US012685789B2

(12) United States Patent
Xiong et al.

(10) Patent No.: US 12,685,789 B2
(45) Date of Patent: Jul. 21, 2026

(54) NEUROPEPTIDE Y1 RECEPTOR (NPY1R) TARGETED THERAPEUTICS AND USES THEREOF

(71) Applicant: Radionetics Oncology, Inc., San Diego, CA (US)

(72) Inventors: Yifeng Xiong, San Diego, CA (US); Junjie Liu, San Diego, CA (US); Yunfei Zhu, San Diego, CA (US)

(73) Assignee: RADIONETICS ONCOLOGY, INC., San Diego, CA (US)

( * ) Notice: Subject to any disclaimer, the term of this patent is extended or adjusted under 35 U.S.C. 154(b) by 0 days.

(21) Appl. No.: 19/002,144

(22) Filed: Dec. 26, 2024

(65) Prior Publication Data

US 2025/0213735 A1 Jul. 3, 2025

Related U.S. Application Data

(60) Provisional application No. 63/682,568, filed on Aug. 13, 2024, provisional application No. 63/646,056, filed on May 13, 2024, provisional application No. 63/615,410, filed on Dec. 28, 2023.

(51) Int. Cl.
*A61K 51/04* (2006.01)
*C07B 59/00* (2006.01)

(52) U.S. Cl.
CPC ........ *A61K 51/0497* (2013.01); *C07B 59/002* (2013.01); *A61K 2121/00* (2013.01); *C07B 2200/05* (2013.01)

(58) Field of Classification Search
CPC ........... A61K 51/0497; A61K 2121/00; C07B 59/002; C07B 2200/05
USPC ........................................................ 424/1.65
See application file for complete search history.

(56) References Cited

U.S. PATENT DOCUMENTS

| | | | | |
|---|---|---|---|---|
| 5,616,620 | A | 4/1997 | Rudolf et al. | |
| 5,807,875 | A | 9/1998 | Rudolf et al. | |
| 2015/0299133 | A1* | 10/2015 | Osterkamp ............. | A61P 43/00 424/1.65 |
| 2024/0226343 | A1 | 7/2024 | Xiong et al. | |

FOREIGN PATENT DOCUMENTS

| | | | |
|---|---|---|---|
| WO | WO-9915498 | A1 | 4/1999 |
| WO | WO-2024112612 | A1 | 5/2024 |

OTHER PUBLICATIONS

Mancilla et al. Org. Prep. Proc. Int. 33 (2001), 341-349. (Year: 2001).*

Killoran et al. Molecules 2021, 26, 1-21. (Year: 2021).*

Killoran et al. Molecules 2021, 26, (Supp) S1-S75. (Year: 2021).*

Berge, Stephen M. et al. Pharmaceutical Salts. Journal of Pharmaceutical Sciences 66(1):1-19 (1977).

Bundgaard, Hans. Chapter 5: Design and Application of Prodrugs. In: Textbook of Drug Design and Development :113-191 (1991).

Bundgaard, Hans. Means to Enhance Penetration: Prodrugs as a Means to Improve the Delivery of Peptide Drugs. Advanced Drug Delivery Review 8(1):1-38 (1992).

Chatenet et al., Novel Dimeric DOTA-Coupled Peptidic Y1-Receptor Antagonists for Targeting of Neuropeptide Y Receptor-Expressing Cancers. EJNNMI Research 1(21):21 (2011).

Fonseca et al., PET Imaging of the Neuropeptide Y System: A Systematic Review. Molecules 27(12):3726 (2022).

Hofmann et al. Synthesis and in vitro and in vivo evaluation of an (18)F-labeled neuropeptide Y analogue for imaging of breast cancer by PET. Mol Phamr 12(4):1121-1130 (2015).

Keller et al. Argininamide-type neuropeptide Y Y1 receptor antagonists: the nature of N ω-carbamoyl substituents determines Y1R binding mode and affinity. RSC Med Chem 11(2):274-282 (2020).

Keller et al. N(ω)-Carbamoylation of the Argininamide Moiety: An Avenue to Insurmountable NPY Y1 Receptor Antagonists and a Radiolabeled Selective High-Affinity Molecular Tool ([(3)H]UR-MK299) with Extended Residence Time. J Med Chem 58(22):8834-8849 (2015).

Keller et al., Prototypic 18F-Labeled Argininamide-Type Neuropeptide Y Y1R Antagonists as Tracers for PET Imaging of Mammary Carcinoma. ACS Medicinal Chemistry Letters 8(3):304-309 (2017).

Keller et al. Structure-Based Design of High-Affinity Fluorescent Probes for the Neuropeptide Y Y1 Receptor. J Med Chem 65(6):4832-4853 (2022).

PCT/US2023/080387 International Search Report and Written Opinion dated Feb. 14, 2024.

Price, Eric W, and Chris Orvig. Matching Chelators to Radiometals for Radiopharmaceuticals. Chemical Society Reviews 43(1):260-290 (2014). Published Online Oct. 30, 2013.

Reubi et al. Y(1)-mediated effect of neuropeptide Y in cancer: breast carcinomas as targets. Cancer Res 61(11):4636-4641 (2001).

Widder, Kenneth J. et al. Method in Enzymology. Academic Press 112:309-396 (1985).

Zhang et al. Targeting the Neuropeptide Y1 Receptor for Cancer Imaging by Positron Emission Tomography Using Novel Truncated Peptides. Mol Pharm 13(11):3657-3664 (2016).

Müller, Christoph. Structure-based development of nonpeptidic fluorescent probes, PET tracers and homobivalent neuropeptide Y $Y_1$ receptor ligands with picomolar binding affinities. Dissertation zur Erlangung des Doktorgrades der Naturwissenschaften (Dr. rer. nat.) an der Fakultät für Chemie und Pharmazie der Universität Regensburg (pp. 1-262) (2022).

PCT/US2024/061942 International Search Report and Written Opinion dated Mar. 6, 2025.

Aiglstorfer, Iris et al. NPY Y1 antagonists: structure-activity relationships of arginine derivatives and hybrid compounds with arpromidine-like partial structures. Regulatory peptides (75-76):9-21 (1998).

(Continued)

*Primary Examiner* — Michael G. Hartley
*Assistant Examiner* — Sean R Donohue
(74) *Attorney, Agent, or Firm* — WILSON SONSINI GOODRICH & ROSATI

(57) ABSTRACT

Described herein are radiotherapeutics that target tumor cells expressing the neuropeptide $Y_1$ receptor ($NPY_1R$) and their use in the treatment and/or diagnosis of cancer.

29 Claims, 2 Drawing Sheets

(56) References Cited

OTHER PUBLICATIONS

Aiglstorfer, Iris et al. Structure-Activity Relationships of Neuropeptide Y $Y_1$ Receptor Antagonists Related to BIBP 3226. Bioorganic & Medicinal Chemistry Letters 10:1597-1600 (2000).
Beck-Sickinger, Annette G. et al. Complete Lalanine scan of neuropeptide Y reveals ligands binding to Y1 and Y2 receptors with distinguished conformations. European journal of biochemistry 225(3):947-958 (1994).
Brennauer, Albert et al. Chapter 17: Structure-activity relationships of nonpeptide neuropeptide Y receptor antagonists. In: Michel, M.C. (eds) Neuropeptide Y and Related Peptides. Handbook of Experimental Pharmacology 162:506-546 (2004).
Buschmann, Jonas et al. Argininamide-type neuropeptide YY 1 receptor antagonists: the nature of N-carbamoyl substituents determines Y 1 R binding mode and affinity. RSC Medicinal Chemistry 11(2):274-282 (2020).
Doods, Henri N. et al. BIBP 3226, the first selective neuropeptide Y1 receptor antagonist: a review of its pharmacological properties. Regulatory peptides 65(1):71-77 (1996).
Keller, Max Dr. Prof., Institute of Pharmacy, University of Regensburg (2 pgs) (Downloaded Apr. 3, 2025).
Keller, Max Dr. Prof., Publications in Journals with Scientific Quality Assurance. Institute of Pharmacy, University of Regensburg (pp. 1-6) (2007-2025).
Keller, Max et al. Bivalent ArgininamideType Neuropeptide Y $Y_1$ Antagonists Do Not Support the Hypothesis of Receptor Dimerisation. ChemMedChem: Chemistry Enabling Drug Discovery 4(10):1733-1745 (2009).
Keller, Max et al. Dimeric argininamide-type neuropeptide Y receptor antagonists: chiral discrimination between $Y_1$ and $Y_4$ receptors. Bioorganic & Medicinal Chemistry 21(21):6303-6322 (2013).
Keller, Max et al. Guanidine Acylguanidine Bioisosteric Approach in the Design of Radioligands: Synthesis of a Tritium-Labeled N G-Propionylargininamide ([$^3$H]-UR-MK114) as a Highly Potent and Selective Neuropeptide Y $Y_1$ Receptor Antagonist. Journal of medicinal chemistry 51(24):8168-8172 (2008).
Keller, Max et al. Mimicking of arginine by functionalized N-carbamoylated arginine as a new broadly applicable approach to labeled bioactive peptides: high affinity angiotensin, neuropeptide Y, neuropeptide FF, and neurotensin receptor ligands as examples. Journal of medicinal chemistry 59(5):1925-1945 (2016).
Keller, Max et al. Red-fluorescent argininamide-type NPY $Y_1$ receptor antagonists as pharmacological tools. Bioorganic & medicinal chemistry 19(9):2859-2878 (2011).
Keller, Max et al. Toward Labeled ArgininamideType NPY $Y_1$ Receptor Antagonists: Identification of a Favorable Propionylation Site in BIBO3304. Archiv der Pharmazie 348(6):390-398 (2015).
Maschauer, Simone et al. $^{18}$F-labelled triazolyl-linked argininamides targeting the neuropeptide $YY_1R$ for PET imaging of mammary carcinoma. Scientific Reports 9(1):12990, 1-12 (2019).
Memminger, Martin et al. The Neuropeptide $YY_1$ receptor: a diagnostic marker? Expression in MCF-7 breast cancer cells is downregulated by antiestrogens in vitro and in xenografts. PLoS One 7(12):e51032, 1-11 (2012).
Park, Chaehee et al. Structural basis of neuropeptide Y signaling through Y1 receptor. Nature communications 13(1):853, 1-12 (2022).
Rudolf, Klaus et al. Chapter 9—BIBP 3226, a potent and selective neuropeptide Y Y1-receptor antagonist. Structure-activity studies and localization of the human Y1 receptor binding site. Neuropeptide Y and drug development :175-190 (1997).
Rudolf, Klaus et al. The first highly potent and selective non-peptide neuropeptide $YY_1$ receptor antagonist: BIBP3226. European journal of pharmacology 271(2-3):R11-R13 (1994).
Schmidt, Michael M et al. A modeling analysis of the effects of molecular size and binding affinity on tumor targeting. Mol Cancer Ther 8(10):2861-2871 (2009).
Schneider, Erich et al. Synthesis and characterization of the first fluorescent nonpeptide NPY Y1 receptor antagonist. ChemBioChem 8(16):1981-1988 (2007).
Sjodin, Paula et al. Re-evaluation of receptor-ligand interactions of the human neuropeptide Y receptor Y1: a site-directed mutagenesis study. Biochemical Journal 393(1):161-169 (2006).
Srinivasarao, Madduri et al. Ligand-Targeted Drug Delivery. Chem. Rev. 17(19):12133-12164 (2017).
Srinivasarao, Madduri et al., Principles in the Design of Ligand-targeted Cancer Therapeutics and Imaging Agents. Nat Rev Drug Discov 14(3):203-219 (2015).
Tang, Tingting et al. Receptor-specific recognition of NPY peptides revealed by structures of NPY receptors. Science Advances 8(18):eabm1232, 1-15 (2022).
Weiss, Stefan et al. Modular synthesis of non-peptidic bivalent NPY Y1 receptor antagonists. Bioorganic & medicinal chemistry 16(22):9858-9866 (2008).
Weiss, Stefan et al. $N^G$-Acyl-argininamides as NPY Y1 receptor antagonists: Influence of structurally diverse acyl substituents on stability and affinity. Bioorganic & medicinal chemistry 18(17):6292-6304 (2010).
Wieland, H. A. et al. Subtype selectivity of the novel nonpeptide neuropeptide Y Y1 receptor antagonist BIBO 3304 and its effect on feeding in rodents. British journal of pharmacology 125(3):549-555 (1998).
Wieland, Heike A. et al. Subtype selectivity and antagonistic profile of the nonpeptide Y1 receptor antagonist BIBP 3226. The Journal of pharmacology and experimental therapeutics 275(1):143-149 (1995).
Wright, Jon. Design and discovery of neuropeptide Y1 receptor antagonists. Drug discovery today 2(1):19-24 (1997).
Yang, Zhenlin et al. Structural basis of ligand binding modes at the neuropeptide Y Y1 receptor. Nature 556(7702):520-524 (2018).

* cited by examiner

NEUROPEPTIDE Y1 RECEPTOR (NPY1R) TARGETED THERAPEUTICS AND USES THEREOF

CROSS-REFERENCE TO RELATED APPLICATIONS

This application claims the benefit of U.S. Provisional Patent Application No. 63/682,568, filed Aug. 13, 2024, U.S. Provisional Patent Application No. 63/646,056, filed May 13, 2024, and U.S. Provisional Patent Application No. 63/615,410, filed Dec. 28, 2023, which are incorporated herein by reference in their entireties.

FIELD OF THE INVENTION

Described herein are radiotherapeutics that target tumor cells expressing the neuropeptide $Y_1$ receptor ($NPY_1R$) and methods of using such radiotherapeutics as cancer therapeutics, diagnostics, or both.

BACKGROUND OF THE INVENTION

Neoplasms are an abnormal growth of cells and cause enormous medical burdens, including morbidity and mortality, in humans. Neoplasms include benign or noncancerous neoplasms which do not display malignant features and are generally unlikely to become dangerous (e.g., adenomas). Malignant neoplasms display features such as genetic mutations, loss of normal function, rapid division, and ability metastasize (invade) to other tissues; and neoplasms of uncertain or unknown behavior. Malignant neoplasms (i.e., cancerous solid tumors) are the leading cause of death in industrialized countries. Noncancerous neoplasms including benign adenomas can also cause significant morbidity and mortality. Although standard treatments can achieve significant effects in tumor growth inhibition and even tumor elimination, the applied drugs exhibit only minor selectivity for the malignant tissue over healthy tissue and their severe side effects limit their efficacy and use. Specific targeting of neoplastic cells without affecting healthy tissue is a major desire for effective solid tumor therapy.

As one of three main classes of cell surface receptors, G protein-coupled receptors (GPCRs) are frequently overexpressed in tumor cells and are considered promising targets for selective tumor therapy. Specifically, $NPY_1R$ is overexpressed in multiple cancer types, including, but not limited to, breast carcinomas, adrenal gland and related tumors, renal cell carcinomas, and ovarian cancers, in both tumor cells and tumor-associated blood vessels. Targeted delivery of radionuclides to tumors with small molecule $NPY_1R$ ligand-based conjugates offers a novel approach to treat and diagnose various cancers, including, but not limited to, breast cancer, kidney cancer (e.g., renal cell carcinoma (RCC)), ovarian cancer, melanoma, gastrointestinal stromal tumor (GIST), Ewing's sarcoma, nephroblastoma, or adrenal gland tumors.

SUMMARY OF THE INVENTION

Described herein are radiopharmaceuticals for use in the diagnosis and/or treatment of tumors. The present disclosure provides an alternative and improved method for the treatment of tumors by targeting tumors that overexpress the neuropeptide $Y_1$ receptor ($NPY_1R$). In some embodiments, the radiopharmaceuticals disclosed herein are useful in the treatment of tumors that overexpress $NPY_1R$. In some other embodiments, the radiopharmaceuticals disclosed herein are useful in the identification of tissues or organs in a subject comprising tumors overexpressing $NPY_1R$. The radiopharmaceuticals disclosed herein are also useful for in vivo imaging of a subject for the presence of and distribution of tumors that overexpress $NPY_1R$ in the subject.

In one aspect, described herein is a compound of Formula (I), or a pharmaceutically acceptable salt thereof:

Formula (I)

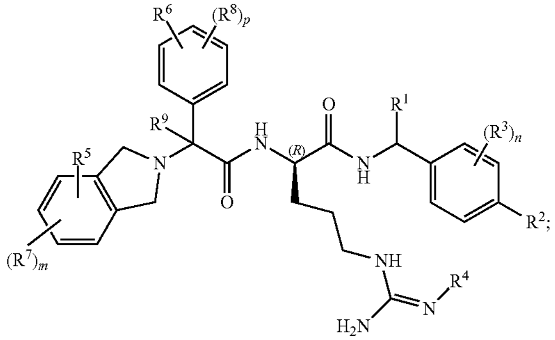

wherein:

$R^1$ is H, $-C_1$-$C_6$ alkyl, or $-C(=O)NH_2$;

$R^2$ is $-OH$, $-NH_2$, $-C(=O)NH_2$, or $-CH_2NHC(=O)NH_2$;

each $R^3$ is independently selected from the group consisting of $R^{3a}$, $R^{3b}$, $R^{3c}$, and $R^{3d}$;

$R^{3a}$, $R^{3b}$, $R^{3c}$, and $R^{3d}$ are each independently selected from the group consisting of H, F, Cl, Br, I, $-CN$, substituted or unsubstituted $-C_1$-$C_6$ alkyl, and substituted or unsubstituted $-C_1$-$C_6$ alkoxy;

$R^4$ is H, $-C(=O)R^{10}$; $-C(=O)NHR^{10}$, or $-C(=O)N(CH_3)R^{10}$;

$R^{10}$ is substituted or unsubstituted $-C_1$-$C_6$ alkyl, substituted or unsubstituted 2 to 6-membered heteroalkyl, $-(CH_2)_u-NH_2$, $-(CH_2)_tC(=O)O(CH_2)_uCH_3$, $-(CH_2)_tNHC(=O)(CH_2)_uCH_3$, or $-(CH_2)_t$-substituted or unsubstituted 5 to 6 membered heteroaryl ring;

t is 1, 2, 3, 4, 5, or 6;

u is 1, 2, 3, or 4;

$R^5$ is absent or $-Z^B$-$L^B$-$R^B$;

$Z^B$ is absent, $-C_1$-$C_6$ alkylene-, $-C_1$-$C_6$ alkylene-O-, $-O-C_1$-$C_6$ alkylene-, $-C(=O)NR^{12}-$, $-NR^{12}C(=O)-$, $-O-$, $-NR^{11}-$, $-S-$, $-S(=O)-$, $-SO_2-$, or $-NHC(=O)NH-$;

$L^B$ is a linker;

$R^B$ is a chelating moiety or a radionuclide complex thereof, $R^6$ is absent or $-Z^A$-$L^A$-$R^A$;

$Z^A$ is absent, $-C_1$-$C_6$ alkylene-, $-C_1$-$C_6$ alkylene-O-, $-O-C_1$-$C_6$ alkylene-, $-C(=O)NR^{12}-$, $-NR^{12}C(=O)-$, $-O-$, $-NR^{12}-$, $-S-$, $-S(=O)-$, $-SO_2-$, or $-NHC(=O)NH-$;

$L^A$ is a linker;

$R^A$ is a chelating moiety or a radionuclide complex thereof;

each $R^7$ is independently selected from F, Cl, Br, I, $-CN$, $-OH$, substituted or unsubstituted $-C_1$-$C_6$ alkyl, or substituted or unsubstituted $-C_1$-$C_6$ alkoxy;

each $R^8$ is independently selected from F, Cl, Br, I, —CN, —OH, substituted or unsubstituted —$C_1$-$C_6$ alkyl, or substituted or unsubstituted —$C_1$-$C_6$ alkoxy;

$R^9$ is H, substituted or unsubstituted —$C_1$-$C_4$ alkyl, or substituted or unsubstituted —$C_1$-$C_6$ alkoxy;

each $R^{11}$ is independently H or unsubstituted —$C_1$-$C_4$ alkyl;

each $R^{12}$ is independently H or unsubstituted —$C_1$-$C_4$ alkyl;

n is 0, 1, 2, 3, or 4;

m is 0, 1, 2, or 3;

p is 0, 1, 2, or 3; and wherein $R^5$ is —$Z^B$-$L^B$-$R^B$ when $R^6$ is absent; or $R^6$ is —$Z^A$-$L^A$-$R^A$ when $R^5$ is absent.

In some embodiments, $R^A$ and $R^B$, if present, are each independently selected from the group consisting of: 1,4,7,10-tetraazacyclododecane-1,4,7,10-tetraacetic acid (DOTA); 1,4,7,10-tetraazacyclododecane-1,4,7-triacetic acid (DO3A); 1,4,7,10-tetraazacyclododecane-1,7-diacetic acid (DO2A); α,α',α'',α'''-tetramethyl-1,4,7,10-tetraazacyclododecane-1,4,7,10-tetraacetic acid (DOTMA); 1,4,7,10-tetrakis(carbamoylmethyl)-1,4,7,10-tetraazacyclododecane (DOTAM); 1,4,7,10-tetraazacyclododecane-1,4,7,10-tetrapropionic acid (DOTPA); 2,2',2''-(10-(2-amino-2-oxoethyl)-1,4,7,10-tetraazacyclododecane-1,4,7-triyl)triacetic acid; benzyl-1,4,7,10-tetraazacyclododecane-1,4,7,10-tetraacetic acid (Bn-DOTA); p-hydroxy-benzyl-1,4,7,10-tetraazacyclododecane-1,4,7,10-tetraacetic acid (p-OH-Bn-DOTA); 6,6'-(((pyridine-2,6-diylbis(methylene))bis((carboxymethyl)azanediyl))bis(methylene))-dipicolinic acid ($H_4$pypa); $H_4$pypa-benzyl; 6,6',6'',6'''-(((pyridine-2,6-diylbis(methylene))bis(azanetriyl))-tetrakis(methylene))-tetrapicolinic acid ($H_4$py4pa); $H_4$py4pa-benzyl; 2,2',2''-(1,4,7-triazacyclononane-1,4,7-triyl)triacetic acid (NOTA); 6,6'-((1,4,10,13-tetraoxa-7,16-diazacyclooctadecane-7,16-diyl)bis(methylene))dipicolinic acid (macropa); 2,2',2'',2'''-(1,10-dioxa-4,7,13,16-tetraazacyclooctadecane-4,7,13,16-tetrayl)tetraacetic acid (crown); 6,6'-((ethane-1,2-diylbis((carboxymethyl)azanediyl))bis(methylene))dipicolinic acid ($H_4$octapa); $H_4$octapa-benzyl; and 3,6,9,12-tetrakis(carboxymethyl)-3,6,9,12-tetraazatetradecanedioic acid (TTHA); or a radionuclide complex thereof.

In some embodiments, $R^A$ and $R^B$, if present, are independently selected from the group consisting of:

(CM-1)

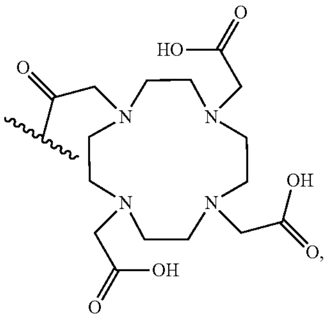

-continued (CM-2)

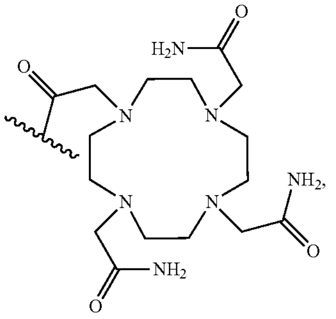

(CM-3)

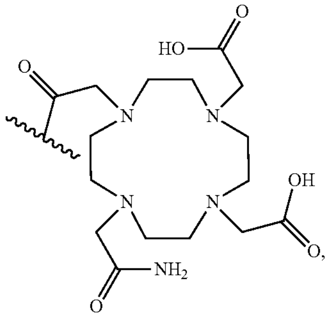

(CM-4)

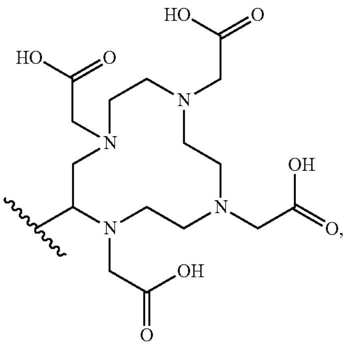

and (CM-5)

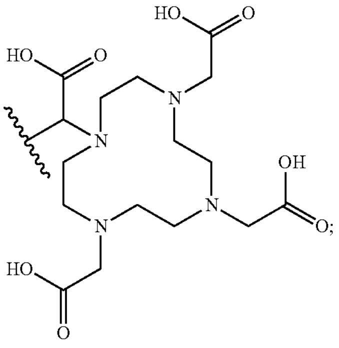

or a radionuclide complex thereof.

In some embodiments, $R^A$ and $R^B$, if present, are (CM-6)

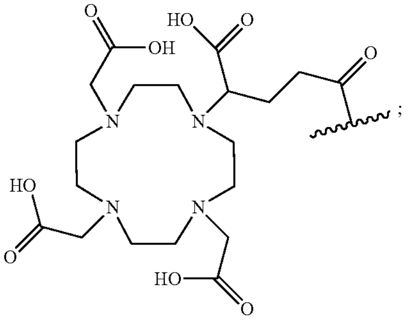

or a radionuclide complex thereof.

In some embodiments, $L^A$ and $L^B$, if present, are each independently selected from: $-L^2-$, $-L^3-$, $-L^4-$, $-L^5-$, $-L^6-$, $-L^7-$, $-L^2-L^3-$, $-L^2-L^4-$, $-L^2-L^6-$, $-L^2-L^7-$, $-L^4-L^6-$, $-L^4-L^7-$, $-L^6-L^7-$, $-L^2-L^3-L^7$, $-L^2-L^4-L^7-$, $-L^2-L^5-L^7-$, $-L^2-L^6-L^7-$, $-L^3-L^4-L^7-$, $-L^4-L^5-L^7-$, $-L^2-L^3-L^4-L^7-$, $-L^2-L^4-L^5-L^7-$, $-L^2-L^4-L^6-L^7-$, $-L^4-L^5-L^6-L^7-$, $-L^2-L^4-L^5-L^6-L^7-$, or $-L^2-L^3-L^4-L^5-L^6-L^7-$; $L^2$ is absent, substituted or unsubstituted $—C_1-C_{20}$ alkylene, substituted or unsubstituted $—C_1-C_{20}$ alkylene-$NR^{16}$—, substituted or unsubstituted $—C_1-C_{20}$ alkylene-C(=O)—, substituted or unsubstituted $—C_1-C_{20}$ alkylene-C(=O)$NR^{16}$—, substituted or unsubstituted $—C_1-C_{20}$ alkylene-$NR^{16}$C(=O)—, substituted or unsubstituted 2 to 20 membered heteroalkylene, $—(CH_2CH_2O)_w—$, $—(OCH_2CH_2)_w—$, or $—(CH_2CH_2O)_w—CH_2CH_2—$; each $R^{16}$ is independently selected from H and $C_1-C_4$ alkyl; w is 1, 2, 3, 4, 5, or 6; $L^3$ is absent or a natural or unnatural amino acid or peptide that is formed from two or more independently selected natural and unnatural amino acids, wherein when two or more amino acids are present then the N atom of the amide linking the amino acids is optionally substituted with $—C_1-C_6$ alkyl; $L^4$ is absent, substituted or unsubstituted 2 to 10-membered heteroalkylene, $—(CH_2)_v—$, $—CH_2—(OCH_2CH_2)_v—$, $—(CH_2CH_2O)_v—CH_2CH_2—$, $—C(=O)CH_2CH_2—$, $—CH_2CH_2C(=O)—$, $—(CH_2)_v—NR^{17}C(=O)—$, $—CH_2CH_2C(=O)NHCH_2CH_2—$, $—CH_2CH_2—C(=O)NH—(CH_2CH_2O)_vCH_2CH_2—$, $—(CH_2)_x—NR^{17}—(CH_2)_v$, $—NHC(=O)NH—O—(CH_2)_v—$, $—NHC(=O)NH—(CH_2)_v—$, $—(CH_2)_x—NHC(=O)NH—(CH_2)_v—$, $—(CH_2)_x—C(=O)NH—(CH_2)_v—$, $—(CH_2)_x—NHC(=O)—(CH_2)_v—$, $—CH_2C(—OH)CH_2—C(OH)—CH_2CH_2—$, $—CH_2C(—OH)CH_2—C(OH)—CH_2CH_2—NHC(=O)CH_2CH_2C(=O)—NHCH_2CH_2—$, or $—NHC(=O)CH_2—O—NH—C(=O)(CH_2)_v—$; each $R^{17}$ is independently H or $—C_1-C_6$ alkyl; each x is independently 1, 2, 3, 4, 5 or 6; each v is independently 1, 2, 3, 4, 5, 6, 7, 8, 9, or 10; $L^5$ is absent, —O—, $—NR^3—$, —C(=O)—, $—C(=O)NR^{13}—$, $—NR^{13}C(=O)$, $—NR^{13}C(=O)O—$, $—NR^{13}C(=O)NR^{13}—$, or $—OC(=O)NR^{13}—$; each $R^{13}$ is independently selected from H and $—C_1-C_4$ alkyl; $L^6$ is absent or $-L^8-L^9-L^{10}-$; $L^8$ is absent, $—(CH_2)_r—$, $—(CH_2)_r—C(=O)—$, $—(CH_2)_r—NR^{14}—$, $—(CH_2)_r—NR^{14}C(=O)—$, $—(CH_2)_r—C(=O)NR^{14}—$, or substituted or unsubstituted heterocycloalkylene; r is 0, 1, 2, or 3; $L^9$ is substituted or unsubstituted cycloalkylene, substituted or unsubstituted heterocycloalkylene, substituted or unsubstituted arylene, or substituted or unsubstituted heteroarylene; $L^{10}$ is absent, $—(CH_2)_q—$, $—NR^{15}—$, $—NR^{15}—(CH_2)_q—$, $—(CH_2)_q—C(=O)—$, $—C(=O)—(CH_2)_q—$, $—(CH_2)_q—NR^{15}—$, $—(CH_2)_q—NR^{15}C(=O)—$, $—(CH_2)_q—C(=O)NR^{15}—$, $—NR^{15}C(=O)—(CH_2)_q—$, or $—C(=O)NR^{15}—(CH_2)_q—$; q is 1, 2, 3, 4, 5 or 6; $R^{14}$ and $R^{15}$ are each independently selected from H or $—C_1-C_6$ alkyl; p is 1, 2, 3, 4, 5, or 6; and $L^7$ is absent, —NH—, or $—N(CH_3)—$.

In some embodiments, the radionuclide of the radionuclide complex is a lanthanide or an actinide. In some embodiments, the radionuclide of the radionuclide complex is actinium, bismuth, cesium, cobalt, copper, dysprosium, erbium, gold, indium, iridium, gallium, lead, lutetium, manganese, palladium, platinum, radium, rhenium, samarium, strontium, technetium, ytterbium, yttrium, or zirconium. In some embodiments, the radionuclide of the radionuclide complex is a diagnostic or therapeutic radionuclide. In some embodiments, the radionuclide of the radionuclide complex is an Auger electron-emitting radionuclide, α-emitting radionuclide, 3-emitting radionuclide, or γ-emitting radionuclide. In some embodiments, the radionuclide of the radionuclide complex is 111-indium ($^{111}In$), 115-indium ($^{115}In$), 67-gallium ($^{67}Ga$), 68-gallium ($^{68}Ga$), 69-gallium ($^{69}Ga$), 71-gallium ($^{71}Ga$), 225-actinium ($^{225}Ac$), 175-lutetium ($^{175}Lu$), 177-lutetium ($^{177}Lu$), 204-lead ($^{204}Pb$), 206-lead ($^{206}Pb$), 207-lead ($^{207}Pb$), 208-lead ($^{208}Pb$), 212-lead ($^{212}Pb$), 63-copper ($^{63}Cu$), 64-copper ($^{64}Cu$), 65-copper ($^{65}Cu$), or 67-copper ($^{67}Cu$).

Also described herein is a pharmaceutical composition comprising a compound described herein (e.g., a compound of Formula (I), or a pharmaceutically acceptable salt thereof), and at least one pharmaceutically acceptable excipient. In some embodiments, the pharmaceutical composition is formulated for administration to a mammal by intravenous administration or subcutaneous administration. In some embodiments, the pharmaceutical composition is formulated for administration to a mammal by intravenous administration.

In another aspect, described herein is a method for the treatment of cancer comprising administering to a mammal with cancer an effective amount of a compound described herein (e.g., a compound of Formula (I)), or a pharmaceutically acceptable salt thereof). In some embodiments, the cancer comprises tumors and the tumors overexpress the neuropeptide $Y_1$ receptor ($NPY_1R$). In some embodiments, the cancer is breast cancer, kidney cancer (e.g. renal cell carcinoma (RCC)), ovarian cancer, melanoma, gastrointestinal stromal tumor (GIST), Ewing's sarcoma, nephroblastoma, or adrenal gland tumors. In some embodiments, the cancer is breast cancer. In some embodiments, the cancer is kidney cancer (e.g., renal cell carcinoma (RCC)). In some embodiments, the cancer is ovarian cancer. In some embodiments, the cancer is melanoma. In some embodiments, the cancer is gastrointestinal stromal tumor (GIST). In some embodiments, the cancer is Ewing's sarcoma. In some embodiments, the cancer is nephroblastoma. In some embodiments, the cancer is adrenal gland tumors.

In another aspect, described herein is a method for treating tumors in a mammal with a radionuclide comprising administering to the mammal a compound described herein (e.g., a compound of Formula (I), or a pharmaceutically acceptable salt thereof). In some embodiments, the mammal has been diagnosed with breast cancer. In some embodiments, the mammal has been diagnosed with kidney cancer (e.g., renal cell carcinoma (RCC)), ovarian cancer, melanoma, gastrointestinal stromal tumor (GIST), Ewing's sarcoma, nephroblastoma, or adrenal gland tumors.

In another aspect, described herein is a method of targeting delivery of a radionuclide to tumors in a mammal comprising administering to a mammal with tumors a compound described herein (e.g., a compound of Formula (I), or a pharmaceutically acceptable salt thereof); wherein the tumors overexpress the neuropeptide $Y_1$ receptor ($NPY_1R$).

In another aspect, described herein is a method for identifying tissues or organs in a mammal with tumors expressing the neuropeptide $Y_1$ receptor ($NPY_1R$) comprising administering to the mammal a compound described herein (e.g., a compound of Formula (I), or a pharmaceutically acceptable salt thereof); and performing positron emission tomography (PET) analysis, single-photon emission computerized tomography (SPECT), or magnetic resonance imaging (MRI); wherein $R^A$ or $R^B$ are a chelating moiety-diagnostic radionuclide complex.

In yet another aspect, described herein is a method for the in vivo imaging of tissues or organs in a mammal with tumors expressing the neuropeptide $Y_1$ receptor ($NPY_1R$) comprising administering to the mammal a compound described herein (e.g., a compound of Formula (I), or a pharmaceutically acceptable salt thereof); and performing positron emission tomography (PET) analysis, single-photon emission computerized tomography (SPECT), or magnetic resonance imaging (MRI); wherein $R^A$ or $R^B$ are a chelating moiety-diagnostic radionuclide complex.

In any of the embodiments disclosed herein, the mammal is a human.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
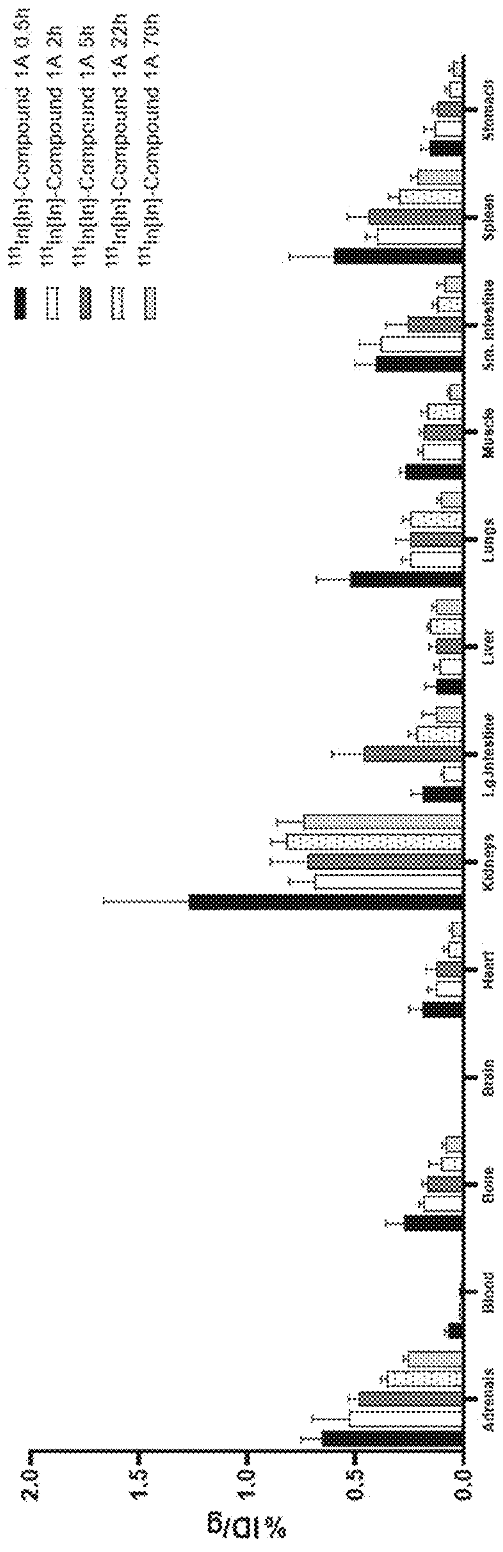
FIG. 1 depicts biodistribution of $^{111}$In[In]-Compound 1A in Wistar Han rats. Timepoints are 0.5, 2.0, 5.0, 24 and 72 hours post IV treatment. Activity is measured as percentage of injected dose per gram of tissue (% ID/g).
Figure 2:
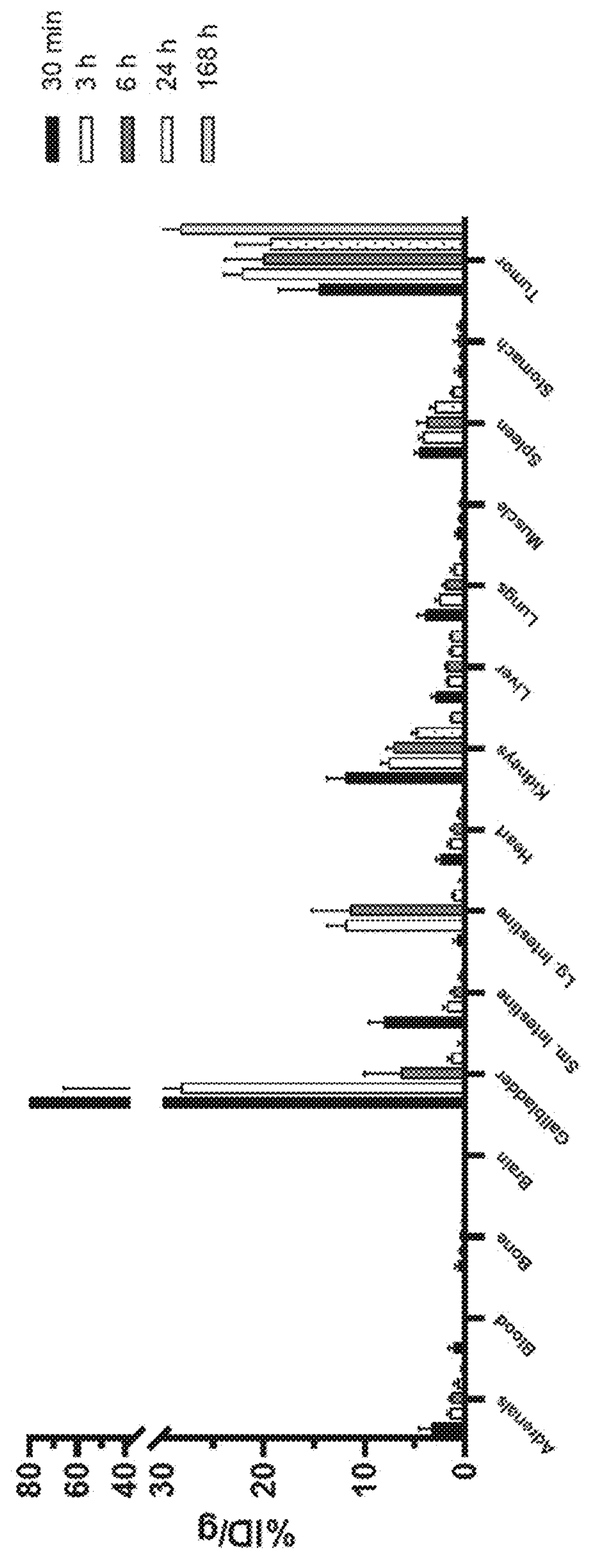
FIG. 2 depicts biodistribution of $^{177}$Lu[Lu]-Compound 1A in tumor bearing Swiss nude mice. Timepoints are 0.5-1, 2-3, 5-6, 22-24 and 168-170 hours post IV treatment. Activity is measured as percentage of injected dose per gram of tissue (% ID/g).

Cancer, a disease in which some cells undergo a genetic change in the control of their growth and replication that results in uncontrolled growth and spreading, is one of the leading causes of death worldwide. General types of cancers include solid tumors (cancers that typically originate in organs), carcinomas (cancers that originate in skin or tissues that line organs), sarcomas (cancers of connective tissues such as bones), leukemias (cancers of bone marrow), and lymphomas and myelomas (cancers of the immune system). Neoplasms are an abnormal growth of cells that result in solid tumors which may be benign (i.e. do not display malignant features and are generally unlikely to become dangerous such as adenomas), malignant (i.e. display features such as genetic mutations, loss of normal function, rapid division, and ability metastasize (invade) to other tissues), and of uncertain or unknown behavior. State-of-the-art treatment of neoplasms is accomplished by a combination of surgical procedures, chemotherapy, and radiation therapy. Surgical procedures can be curative under some conditions, but often require multiple interventions as well as combination with radiation and chemotherapy. Chemotherapy proves to be a potent weapon in the fight against cancer in many cases. Chemotherapy is typically performed by systemic administration of potent cytotoxic drugs, but these compounds often lack tumor selectivity and therefore also kill healthy cells in the body. The resulting non-specific toxicity is the cause of severe side effects of chemotherapy because chemotherapy does not target cancer cells specifically over other cells. Radiotherapy is the use of high-energy radiation to kill cells. The source of radiation may be external-beam radiation (applied using an external source), internal radiation (placement of a radioactive material near the target cells), or radiotherapy from the systemic administration of a radioactive material. Like chemotherapy, many radiation therapy options also lack tumor cell identification properties needed to achieve the ultimate goal of targeted tumor therapy with drug molecules or radionuclides.

Described herein are radiopharmaceuticals that selectively deliver radionuclides to malignant cells that overexpress $NPY_1R$ for use in cancer detection, image guided cancer surgery, and selective tumor killing.

GPCRs are generally poorly antigenic, making them difficult targets for antibody-based strategies. The large size of antibodies can impact homogenous uptake and they may be unable to penetrate deep into solid tumors. Additionally, antibodies may present difficulties during production, including inter-batch variability.

Peptides are intrinsically sensitive to proteolytic enzymes and peptidases present in most tissues may rapidly degrade the peptides into multiple fragments which no longer have significant affinity to the intended receptors. In addition, peptides may cause unwanted immunogenic responses complicating later stages of development by masking the therapeutic effect and impacting the safety assessment.

When peptide ligands are linked to radionuclide payloads, the resulting conjugates often degrade rapidly in blood plasma and produce cytotoxic or radioactive peptide fragments, which may nonspecifically bind to both tumor and normal tissue. Such premature breakdown of peptide radionuclide conjugates reduces the amount of radionuclide payloads distributed to targeted tumors, lowering treatment efficacy, and possibly increasing toxicity. In addition, peptides are most likely excreted exclusively via kidney, which may limit their applications. Marked kidney uptake of some peptide-based therapeutics has limited their routine use.

High affinity, small molecule ligands that bind GPCRs have been described that are cell permeable and can access populations of receptors in endoplasmic reticulum and endosomes. Owing to the low molecular weight of small molecules, vascular permeability and tumor penetration should be improved compared to high molecular weight conjugates based on peptides and antibodies. In many cases, the affinity of small molecule ligands surpasses that of FDA approved antibodies by orders of magnitude.

The Neuropeptide Y Receptor (NPYR)

Neuropeptide Y (NPY) receptors belong to the class A of G-protein coupled receptors (GPCRs). These receptors are involved in the control of a diverse set of behavioral processes including appetite, circadian rhythm, and anxiety. The four functionally expressed subtypes in humans ($NPY_1R$, $NPY_2R$, $NPY_4R$ and $NPY_5R$) are distributed in the central nervous system and in the periphery. They are activated by the endogenous peptides neuropeptide Y (NPY), peptide YY (PYY) and pancreatic polypeptide (PP).

The $NPY_1R$ was shown to be overexpressed in different types of cancer (e.g., breast cancer). Therefore, $NPY_1R$ ligands carrying radionuclide cargoes offer a new modality in the imaging and treatment of cancers.

Breast Cancer

Breast cancer is a type of cancer that starts in the breast. It can start in one or both breasts, and in various parts of the breast. There are many types of breast cancer, and a breast cancer's type is determined by the specific cells in the breast that become cancer.

Breast Cancer Types

Most breast cancers are carcinomas, which are tumors that start in the epithelial cells that line organs and tissues throughout the body. When carcinomas form in the breast, they are usually a more specific type called adenocarcinoma, which starts in cells in the ducts (the milk ducts) or the lobules (glands in the breast that make milk).

The type of breast cancer can also refer to whether the cancer has spread or not. In situ breast cancer (ductal carcinoma in situ or DCIS) is a pre-cancer that starts in a milk duct and has not grown into the rest of the breast tissue. The term invasive (or infiltrating) breast cancer is used to describe any type of breast cancer that has spread (invaded) into the surrounding breast tissue.

Breast Cancer Staging

The staging system most often used for breast cancer is the American Joint Committee on Cancer (AJCC) TNM system. The most recent AJCC system, effective January 2018, has both clinical and pathologic staging systems for breast cancer:

The pathologic stage (also called the surgical stage) is determined by examining tissue removed during an operation.

Sometimes, if surgery is not possible right away or at all, the cancer will be given a clinical stage instead. This is based on the results of a physical exam, biopsy, and imaging tests. The clinical stage is used to help plan treatment. Sometimes, though, the cancer has spread further than the clinical stage estimates, and may not predict the patient's outlook as accurately as a pathologic stage.

In both staging systems, seven key pieces of information are used:

i. The extent (size) of the tumor (T);
ii. The spread to nearby lymph nodes (N);
iii. The spread (metastasis) to distant sites (M);
iv. Estrogen Receptor (ER) status;
v. Progesterone Receptor (PR) status;
vi. HER2 status; and
vii. Grade of the cancer (G).

In addition, Oncotype Dx® Recurrence Score results may also be considered in the stage in certain situations. Once all of these factors have been determined, this information is combined in a process called stage grouping to assign an overall stage.

Breast Cancer Treatment

Tumors can form in the breasts. The types of treatment currently used to treat breast tumors include: surgery, radiation therapy, chemotherapy, hormone therapy, targeted drug therapy and immunotherapy.

There are two main types of surgery to remove breast cancer: breast-conserving surgery and mastectomy. Breast-conserving surgery is surgery to remove the cancer as well as some surrounding normal tissue. Only the part of the breast containing the cancer is removed. How much breast is removed depends on where and how big the tumor is, as well as other factors. This surgery is also called a lumpectomy, quadrantectomy, partial mastectomy, or segmental mastectomy. Mastectomy is a surgery in which the entire breast is removed, including all of the breast tissue and sometimes other nearby tissues. There are several different types of mastectomies. Some women may also have both breasts removed in a double mastectomy. Sometimes surgery is done to remove the nearby lymph nodes and other tissue where the cancer has spread.

Radiation therapy uses high-energy x-rays or other types of radiation to kill cancer cells or keep them from growing. There are two types of radiation therapy: external radiation therapy uses a machine outside the body to send radiation toward the area of the body with cancer; internal radiation therapy uses a radioactive substance sealed in needles, seeds, wires, or catheters that are placed directly into or near the cancer. Additionally, targeted radiopharmaceuticals can provide targeted radiation to the site of the tumor. Chemotherapy is a cancer treatment that uses drugs to stop the growth of cancer cells, either by killing the cells or by stopping them from dividing.

Thus, a need exists for treatment options for breast tumors. Described herein are radiopharmaceuticals that target delivery of radionuclides to breast tumors, which overexpress the $NPY_1R$. Targeted therapies usually cause less harm to normal cells than chemotherapy or radiation therapy do.

Solid Tumors: Benign and/or Malignant Neoplasms (Cancer)

In one aspect, the $NPY_1R$ radiopharmaceuticals described herein are used to treat benign and/or malignant neoplasms (solid tumors), wherein the neoplasm comprises cells that overexpress $NPY_1R$ on the cell surface.

The term "neoplasm" as used herein, refers to an abnormal growth of cells that may proliferate in an uncontrolled way and may have the ability to metastasize (spread).

Neoplasms include solid tumors, adenomas, carcinomas, sarcomas, leukemias and lymphomas, at any stage of the disease with or without metastases.

A solid tumor is an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas. Leukemias (cancers of the blood) generally do not form solid tumors.

Solid tumors are cancers that typically originate in organs, such as the bladder, bowel, brain, breast, endometrium, heart, kidney, lung, liver, uterus, ovaries, pancreas or other endocrine organs (thyroid), and prostate.

In some embodiments, the $NPY_1R$ radiopharmaceuticals described herein are used to treat an adenoma. An adenoma is a tumor that is not cancer. It starts in gland-like cells of the epithelial tissue (thin layer of tissue that covers organs, glands, and other structures within the body). An adenoma can grow from many glandular organs, including the adrenal glands, pituitary gland, thyroid, prostate, and others. Even though benign, they have the potential to cause serious health complications by compressing other structures (mass effect) and by producing large amounts of hormones in an unregulated, non-feedback-dependent manner (causing paraneoplastic syndromes). Over time adenomas may transform to become malignant, at which point they are called adenocarcinomas.

Adenomas may be found in the colon (e.g. adenomatous polyps, which have a tendency to become malignant and to lead to colon cancer), kidneys (e.g. renal adenomas may be precursor lesions to renal carcinomas), adrenal glands (e.g. adrenal adenomas; some secrete hormones such as cortisol, causing Cushing's syndrome, aldosterone causing Conn's syndrome, or androgens causing hyperandrogenism), thyroid (e.g. thyroid adenoma), pituitary (e.g. pituitary adenomas, such as prolactinoma, Cushing's disease and acromegaly), parathyroid (e.g. an adenoma of a parathyroid gland may secrete inappropriately high amounts of parathyroid hormone and thereby cause primary hyperparathyroidism), liver (e.g. hepatocellular adenoma), breast (e.g. fibroadenomas), appendix (e.g. cystadenoma), bronchial (e.g. bronchial adenomas may cause carcinoid syndrome, a type of paraneoplastic syndrome), prostate (e.g. prostate adenoma), sebaceous gland (e.g. sebaceous adenoma), and salivary glands.

Metastasis is the spread of malignant cells to new areas of the body, often by way of the lymph system or bloodstream. A metastatic tumor is one that has spread from the primary site of origin, or where it started, into different areas of the body. Metastatic tumors comprise malignant cells that may express cell surface $NPY_1R$.

Tumors formed from cells that have spread are called secondary tumors. Tumors may have spread to areas near the primary site, called regional metastasis, or to parts of the body that are farther away, called distant metastasis.

In some embodiments, the tumor to be treated comprises tumor cells expressing $NPY_1R$, wherein the tumor is a primary or metastatic tumor. In some embodiments, the tumor to be treated comprises tumor cells expressing $NPY_1R$, wherein the tumor is a primary or metastatic tumor of breast origin. In some embodiments, the tumor to be treated comprises tumor cells expressing $NPY_1R$, wherein the tumor is a primary or metastatic tumor of kidney origin. In some embodiments, the tumor to be treated comprises tumor cells expressing $NPY_1R$, wherein the tumor is a primary or metastatic tumor of ovarian origin. In some embodiments, the tumor to be treated comprises tumor cells expressing $NPY_1R$, wherein the tumor is a primary or metastatic tumor of melanoma origin. In some embodiments, the tumor to be treated comprises tumor cells expressing $NPY_1R$, wherein the tumor is a primary or metastatic tumor of gastrointestinal stromal tumor origin. In some embodiments, the tumor to be treated comprises tumor cells expressing $NPY_1R$, wherein the tumor is a primary or metastatic tumor of Ewing's sarcoma origin. In some embodiments, the tumor to be treated comprises tumor cells expressing $NPY_1R$, wherein the tumor is a primary or metastatic tumor of nephroblastoma origin. In some embodiments, the tumor to be treated comprises tumor cells expressing $NPY_1R$, wherein the tumor is a primary or metastatic tumor of adrenal gland origin.

In some embodiments, the $NPY_1R$ radiopharmaceuticals described herein are used to treat a carcinoma. Carcinomas include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

In some embodiments, the $NPY_1R$ radiopharmaceuticals described herein are used to treat a sarcoma. Sarcomas include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Solid tumors include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Benign solid tumors include adenomas.

Primary and metastatic tumors include, for example, lung cancer (including, but not limited to, lung adenocarcinoma, squamous cell carcinoma, large cell carcinoma, bronchioloalveolar carcinoma, non-small-cell carcinoma, small cell carcinoma, and mesothelioma); breast cancer (including, but not limited to, ductal carcinoma, lobular carcinoma, inflammatory breast cancer, clear cell carcinoma, and mucinous carcinoma); colorectal cancer (including, but not limited to, colon cancer, rectal cancer); anal cancer; pancreatic cancer (including, but not limited to, pancreatic adenocarcinoma, islet cell carcinoma, and neuroendocrine tumors); prostate cancer; ovarian carcinoma (including, but not limited to, ovarian epithelial carcinoma or surface epithelial-stromal tumor including serous tumor, endometrioid tumor and mucinous cystadenocarcinoma, sex-cord-stromal tumor); liver and bile duct carcinoma (including, but not limited to, hepatocellular carcinoma, cholangiocarcinoma, hemangioma); esophageal carcinoma (including, but not limited to, esophageal adenocarcinoma and squamous cell carcinoma); non-Hodgkin's lymphoma; bladder carcinoma; carcinoma of the uterus (including, but not limited to, endometrial adenocarcinoma, uterine papillary serous carcinoma, uterine clear-cell carcinoma, uterine sarcomas and leiomyosarcomas, mixed mullerian tumors); glioma, glioblastoma, medulloblastoma, and other tumors of the brain; kidney cancers (including, but not limited to, renal cell carcinoma, clear cell carcinoma, Wilm's tumor); cancer of the head and neck (including, but not limited to, squamous cell carcinomas); cancer of the stomach (including, but not limited to, stomach adenocarcinoma, gastrointestinal stromal tumor); multiple myeloma; testicular cancer; germ cell tumor; neuroendocrine tumor; cervical cancer; carcinoids of the gastrointestinal tract, breast, and other organs; and signet ring cell carcinoma.

Representative Neuropeptide Y Receptor ($NPY_1R$) Targeting Ligands

In some embodiments, the $NPY_1R$ radiopharmaceuticals described herein have an affinity to $NPY_1R$ that is at least 10-fold, at least 50-fold, at least 100-fold, at least 200-fold, at least 500-fold, or at least 1000-fold greater than the affinity for other non-target receptors. In some embodiments, the radiopharmaceuticals described herein are selective for $NPY_1R$ as compared to any one of the other neuropeptide Y subtypes, including $NPY_2R$, $NPY_4R$ and $NPY_5R$. In some embodiments, the $NPY_1R$ radiopharmaceuticals described herein have an affinity to $NPY_1R$ that is at least 10-fold, at least 50-fold, at least 100-fold, at least 200-fold, at least 500-fold, or at least 1000-fold greater than the affinity for any one of $NPY_2R$, $NPY_4R$ and $NPY_5R$.

In some embodiments, the $NPY_1R$ radiopharmaceuticals described herein preferentially accumulate in tumor tissues that express the targeted $NPY_1R$. In some embodiments, the $NPY_1R$ radiopharmaceuticals described herein preferentially accumulates in tissues or organs comprising tumor cells that express $NPY_1R$ as compared to tissues or organ(s) lacking tumor cells that express $NPY_1R$. In some embodiments, the compound of Formula (I) preferentially accumulates at least 1-fold, at least 2-fold, 3-fold, at least 4-fold, at least 5-fold, or greater than 5-fold more in tissues or organ(s) comprising tumor cells that express $NPY_1R$ as compared to tissues or organs lacking tumor cells that express $NPY_1R$. It is understood that the compound may accumulate in certain tissues and organs involved in the metabolism and/or excretion of therapeutics, including but not limited to the kidneys and liver.

In one aspect, the $NPY_1R$ radiopharmaceutical described herein has the structure of Formula (I), or a pharmaceutically acceptable salt thereof. In some embodiments, described herein is a compound of Formula (I), or a pharmaceutically acceptable salt thereof:

Formula (I)

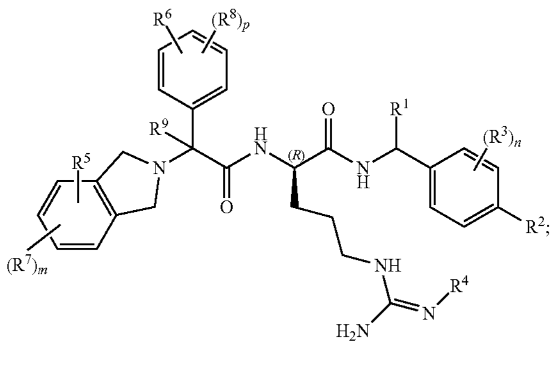

wherein:

$R^1$ is H, $—C_1-C_6$ alkyl, or $—C(═O)NH_2$;

$R^2$ is $—OH$, $—NH_2$, $—C(═O)NH_2$, or $—CH_2NHC(═O)NH_2$;

each $R^3$ is independently selected from the group consisting of $R^{3a}$, $R^{3b}$, $R^{3c}$, and $R^{3d}$;

$R^{3a}$, $R^{3b}$, $R^{3c}$, and $R^{3d}$ are each independently selected from the group consisting of H, F, Cl, Br, I, —CN, substituted or unsubstituted $—C_1-C_6$ alkyl, and substituted or unsubstituted $—C_1-C_6$ alkoxy;

$R^4$ is H, $—C(═O)R^{10}$, $—C(═O)NHR^{10}$, or $—C(═O)N(CH_3)R^{10}$;

$R^{10}$ is substituted or unsubstituted $—C_1-C_6$ alkyl, substituted or unsubstituted 2 to 6-membered heteroalkyl, $—(CH_2)_t—NH_2$, $—(CH_2)_tC(═O)O(CH_2)_uCH_3$, $—(CH_2)_tNHC(═O)(CH_2)_uCH_3$, or $—(CH_2)_t$-substituted or unsubstituted 5 to 6 membered heteroaryl ring;

tis 1, 2, 3, 4, 5, or 6;

u is 1, 2, 3, or 4;

$R^5$ is absent or $—Z^B-L^B-R^B$;

$Z^B$ is absent, $—C_1-C_6$ alkylene-, $—C_1-C_6$ alkylene-O—, $—O—C_1-C_6$ alkylene-, $—C(═O)NR^{11}—$, $—NR^{11}C(═O)—$, —O—, $—NR^{11}—$, —S—, —S(═O)—, $—SO_2—$, or —NHC(═O)NH—;

$L^B$ is a linker;

$R^B$ is a chelating moiety or a radionuclide complex thereof, $R^6$ is absent or $—Z^A-L^A-R^A$;

$Z^A$ is absent, $—C_1-C_6$ alkylene-, $—C_1-C_6$ alkylene-O—, $—O—C_1-C_6$ alkylene-, $—C(═O)NR^{12}—$, $—NR^{12}C(═O)—$, —O—, $—NR^{12}—$, —S—, —S(═O)—, $—SO_2—$, or —NHC(═O)NH—;

$L^A$ is a linker;

$R^A$ is a chelating moiety or a radionuclide complex thereof;

each $R^7$ is independently selected from F, Cl, Br, I, —CN, —OH, substituted or unsubstituted $—C_1-C_6$ alkyl, or substituted or unsubstituted $—C_1-C_6$ alkoxy;

each $R^8$ is independently selected from F, Cl, Br, I, —CN, —OH, substituted or unsubstituted $—C_1-C_6$ alkyl, or substituted or unsubstituted $—C_1-C_6$ alkoxy;

$R^9$ is H, substituted or unsubstituted $—C_1-C_4$ alkyl, or substituted or unsubstituted $—C_1-C_6$ alkoxy;

each $R^{11}$ is independently H or unsubstituted $—C_1-C_4$ alkyl;

each $R^{12}$ is independently H or unsubstituted $—C_1-C_4$ alkyl;

n is 0, 1, 2, 3, or 4;

m is 0, 1, 2, or 3;

p is 0, 1, 2, or 3; and wherein $R^5$ is $—Z^B-L^B-R^B$ when $R^6$ is absent; or $R^6$ is $—Z^A-L^A-R^A$ when $R^5$ is absent.

In some embodiments, $R^1$ is H;

$R^2$ is $—OH$, $—NH_2$, $—C(═O)NH_2$, or $—CH_2NHC(═O)NH_2$;

each $R^3$ is independently selected from the group consisting of $R^{3a}$, $R^{3b}$, $R^{3c}$, and $R^{3d}$;

$R^{3a}$, $R^{3b}$, $R^{3c}$, and $R^{3d}$ are each independently selected from the group consisting of H, F, Cl, Br, I, —CN, substituted or unsubstituted $—C_1-C_6$ alkyl, and substituted or unsubstituted $—C_1-C_6$ alkoxy;

$R^4$ is H, $—C(═O)R^{10}$, $—C(═O)NHR^{10}$, or $—C(═O)N(CH_3)R^{10}$;

$R^{10}$ is substituted or unsubstituted $—C_1-C_6$ alkyl, substituted or unsubstituted 2 to 6-membered heteroalkyl, or $—(CH_2)_tNHC(═O)(CH_2)_uCH_3$;

t is 1, 2, 3, 4, 5, or 6;

u is 1, 2, 3, or 4;

$R^5$ is absent or $—Z^B-L^B-R^B$;

$Z^B$ is absent, $—C_1-C_6$ alkylene-, $—C_1-C_6$ alkylene-O—, $—O—C_1-C_6$ alkylene-, $—C(═O)NR^{11}—$, $—NR^{11}C(═O)—$, —O—, or $—NR^{11}—$;

$L^B$ is a linker $R^B$ is a chelating moiety or a radionuclide complex thereof, $R^6$ is absent or $—Z^A-L^A-R^A$;

$Z^A$ is absent, $—C_1-C_6$ alkylene-, $—C_1-C_6$ alkylene-O—, $—O—C_1-C_6$ alkylene-, $—C(═O)NR^{12}—$, $—NR^{12}C(═O)—$, —O—, or $—NR^{12}—$;

$L^A$ is a linker $R^A$ is a chelating moiety or a radionuclide complex thereof;

$R^9$ is H;

each $R^{11}$ is independently H or unsubstituted $—C_1-C_4$ alkyl;

each $R^{12}$ is independently H or unsubstituted $—C_1-C_4$ alkyl;

n is 0, 1, 2, 3, or 4;

m is 0;

p is 0; and wherein $R^5$ is $—Z^B$-$L^B$-$R^B$ when $R^6$ is absent; or $R^6$ is $—Z^A$-$L^A$-$R^A$ when $R^5$ is absent.

In some embodiments, the compound of Formula (I) has the structure of Formula (Ia), or a pharmaceutically acceptable salt thereof:

(Ia)

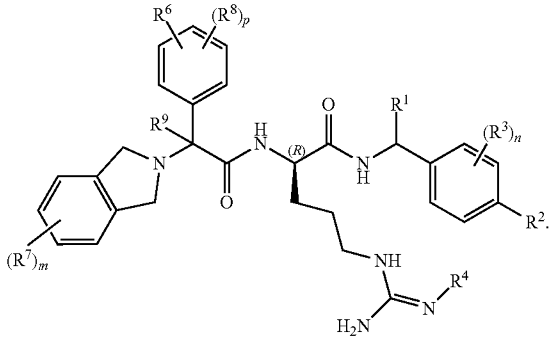

In some embodiments, the compound of Formula (I) has the structure of Formula (Ia-1S), or a pharmaceutically acceptable salt thereof:

(Ia-1S)

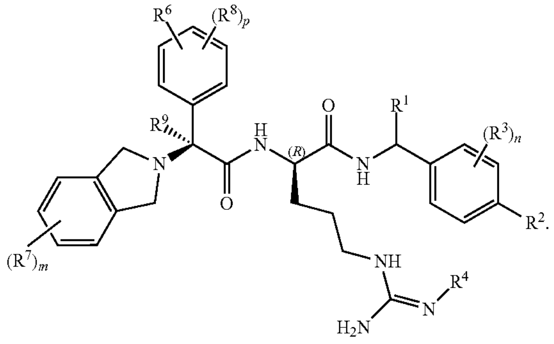

(IIa)

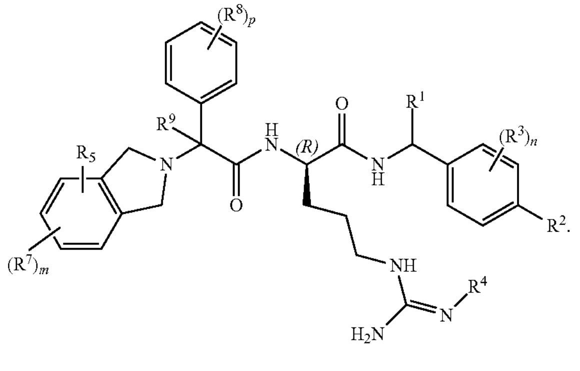

In some embodiments, the compound of Formula (I) has the structure of Formula (IIa-S), or a pharmaceutically acceptable salt thereof:

(IIa-S)

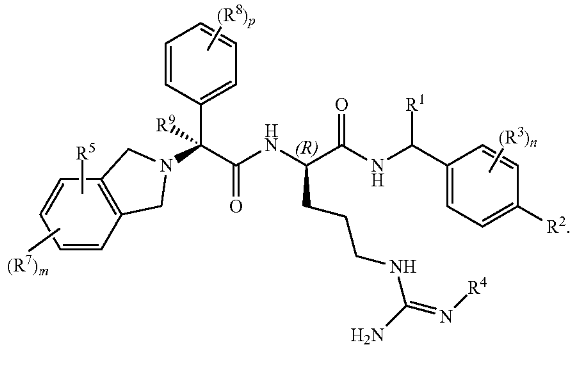

In some embodiments, the compound of Formula (I) has the structure of Formula (Ib), or a pharmaceutically acceptable salt thereof:

(Ib)

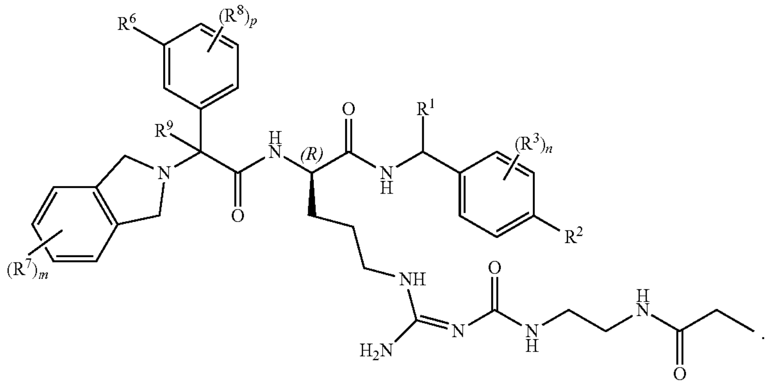

In some embodiments, the compound of Formula (I) has the structure of Formula (IIa), or a pharmaceutically acceptable salt thereof:

In some embodiments, the compound of Formula (I) has the structure of Formula (Ib-1S), or a pharmaceutically acceptable salt thereof:

(Ib-1S)

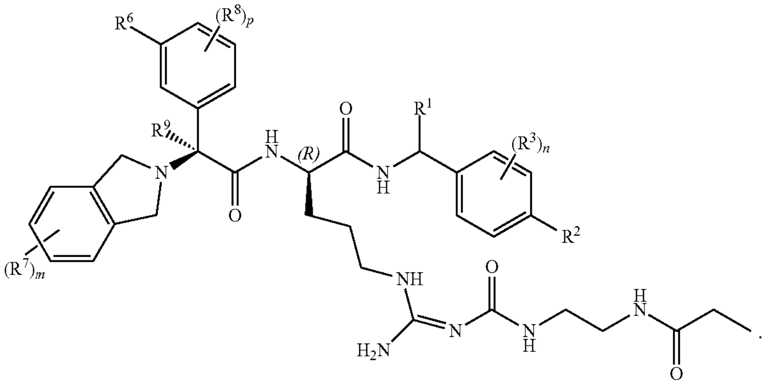

In some embodiments, the compound of Formula (I) has the structure of Formula (IIb), or a pharmaceutically acceptable salt thereof:

(IIb)

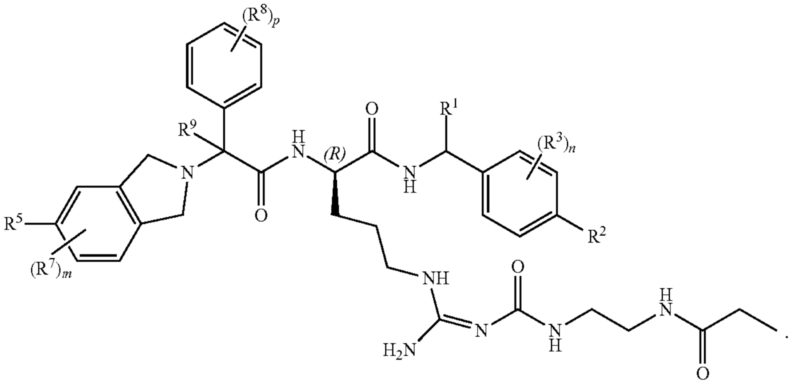

In some embodiments, the compound of Formula (I) has the structure of Formula (IIb-S), or a pharmaceutically acceptable salt thereof:

(IIb-S)

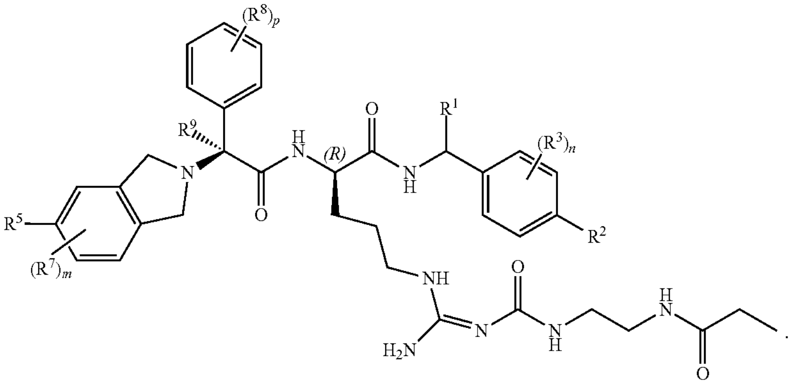

In some embodiments, the compound of Formula (I) has the structure of Formula (Ic), or a pharmaceutically acceptable salt thereof:

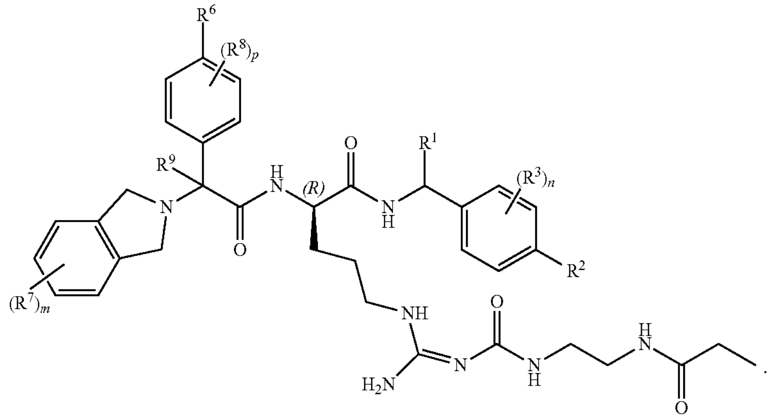

(Ic)

In some embodiments, the compound of Formula (I) has the structure of Formula (Ic-1S), or a pharmaceutically acceptable salt thereof:

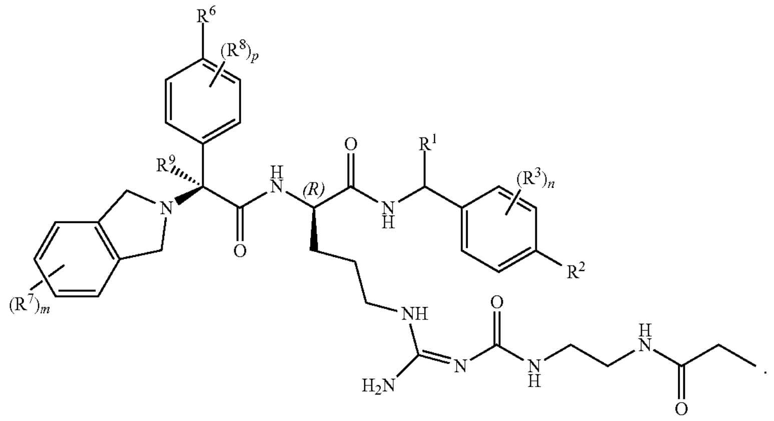

(Ic-1S)

In some embodiments, the compound of Formula (I) has the structure of Formula (IIc), or a pharmaceutically acceptable salt thereof:

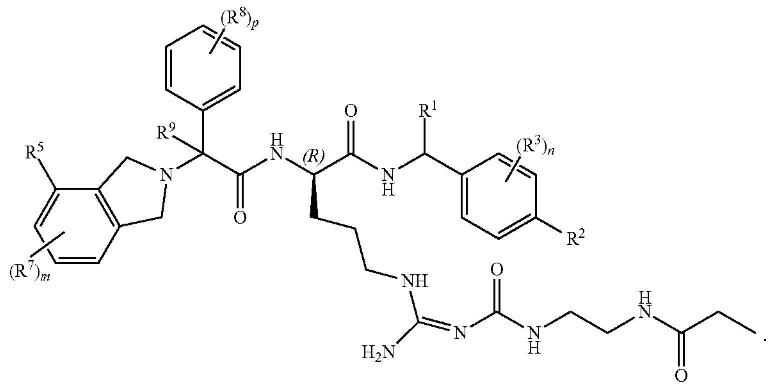

(IIc)

In some embodiments, the compound of Formula (I) has the structure of Formula (IIc-S), or a pharmaceutically acceptable salt thereof:

(IIc-S)

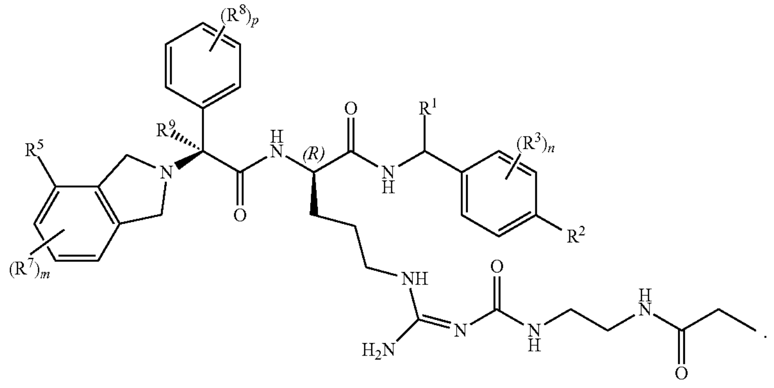

In some embodiments, the compound of Formula (I) has the structure of Formula (Id), or a pharmaceutically acceptable salt thereof:

(Id)

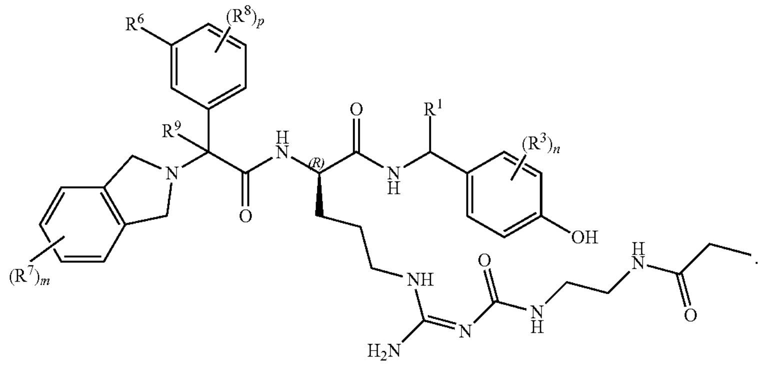

In some embodiments, the compound of Formula (I) has the structure of Formula (Id-1S), or a pharmaceutically acceptable salt thereof:

(Id-1S)

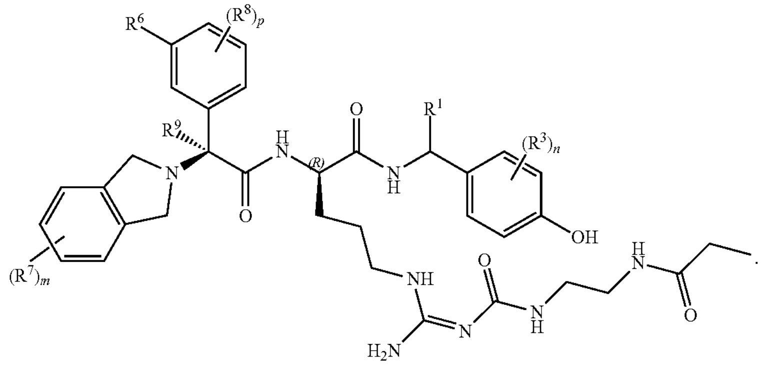

In some embodiments, the compound of Formula (I) has the structure of Formula (IId), or a pharmaceutically acceptable salt thereof:

(IId)

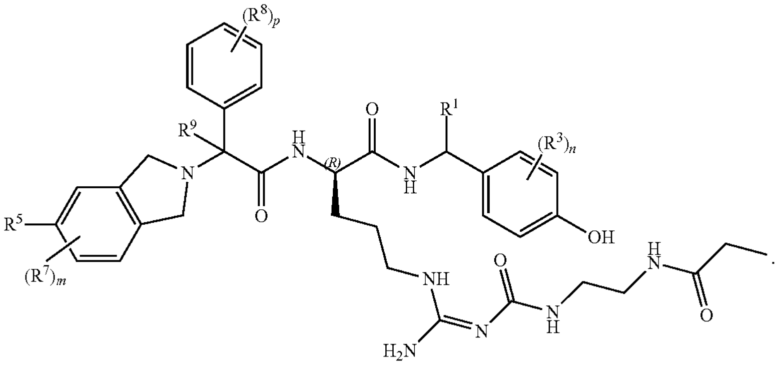

In some embodiments, the compound of Formula (I) has the structure of Formula (IId-1S), or a pharmaceutically acceptable salt thereof:

(IId-1S)

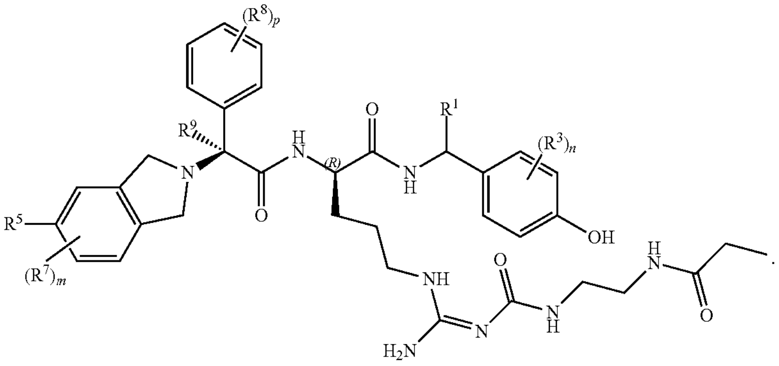

In some embodiments, the compound of Formula (I) has the structure of Formula (Ie), or a pharmaceutically acceptable salt thereof:

(Ie)

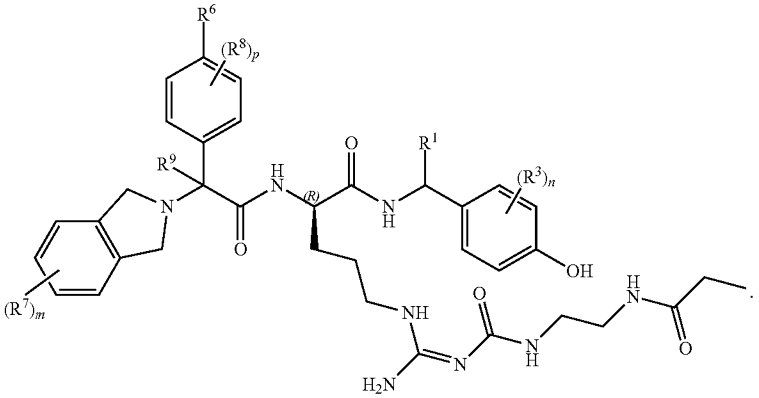

In some embodiments, the compound of Formula (I) has the structure of Formula (Ie-1S), or a pharmaceutically acceptable salt thereof:

(Ie-1S)

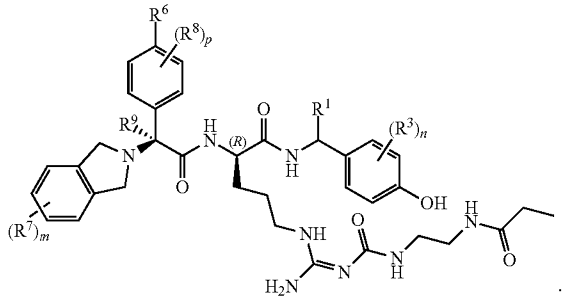

In some embodiments, the compound of Formula (I) has the structure of Formula (IIe), or a pharmaceutically acceptable salt thereof.

(IIe)

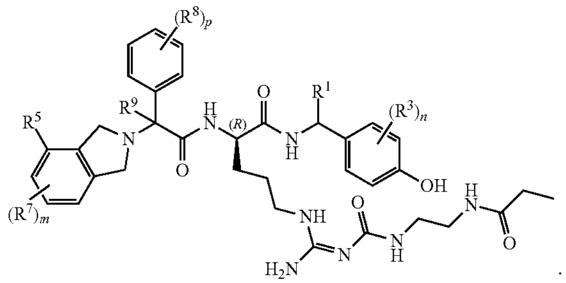

In some embodiments, the compound of Formula (I) has the structure of Formula (IIe-1S), or a pharmaceutically acceptable salt thereof:

(IIe-1S)

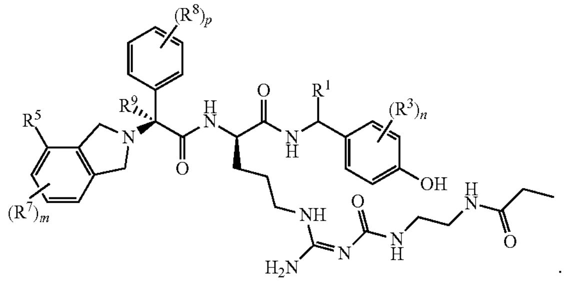

In some embodiments, the compound of Formula (I) has the structure of Formula (If), or a pharmaceutically acceptable salt thereof:

(If)

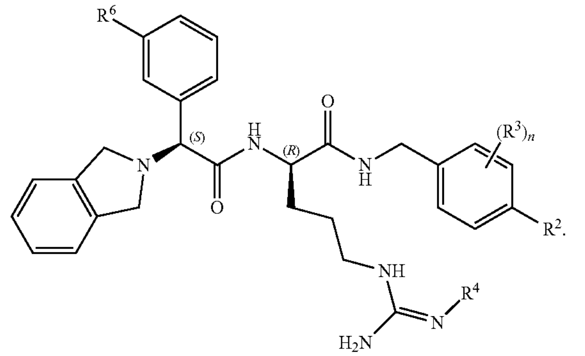

In some embodiments, the compound of Formula (I) has the structure of Formula (If-1S), or a pharmaceutically acceptable salt thereof:

(If-1S)

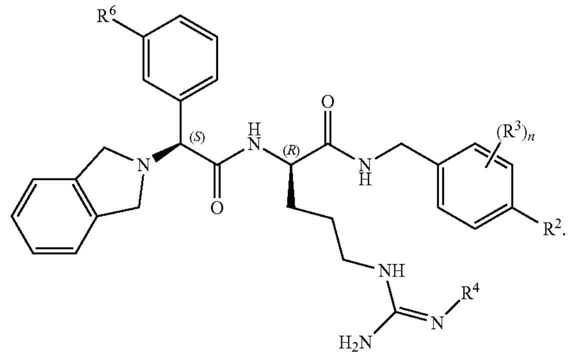

In some embodiments, the compound of Formula (I) has the structure of Formula (IIf), or a pharmaceutically acceptable salt thereof:

(IIf)

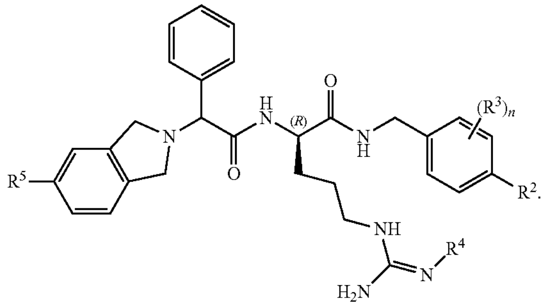

In some embodiments, the compound of Formula (I) has the structure of Formula (IIf-1S), or a pharmaceutically acceptable salt thereof:

(IIf-1S)

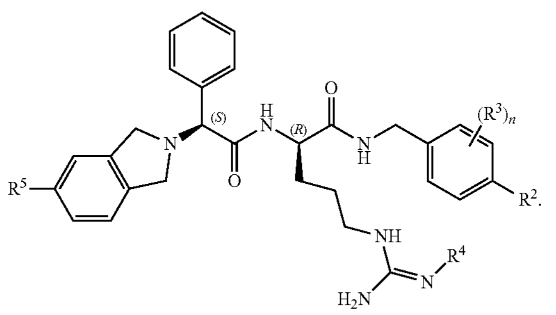

In some embodiments, the compound of Formula (I) has the structure of Formula (Ig), or a pharmaceutically acceptable salt thereof:

(Ig)

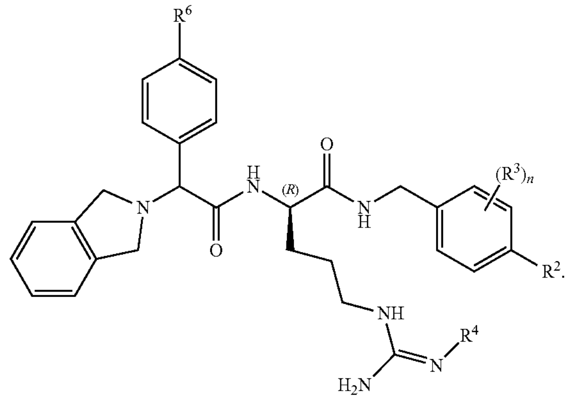

In some embodiments, the compound of Formula (I) has the structure of Formula (Ig-1S), or a pharmaceutically acceptable sale thereon:

(Ig-1S)

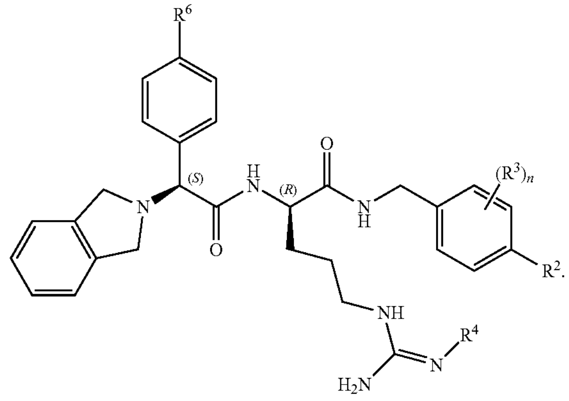

In some embodiments, the compound of Formula (I) has the structure of Formula (If), or Formula (Ig), or a pharmaceutically acceptable salt thereof:

(If)

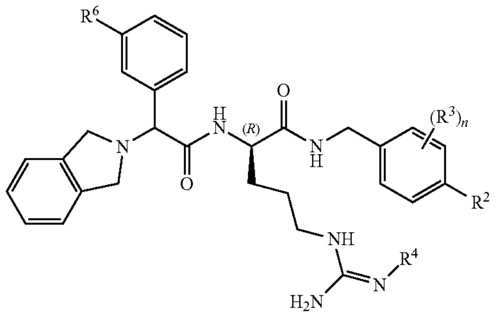

or (Ig)

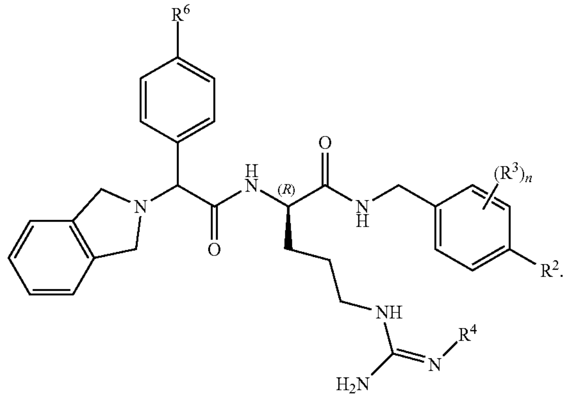

In some embodiments, the compound of Formula (I) has the structure of Formula (IIg), or a pharmaceutically acceptable salt thereof:

(IIg)

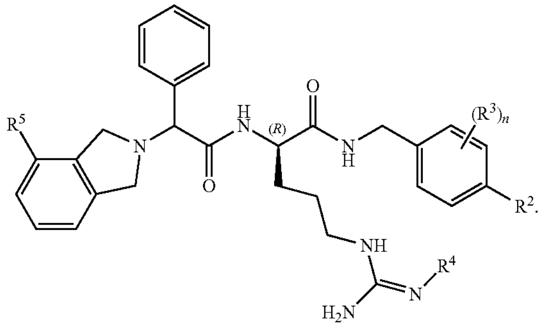

In some embodiments, the compound of Formula (I) has the structure of Formula (IIg-1S), or a pharmaceutically acceptable salt thereof:

(IIg-1S)

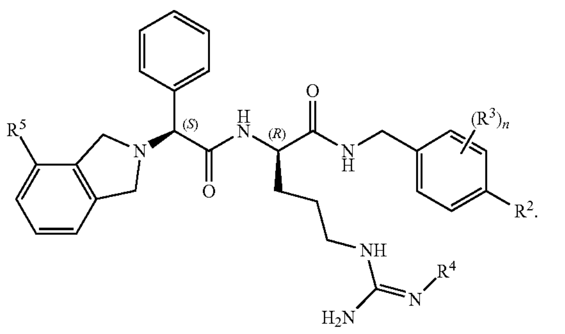

In some embodiments, the compound of Formula (I) has the structure of Formula (Ih), or a pharmaceutically acceptable salt thereof:

(Ih)

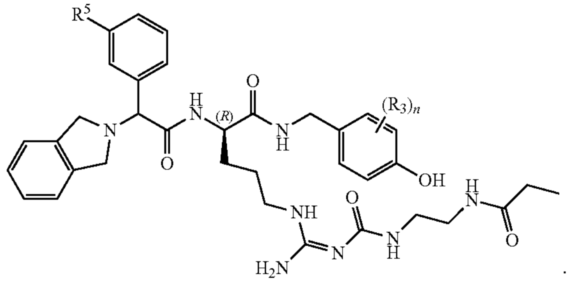

In some embodiments, the compound of Formula (I) has the structure of Formula (Ih-1S), or a pharmaceutically acceptable salt thereof:

(Ih-1S)

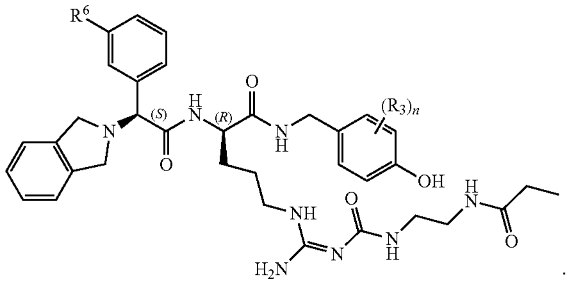

In some embodiments, the compound of Formula (I) has the structure of Formula (IIh), or a pharmaceutically acceptable salt thereof:

(IIh)

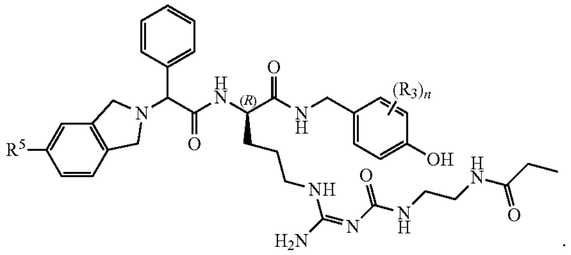

In some embodiments, the compound of Formula (I) has the structure of Formula (IIh-1S), or a pharmaceutically acceptable salt thereof:

(IIh-1S)

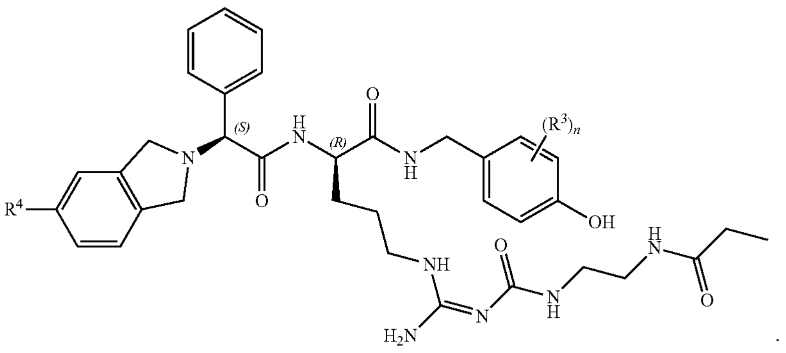

In some embodiments, the compound of Formula (I) has the structure of Formula (Ii), or a pharmaceutically acceptable salt thereof:

(Ii)

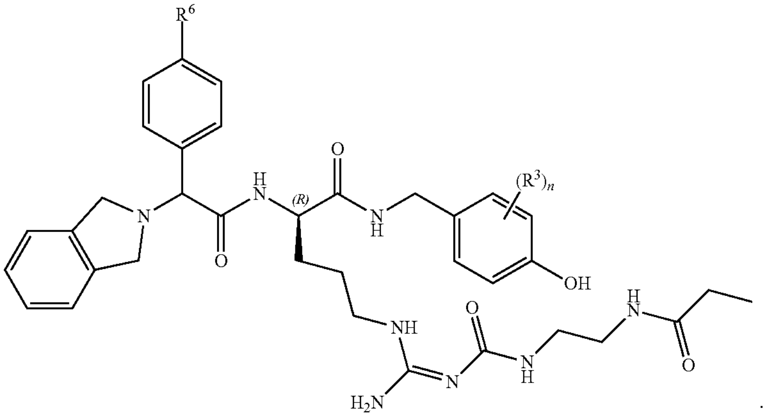

In some embodiments, the compound of Formula (I) has the structure of Formula (Ii-1S), or a or a pharmaceutically acceptable salt thereof:

(Ii-1S)

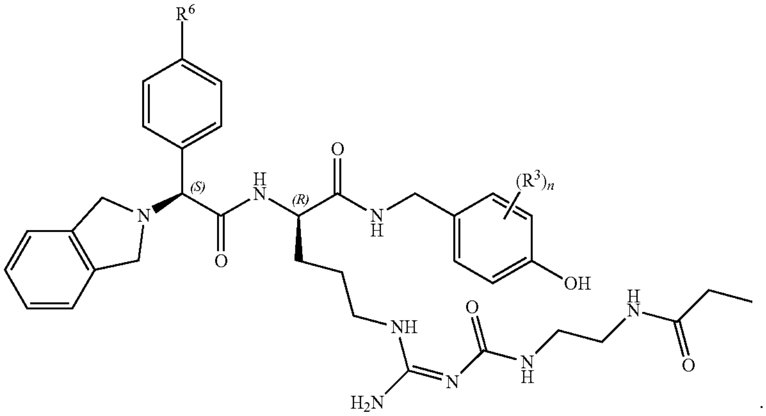

In some embodiments, the compound of Formula (I) has the structure of Formula (IIi), or a pharmaceutically acceptable salt thereof:

(IIi)

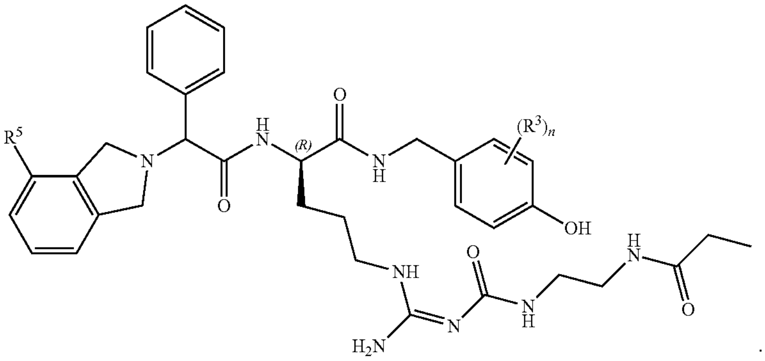

In some embodiments, the compound of Formula (I) has the structure of Formula (IIi-1S), or a pharmaceutically acceptable salt thereof:

(IIi-1S)

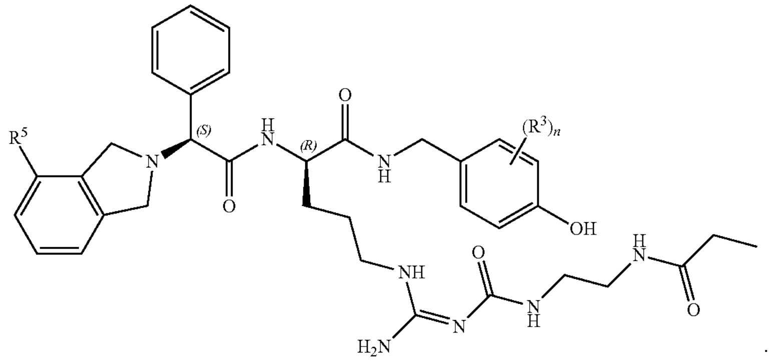

In some embodiments, the compound of Formula (I) has the structure of Formula (Ij), or a pharmaceutically acceptable salt thereof:

(Ij)

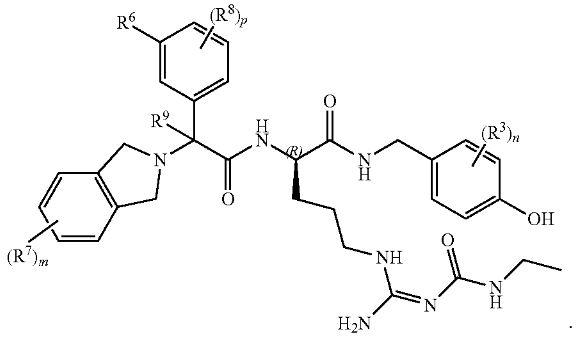

In some embodiments, the compound of Formula (I) has the structure of Formula (Ij-1S), or a pharmaceutically acceptable salt thereof:

(Ij-1S)

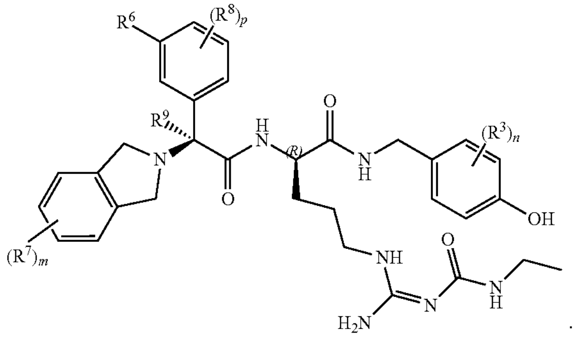

In some embodiments, the compound of Formula (I) has the structure of Formula (IIj), or a pharmaceutically acceptable salt thereof:

(IIj)

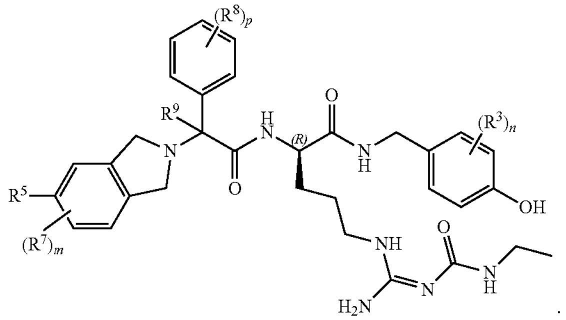

some embodiments, the compound of Formula (I) has the structure of Formula (IIj-1S), or a pharmaceutically acceptable salt thereof:

(IIj-1S)

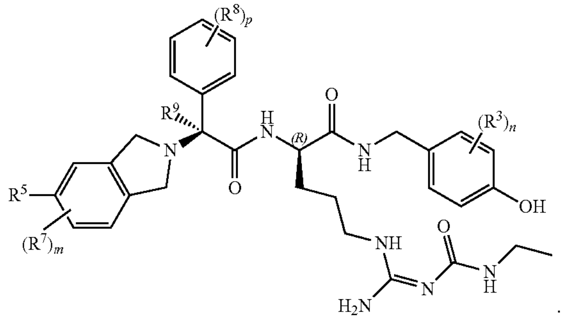

In some embodiments, the compound of Formula (I) has the structure of Formula (Ik), or a pharmaceutically acceptable salt thereof:

(Ik)

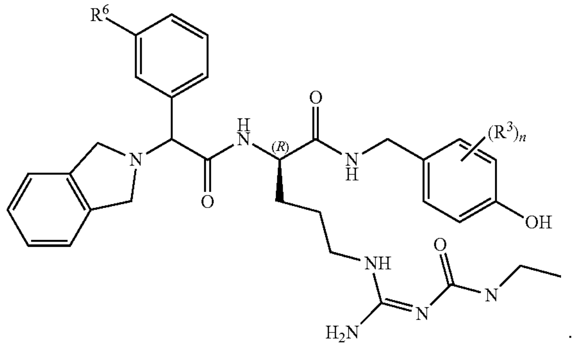

In some embodiments, the compound of Formula (I) has the structure of Formula (Ik-1S), or a pharmaceutically acceptable salt thereof:

(Ik-1S)

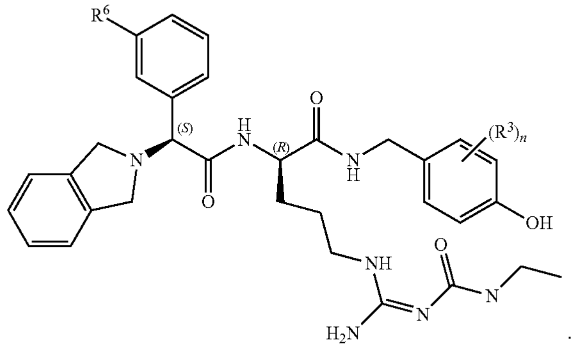

In some embodiments, the compound of Formula (I) has the structure of Formula (IIk), or a pharmaceutically acceptable salt thereof:

(IIk)

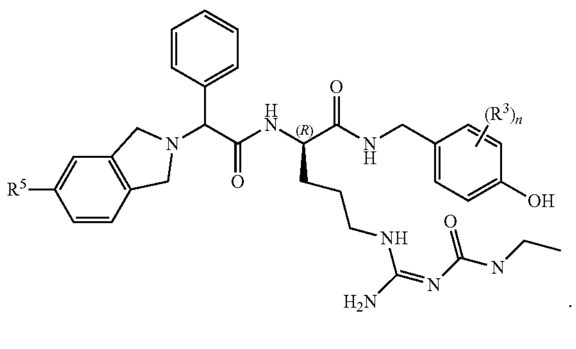

In some embodiments, the compound of Formula (I) has the structure of Formula (IIk-IS), or a pharmaceutically acceptable salt thereof:

(IIk-1S)

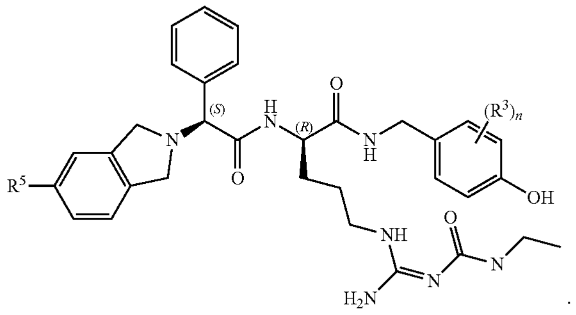

In some embodiments, the compound of Formula (I) has the structure of Formula (II), or a pharmaceutically acceptable salt thereof:

(II)

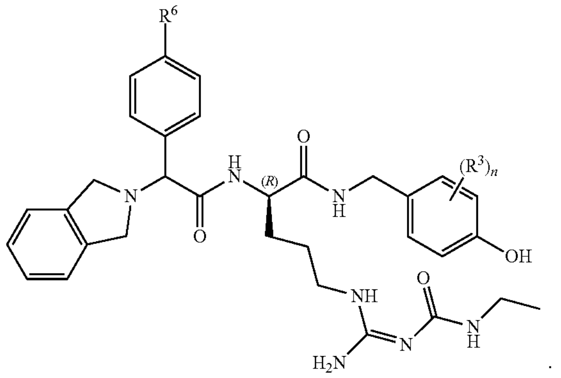

In some embodiments, the compound of Formula (I) has the structure of Formula (II-1S), or a pharmaceutically acceptable salt thereof:

(II-1S)

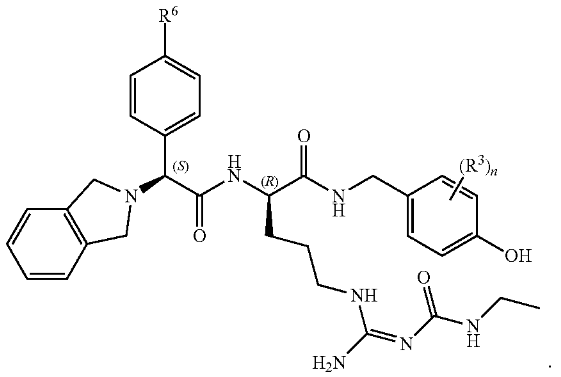

In some embodiments, the compound of Formula (I) has the structure of Formula (II1), or a pharmaceutically acceptable salt thereof:

(Il1)

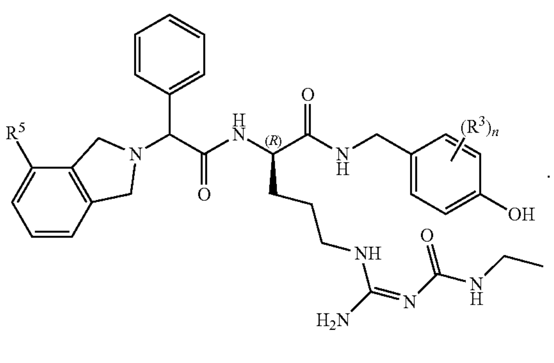

In some embodiments, the compound of Formula (I) has the structure of Formula (Il1-1S), or a pharmaceutically acceptable salt thereof:

(Il1-1S)

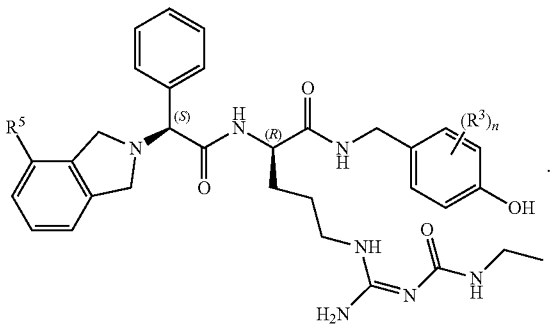

In some embodiments, $R^5$ is absent. In some embodiments, $R^5$ is $—Z^B\text{-}L^B\text{-}R^B$.

In some embodiments, $Z^B$ is absent. In some embodiments, $Z^B$ is —O—, —NH—, or $—N(—CH_3)—$. In some embodiments, $Z^B$ is $—C_1\text{-}C_6$ alkylene-. In some embodiments, $Z^B$ is $—C_1\text{-}C_6$ alkylene-O—. In some embodiments, $Z^B$ is $—O—C_1\text{-}C_6$ alkylene-. In some embodiments, $Z^B$ is $—C(═O)NR^{11}—$. In some embodiments, $Z^B$ is —C(═O)NH—. In some embodiments, $Z^B$ is $—NR^{11}C(═O)—$. In some embodiments, $Z^B$ is —NHC(═O)—. In some embodiments, $Z^B$ is —O—. In some embodiments, $Z^B$ is $—NR^{11}—$. In some embodiments, $Z^B$ is $—N(—CH_3)—$. In some embodiments, $Z^B$ is —NH—.

In some embodiments, $R^6$ is absent. In some embodiments, $R^6$ is $—Z^A\text{-}L^A\text{-}R^A$.

In some embodiments, $Z^A$ is absent. In some embodiments, $Z^A$ is $—C_1\text{-}C_6$ alkylene-, —O—, —NH—, or $—N(—CH_3)—$. In some embodiments, $Z^A$ is $—C_1\text{-}C_6$ alkylene-. In some embodiments, $Z^A$ is $—C_1\text{-}C_6$ alkylene-O—. In some embodiments, $Z^A$ is $—O—C_1\text{-}C_6$ alkylene-. In some embodiments, $Z^A$ is $—C(═O)NR^{12}—$. In some embodiments, $Z^A$ is —C(═O)NH—. In some embodiments, $Z^A$ is $—NR^{12}C(═O)—$. In some embodiments, $Z^A$ is —NHC(═O)—. In some embodiments, $Z^A$ is —O—. In some embodiments, $Z^A$ is $—NR^{12}—$. In some embodiments, $Z^A$ is $—N(—CH_3)—$. In some embodiments, $Z^A$ is —NH—.

In some embodiments, $R^1$ is H. In some embodiments, $R^1$ is $—C_1\text{-}C_6$ alkyl. In some embodiments, $R^1$ is $—CH_3$. In some embodiments, $R^1$ is $—CH_2CH_3$.

In some embodiments, n is 0. In some embodiments, n is 1. In some embodiments, n is 2. In some embodiments, n is 3. In some embodiments, n is 4.

In some embodiments, m is 0. In some embodiments, m is 1. In some embodiments, m is 2. In some embodiments, m is 3.

In some embodiments, p is 0. In some embodiments, p is 1. In some embodiments, p is 2. In some embodiments, p is 3.

In some embodiments, each $R^3$ is independently H, F, Cl, Br, I, —CN, $—CH_3$, $—CF_3$, or $—OCH_3$. In some embodiments, each $R^3$ is independently F, Cl, Br, I, $—CH_3$, $—CF_3$, or $—OCH_3$. In some embodiments, each $R^3$ is independently F, Cl, Br, I, or $—CH_3$. In some embodiments, $R^3$ is F. In some embodiments, $R^3$ is $C_1$. In some embodiments, $R^3$ is Br. In some embodiments, $R^3$ is I. In some embodiments, $R^3$ is —CN. In some embodiments, $R^3$ is independently substituted or unsubstituted $—C_1\text{-}C_6$ alkyl. In some embodiments, $R^3$ is $—CH_3$. In some embodiments, $R^3$ is $—CF_3$. In some embodiments, $R^3$ is substituted or unsubstituted $—C_1\text{-}C_6$ alkoxy. In some embodiments, $R^3$ is $—OCH_3$. In some embodiments, $R^3$ is H.

In some embodiments, each $R^7$ is independently selected from F, Cl, Br, I, or $—CH_3$. In some embodiments, $R^7$ is independently F. In some embodiments, $R^7$ is independently Cl. In some embodiments, $R^7$ is independently Br. In some embodiments, $R^7$ is independently I. In some embodiments, $R^7$ is independently —CN. In some embodiments, $R^7$ is independently substituted or unsubstituted $—C_1\text{-}C_6$ alkyl. In some embodiments, $R^7$ is independently $—CH_3$. In some embodiments, $R^7$ is independently substituted or unsubstituted $—C_1\text{-}C_6$ alkoxy. In some embodiments, $R^7$ is independently $—OCH_3$.

In some embodiments, each $R^8$ is independently selected from F, Cl, Br, I, or $—CH_3$. In some embodiments, $R^8$ is independently F. In some embodiments, $R^8$ is independently Cl. In some embodiments, $R^8$ is independently Br. In some embodiments, $R^8$ is independently I. In some embodiments, $R^8$ is independently —CN. In some embodiments, $R^8$ is independently substituted or unsubstituted $—C_1\text{-}C_6$ alkyl. In some embodiments, $R^8$ is $—CH_3$. In some embodiments, $R^8$ is independently substituted or unsubstituted $—C_1\text{-}C_6$ alkoxy. In some embodiments, $R^8$ is $—OCH_3$.

In some embodiments, $R^9$ is H. In some embodiments, $R^9$ is substituted or unsubstituted $—C_1\text{-}C_4$ alkyl. In some embodiments, $R^9$ is $—CH_3$.

In some embodiments, $R^{11}$ is H. In some embodiments, $R^{11}$ is $—CH_3$. In some embodiments, $R^{11}$ is $—CH_2CH_3$.

In some embodiments, $R^{12}$ is H. In some embodiments, $R^{12}$ is $—CH_3$. In some embodiments, $R^{12}$ is $—CH_2CH_3$.

In some embodiments, the compound of Formula (I) has the structure of Formula (Im), or a pharmaceutically acceptable salt thereof:

(Im)

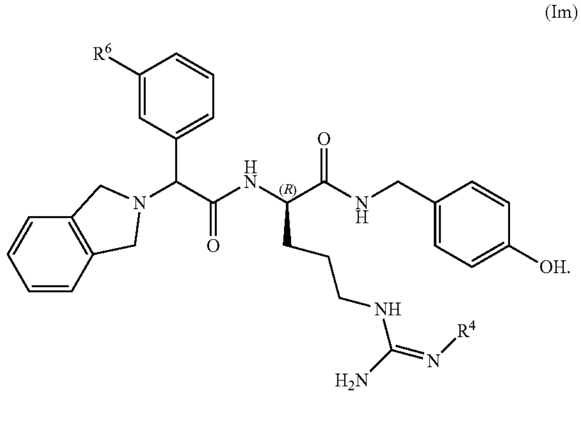

In some embodiments, the compound of Formula (I) has the structure of Formula (Im-1 S), or a pharmaceutically acceptable salt thereof:

(Im-1S)

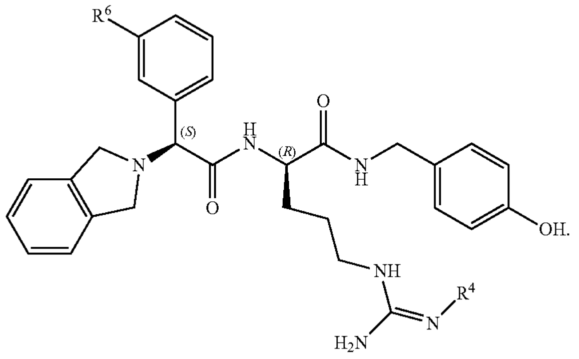

In some embodiments, the compound of Formula (I) has the structure of Formula (IIm), or a pharmaceutically acceptable salt thereof:

(IIm)

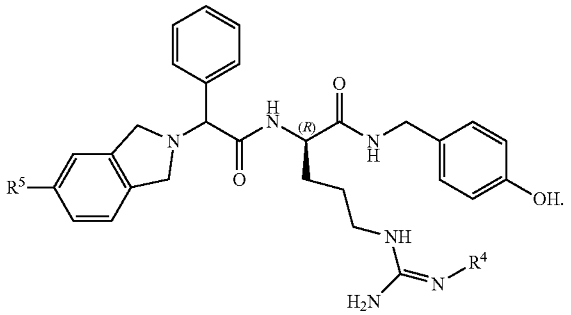

In some embodiments, the compound of Formula (I) has the structure of Formula (IIm-1S), or a pharmaceutically acceptable salt thereof:

(IIm-1S)

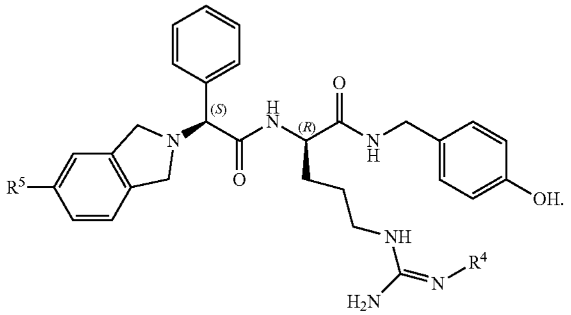

In some embodiments, the compound of Formula (I) has the structure of Formula (In), or a pharmaceutically acceptable salt thereof:

(In)

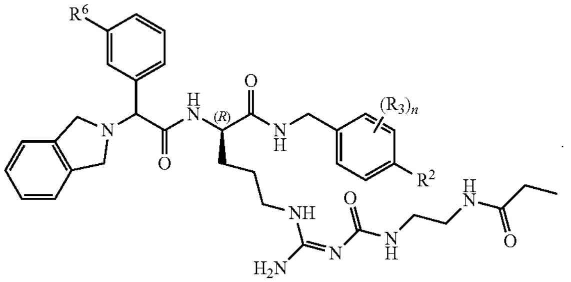

In some embodiments, the compound of Formula (I) has the structure of Formula (In-1S), or a pharmaceutically acceptable salt thereof:

(In-1S)

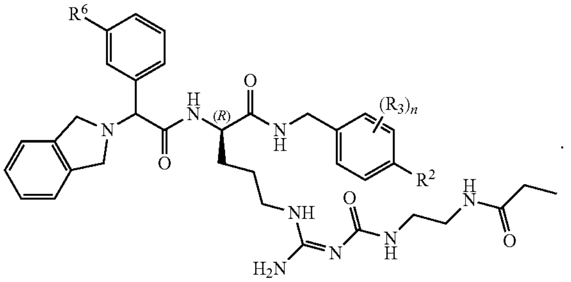

In some embodiments, the compound of Formula (I) has the structure of Formula (IIn), or a pharmaceutically acceptable salt thereof:

(In)

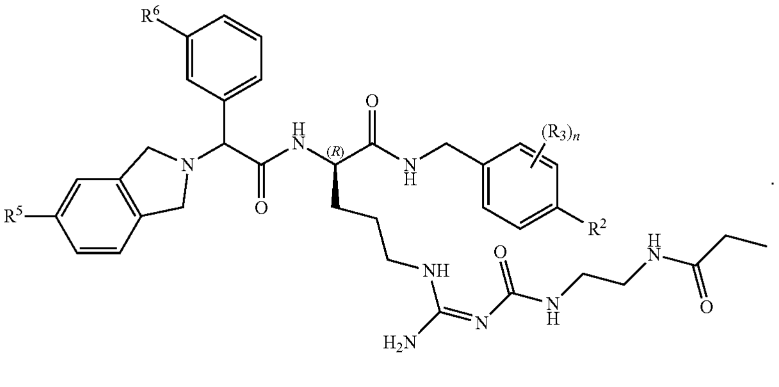

In some embodiments, the compound of Formula (I) has the structure of Formula (IIn-1S), or a pharmaceutically acceptable salt thereof:

(IIn-1S)

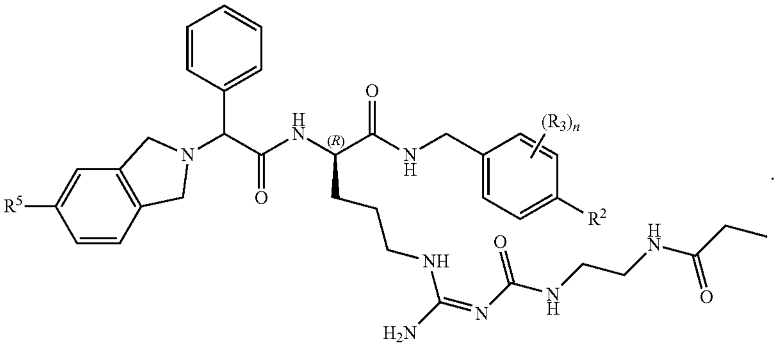

In some embodiments, the compound of Formula (I) has the structure of Formula (Io), or a pharmaceutically acceptable salt thereof:

(Io)

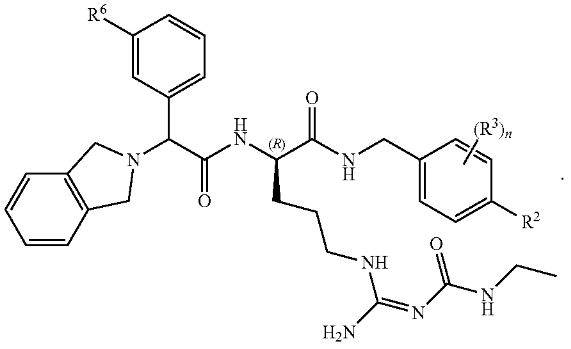

In some embodiments, the compound of Formula (I) has the structure of Formula (Io-1S), or a pharmaceutically acceptable salt thereof:

(Io-1S)

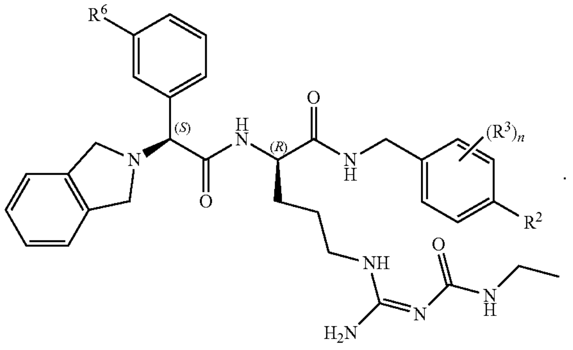

In some embodiments, the compound of Formula (I) has the structure of Formula (IIo), or a pharmaceutically acceptable salt thereof:

(IIo)

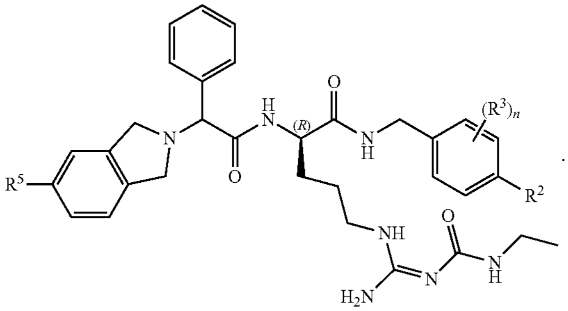

In some embodiments, the compound of Formula (I) has the structure of Formula (IIo-1S), or a pharmaceutically acceptable salt thereof:

(IIo-1S)

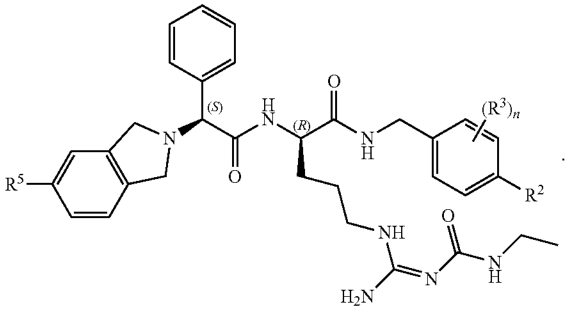

In some embodiments, the compound of Formula (I) has the structure of Formula (Ip), or a pharmaceutically acceptable salt thereof:

(Ip)

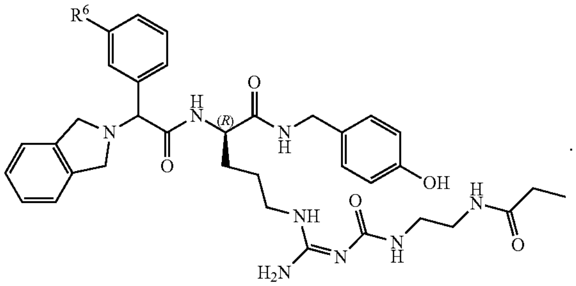

In some embodiments, the compound of Formula (I) has the structure of Formula (Ip-1S), or a pharmaceutically acceptable salt thereof:

(Ip-1S)

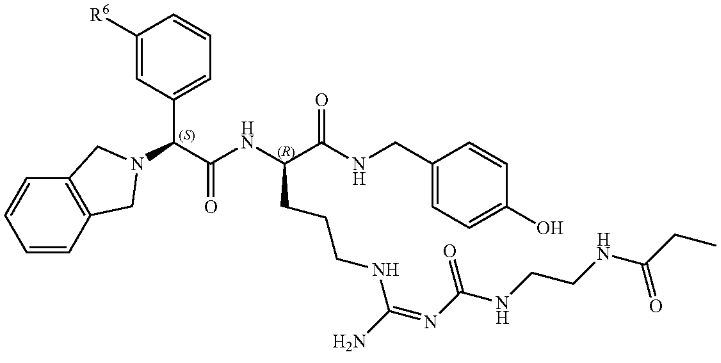

In some embodiments, the compound of Formula (I) has the structure of Formula (IIp), or a pharmaceutically acceptable salt thereof:

(IIp)

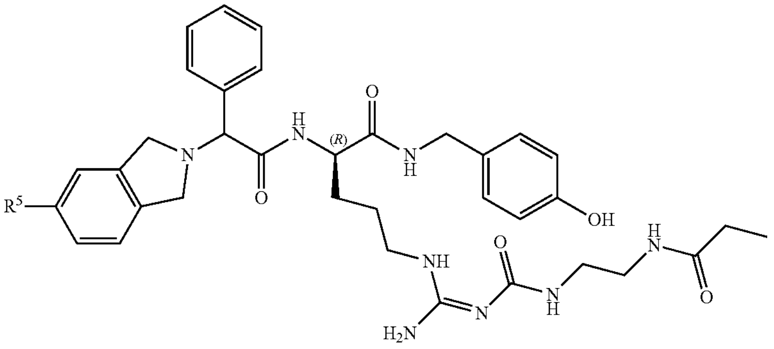

In some embodiments, the compound of Formula (I) has the structure of Formula (IIp-1S), or a pharmaceutically acceptable salt thereof:

(IIp-1S)

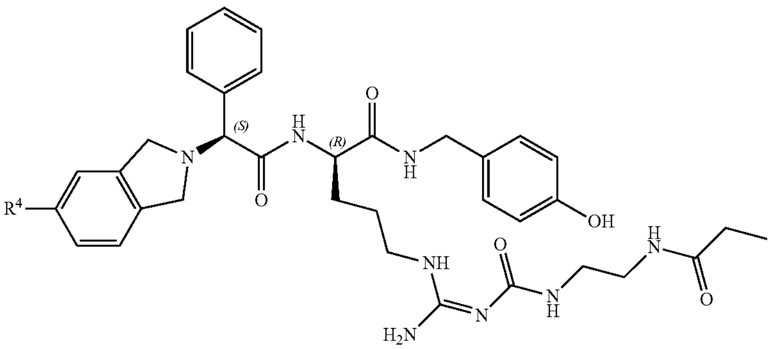

In some embodiments, the compound of Formula (I) has the structure of Formula (Iq), or a pharmaceutically acceptable salt thereof:

(Iq)

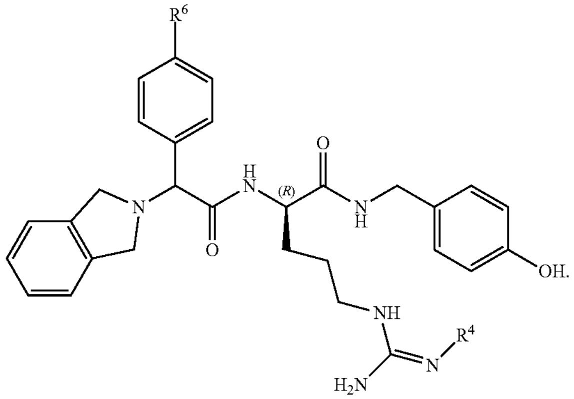

In some embodiments, the compound of Formula (I) has the structure of Formula (Iq-1S), or a pharmaceutically acceptable salt thereof:

(Iq-1S)

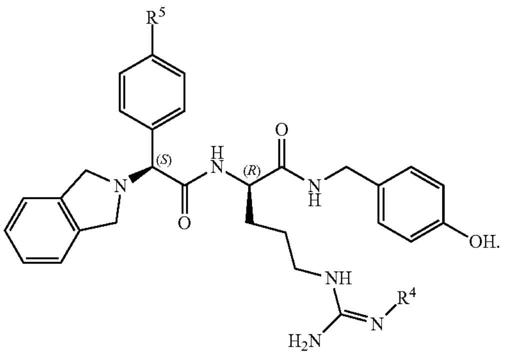

In some embodiments, the compound of Formula (I) has the structure of Formula (IIq), or a pharmaceutically acceptable salt thereof:

(IIq)

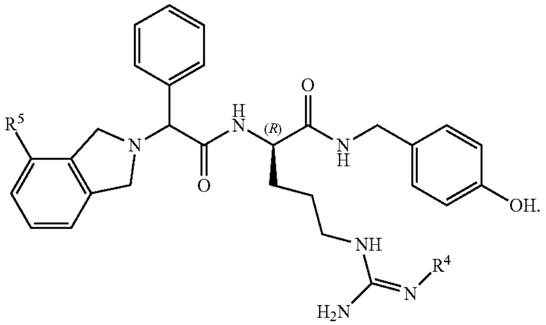

In some embodiments, the compound of Formula (I) has the structure of Formula (IIq-1S), or a pharmaceutically acceptable salt thereof:

(IIq-1S)

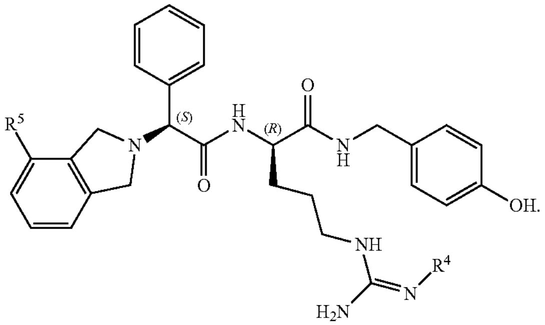

In some embodiments, the compound of Formula (I) has the structure of Formula (Ir), or a pharmaceutically acceptable salt thereof:

(Ir)

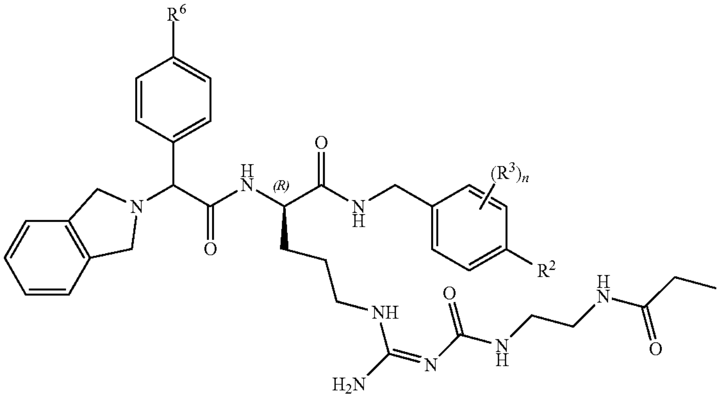

In some embodiments, the compound of Formula (I) has the structure of Formula (Ir-1S), or a pharmaceutically acceptable salt thereof:

(Ir-1S)

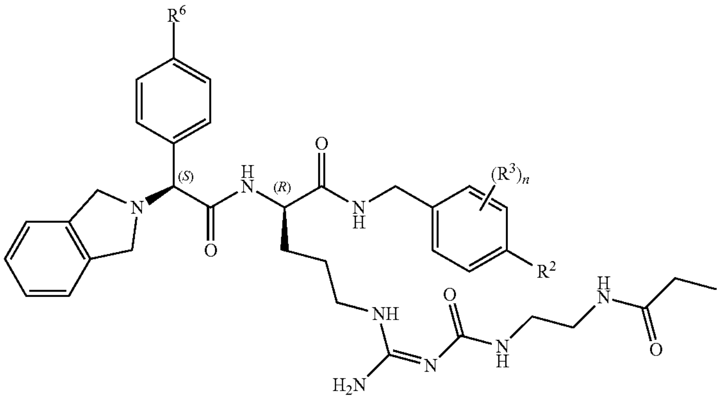

In some embodiments, the compound of Formula (I) has the structure of Formula (IIr), or a pharmaceutically acceptable salt thereof:

(IIr)

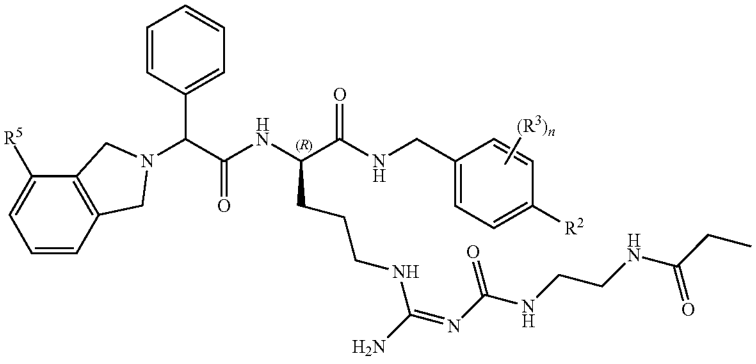

In some embodiments, the compound of Formula (I) has the structure of Formula (IIr-1S), or a pharmaceutically acceptable salt thereof:

(IIr-1S)

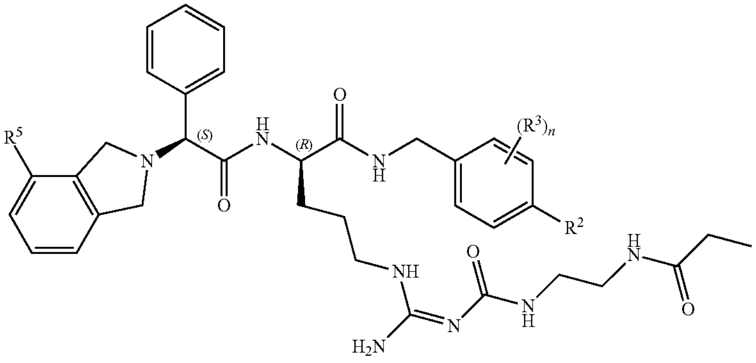

In some embodiments, the compound of Formula (I) has the structure of Formula (Is), or a pharmaceutically acceptable salt thereof:

(Is)

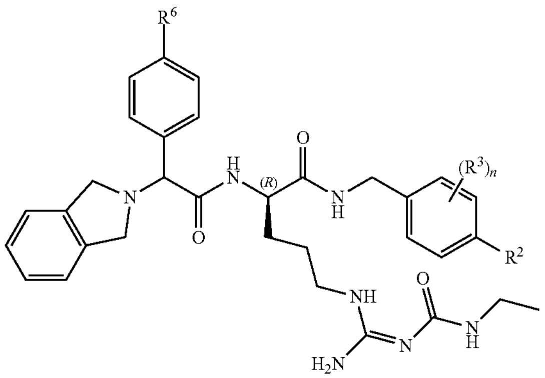

In some embodiments, the compound of Formula (I) has the structure of Formula (Is-1S), or a pharmaceutically acceptable salt thereof:

(Is-1S)

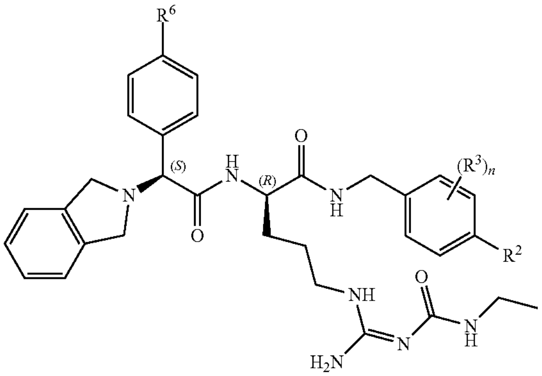

In some embodiments, the compound of Formula (I) has the structure of Formula (Is), or a pharmaceutically acceptable salt thereof:

(IIs)

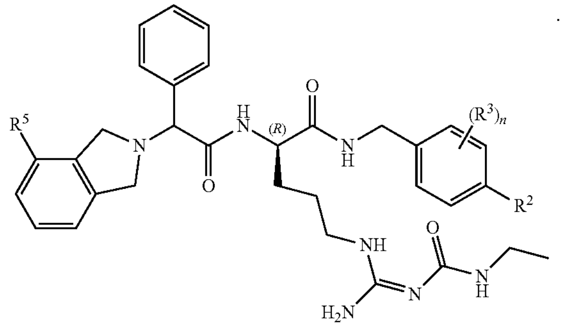

In some embodiments, the compound of Formula (I) has the structure of Formula (IIs-1S), or a pharmaceutically acceptable salt thereof:

(IIs-1S)

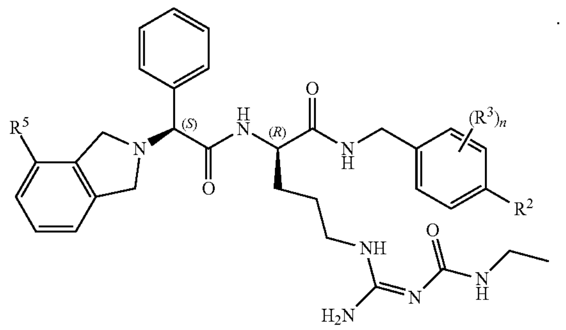

In some embodiments, the compound of Formula (I) has the structure of Formula (It), or a pharmaceutically acceptable salt thereof:

(It)

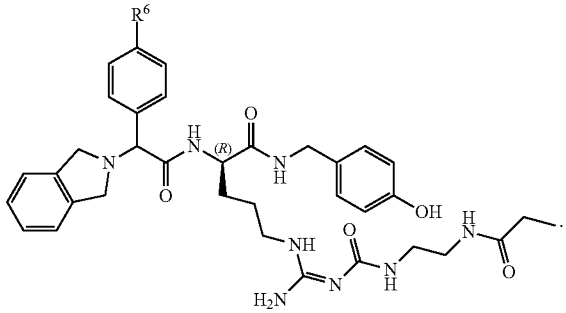

In some embodiments, the compound of Formula (I) has the structure of Formula (It-1S), or a pharmaceutically acceptable salt thereof:

(It-1S)

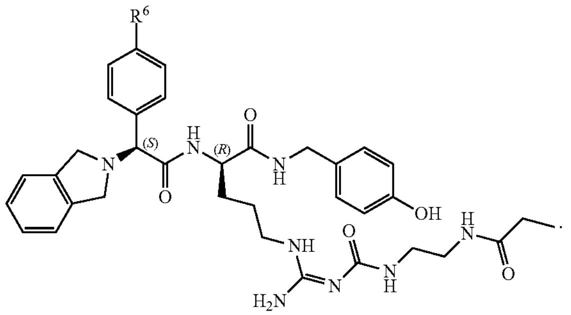

In some embodiments, the compound of Formula (I) has the structure of Formula (IIt), or a pharmaceutically acceptable salt thereof:

(IIt)

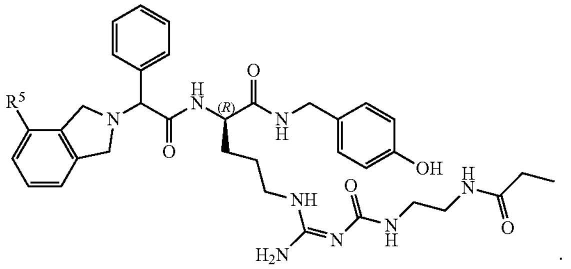

In some embodiments, the compound of Formula (I) has the structure of Formula (IIt-1S), or a pharmaceutically acceptable salt thereof:

(IIt-1S)

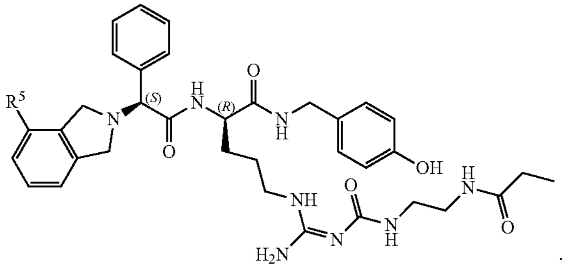

In some embodiments, the compound of Formula (I) has the structure of Formula (Iu), or a pharmaceutically acceptable salt thereof:

(Iu)

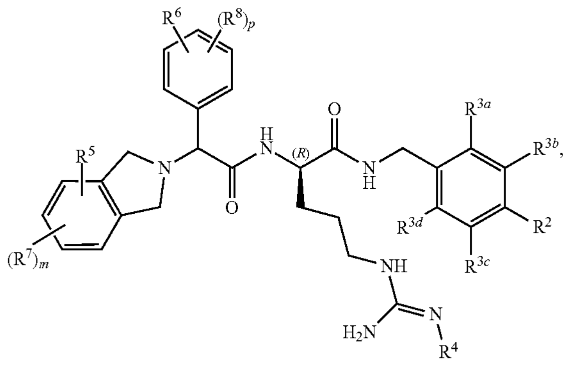

wherein each $R^{3a}$, $R^{3b}$, $R^{3c}$ and $R^{3d}$ is independently selected from the group consisting of H, F, Cl, Br, I, —CN, substituted or unsubstituted —$C_1$-$C_6$ alkyl, and substituted or unsubstituted —$C_1$-$C_6$ alkoxy. In some embodiments, each $R^{3a}$, $R^{3b}$, $R^{3c}$ and $R^{3d}$ is independently selected from the group consisting of H, F, Cl, Br, I, —CN, —$CH_3$, —$CF_3$, and —$OCH_3$. In some embodiments, the compound of Formula (I) has the structure of Formula (Iu-1S), or a pharmaceutically acceptable salt thereof:

(Iu-1S)

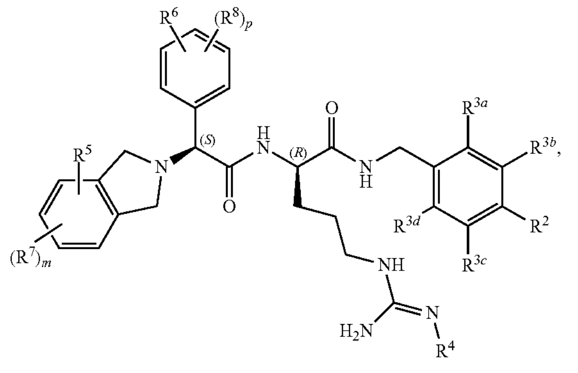

Wherein each $R^{3a}$, $R^{3b}$, $R^{3c}$ and $R^{3d}$ is independently selected from the group consisting of H, F, Cl, Br, I, —CN, substituted or unsubstituted —$C_1$-$C_6$ alkyl, and substituted or unsubstituted —$C_1$-$C_6$ alkoxy. In some embodiments, each $R^{3a}$, $R^{3b}$, $R^{3c}$ and $R^{3d}$ is independently selected from the group consisting of H, F, Cl, Br, I, —CN, —$CH_3$, —$CF_3$, and —$OCH_3$.

In some embodiments, the compound of Formula (I) has the structure of Formula (Iv), or a pharmaceutically acceptable salt thereof:

(Iv)

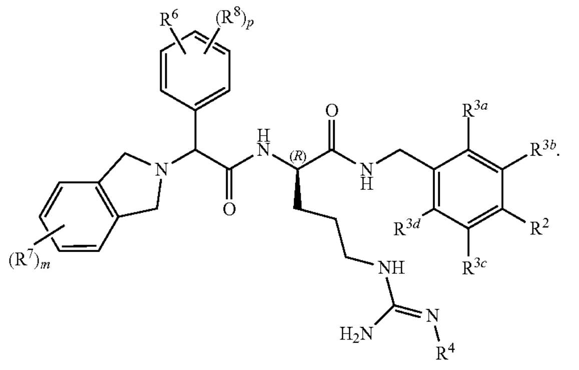

In some embodiments, the compound of Formula (I) has the structure of Formula (Iw), or a pharmaceutically acceptable salt thereof:

(Iw)

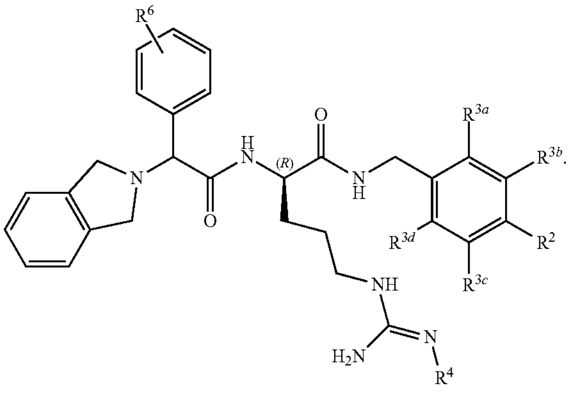

In some embodiments, the compound of Formula (I) has the structure of Formula (Iv-1S), or a pharmaceutically acceptable salt thereof:

(Iv-1S)

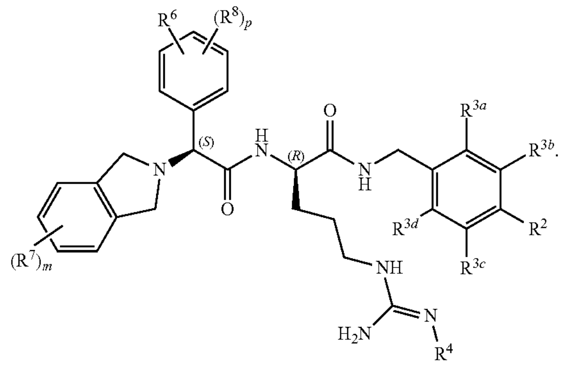

In some embodiments, the compound of Formula (I) has the structure of Formula (Iw-1S), or a pharmaceutically acceptable salt thereof:

(Iw-1S)

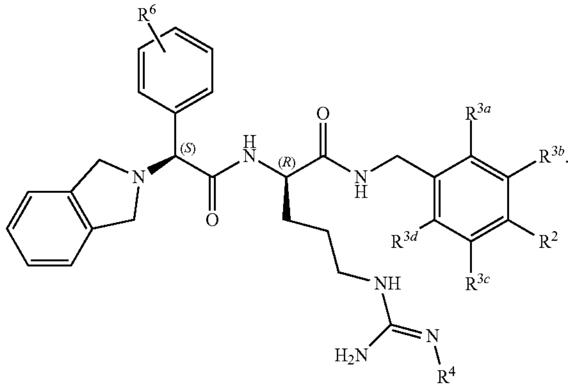

In some embodiments, the compound of Formula (I) has the structure of Formula (IIv), or a pharmaceutically acceptable salt thereof:

(IIv)

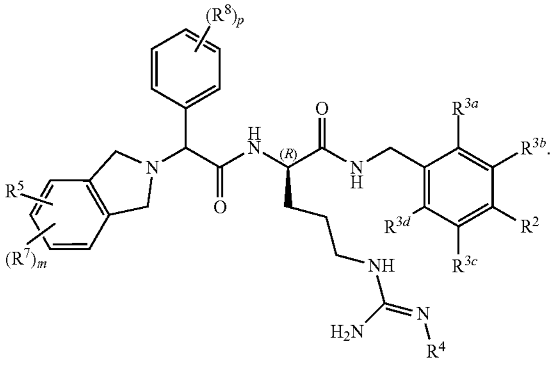

In some embodiments, the compound of Formula (I) has the structure of Formula (IIw), or a pharmaceutically acceptable salt thereof:

(IIw)

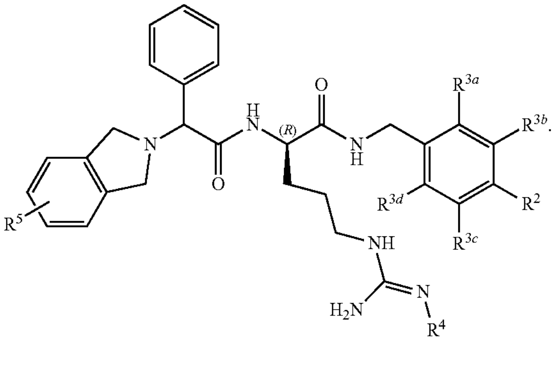

In some embodiments, the compound of Formula (I) has the structure of Formula (IIv-1S), or a pharmaceutically acceptable salt thereof:

(IIv-1S)

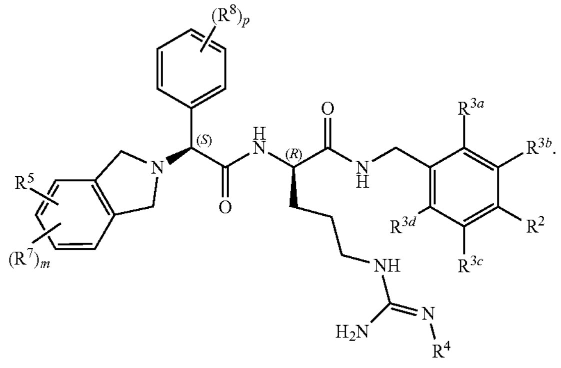

In some embodiments, the compound of Formula (I) has the structure of Formula (IIw-1S), or pharmaceutically acceptable salt thereof:

(IIw-1S)

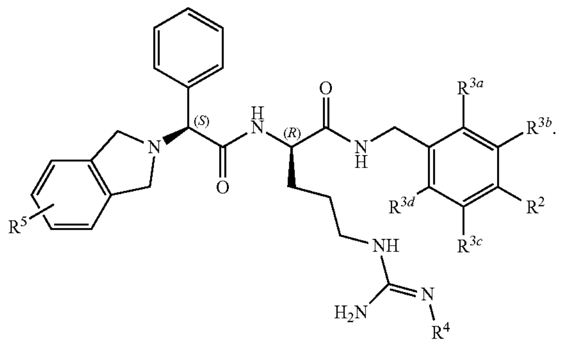

In some embodiments, the compound of Formula (I) has the structure of Formula (Iw), or Formula (IIw), or a pharmaceutically acceptable salt thereof:

(Iw)

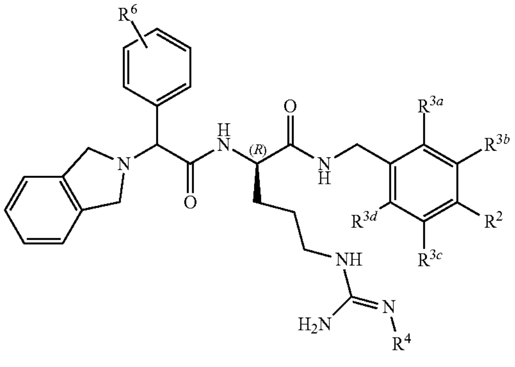

or

-continued (IIw)

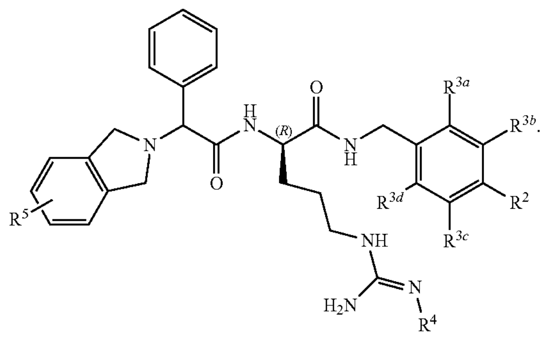

In some embodiments, the compound of Formula (I) has the structure of Formula (Iw-1S), or Formula (IIw-1S), or a pharmaceutically acceptable salt thereof:

(Iw-1S)

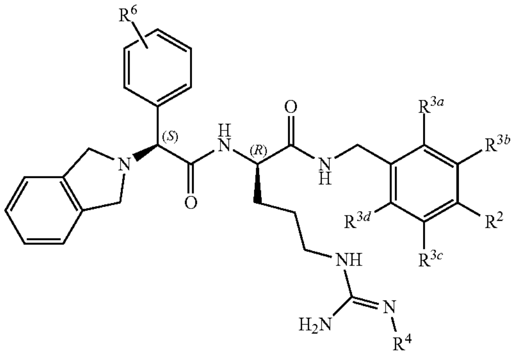

or (IIw-1S)

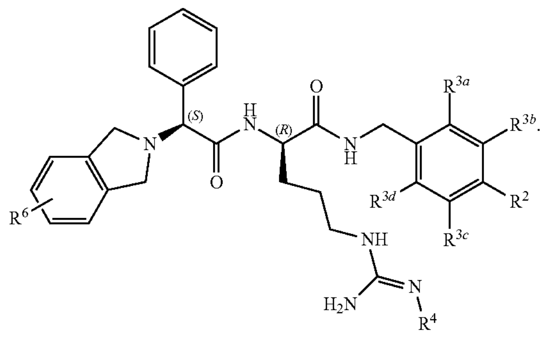

In some embodiments, the compound of Formula (I) has the structure of Formula (Ix), or a pharmaceutically acceptable salt thereof:

(Ix)

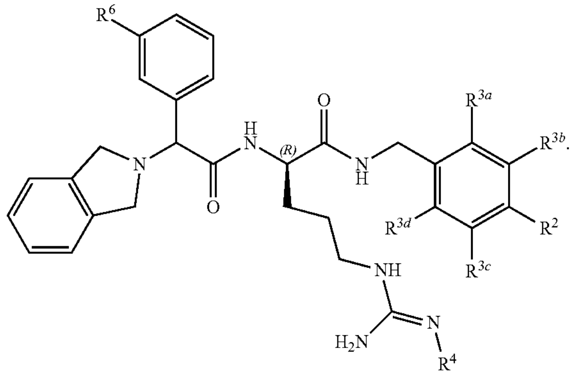

In some embodiments, the compound of Formula (I) has the structure of Formula (Iy), or a pharmaceutically acceptable salt thereof:

(Iy)

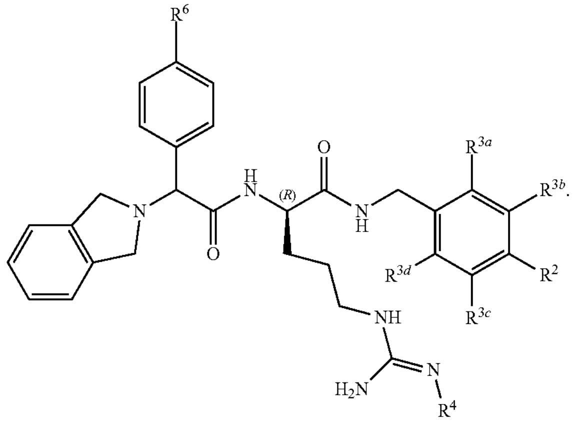

In some embodiments, the compound of Formula (I) has the structure of Formula (Ix-1S), or a pharmaceutically acceptable salt thereof:

(Ix-1S)

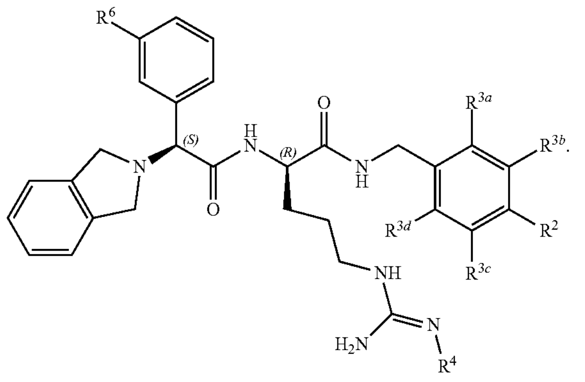

In some embodiments, the compound of Formula (I) has the structure of Formula (Iy-1S), or a pharmaceutically acceptable salt thereof:

(Iy-1S)

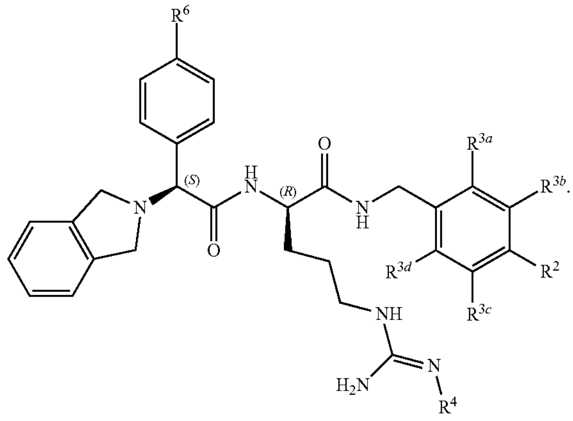

In some embodiments, the compound of Formula (I) has the structure of Formula (IIx), or a pharmaceutically acceptable salt thereof:

(IIx)

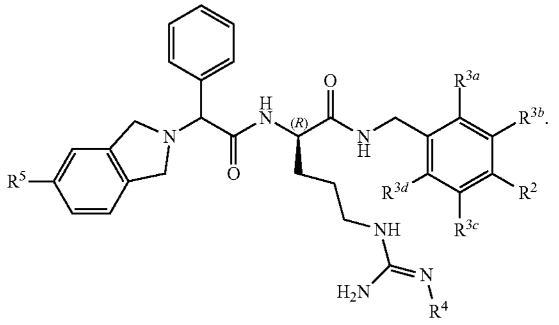

In some embodiments, the compound of Formula (I) has the structure of Formula (IIy), or a pharmaceutically acceptable salt thereof:

(IIy)

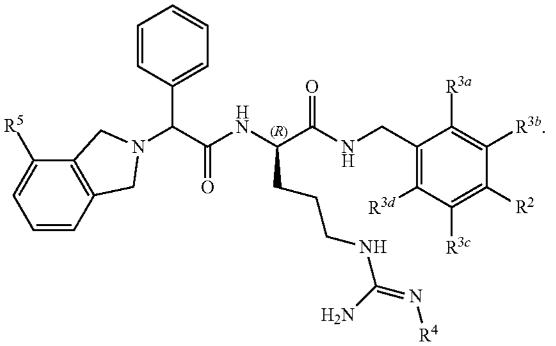

In some embodiments, the compound of Formula (I) has the structure of Formula (IIx-1S), or a pharmaceutically acceptable salt thereof:

(IIx-1S)

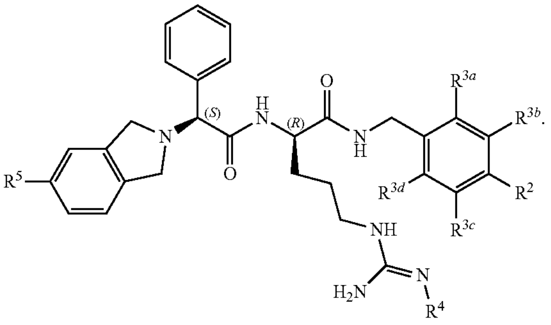

In some embodiments, the compound of Formula (I) has the structure of Formula (IIy-1S), or a pharmaceutically acceptable salt thereof:

(IIy-1S)

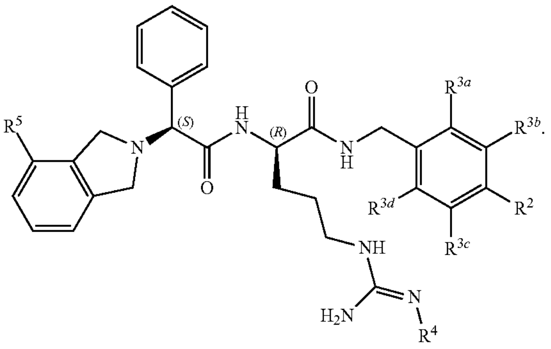

In some embodiments, the compound of Formula (I) has the structure of Formula (Iz), or a pharmaceutically acceptable salt thereof:

(Iz)

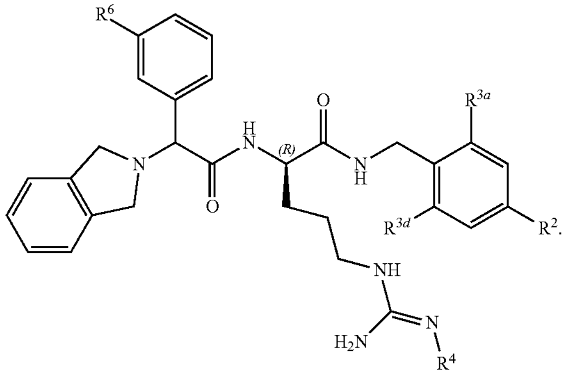

In some embodiments, the compound of Formula (I) has the structure of Formula (Iz-1S), or a pharmaceutically acceptable salt thereof:

(Iz-1S)

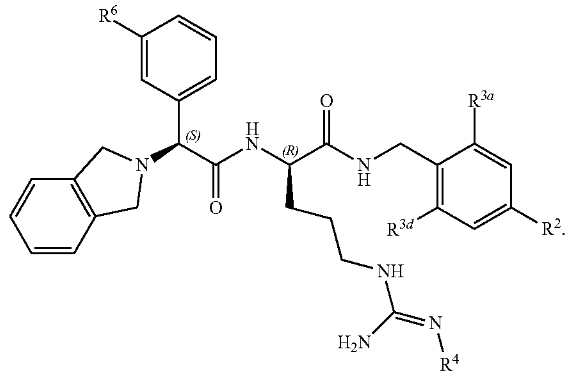

In some embodiments, the compound of Formula (I) has the structure of Formula (Iaa), or a pharmaceutically acceptable salt thereof:

(Iaa)

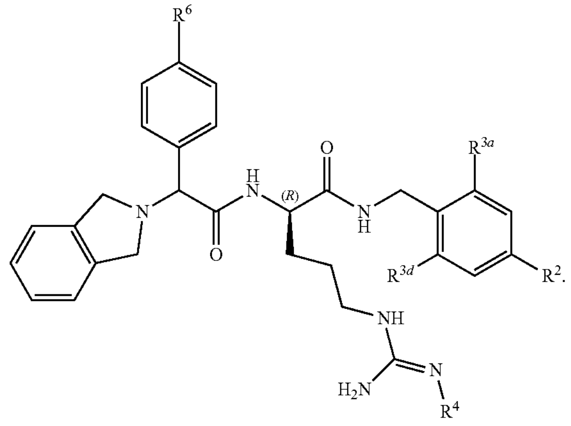

In some embodiments, the compound of Formula (I) has the structure of Formula (Iaa-1S), or a pharmaceutically acceptable salt thereof:

(Iaa-1S)

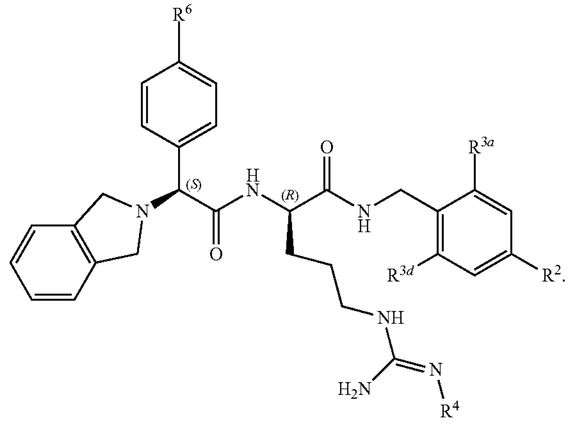

In some embodiments, the compound of Formula (I) has the structure of Formula (IIz), or a pharmaceutically acceptable salt thereof:

(IIz)

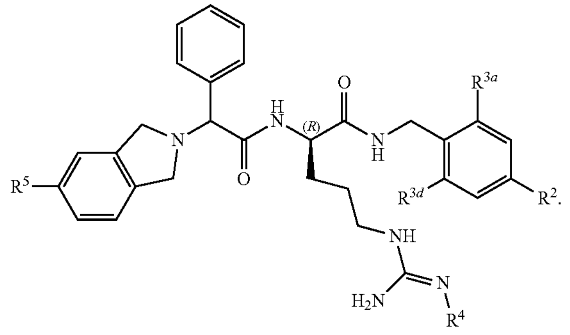

In some embodiments, the compound of Formula (I) has the structure of Formula (IIz-1S), or a pharmaceutically acceptable salt thereof:

(IIz-1S)

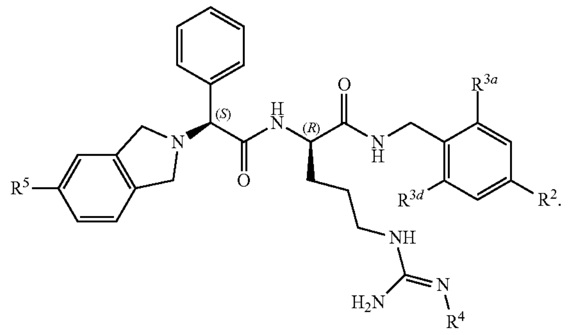

In some embodiments, the compound of Formula (I) has the structure of Formula (IIaa), or a pharmaceutically acceptable salt thereof:

(IIaa)

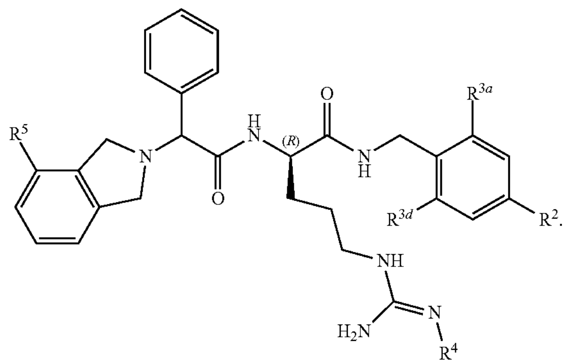

In some embodiments, the compound of Formula (I) has the structure of Formula (IIaa-1S), or a pharmaceutically acceptable salt thereof:

(IIaa-1S)
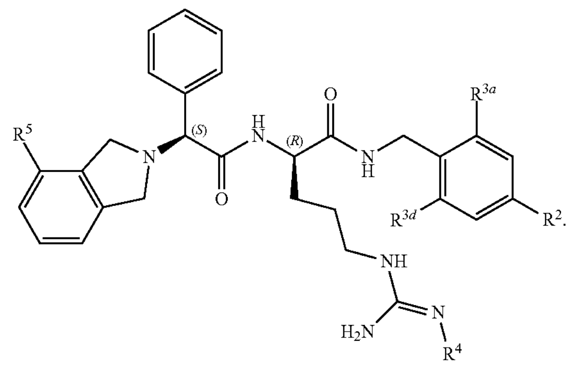
In some embodiments, the compound of Formula (I) has the following structure, or a pharmaceutically acceptable salt thereof:
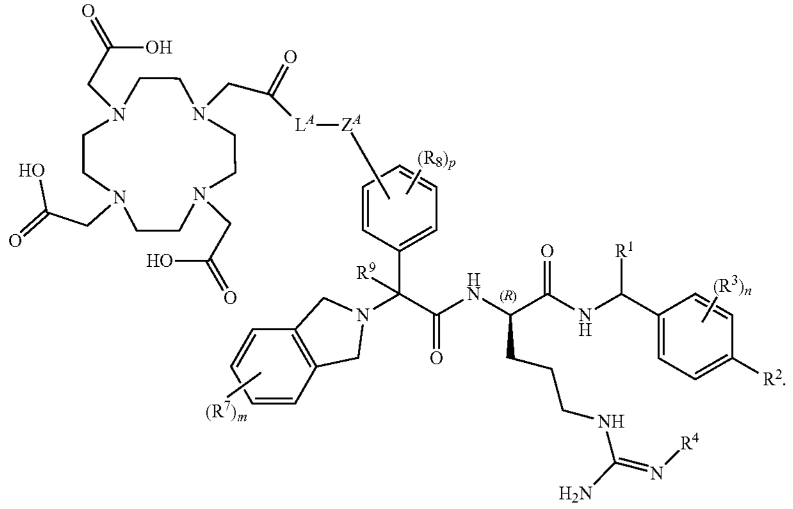
In some embodiments, the compound of Formula (I) has the following structure, or a pharmaceutically acceptable salt thereof:
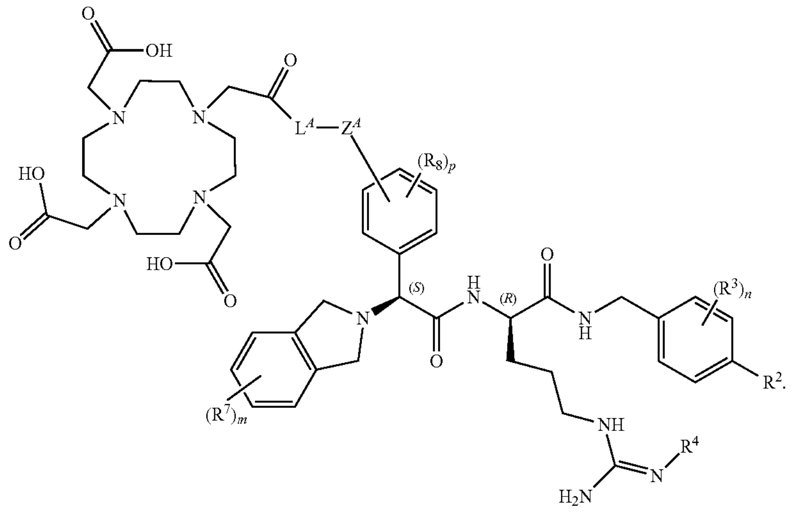

In some embodiments, the compound of Formula (I) has the following structure, or a pharmaceutically acceptable salt thereof:

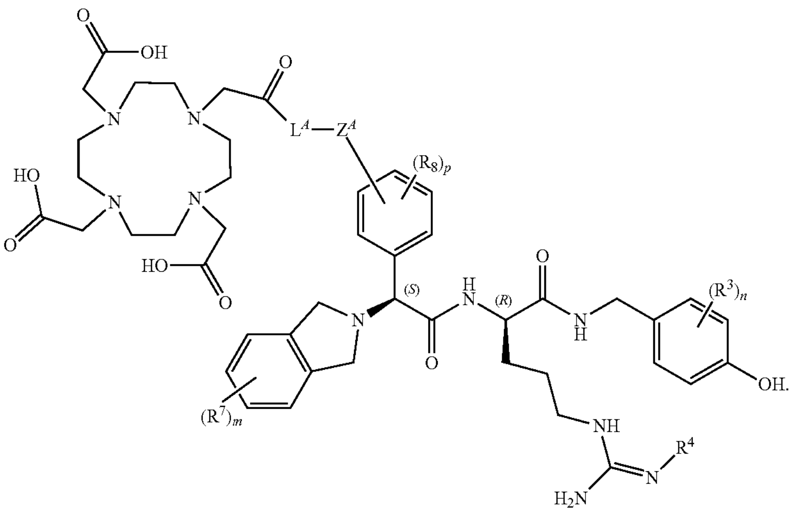

In some embodiments, the compound of Formula (I) has the following structure, or a pharmaceutically acceptable salt thereof:

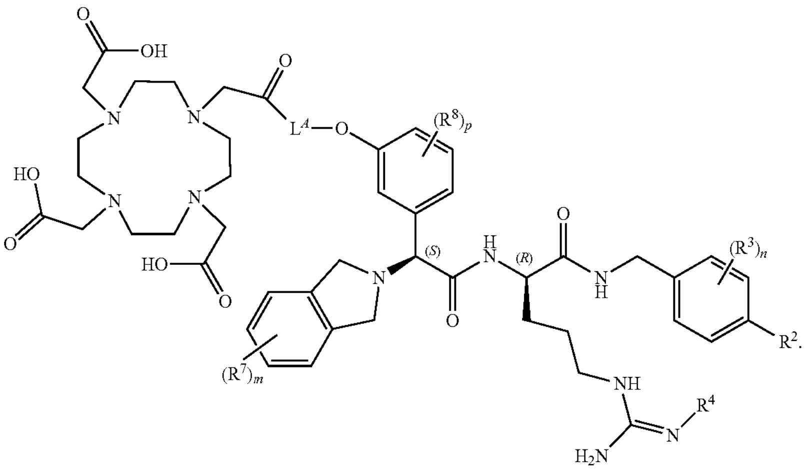

In some embodiments, the compound of Formula (I) has the following structure, or a pharmaceutically acceptable salt thereof:

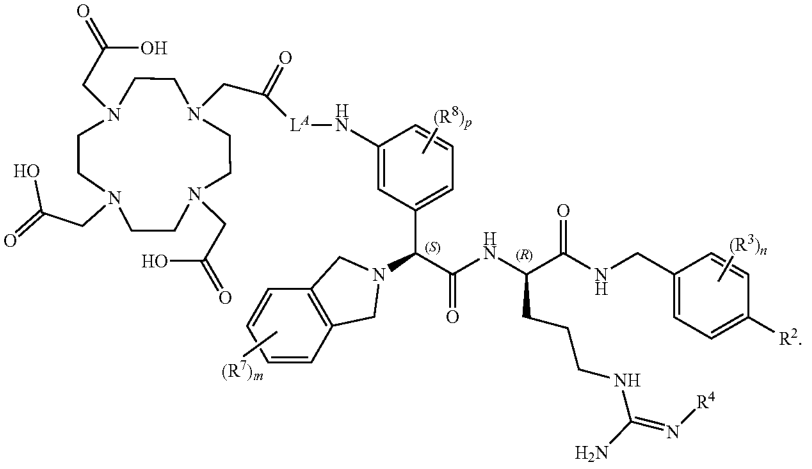
In some embodiments, the compound of Formula (I) has the following structure, or a pharmaceutically acceptable salt thereof:
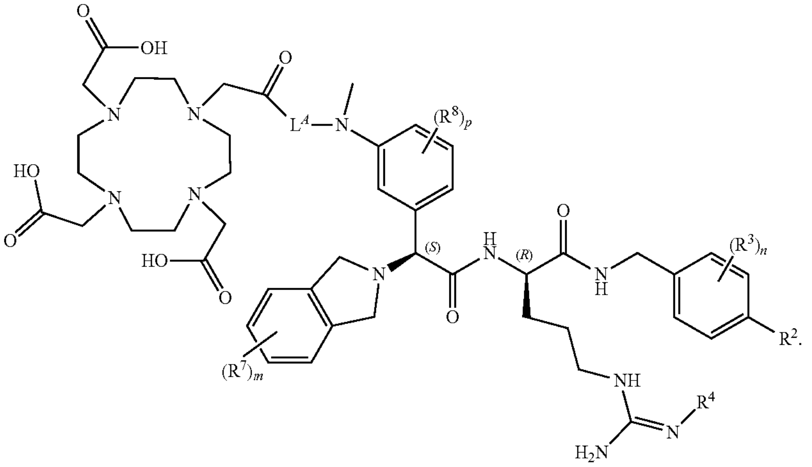
In some embodiments, the compound of Formula (I) has the following structure, or a pharmaceutically acceptable salt thereof:
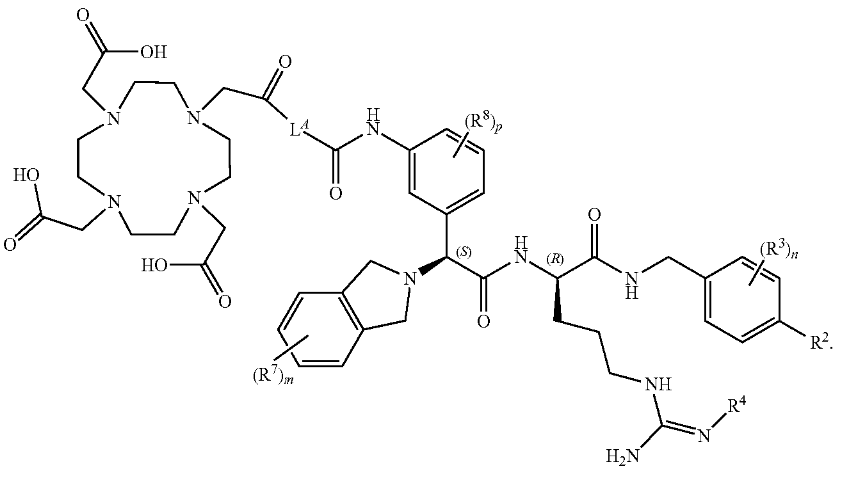

In some embodiments, the compound of Formula (I) has the following structure, or a pharmaceutically acceptable salt thereof:

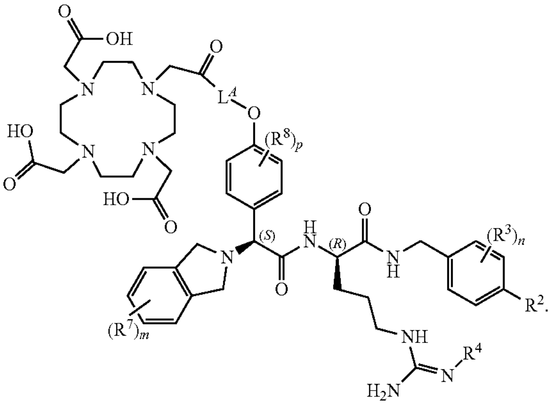

In some embodiments, the compound of Formula (I) has the following structure, or a pharmaceutically acceptable salt thereof:

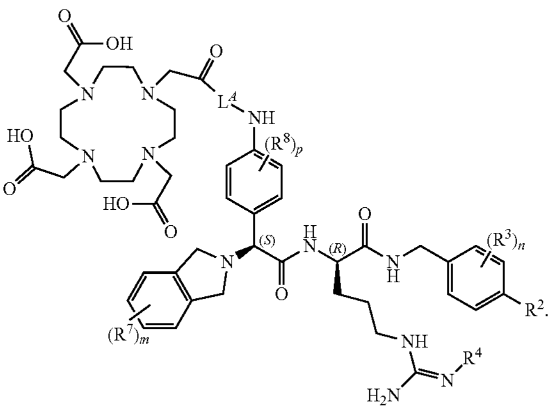

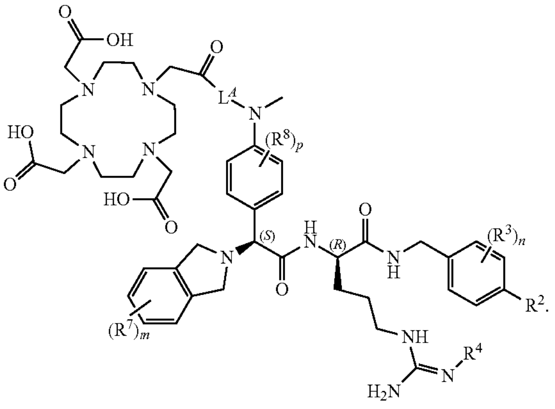

In some embodiments, the compound of Formula (I) has the following structure, or a pharmaceutically acceptable salt thereof:

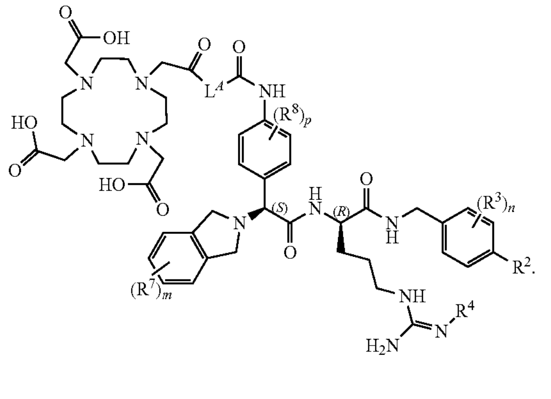

In some embodiments, the compound of Formula (I) has the following structure, or a pharmaceutically acceptable salt thereof:

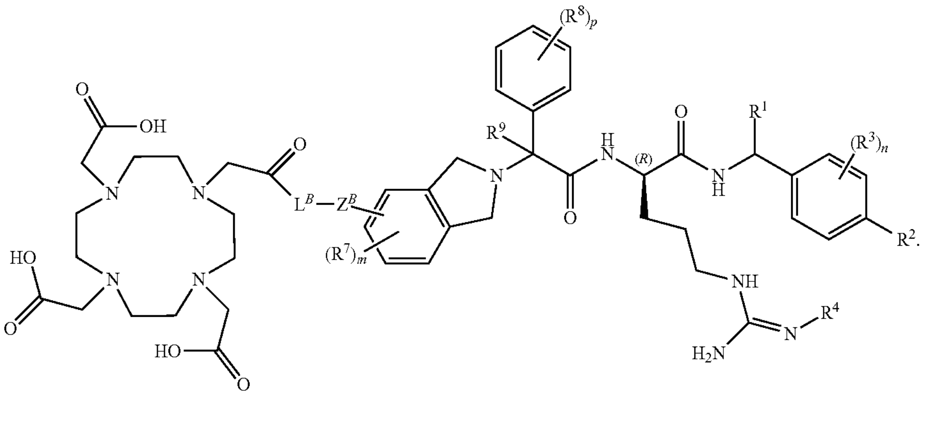

In some embodiments, the compound of Formula (I) has the following structure, or a pharmaceutically acceptable salt thereof:

In some embodiments, the compound of Formula (I) has the following structure, or a pharmaceutically acceptable salt thereof:

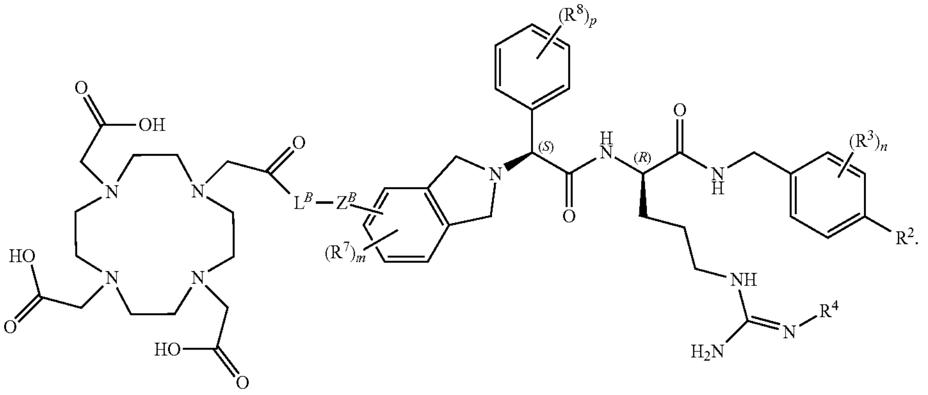

In some embodiments, the compound of Formula (I) has the following structure, or a pharmaceutically acceptable salt thereof:

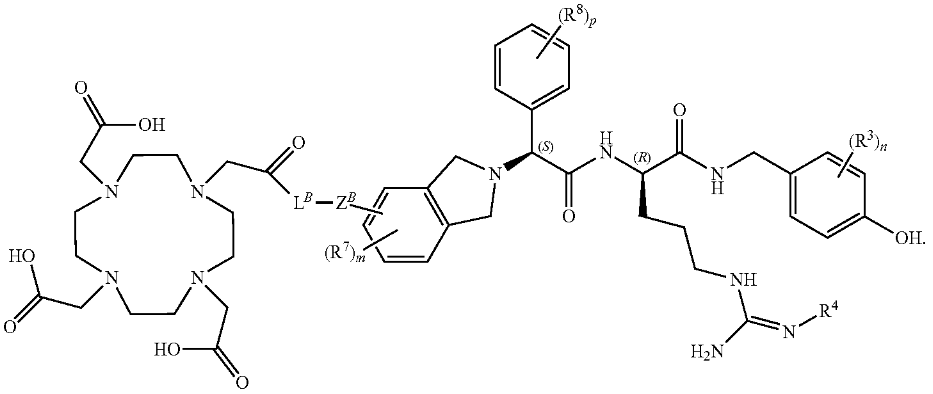

In some embodiments, the compound of Formula (I) has the following structure, or a pharmaceutically acceptable salt thereof:

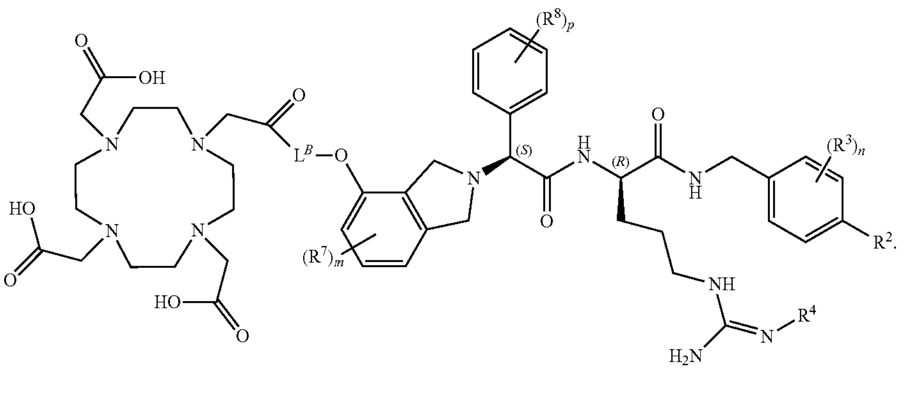

In some embodiments, the compound of Formula (I) has the following structure, or a pharmaceutically acceptable salt thereof:

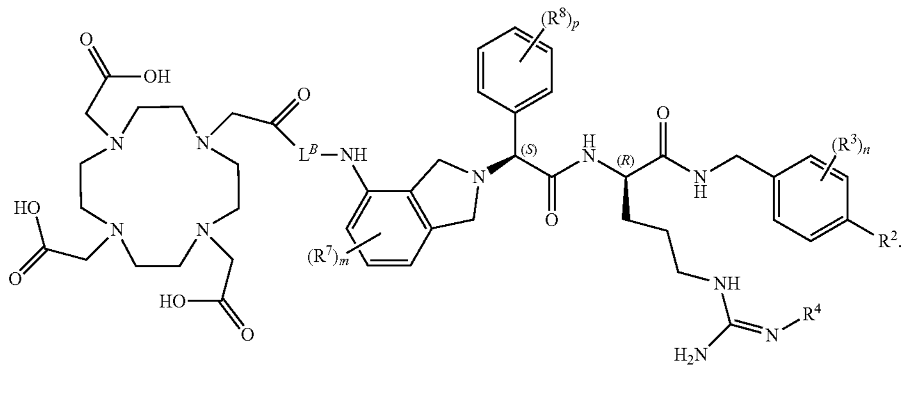

In some embodiments, the compound of Formula (I) has the following structure, or a pharmaceutically acceptable salt thereof:

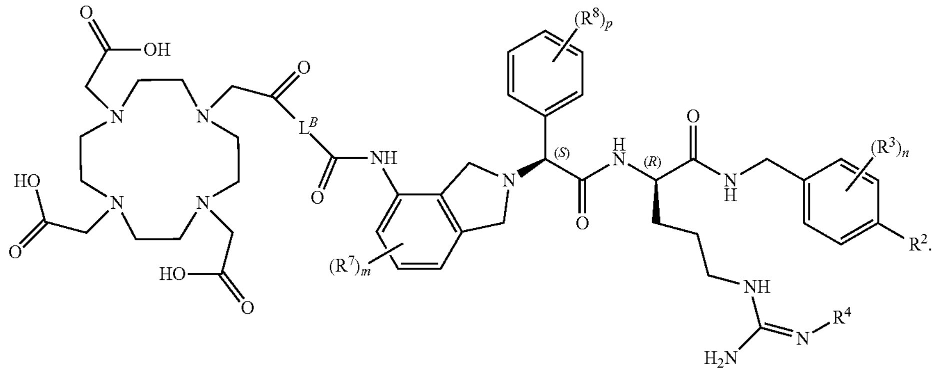

In some embodiments, $R^{3a}$ is H, F, Cl, Br, I, —CN, —$CH_3$, —$CF_3$, or —$OCH_3$. In some embodiments, $R^{3a}$ is H. In some embodiments, $R^{3a}$ is F. In some embodiments, $R^{3a}$ is Cl. In some embodiments, $R^{3a}$ is Br. In some embodiments, $R^{3a}$ is I. In some embodiments, $R^{3a}$ is —CN. In some embodiments, $R^{3a}$ is —$CH_3$. In some embodiments, $R^{3a}$ is —$CF_3$. In some embodiments, $R^{3a}$ is —$OCH_3$. In some embodiments, $R^{3b}$ is H, F, Cl, Br, I, —CN, —$CH_3$, —$CF_3$, or —$OCH_3$. In some embodiments, $R^{3b}$ is H. In some embodiments, $R^{3b}$ is F. In some embodiments, $R^{3b}$ is $C_1$. In some embodiments, $R^{3b}$ is Br. In some embodiments, $R^{3b}$ is I. In some embodiments, $R^{3b}$ is —CN. In some embodiments, $R^{3b}$ is —$CH_3$. In some embodiments, $R^{3b}$ is —$CF_3$. In some embodiments, $R^{3b}$ is —$OCH_3$. In some embodiments, $R^{3c}$ is H, F, Cl, Br, I, —CN, —$CH_3$, —$CF_3$, or —$OCH_3$. In some embodiments, $R^{3c}$ is H. In some embodiments, $R^{3c}$ is F. In some embodiments, $R^{3c}$ is $C_1$. In some embodiments, $R^{3c}$ is Br. In some embodiments, $R^{3c}$ is I. In some embodiments, $R^{3c}$ is —CN. In some embodiments, $R^{3c}$ is —$CH_3$. In some embodiments, $R^{3c}$ is —$CF_3$. In some embodiments, $R^{3c}$ is —$OCH_3$. In some embodiments, $R^{3d}$ is H, F, Cl, Br, I, —CN, —$CH_3$, —$CF_3$, or —$OCH_3$. In some embodiments, $R^{3d}$ is H. In some embodiments, $R^{3d}$ is F. In some embodiments, $R^{3d}$ is $C_1$. In some embodiments, $R^{3d}$ is Br. In some embodiments, $R^{3d}$ is I. In some embodiments, $R^{3d}$ is —CN. In some embodiments, $R^{3d}$ is —$CH_3$. In some embodiments, $R^{3d}$ is —$CF_3$. In some embodiments, $R^{3d}$ is —$OCH_3$. In some embodiments, $R^{3a}$ and $R^{3d}$ are F or Cl and $R^{3b}$ and $R^{3c}$ are H. In some embodiments, $R^{3a}$ and $R^{3d}$ are F and $R^{3b}$ and $R^{3c}$ are H. In some embodiments, $R^{3a}$ and $R^{3d}$ are $C_1$ and $R^{3b}$ and $R^{3c}$ are H. In some embodiments, $R^{3a}$ is F, Cl, or Br and $R^{3b}$, $R^{3c}$, and $R^{3d}$ are H. In some embodiments, $R^{3a}$ is F and $R^{3b}$, $R^{3c}$, and $R^{3d}$ are H. In some embodiments, $R^{3a}$ is $C_1$ and $R^{3b}$, $R^{3c}$, and $R^{3d}$ are H. In some embodiments, $R^{3a}$ is Br and $R^{3b}$, $R^{3c}$, and $R^{3d}$ are H.

In some embodiments, the compound of Formula (I) has the structure of Formula (Jab), or a pharmaceutically acceptable salt thereof:

(Iab)

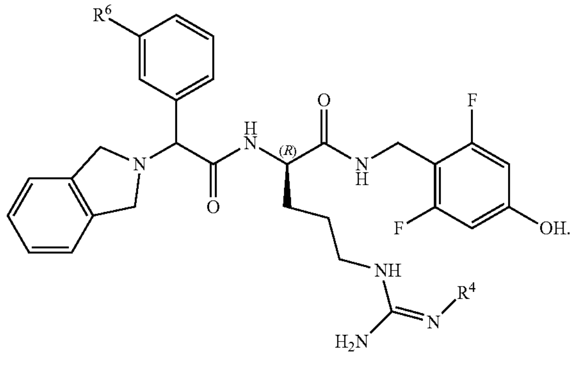

In some embodiments, the compound of Formula (I) has the structure of Formula (Iac), or a pharmaceutically acceptable salt thereof:

(Iac)

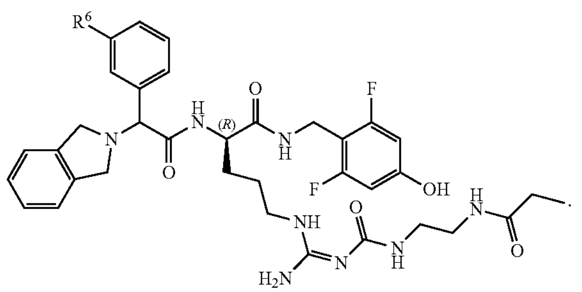

In some embodiments, the compound of Formula (I) has the structure of Formula (Iad), or a pharmaceutically acceptable salt thereof:

(Iad)

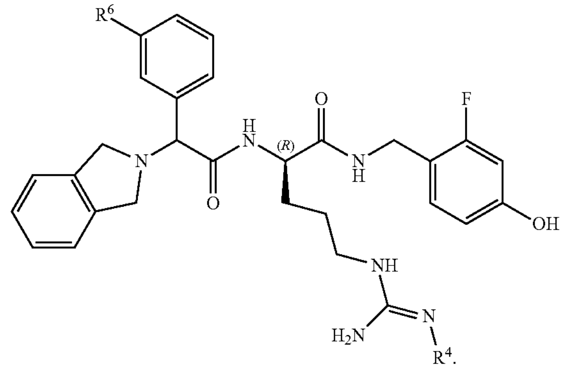

In some embodiments, the compound of Formula (I) has the structure of Formula (Iab-1S), or a pharmaceutically acceptable salt thereof:

(Iab-1S)

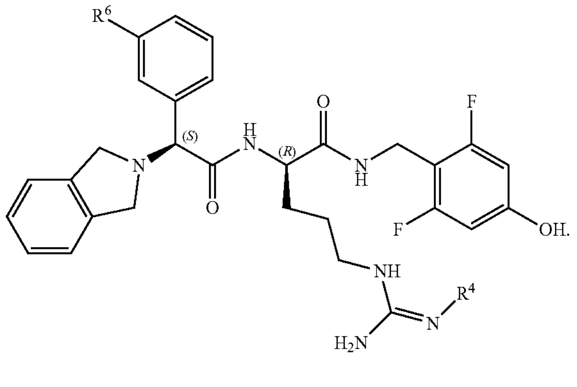

In some embodiments, the compound of Formula (I) has the structure of Formula (Iac-1S), or a pharmaceutically acceptable salt thereof:

(Iac-1S)

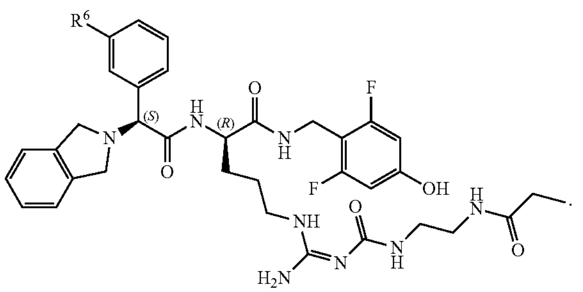

In some embodiments, the compound of Formula (I) has the structure of Formula (Iad-1S), or a pharmaceutically acceptable salt thereof:

(Iad-1S)

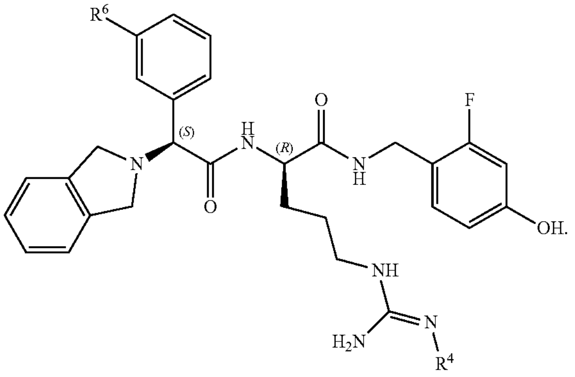

In some embodiments, the compound of Formula (I) has the structure of Formula (IIav), or a pharmaceutically acceptable salt thereof:

(IIab)

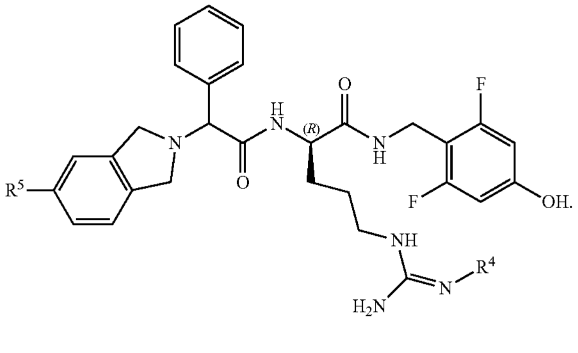

In some embodiments, the compound of Formula (I) has the structure of Formula (IIac), or a pharmaceutically acceptable salt thereof:

(IIac)

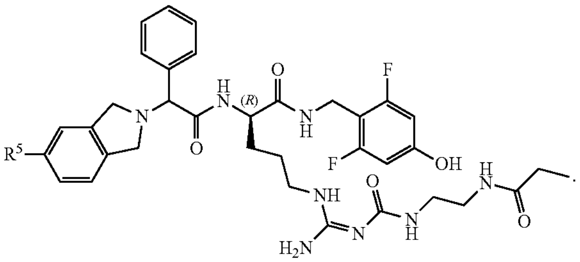

In some embodiments, the compound of Formula (I) has the structure of Formula (Had), or a pharmaceutically acceptable salt thereof:

(IIad)

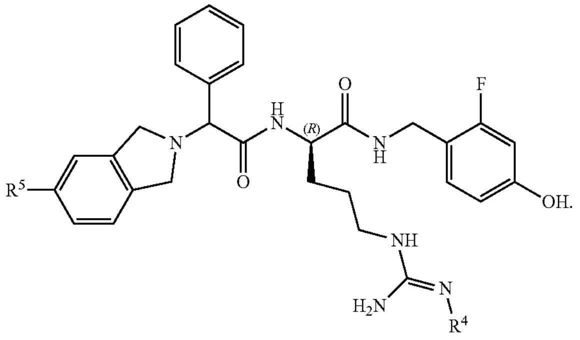

In some embodiments, the compound of Formula (I) has the structure of Formula (IIab-1S), or a pharmaceutically acceptable salt thereof:

(IIab-1S)

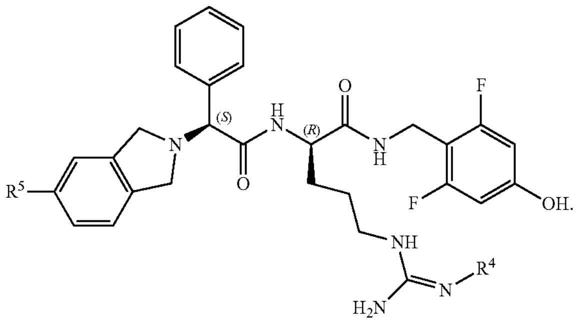

In some embodiments, the compound of Formula (I) has the structure of Formula (IIac-1S), or a pharmaceutically acceptable salt thereof:

(IIac-1S)

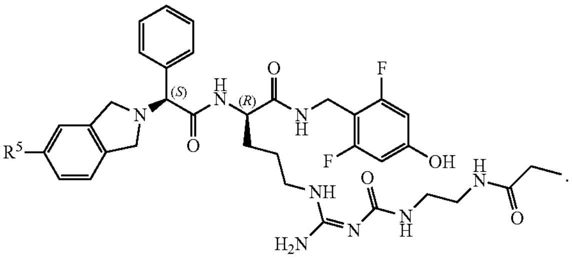

In some embodiments, the compound of Formula (I) has the structure of Formula (Had-1S), or a pharmaceutically acceptable salt thereof:

(IIad-1S)

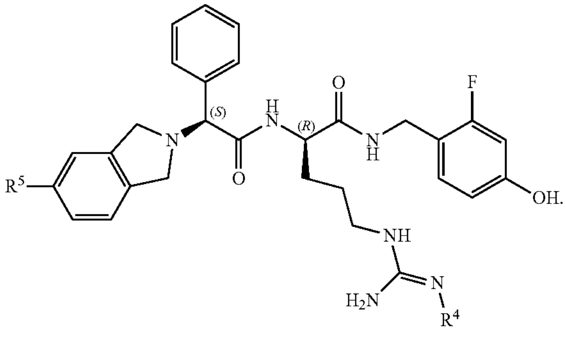

In some embodiments, the compound of Formula (I) has the structure of Formula (Iae), or a pharmaceutically acceptable salt thereof:

(Iae)

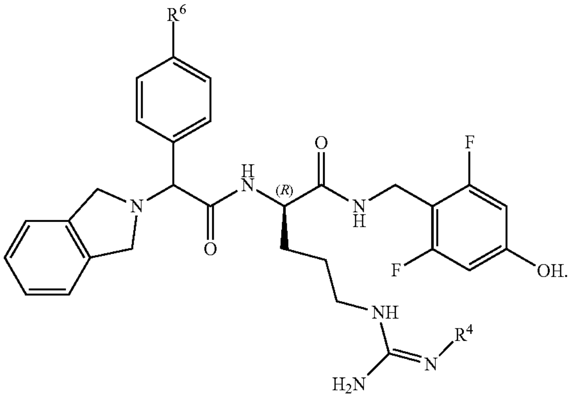

In some embodiments, the compound of Formula (I) has the structure of Formula (Iaf), or a pharmaceutically acceptable salt thereof:

(Iaf)

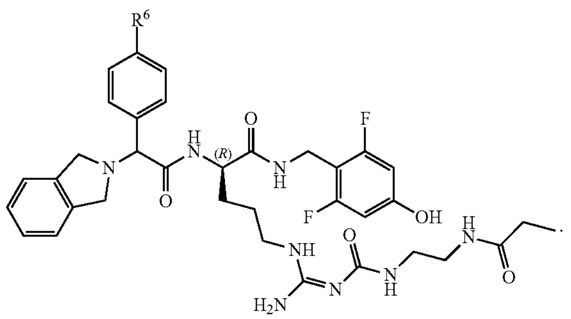

In some embodiments, the compound of Formula (I) has the structure of Formula (hag), or a pharmaceutically acceptable salt thereof:

(Iag)

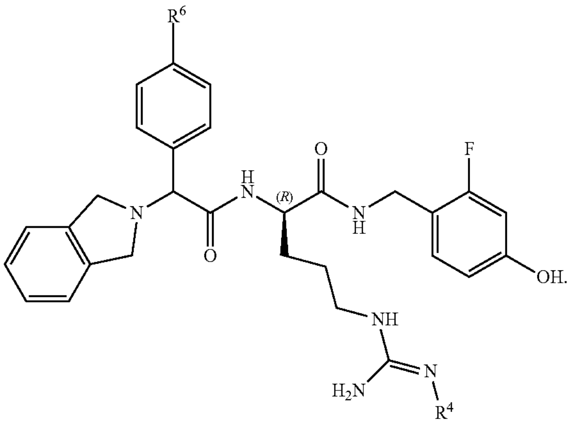

In some embodiments, the compound of Formula (I) has the structure of Formula (Iae-1S), or a pharmaceutically acceptable salt thereof:

(Iae-1S)

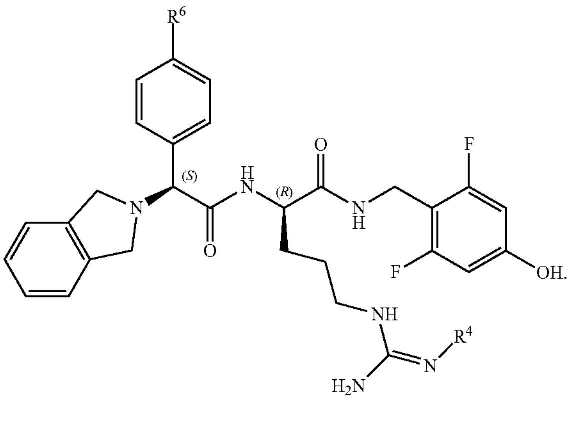

In some embodiments, the compound of Formula (I) has the structure of Formula (Iaf-1S), or a pharmaceutically acceptable salt thereof:

(Iaf-1S)

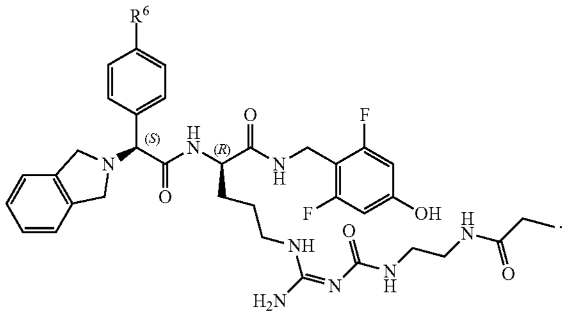

In some embodiments, the compound of Formula (I) has the structure of Formula (Iag-1S), or a pharmaceutically acceptable salt thereof:

(Iag-1S)

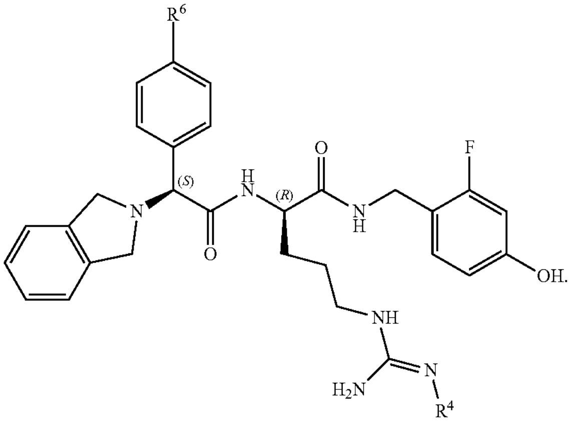

In some embodiments, the compound of Formula (I) has the structure of Formula (IIae), or a pharmaceutically acceptable salt thereof:

(IIae)

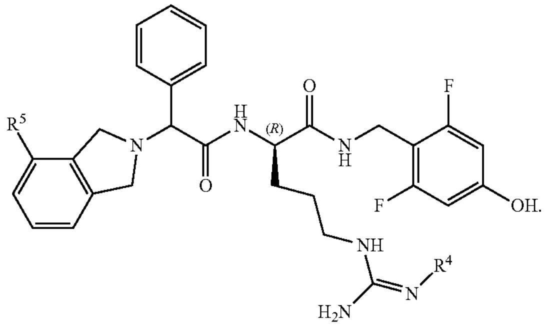

In some embodiments, the compound of Formula (I) has the structure of Formula (IIaf), or a pharmaceutically acceptable salt thereof:

(IIaf)

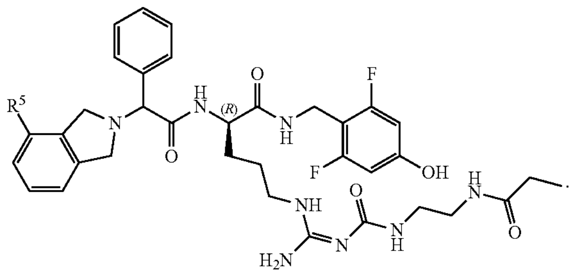

In some embodiments, the compound of Formula (I) has the structure of Formula (IIag), or a pharmaceutically acceptable salt thereof:

(IIag)

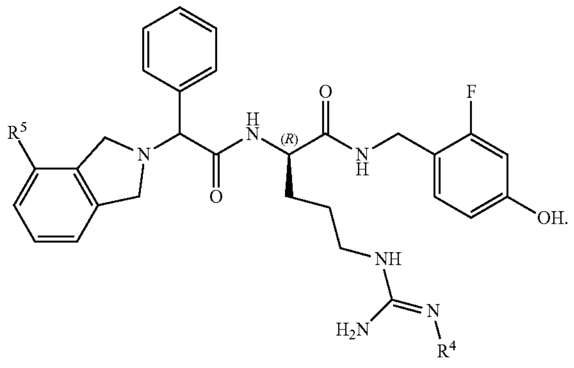

In some embodiments, the compound of Formula (I) has the structure of Formula (IIae-1S), or a pharmaceutically acceptable salt thereof:

(IIae-1S)

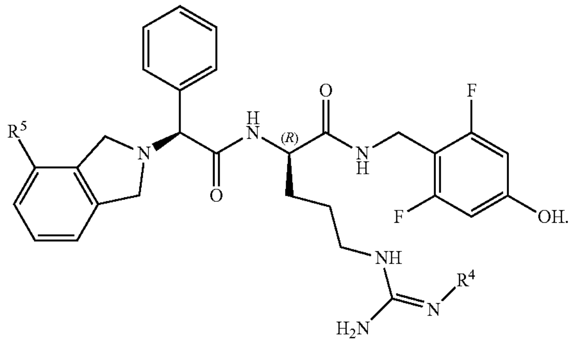

In some embodiments, the compound of Formula (I) has the structure of Formula (IIaf-1S), or a pharmaceutically acceptable salt thereof:

(IIaf-1S)

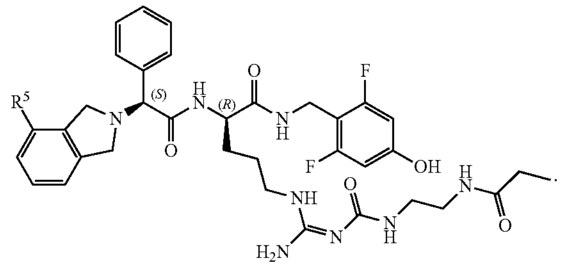

In some embodiments, the compound of Formula (I) has the structure of Formula (IIag-1S), or a pharmaceutically acceptable salt thereof:

(IIag-1S)

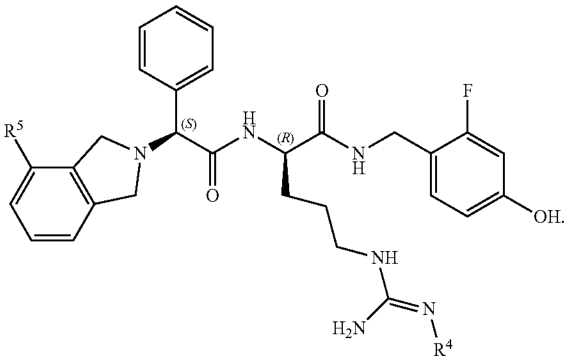

In some embodiments, $R^2$ is $—C(=O)NH_2$ or $—CH_2NHC(=O)NH_2$. In some embodiments, $R^2$ is —OH. In some embodiments, $R^2$ is $—NH_2$. In some embodiments, $R^2$ is $—C(=O)NH_2$. In some embodiments, $R^2$ is $—CH_2NHC(=O)NH_2$.

In some embodiments, $R^4$ is H. In some embodiments, $R^4$ is $—C(=O)R^{10}$. In some embodiments, $R^4$ is $—C(=O)NHR^{10}$. In some embodiments, $R^4$ is $—C(=O)N(CH_3)R^{10}$.

In some embodiments, $R^{10}$ is unsubstituted $—C_1$-$C_6$ alkyl or unsubstituted 2 to 6-membered heteroalkyl. In some embodiments, $R^{10}$is $—(CH_2)_tCH_3$. In some embodiments, $R^{10}$is $—CH_2CH_3$. In some embodiments, $R^{10}$ is $—(CH_2)_tNHC(=O)(CH_2)_uCH_3$. In some embodiments, t is 1. In some embodiments, t is 2. In some embodiments, t is 4. In some embodiments, u is 1. In some embodiments, t is 2 and u is 1. In some embodiments, $R^{10}$ is $—(CH_2)_2NHC(=O)(CH_2)_uCH_3$. In some embodiments, $R^{10}$ is $—(CH_2)_2NHC(=O)CH_2CH_3$.

In some embodiments, $R^4$ is $—C(=O)NH(CH_2)_tCH_3$ or $—C(=O)NH(CH_2)_tNHC(=O)(CH_2)_uCH_3$. In some embodiments, t is 1. In some embodiments, t is 2. In some embodiments, t is 4. In some embodiments, u is 1. In some embodiments, t is 2 and u is 1. In some embodiments, t is 4 and u is 1. In some embodiments, $R^4$ is $—C(=O)NHCH_2CH_3—$. In some embodiments, $R^4$ is $—C(=O)NH(CH_2)_2NHC(=O)CH_2CH_3$.

In some embodiments, t is 1. In some embodiments, t is 2. In some embodiments, t is 3. In some embodiments, t is 4. In some embodiments, t is 5. In some embodiments, t is 6.

In some embodiments, u is 1. In some embodiments, u is 2. In some embodiments, u is 3. In some embodiments, u is 4.

In some embodiments, $R^A$ and $R^B$, if present, are independently selected from the group consisting of: cyclen, DO2A, DO3A, HP-DO3A, DO3A-Nprop, DO3AP, $DO3AP^{PrA}$, $DO3AP^{ABn}DO3AM^{nBu}$, BT-DO3A, DOTA, DOTAGA, $DOTA(GA)_2$, DOTAM, DOTA-4AMP, DOTMA, DOTP, CB-DO2A, DOTPA, DOTMP, DOTAMAP, TRITA, $L^{py}$, cyclam, TETA, CB-Cyclam, CB-TE2A, TE2A, NOTA, NODAGA, NODA-MPAA, TACN, TACN-TM, NOTP, Sarcophagine (Sar), DiAmSar, SarAr, AmBaSar, cis-DO2A2P, trans-DO2A2P, DOTEP, p-$NO_2$-Bn-DOTA, BAT, DO3TMP-Monoamide, CHX-A"-DTPA, c-DEPA, PCTA, p-$NO_2$-Bn-PCTA, TRAP, TRAPH, TRAP-OH, TRAP-Ph, NOPO, AAZTA, DATAM, HEHA, PEPA, DTA, EDTMP, DTPMP, NTA, EDTA, DTPA, CyDTPA, DFO, DFO*, deferiprone, TTHA, HBED, HBED-CC, HBED-CC TFP, $H_4$pypa, $H_4$py4pa, CP256, THP, YM103, t-Bu-calix[4]arene-tetracarboxylic acid, CHX-A"-DTPA, $H_6$phospha, p-$NH_2$-Bn-CHXA"-DTPA, DEDPA, $H_4$octox, $H_4$octapa, $H_4$CHXoctapa, HYNIC, macropa, crown, macropid, HOPO, Bis(2-mercaptoacetamide), Bis (aminothiolate), or SBTG2DAP.

In some embodiments, $R^A$ and $R^B$, if present, are each independently selected from the group consisting of: 1,4,7,10-tetraazacyclododecane-1,4,7,10-tetraacetic acid (DOTA); 1,4,7,10-tetraazacyclododecane-1,4,7-triacetic acid (DO3A); 1,4,7,10-tetraazacyclododecane-1,7-diacetic acid (DO2A); α,α',α",α'"-tetramethyl-1,4,7,10-tetraazacyclododecane-1,4,7,10-tetraacetic acid (DOTMA); 1,4,7,10-tetrakis(carbamoylmethyl)-1,4,7,10-tetraazacyclododecane (DOTAM); 1,4,7,10-tetraazacyclododecane-1,4,7,10-tetrapropionic acid (DOTPA); 2,2',2"-(10-(2-amino-2-oxoethyl)-1,4,7,10-tetraazacyclododecane-1,4,7-triyl)triacetic acid; benzyl-1,4,7,10-tetraazacyclododecane-1,4,7,10-tetraacetic acid (Bn-DOTA); p-hydroxy-benzyl-1,4,7,10-tetraazacyclododecane-1,4,7,10-tetraacetic acid (p-OH-Bn-DOTA); 6,6'-(((pyridine-2,6-diylbis(methylene))bis((carboxymethyl)azanediyl))bis(methylene))dipicolinic acid ($H_4$pypa); $H_4$pypa-benzyl; 6,6',6",6'"-(((pyridine-2,6-diylbis(methylene))bis(azanetriyl))-tetrakis(methylene))-tetrapicolinic acid ($H_4$py4pa); $H_4$py4pa-benzyl; 2,2',2"-(1,4,7-triazacyclononane-1,4,7-triyl)triacetic acid (NOTA); 6,6'-((1,4,10,13-tetraoxa-7,16-diazacyclooctadecane-7,16-diyl)bis(methylene))dipicolinic acid (macropa); 2,2',2",2'"-(1,10-dioxa-4,7,13,16-tetraazacyclooctadecane-4,7,13,16-tetrayl)tetraacetic acid (crown); 6,6'-((ethane-1,2-diylbis((carboxymethyl)azanediyl))bis(methylene))dipicolinic acid ($H_4$octapa); $H_4$octapa-benzyl; and 3,6,9,12-tetrakis(carboxymethyl)-3,6,9,12-tetraazatetradecanedioic acid (TTHA); or a radionuclide complex thereof.

In some embodiments, $R^A$ and $R^B$, if present, are each independently selected from the group consisting of: DOTA; DO3A; DO2A; DOTMA; DOTAM; DOTPA; $H_4$pypa; $H_4$py4pa; macropa; crown; $H_4$octapa; and TTHA; or a radionuclide complex thereof.

In some embodiments, $R^A$ is DOTA or a radionuclide complex thereof. In some embodiments, $R^A$ is DO3A or a radionuclide complex thereof. In some embodiments, $R^A$ is DO2A or a radionuclide complex thereof. In some embodiments, $R^A$ is DOTMA or a radionuclide complex thereof. In some embodiments, $R^A$ is DOTAM or a radionuclide complex thereof. In some embodiments, $R^A$ is DOTPA or a radionuclide complex thereof. In some embodiments, $R^A$ is 2,2',2'-(10-(2-amino-2-oxoethyl)-1,4,7,10-tetraazacyclododecane-1,4,7-triyl)triacetic acid or a radionuclide complex thereof. In some embodiments, $R^A$ is $H_4$pypa or a radionuclide complex thereof. In some embodiments, $R^A$ is $H_4$py4pa or a radionuclide complex thereof. In some embodiments, $R^A$ is NOTA or a radionuclide complex thereof. In some embodiments, $R^A$ is macropa or a radionuclide complex thereof. In some embodiments, $R^A$ is crown or a radionuclide complex thereof. In some embodiments, $R^A$ is $H_4$octapa or a radionuclide complex thereof. In some embodiments, $R^A$ is TTHA or a radionuclide complex thereof.

In some embodiments, $R^B$ is DOTA or a radionuclide complex thereof. In some embodiments, $R^B$ is DO3A or a radionuclide complex thereof. In some embodiments, $R^B$ is DO2A or a radionuclide complex thereof. In some embodiments, $R^B$ is DOTMA or a radionuclide complex thereof. In some embodiments, $R^B$ is DOTAM or a radionuclide complex thereof. In some embodiments, $R^B$ is DOTPA or a radionuclide complex thereof. In some embodiments, $R^B$ is 2,2',2"-(10-(2-amino-2-oxoethyl)-1,4,7,10-tetraazacyclododecane-1,4,7-triyl)triacetic acid or a radionuclide complex thereof. In some embodiments, $R^B$ is $H_4$pypa or a radionuclide complex thereof. In some embodiments, $R^B$ is $H_4$py4pa or a radionuclide complex thereof. In some embodiments, $R^B$ is NOTA or a radionuclide complex thereof. In some embodiments, $R^B$ is macropa or a radionuclide complex thereof. In some embodiments, $R^B$ is crown or a radionuclide complex thereof. In some embodiments, $R^B$ is $H_4$octapa or a radionuclide complex thereof. In some embodiments, $R^B$ is TTHA or a radionuclide complex thereof.

In some embodiments, the chelating moieties of $R^A$ and $R^B$ are independently selected from the group consisting of: DOTA, DO3A and DOTAGA; or a radionuclide complex thereof.

In some embodiments, the chelating moieties of $R^A$ and $R^B$ are independently selected from the group consisting of: DOTA and DO3A; or a radionuclide complex thereof.

In some embodiments, the chelating moieties of $R^A$ and $R^B$ are independently selected from the group consisting of:

(CM-1)

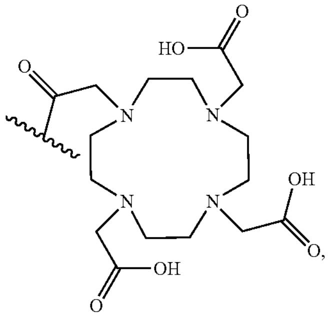

(CM-2)

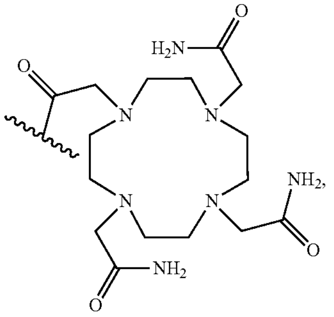

-continued (CM-4)

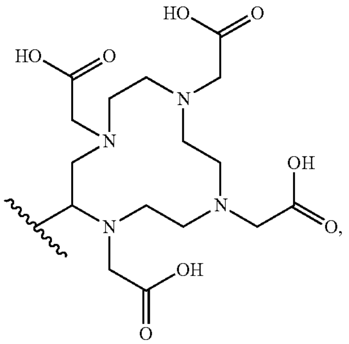

and (CM-5)

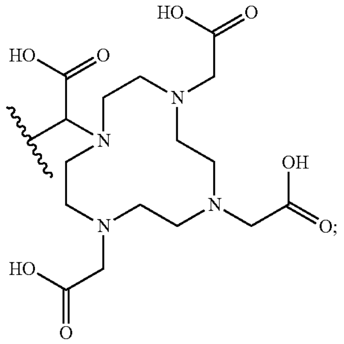

or a radionuclide complex thereof. In some embodiments, $R^A$ and $R^B$, if present, are (CM-6)

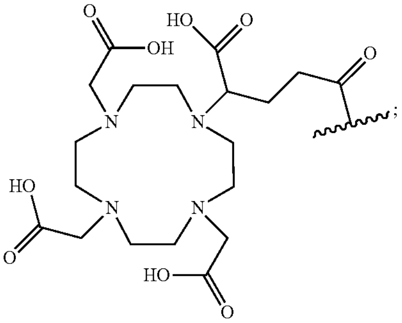

In some embodiments, $R^A$ is CM-1; or a radionuclide complex thereof. In some embodiments, $R^A$ is CM-2, CM-4, or CM-5; or a radionuclide complex thereof. In some embodiments, $R^A$ is CM-2; or a radionuclide complex thereof. In some embodiments, $R^A$ is CM-4; or a radionuclide complex thereof. In some embodiments, $R^A$ is CM-5; or a radionuclide complex thereof.

In some embodiments, $R^B$ is CM-1; or a radionuclide complex thereof. In some embodiments, $R^B$ is CM-2, CM-4, or CM-5; or a radionuclide complex thereof. In some embodiments, $R^B$ is CM-2; or a radionuclide complex thereof. In some embodiments, $R^B$ is CM-4; or a radionuclide complex thereof. In some embodiments, $R^B$ is CM-5; or a radionuclide complex thereof.

Radionuclide Complexes

Radiopharmaceuticals have increasingly become particularly useful tools for physicians to diagnose, stage, treat, and monitor the progression of several diseases, especially cancer. The primary difference between radiopharmaceuticals and other pharmaceutical drugs is that radiopharmaceuticals contain a radionuclide. The nuclear decay properties of the radionuclide determine whether a radiopharmaceutical will be used clinically as a diagnostic agent or as a therapeutic agent. Diagnostic radiopharmaceuticals require radionuclides that emit either gamma (γ) rays or positrons (β+), which subsequently annihilate with nearby electrons to produce two 511 keV annihilation photons emitted approximately 180° away from each other. Gamma ray-emitting radionuclides (e. g. $^{99m}$Tc, $^{111}$In, $^{201}$Tl, etc.) are useful for single photon emission computed tomography (SPECT), while positron-emitting radionuclides (e. g. $^{18}$F, $^{89}$Zr, $^{68}$Ga, etc.) are useful for positron emission tomography (PET).

In contrast, therapeutic radiopharmaceuticals require radionuclides that emit particulate radiation, such as alpha (α) particles, beta (β—) particles, or Auger electrons. These particles, which strongly interact with target tissues (e. g. cancerous tumor) and lead to extensive localized ionization, can damage chemical bonds in DNA molecules and potentially induce cytotoxicity.

For most nuclear medicine applications, it is desired that a diagnostic radiopharmaceutical is paired with a therapeutic radiopharmaceutical. This concept is commonly known as "theranostics". As a first step in the theranostic concept, a target molecule labeled with a diagnostic radionuclide is used for quantitative imaging of a tumor imaging biomarker, either by positron emission tomography (PET) or single photon emission computed tomography (SPECT). Then it is demonstrated that, with this targeted molecule, a tumoricidal radiation absorbed dose can be delivered to tumor and metastases, as a second step, via administration of the same or a similar target molecule labeled with a therapeutic radionuclide.

In some embodiments, the chemical and pharmacokinetic behaviors of both the diagnostic and therapeutic radiopharmaceuticals match. In some embodiments, the diagnostic and therapeutic radionuclides are a chemically identical radioisotope pair (also known as a "matched pair"). One example of a matched pair for theranostic radiopharmaceutical applications is the $^{123}$I/$^{131}$I pair, where $^{123}$I-labeled compounds are used for diagnosis, while $^{131}$I-labeled compounds are used for therapy. Other theranostic matched pairs include $^{44}$Sc/$^{47}$Sc, $^{64}$Cu/$^{67}$Cu, $^{72}$As/$^{77}$As, $^{86}$Y/$^{90}$Y, and $^{203}$Pb/$^{212}$Pb, among others. Alternatively, radionuclide pairs from different elements can be utilized for theranostic radiopharmaceutical development when their chemistry is very similar (e. g. $^{99m}$Tc/$^{186/188}$Re) and there is no significant difference in the pharmacokinetic behavior between the diagnostic and therapeutic analogues. Another example is the $^{68}$Ga/$^{177}$Lu pair, where $^{68}$Ga is used for diagnosis and $^{177}$Lu is used for therapy. For example, gastroenteropancreatic endocrine tumors express high amounts of SST2 receptor that can be targeted with somatostatin receptor scintigraphy for diagnostic purposes with a $^{68}$Ga SST2 ligand conjugate ([$^{68}$Ga]Ga-DOTA-TATE (NETSPOT™) or [$^{68}$Ga]Ga-DOTA-TOC (DOTA-(D-Phel,Tyr3)-octreotide, SomaKit TOC®)), followed by treatment with a $^{177}$Lu SST2 ligand conjugate ([$^{177}$Lu]Lu-DOTA-TATE) for endoradiotherapy.

Chelating Moieties Used to Generate Metal (Radionuclide) Complexes

The compounds described herein comprise at least one $R^A$ or $R^B$ group, wherein $R^A$ or $R^B$ is a chelating moiety capable of chelating a radionuclide (Z'), or radionuclide complex thereof. In some embodiments, any suitable group or atom(s) of the chelator are used to connect, via an optional linker, to the NPY$^1$R targeting ligand.

In some embodiments, the chelator is capable of binding a radioactive atom. In some embodiments, the binding is direct, e.g., the chelator makes hydrogen bonds or electrostatic interactions with a radioactive atom. In some embodiments, the binding is indirect, e.g., the chelator binds to a molecule that comprises a radioactive atom. In some embodiments, the chelator is or comprises a macrocycle.

In some embodiments, the chelator comprises one or more amine groups. In some embodiments, the metal chelator comprises two or more amine groups. In some embodiments, the chelator comprises three or more amine groups. In some embodiments, the chelator comprises four or more amine groups. In some embodiments, the chelator includes 4 or more N atoms, 4 or more carboxylic acid groups, or a combination thereof. In some embodiments, the chelator does not comprise S. In some embodiments, the chelator comprises a ring. In some embodiments, the ring comprises an O and/or a N atom. In some embodiments, the chelator is a ring that includes 3 or more N atoms, 3 or more carboxylic acid groups, or a combination thereof. In some embodiments, the chelator is a polydentate ligand, bidentate ligand, or monodentate ligand. Polydentate ligands range in the number of atoms used to bond to a metal atom or ion. EDTA, a hexadentate ligand, is an example of a polydentate ligand that has six donor atoms with electron pairs that can be used to bond to a central metal atom or ion. Bidentate ligands have two donor atoms which allow them to bind to a central metal atom or ion at two points. Ethylenediamine (en) and the oxalate ion (ox) are examples of bidentate ligands.

In some embodiments, a chelator described herein comprises a cyclic chelating agent or an acyclic chelating agent. In some embodiments, a chelator described herein comprises a cyclic chelating agent. In some embodiments, a chelator described herein comprises an acyclic chelating agent.

In some embodiments, a chelator described herein comprises cyclen, DO2A, DO3A, HP-DO3A, DO3A-Nprop, DO3AP, $DO3AP^{PrA}$, $DO3AP^{Abn}$, $DO3AM^{nBu}$, BT-DO3A, DOTA, PSC, DOTAGA, $DOTA(GA)_2$, DOTAM, DOTA-4AMP, DOTMA, DOTP, CB-DO2A, DOTPA, DOTMP, DOTAMAP, TRITA, IP, cyclam, TETA, CB-Cyclam, CB-TE2A, TE2A, NOTA, NODAGA, NODA-MPAA, TACN, TACN-TM, NOTP, Sarcophagine (Sar), DiAmSar, SarAr, AmBaSar, cis-DO2A2P, trans-DO2A2P, DOTEP, p-NO2-Bn-DOTA, BAT, DO3TMP-Monoamide, CHX-A"-DTPA, c-DEPA, PCTA, p-NO2-Bn-PCTA, TRAP, TRAPH, TRAP-OH, TRAP-Ph, NOPO, AAZTA, DATAM, HEHA, PEPA, DTA, EDTMP, DTPMP, NTA, EDTA, DTPA, CyDTPA, DFO, DFO*, deferiprone, TTHA, HBED, HBED-CC, HBED-CC TFP, $H_4$pypa, $H_4$py4pa, CP256, THP, YM103, t-Bu-calix[4]arene-tetracarboxylic acid, CHX-A"-DTPA, $H_6$phospha, p-$NH_2$-Bn-CHXA"-DTPA, DEDPA, $H_4$octox, $H_4$octapa, $H_4$CHXoctapa, HYNIC, macropa, crown, macropid, HOPO, Bis(2-mercaptoacetamide), Bis (aminothiolate), or SBTG2DAP.

In some embodiments, a chelator described herein comprises DOTA, DOTAGA, $DOTA(GA)_2$, NOTA, NODAGA, TRITA, TETA, DOTA-MA, HP-DO3A, DOTMA, DOTA-pNB, DOTP, DOTMP, DOTEP, DOTMPE, F-DOTPME, DOTPP, DOTBzP, DOTA-monoamide, BAT, DO3TMP-Monoamide, or CHX-A"-DTPA.

In some embodiments, a chelator described herein comprises DTA, CyEDTA, EDTMP, DTPMP, DTPA, CyDTPA, Cy2DTPA, DTPA-MA, DTPA-BA, or BOPA.

In some embodiments, a chelator described herein comprises DOTA, PSC, DOTAGA, $DOTA(GA)_2$, DOTP, DOTMA, DOTAM, DTPA, NTA, EDTA, DO3A, DO2A, NOC, NOTA, TETA, TACN, DiAmSar, CB-Cyclam, CB-TE2A, DOTA-4AMP, or NOTP.

In some embodiments, a chelator described herein comprises DOTA, DOTAGA, $DOTA(GA)_2$, DOTP, DOTMA, DOTAM, DTPA, NTA, EDTA, DO3A, DO2A, NOC, NOTA, TETA, TACN, DiAmSar, CB-Cyclam, CB-TE2A, DOTA-4AMP, or NOTP.

In some embodiments, a chelator described herein comprises HP-DO3A, BT-DO3A, DO3A-Nprop, DO3AP, DO2A2P, DOA3P, DOTP, DOTPMB, DOTAMAE, DOTAMAP, $DO3AM^{Bu}$, DOTMA, TCE-DOTA, DEPA, PCTA, p-$NO_2$-Bn-PCTA, p-$NO_2$-Bn-DOTA, symPC2APA, symPCA2PA, asymPC2APA, asymPCA2PA, TRAP, AAZTA, $DATA^m$, THP, HEHA, HBED, or HBED-CC TFP.

In some embodiments, a chelator described herein comprises DOTA, NOTA, NODAGA, DOTAGA, HBED, HBED-CC TFP, H2DEPDPA, DFO-B, Deferiprone, CP256, YM103, TETA, CB-TE2A, TE2A, Sar, DiAmSar, TRAPH, TRAP-Pr, TRAP-OH, TRAP-Ph, NOPO, DEADPA, PCTA, EDTA, PEPA, HEHA, DTPA, EDTMP, AAZTA, DO3AP, $DO3AP^{PrA}$, $DO3AP^{Abn}$, or DOTAM.

In some embodiments, the chelator is or comprises DOTA, HBED-CC, DOTAGA, $DOTA(GA)_2$, NOTA, and/or DOTAM. In some embodiments, the chelator is or comprises NODAGA, NOTA, DOTAGA, $DOTA(GA)_2$, TRAP, NOPO, NCTA, DFO, DTPA, and/or HYNIC.

In some embodiments, the chelator comprises a macrocycle, e.g., a macrocycle comprising an O and/or a N atom, DOTA, HBED-CC, DOTAGA, $DOTA(GA)_2$, NOTA, DOTAM, one or more amines, one or more ethers, one or more carboxylic acids, EDTA, DTPA, TETA, DO3A, PCTA, and/or desferrioxamine.

In some embodiments, a metal chelator described herein comprises one of the following structures.

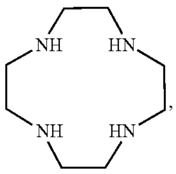
, (Cyclen)

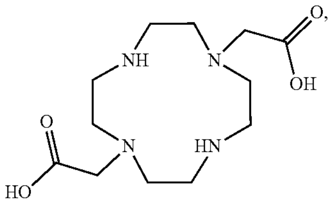
, (DO2A)

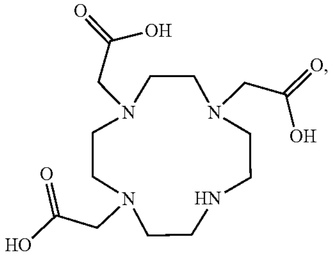

(DO3A)

-continued
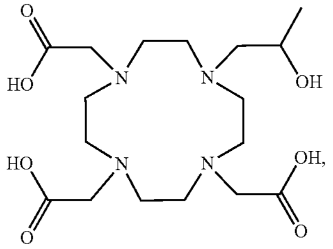
(HP-DO3A)
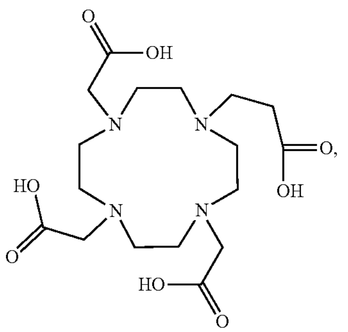
(DO3A-Nprop)
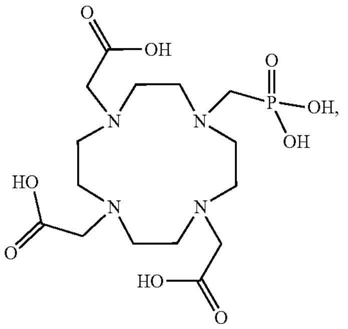
(DO3AP)
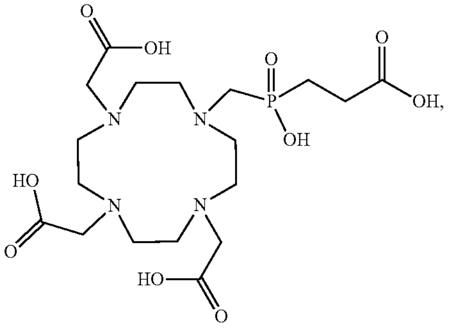
(DO3AP$^{PrA}$)
-continued
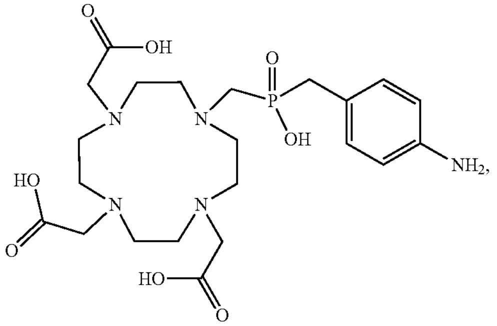
(DO3AP$^{Abn}$)
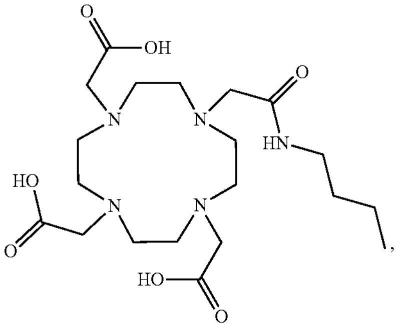
(DO3AM$^{nBu}$)
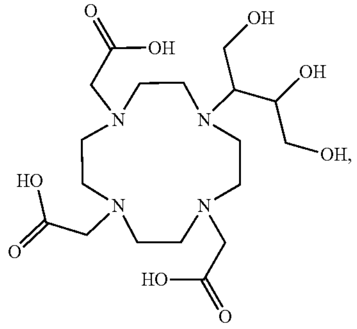
(BT-DO3A)
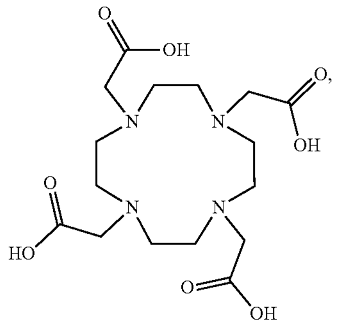
(DOTA)

-continued
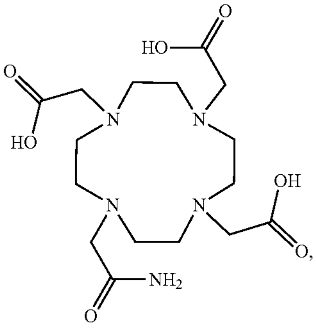
(PSC)
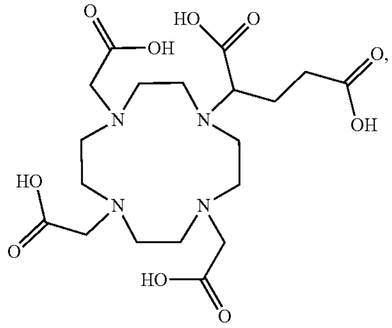
(DOTAGA)
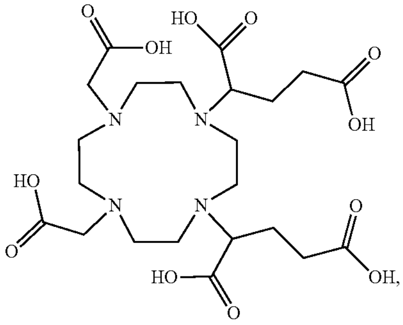
(DOTA(GA)$_2$)
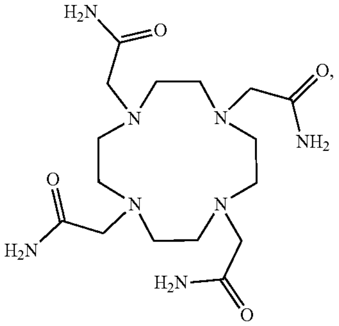
(DOTAM)
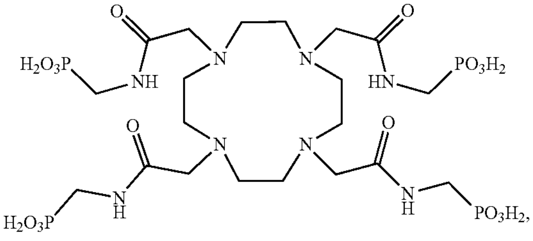
(DOTA-4AMP)
-continued
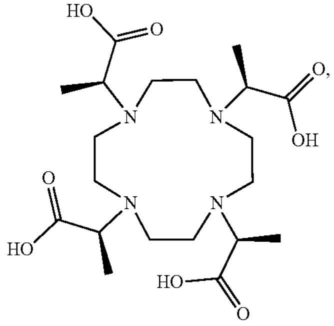
(DOTMA)
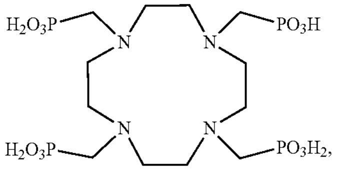
(DOTP)
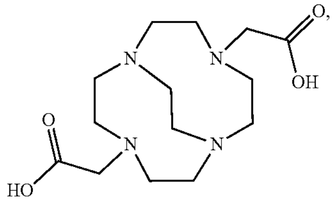
(CB-DO2A)
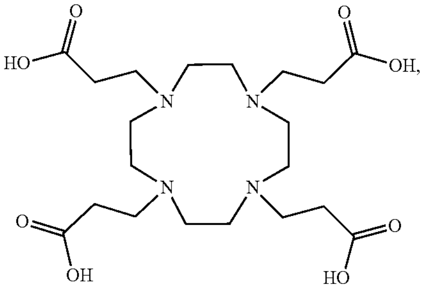
(DOTPA)
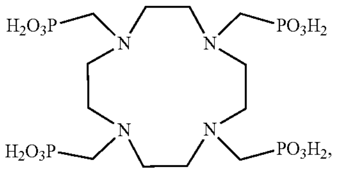
(DOTMP)
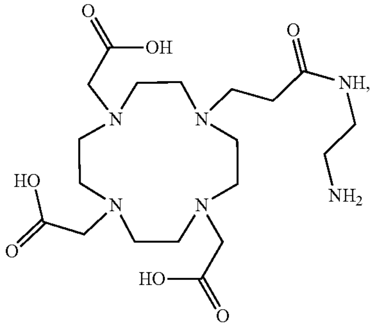
(DOTAMAP)

-continued
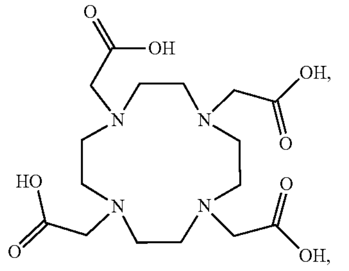
(TRITA)
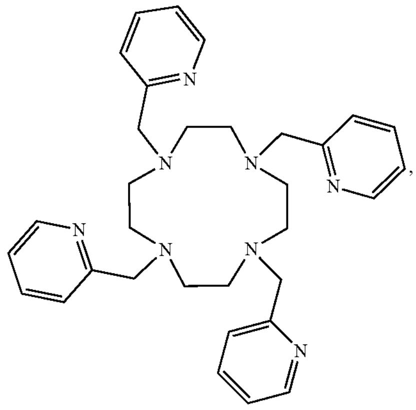
($L^{py}$)
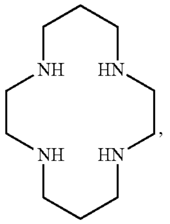
(cyclam)
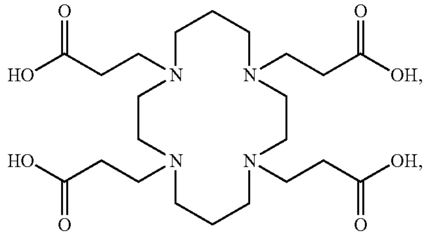
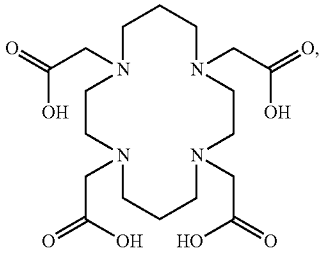
(TETA)
-continued
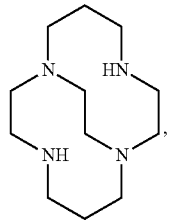
(CB-Cyclam)
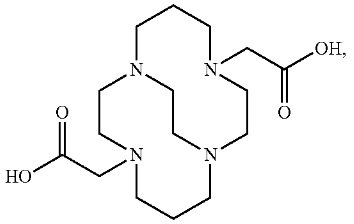
(CB-TE2A)
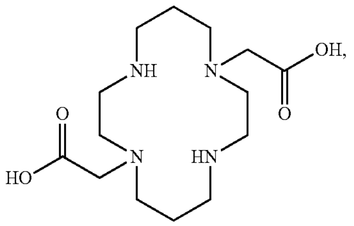
(TE2A)
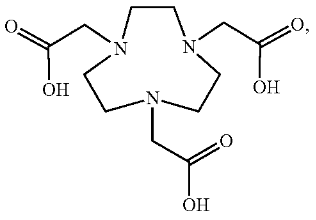
(NOTA)
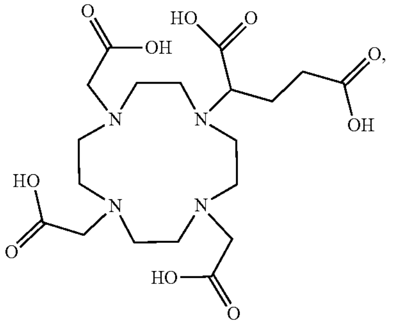
(NODAGA)
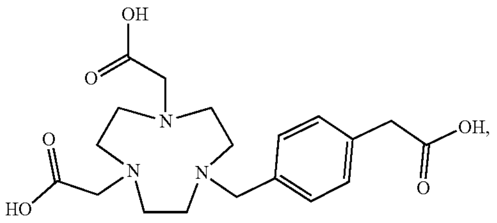
(NODA-MPAA)

-continued
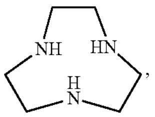
(TACN)
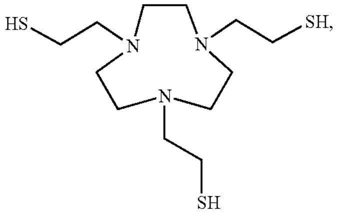
(TACN-TM)
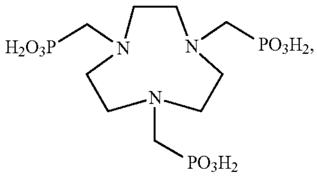
(NOTP)
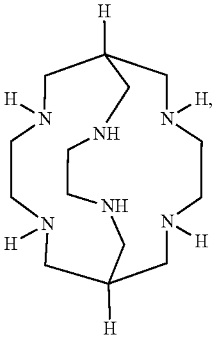
(Sar)
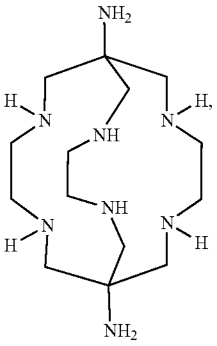
(DiAmSar)
-continued
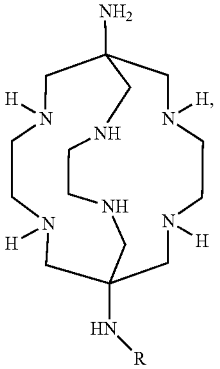
(SarAr, R = p-$NH_2$—Bn; AmBaSar, R = p-C(=O)OH—Bn)
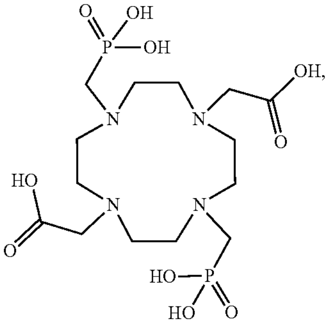
(cis-DO2A2P)
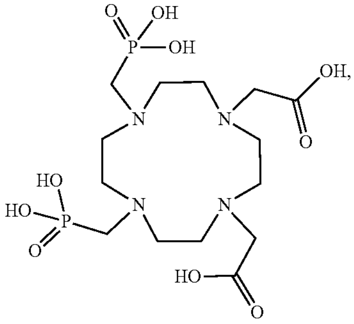
(trans-DO2A2P)
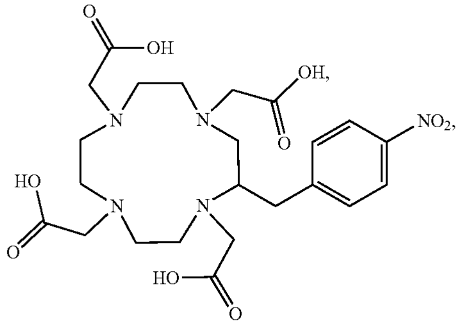
(p-$NO_2$—Bn-DOTA)

-continued
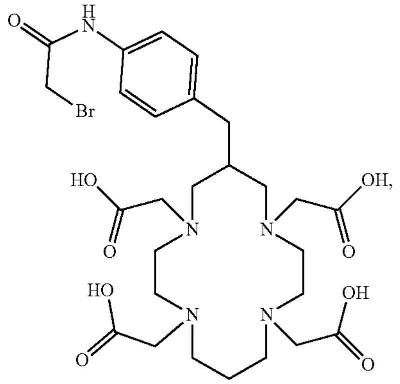
(BAT)
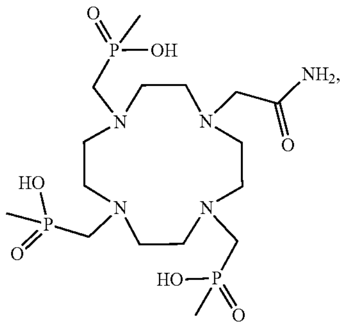
(DO3TMP-Monoamide)
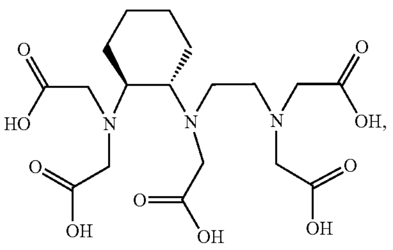
(CHX-A"-DTPA)
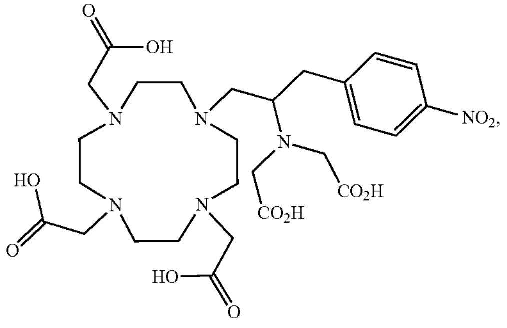
(c-DEPA)
-continued
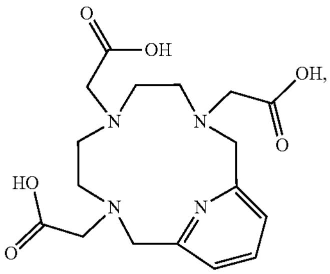
(PCTA)
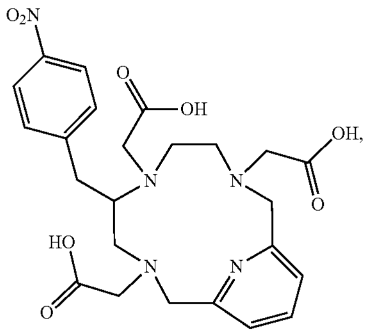
(p-$NO_2$—Bn-PCTA)
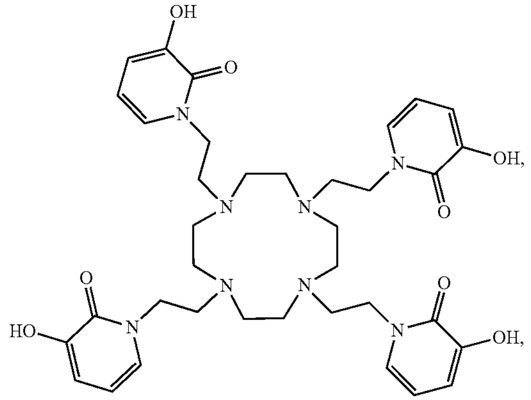
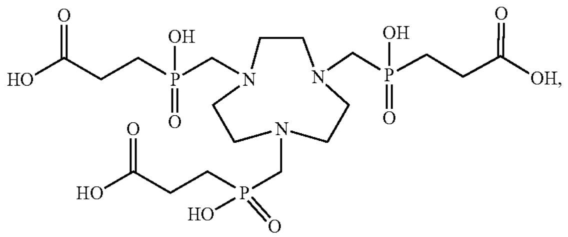
(TRAP)
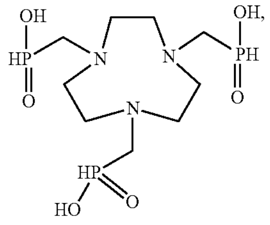
(TRAPH)

-continued
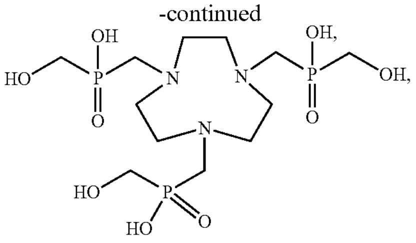
(TRAP-OH)
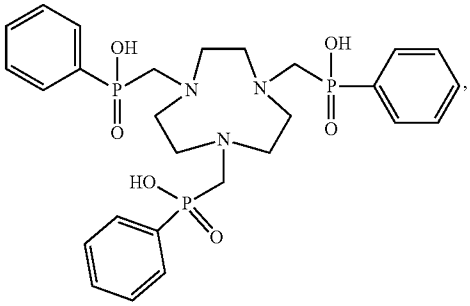
,
(TRAP-Ph)
-continued
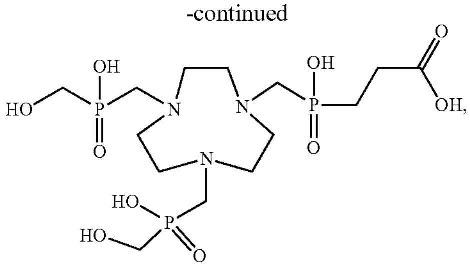
(NOPO)
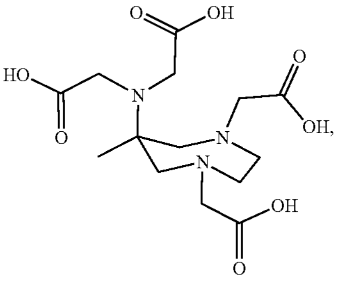
(AAZTA)
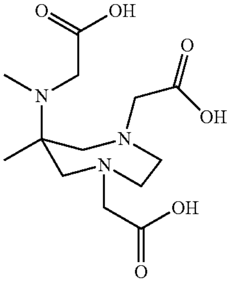
,
(DATAM)
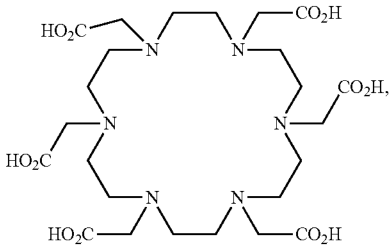
(HEHA)
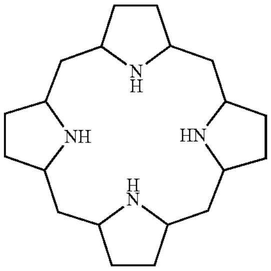
,
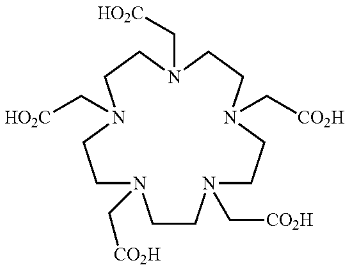
,
(PEPA)
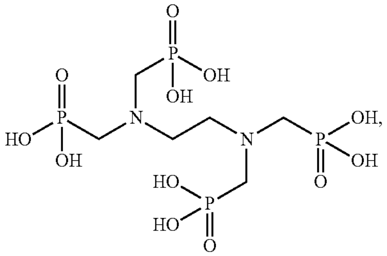
(EDTMP)
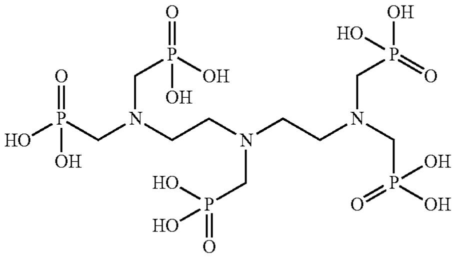
,
(DTPMP)
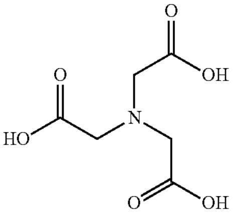
,
(NTA)
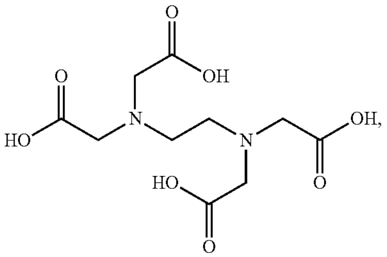
(EDTA)

-continued
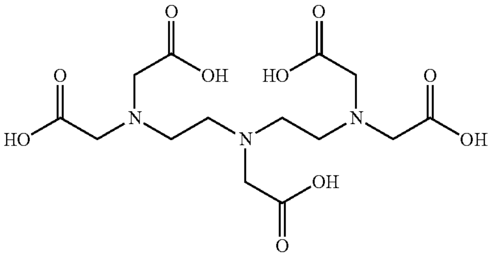
,
(DTPA)
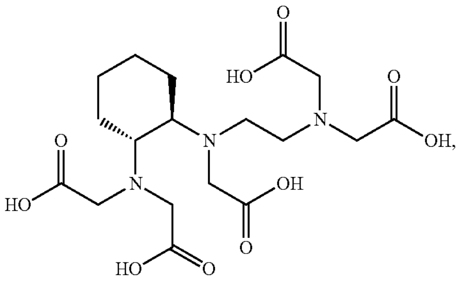
(CyDTPA)
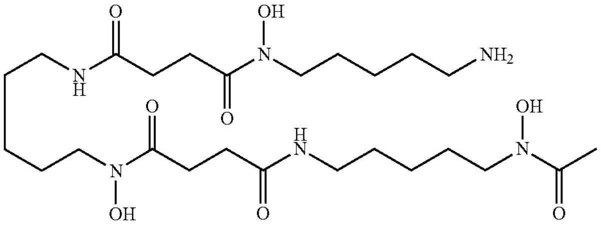
,
(DFO)
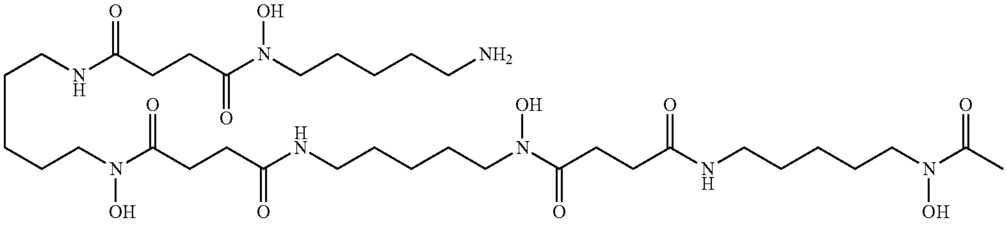
,
(DFO*)
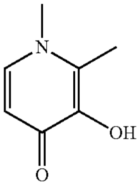
,
(deferiprone)
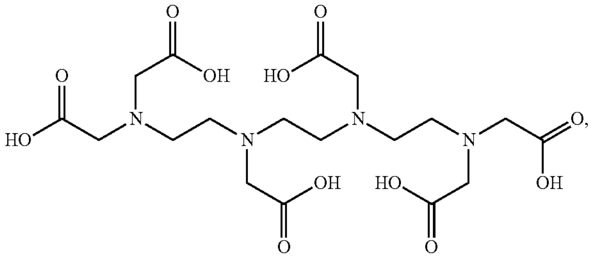
(TTHA)
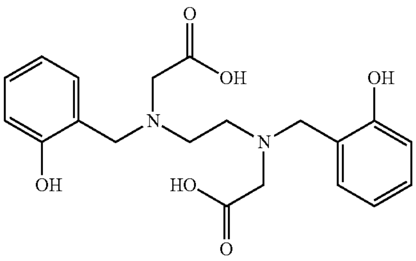
,
(HBED)
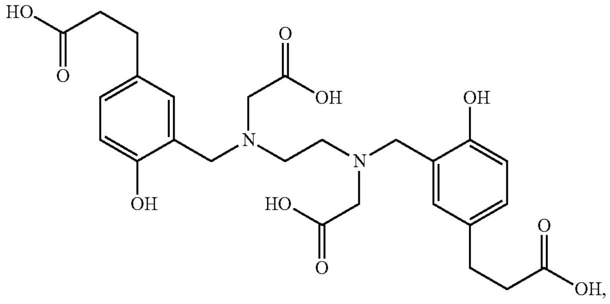
(HBED-CC)

-continued
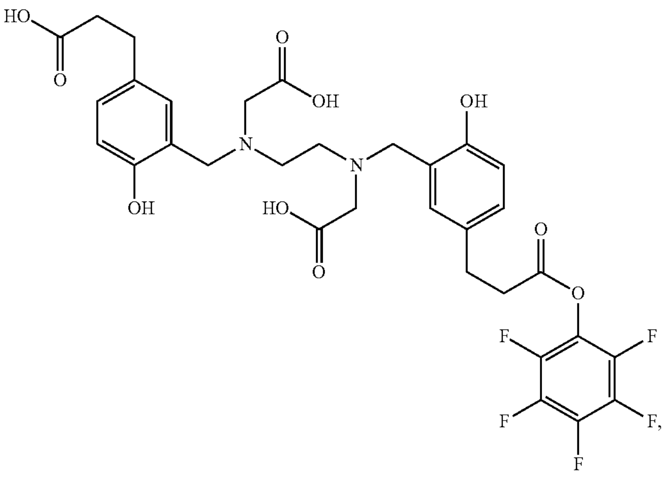
(HBED-CC-TFP)
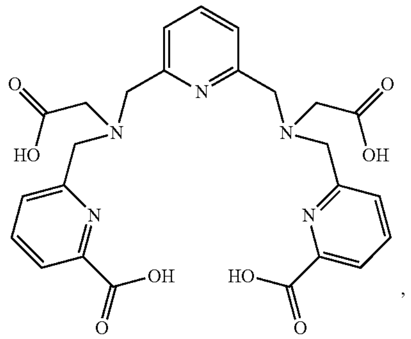
(H4pypa)
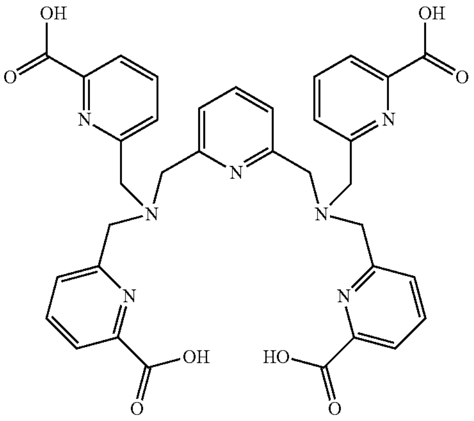
(H4py4pa)
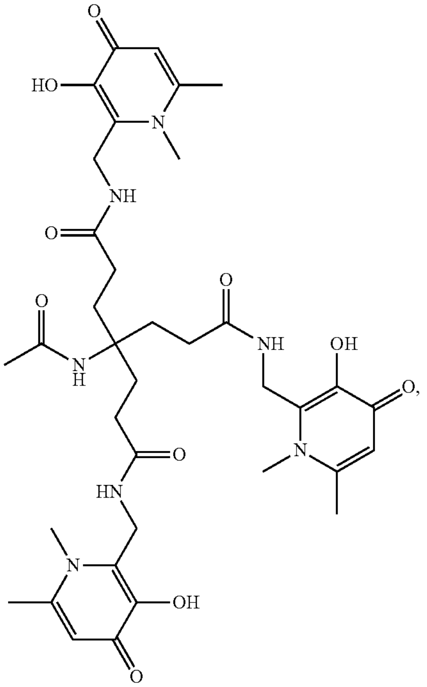
(CP256)

-continued
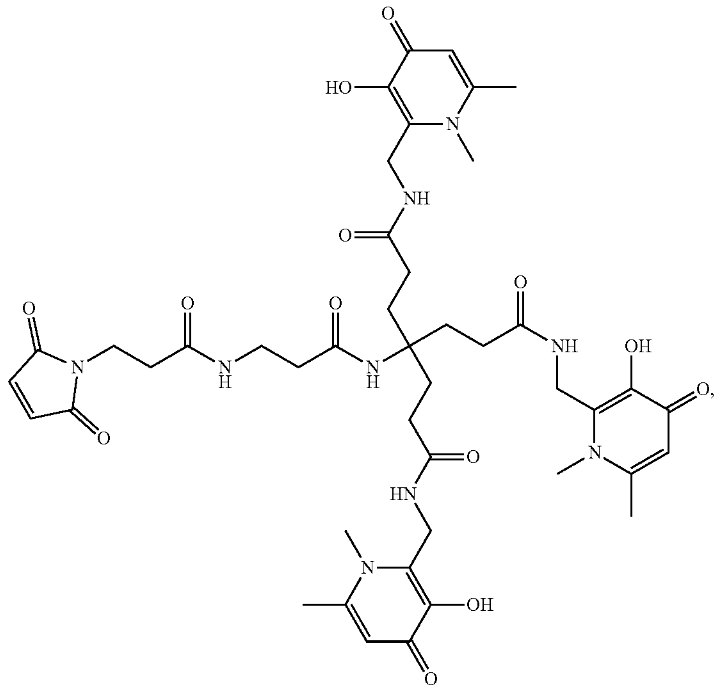
(YM103)
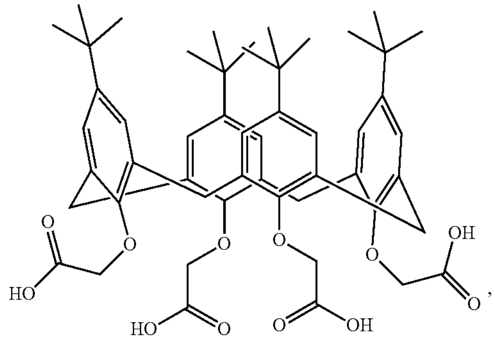
,
(t-Bu-calix[4]arene-tetracarboxylic acid)
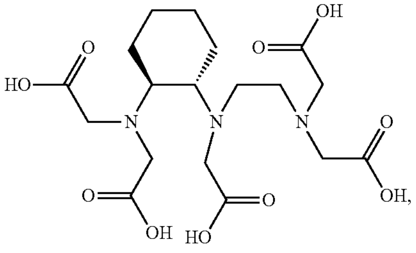
(CHX-A"-DTPA)
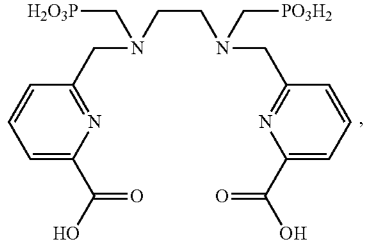
,
($H_6$phospha)
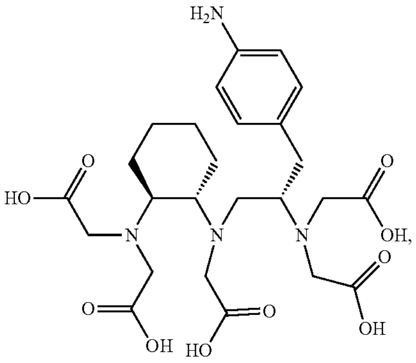
(p-$NH_2$-Bn-CHXA"-DTPA)

-continued
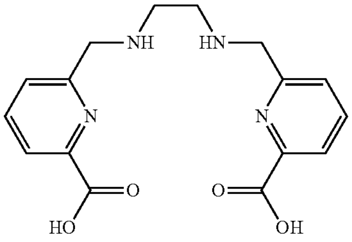
,
(DEDPA)
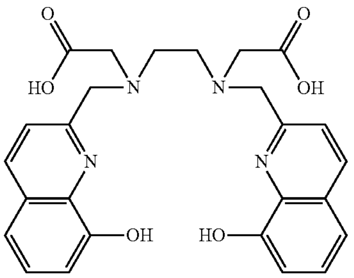
,
($H_4$octox)
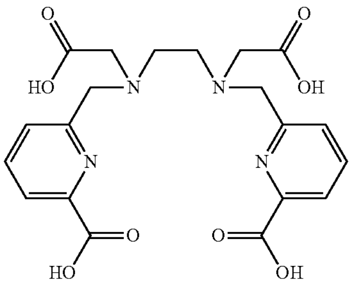
,
($H_4$octapa)
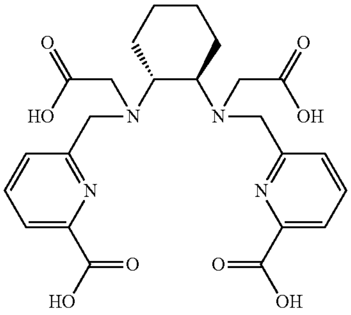
,
($H_4$CHXoctapa)
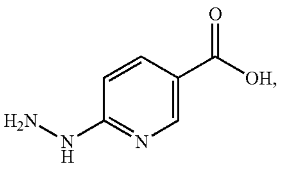
(HYNIC)
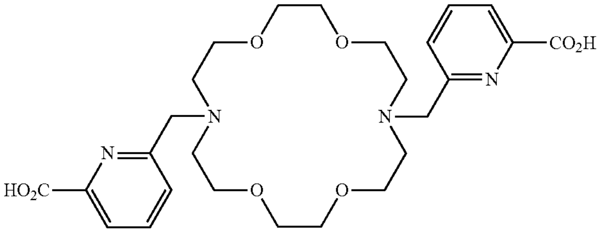
,
(macropa)
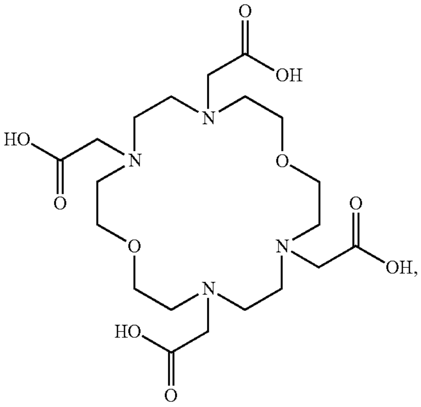
(crown)
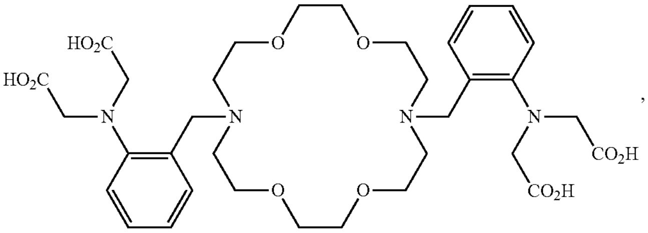
,
(macropid)

-continued

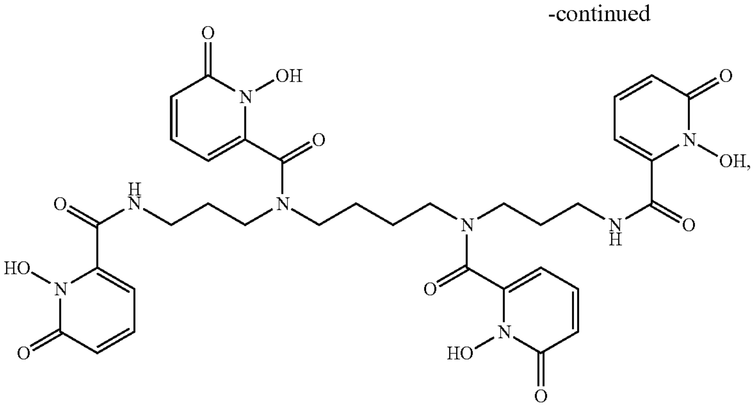

(HOPO)

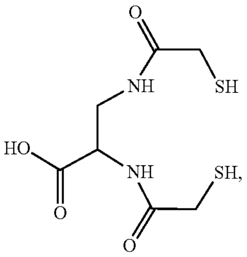

(Bis(2-mercaptoacetamide))

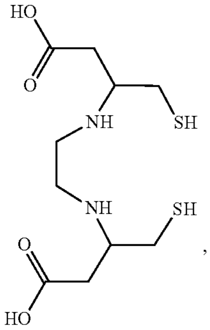

(Bis(aminothiolate))

, or

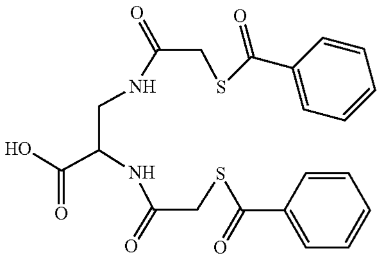

(SBTG$_2$DAP)

.

In some embodiments, $R^A$ and $R^B$, if present, each independently comprise a radionuclide and DOTA. In some embodiments, $R^A$ and $R^B$, if present, each independently comprise a radionuclide and a DOTA derivative. In some embodiments, $R^A$ and $R^B$, if present, are each independently chelators, and at least one or both are DOTA.

In some embodiments, $R^A$ and $R^B$, if present, each independently comprise a radionuclide and DOTAGA. In some embodiments, $R^A$ and $R^B$, if present, each independently comprise a radionuclide and a DOTAGA derivative. In some embodiments, $R^A$ and $R^B$, if present, are each independently chelators, and at least one or both are DOTAGA.

In some embodiments, the chelating moiety comprises a radionuclide and a chelator configured to bind the radionuclide (Z'), wherein the chelator comprises DOTA, DOTP, DOTMA, DOTAM, DTPA, NOTA, NTA, NODAGA, EDTA, DO3A, DO2A, NOC, TETA, CB-TE2A, DiAmSar, CB-Cyclam, DOTA-4AMP, $H_4$pypa, $H_4$octox, $H_4$octapa, p-$NO_2$-Bn-neunpa, or NOTP.

In some embodiments, the metal chelator described herein comprises macropa or crown. In some embodiments, the metal chelator described herein comprises macropa. In some embodiments, the metal chelator described herein comprises crown. In some embodiments, the metal chelator described herein comprises (macropa)

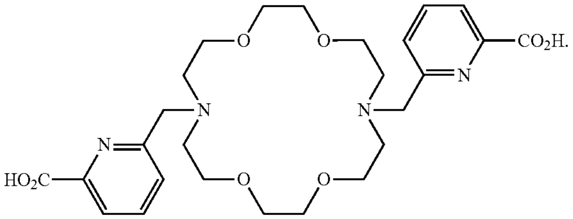

.

In some embodiments, the metal chelator described herein comprises (crown)

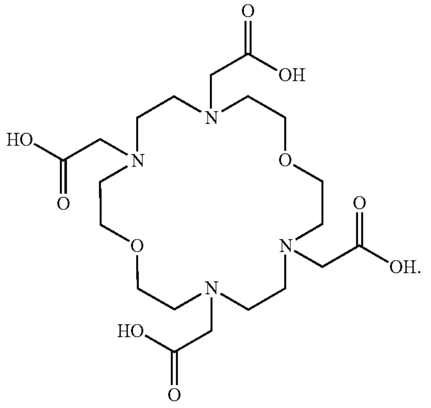

In some embodiments, $R^A$ and $R^B$, if present, are each independently selected from the group consisting of: 1,4,7,10-tetraazacyclododecane-1,4,7,10-tetraacetic acid (DOTA); 2,2',2"-(10-(2-amino-2-oxoethyl)-1,4,7,10-tetraazacyclododecane-1,4,7-triyl)triacetic acid (PSC); 1,4,7,10-tetraazacyclododecane-1,4,7-triacetic acid (DO3A); 1,4,7,10-tetraazacyclododecane-1,7-diacetic acid (DO2A); α,α',α",α'"-tetramethyl-1,4,7,10-tetraazacyclododecane-1,4,7,10-tetraacetic acid (DOTMA); 1,4,7,10-tetrakis(carbamoylmethyl)-1,4,7,10-tetraazacyclododecane (DOTAM); 1,4,7,10-tetraazacyclododecane-1,4,7,10-tetrapropionic acid (DOTPA); 2,2',2"-(10-(2-amino-2-oxoethyl)-1,4,7,10-tetraazacyclododecane-1,4,7-triyl)triacetic acid; benzyl-1,4,7,10-tetraazacyclododecane-1,4,7,10-tetraacetic acid (Bn-DOTA); p-hydroxy-benzyl-1,4,7,10-tetraazacyclododecane-1,4,7,10-tetraacetic acid (p-OH-Bn-DOTA); 6,6'-(((pyridine-2,6-diylbis(methylene))bis((carboxymethyl)azanediyl))bis(methylene))dipicolinic acid ($H_4$pypa); $H_4$pypa-benzyl; 6,6',6",6'"-(((pyridine-2,6-diylbis(methylene))bis(azanetriyl))-tetrakis(methylene))-tetrapicolinic acid ($H_4$py4pa); $H_4$py4pa-benzyl; 2,2',2"-(1,4,7-triazacyclononane-1,4,7-triyl)triacetic acid (NOTA); 6,6'-((1,4,10,13-tetraoxa-7,16-diazacyclooctadecane-7,16-diyl)bis(methylene))dipicolinic acid (macropa); 2,2',2",2'"-(1,10-dioxa-4,7,13,16-tetraazacyclooctadecane-4,7,13,16-tetrayl)tetraacetic acid (crown); 6,6'-((ethane-1,2-diylbis((carboxymethyl)azanediyl))bis(methylene))dipicolinic acid ($H_4$octapa); $H_4$octapa-benzyl; and 3,6,9,12-tetrakis(carboxymethyl)-3,6,9,12-tetraazatetradecanedioic acid (TTHA); or a radionuclide complex thereof.

In some embodiments, $R^A$ and $R^B$, if present, are each independently selected from the group consisting of: DOTA and DO3A; or a radionuclide complex thereof.

In some embodiments, $R^A$ and $R^B$, if present, are each independently selected from the group consisting of:

(CM-1)

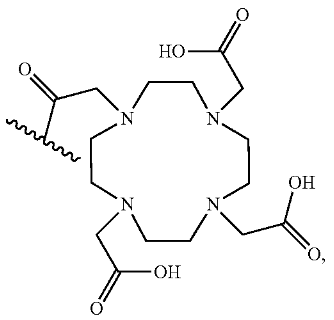

-continued (CM-2)

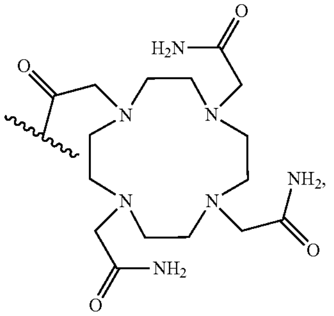

(CM-3)

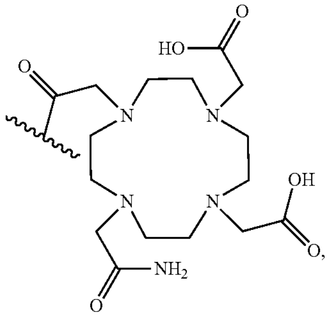

(CM-4)

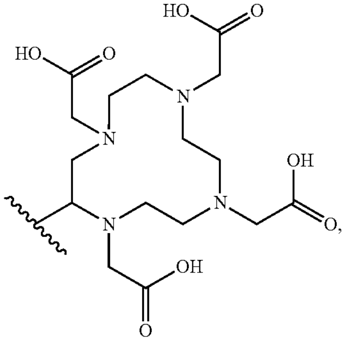

and (CM-5)

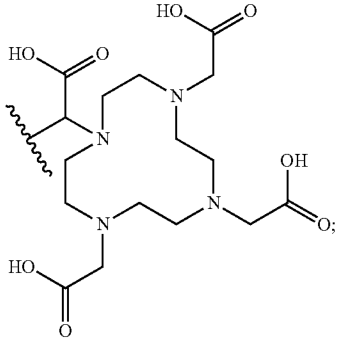

or a radionuclide complex thereof.

In some embodiments, $R^A$ and $R^B$, if present, are each independently selected from the group consisting of: CM-1, CM-2, CM-4, and CM-5; or a radionuclide complex thereof.

In some embodiments, $R^A$ or $R^B$ is: CM-1; or a radionuclide complex thereof.

In some embodiments, $R^A$ or $R^B$ is: CM-2, CM-3, CM-4, or CM-5; or a radionuclide complex thereof.

In some embodiments, $R^A$ or $R^B$ is: CM-2; or a radionuclide complex thereof. In some embodiments, $R^A$ or $R^B$ is: CM-3; or a radionuclide complex thereof. In some embodiments, $R^A$ or $R^B$ is: CM-5; or a radionuclide complex thereof. In some embodiments, $R^A$ or $R^B$ is: CM-4; or a radionuclide complex thereof.

In some embodiments, $R^A$ or $R^B$ is: (CM-6); or a radionuclide complex thereof.

In some embodiments, $R^A$ or $R^B$ is:

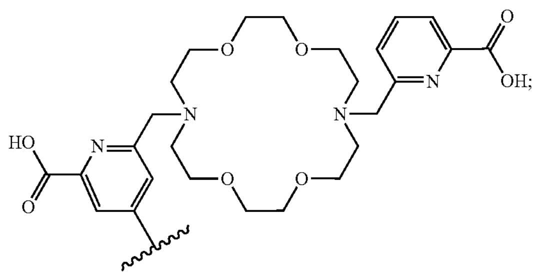 [SMILES: *c1cc(CN2CCOCCOCCN(Cc3cccc(C(=O)O)n3)CCOCCOCC2)nc(C(=O)O)c1]

or a radionuclide complex thereof. In some embodiments, $R^A$ or $R^B$ is:

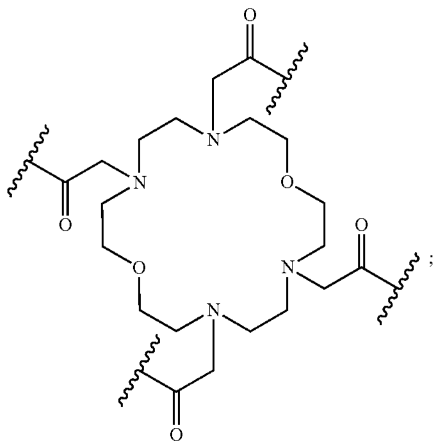 [SMILES: *C(=O)CN1CCOCCN(CC(*)=O)CCN(CC(*)=O)CCOCCN(CC(*)=O)CC1]

or a radionuclide complex thereof.

In some embodiments, $R^A$ or $R^B$ is:

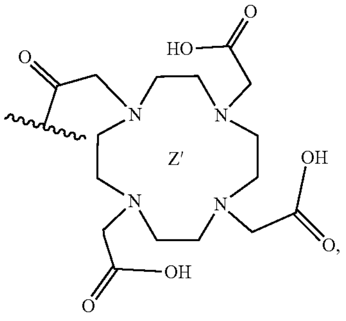

-continued

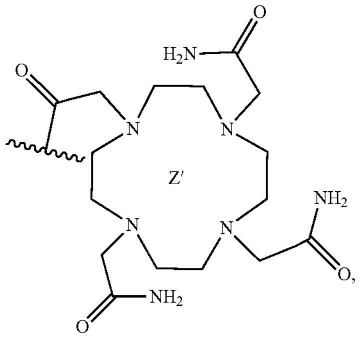

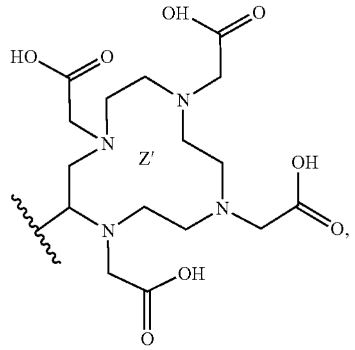

or

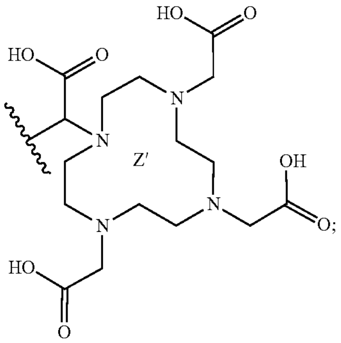

wherein Z' is a diagnostic or therapeutic radionuclide.

In some embodiments, $R^A$ or $R^B$ is:

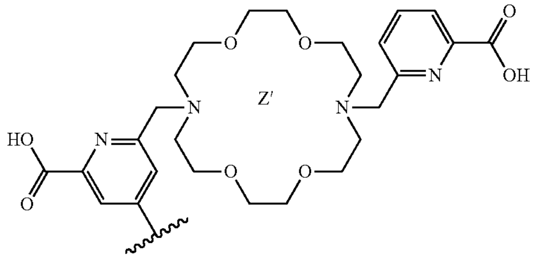

or

-continued

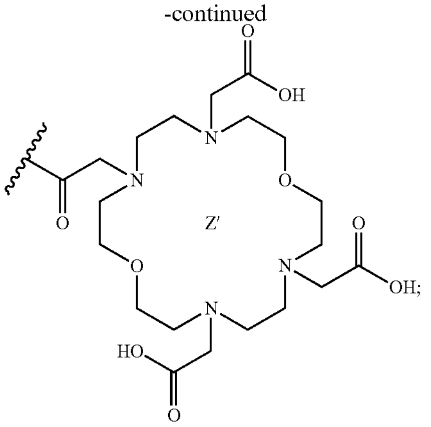

wherein Z' is a diagnostic or therapeutic radionuclide.

In some embodiments, Z' is an Auger electron-emitting radionuclide, α-emitting radionuclide, β-emitting radionuclide, or γ-emitting radionuclide. In some embodiments, Z' is an Auger electron-emitting radionuclide that is 111-indium ($^{111}$In), 67-gallium ($^{67}$Ga), 68-gallium ($^{68}$Ga), 99m-technetium ($^{99m}$Tc), or 195m-platinum ($^{195m}$Pt). In some embodiments, Z' is an α-emitting radionuclide that is 225-actinium ($^{225}$Ac), 213-bismuth ($^{213}$Bi), 223-Radium ($^{223}$Ra), or 212-lead ($^{212}$Pb). In some embodiments, Z' is a β-emitting radionuclide that is 90-yttrium ($^{90}$Y) 177-lutetium ($^{177}$Lu), iodine-131 ($^{131}$I), 186-rhenium ($^{186}$Re), 188-rhenium ($^{188}$Re), 64-copper ($^{64}$Cu), 67-copper ($^{67}$Cu), 153-samarium ($^{153}$Sm), 89-strontium ($^{89}$Sr), 198-gold ($^{198}$Au), 169-Erbium ($^{169}$Er), 165-dysprosium ($^{165}$Dy), 99m-technetium ($^{99m}$Tc), 89-zirconium ($^{89}$Zr), or 52-manganese ($^{52}$Mn). In some embodiments, Z' is a γ-emitting radionuclide that is 60-cobalt ($^{60}$Co), 103-palldium ($^{103}$Pd), 137-cesium ($^{137}$Cs), 169-ytterbium ($^{169}$Yb) 192-iridium ($^{192}$Ir), or 226-radium ($^{226}$Ra).

In some embodiments, $R^6$ comprises a radionuclide (Z') and a chelator configured to bind the radionuclide (Z'), wherein the radionuclide is suitable for positron emission tomography (PET) analysis, single-photon emission computerized tomography (SPECT), or magnetic resonance imaging (MRI). In some embodiments, the radionuclide is copper-64 ($^{64}$Cu), gallium-68 ($^{68}$Ga), 111-indium ($^{111}$In), or technetium-99m ($^{99m}$Tc).

Metals (Radionuclides)

In some embodiments, Z' is an Auger electron-emitting radionuclide. In some embodiments, Z' is an α-emitting radionuclide. In some embodiments, Z' is a β-emitting radionuclide. In some embodiments, Z' is a γ-emitting radionuclide. In some embodiments, the type of radionuclide used in a non-peptide targeted therapeutic compound can be tailored to the specific type of cancer, the type of targeting moiety (e.g., non-peptide ligand), etc. Radionuclides that undergo α-decay emit α-particles (helium ions with a +2 charge) from their nuclei. As a result of α-decay the daughter nuclide has 2 protons less and 2 neutrons less than the parent nuclide. This means that in α-decay, the proton number is reduced by 2 while the nucleon number is reduced by 4. Radionuclides that undergo β-decay emit β-particles (electrons) from their nuclei. During β-decay, one of the neutrons changes into a proton and an electron. The proton remains in the nucleus while the electron is emitted as a β-particle. This means that in (3-decay, the nucleus loses a neutron but gains a proton. In γ-decay, a nucleus in an excited state (higher energy state) emits a γ-ray photon to change to a lower energy state. There is no change in the proton number and nucleon number during the γ-decay. The emission of γ-rays often accompanies the emission of α-particles and β-particles.

Auger electrons (Aes) are very low energy electrons that are emitted by radionuclides that decay by electron capture (EC) (e.g. $^{111}$In, $^{67}$Ga, $^{99m}$Tc, $^{195m}$Pt, $^{125}$I and $^{123}$I). This energy is deposited over nanometer-micrometer distances, resulting in high linear energy transfer that is potent for causing lethal damage in cancer cells. Thus, AE-emitting radiotherapeutic agents have great potential for treatment of cancer.

β-Particles are electrons emitted from the nucleus. They typically have a longer range in tissue (on the order of 1-5 mm) and are the most frequently used.

α-Particles are helium nuclei (two protons and two neutrons) that are emitted from the nucleus of a radioactive atom. Depending on their emission energy, they can travel 50-100 μm in tissue. They are positively charged and are orders of magnitude larger than electrons. The amount of energy deposited per path length travelled (designated 'linear energy transfer') of α-particles is approximately 400 times greater than that of electrons. This leads to substantially more damage along their path than that caused by electrons. An α-particle track leads to a preponderance of complex and largely irreparable DNA double-strand breaks. The absorbed dose required to achieve cytotoxicity relates to the number of α-particles traversing the cell nucleus. With use of this as a measure, cytotoxicity may be achieved with a range of 1 to 20 α-particle traversals of the cell nucleus. The resulting high potency, combined with the short range of α-particles (which reduces normal organ toxicity), has led to substantial interest in developing α-particle-emitting agents. The α-particle emitters typically used include bismuth-212, lead-212, bismuth-213, actinium-225, radium-223 and thorium-227.

In some embodiments, Z' is a diagnostic or therapeutic radionuclide.

Representative Radionuclides

| Isotope | Radionuclide $t_{1/2}$ (h) | Decay mode |
|---|---|---|
| $^{60}$Cu | 0.4 | β+ (93%), EC (7%) |
| $^{61}$Cu | 3.3 | β+ (62%), EC (38%) |
| $^{62}$Cu | 0.16 | β+ (98%), EC (2%) |
| $^{64}$Cu | 12.7 | β+ (19%), EC (41%), β− (40%) |
| $^{67}$Cu | 61.9 | β− (100%) |
| $^{66}$Ga | 9.5 | β+ (56%), EC (44%) |
| $^{67}$Ga | 78.2 | EC (100%) |
| $^{68}$Ga | 1.1 | β+ (90%), EC (10%) |
| $^{44}$Sc | 3.9 | β+ (94%), EC (6%) |
| $^{47}$Sc | 80.2 | β− (100%) |
| $^{111}$In | 67.2 | EC (100%) |
| $^{114m}$In | 49.5 d | EC (100%) |
| $^{114}$In (daughter) | 73 s | β− (100%) |
| $^{177}$Lu | 159.4 | β− (100%) |
| $^{86}$Y | 14.7 | β+ (33%), EC (66%) |
| $^{90}$Y | 64.1 | β− (100%) |
| $^{89}$Zr | 78.5 | β+ (23%), EC (77%) |
| $^{212}$Bi | 1.1 | α (36%), β− (64%) |
| $^{213}$Bi | 0.76 | α (2.2%), β− (97.8%) |
| $^{212}$Pb (daughter is $^{212}$Bi) | 10.6 | β− (100%) |
| $^{225}$Ac | 240 | α (100%) |
| $^{227}$Th | 448.8 | α |
| $^{211}$At | 7.2 | α |

In some embodiments, Z' is an Auger electron-emitting radionuclide. In some embodiments, Z' is an Auger electron-emitting radionuclide that is 111-indium ($^{111}$In), 67-gallium ($^{67}$Ga), 68-gallium ($^{68}$Ga), 99m-technetium ($^{99m}$Tc), or 195m-platinum ($^{195m}$pt).

In some embodiments, Z' is an α-emitting radionuclide. In some embodiments, Z' is an α-emitting radionuclide that is 225-actinium ($^{225}$Ac), 213-bismuth ($^{213}$Bi), 223-Radium ($^{223}$Ra), or 212-lead ($^{212}$Pb).

In some embodiments, Z' is an β-emitting radionuclide. In some embodiments, Z' is a β-emitting radionuclide that is 90-yttrium ($^{90}$Y), 177-lutetium ($^{177}$Lu), 186-rhenium ($^{186}$Re), 188-rhenium ($^{188}$Re), 64-copper ($^{64}$Cu), 67-copper ($^{67}$Cu), 153-samarium ($^{153}$Sm), 89-strontium ($^{89}$Sr), 198-gold ($^{198}$Au), 169-Erbium ($^{169}$Er), 165-dysprosium ($^{165}$Dy), 99m-technetium ($^{99m}$Tc), 89-zirconium ($^{89}$Zr), or 52-manganese ($^{52}$Mn).

In some embodiments, Z' is a γ-emitting radionuclide. In some embodiments, Z' is a γ-emitting radionuclide that is 60-cobalt ($^{60}$Co), 103-palldium ($^{103}$Pd), 137-cesium ($^{137}$Cs), 169-ytterbium ($^{169}$Yb) 192-iridium ($^{192}$Ir), or 226-radium ($^{226}$Ra).

In some embodiments, Z' is an Auger electron-emitting radionuclide that is 111-indium ($^{111}$In), 67-gallium ($^{67}$Ga), 68-gallium ($^{68}$Ga), 99m-technetium ($^{99m}$Tc), or 195m-platinum ($^{195m}$Pt); or Z' is an α-emitting radionuclide that is 225-actinium ($^{225}$Ac), 213-bismuth ($^{213}$Bi), 223-Radium ($^{223}$Ra), or 212-lead ($^{212}$Pb); or Z' is a β-emitting radionuclide that is 90-yttrium ($^{90}$Y), 177-lutetium ($^{177}$Lu), 186-rhenium ($^{186}$Re), 188-rhenium ($^{188}$Re), 64-copper ($^{64}$Cu), 67-copper ($^{67}$Cu), 153-samarium ($^{153}$Sm), 89-strontium ($^{89}$Sr), 198-gold ($^{198}$Au), 169-Erbium ($^{169}$Er), 165-dysprosium ($^{165}$Dy), 99m-technetium ($^{99m}$Tc), 89-zirconium ($^{89}$Zr), or 52-manganese ($^{52}$Mn); or Z' is a 7-emitting radionuclide that is 60-cobalt ($^{60}$Co), 103-palldium ($^{103}$Pd), 137-cesium ($^{137}$Cs), 169-ytterbium ($^{169}$Yb) 192-iridium ($^{192}$Ir), or 226-radium ($^{226}$Ra).

In some embodiments, Z' is 90-yttrium ($^{90}$Y), 177-lutetium ($^{177}$Lu), 186-rhenium ($^{186}$Re), 188-rhenium ($^{188}$Re), 67-copper ($^{67}$Cu), 153-samarium ($^{153}$Sm), 89-strontium ($^{89}$Sr), 198-gold ($^{198}$Au), 169-Erbium ($^{169}$Er), 165-dysprosium ($^{165}$Dy), or technetium-99m ($^{99m}$Tc).

In some embodiments, Z' is $^{94}$Tc, $^{90}$n $^{11}$In, $^{67}$Ga, $^{68}$Ga, $^{86}$Y, $^{90}$Y, $^{177}$Lu, $^{161}$Tb, $^{186}$Re, $^{188}$Re, $^{64}$Cu, $^{67}$Cu, $^{55}$Co, $^{57}$Co, $^{43}$Sc, $^{44}$Sc, $^{47}$Sc, $^{225}$Ac, $^{213}$Bi, $^{212}$Bi, $^{212}$Pb, 227Th $^{153}$Sm, $^{166}$Ho, $^{152}$Gd, $^{153}$Gd, $^{157}$Gd, or $^{166}$Dy.

In some embodiments, Z' is $^{67}$Cu, $^{64}$Cu, $^{90}$Y $^{109}$Pd, $^{111}$Ag, $^{149}$Pm, $^{153}$Sm, $^{166}$Ho, $^{99m}$Tc, $^{67}$Ga $^{68}$Ga$^{111}$In, $^{90}$Y $^{177}$Lu, $^{186}$Re, $^{188}$Re, $^{197}$Au, $^{198}$Au, $^{199}$Au, $^{105}$Rh, $^{165}$Ho, $^{161}$Tb, $^{149}$Pm, $^{44}$Sc, $^{47}$Sc, $^{70}$As, $^{71}$As, $^{72}$As, $^{73}$As, $^{74}$As, $^{76}$As, $^{77}$As, $^{212}$Pb, $^{212}$Bi, $^{213}$Bi, $^{225}$Ac, $^{117m}$Sn, $^{67}$Ga, $^{201}$Tl, $^{160}$Gd, $^{148}$Nd, or $^{89}$Sr.

In some embodiments, Z' is $^{68}$Ga, $^{43}$Sc, $^{44}$Sc, $^{47}$Sc, $^{177}$Lu, $^{161}$Tb, $^{225}$Ac, $^{213}$Bi, $^{212}$Bi, or $^{212}$Pb. In some embodiments, Z' is $^{67}$Ga, $^{99m}$Tc, $^{111}$In, or $^{201}$Tl. In some embodiments, the radionuclide (Z') is $^{44}$Sc, $^{64}$Cu, $^{67}$Ga, $^{68}$Ga, $^{86}$Y $^{89}$Zr, $^{99m}$Tc, $^{111}$In, or $^{177}$Lu. In some embodiments, Z' is $^{44}$Sc, $^{64}$Cu, $^{68}$Ga, $^{86}$Y, or $^{89}$Zr. In some embodiments, Z' is $^{67}$Ga, $^{99m}$Tc, $^{111}$In, or 177Lu.

In some embodiments, Z' is $^{67}$Cu, $^{90}$Y $^{111}$In, $^{177}$Lu, $^{225}$Ac, $^{212}$Pb, or $^{213}$Bi.

In some embodiments, Z' is 111-indium ($^{111}$In), 115-indium ($^{11}$5In), 67-gallium ($^{67}$Ga), 68-gallium ($^{68}$Ga), 69-gallium ($^{69}$Ga), 71-gallium ($^{71}$Ga), 225-actinium ($^{225}$Ac), 175-lutetium ($^{175}$Lu), 177-lutetium ($^{177}$Lu), 204-lead ($^{204}$Pb), 206-lead ($^{206}$Pb), 207-lead ($^{207}$Pb), 208-lead ($^{208}$Pb), 212-lead ($^{212}$Pb), 63-copper ($^{63}$Cu), 64-copper ($^{64}$Cu), 65-copper ($^{65}$Cu), or 67-copper ($^{67}$Cu).

In some embodiments, Z' is 111-indium ($^{111}$In). In some embodiments, Z' is 115-indium ($^{115}$In). In some embodiments, Z' is 67-gallium ($^{67}$Ga). In some embodiments, Z' is 68-gallium ($^{68}$Ga). In some embodiments, Z' is 69-gallium ($^{69}$Ga), 71-gallium ($^{71}$Ga), or a mixture thereof. In some embodiments, Z' is 225-actinium ($^{225}$Ac). In some embodiments, Z' is 175-lutetium ($^{175}$Lu). In some embodiments, Z' is 177-lutetium ($^{177}$Lu). In some embodiments, Z' is 204-lead ($^{204}$Pb), 206-lead ($^{206}$Pb), 207-lead ($^{207}$Pb), 208-lead ($^{208}$Pb), or a mixture thereof. In some embodiments, Z' is 212-lead ($^{212}$Pb). In some embodiments, Z' is 64-copper ($^{64}$Cu). In some embodiments, Z' is 63-copper ($^{63}$Cu), 65-copper ($^{65}$Cu), or a mixture thereof. In some embodiments, Z' is 67-copper ($^{67}$Cu).

In some embodiments, Z' is 111-indium ($^{111}$In), 115-indium ($^{11}$5In), 67-gallium ($^{67}$Ga), 68-gallium ($^{68}$Ga), 225-actinium ($^{225}$Ac), 175-lutetium ($^{175}$Lu) or 177-lutetium ($^{177}$Lu).

Exemplary Chelator and Radionuclide Complexes

Radionuclides have useful emission properties that can be used for diagnostic imaging techniques, such as single photon emission computed tomography (SPECT, e.g. $^{67}$Ga, $^{99m}$Tc, $^{11}$In, $^{177}$Lu) and positron emission tomography (PET, e.g. $^{68}$Ga, $^{64}$Cu, $^{44}$Sc, $^{86}$Y, $^{89}$Zr), as well as therapeutic applications (e.g. $^{47}$Sc, $^{114}$mIn, $^{177}$Lu, $^{90}$Y, $^{212/213}$Bi, $^{212}$Pb, $^{225}$Ac, $^{186/188}$Re). A fundamental component of a radiometal-based radiopharmaceutical is the chelator, the ligand system that binds the radiometal ion in a tight stable coordination complex so that it can be properly directed to a desirable molecular target in vivo. Guidance for selecting the optimal match between chelator and radiometal for a particular use is provided in the art (e.g., see Price et al., "Matching chelators to radiometals for radiopharmaceuticals", *Chem. Soc. Rev.,* 2014, 43, 260-290).

In some embodiments, $R^A$ and $R^B$, if present, are each independently selected from the group consisting of: DOTA; DO3A; DO2A; DOTMA; DOTAM; DOTPA; Bn-DOTA; p-OH-Bn-DOTA; $H_4$pypa; $H_4$pypa-benzyl; $H_4$py4pa; $H_4$py4pa-benzyl; $H_4$octapa; $H_4$octapa-benzyl; and TTHA; or a radionuclide complex thereof.

In some embodiments, $R^A$ or $R^B$ is:

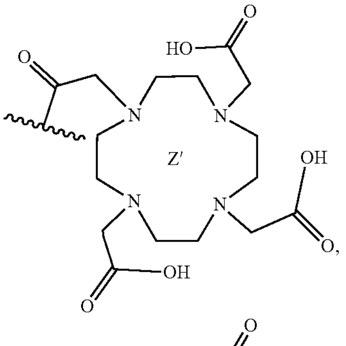

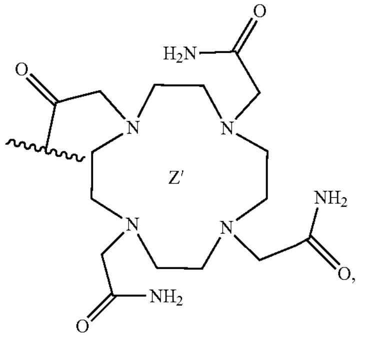

-continued

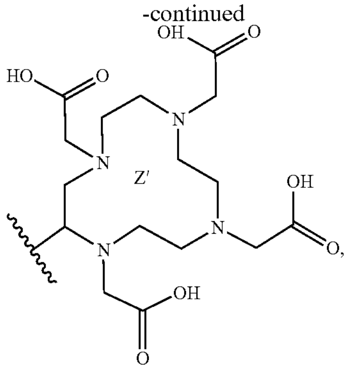

or

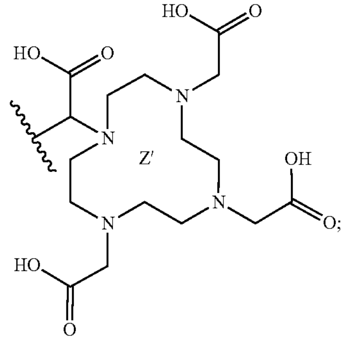

wherein Z' is a diagnostic or therapeutic radionuclide.

In some embodiments, the radionuclide (Z') is $^{44}Sc$, $^{64}Cu$, $^{67}Ga$, $^{68}Ga$, $^{86}Y$ $^{89}Zr$, $^{99m}Tc$, $^{111}In$, or $^{177}Lu$. In some embodiments, the radionuclide (Z') is $^{44}Sc$, $^{64}Cu$, $^{68}Ga$, $^{86}Y$, or $^{89}Zr$. In some embodiments, the radionuclide (Z') is $^{67}Ga$, $^{99m}Tc$, $^{111}In$, or $^{177}Lu$.

In some embodiments, the radionuclide (Z') is $^{67}Cu$, $^{90}Y$, $^{111}n$, $^{177}Lu$, $^{225}Ac$, $^{212}Pb$, or 213Bi.

In some embodiments, the radionuclide (Z') is 111-indium ($^{111}In$), 115-indium ($^{115}In$), 67-gallium ($^{67}Ga$), 68-gallium ($^{68}Ga$), 69-gallium ($^{69}Ga$), 71-gallium ($^{71}Ga$), 225-actinium ($^{225}Ac$), 175-lutetium ($^{175}Lu$), 177-lutetium ($^{177}Lu$), 204-lead ($^{204}Pb$), 206-lead ($^{206}Pb$), 207-lead ($^{207}Pb$), 208-lead ($^{208}Pb$), 212-lead ($^{212}Pb$), 63-copper ($^{63}Cu$), 64-copper ($^{64}Cu$), 65-copper ($^{65}Cu$), or 67-copper ($^{67}Cu$).

In some embodiments, radionuclide (Z') is 111-indium ($^{111}In$). In some embodiments, radionuclide (Z') is 115-indium ($^{115}In$). In some embodiments, radionuclide (Z') is 67-gallium ($^{67}Ga$). In some embodiments, Z' is 68-gallium ($^{68}Ga$). In some embodiments, radionuclide (Z') is 69-gallium ($^{69}Ga$), 71-gallium ($^{71}Ga$), or a mixture thereof. In some embodiments, radionuclide (Z')' is 225-actinium ($^{225}Ac$). In some embodiments, radionuclide (Z') is 175-lutetium ($^{175}Lu$). In some embodiments, radionuclide (Z') is 177-lutetium ($^{177}Lu$). In some embodiments, radionuclide (Z') is 204-lead ($^{204}Pb$), 206-lead ($^{206}Pb$), 207-lead ($^{207}Pb$), 208-lead ($^{208}Pb$), or a mixture thereof. In some embodiments, radionuclide (Z') is 212-lead ($^{212}Pb$). In some embodiments, radionuclide (Z') is 64-copper ($^{64}Cu$). In some embodiments, radionuclide (Z') is 63-copper ($^{63}Cu$), 65-copper ($^{65}Cu$), or a mixture thereof. In some embodiments, radionuclide (Z') is 67-copper ($^{67}Cu$).

In some embodiments, the radionuclide (Z') is 111-indium ($^{111}In$), 115-indium ($^{115}In$), 67-gallium ($^{67}Ga$), 68-gallium ($^{68}Ga$), 225-actinium ($^{225}Ac$), 175-lutetium ($^{175}Lu$) or 177-lutetium ($^{177}Lu$).

In some embodiments, the radionuclide (Z') is 90-yttrium ($^{90}Y$), 177-lutetium ($^{177}Lu$), 186-rhenium ($^{186}Re$), 188-rhenium ($^{188}Re$), 67-copper ($^{67}Cu$), 153-samarium ($^{153}Sm$), 89-strontium ($^{89}Sr$), 198-gold ($^{198}Au$), 169-Erbium ($^{169}Er$), 165-dysprosium ($^{165}Dy$), or technetium-99m ($^{99m}Tc$).

Emission Tomography

In some embodiments, $R^A$ or $R^B$ comprises a chelated radionuclide that is suitable for positron emission tomography (PET) analysis or single-photon emission computerized tomography (SPECT). In some embodiments, $R^A$ or $R^B$ comprises a chelated radionuclide that is suitable for single-photon emission computerized tomography (SPECT). In some embodiments, $R^A$ or $R^B$ comprises a chelated radionuclide that is suitable for positron emission tomography (PET) analysis. In some embodiments, $R^A$ or $R^B$ comprises a chelated radionuclide that is suitable for positron emission tomography imaging, positron emission tomography with computed tomography imaging, or positron emission tomography with magnetic resonance imaging (MRI).

In some embodiments, $R^A$ or $R^B$ is a chelating moiety selected from the group consisting of: DOTA; DO3A; DO2A; DOTMA; DOTAM; DOTPA; Bn-DOTA; p-OH-Bn-DOTA; $H_4$pypa; $H_4$pypa-benzyl; $H_4$py4pa; $H_4$py4pa-benzyl; $H_4$octapa; $H_4$octapa-benzyl; and TTHA; or a radionuclide complex thereof. In some embodiments, the radionuclide is copper-64 ($^{64}Cu$), gallium-68 ($^{68}Ga$), or technetium-99m ($^{99m}Tc$).

In some embodiments, a conjugate described herein is designed to have a prescribed elimination profile. The elimination profile can be designed by adjusting the sequence and length of the non-peptide ligand, the property of the linker, the type of radionuclide, etc. In some embodiments, the conjugate has an elimination half-life of about 5 minutes to about 12 hours. In some embodiments, the conjugate has an elimination half-life of about 10 minutes to about 8 hours. In some embodiments, the conjugate has an elimination half-life of at least about 15 minutes, at least about 30 minutes, at least about 1 hour, at least about 2 hours, at least about 3 hours, at least about 4 hours, at least about 5 hours, at least about 6 hours, at least about 8 hours. In some embodiments, the conjugate has an elimination half-life of at most about 15 minutes, at most about 30 minutes, at most about 1 hour, at most about 2 hours, at most about 3 hours, at most about 4 hours, at most about 5 hours, at most about 6 hours, or at most about 8 hours. In some embodiments, the elimination half-life is determined in rats. In some embodiments, the elimination half-life is determined in humans.

A herein described conjugate can have an elimination half-life in a tumor and non-tumor tissue of the subject. The elimination half-life in a tumor can be the same as or different from (either longer or shorter than) the elimination half-life in a non-tumor issue. In some embodiments, the elimination half-life of the conjugate in a tumor is about 15 minutes to about 1 day. In some embodiments, the elimination half-life of the conjugate in a tumor is at least 1.1, at least 1.2, at least 1.3, at least 1.4, at least 1.5, at least 2.0, at least 2.5, at least 3.0, at least 4.0, or at least 5.0-fold of the elimination half-life of the conjugate in a non-tumor tissue of the subject.

As used herein, the "elimination half-life" can refer to the time it takes from the maximum concentration after administration to half maximum concentration. In some embodiments, the elimination half-life is determined after intravenous administration. In some embodiments, the elimination half-life is measured as biological half-life, which is the half-life of the pharmaceutical in the living system. In some embodiments, the elimination half-life is measured as effective half-life, which is the half-life of a radiopharmaceutical in a living system taking into account the half-life of the radionuclide.

Response and toxicity prediction is essential for the rational implementation of cancer therapy. The biological effects of radionuclide therapy are mediated by a well-defined physical quantity, the absorbed dose (D), which is defined as the energy absorbed per unit mass of tissue.

Radiation dosimetry is the measurement, calculation and assessment of the ionizing radiation dose absorbed by an object, usually the human body, and may be thought of as the ability to perform the equivalent of a pharmacodynamic study in treated patients in real time. This applies both internally, due to ingested or inhaled radioactive substances, or externally due to irradiation by sources of radiation. Dosimetry analysis may be performed as part of patient treatment to calculate tumor versus normal organ absorbed dose and therefore the likelihood of treatment success.

A conjugate described herein can have a prescribed time-integrated activity coefficient (i.e., a) in a tumor or non-tumor tissues of a subject. As used herein, a represents the cumulative number of nuclear transformations occurring in a source tissue over a dose-integration period per unit administered activity. The ã value of a conjugate can be tuned by modifications of the NPDC. The ã value can be determined using a method known in the art. In some embodiments, the ã value of the conjugate in a tumor is from about 10 minutes to about 1 day. The ã value of the conjugate in a tumor can be the same as the ã value of the conjugate in a non-tumor tissue of the subject. The ã value of the conjugate in a tumor can be longer or shorter than the ã value of the conjugate in a non-tumor tissue of the subject. In some embodiments, the ã value of the conjugate in a tumor is at least 1.1, at least 1.2, at least 1.3, at least 1.4, at least 1.5, at least 2.0, at least 2.5, at least 3.0, at least 4.0, or at least 5.0-fold of the ã value of the conjugate in a non-tumor tissue of the subject.

A conjugate described herein can have and value in an organ of a subject. In some embodiments, the conjugate has an ã value in a kidney of the subject of at most 24 hours. In some embodiments, the ã value of the conjugate in a kidney of the subject is at most 18 hours, 15 hours, 12 hours, 10 hours, 8 hours, 6 hours, or 5 hours. In some embodiments, the ã value of the conjugate in a kidney of the subject is about 30 minutes to about 24 hours. In some embodiments, the ã value of the conjugate in a kidney of the subject is about 2 to 24 hours. In some embodiments, the ã value of the conjugate in a kidney of the subject is more than 24 hours. In some embodiments, the ã value of the conjugate in a liver of the subject is at most 24 hours. In some embodiments, the ã value of the conjugate in a liver of the subject is at most 18 hours, 15 hours, 12 hours, 10 hours, 8 hours, 6 hours, or 5 hours. In some embodiments, the ã value of the conjugate in a liver of the subject is about 30 minutes to about 24 hours. In some embodiments, the ã value of the conjugate in a liver of the subject is about 2 to 24 hours. In some embodiments, the ã value of the conjugate in a liver of the subject is more than 24 hours.

Linkers

In some embodiments, the linker has a prescribed length thereby linking the neuropeptide $Y_1$ receptor ($NPY_1R$) targeting ligand and the chelating moiety or a radionuclide complex thereof ($R^A$ or $R^B$) while allowing an appropriate distance therebetween.

In some embodiments, the linker is flexible. In some embodiments, the linker is rigid.

In some embodiments, the linker comprises a linear structure. In some embodiments, the linker comprises a non-linear structure. In some embodiments, the linker comprises a branched structure. In some embodiments, the linker comprises a cyclic structure.

In some embodiments, the linker comprises one or more linear structures, one or more non-linear structures, one or more branched structures, one or more cyclic structures, one or more flexible moieties, one or more rigid moieties, or combinations thereof.

In some embodiments, a linker comprises one or more amino acid residues. In some embodiments, the linker comprises 1 to 3, 1 to 5, 1 to 10, 5 to 10, or 5 to 20 amino acid residues. In some embodiments, one or more amino acids of the linker are unnatural amino acids.

In some embodiments, the linker comprises a peptide linkage. The peptide linkage comprises L-amino acids and/or D-amino acids. In some embodiments, D-amino acids are preferred in order to minimize immunogenicity and nonspecific cleavage by background peptidases or proteases. Cellular uptake of oligo-D-arginine sequences is known to be as good as or better than that of oligo-L-arginines.

In some embodiments, a linker has 1 to 100 atoms, 1 to 50 atoms, 1 to 30 atoms, 1 to 20 atoms, 1 to 15 atoms, 1 to 10 atoms, or 1 to 5 atoms in length. In some embodiments, the linker has 1 to 10 atoms in length. In some embodiments, the linker has 1 to 20 atoms in length.

In some embodiments, a linker can comprise flexible and/or rigid regions. Exemplary flexible linker regions include those comprising Gly and Ser residues ("GS" linker), glycine residues, alkylene chain, PEG chain, etc. Exemplary rigid linker regions include those comprising alpha helix-forming sequences, proline-rich sequences, and regions rich in double and/or triple bonds.

In some embodiments, the cleavable linker comprises one or more of substituted or unsubstituted alkylene, substituted or unsubstituted cycloalkylene, substituted or unsubstituted heterocycloalkylene, substituted or unsubstituted arylene, and substituted or unsubstituted heteroarylene.

In some embodiments, the linker comprises a click chemistry residue. In some embodiments, the linker is attached to a non-peptide ligand, to a metal chelator or both via click chemistry. For example, in some embodiments, a non-peptide ligand comprises an azide group that reacts with an alkyne moiety of the linker. For another example, in some embodiments, a non-peptide ligand comprises an alkyne group that reacts with an azide of the linker. The metal chelator and the linker can be attached similarly. In some embodiments, the linker comprises an azide moiety, an alkyne moiety, or both. In some embodiments, the linker comprises a triazole moiety.

In some embodiments, $L^A$ and $L^B$ are independently selected from: $-L^2-$, $-L^3-$, $-L^4-$, $-L^5-$, $-L^6-$, $-L^7-$, $-L^2-L^3-$, $-L^2-L^4-$, $-L^2-L^6-$, $-L^2-L^7-$, $-L^4-L^6-$, $-L^4-L^7-$, $-L^6-L^7-$, $-L^2-L^3-L^7-$, $-L^2-L^4-L^7-$, $-L^2-L^5-L^7-$, $-L^2-L^6-L^7-$, $-L^3-L^4-L^7-$, $-L^4-L^5-L^7-$, $-L^2-L^3-L^4-L^7-$, $-L^2-L^4-L^5-L^7-$, $-L^2-L^4-L^6-L^7-$, $-L^4-L^5-L^6-L^7-$, $-L^2-L^4-L^5-L^6-L^7-$, or $-L^2-L^3-L^4-L^5-L^6-L^7-$, or a combination thereof; $L^2$ is absent, substituted or unsubstituted $—C_1-C_{20}$ alkylene, substituted or unsubstituted $—C_1-C_{20}$ alkylene-$NR^{16}$—, substituted or unsubstituted $—C_1-C_{20}$ alkylene-C(=O)—, substituted or unsubstituted $—C_1-C_{20}$ alkylene-C(=O)$NR^{16}$—, substituted or unsubstituted $—C_1-C_{20}$ alkylene-$NR^{16}$C(=O)—, substituted or unsubstituted 2 to 20 membered heteroalkylene, $—(CH_2CH_2O)_w—$, $—(OCH_2CH_2)_w—$, or $—(CH_2CH_2O)_w—CH_2CH_2—$; each $R^{16}$ is independently selected from H or $C_1-C_4$ alkyl; w is 1, 2, 3, 4, 5, or 6; $L^3$ is absent or a natural or unnatural amino acid or peptide that is formed from two or more independently selected natural and unnatural amino acids, wherein when two or more amino acids are present then the N atom of the amide linking the amino acids is optionally substituted with —$C_1$-$C_6$ alkyl; $L^4$ is absent, substituted or unsubstituted 2 to 10-membered heteroalkylene, —$(CH_2)_v$—, —$CH_2$—$(OCH_2CH_2)_v$—, —$(CH_2CH_2O)_v$—$CH_2CH_2$—, —C(═O)$CH_2CH_2$—, —$CH_2CH_2C$(═O)—, —$(CH_2)_v$—$NR^{17}C$(═O)—, —$CH_2CH_2C$(═O)$NHCH_2CH_2$—, —$CH_2CH_2$—C(═O)NH—$(CH_2CH_2O)_vCH_2CH_2$—, —$(CH_2)_x$—$NR^{17}$—$(CH_2)_v$—, —NHC(═O)NH—O—$(CH_2)_v$—, —NHC(═O)NH—$(CH_2)_v$—, —$(CH_2)_x$—NHC(═O)NH—$(CH_2)_v$—, —$(CH_2)_x$—C(═O)NH—$(CH_2)_v$—, —$(CH_2)_x$—NHC(═O)—$(CH_2)_v$—, —$CH_2C$(—OH)$CH_2$—C(OH)—$CH_2CH_2$—, —$CH_2C$(—OH)$CH_2$—C(OH)—$CH_2CH_2$—NHC(═O)$CH_2CH_2C$(═O)—$NHCH_2CH_2$—, or —NHC(═O)$CH_2$—O—NH—C(═O)$(CH_2)_v$—; $R^{17}$ is H or —$C_1$-$C_6$ alkyl; each x is independently 1, 2, 3, 4, 5 or 6; each v is independently 1, 2, 3, 4, 5, 6, 7, 8, 9, or 10; $L^5$ is absent, —O—, —$NR^{13}$—, —C(═O)—, —C(═O)$NR^{13}$—, —$NR^{13}C$(═O), —$NR^{13}C$(═O)O—, —$NR^{13}C$(═O)$NR^{13}$—, or —OC(═O)$NR^{13}$—; each $R^{13}$ is independently selected from H or —$C_1$-$C_4$ alkyl; $L^6$ is absent or -$L^8$-$L^9$-$L^{10}$-; $L^8$ is absent, —$(CH_2)_r$—, —$(CH_2)_r$—C(═O)—, —$(CH_2)_r$—$NR^{14}$—, —$(CH_2)_r$—$NR^{14}C$(═O)—, —$(CH_2)_r$—C(═O)$NR^{14}$—, or substituted or unsubstituted heterocycloalkylene; r is 0, 1, 2, or 3; $L^9$ is substituted or unsubstituted cycloalkylene, substituted or unsubstituted heterocycloalkylene, substituted or unsubstituted arylene or substituted or unsubstituted heteroarylene; $L^{10}$ is absent, —$(CH_2)_q$—, —$NR^{15}$—, —$NR^{15}$—$(CH_2)_q$—, —$(CH_2)_q$—C(═O)—, —C(═O)—$(CH_2)_q$—, —$(CH_2)_q$—$NR^{15}$—, —$(CH_2)_q$—$NR^{15}C$(═O)—, —$(CH_2)_q$—C(═O)$NR^{15}$—, —$NR^{15}C$(═O)—$(CH_2)_q$—, or —C(═O)$NR^{15}$—$(CH_2)_q$—; q is 1, 2, 3, 4, 5, or 6; $R^{14}$ and $R^{15}$ are each independently selected from H or —$C_1$-$C_6$ alkyl; and $L^7$ is absent, —NH—, or —N($CH_3$)—.

In some embodiments, $L^A$ and $L^B$ are independently selected from: -$L^2$-, -$L^3$-, -$L^4$-, -$L^5$-, -$L^6$-, -$L^7$-, -$L^2$-$L^3$-, -$L^2$-$L^7$-, -$L^4$-$L^7$-, -$L^2$-$L^4$-$L^7$-, -$L^2$-$L^6$-$L^7$-, -$L^2$-$L^3$-$L^4$-$L^7$-, -$L^2$-$L^4$-$L^5$-$L^7$-, -$L^2$-$L^4$-$L^6$-$L^7$-, or -$L^2$-$L^4$-$L^5$-$L^6$-$L^7$-, or a combination thereof; $L^2$ is absent, substituted or unsubstituted —$C_1$-$C_{20}$ alkylene-$NR^{16}$—, substituted or unsubstituted —$C_1$-$C_{20}$ alkylene-NR $^{16}C$(═O)—, or —$(CH_2CH_2O)_w$—$CH_2CH_2$—; each $R^{16}$ is independently selected from H or $C_1$-$C_4$ alkyl; w is 1, 2, 3, 4, 5, or 6; $L^3$ is absent or a natural or unnatural amino acid or peptide that is formed from two or more independently selected natural and unnatural amino acids, wherein when two or more amino acids are present then the N atom of the amide linking the amino acids is optionally substituted with —$C_1$-$C_6$ alkyl; $L^4$ is absent, substituted or unsubstituted 2 to 10-membered heteroalkylene, —$(CH_2)_v$—, —$(CH_2CH_2O)_v$—$CH_2CH_2$—, —C(═O)$CH_2CH_2$—, —$(CH_2)_v$—$NR^{17}C$(═O)—, —$CH_2CH_2C$(═O)$NHCH_2CH_2$—, —$CH_2CH_2$—C(═O)NH—$(CH_2CH_2O)_vCH_2CH_2$—, —$(CH_2)_x$—$NR^{17}$—$(CH_2)_v$, —NHC(═O)NH—O—$(CH_2)_v$—, —NHC(═O)NH—$(CH_2)_v$—, —$(CH_2)_x$—NHC(═O)NH—$(CH_2)_v$—, —$CH_2C$(—OH)$CH_2$—C(OH)—$CH_2CH_2$—, —$CH_2C$(—OH)$CH_2$—C(OH)—$CH_2CH_2$—NHC(═O)$CH_2CH_2C$(═O)—$NHCH_2CH_2$—, or —NHC(═O)$CH_2$—O—NH—C(═O)$(CH_2)_v$—; $R^{17}$ is H or —$C_1$-$C_6$ alkyl; each x is independently 1, 2, 3, 4, 5 or 6; each v is independently 1, 2, 3, 4, 5, 6, 7, 8, 9, or 10; $L^5$ is absent, —O—, or —$NR^{13}C$(═O); $R^{13}$ is H or —$C_1$-$C_4$ alkyl; $L^6$ is -$L^8$-$L^9$-$L^{10}$-; $L^8$ is absent, —$(CH_2)_r$— or substituted or unsubstituted heterocycloalkylene; r is 0, 1, 2, or 3; $L^9$ is substituted or unsubstituted cycloalkylene, substituted or unsubstituted heterocycloalkylene, or substituted or unsubstituted arylene; $L^{10}$ is absent, —$(CH_2)_q$—, —$NR^{15}$—$(CH_2)_q$—, or —C(═O)—$(CH_2)_q$—; q is 1, 2, 3, 4, 5, or 6; $R^{14}$ and $R^{15}$ are each independently selected from H or —$C_1$-$C_6$ alkyl; and $L^7$ is —NH—.

In some embodiments, $L^A$ is -$L^2$-$L^3$-, -$L^2$-$L^7$-, -$L^4$-$L^7$-, -$L^2$-$L^4$-$L^7$-, -$L^2$-$L^6$-$L^7$-, -$L^2$-$L^3$-$L^4$-$L^7$-, -$L^2$-$L^4$-$L^5$-$L^7$-, -$L^2$-$L^4$-$L^6$-$L^7$-, or -$L^2$-$L^4$-$L^5$-$L^6$-$L^7$-. In some embodiments, $L^A$ is -$L^2$-$L^3$-. In some embodiments, $L^A$ is -$L^2$-$L^7$-. In some embodiments, $L^A$ is -$L^4$-$L^7$-. In some embodiments, $L^A$ is -$L^2$-$L^4$-$L^7$-. In some embodiments, $L^A$ is -$L^2$-$L^6$-$L^7$-. In some embodiments, $L^A$ is -$L^2$-$L^3$-$L^4$-$L^7$-. In some embodiments, $L^A$ is -$L^2$-$L^4$-$L^5$-$L^7$-. In some embodiments, $L^A$ is -$L^2$-$L^4$-$L^6$-$L^7$-. In some embodiments, $L^A$ is -$L^2$-$L^4$-$L^5$-$L^6$-$L^7$-.

In some embodiments, $L^B$ is -$L^2$-$L^3$-, -$L^2$-$L^7$-, -$L^4$-$L^7$-, -$L^2$-$L^4$-$L^7$-, -$L^2$-$L^6$-$L^7$-, -$L^2$-$L^3$-$L^4$-$L^7$-, -$L^2$-$L^4$-$L^5$-$L^7$-, -$L^2$-$L^4$-$L^6$-$L^7$-, or -$L^2$-$L^4$-$L^5$-$L^6$-$L^7$-. In some embodiments, $L^B$ is -$L^2$-$L^3$-. In some embodiments, $L^B$ is -$L^2$-$L^7$-. In some embodiments, $L^B$ is -$L^4$-$L^7$-. In some embodiments, $L^B$ is -$L^2$-$L^4$-$L^7$-. In some embodiments, $L^B$ is -$L^2$-$L^6$-$L^7$-. In some embodiments, $L^B$ is -$L^2$-$L^3$-$L^4$-$L^7$-. In some embodiments, $L^B$ is -$L^2$-$L^4$-$L^5$-$L^7$-. In some embodiments, $L^B$ is -$L^2$-$L^4$-$L^6$-$L^7$-. In some embodiments, $L^B$ is -$L^2$-$L^4$-$L^5$-$L^6$-$L^7$-.

In some embodiments, $L^2$is absent. In some embodiments, $L^2$ is substituted or unsubstituted —$C_1$-$C_{20}$ alkylene-, substituted or unsubstituted —$C_1$-$C_{20}$ alkylene-NH—, substituted or unsubstituted —$C_1$-$C_{20}$ alkylene-N($CH_3$)—, substituted or unsubstituted —$C_1$-$C_{20}$ alkylene-NHC(═O)—, or —$(CH_2CH_2O)_w$—$CH_2CH_2$—. In some embodiments, $L^2$ is substituted or unsubstituted —$C_1$-$C_{20}$ alkylene-. In some embodiments, $L^2$ is substituted or unsubstituted —$C_1$-$C_{20}$ alkylene-NH—. substituted or unsubstituted —$C_1$-$C_{20}$ alkylene-N(—$CH_3$)—. In some embodiments, $L^2$ is substituted or unsubstituted —$C_1$-$C_{20}$ alkylene-NHC(═O)—. In some embodiments, $L^2$ is —$(CH_2CH_2O)_w$—$CH_2CH_2$—.

In some embodiments, $L^2$ is

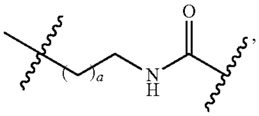
,
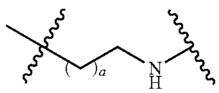
,
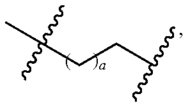
, or
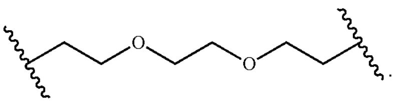
.

wherein a is 1, 2, 3, 4 or 5. In some embodiments, $L^2$is

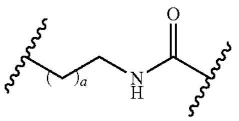
.

In some embodiments, $L^2$is a

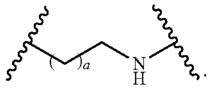 [SMILES: *CCN*]

In some embodiments, $L^2$is

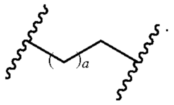 [SMILES: *CC*]

In some embodiments, $L^2$ is

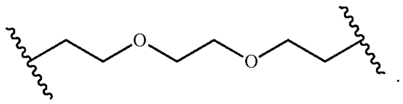 [SMILES: *CCOCCOCC*]

In some embodiments, a is 1. In some embodiments, a is 2. In some embodiments, a is 3. In some embodiments, a is 4. In some embodiments, a is 5.

In some embodiments, $L^2$ is

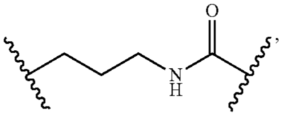
,
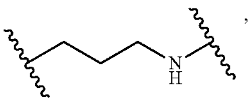
,
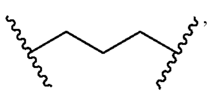
, or
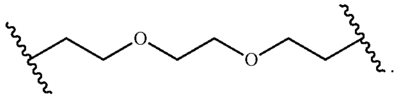

In some embodiments, $L^2$is

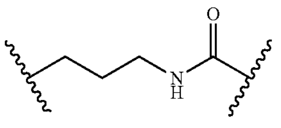

In some embodiments, $L^2$is

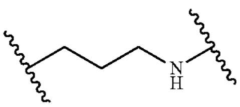

In some embodiments, $L^2$is

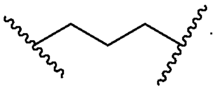 [SMILES: *CCC*]

In some embodiments, $L^2$is

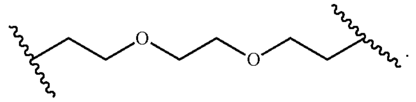 [SMILES: *CCOCCOCC*]

In some embodiments, w is 1. In some embodiments, w is 2. In some embodiments, w is 3. In some embodiments, w is 4.

In some embodiments, $L^3$ is absent. In some embodiments, $L^3$ is a natural amino acid, an unnatural amino acid, or peptide that is formed from two or more independently selected amino acids selected from the group consisting of alanine (Ala), 3-(2-Naphthyl)-alanine (2-Nal), arginine (Arg), asparagine (Asn), aspartate (Asp), cysteine (Cys), cysteic acid, glutamine (Gln), glutamate (Glu), gamma-Carboxyglutamate (Gla), glycine (Gly), histidine (His), isoleucine (Ile), leucine (Leu), lysine (Lys), hydroxylysine (Hyl), ornithine (Orn), methionine (Met), phenylalanine (Phe), p-phenyl phenylalanine (Bip), proline (Pro), hydroxyproline (Hyp), serine (Ser), homoserine (Hse), sarcosine (Sar), threonine (Thr), tryptophan (Trp), tyrosine (Tyr), valine (Val), 4-benzoyl-L-phenylalanine (Bpa), and cyclohexylalanine (Cha), wherein when two or more amino acids are present then the N atom of the amide linking the amino acids is optionally substituted with —$CH_3$. In some embodiments, $L^3$ is a natural amino acid, an unnatural amino acid, or peptide that is formed from two or more independently selected amino acids selected from the group consisting of alanine (Ala), arginine (Arg), asparagine (Asn), aspartate (Asp), cysteine (Cys), cysteic acid, glutamine (Gln), glutamate (Glu), glycine (Gly), leucine (Leu), lysine (Lys), methionine (Met), phenylalanine (Phe), proline (Pro), serine (Ser), sarcosine (Sar), tyrosine (Tyr), and valine (Val), wherein when two or more amino acids are present then the N atom of the amide linking the amino acids is optionally substituted with —$CH_3$. In some embodiments, the peptide is formed from one or more independently selected L-amino acids. In some embodiments, the peptide is formed from one or more independently selected D-amino acids. In some embodiments, the peptide is formed from one or more independently selected L-amino acids and one or more independently selected D-amino acids.

In some embodiments, $L^3$ is a natural amino acid. In some embodiments, $L^3$ is lysine. In some embodiments, $L^3$ is glutamic acid. In some embodiments, $L^3$ is glutamine. In some embodiments, $L^3$ is asparagine. In some embodiments, $L^3$ is serine. In some embodiments, $L^3$ is an unnatural amino acid. In some embodiments, $L^3$ is a dipeptide. In some embodiments, $L^3$ is Asn-Ser. In some embodiments, $L^3$ is a tripeptide. In some embodiments, $L^3$ is Ser-Ser-Ser. In some embodiments, $L^3$ is Gly-Gly-Gly.

In some embodiments, $L^3$ is $NH_2NH_2$

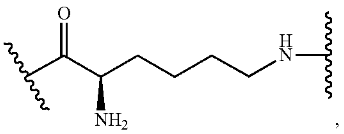
,
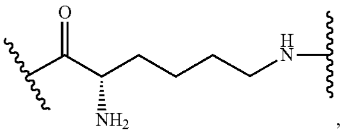
,

-continued
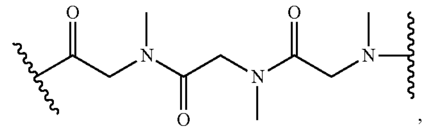,
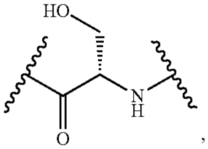, 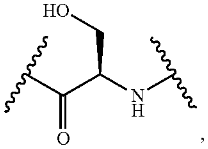,
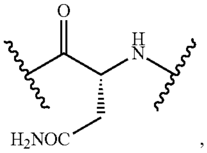, 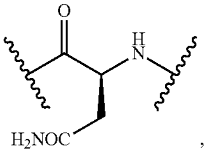,
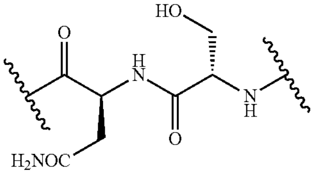,
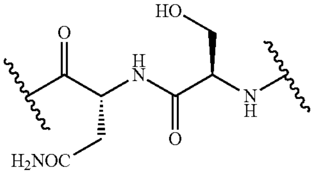,
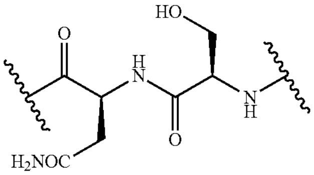,
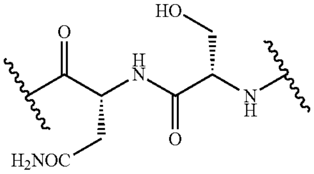,
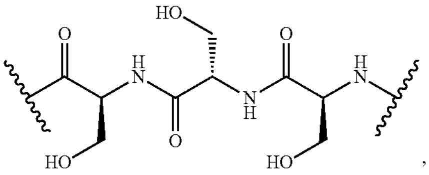, or
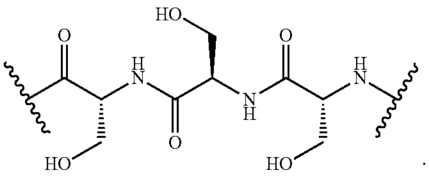.
In some embodiments, $L^3$ is
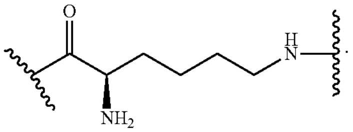 [SMILES: *NCCCC[C@@H](N)C(*)=O]
some embodiments, $L^3$ is
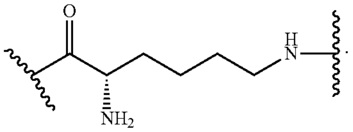 [SMILES: *NCCCC[C@H](N)C(*)=O]
In some embodiments, $L^3$ is
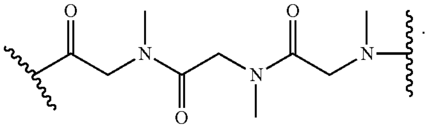 [SMILES: *C(=O)CN(C)C(=O)CN(C)C(=O)CN(*)C ; "."]
In some embodiments, $L^3$ is
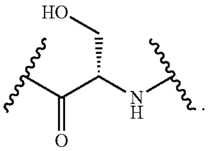 [SMILES: *N[C@@H](CO)C(*)=O]
In some embodiments, $L^3$ is
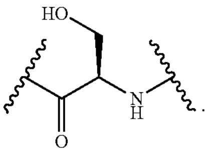 [SMILES: *N[C@H](CO)C(*)=O]
In some embodiments, $L^3$ is
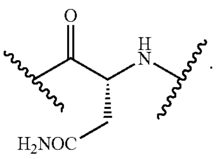 [SMILES: *N[C@H](CC(N)=O)C(*)=O]
In some embodiments, $L^3$ is
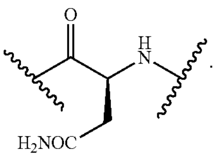 [SMILES: *N[C@@H](CC(N)=O)C(*)=O]

In some embodiments, $L^3$ is

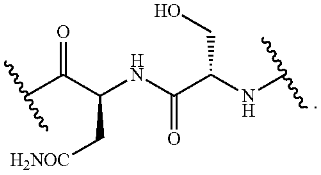 [SMILES: *N[C@@H](CO)C(=O)N[C@@H](CC(N)=O)C(*)=O]

In some embodiments, $L^3$ is

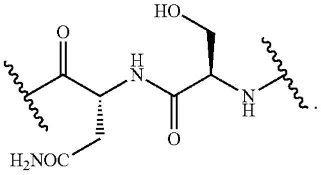 [SMILES: *N[C@H](CO)C(=O)N[C@H](CC(N)=O)C(*)=O]

In some embodiments, $L^3$ is

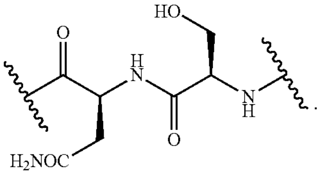 [SMILES: *N[C@H](CO)C(=O)N[C@@H](CC(N)=O)C(*)=O]

In some embodiments, $L^3$ is

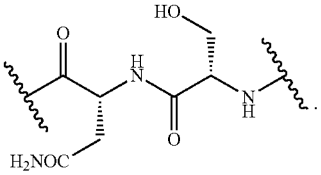 [SMILES: *N[C@@H](CO)C(=O)N[C@H](CC(N)=O)C(*)=O]

In some embodiments, $L^3$ is

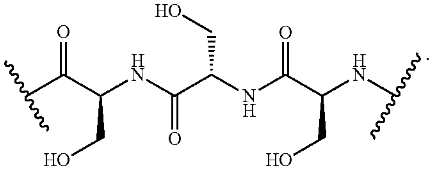 [SMILES: *N[C@@H](CO)C(=O)N[C@@H](CO)C(=O)N[C@@H](CO)C(*)=O]

In some embodiments, $L^3$ is

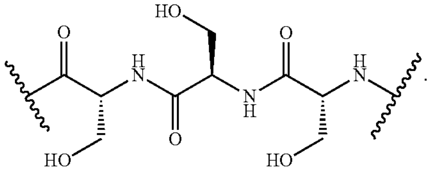 [SMILES: *N[C@H](CO)C(=O)N[C@H](CO)C(=O)N[C@H](CO)C(*)=O]

In some embodiments, $L^4$ is absent. In some embodiments, $L^4$ is $-(CH_2)_v-$. In some embodiments, $L^4$ is $-CH_2-$. In some embodiments, $L^4$ is $-CH_2-CH_2-$. In some embodiments, $L^4$ is $-(CH_2CH_2O)_v-CH_2CH_2-$. In some embodiments, $L^4$ is $-C(=O)CH_2CH_2-$. In some embodiments, $L^4$ is $-(CH_2)_v-NR^{17}C(=O)-$. In some embodiments, $L^4$ is $-CH_2CH_2C(=O)NHCH_2CH_2-$. In some embodiments, $L^4$ is $-CH_2CH_2C(=O)NH-(CH_2CH_2O)_vCH_2CH_2-$. In some embodiments, $L^4$ is $-(CH_2)_x-NR^{17}-(CH_2)_v-$. In some embodiments, $L^4$ is $-NHC(=O)NH-O-(CH_2)_v-$. In some embodiments, $L^4$ is $-NHC(=O)NH-(CH_2)_v-$. In some embodiments, $L^4$ is $-(CH_2)_x-NHC(=O)NH-(CH_2)_v-$. In some embodiments, $L^4$ is $-CH_2C(-OH)CH_2-C(OH)-CH_2CH_2-$. In some embodiments, $L^4$ is $-CH_2C(-OH)CH_2-C(OH)-CH_2CH_2-NHC(=O)CH_2CH_2C(=O)-NHCH_2CH_2-$. In some embodiments, $L^4$ is or $-NHC(=O)CH_2-O-NH-C(=O)(CH_2)_v-$. In some embodiments, $L^4$ is $-CH_2CH_2C(=O)NH-(CH_2CH_2O)_v-CH_2CH_2-$. In some embodiments, $L^4$ is $-CH_2C(-OH)CH_2-C(OH)-CH_2CH_2-NH(C=O)CH_2CH_2(C=O)NHCH_2CH_2-$. In some embodiments, v is 1, 2, 3, 4, 5, or 6. In some embodiments, $R^{17}$ is H. In some embodiments, $R^{17}$ is $CH_3$.

In some embodiments, $L^4$ is

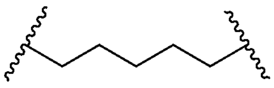
,
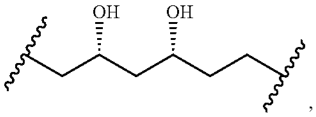
,
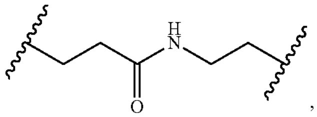
,
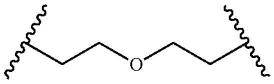
,
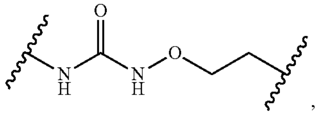
,
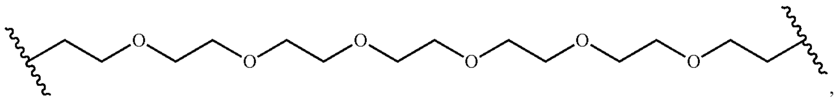
,
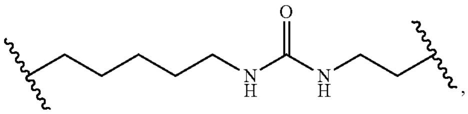
,
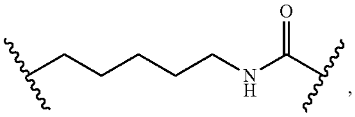
,
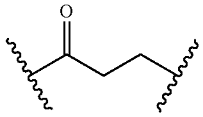
, -continued
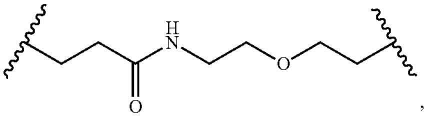,
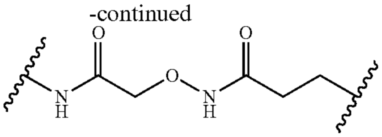,
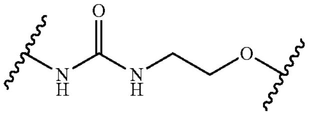,
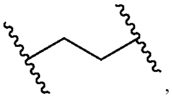,
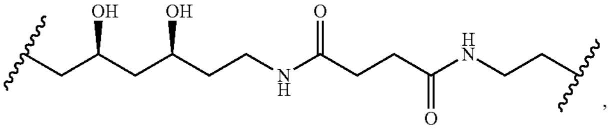,
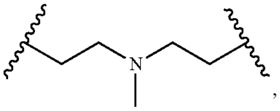,
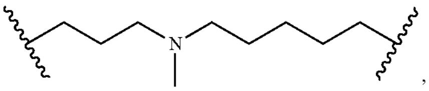,
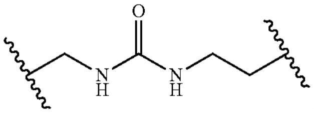, or
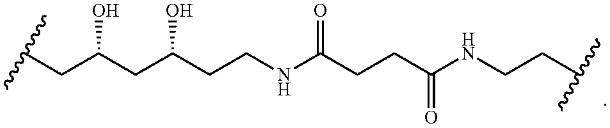.
In some embodiments $L^4$ is
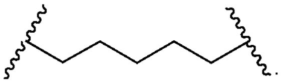 [SMILES: *CCCCC*].
In some embodiments, $L^4$ is
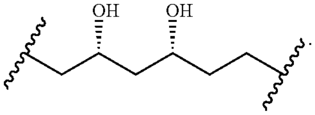 [SMILES: *CC[C@@H](O)C[C@@H](O)C*].
In some embodiments, $L^4$ is
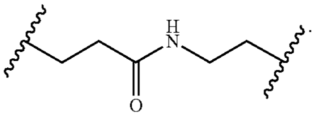 [SMILES: *CCNC(=O)CC*].
In some embodiments, $L^4$ is
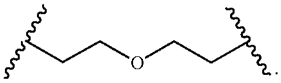 [SMILES: *CCOCC*].
In some embodiments, $L^4$ is
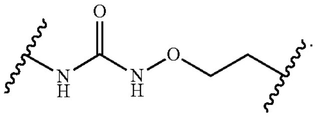 [SMILES: *CCONC(=O)N*].
In some embodiments, $L^4$ is
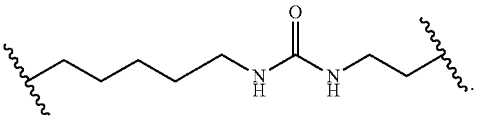 [SMILES: *CCCCCCNC(=O)NCC*].
In some embodiments, $L^4$ is
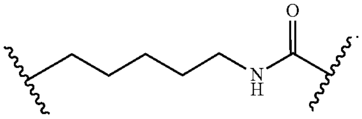 [SMILES: *CCCCC(C)CNC(*)=O].
In some embodiments, $L^4$ is
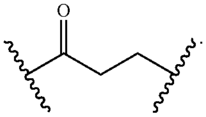 [SMILES: *CCC(*)=O].
In some embodiments, $L^4$ is
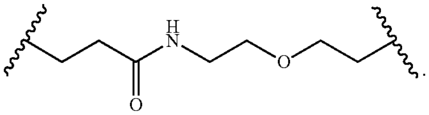 [SMILES: *CCOCCNC(=O)CC*].
In some embodiments $L^4$ is
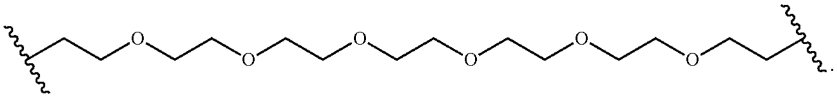.

In some embodiments, $L^4$ is

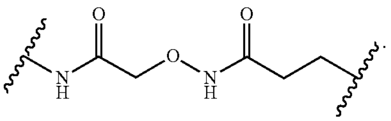 [SMILES: *CCC(=O)NOCC(=O)N*]

In some embodiments, $L^4$ is

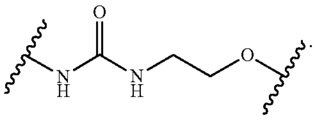 [SMILES: *NC(=O)NCCO*]

In some embodiments, $L^4$ is

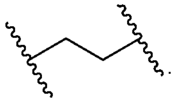 [SMILES: *CC*]

In some embodiments, $L^4$ is

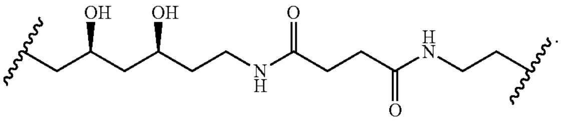 [SMILES: *CCNC(=O)CCC(=O)NCC[C@H](O)C[C@H](O)C*]

In some embodiments, $L^4$ is

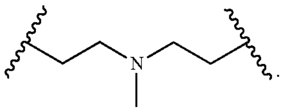 [SMILES: *CCN(C)CC*]

In some embodiments, $L^4$ is

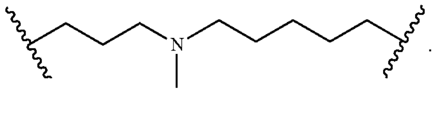 [SMILES: *CCCCCN(C)CCC*]

In some embodiments, $L^4$ is

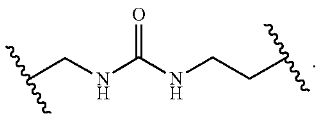 [SMILES: *CCNC(=O)NC*]

In some embodiments, $L^4$ is

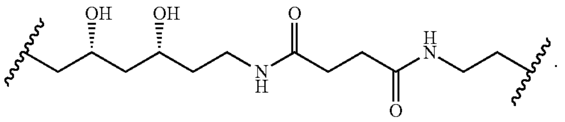 [SMILES: *CCNC(=O)CCC(=O)NCC[C@@H](O)C[C@@H](O)C*]

In some embodiments, $R^{17}$ is H. In some embodiments, $R^{17}$ is —$CH_3$. In some embodiments, $R^{17}$ is —$CH_2CH_3$.

In some embodiments, $L^5$ is absent. In some embodiments, $L^5$ is —O—. In some embodiments, $L^5$ is —C(=O)$NR^{13}$— or —$NR^{13}$C(=O)—. In some embodiments, $L^5$ is —C(=O)NH— or —NHC(=O)—. In some embodiments, $L^5$ is —C(=O)NH—. In some embodiments, $L^5$ is —NHC(=O)—.

In some embodiments, $L^6$ is absent. In some embodiments, $L^6$ is -$L^8$-$L^9$-$L^{10}$-.

In some embodiments, $L^6$ is

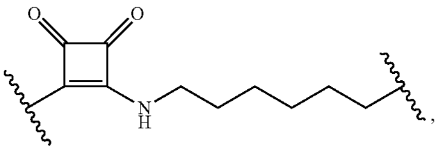

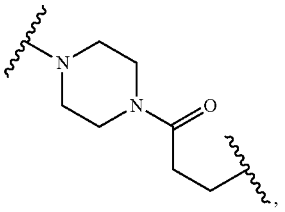

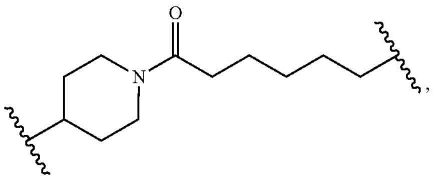

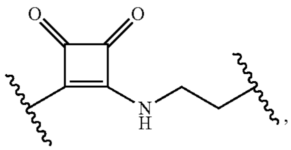

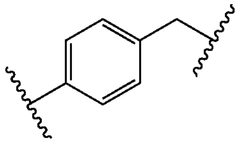

,

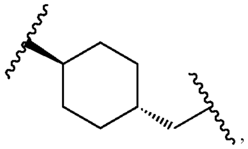

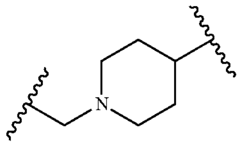

,

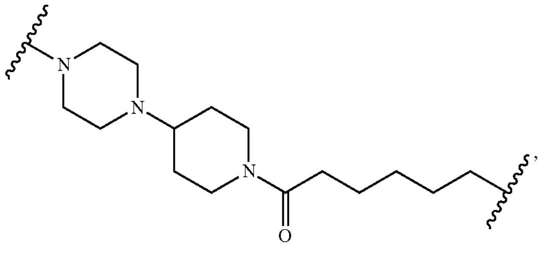

-continued
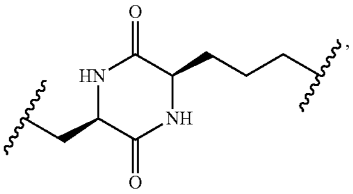
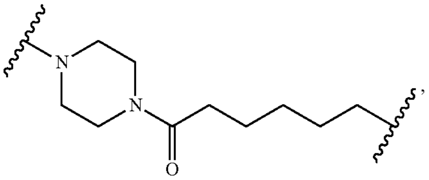
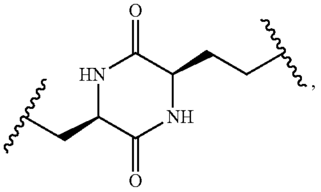
or
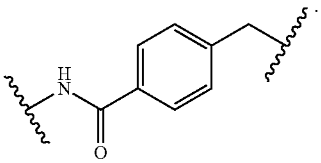
In some embodiments, $L^6$ is
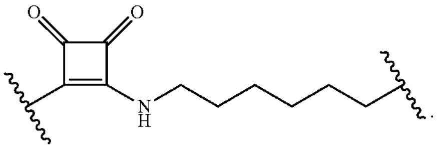 [SMILES: *CCCCCCNc1c(*)c(=O)c1=O]
In some embodiments, $L^6$ is
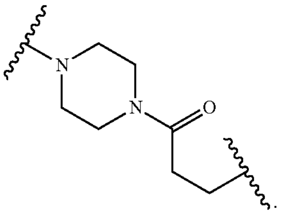 [SMILES: *CCC(=O)N1CCN(*)CC1]
In some embodiments, $L^6$ is
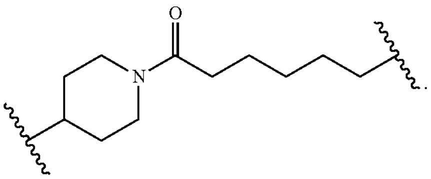 [SMILES: *CCCCCC(=O)N1CCC(*)CC1]
In some embodiments, $L^6$ is
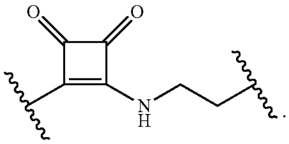 [SMILES: *CCNc1c(*)c(=O)c1=O]
In some embodiments, $L^6$ is
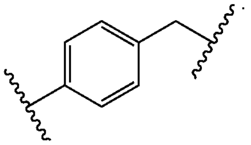 [SMILES: *Cc1ccc(*)cc1]
In some embodiments, $L^6$ is
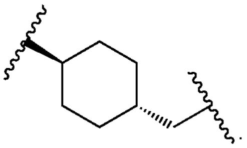 [SMILES: *C[C@H]1CC[C@H](*)CC1]
In some embodiments, $L^6$ is
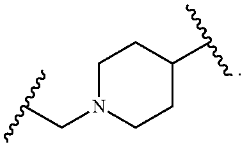 [SMILES: *CN1CCC(*)CC1]
In some embodiments, $L^6$ is
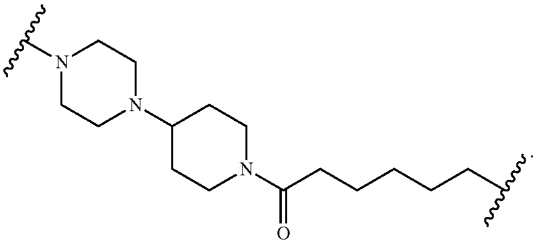 [SMILES: *CCCCCC(=O)N1CCC(N2CCN(*)CC2)CC1]
In some embodiments, $L^6$ is
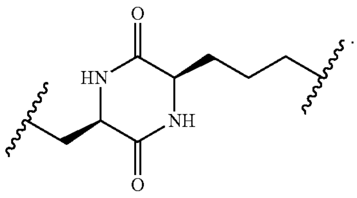 [SMILES: *CCC[C@H]1NC(=O)[C@@H](C*)NC1=O]

In some embodiments, $L^6$ is

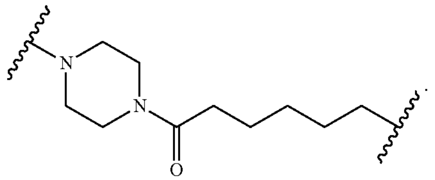 [SMILES: *CCCCCC(=O)N1CCN(*)CC1]

In some embodiments, $L^6$ is

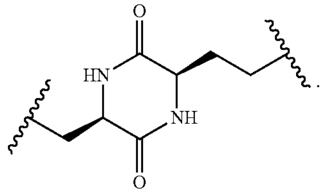 [SMILES: *CC[C@H]1NC(=O)[C@@H](C*)NC1=O]

In some embodiments, $L^6$ is

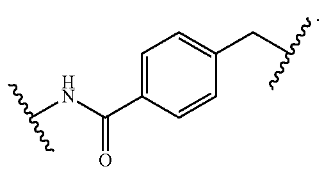 [SMILES: *Cc1ccc(C(=O)N*)cc1]

In some embodiments, $L^6$ is absent. In some embodiments, $L^8$ is $-(CH_2)_r$. In some embodiments, $L^8$ is substituted or unsubstituted heterocycloalkylene. In some embodiments, $L^8$ is $-(CH_2)_r-NR^{14}C(=O)-$. In some embodiments, r is 0. In some embodiments, r is 1 or 2. In some embodiments, r is 3. In some embodiments, $R^{14}$ is H.

In some embodiments, $L^9$ is a substituted or unsubstituted heterocycloalkylene. In some embodiments, $L^9$ is a substituted or unsubstituted 3 to 8 membered heterocycloalkylene. In some embodiments, $L^9$ is a substituted or unsubstituted 4 to 6 membered heterocycloalkylene. In some embodiments, $L^9$ is azetidinylene, pyrrolidinylene, piperidinylene or piperazinylene. In some embodiments, $L^9$ is a substituted or unsubstituted cycloalkylene. In some embodiments, $L^9$ is a substituted or unsubstituted $C_4$-$C_8$ cycloalkylene. In some embodiments, $L^9$ is

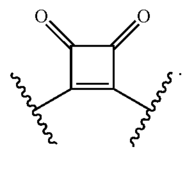 [SMILES: *c1c(*)c(=O)c1=O]

In some embodiments, $L^9$ is a substituted or unsubstituted arylene. In some embodiments, $L^9$ is substituted or unsubstituted phenylene. In some embodiments, $L^9$ is unsubstituted phenylene. In some embodiments, $L^9$ is a substituted or unsubstituted heteroarylene.

In some embodiments, $L^{10}$ is absent. In some embodiments, $L^{10}$ is $-(CH_2)_q-$. In some embodiments, $L^{10}$ is $-NR^{15}-(CH_2)_q-$. In some embodiments, $L^{10}$ is $-NH(CH_2)_q-$. In some embodiments, $L^{10}$ is $-C(=O)-(CH_2)_q-$. In some embodiments, $R^{15}$ is H. In some embodiments, q is 1. In some embodiments, q is 2. In some embodiments, q is 3. In some embodiments, q is 4. In some embodiments, q is 5. In some embodiments, q is 6. In some embodiments, $L^{10}$ is $-(CH_2)-$.

In some embodiments, $L^7$ is absent. In some embodiments, $L^7$ is $-NH-$.

In some embodiments, w is 1. In some embodiments, w is 2. In some embodiments, w is 3. In some embodiments, w is 4. In some embodiments, w is 5. In some embodiments, w is 6.

In some embodiments, v is 1, 2, 3, 4, 5, or 6. In some embodiments, v is 1. In some embodiments, v is 2. In some embodiments, v is 3. In some embodiments, v is 4. In some embodiments, v is 5. In some embodiments, v is 6. In some embodiments, v is 7. In some embodiments, v is 8. In some embodiments, v is 9. In some embodiments, v is 10.

In some embodiments, x is 1. In some embodiments, x is 2. In some embodiments, x is 3. In some embodiments, x is 4. In some embodiments, x is 5. In some embodiments, x is 6.

In some embodiments, r is 0. In some embodiments, r is 1. In some embodiments, r is 2. In some embodiments, r is 3.

In some embodiments, q is 1, 2 or 3. In some embodiments, q is 4, 5 or 6. In some em, q is 1. In some embodiments, q is 2. In some embodiments, q is 3. In some embodiments, q is 4. In some embodiments, q is 5. In some embodiments, q is 6.

In some embodiments, $L^A$ is $-L^2-L^3-$; $L^2$ is unsubstituted $-C_1$-$C_6$ alkylene-NH—; and $L^3$ is a natural or unnatural amino acid or natural or unnatural peptide, wherein the N atom of the amide linking the amino acids is optionally substituted with $-CH_3$. In some embodiments, the natural or unnatural amino acid is lysine. In some embodiments, the peptide is a tripeptide consisting of three glycines wherein the N atom of the amide linking the amino acids is substituted with $-CH_3$.

In some embodiments, $L^A$ is $-L^2-L^7-$; $L^2$ is $-(CH_2CH_2O)_w-CH_2CH_2-$ or substituted or unsubstituted $C_1$-$C_6$ alkylene; and $L^7$ is $-NH-$. In some embodiments, $L^A$ is $-L^2-L^7-$; $L^2$ is $-(CH_2CH_2O)_w-CH_2CH_2-$; and $L^7$ is $-NH-$. In some embodiments, w is 2. In some embodiments, $L^A$ is $-L^2-L^7-$; $L^2$ is unsubstituted $C_1$-$C_6$ alkylene; and $L^7$ is $-NH-$.

In some embodiments, $L^A$ is $-L^4-L^7-$; $L^4$ is $-(CH_2)_x-NR^{17}-(CH_2)_v$; and $L^7$ is $-NH-$. In some embodiments, x is 3. In some embodiments, v is 5. In some embodiments, $R^{17}$ is $-CH_3$.

In some embodiments, $L^A$ is $-L^2-L^3-L^7$; $L^2$ is unsubstituted $-C_1$-$C_6$ alkylene-; $L^3$ is natural or unnatural amino acid or natural or unnatural peptide, wherein the N atom of the amide linking the amino acids is optionally substituted with $-CH_3$; and $L^7$ is absent or $-NH-$. In some embodiments, $L^3$ is Lys. In some embodiments, $L^3$ is Gly-Gly-Gly, wherein the N atom of the amide linking the amino acids is substituted with $-CH_3$.

In some embodiments, $L^A$ is $-L^2-L^4-L^7$; $L^2$ is unsubstituted $-C_1$-$C_6$ alkylene-, unsubstituted $-C_1$-$C_{20}$ alkylene-N($CH_3$)—, or unsubstituted $-C_1$-$C_6$ alkylene-NHC(=O)—; $L^4$ is $-(CH_2)_v-$, $-(CH_2CH_2O)_v-CH_2CH_2-$, $-(CH_2)_v-NR^{17}-(CH_2)_v$, $-NHC(=O)NH-O-(CH_2)_v-$, $-NHC(=O)CH_2-O-NH-C(=O)(CH_2)_v-$, $-CH_2C(-OH)CH_2-C(OH)-CH_2CH_2-$, $-CH_2CH_2C(=O)NHCH_2CH_2-$, $-CH_2CH_2-C(=O)NH-(CH_2CH_2O)_vCH_2CH_2-$, $-CH_2C(-OH)CH_2-C$ (OH)—$CH_2CH_2$—NHC(=O)$CH_2CH_2$C(=O)—NH$CH_2CH_2$—, or —$CH_2CH_2$C(=O)NH—$(CH_2CH_2O)_v$—$CH_2CH_2$—; and $L^7$ is —NH—. In some embodiments, $L^A$ is -$L^2$-$L^4$-$L^7$; $L^2$ is unsubstituted —$C_1$-$C_6$ alkylene- or unsubstituted —$C_1$-$C_6$ alkylene-NHC(=O)—; $L^4$ is —$(CH_2)_v$—, —$(CH_2CH_2O)_v$—$CH_2CH_2$—, —$(CH_2)_v$—$NR^{17}$—$(CH_2)_v$, —NHC(=O)NH—O—$(CH_2)_v$—, —NHC(=O)$CH_2$—O—NH—C(=O)$(CH_2)_v$—, —$CH_2$C(—OH)$CH_2$—C(OH)—$CH_2CH_2$—, —$CH_2CH_2$C(=O)NH$CH_2CH_2$—, —$CH_2CH_2$—C(=O)NH—$(CH_2CH_2O)_v$$CH_2CH_2$—, or —$CH_2$C(—OH)$CH_2$—C(OH)—$CH_2CH_2$—NHC(=O)$CH_2CH_2$C(=O)—NH$CH_2CH_2$—; and $L^7$ is —NH—. In some embodiments, $L^A$ is -$L^2$-$L^4$-$L^7$; $L^2$ is unsubstituted —$C_1$-$C_6$ alkylene-NHC(=O)—; $L^4$ is —$(CH_2)_v$—; and $L^7$ is —NH—. In some embodiments, v is 1. In some embodiments, v is 2. In some embodiments, v is 6. In some embodiments, $R^{17}$ is —$CH_3$.

In some embodiments, $L^A$ is -$L^2$-$L^6$-$L^7$-; $L^2$ is unsubstituted —$C_1$-$C_6$ alkylene-, unsubstituted —$C_1$-$C_6$ alkylene-NH—, or unsubstituted —$C_1$-$C_6$ alkylene-NHC(=O)—; $L^6$ is -$L^8$-$L^9$-$L^{10}$-; and $L^7$ is —NH—. In some embodiments, $L^8$ is absent. In some embodiments, $L^8$ is —$(CH_2)_r$—. In some embodiments, $L^8$ is substituted or unsubstituted heterocycloalkylene. In some embodiments, $L^9$ is substituted or unsubstituted cycloalkylene. In some embodiments, $L^9$ is substituted or unsubstituted heterocycloalkylene. In some embodiments, $L^{10}$ is —$NR^w$—$(CH_2)_q$—. In some embodiments, $L^{10}$ is —$(CH_2)_q$—. In some embodiments, $L^{10}$ is —C(=O)—$(CH_2)_q$—. In some embodiments, q is 1. In some embodiments, q is 2. In some embodiments, q is 3. In some embodiments, q is 5. In some embodiments, q is 6. In some embodiments, r is 1.

In some embodiments, $L^A$ is -$L^2$-$L^3$-$L^4$-$L^7$-; $L^2$ is unsubstituted —$C_1$-$C_6$ alkylene-NH—; $L^3$ is serine, asparagine, Asn-Ser, or Ser-Ser-Ser; $L^4$ is —C(=O)$CH_2CH_2$—; and $L^7$ is —NH—.

In some embodiments, $L^A$ is -$L^2$-$L^4$-$L^5$-$L^7$-; $L^2$ is unsubstituted —$C_1$-$C_6$ alkylene- or unsubstituted —$C_1$-$C_6$ alkylene-NHC(=O)—; $L^4$ is —$(CH_2)_x$—NHC(=O)NH—$(CH_2)_v$— or —NHC(=O)NH—$(CH_2)_v$—; $L^5$ is —O—; and $L^7$ is —NH—. In some embodiments, x is 1. In some embodiments, x is 5. In some embodiments, v is 2.

In some embodiments, $L^A$ is -$L^2$-$L^4$-$L^6$-$L^7$-; $L^2$ is unsubstituted $C_1$-$C_6$ alkylene-NHC(=O)—; $L^4$ is —$(CH_2CH_2O)_v$—$CH_2CH_2$— or —$(CH_2)_x$—$NR^{17}$C(=O)—; $L^6$ is -$L^8$-$L^9$-$L^{10}$-; and $L^7$ is —NH—. In some embodiments, $L^A$ is -$L^2$-$L^4$-$L^6$-$L^7$-; $L^2$ is unsubstituted $C_1$-$C_6$ alkylene-NHC(=O)—; $L^4$ is —$(CH_2)_x$—$NR^{17}$C(=O)—; $L^6$ is -$L^8$-$L^9$-$L^{10}$-; and $L^7$ is —NH—. In some embodiments, v is 5. In some embodiments, $L^9$ is substituted or unsubstituted heterocycloalkylene. In some embodiments, $L^8$ is —$(CH_2)_r$—. In some embodiments, $L^8$ is —$(CH_2)_r$—$NR^{14}$C(=O)—. In some embodiments, $L^9$ is substituted or unsubstituted arylene. In some embodiments, $L^{10}$ is absent. In some embodiments, $L^{10}$ is —$(CH_2)_q$—. In some embodiments, $L^A$ is -$L^2$-$L^4$-$L^5$-$L^6$-$L^7$-; $L^2$ is substituted or unsubstituted —$C_1$-$C_6$ alkylene-NHC(=O)—; $L^4$ is —$(CH_2CH_2O)_v$—$CH_2CH_2$—; $L^5$ is —NHC(=O)—; $L^6$ is -$L^8$-$L^9$-$L^{10}$-; and $L^7$ is —NH—. In some embodiments, $L^9$ is unsubstituted phenylene.

In some embodiments, $L^B$ is -$L^2$-$L^3$-; $L^2$ is unsubstituted —$C_1$-$C_6$ alkylene-NH—; and $L^3$ is a natural or unnatural amino acid or natural or unnatural peptide, wherein the N atom of the amide linking the amino acids is optionally substituted with —$CH_3$. In some embodiments, the natural or unnatural amino acid is lysine. In some embodiments, the peptide is a tripeptide consisting of three glycines wherein the N atom of the amide linking the amino acids is substituted with —$CH_3$.

In some embodiments, $L^B$ is -$L^2$-$L^7$-; $L^2$ is —$(CH_2CH_2O)_w$—$CH_2CH_2$— or substituted or unsubstituted $C_1$-$C_6$ alkylene; and $L^7$ is —NH—. In some embodiments, $L^B$ is -$L^2$-$L^7$-; $L^2$ is —$(CH_2CH_2O)_w$—$CH_2CH_2$—; and $L^7$ is —NH—. In some embodiments, w is 2. In some embodiments, $L^B$ is -$L^2$-$L^7$-; $L^2$ is unsubstituted $C_1$-$C_6$ alkylene; and $L^7$ is —NH—.

In some embodiments, $L^B$ is -$L^4$-$L^7$-; $L^4$ is —$(CH_2)_x$—$NR^{17}$—$(CH_2)_v$; and $L^7$ is —NH—. In some embodiments, x is 3. In some embodiments, v is 5. In some embodiments, $R^{17}$ is —$CH_3$.

In some embodiments, $L^B$ is -$L^2$-$L^3$-$L^7$; $L^2$ is unsubstituted —$C_1$-$C_6$ alkylene-; $L^3$ is natural or unnatural amino acid or natural or unnatural peptide, wherein the N atom of the amide linking the amino acids is optionally substituted with —$CH_3$; and $L^7$ is absent or —NH—. In some embodiments, $L^3$ is Lys. In some embodiments, $L^3$ is Gly-Gly-Gly, wherein the N atom of the amide linking the amino acids is substituted with —$CH_3$.

In some embodiments, $L^B$ is -$L^2$-$L^4$-$L^7$; $L^2$ is unsubstituted —$C_1$-$C_6$ alkylene- or unsubstituted —$C_1$-$C_6$ alkylene-NHC(=O)—; $L^4$ is —$(CH_2)_v$—, —$(CH_2CH_2O)_v$—$CH_2CH_2$—, —$(CH_2)_v$—$NR^{17}$—$(CH_2)_v$, —NHC(=O)NH—O—$(CH_2)_v$—, —NHC(=O)$CH_2$—O—NH—C(=O)$(CH_2)_v$—, —$CH_2$C(—OH)$CH_2$—C(OH)—$CH_2CH_2$—, —$CH_2CH_2$C(=O)NH$CH_2CH_2$—, —$CH_2CH_2$—C(=O)NH—$(CH_2CH_2O)_v$$CH_2CH_2$—, —$CH_2$C(—OH)$CH_2$—C(OH)—$CH_2CH_2$—NHC(=O)$CH_2CH_2$C(=O)—NH$CH_2CH_2$—, or —$CH_2CH_2$C(=O)NH—$(CH_2CH_2O)_v$—$CH_2CH_2$—; and $L^7$ is —NH—. In some embodiments, $L^B$ is -$L^2$-$L^4$-$L^7$; $L^2$ is unsubstituted —$C_1$-$C_6$ alkylene- or unsubstituted —$C_1$-$C_6$ alkylene-NHC(=O)—; $L^4$ is —$(CH_2)_v$—, —$(CH_2CH_2O)_v$—$CH_2CH_2$—, —$(CH_2)_v$—$NR^{17}$—$(CH_2)_v$, —NHC(=O)NH—O—$(CH_2)_v$—, —NHC(=O)$CH_2$—O—NH—C(=O)$(CH_2)_v$—, —$CH_2$C(—OH)$CH_2$—C(OH)—$CH_2CH_2$—, —$CH_2CH_2$C(=O)NH$CH_2CH_2$—, —$CH_2CH_2$—C(=O)NH—$(CH_2CH_2O)_v$$CH_2CH_2$—, or —$CH_2$C(—OH)$CH_2$—C(OH)—$CH_2CH_2$—NHC(=O)$CH_2CH_2$C(=O)—NH$CH_2CH_2$—; and $L^7$ is —NH—. In some embodiments, $L^B$ is -$L^2$-$L^4$-$L^7$; $L^2$ is unsubstituted —$C_1$-$C_6$ alkylene-NHC(=O)—; $L^4$ is —$(CH_2)_v$—; and $L^7$ is —NH—. In some embodiments, v is 1. In some embodiments, v is 2. In some embodiments, v is 6. In some embodiments, $R^{17}$ is —$CH_3$.

In some embodiments, $L^B$ is -$L^2$-$L^6$-$L^7$-; $L^2$ is unsubstituted —$C_1$-$C_6$ alkylene-, unsubstituted —$C_1$-$C_6$ alkylene-NH—, or unsubstituted —$C_1$-$C_6$ alkylene-NHC(=O)—; $L^6$ is -$L^8$-$L^9$-$L^{10}$-; and $L^7$ is —NH—. In some embodiments, $L^8$ is absent. In some embodiments, $L^8$ is —$(CH_2)_r$—. In some embodiments, $L^8$ is substituted or unsubstituted heterocycloalkylene. In some embodiments, $L^9$ is substituted or unsubstituted cycloalkylene. In some embodiments, $L^9$ is substituted or unsubstituted heterocycloalkylene. In some embodiments, $L^{10}$ is —$NR^w$—$(CH_2)_q$—. In some embodiments, $L^{10}$ is —$(CH_2)_q$—. In some embodiments, $L^{10}$ is —C(=O)—$(CH_2)_q$—. In some embodiments, q is 1. In some embodiments, q is 2. In some embodiments, q is 3. In some embodiments, q is 5. In some embodiments, q is 6. In some embodiments, r is 1.

In some embodiments, $L^B$ is -$L^2$-$L^3$-$L^4$-$L^7$-; $L^2$ is unsubstituted —$C_1$-$C_6$ alkylene-NH—; $L^3$ is serine, asparagine, Asn-Ser, or Ser-Ser-Ser; $L^4$ is —C(=O)$CH_2CH_2$—; and $L^7$ is —NH—.

In some embodiments, $L^B$ is $-L^2-L^4-L^5-L^7-$; $L^2$ is unsubstituted $—C_1-C_6$ alkylene- or unsubstituted $—C_1-C_6$ alkylene-NHC(═O)—; $L^4$ is $—(CH_2)_x—$NHC(═O)NH—$(CH_2)_v—$ or —NHC(═O)NH—$(CH_2)_v—$; $L^5$ is —O—; and $L^7$ is —NH—. In some embodiments, x is 1. In some embodiments, x is 5. In some embodiments, v is 2.

In some embodiments, $L^B$ is $-L^2-L^4-L^6-L^7-$; $L^2$ is unsubstituted $C_1-C_6$ alkylene-NH—C(═O)—; $L^4$ is $—(CH_2CH_2O)_v—CH_2CH_2—$ or $—(CH_2)_x—NR^{17}C$(═O)—; $L^6$ is $-L^8-L^9-L^{10}-$; and $L^7$ is —NH—. In some embodiments, $L^B$ is $-L^2-L^4-L^6-L^7-$; $L^2$ is unsubstituted $C_1-C_6$ alkylene-NHC(═O)—; $L^4$ is $—(CH_2)_x—NR^{17}C$(═O)—; $L^6$ is $-L^8-L^9-L^{10}-$; and $L^7$ is —NH—. In some embodiments, v is 5. In some embodiments, $L^9$ is substituted or unsubstituted heterocycloalkylene. In some embodiments, $L^8$ is $—(CH_2)_r—$. In some embodiments, $L^8$ is $—(CH_2)_r—NR^{14}C$(═O)—. In some embodiments, $L^9$ is substituted or unsubstituted arylene. In some embodiments, $L^{10}$ is absent. In some embodiments, $L^{10}$ is $—(CH_2)_q—$.

In some embodiments, $L^B$ is $-L^2-L^4-L^5-L^6-L^7-$; $L^2$ is substituted or unsubstituted $—C_1-C_6$ alkylene-NHC(═O)—; $L^4$ is $—(CH_2CH_2O)_v—CH_2CH_2—$; $L^5$ is —NHC(═O)—; $L^6$ is $-L^8-L^9-L^{10}-$; and $L^7$ is —NH—. In some embodiments, $L^9$ is unsubstituted phenylene.

In some embodiments, $L^A-R^A$ is $-L^2-L^3-R^A$; $L^2$ is unsubstituted $—C_1-C_6$ alkylene-NH—; and $L^3$ is a natural or unnatural amino acid or natural or unnatural peptide, wherein the N atom of the amide linking the amino acids is optionally substituted with $—CH_3$. In some embodiments, the natural or unnatural amino acid is lysine. In some embodiments, the peptide is a tripeptide consisting of three glycines wherein the N atom of the amide linking the amino acids is substituted with $—CH_3$.

In some embodiments, $L^A-R^A$ is $-L^2-L^7-R^A$; $L^2$ is $—(CH_2CH_2O)_w—CH_2CH_2—$ or substituted or unsubstituted $C_1-C_6$ alkylene; and $L^7$ is —NH—. In some embodiments, $L^A-R^A$ is $-L^2-L^7-R^A$; $L^2$ is $—(CH_2CH_2O)_w—CH_2CH_2—$; and $L^7$ is —NH—. In some embodiments, w is 2. In some embodiments, $L^A-R^A$ is $-L^2-L^7-R^A$; $L^2$ is unsubstituted $C_1-C_6$ alkylene; and $L^7$ is —NH—.

In some embodiments, $L^A-R^A$ is $-L^4-L^7-R^A$; $L^4$ is $—(CH_2)_x—NR^{17}—(CH_2)_v$; and $L^7$ is —NH—. In some embodiments, x is 3. In some embodiments, v is 5. In some embodiments, $R^{17}$ is $—CH_3$.

In some embodiments, $L^A-R^A$ is $-L^2-L^3-L^7-R^A$; $L^2$ is unsubstituted $—C_1-C_6$ alkylene-; $L^3$ is natural or unnatural amino acid or natural or unnatural peptide, wherein the N atom of the amide linking the amino acids is optionally substituted with $—CH_3$; and $L^7$ is absent or —NH—. In some embodiments, $L^3$ is Lys. In some embodiments, $L^3$ is Gly-Gly-Gly, wherein the N atom of the amide linking the amino acids is substituted with $—CH_3$.

In some embodiments, $L^A-R^A$ is $-L^2-L^4-L^7-R^A$; $L^2$ is unsubstituted $—C_1-C_6$ alkylene-, unsubstituted $—C_1-C_{20}$ alkylene-N$(CH_3)$—, unsubstituted $—C_1-C_6$ alkylene-NHC(═O)—; $L^4$ is $—(CH_2)_v—$, $—(CH_2CH_2O)_v—CH_2CH_2—$, $—(CH_2)_v—NR^{17}—(CH_2)_v$, —NHC(═O)NH—O—$(CH_2)_v—$, —NHC(═O)$CH_2$—O—NH—C(═O)$(CH_2)_v—$, $—CH_2C$(—OH)$CH_2$—C(OH)—$CH_2CH_2$—, $—CH_2CH_2C$(═O)$NHCH_2CH_2$—, $—CH_2CH_2$—C(═O)NH—$(CH_2CH_2O)_vCH_2CH_2$—, or $—CH_2C$(—OH)$CH_2$—C(OH)—$CH_2CH_2$—NHC(═O)$CH_2CH_2C$(═O)—$NHCH_2CH_2$—, or $—CH_2CH_2C$(═O)NH—$(CH_2CH_2O)_v—CH_2CH_2$—; and $L^7$ is —NH—. In some embodiments, $L^A-R^A$ is $-L^2-L^4-L^7-R^A$; $L^2$ is unsubstituted $—C_1-C_6$ alkylene- or unsubstituted $—C_1-C_6$ alkylene-NHC(═O)—; $L^4$ is $—(CH_2)_v—$, $—(CH_2CH_2O)_v—CH_2CH_2—$, $—(CH_2)_v—NR^{17}—(CH_2)_v$, —NHC(═O)NH—O—$(CH_2)_v—$, —NHC(═O)$CH_2$—O—NH—C(═O)$(CH_2)_v—$, $—CH_2C$(—OH)$CH_2$—C(OH)—$CH_2CH_2$—, $—CH_2CH_2C$(═O)$NHCH_2CH_2$—, $—CH_2CH_2$—C(═O)NH—$(CH_2CH_2O)_vCH_2CH_2$—, or $—CH_2C$(—OH)$CH_2$—C(OH)—$CH_2CH_2$—NHC(═O)$CH_2CH_2C$(═O)—$NHCH_2CH_2$—; and $L^7$ is —NH—. In some embodiments, v is 1. In some embodiments, v is 2. In some embodiments, v is 6. In some embodiments, $R^{17}$ is $—CH_3$.

In some embodiments, $L^A-R^A$ is $-L^2-L^6-L^7-R^A$; $L^2$ is unsubstituted $—C_1-C_6$ alkylene-, unsubstituted $—C_1-C_6$ alkylene-NH—, or unsubstituted $—C_1-C_6$ alkylene-NHC(═O)—; $L^6$ is $-L^8-L^9-L^{10}-$; and $L^7$ is —NH—. In some embodiments, $L^8$ is absent. In some embodiments, $L^8$ is $—(CH_2)_r—$. In some embodiments, $L^8$ is substituted or unsubstituted heterocycloalkylene. In some embodiments, $L^9$ is substituted or unsubstituted cycloalkylene. In some embodiments, $L^9$ is substituted or unsubstituted heterocycloalkylene. In some embodiments, $L^{10}$ is $—NR^w—(CH_2)_q—$. In some embodiments, $L^{10}$ is $—(CH_2)_q—$. In some embodiments, $L^{10}$ is —C(═O)—$(CH_2)_q—$. In some embodiments, q is 1. In some embodiments, q is 2. In some embodiments, q is 3. In some embodiments, q is 5.

In some embodiments, $L^A-R^A$ is $-L^2-L^3-L^4-L^7-R^A$. $L^2$ is unsubstituted $—C_1-C_6$ alkylene-NH—; $L^3$ is serine, asparagine, Asn-Ser, or Ser-Ser-Ser; $L^4$ is —C(═O)$CH_2CH_2$—; and $L^7$ is —NH—.

In some embodiments, $L^A-R^A$ is $-L^2-L^4-L^5-L^7-R^A$. $L^2$ is unsubstituted $—C_1-C_6$ alkylene- or unsubstituted $—C_1-C_6$ alkylene-NHC(═O)—; $L^4$ is $—(CH_2)_x—$NHC(═O)NH—$(CH_2)_v—$ or —NHC(═O)NH—$(CH_2)_v—$; $L^5$ is —O—; and $L^7$ is —NH—. In some embodiments, x is 1. In some embodiments, x is 5. In some embodiments, v is 2.

In some embodiments, $L^A-R^A$ is $-L^2-L^4-L^6-L^7-$; $L^2$ is unsubstituted $C_1-C_6$ alkylene-NH—C(═O)—; $L^4$ is $—(CH_2CH_2O)_v—CH_2CH_2—$ or $—(CH_2)_x—NR^{17}C$(═O)—; $L^6$ is $-L^8-L^9-L^{10}-R^A$; and $L^7$ is —NH—. In some embodiments, $L^A-R^A$ is $-L^2-L^4-L^6-L^7-R^A$. $L^2$ is unsubstituted $C_1-C_6$ alkylene-NHC(═O)—; $L^4$ is $—(CH_2)_x—NR^{17}C$(═O)—; $L^6$ is $-L^8-L^9-L^{10}-$; and $L^7$ is —NH—. In some embodiments, v is 5. In some embodiments, $L^9$ is substituted or unsubstituted heterocycloalkylene. In some embodiments, $L^8$ is $—(CH_2)_r—$. In some embodiments, $L^8$ is $—(CH_2)_r—NR^{14}C$(═O)—. In some embodiments, $L^9$ is substituted or unsubstituted arylene. In some embodiments, $L^{10}$ is absent. In some embodiments, $L^{10}$ is $—(CH_2)_q—$.

In some embodiments, $L^A-R^A$ is $-L^2-L^4-L^5-L^6-L^7-R^A$. $L^2$ is substituted or unsubstituted $—C_1-C_6$ alkylene-NHC(═O)—; $L^4$ is $—(CH_2CH_2O)_v—CH_2CH_2—$; $L^5$ is —NHC(═O)—; $L^6$ is $-L^8-L^9-L^{10}-$; and $L^7$ is —NH—. In some embodiments, $L^9$ is unsubstituted phenylene.

In some embodiments, $L^B-R^B$ is $-L^2-L^3-R^B$; $L^2$ is unsubstituted $—C_1-C_6$ alkylene-NH—; and $L^3$ is a natural or unnatural amino acid or natural or unnatural peptide, wherein the N atom of the amide linking the amino acids is optionally substituted with $—CH_3$. In some embodiments, the natural or unnatural amino acid is lysine. In some embodiments, the peptide is a tripeptide consisting of three glycines wherein the N atom of the amide linking the amino acids is substituted with $—CH_3$.

In some embodiments, $L^B-R^B$ is $-L^2-L^7-R^B$; $L^2$ is $—(CH_2CH_2O)_w—CH_2CH_2—$ or substituted or unsubstituted $C_1-C_6$ alkylene; and $L^7$ is —NH—. In some embodiments, $L^B-R^B$ is $-L^2-L^7-R^B$; $L^2$ is $—(CH_2CH_2O)_w—CH_2CH_2—$; and $L^7$ is —NH—. In some embodiments, w is 2. In some embodiments, $L^B$ is $-L^2-L^7-$; $L^2$ is unsubstituted $C_1-C_6$ alkylene; and $L^7$ is —NH—.

In some embodiments, $L^B$-$R^B$ is -$L^4$-$L^7$-$R^B$; $L^4$ is —$(CH_2)_x$—$NR^{17}$—$(CH_2)_v$; and $L^7$ is —NH—. In some embodiments, x is 3. In some embodiments, v is 5. In some embodiments, $R^{17}$ is —$CH_3$.

In some embodiments, $L^B$-$R^B$ is -$L^2$-$L^3$-$L^7$-$R^B$; $L^2$ is unsubstituted —$C_1$-$C_6$ alkylene-; $L^3$ is natural or unnatural amino acid or natural or unnatural peptide, wherein the N atom of the amide linking the amino acids is optionally substituted with —$CH_3$; and $L^7$ is absent or —NH—. In some embodiments, $L^3$ is Lys. In some embodiments, $L^3$ is Gly-Gly-Gly, wherein the N atom of the amide linking the amino acids is substituted with —$CH_3$.

In some embodiments, $L^B$-$R^B$ is -$L^2$-$L^4$-$L^7$-$R^B$; $L^2$ is unsubstituted —$C_1$-$C_6$ alkylene-, unsubstituted —$C_1$-$C_6$ alkylene-NHC(═O)—; $L^4$ is —$(CH_2)_v$—, —$(CH_2CH_2O)_v$—$CH_2CH_2$—, —$(CH_2)_v$—$NR^{17}$—$(CH_2)_v$, —NHC(═O)NH—O—$(CH_2)_v$—, —NHC(═O)$CH_2$—O—NH—C(═O)$(CH_2)_v$—, —$CH_2$C(—OH)$CH_2$—C(OH)—$CH_2CH_2$—, —$CH_2CH_2$C(═O)NH$CH_2CH_2$—, —$CH_2CH_2$—C(═O)NH—$(CH_2CH_2O)_v$$CH_2CH_2$—, —$CH_2$C(—OH)$CH_2$—C(OH)—$CH_2CH_2$—NHC(═O)$CH_2CH_2$C(═O)—NH$CH_2CH_2$—, or —$CH_2CH_2$C(═O)NH—$(CH_2CH_2O)_v$—$CH_2CH_2$—; and $L^7$ is —NH—. In some embodiments, $L^B$ is -$L^2$-$L^4$-$L^7$; $L^2$ is unsubstituted —$C_1$-$C_6$ alkylene- or unsubstituted —$C_1$-$C_6$ alkylene-NHC(═O)—; $L^4$ is —$(CH_2)_v$—, —$(CH_2CH_2O)_v$—$CH_2CH_2$—, —$(CH_2)_v$—$NR^{17}$—$(CH_2)_v$, —NHC(═O)NH—O—$(CH_2)_v$—, —NHC(═O)$CH_2$—O—NH—C(═O)$(CH_2)_v$—, —$CH_2$C(—OH)$CH_2$—C(OH)—$CH_2CH_2$—, —$CH_2CH_2$C(═O)NH$CH_2CH_2$—, —$CH_2CH_2$—C(═O)NH—$(CH_2CH_2O)_v$$CH_2CH_2$—, or —$CH_2$C(—OH)$CH_2$—C(OH)—$CH_2CH_2$—NHC(═O)$CH_2CH_2$C(═O)—NH$CH_2CH_2$—; and $L^7$ is —NH—. In some embodiments, v is 1. In some embodiments, v is 2. In some embodiments, v is 6. In some embodiments, $R^{17}$ is —$CH_3$.

In some embodiments, $L^B$-$R^B$ is -$L^2$-$L^6$-$L^7$-$R^B$; $L^2$ is unsubstituted —$C_1$-$C_6$ alkylene-, unsubstituted —$C_1$-$C_6$ alkylene-NH—, or unsubstituted —$C_1$-$C_6$ alkylene-NHC(═O)—; $L^6$ is -$L^8$-$L^9$-$L^{10}$-; and $L^7$ is —NH—. In some embodiments, $L^8$ is absent. In some embodiments, $L^8$ is —$(CH_2)_r$—. In some embodiments, $L^8$ is substituted or unsubstituted heterocycloalkylene. In some embodiments, $L^9$ is substituted or unsubstituted cycloalkylene. In some embodiments, $L^9$ is substituted or unsubstituted heterocycloalkylene. In some embodiments, $L^{10}$ is —$NR^w$—$(CH_2)_q$—. In some embodiments, $L^{10}$ is —$(CH_2)_q$—. In some embodiments, $L^{10}$ is —C(═O)—$(CH_2)_q$—. In some embodiments, q is 1. In some embodiments, q is 2. In some embodiments, q is 3. In some embodiments, q is 5.

In some embodiments, $L^B$-$R^B$ is -$L^2$-$L^3$-$L^4$-$L^7$-$R^B$. $L^2$ is unsubstituted —$C_1$-$C_6$ alkylene-NH—; $L^3$ is serine, asparagine, Asn-Ser, or Ser-Ser-Ser; $L^4$ is —C(═O)$CH_2CH_2$—; and $L^7$ is —NH—.

In some embodiments, $L^B$-$R^B$ is -$L^2$-$L^4$-$L^5$-$L^7$-$R^B$. $L^2$ is unsubstituted —$C_1$-$C_6$ alkylene- or unsubstituted —$C_1$-$C_6$ alkylene-NHC(═O)—; $L^4$ is —$(CH_2)_x$—NHC(═O)NH—$(CH_2)_v$— or —NHC(═O)NH—$(CH_2)_v$—; $L^5$ is —O—; and $L^7$ is —NH—. In some embodiments, x is 1. In some embodiments, x is 5. In some embodiments, v is 2.

In some embodiments, $L^B$-$R^B$ is -$L^2$-$L^4$-$L^6$-$L^7$-$R^B$. $L^2$ is unsubstituted $C_1$-$C_6$ alkylene-NH—C(═O)—; $L^4$ is —$(CH_2)_x$—$NR^{17}$C(═O)—; $L^6$ is -$L^8$-$L^9$-$L^{10}$; and $L^7$ is —NH—. In some embodiments, $L^B$-$R^B$ is -$L^2$-$L^4$-$L^6$-$L^7$-$R^B$. $L^2$ is unsubstituted $C_1$-$C_6$ alkylene-NHC(═O)—; $L^4$ is —$(CH_2CH_2O)_v$—$CH_2CH_2$— or —$(CH_2)_x$—$NR^{17}$C(═O)—; $L^6$ is -$L^8$-$L^9$-$L^{10}$-; and $L^7$ is —NH—. In some embodiments, v is 5. In some embodiments, $L^9$ is substituted or unsubstituted heterocycloalkylene. In some embodiments, $L^8$ is —$(CH_2)_r$—. In some embodiments, $L^8$ is —$(CH_2)_r$—$NR^{14}$C(═O)—. In some embodiments, $L^9$ is substituted or unsubstituted arylene. In some embodiments, $L^{10}$ is absent. In some embodiments, $L^{10}$ is —$(CH_2)_q$—.

In some embodiments, $L^B$-$R^B$ is -$L^2$-$L^4$-$L^5$-$L^6$-$L^7$-$R^B$. $L^2$ is substituted or unsubstituted —$C_1$-$C_6$ alkylene-NHC(═O)—; $L^4$ is —$(CH_2CH_2O)_v$—$CH_2CH_2$—; $L^5$ is —NHC(═O)—; $L^6$ is -$L^8$-$L^9$-$L^{10}$-; and $L^7$ is —NH—. In some embodiments, $L^9$ is unsubstituted phenylene.

In some embodiments, $R^5$ is absent or —$Z^B$-$L^B$-$R^B$; $Z^B$ is —O—, —NH—, —N(—$CH_3$)—, —C(═O)NH—, —C(═O)N(—$CH_3$)—, —NHC(═O)—; or —N(—$CH_3$)—C(═O)—; -$L^B$-$R^B$ is -$L^2$-$L^4$-$L^7$-$R^B$; $L^2$ is —$C_1$-$C_{20}$ alkylene, —$C_1$-$C_{20}$ alkylene-C(═O)$NR^{16}$—, —$C_1$-$C_{20}$ alkylene-NR $^{16}$C(═O)—, —$(CH_2CH_2O)_w$—, or —$(CH_2CH_2O)_w$—$CH_2CH_2$—; each $R^{16}$ is independently selected from H or $C_1$-$C_4$ alkyl; w is 1, 2, 3, 4, 5, or 6; $L^4$ is absent, —$(CH_2)_v$—, —$CH_2$—$(OCH_2CH_2)_v$—, —$(CH_2CH_2O)_v$—$CH_2CH_2$—, —C(═O)$CH_2CH_2$—, —$(CH_2)_x$—NHC(═O)—$(CH_2)_v$—, —$(CH_2)_x$—C(═O)NH—$(CH_2)_v$—, —$CH_2CH_2$—C(═O)NH—$(CH_2CH_2O)_v$$CH_2CH_2$—, —$(CH_2)_x$—$NR^{17}$—$(CH_2)_v$—; $R^{17}$ is H or —$C_1$-$C_6$ alkyl; each x is independently 1, 2, 3, 4, 5 or 6; each v is independently 1, 2, 3, 4, 5, 6, 7, 8, 9, or 10; $L^7$ is absent, —NH—, or —N($CH_3$)—; $R^B$ is a chelating moiety or a radionuclide complex thereof. In some embodiments, $R^5$ is absent or —$Z^B$-$L^B$-$R^B$; $Z^B$ is —O—, —NH—, —C(═O)NH—, or —NHC(═O)—; -$L^B$-$R^B$ is -$L^2$-$L^4$-$L^7$-$R^B$; $L^2$ is —$C_1$-$C_6$ alkylene, or —$(CH_2CH_2O)_w$—$CH_2CH_2$—; w is 1, 2, 3, 4, 5, or 6; $L^4$ is absent; $L^7$ is —NH—; $R^B$ is a chelating moiety or a radionuclide complex thereof. In some embodiments, $R^5$ is absent or —$Z^B$-$L^B$-$R^B$; $Z^B$ is —O—, —NH—, —C(═O)NH—, or —NHC(═O)—; -$L^B$-$R^B$ is -$L^2$-$L^4$-$L^7$-$R^B$; $L^2$ is —$C_1$-$C_6$ alkylene, —$C_1$-$C_6$ alkylene-C(═O)NH—, —$C_1$-$C_6$ alkylene-NHC(═O)—; $L^4$ is absent, —$(CH_2)_v$—, —$CH_2$—$(OCH_2CH_2)_v$—, —$(CH_2CH_2O)_v$—$CH_2CH_2$—, —C(═O)$CH_2CH_2$—, —$(CH_2)_x$—NHC(═O)—$(CH_2)_v$—, —$(CH_2)_x$—C(═O)NH—$(CH_2)_v$—, —$CH_2CH_2$—C(═O)NH—$(CH_2CH_2O)_v$$CH_2CH_2$—; each x is independently 1, 2, 3, 4, 5 or 6; each v is independently 1, 2, 3, 4, 5, or 6; $L^7$ is —NH—; $R^B$ is a chelating moiety or a radionuclide complex thereof. In some embodiments, $R^5$ is absent or —$Z^B$-$L^B$-$R^B$; $Z^B$ is —O—, —NH—, —C(═O)NH—, or —NHC(═O)—; -$L^B$-$R^B$ is -$L^2$-$L^4$-$L^7$-$R^B$; $L^2$ is —$C_1$-$C_6$ alkylene, —$C_1$-$C_6$ alkylene-C(═O)NH—, —$C_1$-$C_6$ alkylene-NHC(═O)—; $L^4$ is absent, —$(CH_2)_v$—, —$(CH_2)_x$—NHC(═O)—$(CH_2)_v$—, or —$(CH_2)_x$—C(═O)NH—$(CH_2)_v$—; each x is independently 1, 2, 3, 4, 5 or 6; each v is independently 1, 2, 3, 4, 5, or 6; $L^7$ is —NH—; $R^B$ is a chelating moiety or a radionuclide complex thereof. In some embodiments, $R^B$ is

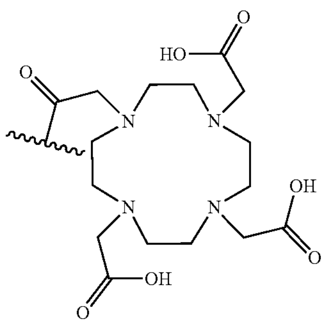

or

-continued

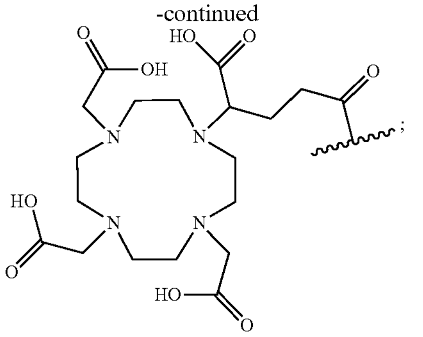

or a radionuclide complex thereof. In some embodiments, $R^B$ is

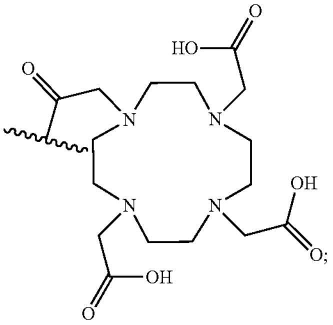 [SMILES: *C(=O)CN1CCN(CC(=O)O)CCN(CC(=O)O)CCN(CC(=O)O)CC1]

or a radionuclide complex thereof.

In some embodiments, $R^6$ is absent or $-Z^A-L^A-R^A$; $Z^A$ is —O—, —NH—, —N(—$CH_3$)—, —C(═O)NH—, —C(═O)N(—$CH_3$)—, —NHC(═O)—; or —N(—$CH_3$)—C(═O)—; $L^A-R^A$ is $-L^2-L^4-L^7-R^A$; $L^2$ is —$C_1$-$C_{20}$ alkylene, —$C_1$-$C_{20}$ alkylene-C(═O)$NR^{16}$—, —$C_1$-$C_{20}$ alkylene-$NR^{16}$C(═O)—, —$(CH_2CH_2O)_w$—, or —$(CH_2CH_2O)_w$—$CH_2CH_2$—; each $R^{16}$ is independently selected from H or $C_1$-$C_4$ alkyl; w is 1, 2, 3, 4, 5, or 6; $L^4$ is absent, —$(CH_2)_v$—, —$CH_2$—$(OCH_2CH_2)_v$—, —$(CH_2CH_2O)_v$—$CH_2CH_2$—, —C(═O)$CH_2CH_2$—, —$(CH_2)_x$—NHC(═O)—$(CH_2)_v$—, —$(CH_2)_x$—C(═O)NH—$(CH_2)_v$—, —$CH_2CH_2$—C(═O)NH—$(CH_2CH_2O)_v CH_2CH_2$—, —$(CH_2)_x$—$NR^{17}$—$(CH_2)_v$—; $R^{17}$ is H or —$C_1$-$C_6$ alkyl; each x is independently 1, 2, 3, 4, 5 or 6; each v is independently 1, 2, 3, 4, 5, 6, 7, 8, 9, or 10; $L^7$ is —NH— or —N($CH_3$)—; $R^A$ is a chelating moiety or a radionuclide complex thereof. In some embodiments, $R^6$ is absent or $-Z^A-L^A-R^A$; $Z^A$ is —O—, —NH—, —C(═O)NH—, or —NHC(═O)—; $L^A-R^A$ is $-L^2-L^4-L^7-R^A$; $L^2$ is —$C_1$-$C_6$ alkylene, or —$(CH_2CH_2O)_w$—$CH_2CH_2$—; w is 1, 2, 3, 4, 5, or 6; $L^4$ is absent; $L^7$ is —NH—; $R^A$ is a chelating moiety or a radionuclide complex thereof. In some embodiments, $R^6$ is absent or $-Z^A-L^A-R^A$; $Z^A$ is —O—, —NH—, —C(═O)NH—, or —NHC(═O)—; $L^A-R^A$ is $-L^2-L^4-L^7-R^A$; $L^2$ is —$C_1$-$C_6$ alkylene, —$C_1$-$C_6$ alkylene-C(═O)NH—, —$C_1$-$C_6$ alkylene-NHC(═O)—; $L^4$ is absent, —$(CH_2)_v$—, —$CH_2$—$(OCH_2CH_2)_v$—, —$(CH_2CH_2O)_v$—$CH_2CH_2$—, —C(═O)$CH_2CH_2$—, —$(CH_2)_x$—NHC(═O)—$(CH_2)_v$—, —$(CH_2)_x$—C(═O)NH—$(CH_2)_v$—, —$CH_2CH_2$—C(═O)NH—$(CH_2CH_2O)_v CH_2CH_2$—; each x is independently 1, 2, 3, 4, 5 or 6; each v is independently 1, 2, 3, 4, 5, or 6; $L^7$ is —NH—; $R^A$ is a chelating moiety or a radionuclide complex thereof. In some embodiments, $R^6$ is absent or $-Z^A-L^A-R^A$; $Z^A$ is —O—, —NH—, —C(═O)NH—, or —NHC(═O)—; $L^A-R^A$ is $-L^2-L^4-L^7-R^A$; $L^2$ is —$C_1$-$C_6$ alkylene, —$C_1$-$C_6$ alkylene-C(═O)NH—, —$C_1$-$C_6$ alkylene-NHC(═O)—; $L^4$ is absent, —$(CH_2)_v$—, —$(CH_2)_x$—NHC(═O)—$(CH_2)_v$—, or —$(CH_2)_x$—C(═O)NH—$(CH_2)_v$—; each x is independently 1, 2, 3, 4, 5 or 6; each v is independently 1, 2, 3, 4, 5, or 6; $L^7$ is —NH—; $R^A$ is a chelating moiety or a radionuclide complex thereof. In some embodiments, $R^A$ is:

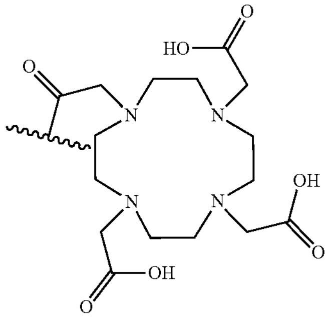

or

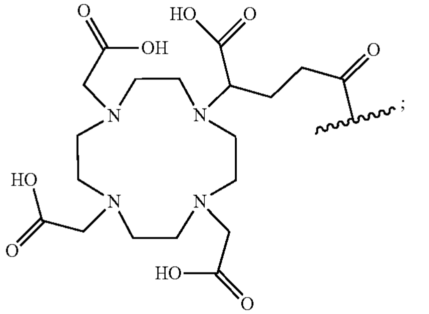

or a radionuclide complex thereof. In some embodiments, $R^A$ is:

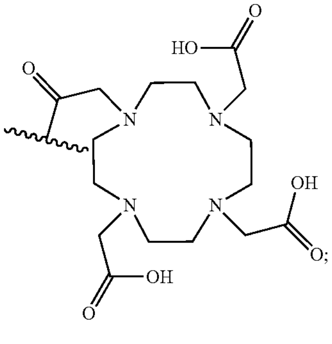 [SMILES: *C(=O)CN1CCN(CC(=O)O)CCN(CC(=O)O)CCN(CC(=O)O)CC1]

or a radionuclide complex thereof.

In some embodiments, the linker $-L^A-$ or $-L^B-$ is selected from (if one is present), or $-L^A-$ and $-L^B-$ each are independently selected from (if both are present) the following linkers:

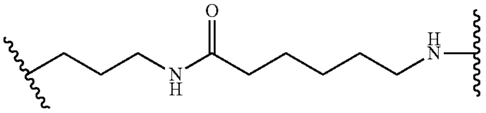,
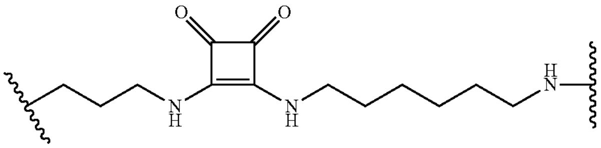,
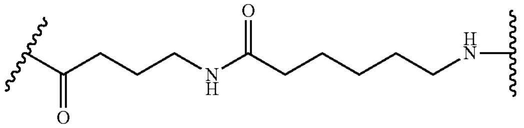,
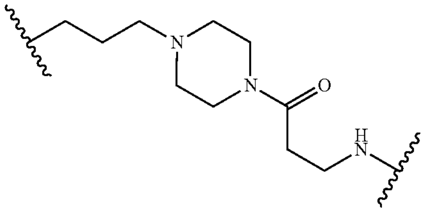,
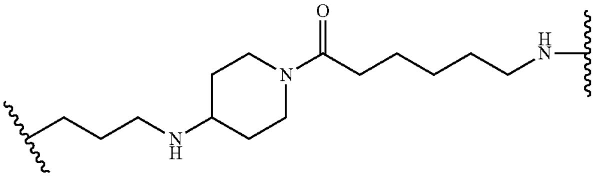,
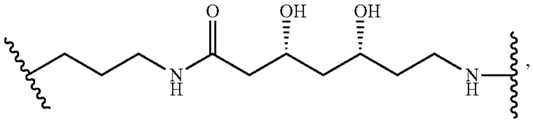,
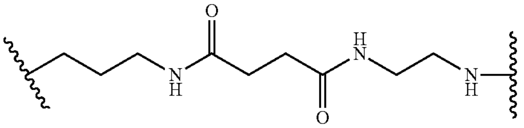,
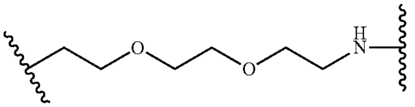,
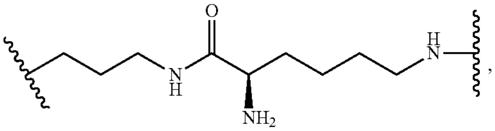,
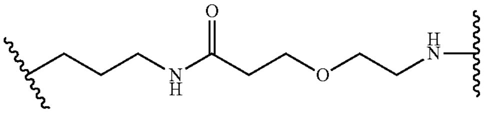,
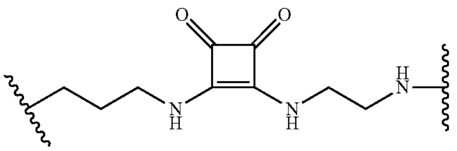,
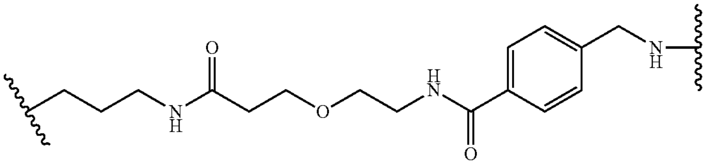,
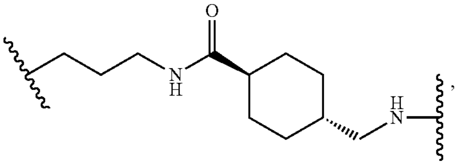,
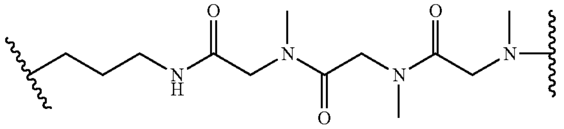,
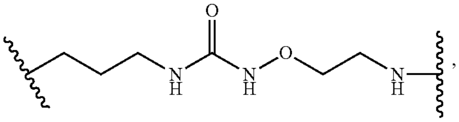,
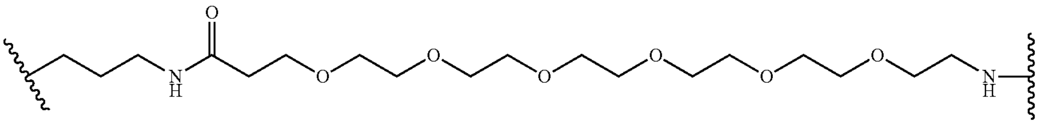,
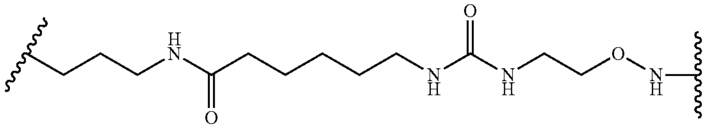,
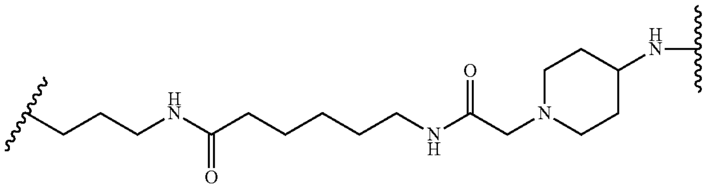, -continued
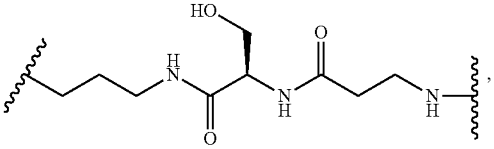,
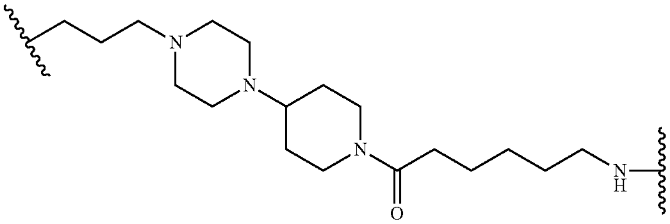,
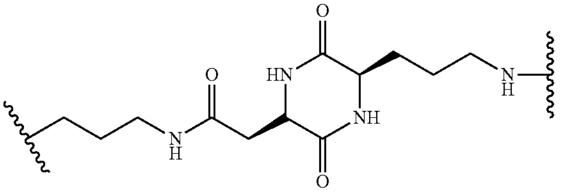,
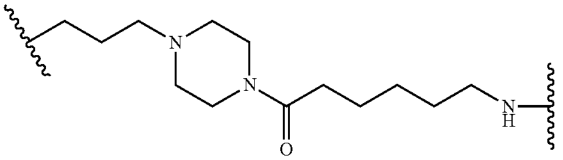,
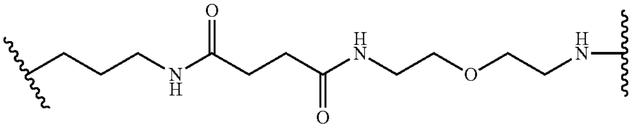,
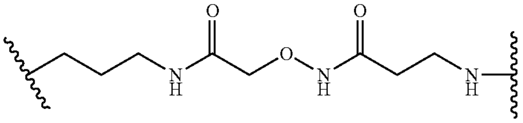,
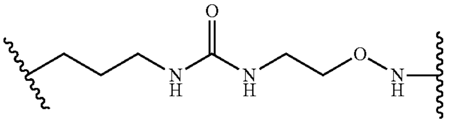,
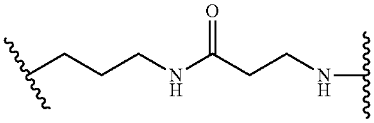,
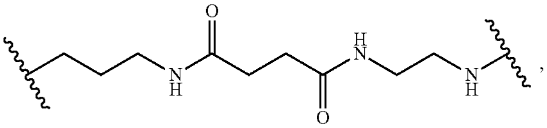,
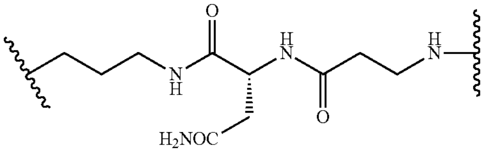,
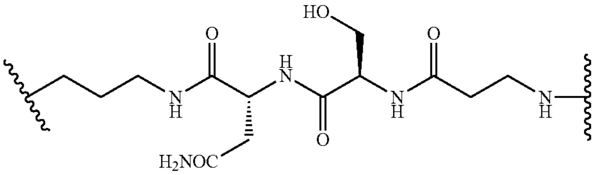,
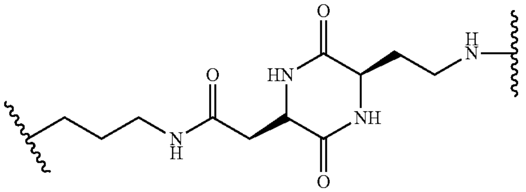,
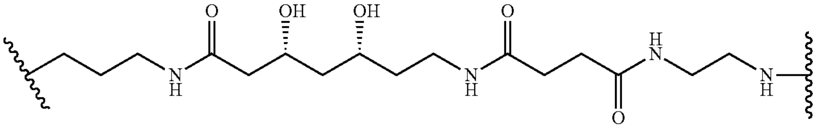,
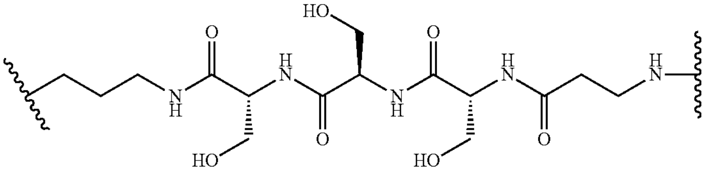,
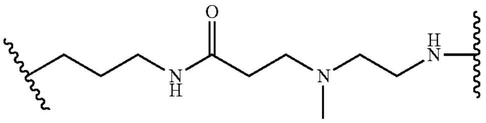,
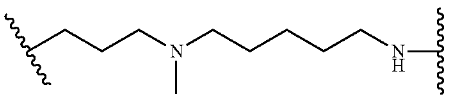,
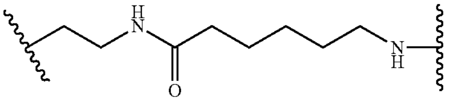, or
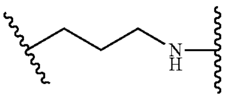.

some embodiments, the linker is -$L^A$-. In some embodiments, the linker is -$L^B$-.

In some embodiments, the linker -$L^A$- or -$L^B$- (whichever is present) is

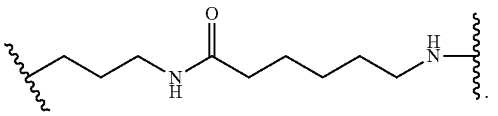 [SMILES: *CCCNC(=O)CCCCCN*]

In some embodiments, the linker -$L^A$- or -$L^B$- (whichever is present) is

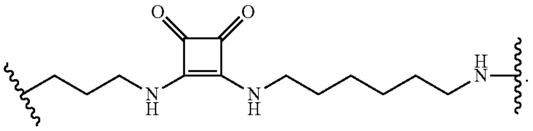 [SMILES: *CCCNc1c(NCCCCCCN*)c(=O)c1=O]

In some embodiments, the linker -$L^A$- or -$L^B$- (whichever is present) is

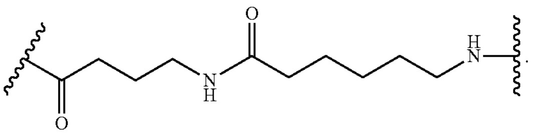 [SMILES: *NCCCCCC(=O)NCCCC(*)=O]

In some embodiments, -$L^A$ is

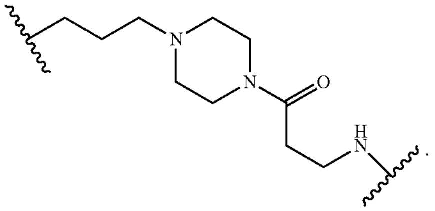 [SMILES: *CCCN1CCN(C(=O)CCN*)CC1]

In some embodiments, the linker -$L^A$- or -$L^B$- (whichever is present) is

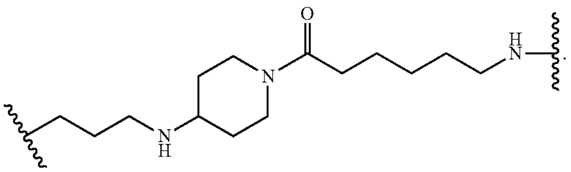 [SMILES: *CCCNC1CCN(C(=O)CCCCCN*)CC1]

In some embodiments, the linker -$L^A$- or -$L^B$- (whichever is present) is

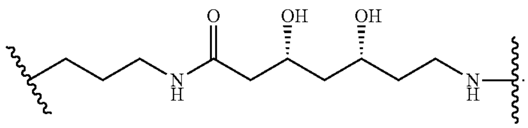 [SMILES: *CCCNC(=O)C[C@H](O)C[C@H](O)CCN*]

In some embodiments, the linker -$L^A$- or -$L^B$- (whichever is present) is

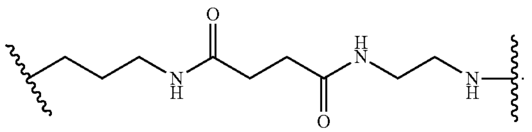 [SMILES: *CCCNC(=O)CCC(=O)NCCN*]

In some embodiments, the linker -$L^A$- or -$L^B$- (whichever is present) is

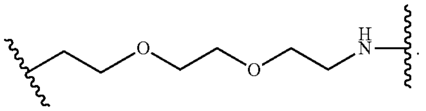 [SMILES: *CCOCCOCCN*]

In some embodiments, the linker -$L^A$- or -$L^B$- (whichever is present) is

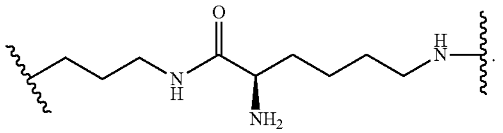 [SMILES: *CCCNC(=O)[C@H](N)CCCCN*]

In some embodiments, the linker -$L^A$- or -$L^B$- (whichever is present) is

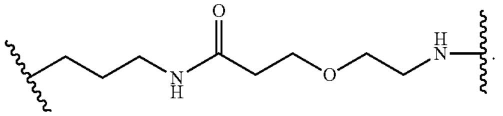 [SMILES: *CCCNC(=O)CCOCCN*]

In some embodiments, the linker -$L^A$- or -$L^B$-(whichever is present) is

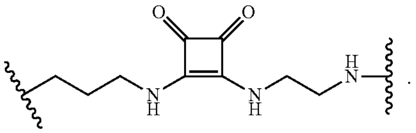 [SMILES: *CCCNc1c(NCCN*)c(=O)c1=O]

In some embodiments, the linker -$L^A$- or -$L^B$- (whichever is present) is

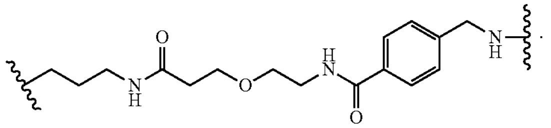 [SMILES: *CCCNC(=O)CCOCCNC(=O)c1ccc(CN*)cc1]

In some embodiments, the linker -$L^A$- or -$L^B$- (whichever is present) is

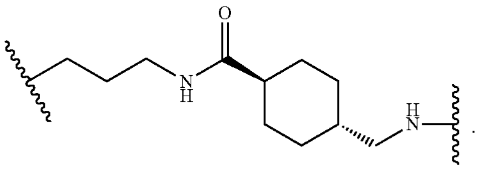 [SMILES: *CCCNC(=O)[C@H]1CC[C@H](CN*)CC1]

In some embodiments, the linker -$L^A$- or -$L^B$- (whichever is present) is

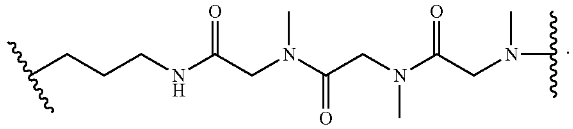 [SMILES: *CCCNC(=O)CN(C)C(=O)CN(C)C(=O)CN(*)C]

In some embodiments, the linker -$L^A$- or -$L^B$- (whichever is present) is

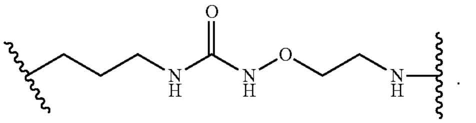 [SMILES: *CCCNC(=O)NOCCN*]

In some embodiments, the linker -$L^A$- or -$L^B$-(whichever is present) is

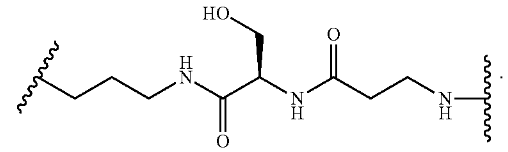

In some embodiments, the linker -$L^A$- or -$L^B$- (whichever is present) is

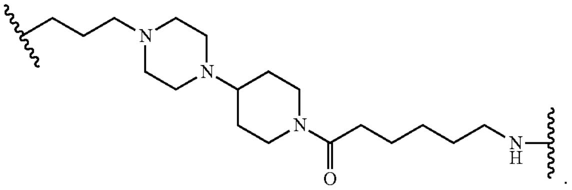

In some embodiments, the linker -$L^A$- or -$L^B$-(whichever is present) is

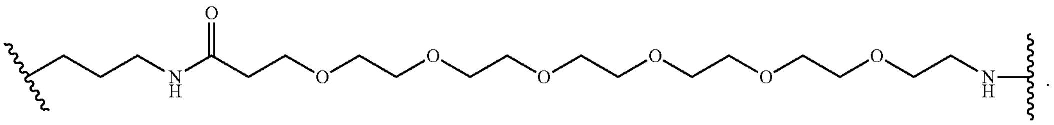 [SMILES: *CCCNC(=O)CCOCCOCCOCCOCCOCCOCCN*]

In some embodiments, the linker -$L^A$- or -$L^B$- (whichever is present) is

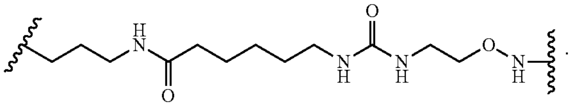 [SMILES: *CCCNC(=O)CCCCCNC(=O)NCCON* ; "."]

In some embodiments, the linker -$L^A$- or -$L^B$-(whichever is present) is

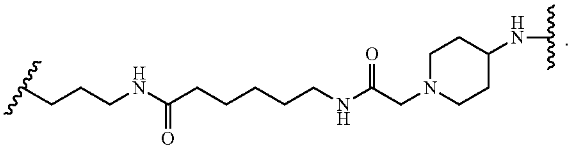 [SMILES: *CCCNC(=O)CCCCCNC(=O)CN1CCC(N*)CC1 ; "."]

n some embodiments, the linker -$L^A$- or -$L^B$- (whichever is present) is

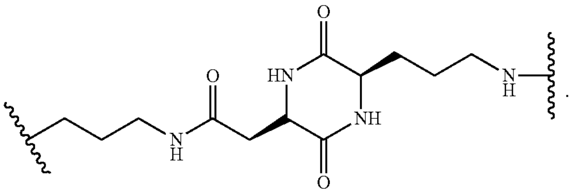

In some embodiments, the linker -$L^A$- or -$L^B$- (whichever is present) is

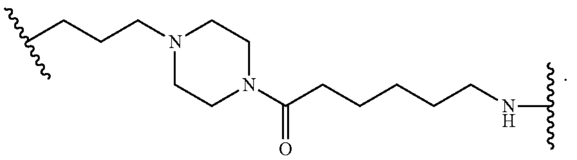 [SMILES: *CCCN1CCN(C(=O)CCCCCN*)CC1 ; "."]

In some embodiments, the linker -$L^A$- or -$L^B$- (whichever is present) is

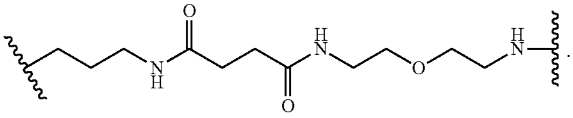 [SMILES: *CCCNC(=O)CCC(=O)NCCOCCN*]

In some embodiments, the linker -$L^A$- or -$L^B$-(whichever is present) is

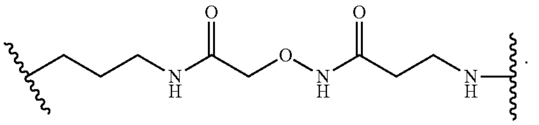 [SMILES: *CCCNC(=O)CONC(=O)CCN*]

In some embodiments, the linker -$L^A$- or -$L^B$- (whichever is present) is

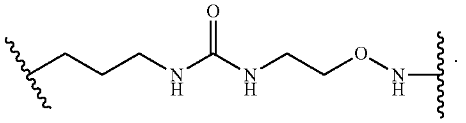 [SMILES: *CCCNC(=O)NCCON* ; "."]

In some embodiments, the linker -$L^A$- or -$L^B$- (whichever is present) is

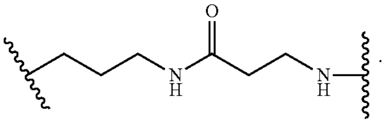 [SMILES: *CCCNC(=O)CCN* ; "."]

In some embodiments, the linker -$L^A$- or -$L^B$- (whichever is present) is

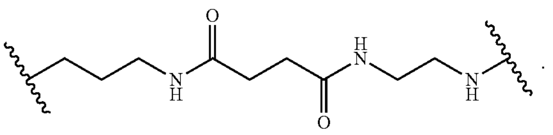 [SMILES: *CCCNC(=O)CCC(=O)NCCN* ; "."]

In some embodiments, the linker -$L^A$- or -$L^B$- (whichever is present) is

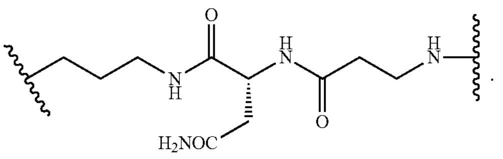 [SMILES: *CCCNC(=O)[C@@H](CC(N)=O)NC(=O)CCN* ; "."]

In some embodiments, the linker -$L^A$- or -$L^B$- (whichever is present) is

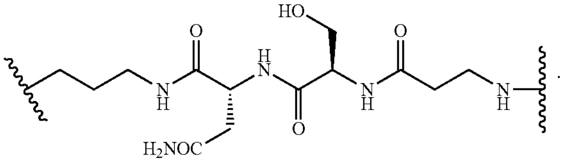 [SMILES: *CCCNC(=O)[C@@H](CC(N)=O)NC(=O)[C@@H](CO)NC(=O)CCN* ; "."]

In some embodiments, the linker -$L^A$- or -$L^B$-(whichever is present) is

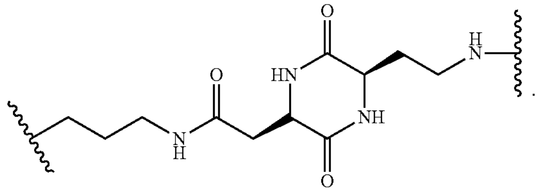

In some embodiments, the linker -$L^A$- or -$L^B$- (whichever is present) is

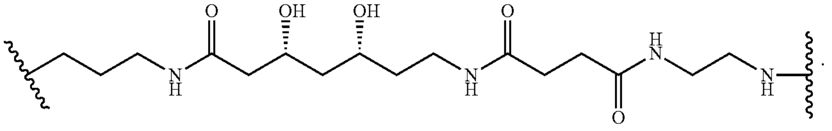 [SMILES: *CCCNC(=O)C[C@H](O)C[C@H](O)CCNC(=O)CCC(=O)NCCN* ; "."]

In some embodiments, the linker -$L^A$- or -$L^B$- (whichever is present) is

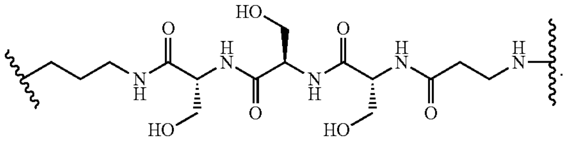 [SMILES: *CCCNC(=O)[C@@H](CO)NC(=O)[C@@H](CO)NC(=O)[C@@H](CO)NC(=O)CCN*]

In some embodiments, the linker -$L^A$- or -$L^B$-(whichever is present) is

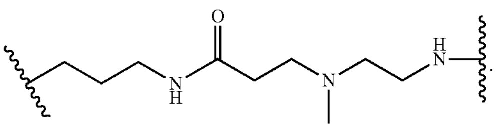 [SMILES: *CCCNC(=O)CCN(C)CCN*]

In some embodiments, the linker $-L^A-$ or $-L^B-$ (whichever is present) is

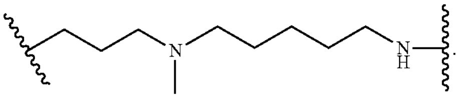 [SMILES: *CCCN(C)CCCCCN*]

In some embodiments, the linker $-L^A-$ or $-L^B-$ (whichever is present) is

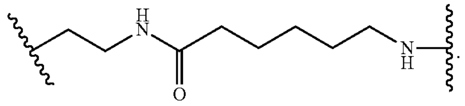 [SMILES: *CCNC(=O)CCCCCN*]

In some embodiments, the linker $-L^A-$ or $-L^B-$ (whichever is present) is

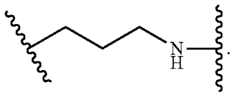 [SMILES: *CCCN*]

In some embodiments, the linker is $-L^A-$. In some embodiments, the linker is $-L^B-$.

Representative Linker and Chelating Moieties

In some embodiments, $-L^A-R^A$ is

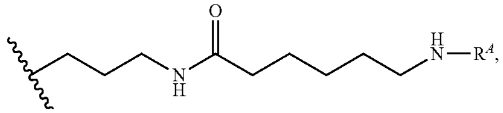

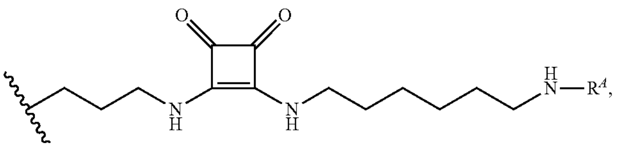

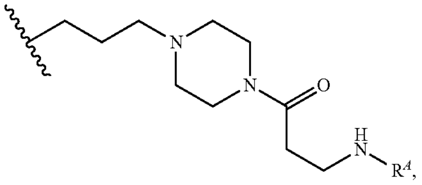

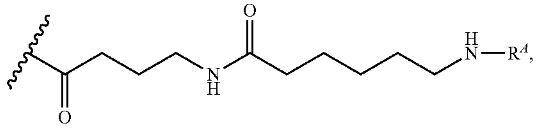

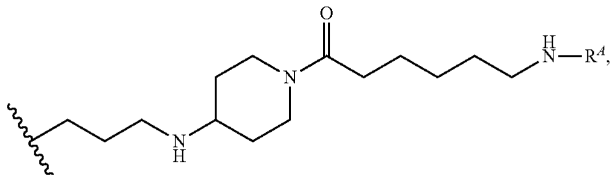

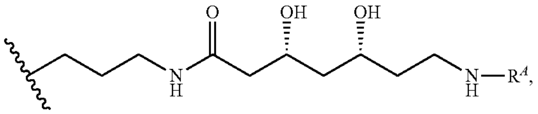

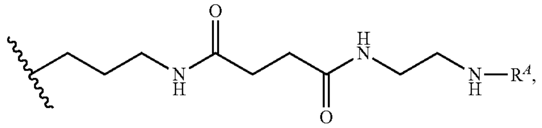

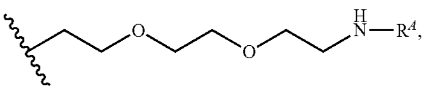

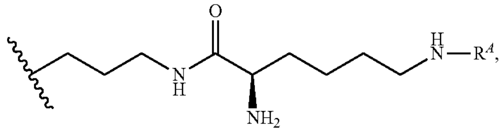

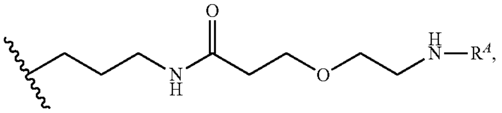

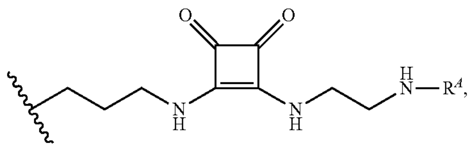

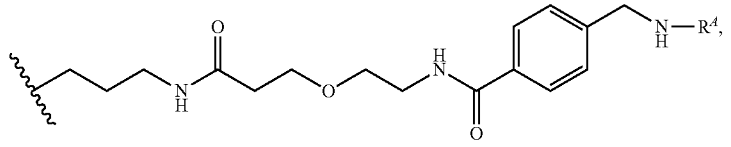

-continued
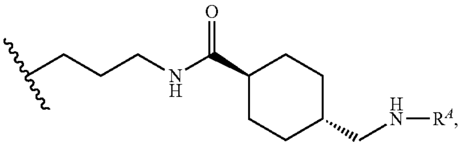
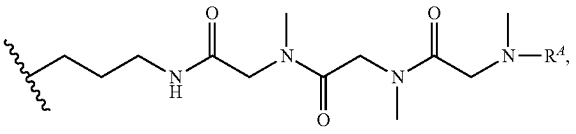
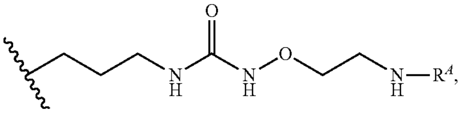
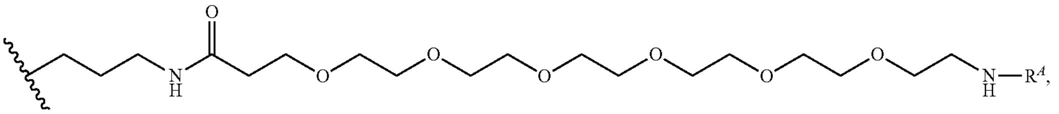
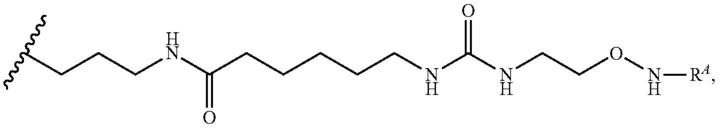
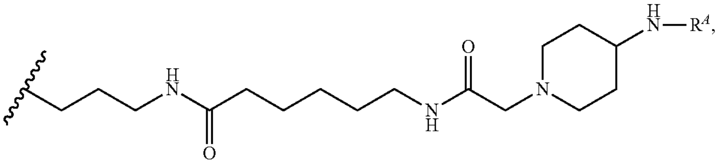
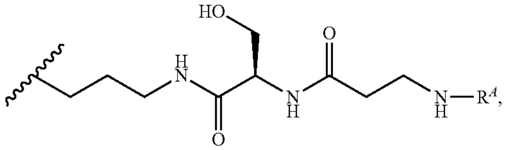
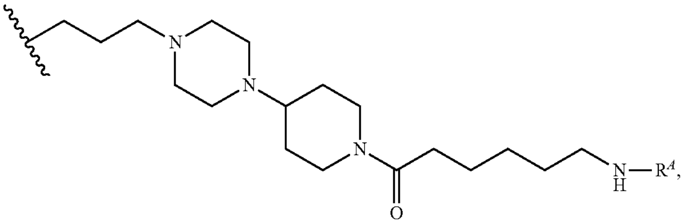
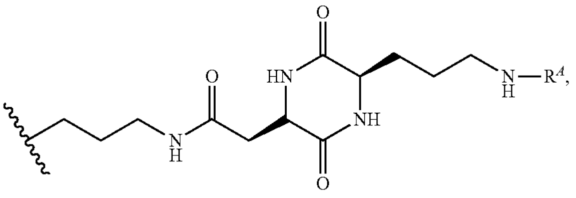
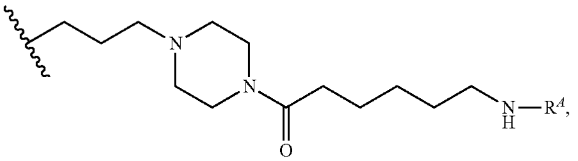
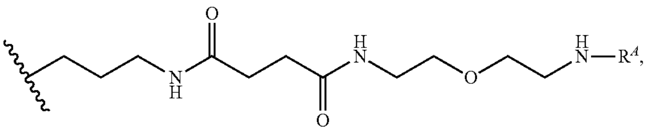
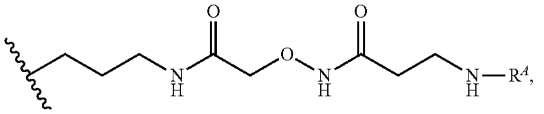
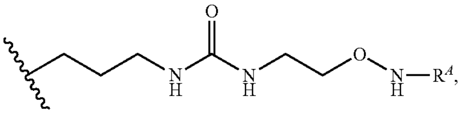
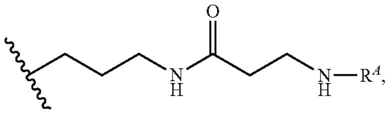
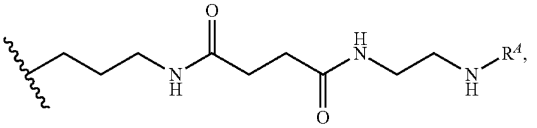
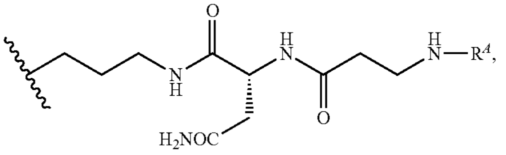

-continued
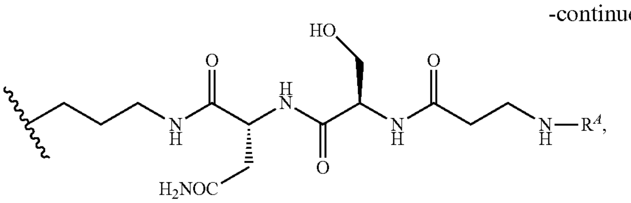
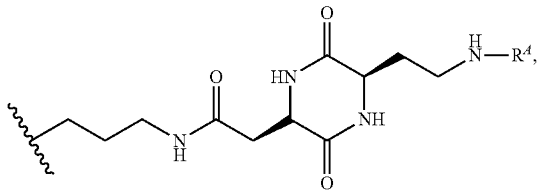
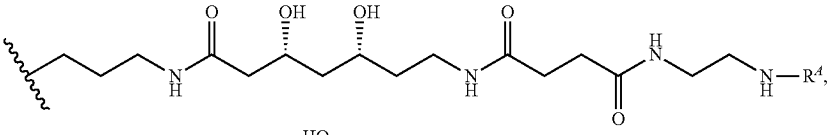
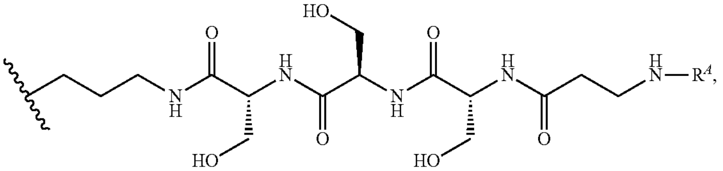
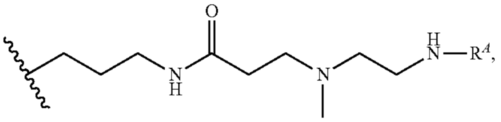
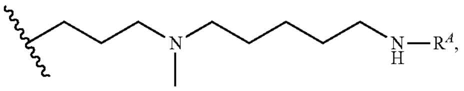
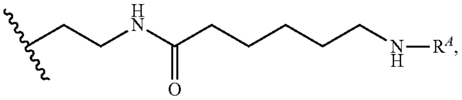
or
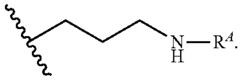
In some embodiments, —$R^A$ in the preceding embodiment is
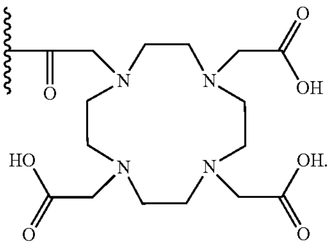 [SMILES: *C(=O)CN1CCN(CC(=O)O)CCN(CC(=O)O)CCN(CC(=O)O)CC1]
In some embodiments, -$L^A$-$R^A$ is
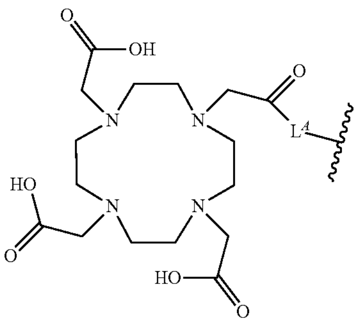
when —$R^A$ in the preceding embodiments is
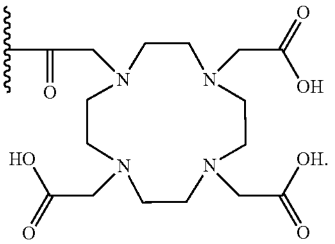 [SMILES: *C(=O)CN1CCN(CC(=O)O)CCN(CC(=O)O)CCN(CC(=O)O)CC1]
In some embodiments, -$L^A$-$R^A$— is
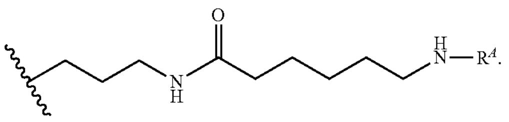
In some embodiments, -$L^A$-$R^A$— is
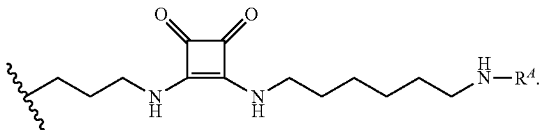

In some embodiments, $-L^A-R^A-$ is

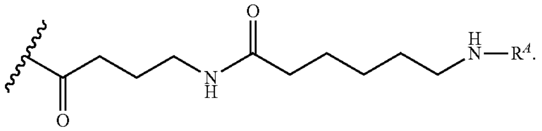

In some embodiments, $-L^A-R^A-$ is

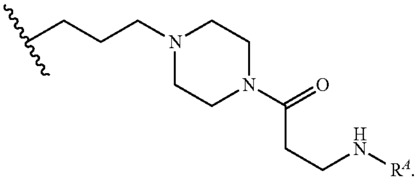

In some embodiments, $-L^A-R^A-$ is

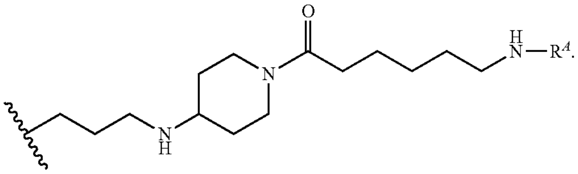

In some embodiments, $-L^A-R^A-$ is

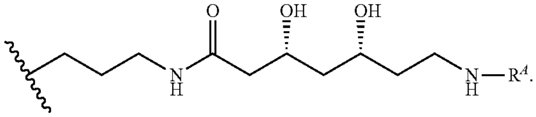

In some embodiments, $-L^A-R^A-$ is

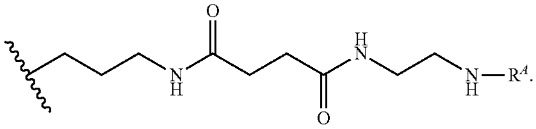

In some embodiments, $-L^A-R^A-$ is

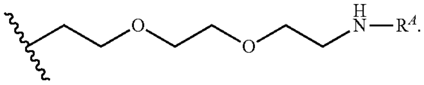

In some embodiments, $-L^A-R^A-$ is

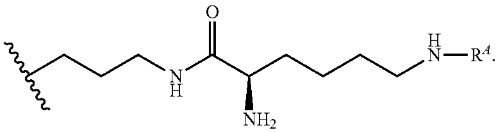

In some embodiments, $-L^A-R^A-$ is

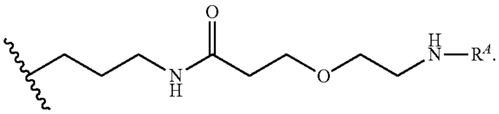

In some embodiments, $-L^A-R^A-$ is

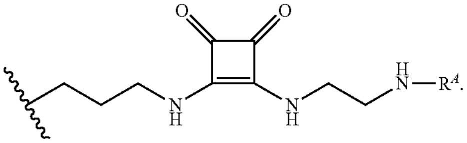

In some embodiments, $-L^A-R^A-$ is

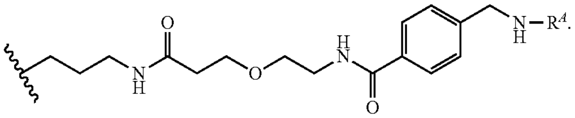

In some embodiments, $-L^A-R^A-$ is

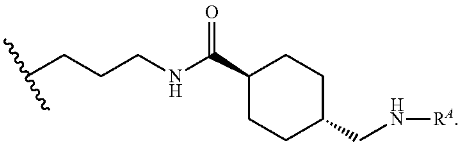

In some embodiments, $-L^A-R^A-$ is

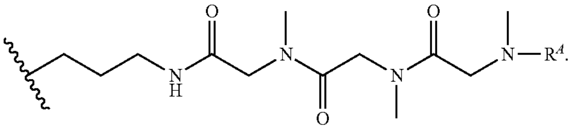

In some embodiments, $-L^A-R^A-$ is

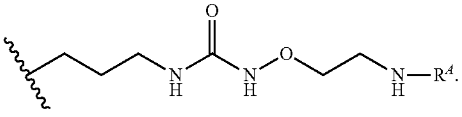

In some embodiments, $-L^A-R^A—$ is

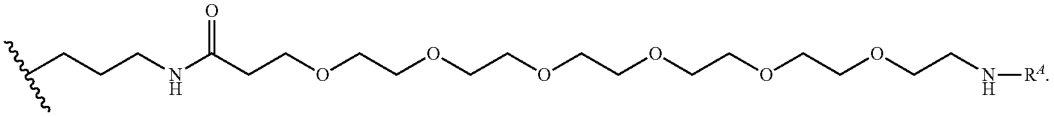

In some embodiments, $-L^A-R^A—$ is

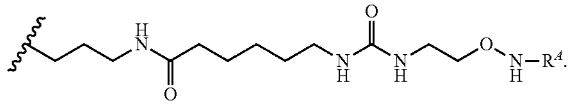

In some embodiments, $-L^A-R^A—$ is

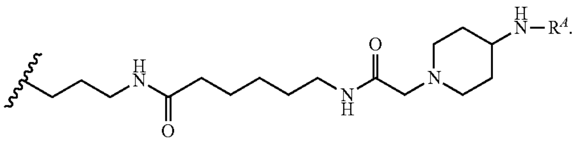

In some embodiments, $-L^A-R^A—$ is

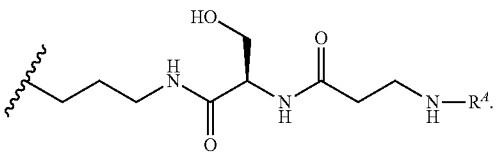

In some embodiments, $-L^A-R^A$ is

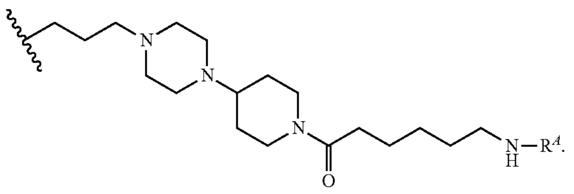

In some embodiments, $-L^A-R^A—$ is

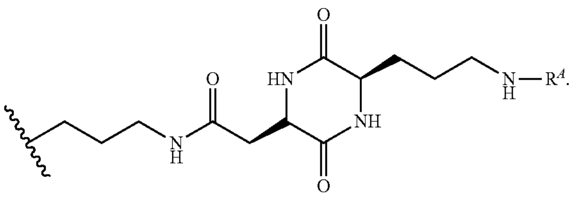

In some embodiments, $-L^A-R^A—$ is

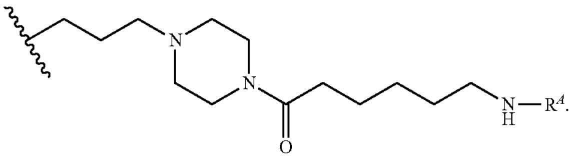

In some embodiments, $-L^A-R^A$ is

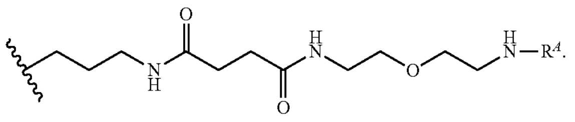

In some embodiments, $-L^A-R^A—$ is

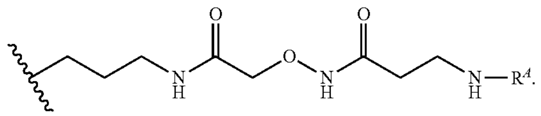

In some embodiments, $-L^A-R^A$ is

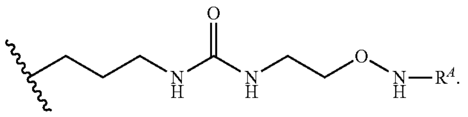

In some embodiments, $-L^A-R^A$ is

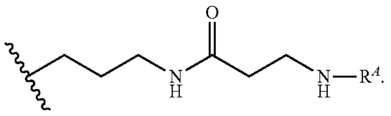

In some embodiments, $-L^A-R^A—$ is

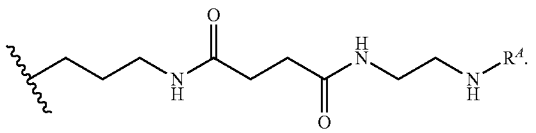

In some embodiments, $-L^A-R^A-$ is

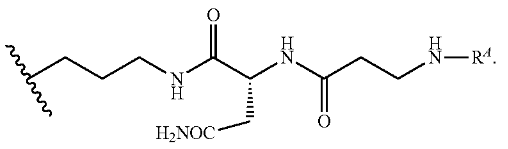

In some embodiments, $-L^A-R^A-$ is

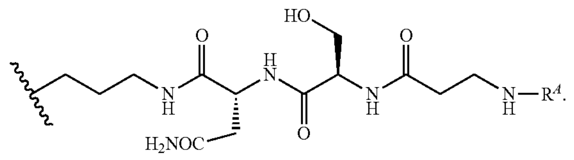

In some embodiments, $-L^A-R^A-$ is

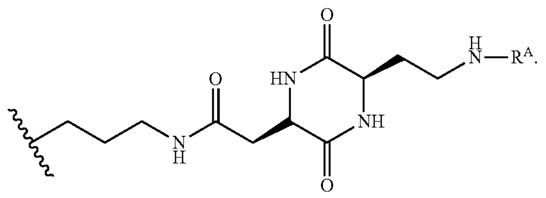

In some embodiments, $-L^A-R^A-$ is

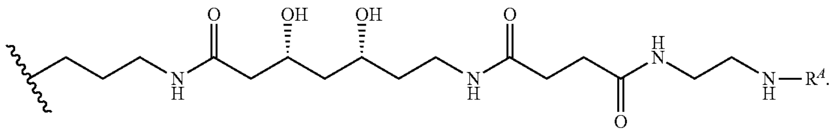

In some embodiments, $-L^A-R^A-$ is

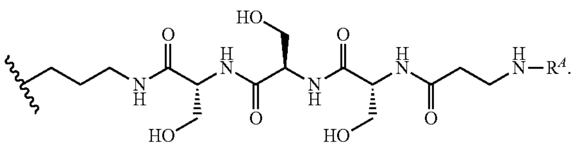

In some embodiments, $-L^A-R^A$ is

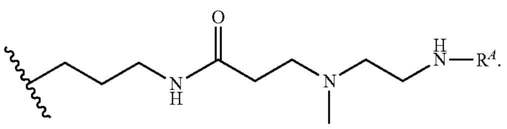

In some embodiments, $-L^A-R^A-$ is

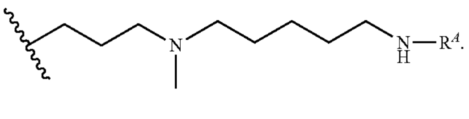

In some embodiments, $-L^A-R^A$ is

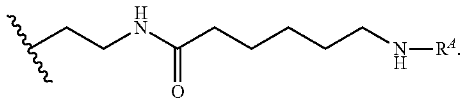

In some embodiments, $-L^A-R^A-$ is

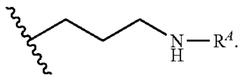

In some embodiments, $-R^A$ in the preceding embodiments is

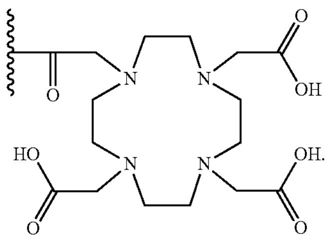 [SMILES: *C(=O)CN1CCN(CC(=O)O)CCN(CC(=O)O)CCN(CC(=O)O)CC1]

In some embodiments, $-L^A-R^A$ is

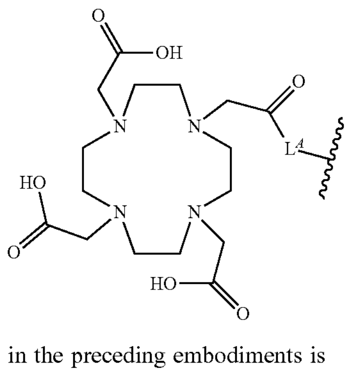

when $-R^A$ in the preceding embodiments is

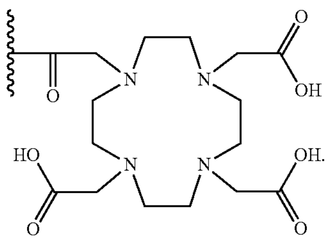 [SMILES: *C(=O)CN1CCN(CC(=O)O)CCN(CC(=O)O)CCN(CC(=O)O)CC1]

In some embodiments, $-L^B-R^B$ is
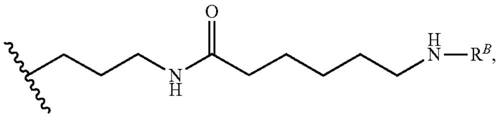
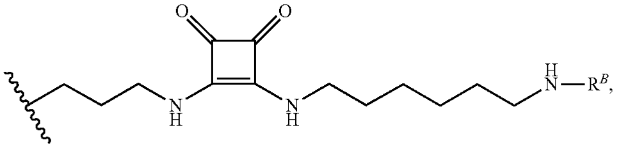
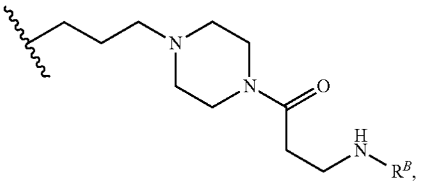
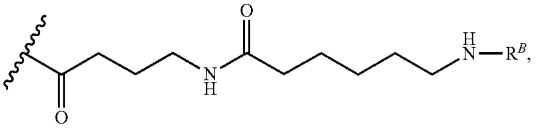
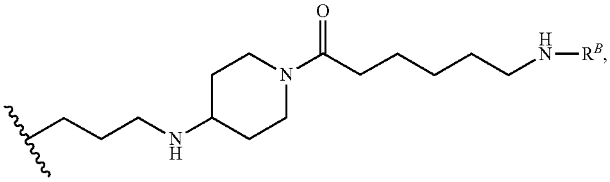
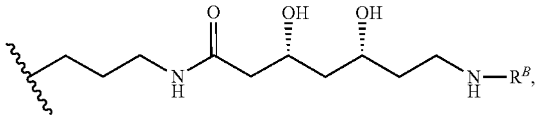
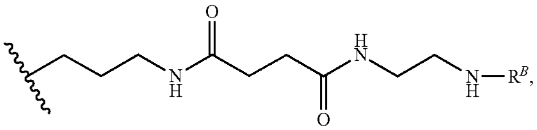
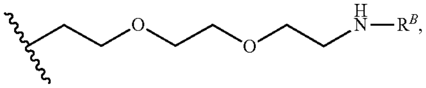
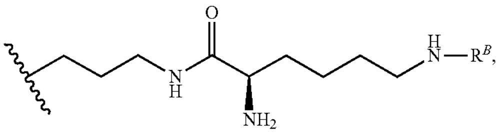
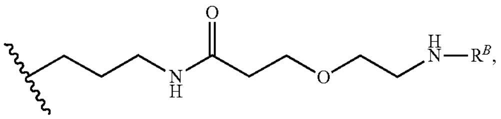
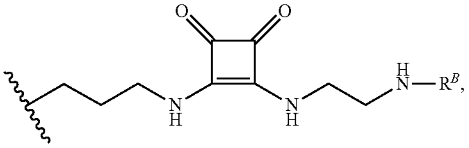
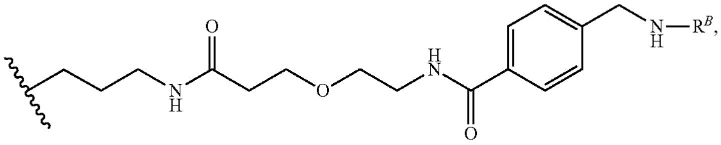
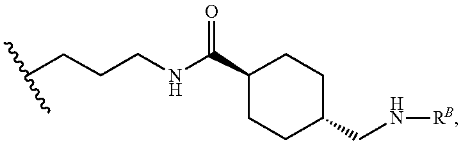
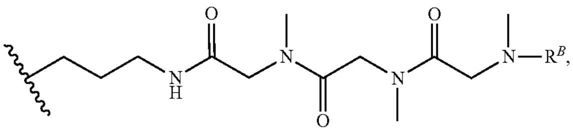
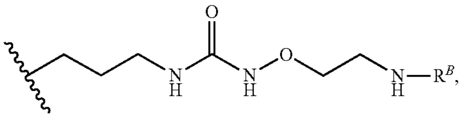
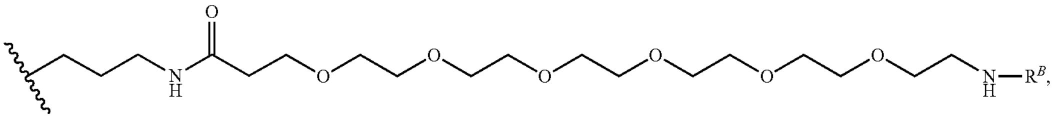

-continued
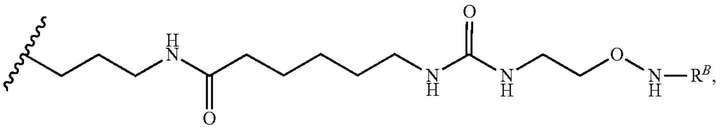
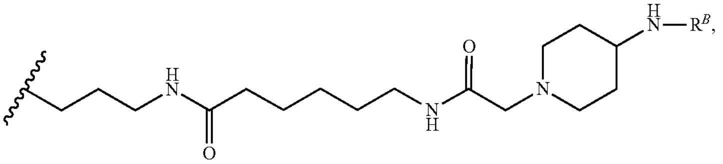
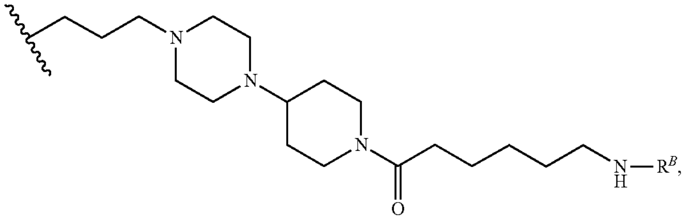
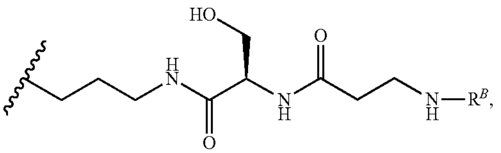
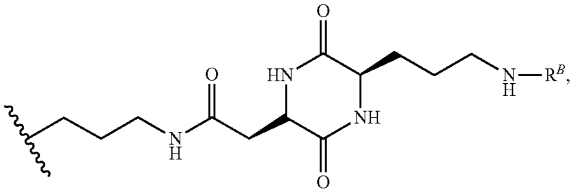
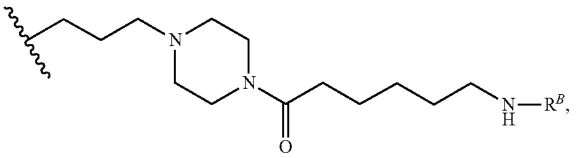
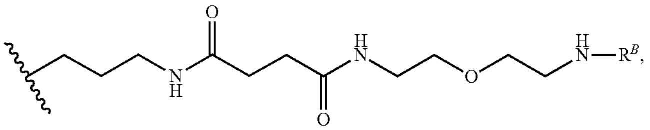
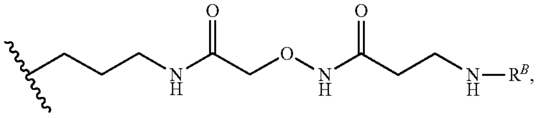
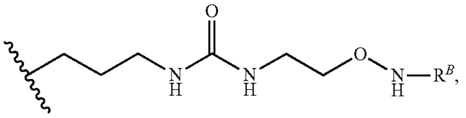
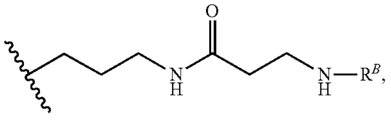
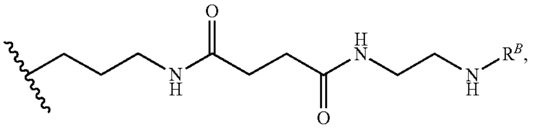
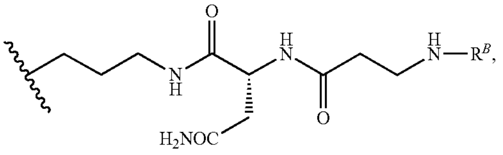
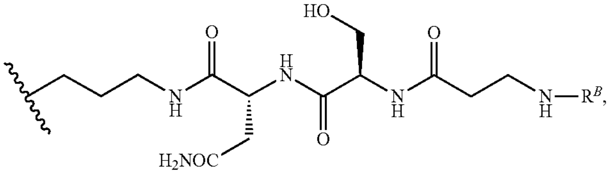
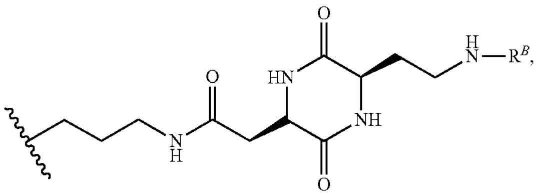
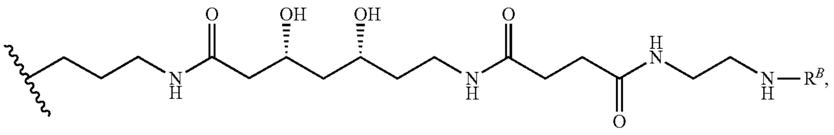
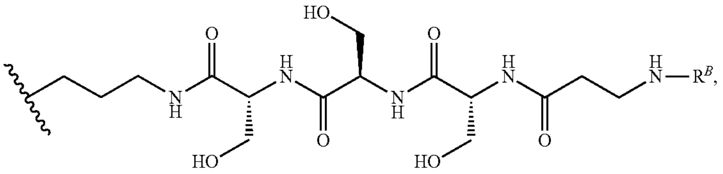

-continued
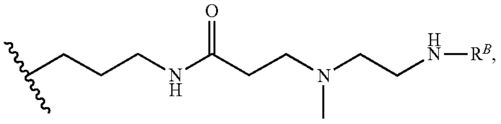
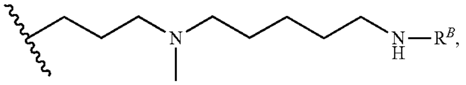
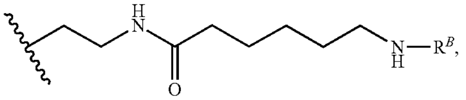
or
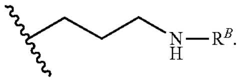
In some embodiments, $R^B$ in the preceding embodiment is
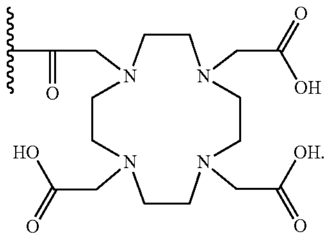 [SMILES: *C(=O)CN1CCN(CC(=O)O)CCN(CC(=O)O)CCN(CC(=O)O)CC1]
In some embodiments, $-L^B-R^B$ is
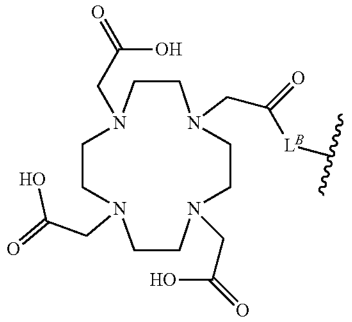
when $R^B$ in the preceding embodiments is
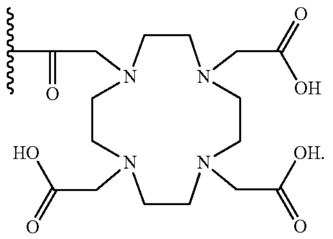 [SMILES: *C(=O)CN1CCN(CC(=O)O)CCN(CC(=O)O)CCN(CC(=O)O)CC1]
In some embodiments, $-L^B-R^B$ is
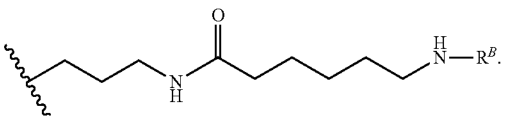
In some embodiments, $-L^B-R^B$ is
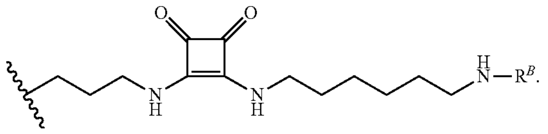
In some embodiments, $-L^B-R^B$ is
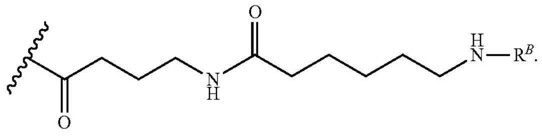
In some embodiments, $-L^B-R^B$ is
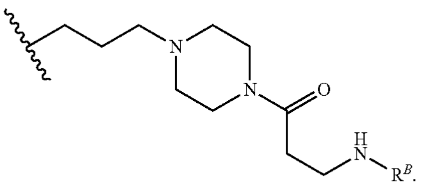
In some embodiments, $-L^B-R^B$ is
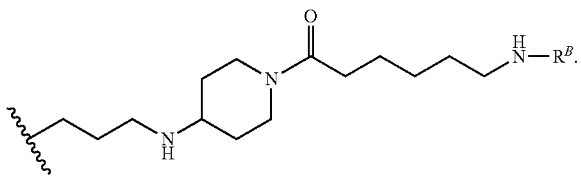
In some embodiments, $-L^B-R^B$ is
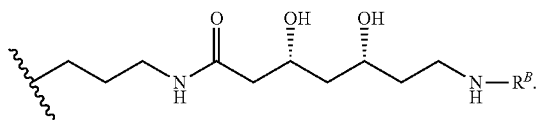

In some embodiments, -$L^B$-$R^B$ is

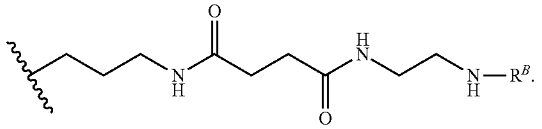

In some embodiments, -$L^B$-$R^B$ is

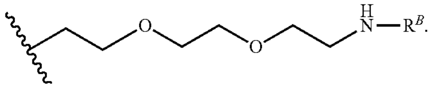

In some embodiments, -$L^B$-$R^B$ is

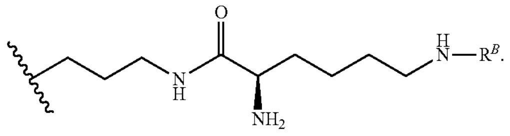

In some embodiments, -$L^B$-$R^B$ is

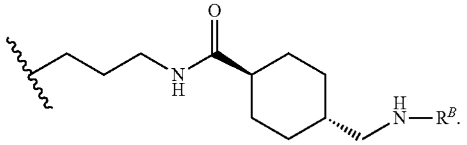

In some embodiments, -$L^B$-$R^B$ is

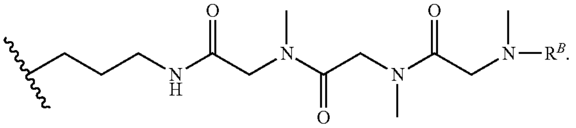

In some embodiments, -$L^B$-$R^B$ is

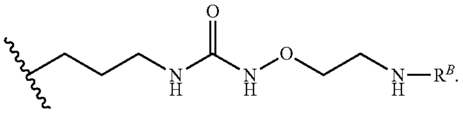

In some embodiments, -$L^B$-$R^B$ is

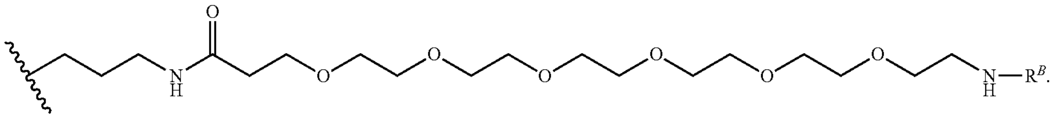

In some embodiments, -$L^B$-$R^B$ is

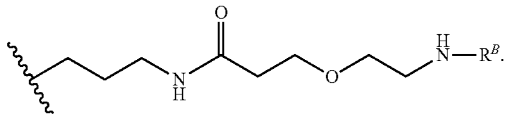

In some embodiments, -$L^B$-$R^B$ is

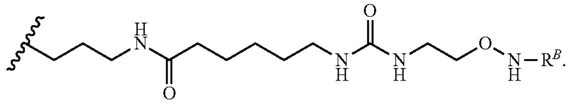

In some embodiments, -$L^B$-$R^B$ is

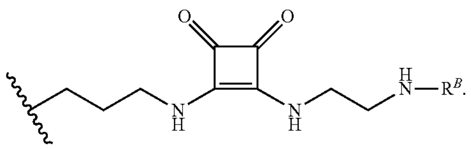

In some embodiments, -$L^B$-$R^B$ is

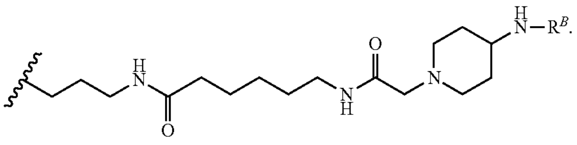

In some embodiments, -$L^B$-$R^B$ is

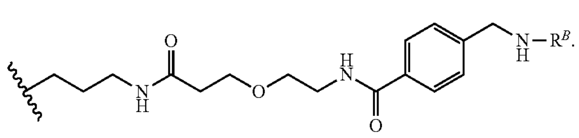

In some embodiments, -$L^B$-$R^B$ is

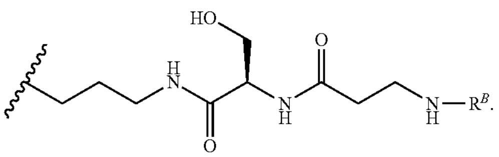

In some embodiments, $-L^B-R^B$ is

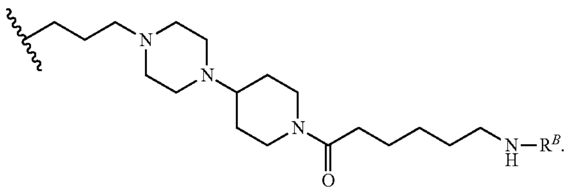

In some embodiments, $-L^B-R^B$ is

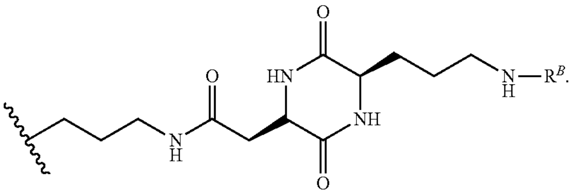

In some embodiments, $-L^B-R^B$ is

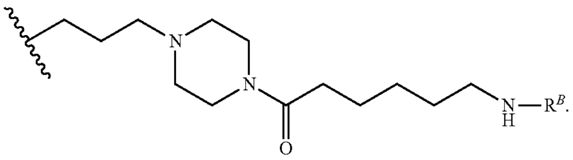

In some embodiments, $-L^B-R^B$ i

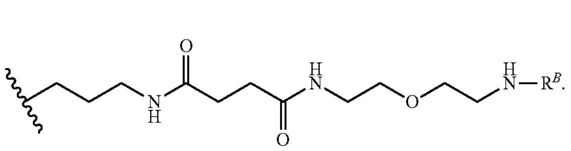

In some embodiments, $-L^B-R^B$ is

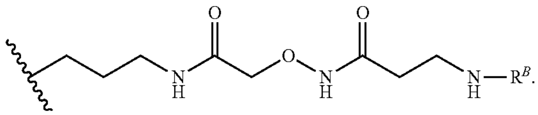

In some embodiments, $-L^B-R^B$ is

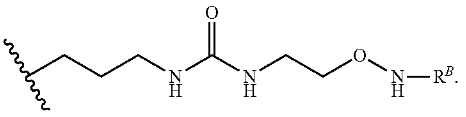

In some embodiments, $-L^B-R^B$ is

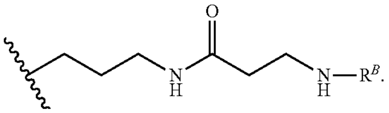

In some embodiments, $-L^B-R^B$ is

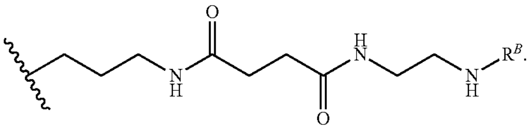

In some embodiments, $-L^B-R^B$ is

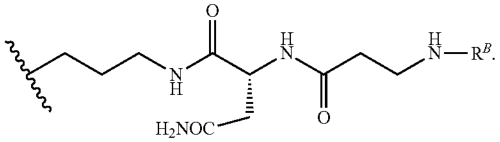

In some embodiments, $-L^B-R^B$ is

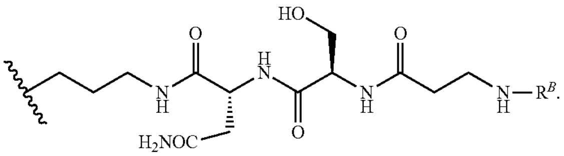

In some embodiments, $-L^B-R^B$ is

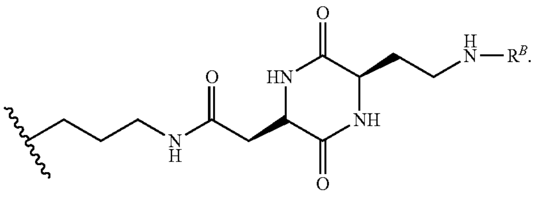

In some embodiments, $-L^B-R^B$ is

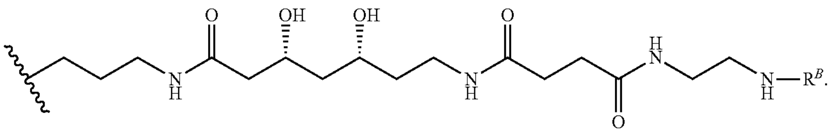

In some embodiments, $-L^B-R^B$ is

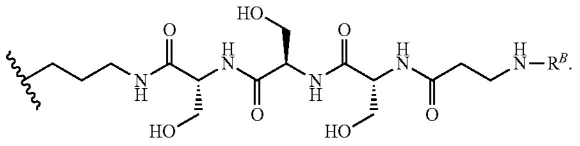

In some embodiments, $-L^B-R^B$ is

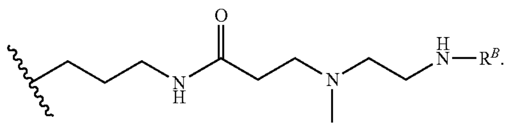

In some embodiments, $-L^B-R^B$ is

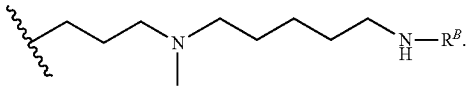

In some embodiments, $-L^B-R^B$ is

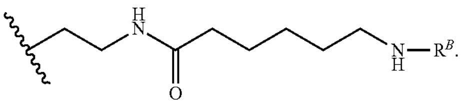

In some embodiments, $-L^B-R^B$ is

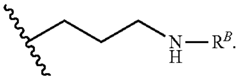

In some embodiments, $—R^B$ in the preceding embodiments is

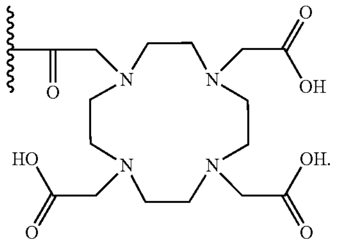 [SMILES: *C(=O)CN1CCN(CC(=O)O)CCN(CC(=O)O)CCN(CC(=O)O)CC1]

In some embodiments, $-L^B-R^B$ is

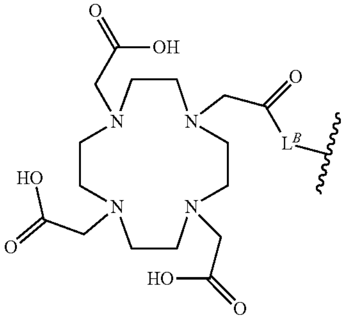

when $R^B$ in the preceding embodiments is

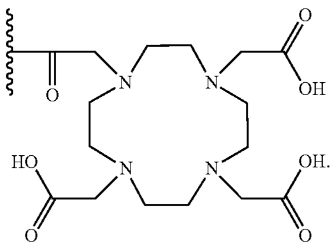 [SMILES: *C(=O)CN1CCN(CC(=O)O)CCN(CC(=O)O)CCN(CC(=O)O)CC1]

In some embodiments, $-L^A-R^A$ or $-L^B-R^B$ is selected from (if one is present), or the -linker-chelating moiety $-L^A-R^A$ and $-L^B-R^B$ each are independently selected from (if both are present) are represented by

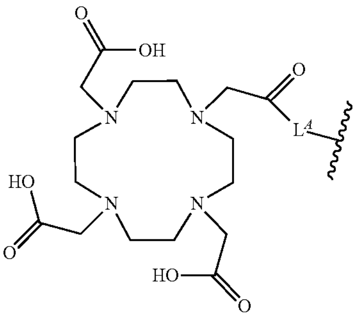

and

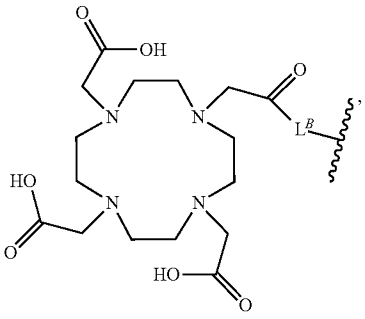

respectively, and selected from the following:
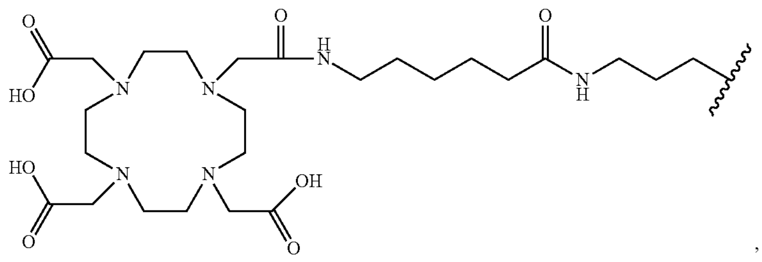
,
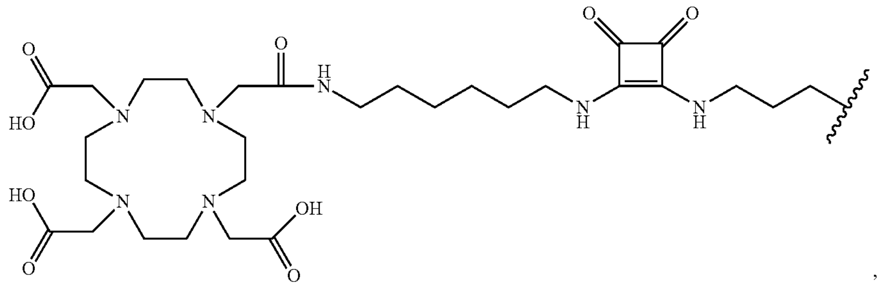
,
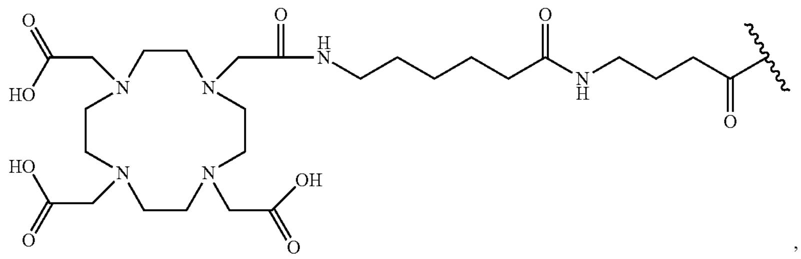
,
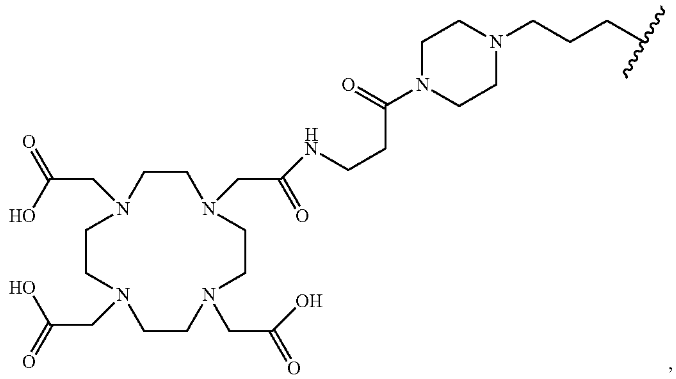
,
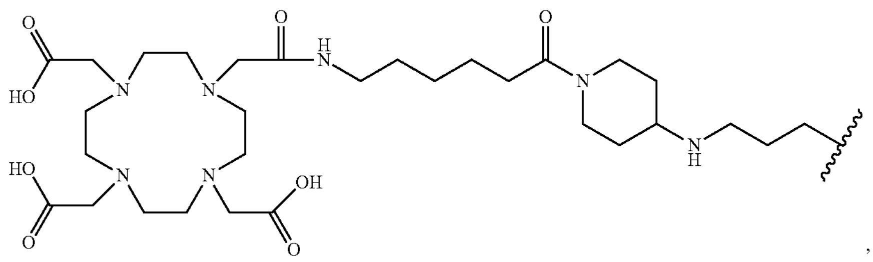
, -continued
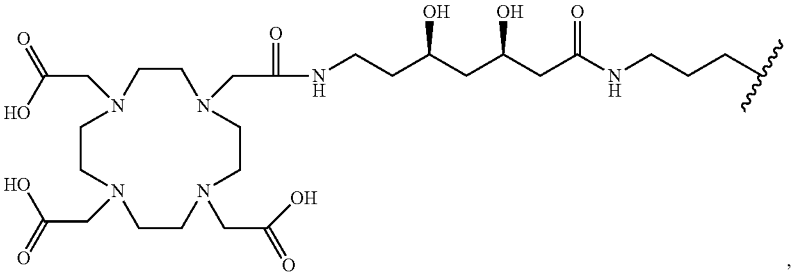
,
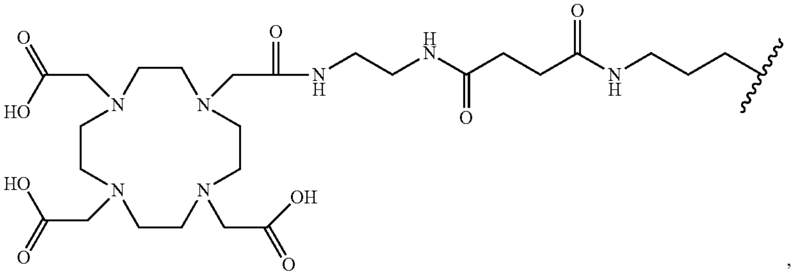
,
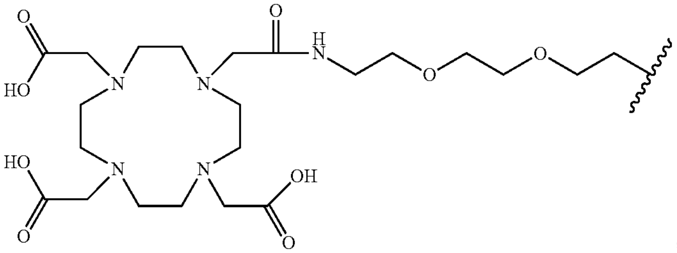
,
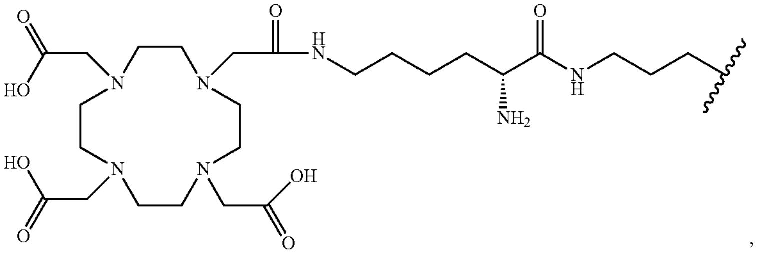
,
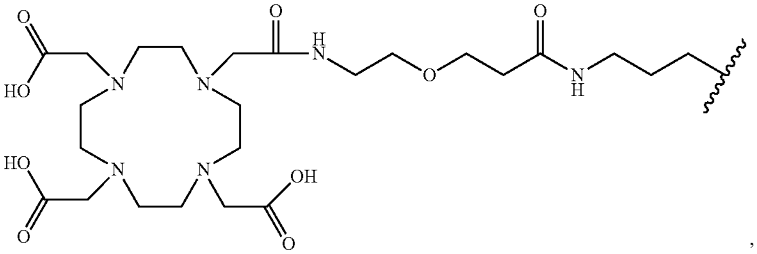
,
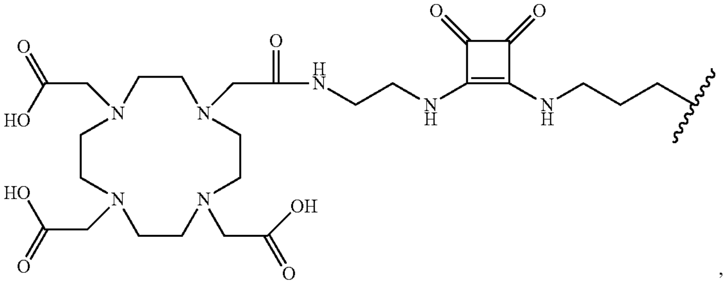
, -continued
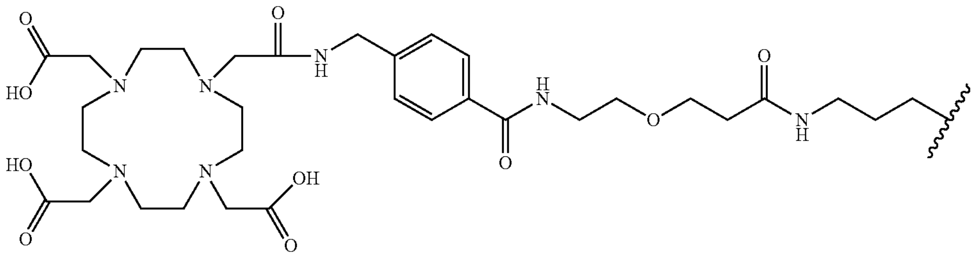
,
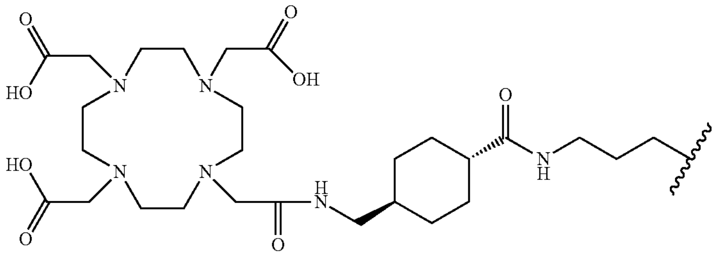
,
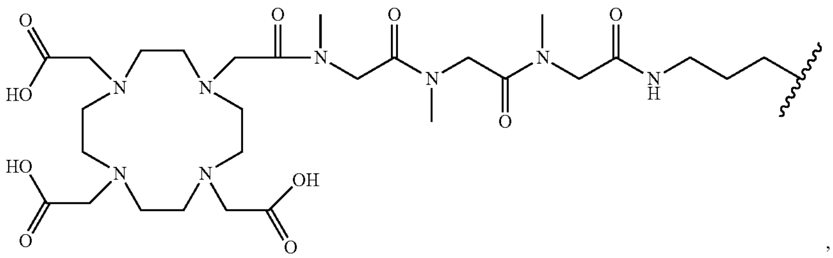
,
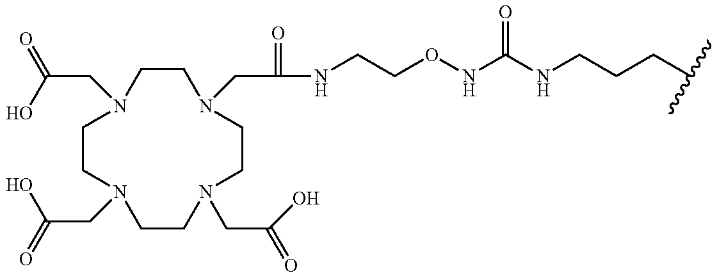
,
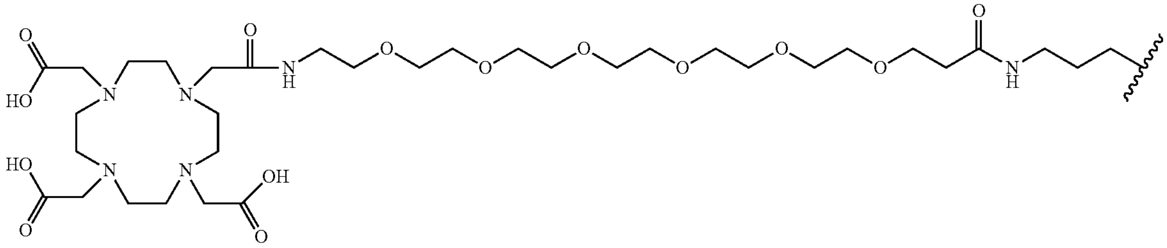
,
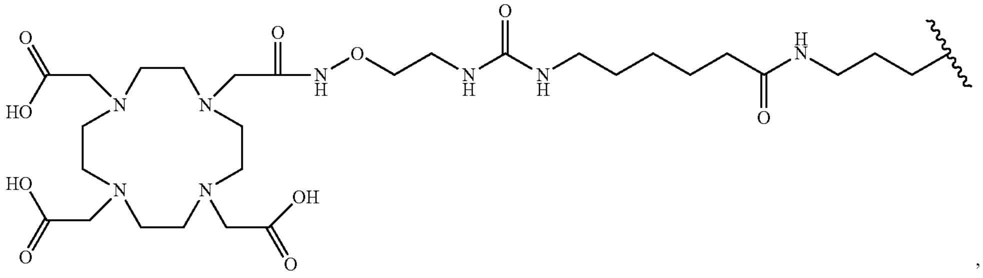
, -continued
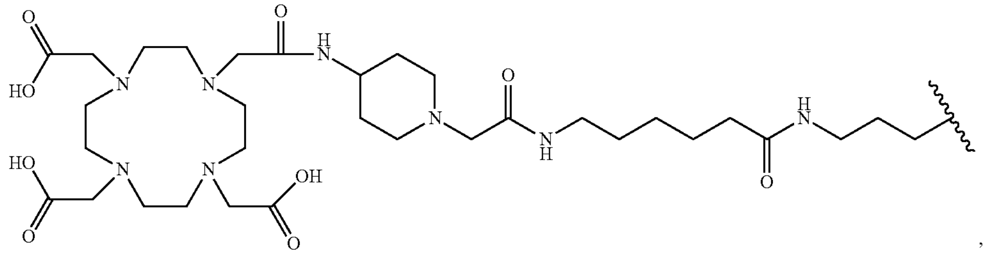
,
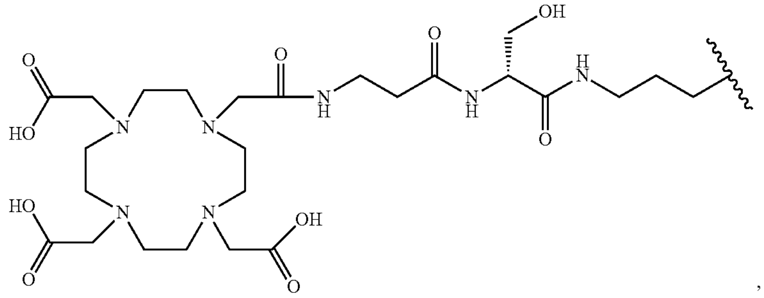
,
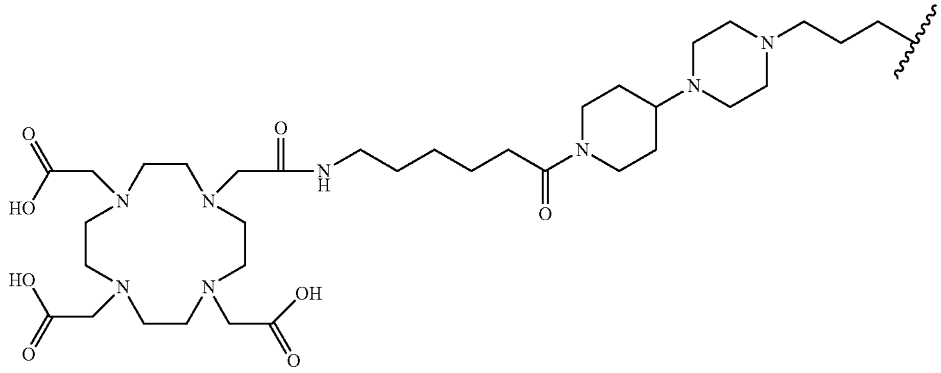
,
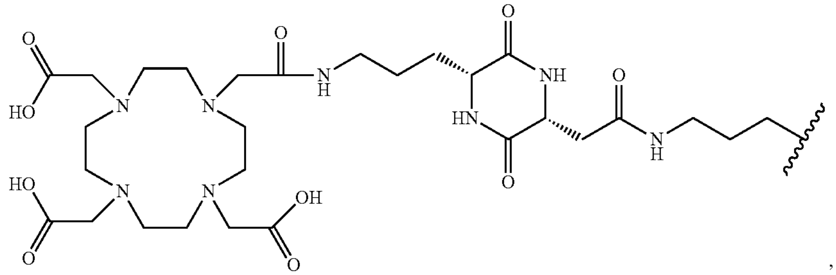
,
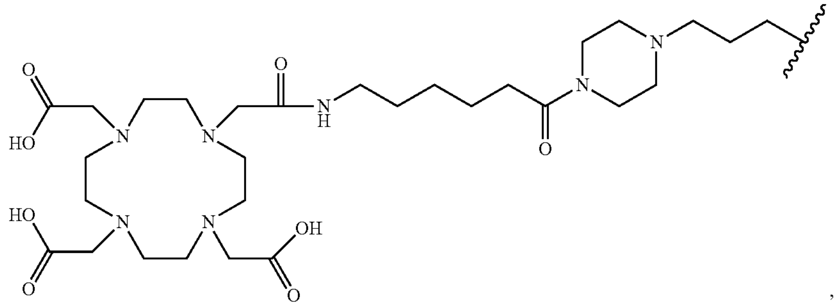
, -continued
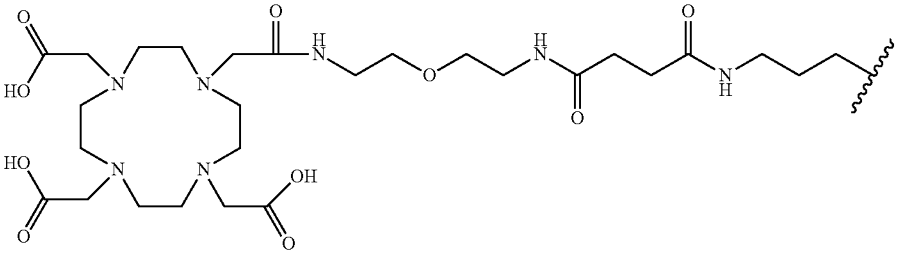
,
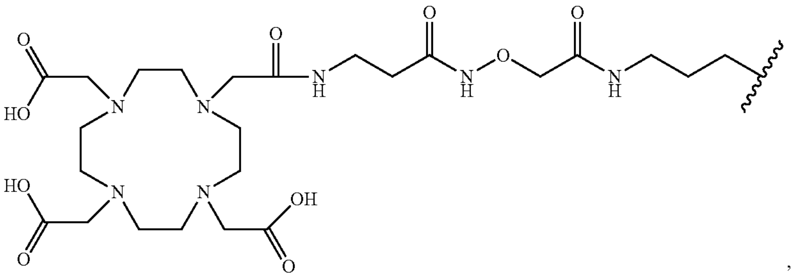
,
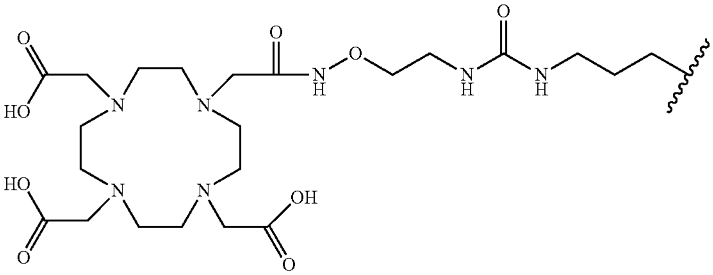
,
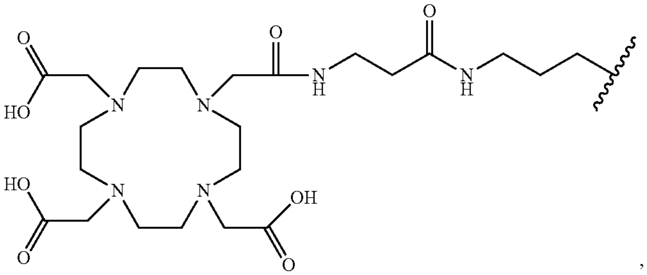
,
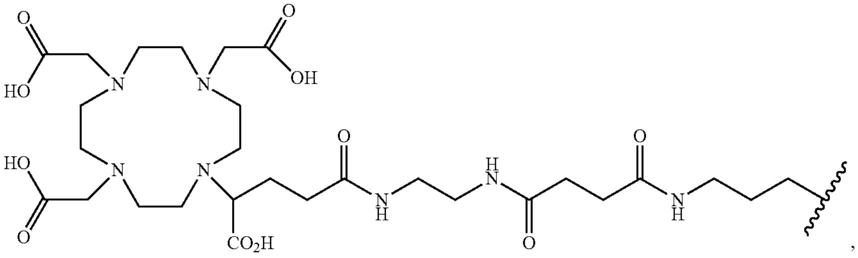
,
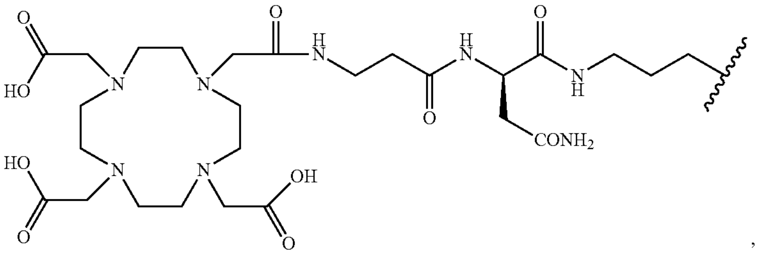
, -continued
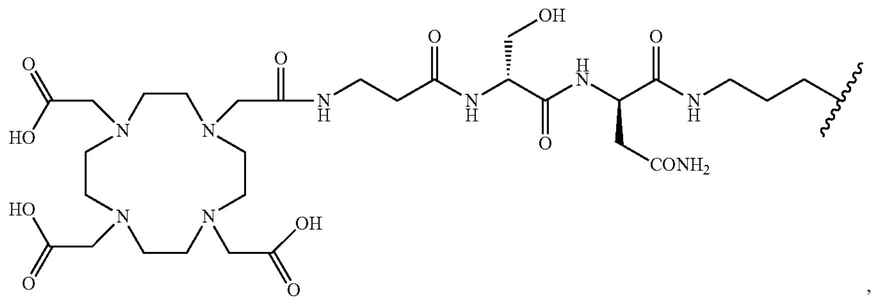
,
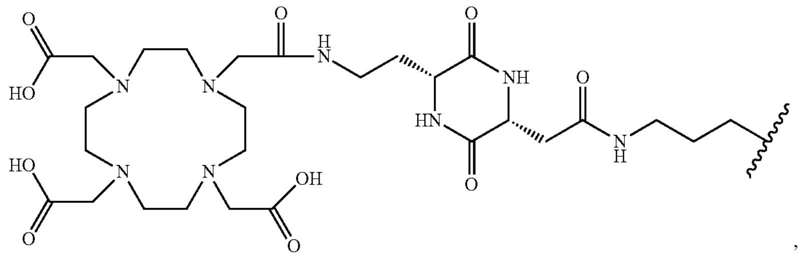
,
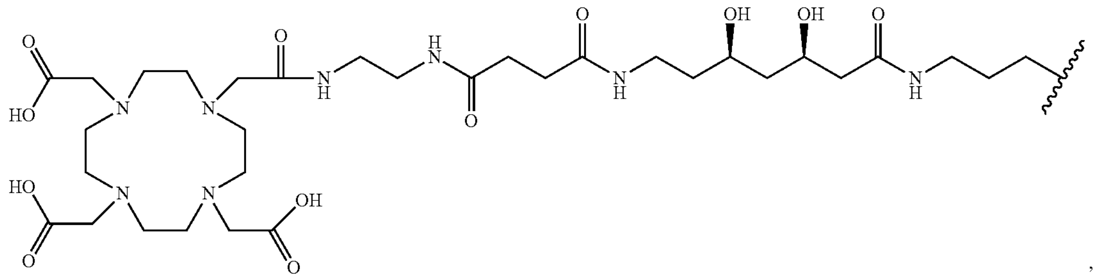
,
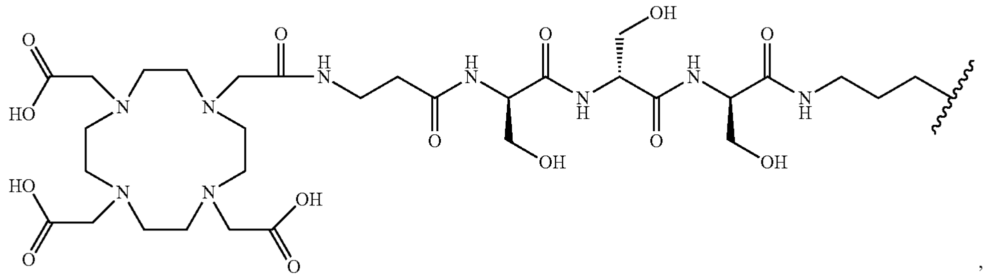
,
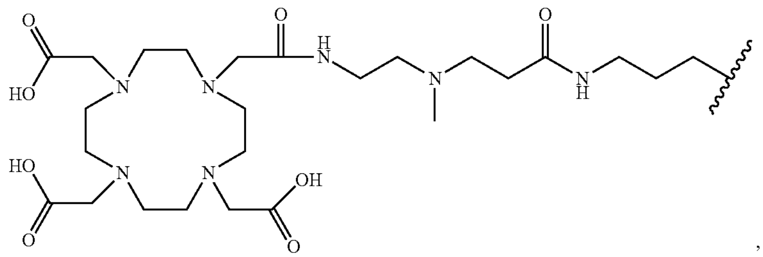
,
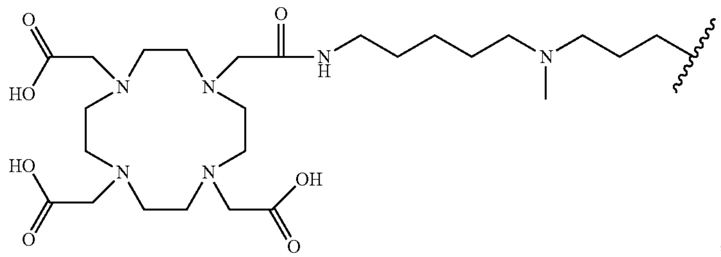
, -continued

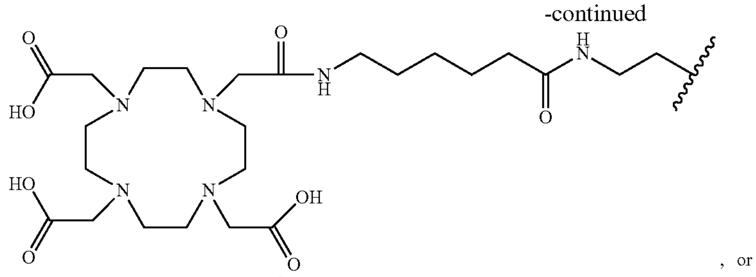

, or

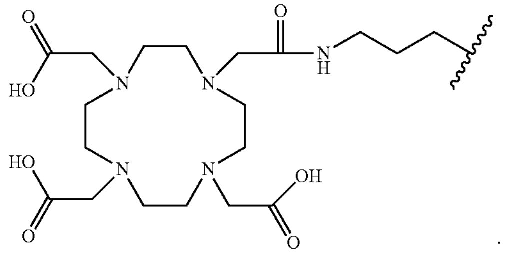

In some embodiments, the -linker-(chelating moiety or a radionuclide complex thereof) is $-L^A-R^A$. In some embodiments, the -linker-(chelating moiety or a radionuclide complex thereof) is $-L^B-R^B$.

Representative Conjugate Compounds

Representative $NPY_1R$ radiopharmaceuticals described herein have one of the following structures, or a pharmaceutically acceptable salt thereof:

TABLE 1

| Cmpd no. | Structure |
| --- | --- |
| 1A | 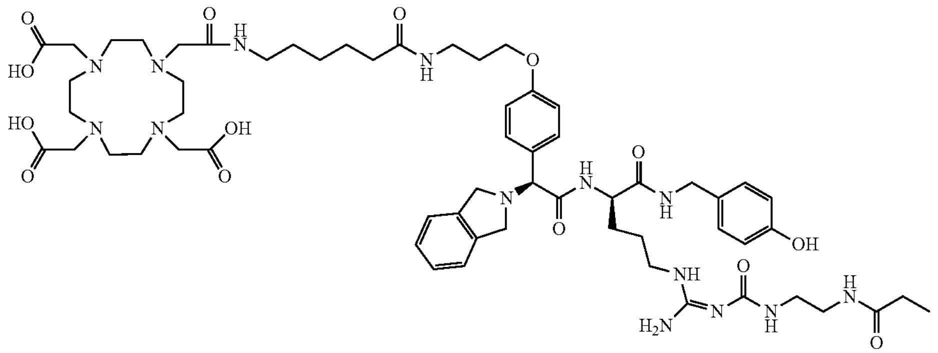 [SMILES: CCC(=O)NCCNC(=O)/N=C(/N)NCCC[C@@H](NC(=O)[C@H](c1ccc(OCCCNC(=O)CCCCCNC(=O)CN2CCN(CC(=O)O)CCN(CC(=O)O)CCN(CC(=O)O)CC2)cc1)N1Cc2ccccc2C1)C(=O)NCc1ccc(O)cc1] |
| 1B | 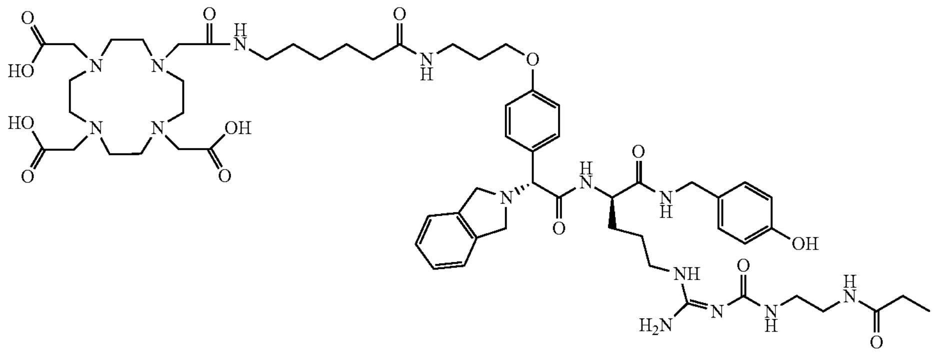 [SMILES: CCC(=O)NCCNC(=O)/N=C(/N)NCCC[C@@H](NC(=O)[C@@H](c1ccc(OCCCNC(=O)CCCCCNC(=O)CN2CCN(CC(=O)O)CCN(CC(=O)O)CCN(CC(=O)O)CC2)cc1)N1Cc2ccccc2C1)C(=O)NCc1ccc(O)cc1] |

TABLE 1-continued
| Cmpd no. | Structure |
| --- | --- |
| 1A-In | 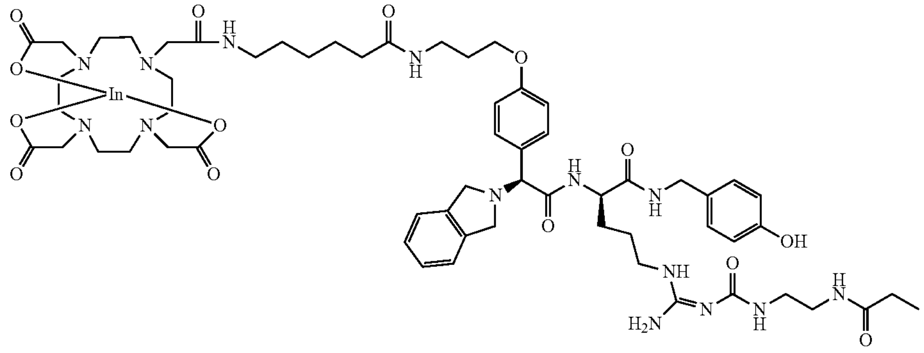 |
| 1A-Lu | 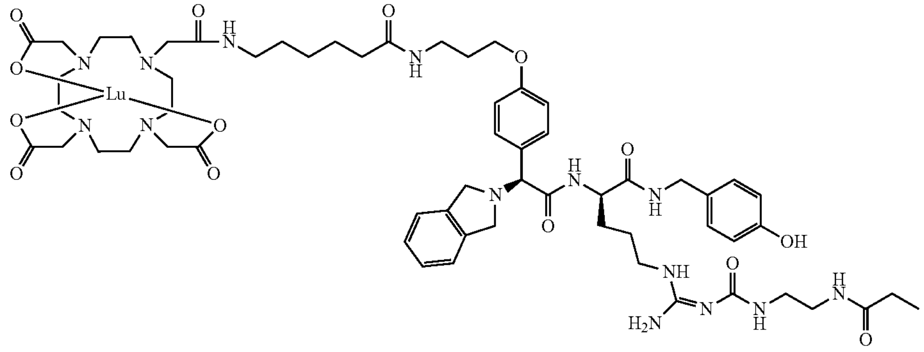 |
| 1A-Ga | 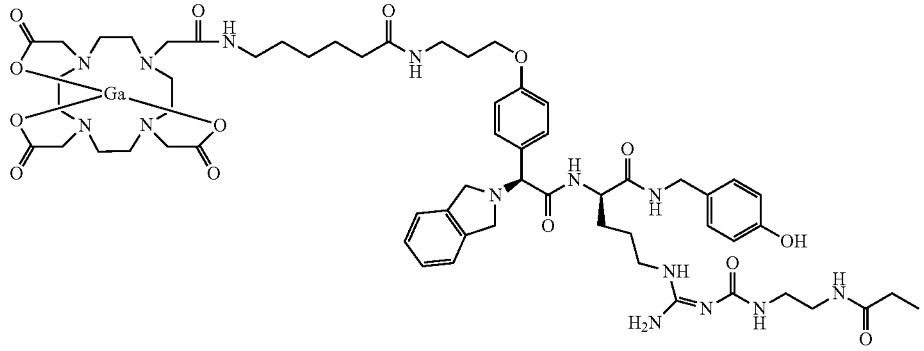 |
| 2 | 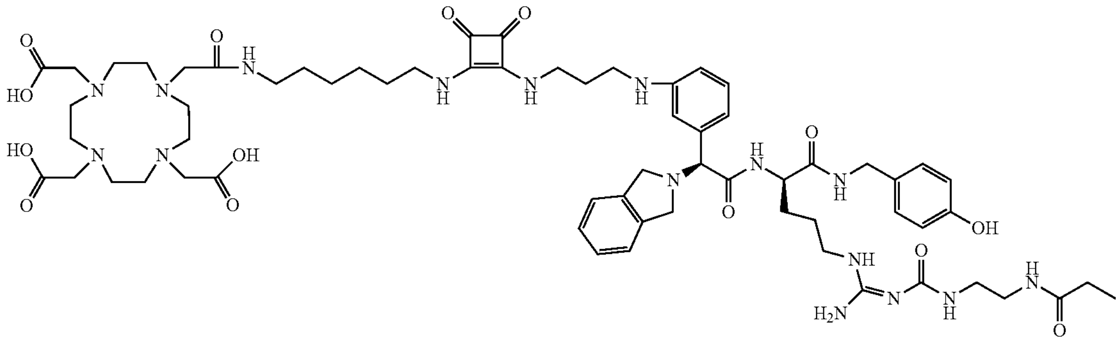 [SMILES: CCC(=O)NCCNC(=O)/N=C(/N)NCCC[C@@H](NC(=O)[C@H](c1cccc(NCCCNc2c(NCCCCCCNC(=O)CN3CCN(CC(=O)O)CCN(CC(=O)O)CCN(CC(=O)O)CC3)c(=O)c2=O)c1)N1Cc2ccccc2C1)C(=O)NCc1ccc(O)cc1] |

TABLE 1-continued
| Cmpd no. | Structure |
| --- | --- |
| 2B | 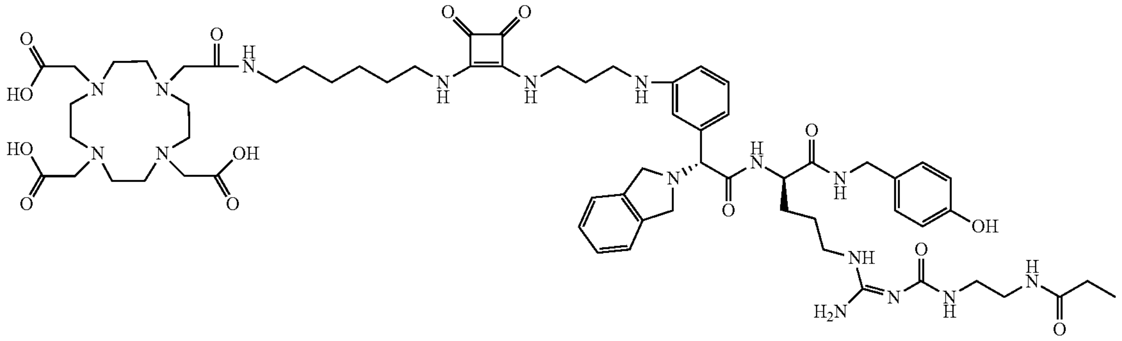 [SMILES: CCC(=O)NCCNC(=O)/N=C(/N)NCCC[C@@H](NC(=O)[C@@H](c1cccc(NCCCNc2c(NCCCCCCNC(=O)CN3CCN(CC(=O)O)CCN(CC(=O)O)CCN(CC(=O)O)CC3)c(=O)c2=O)c1)N1Cc2ccccc2C1)C(=O)NCc1ccc(O)cc1] |
| 3A | 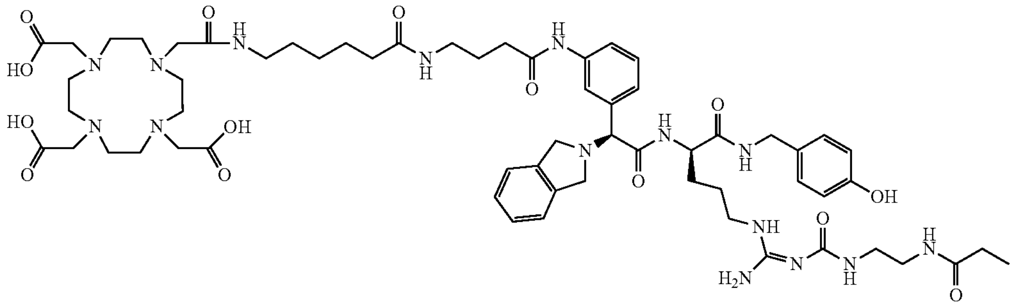 [SMILES: CCC(=O)NCCNC(=O)/N=C(/N)NCCC[C@@H](NC(=O)[C@H](c1cccc(NC(=O)CCCNC(=O)CCCCCNC(=O)CN2CCN(CC(=O)O)CCN(CC(=O)O)CCN(CC(=O)O)CC2)c1)N1Cc2ccccc2C1)C(=O)NCc1ccc(O)cc1] |
| 3B | 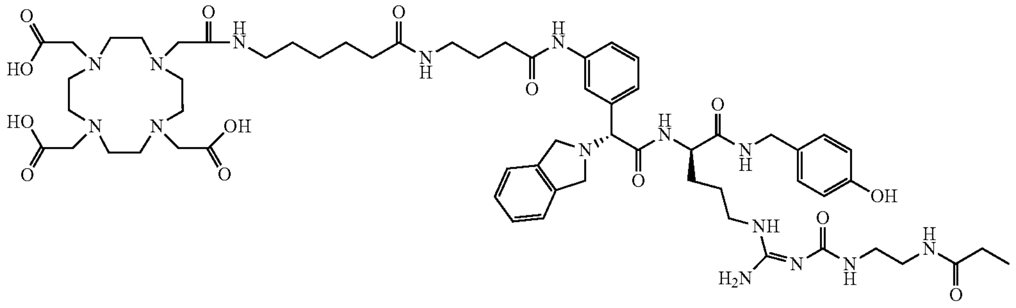 [SMILES: CCC(=O)NCCNC(=O)/N=C(/N)NCCC[C@@H](NC(=O)[C@@H](c1cccc(NC(=O)CCCNC(=O)CCCCCNC(=O)CN2CCN(CC(=O)O)CCN(CC(=O)O)CCN(CC(=O)O)CC2)c1)N1Cc2ccccc2C1)C(=O)NCc1ccc(O)cc1] |
| 4 | 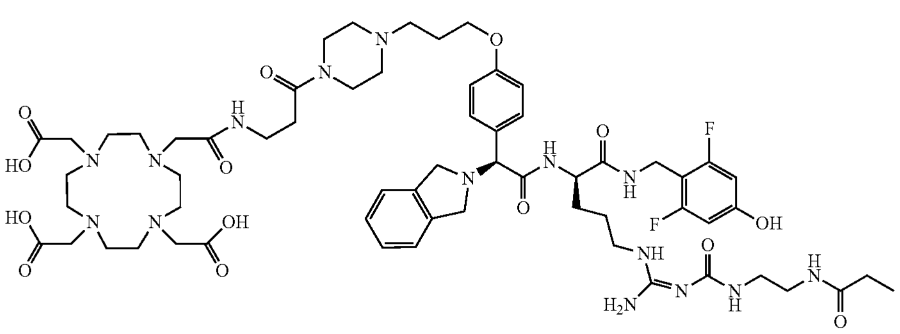 [SMILES: CCC(=O)NCCNC(=O)/N=C(/N)NCCC[C@@H](NC(=O)[C@H](c1ccc(OCCCN2CCN(C(=O)CCNC(=O)CN3CCN(CC(=O)O)CCN(CC(=O)O)CCN(CC(=O)O)CC3)CC2)cc1)N1Cc2ccccc2C1)C(=O)NCc1c(F)cc(O)cc1F] |

TABLE 1-continued
| Cmpd no. | Structure |
| --- | --- |
| 4B | 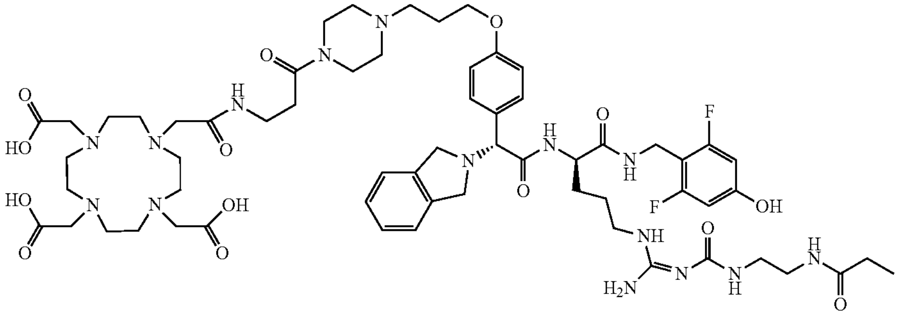 [SMILES: CCC(=O)NCCNC(=O)/N=C(/N)NCCC[C@@H](NC(=O)[C@@H](c1ccc(OCCCN2CCN(C(=O)CCNC(=O)CN3CCN(CC(=O)O)CCN(CC(=O)O)CCN(CC(=O)O)CC3)CC2)cc1)N1Cc2ccccc2C1)C(=O)NCc1c(F)cc(O)cc1F] |
| 5 | 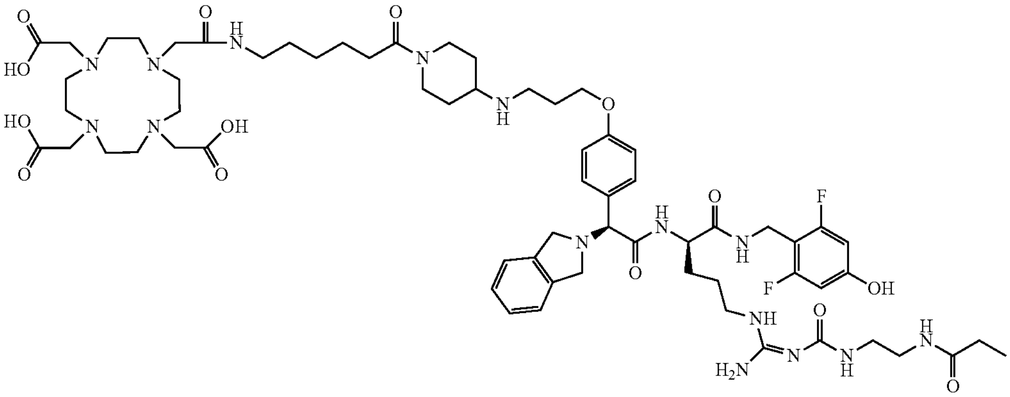 [SMILES: CCC(=O)NCCNC(=O)/N=C(/N)NCCC[C@@H](NC(=O)[C@H](c1ccc(OCCCNC2CCN(C(=O)CCCCCNC(=O)CN3CCN(CC(=O)O)CCN(CC(=O)O)CCN(CC(=O)O)CC3)CC2)cc1)N1Cc2ccccc2C1)C(=O)NCc1c(F)cc(O)cc1F] |
| 5B | 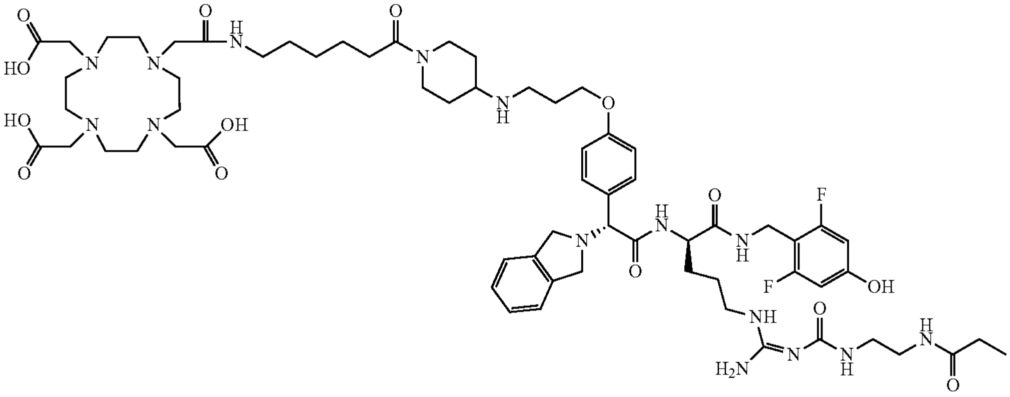 [SMILES: CCC(=O)NCCNC(=O)/N=C(/N)NCCC[C@@H](NC(=O)[C@@H](c1ccc(OCCCNC2CCN(C(=O)CCCCCNC(=O)CN3CCN(CC(=O)O)CCN(CC(=O)O)CCN(CC(=O)O)CC3)CC2)cc1)N1Cc2ccccc2C1)C(=O)NCc1c(F)cc(O)cc1F] |
| 6 | 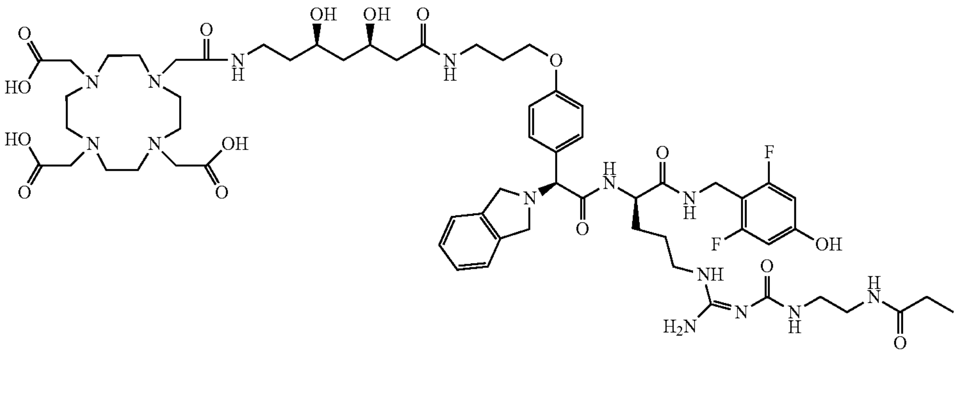 [SMILES: CCC(=O)NCCNC(=O)/N=C(/N)NCCC[C@@H](NC(=O)[C@H](c1ccc(OCCCNC(=O)C[C@H](O)C[C@H](O)CCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |

TABLE 1-continued
| Cmpd no. | Structure |
| --- | --- |
| 6B | 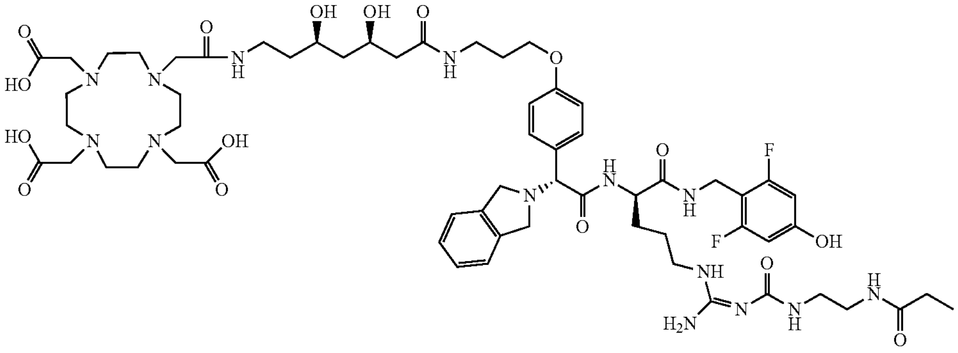 [SMILES: CCC(=O)NCCNC(=O)/N=C(/N)NCCC[C@@H](NC(=O)[C@@H](c1ccc(OCCCNC(=O)C[C@H](O)C[C@H](O)CCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |
| 7 | 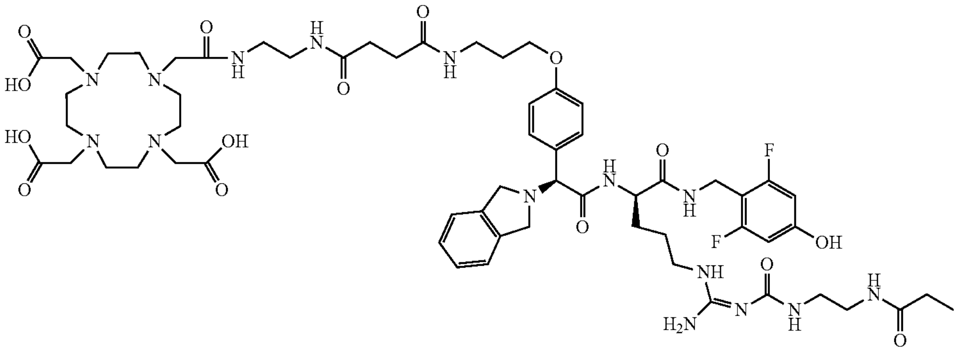 [SMILES: CCC(=O)NCCNC(=O)/N=C(/N)NCCC[C@@H](NC(=O)[C@H](c1ccc(OCCCNC(=O)CCC(=O)NCCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |
| 7B | 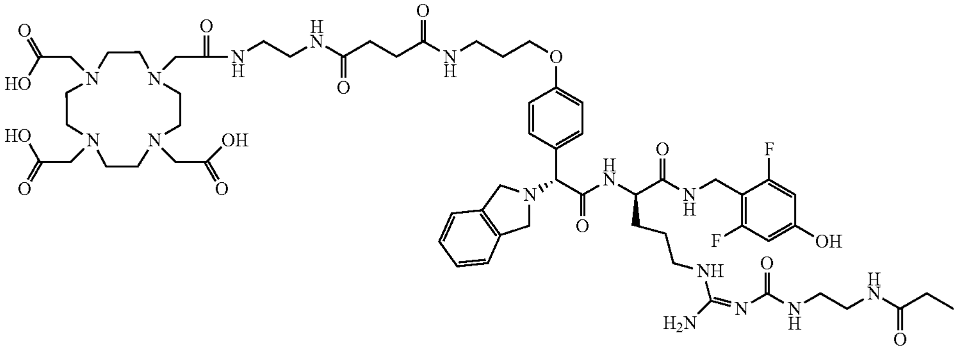 [SMILES: CCC(=O)NCCNC(=O)/N=C(/N)NCCC[C@@H](NC(=O)[C@@H](c1ccc(OCCCNC(=O)CCC(=O)NCCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |
| 8A | 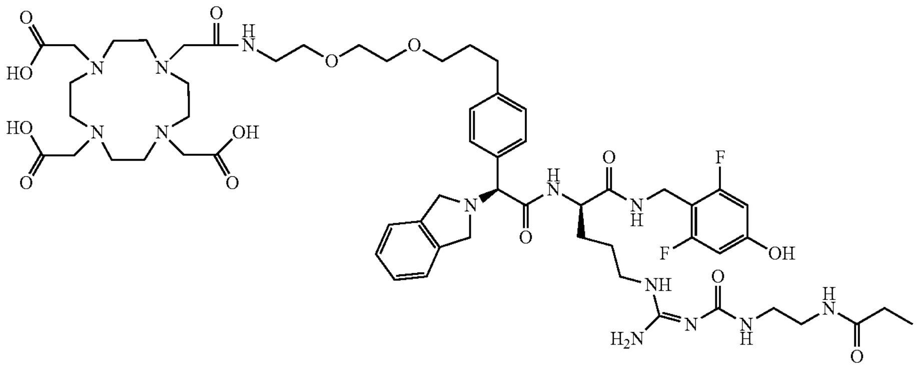<br>(absolute stereochemistry not determined) |

TABLE 1-continued
| Cmpd no. | Structure |
|---|---|
| 8B | 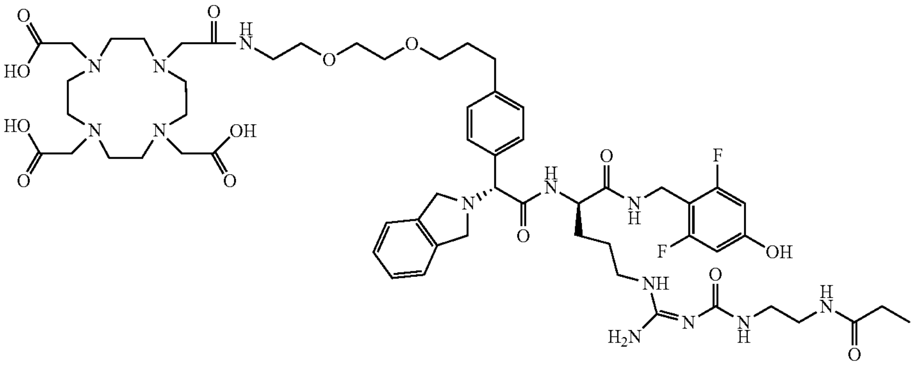 (absolute stereochemistry not determined) |
| 9 | 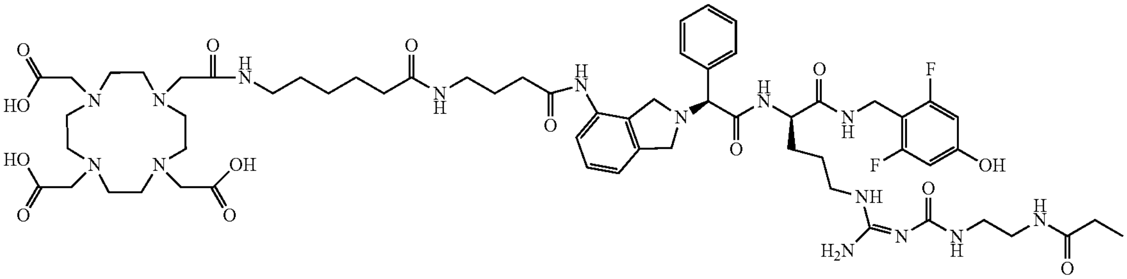 [SMILES: CCC(=O)NCCNC(=O)/N=C(/N)NCCC[C@@H](NC(=O)[C@H](c1ccccc1)N1Cc2cccc(NC(=O)CCCNC(=O)CCCCCNC(=O)CN3CCN(CC(=O)O)CCN(CC(=O)O)CCN(CC(=O)O)CC3)c2C1)C(=O)NCc1c(F)cc(O)cc1F] |
| 10 | 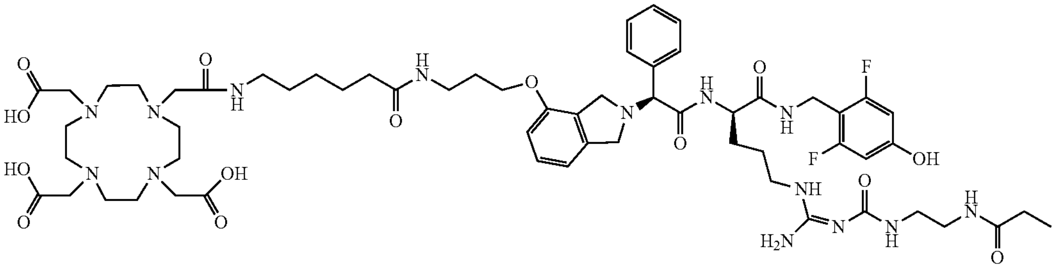 [SMILES: CCC(=O)NCCNC(=O)/N=C(/N)NCCC[C@@H](NC(=O)[C@H](c1ccccc1)N1Cc2cccc(OCCCNC(=O)CCCCCNC(=O)CN3CCN(CC(=O)O)CCN(CC(=O)O)CCN(CC(=O)O)CC3)c2C1)C(=O)NCc1c(F)cc(O)cc1F] |
| 11 | 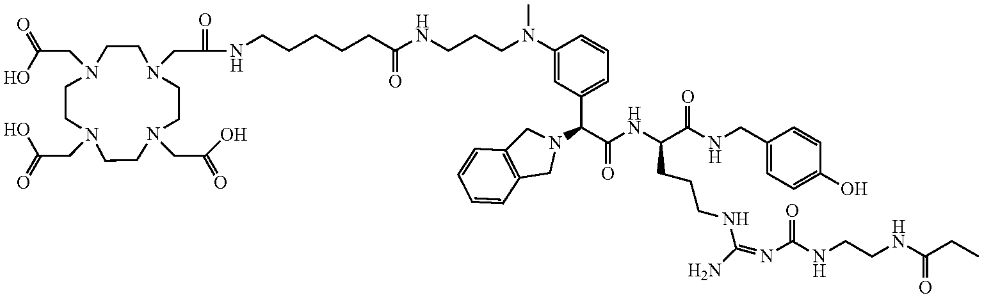 [SMILES: CCC(=O)NCCNC(=O)/N=C(/N)NCCC[C@@H](NC(=O)[C@H](c1cccc(N(C)CCCNC(=O)CCCCCNC(=O)CN2CCN(CC(=O)O)CCN(CC(=O)O)CCN(CC(=O)O)CC2)c1)N1Cc2ccccc2C1)C(=O)NCc1ccc(O)cc1] |
| 12 | 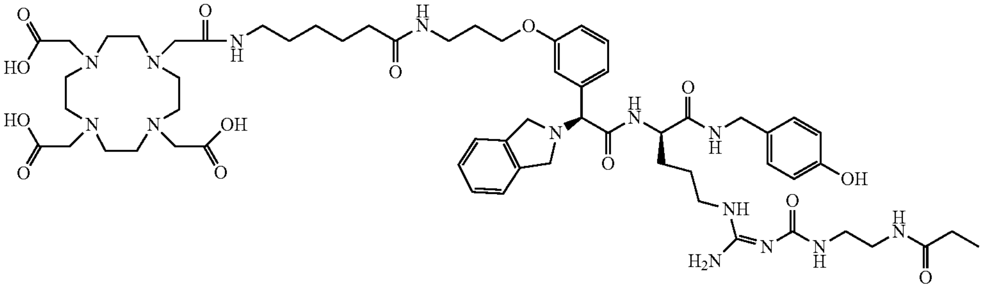 [SMILES: CCC(=O)NCCNC(=O)/N=C(/N)NCCC[C@@H](NC(=O)[C@H](c1cccc(OCCCNC(=O)CCCCCNC(=O)CN2CCN(CC(=O)O)CCN(CC(=O)O)CCN(CC(=O)O)CC2)c1)N1Cc2ccccc2C1)C(=O)NCc1ccc(O)cc1] |

TABLE 1-continued
| Cmpd no. | Structure |
| --- | --- |
| 13 | 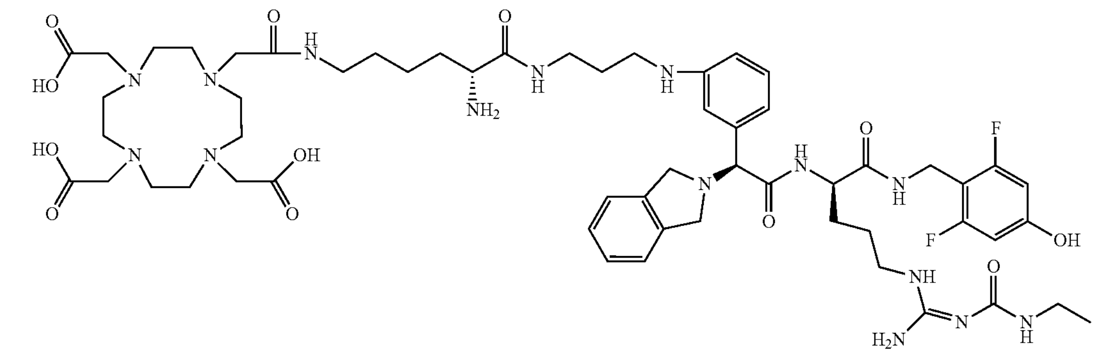 [SMILES: CCNC(=O)/N=C(/N)NCCC[C@@H](NC(=O)[C@H](c1cccc(NCCCNC(=O)[C@H](N)CCCCNC(=O)CN2CCN(CC(=O)O)CCN(CC(=O)O)CCN(CC(=O)O)CC2)c1)N1Cc2ccccc2C1)C(=O)NCc1c(F)cc(O)cc1F] |
| 14 | 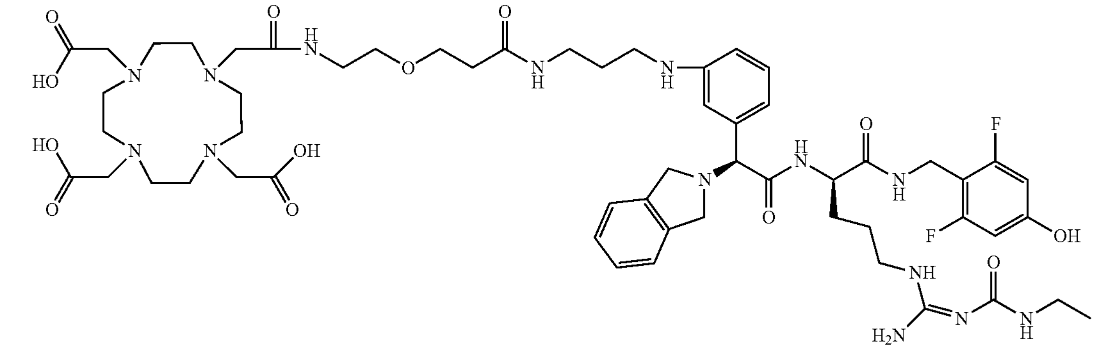 [SMILES: CCNC(=O)/N=C(/N)NCCC[C@@H](NC(=O)[C@H](c1cccc(NCCCNC(=O)CCOCCNC(=O)CN2CCN(CC(=O)O)CCN(CC(=O)O)CCN(CC(=O)O)CC2)c1)N1Cc2ccccc2C1)C(=O)NCc1c(F)cc(O)cc1F] |
| 15 | 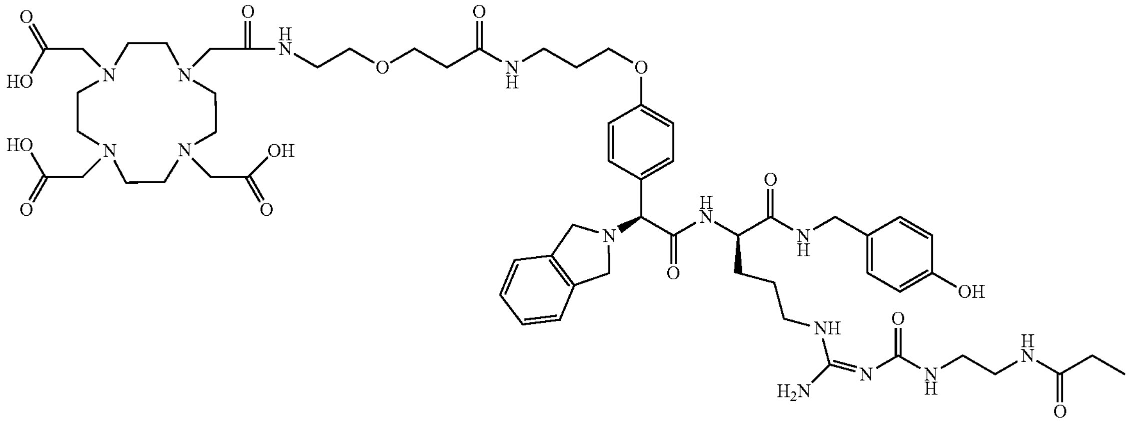 [SMILES: CCC(=O)NCCNC(=O)/N=C(/N)NCCC[C@@H](NC(=O)[C@H](c1ccc(OCCCNC(=O)CCOCCNC(=O)CN2CCN(CC(=O)O)CCN(CC(=O)O)CCN(CC(=O)O)CC2)cc1)N1Cc2ccccc2C1)C(=O)NCc1ccc(O)cc1] |
| 16 | 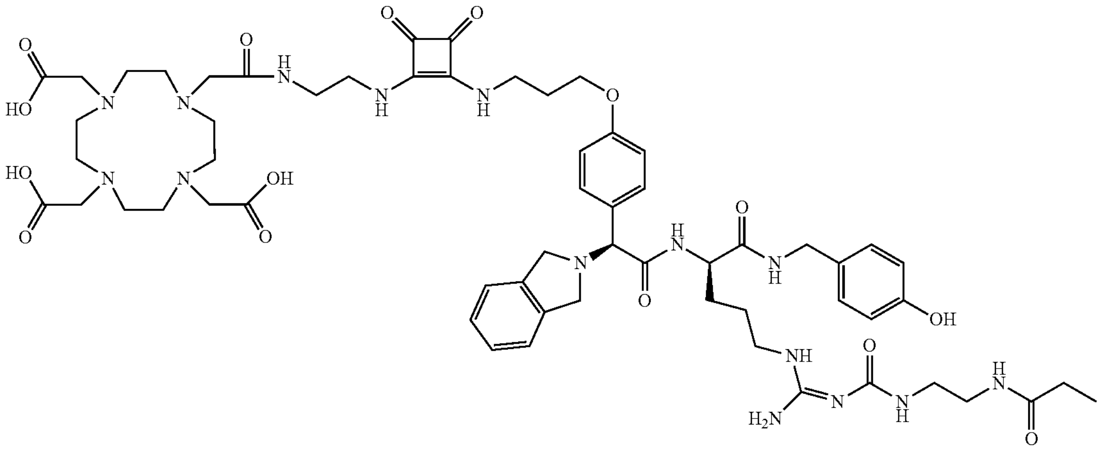 [SMILES: CCC(=O)NCCNC(=O)/N=C(/N)NCCC[C@@H](NC(=O)[C@H](c1ccc(OCCCNc2c(NCCNC(=O)CN3CCN(CC(=O)O)CCN(CC(=O)O)CCN(CC(=O)O)CC3)c(=O)c2=O)cc1)N1Cc2ccccc2C1)C(=O)NCc1ccc(O)cc1] |

TABLE 1-continued
| Cmpd no. | Structure |
|---|---|
| 17 | 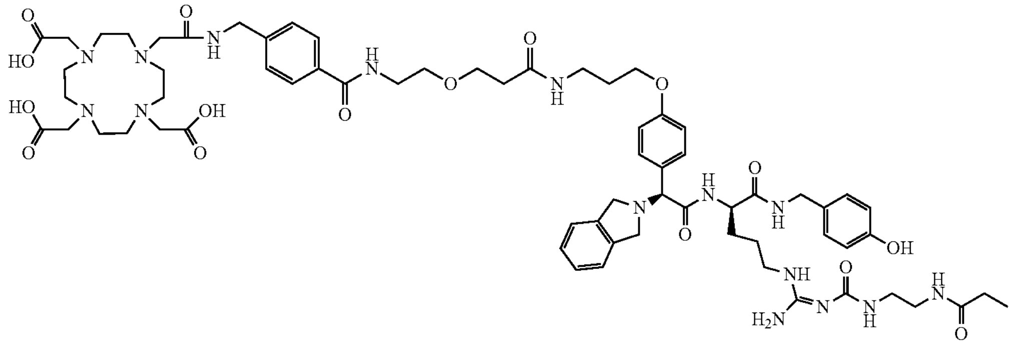 [SMILES: CCC(=O)NCCNC(=O)/N=C(/N)NCCC[C@@H](NC(=O)[C@H](c1ccc(OCCCNC(=O)CCOCCNC(=O)c2ccc(CNC(=O)CN3CCN(CC(=O)O)CCN(CC(=O)O)CCN(CC(=O)O)CC3)cc2)cc1)N1Cc2ccccc2C1)C(=O)NCc1ccc(O)cc1] |
| 18 | 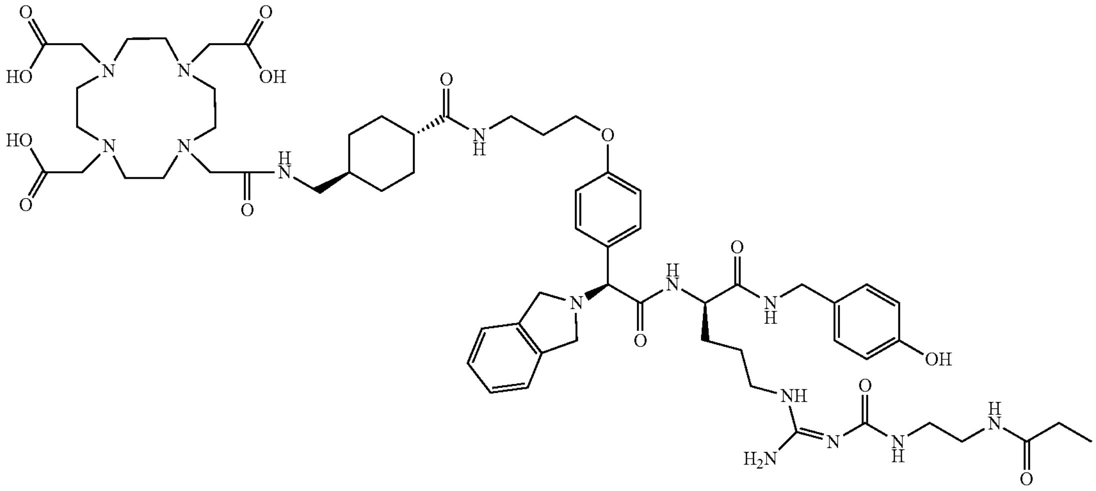 [SMILES: CCC(=O)NCCNC(=O)/N=C(/N)NCCC[C@@H](NC(=O)[C@H](c1ccc(OCCCNC(=O)[C@H]2CC[C@H](CNC(=O)CN3CCN(CC(=O)O)CCN(CC(=O)O)CCN(CC(=O)O)CC3)CC2)cc1)N1Cc2ccccc2C1)C(=O)NCc1ccc(O)cc1] |
| 19 | 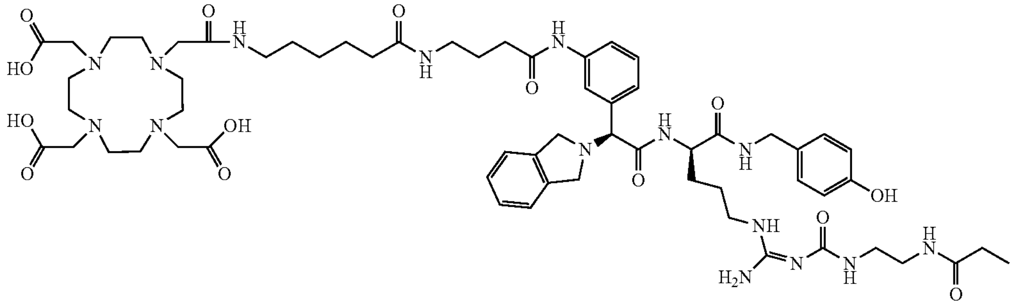 [SMILES: CCC(=O)NCCNC(=O)/N=C(/N)NCCC[C@@H](NC(=O)[C@H](c1cccc(NC(=O)CCCNC(=O)CCCCCNC(=O)CN2CCN(CC(=O)O)CCN(CC(=O)O)CCN(CC(=O)O)CC2)c1)N1Cc2ccccc2C1)C(=O)NCc1ccc(O)cc1] |
| 20 | 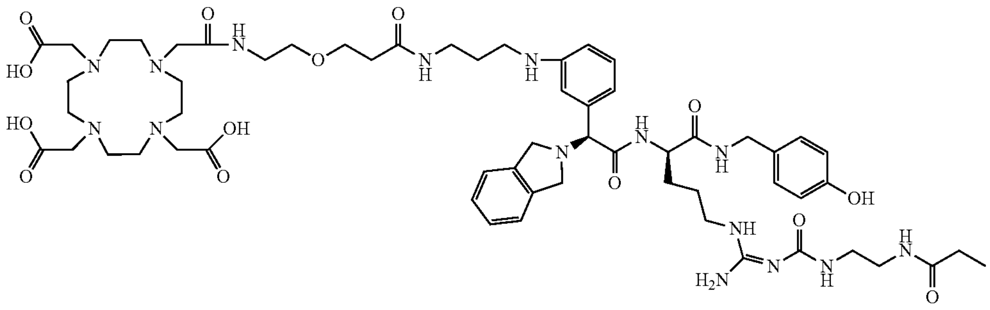 [SMILES: CCC(=O)NCCNC(=O)/N=C(/N)NCCC[C@@H](NC(=O)[C@H](c1cccc(NCCCNC(=O)CCOCCNC(=O)CN2CCN(CC(=O)O)CCN(CC(=O)O)CCN(CC(=O)O)CC2)c1)N1Cc2ccccc2C1)C(=O)NCc1ccc(O)cc1] |

TABLE 1-continued
| Cmpd no. | Structure |
|---|---|
| 21 | 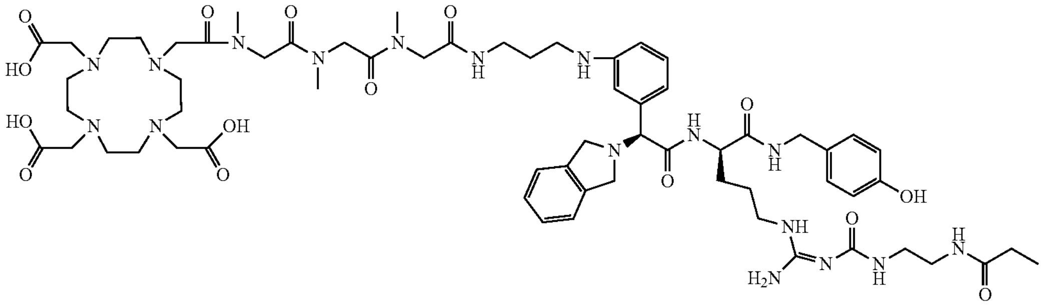 [SMILES: CCC(=O)NCCNC(=O)/N=C(/N)NCCC[C@@H](NC(=O)[C@H](c1cccc(NCCCNC(=O)CN(C)C(=O)CN(C)C(=O)CN(C)C(=O)CN2CCN(CC(=O)O)CCN(CC(=O)O)CCN(CC(=O)O)CC2)c1)N1Cc2ccccc2C1)C(=O)NCc1ccc(O)cc1] |
| 22 | 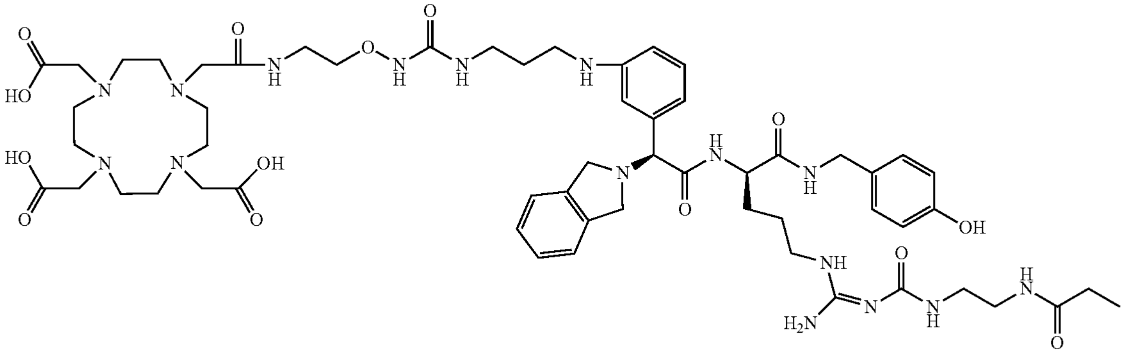 [SMILES: CCC(=O)NCCNC(=O)/N=C(/N)NCCC[C@@H](NC(=O)[C@H](c1cccc(NCCCNC(=O)NOCCNC(=O)CN2CCN(CC(=O)O)CCN(CC(=O)O)CCN(CC(=O)O)CC2)c1)N1Cc2ccccc2C1)C(=O)NCc1ccc(O)cc1] |
| 23 | 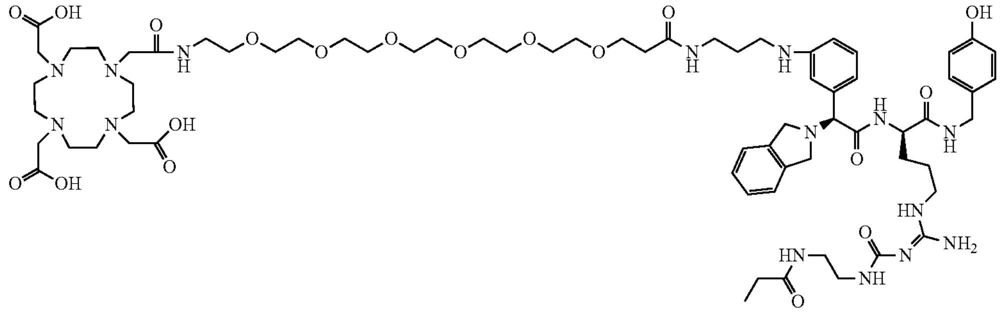 [SMILES: CCC(=O)NCCNC(=O)/N=C(/N)NCCC[C@@H](NC(=O)[C@H](c1cccc(NCCCNC(=O)CCOCCOCCOCCOCCOCCOCCNC(=O)CN2CCN(CC(=O)O)CCN(CC(=O)O)CCN(CC(=O)O)CC2)c1)N1Cc2ccccc2C1)C(=O)NCc1ccc(O)cc1] |
| 25 | 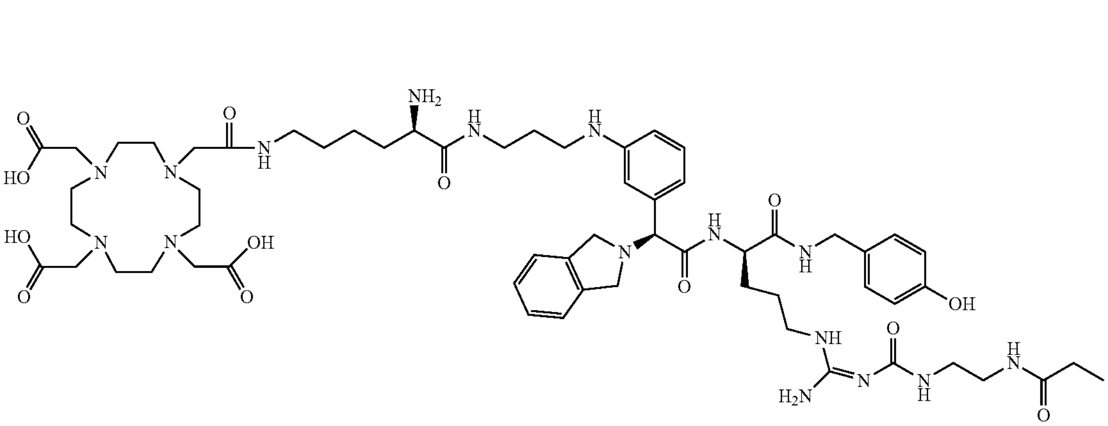 [SMILES: CCC(=O)NCCNC(=O)/N=C(/N)NCCC[C@@H](NC(=O)[C@H](c1cccc(NCCCNC(=O)[C@H](N)CCCCNC(=O)CN2CCN(CC(=O)O)CCN(CC(=O)O)CCN(CC(=O)O)CC2)c1)N1Cc2ccccc2C1)C(=O)NCc1ccc(O)cc1] |

TABLE 1-continued
| Cmpd no. | Structure |
|---|---|
| 26 | 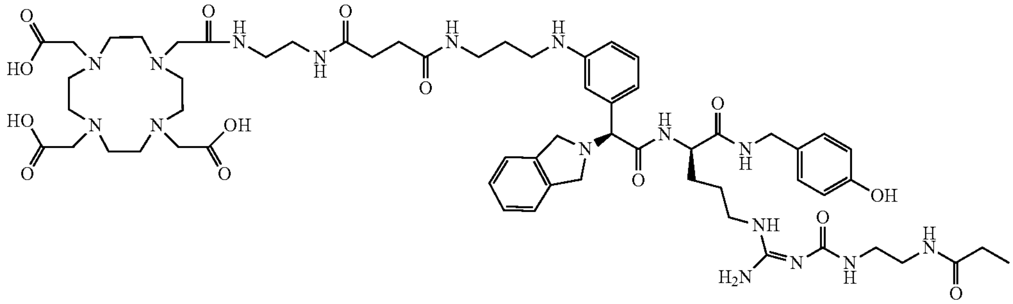 [SMILES: CCC(=O)NCCNC(=O)/N=C(/N)NCCC[C@@H](NC(=O)[C@H](c1cccc(NCCCNC(=O)CCC(=O)NCCNC(=O)CN2CCN(CC(=O)O)CCN(CC(=O)O)CCN(CC(=O)O)CC2)c1)N1Cc2ccccc2C1)C(=O)NCc1ccc(O)cc1] |
| 27 | 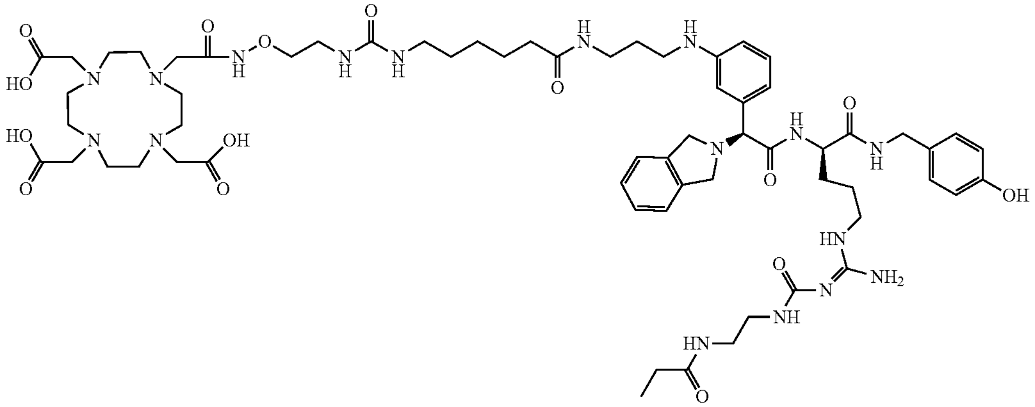 [SMILES: CCC(=O)NCCNC(=O)/N=C(/N)NCCC[C@@H](NC(=O)[C@H](c1cccc(NCCCNC(=O)CCCCCNC(=O)NCCONC(=O)CN2CCN(CC(=O)O)CCN(CC(=O)O)CCN(CC(=O)O)CC2)c1)N1Cc2ccccc2C1)C(=O)NCc1ccc(O)cc1] |
| 28 | 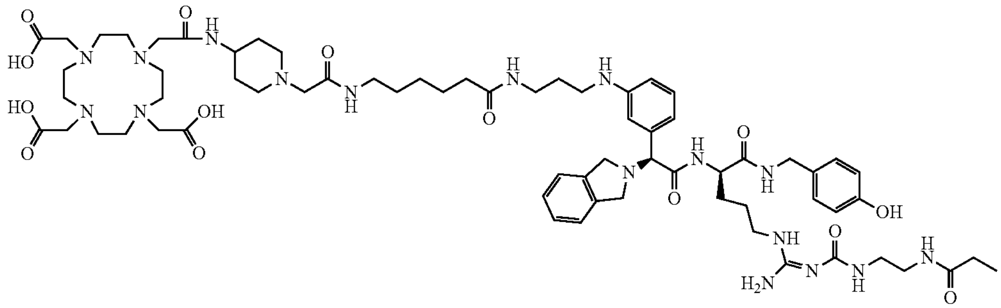 [SMILES: CCC(=O)NCCNC(=O)/N=C(/N)NCCC[C@@H](NC(=O)[C@H](c1cccc(NCCCNC(=O)CCCCCNC(=O)CN2CCC(NC(=O)CN3CCN(CC(=O)O)CCN(CC(=O)O)CCN(CC(=O)O)CC3)CC2)c1)N1Cc2ccccc2C1)C(=O)NCc1ccc(O)cc1] |
| 29 | 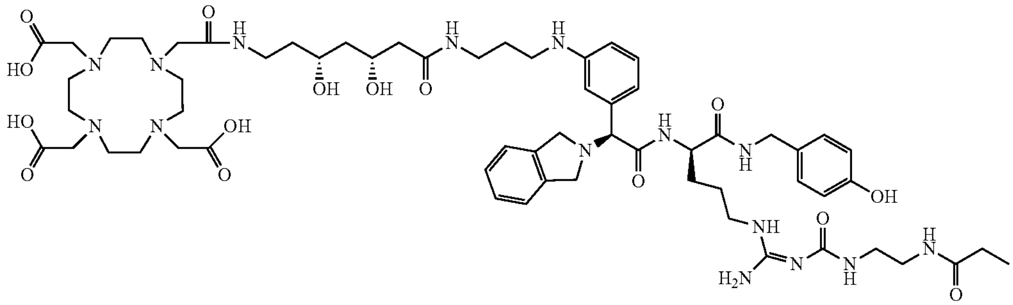 [SMILES: CCC(=O)NCCNC(=O)/N=C(/N)NCCC[C@@H](NC(=O)[C@H](c1cccc(NCCCNC(=O)C[C@H](O)C[C@H](O)CCNC(=O)CN2CCN(CC(=O)O)CCN(CC(=O)O)CCN(CC(=O)O)CC2)c1)N1Cc2ccccc2C1)C(=O)NCc1ccc(O)cc1] |

TABLE 1-continued
| Cmpd no. | Structure |
|---|---|
| 30 | 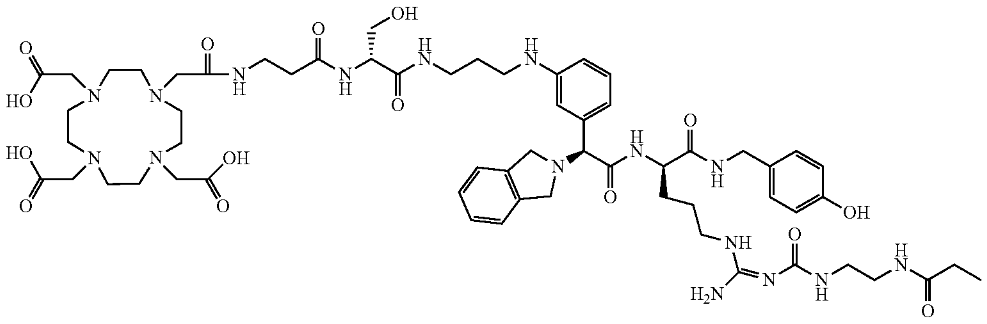 [SMILES: CCC(=O)NCCNC(=O)/N=C(/N)NCCC[C@@H](NC(=O)[C@H](c1cccc(NCCCNC(=O)[C@@H](CO)NC(=O)CCNC(=O)CN2CCN(CC(=O)O)CCN(CC(=O)O)CCN(CC(=O)O)CC2)c1)N1Cc2ccccc2C1)C(=O)NCc1ccc(O)cc1] |
| 31A | 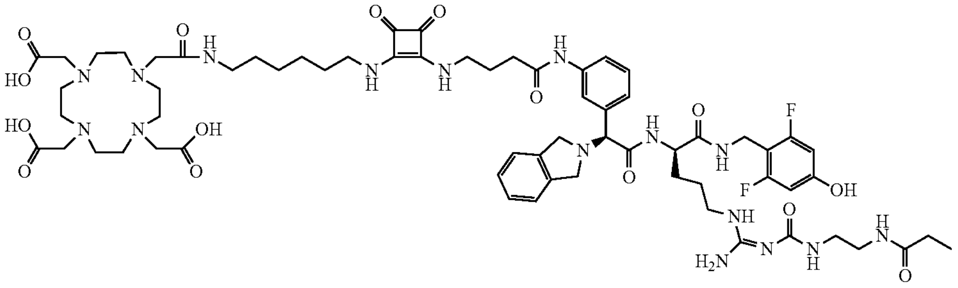<br>(absolute stereochemistry not determined) |
| 31B | 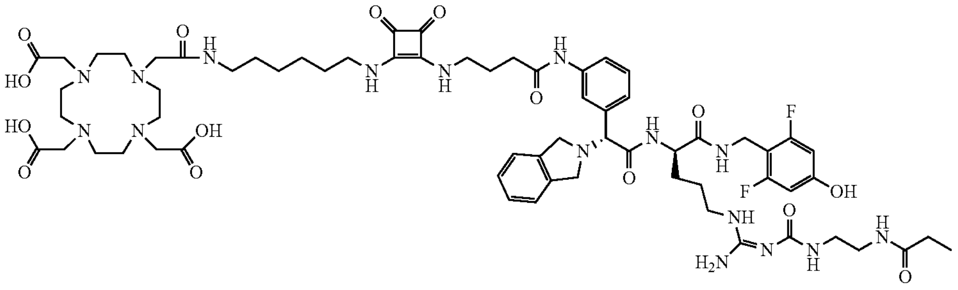<br>(absolute stereochemistry not determined) |
| 32A | 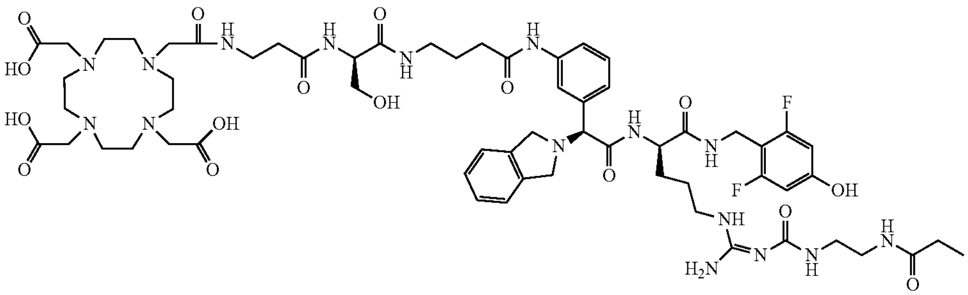<br>(absolute stereochemistry not determined) |

TABLE 1-continued
| Cmpd no. | Structure |
|---|---|
| 32B | 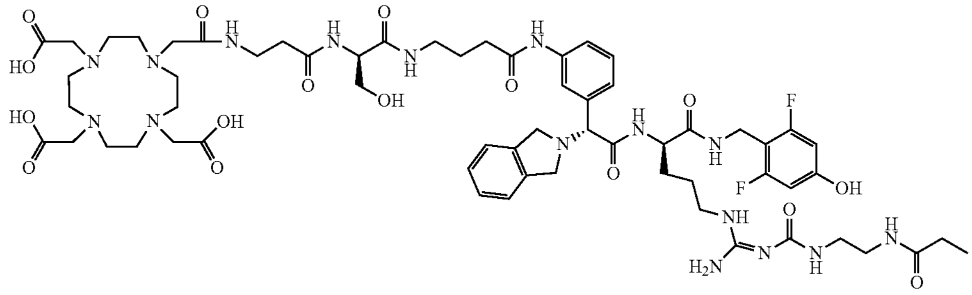 (absolute stereochemistry not determined) |
| 33 | 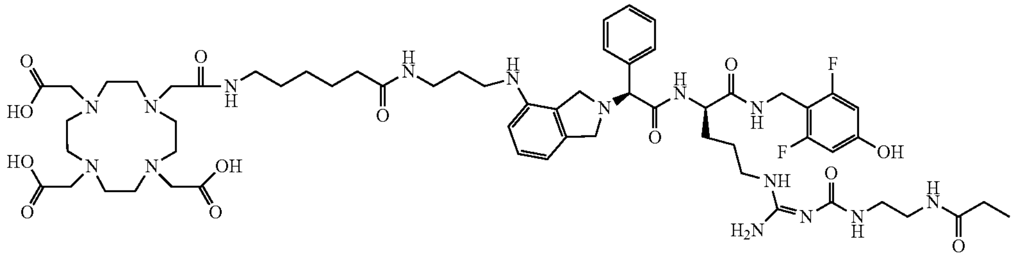 [SMILES: CCC(=O)NCCNC(=O)/N=C(/N)NCCC[C@@H](NC(=O)[C@H](c1ccccc1)N1Cc2cccc(NCCCNC(=O)CCCCCNC(=O)CN3CCN(CC(=O)O)CCN(CC(=O)O)CCN(CC(=O)O)CC3)c2C1)C(=O)NCc1c(F)cc(O)cc1F] |
| 34 | 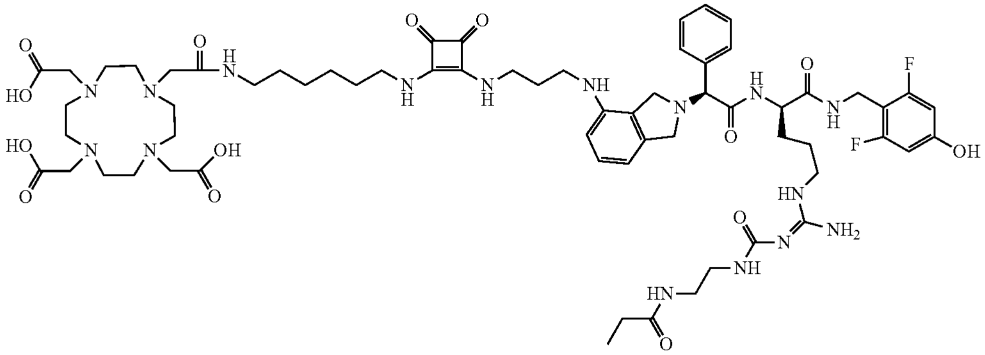 [SMILES: CCC(=O)NCCNC(=O)/N=C(/N)NCCC[C@@H](NC(=O)[C@H](c1ccccc1)N1Cc2cccc(NCCCNc3c(NCCCCCCNC(=O)CN4CCN(CC(=O)O)CCN(CC(=O)O)CCN(CC(=O)O)CC4)c(=O)c3=O)c2C1)C(=O)NCc1c(F)cc(O)cc1F] |
| 35 | 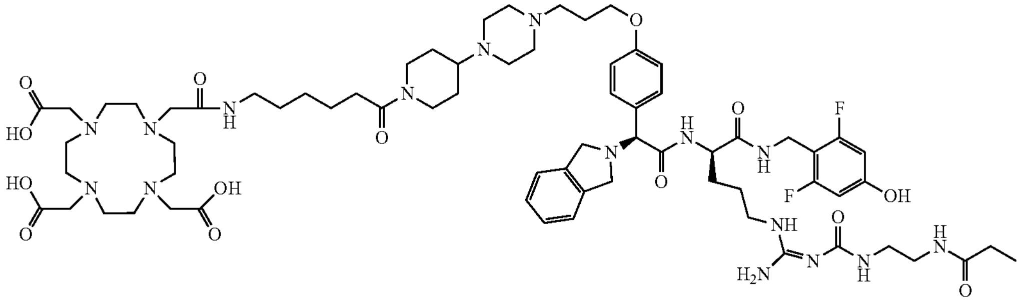 [SMILES: CCC(=O)NCCNC(=O)/N=C(/N)NCCC[C@@H](NC(=O)[C@H](c1ccc(OCCCN2CCN(C3CCN(C(=O)CCCCCNC(=O)CN4CCN(CC(=O)O)CCN(CC(=O)O)CCN(CC(=O)O)CC4)CC3)CC2)cc1)N1Cc2ccccc2C1)C(=O)NCc1c(F)cc(O)cc1F] |

TABLE 1-continued
| Cmpd no. | Structure |
| --- | --- |
| 36 | 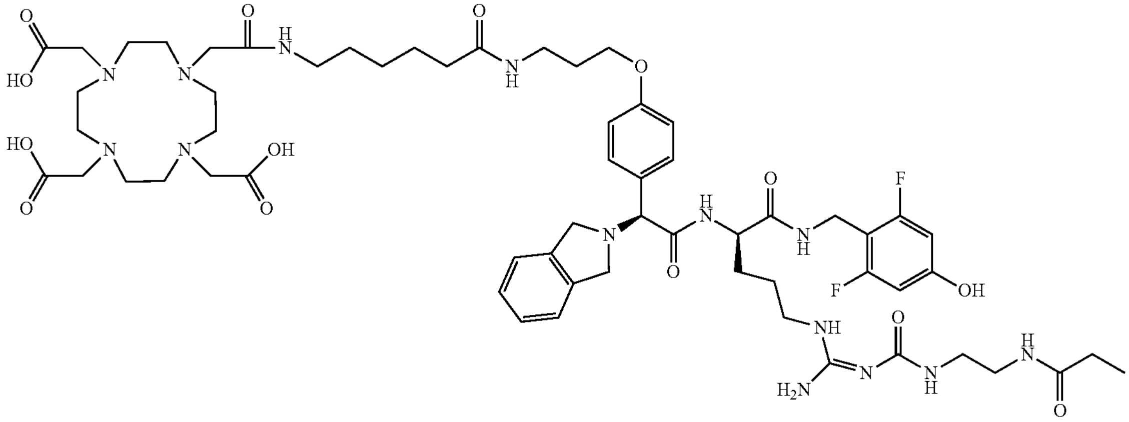 [SMILES: CCC(=O)NCCNC(=O)/N=C(/N)NCCC[C@@H](NC(=O)[C@H](c1ccc(OCCCNC(=O)CCCCCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |
| 37 | 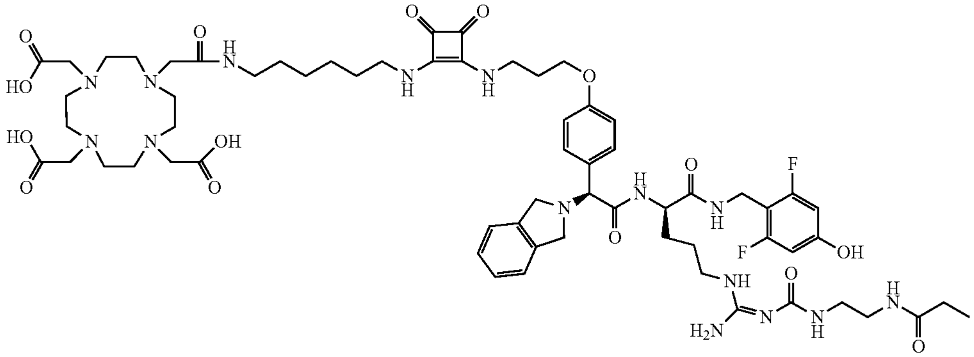 |
| 38 | 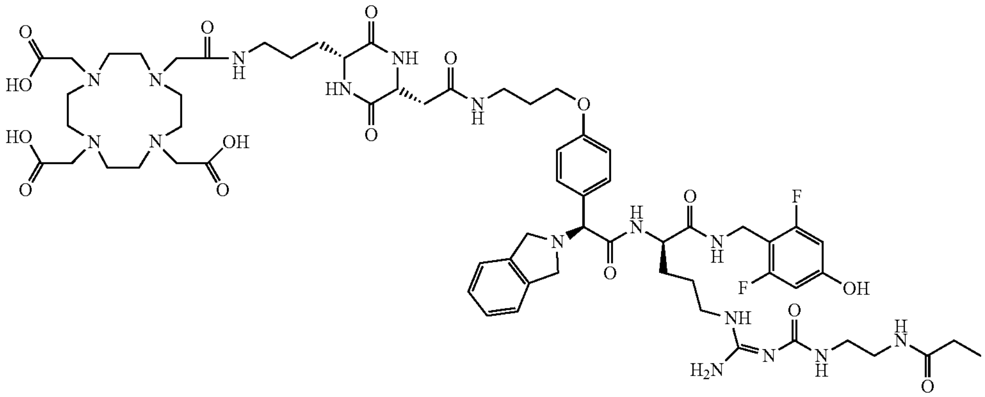 |
| 39 | 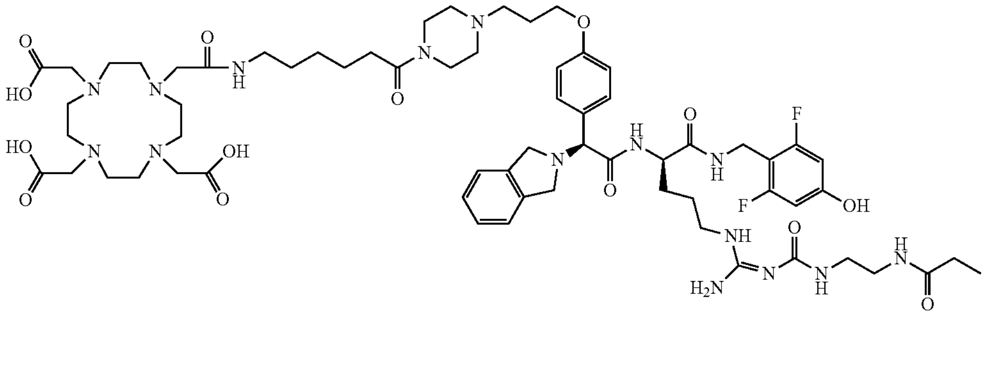 [SMILES: CCC(=O)NCCNC(=O)/N=C(/N)NCCC[C@@H](NC(=O)[C@H](c1ccc(OCCCN2CCN(C(=O)CCCCCNC(=O)CN3CCN(CC(=O)O)CCN(CC(=O)O)CCN(CC(=O)O)CC3)CC2)cc1)N1Cc2ccccc2C1)C(=O)NCc1c(F)cc(O)cc1F] |

TABLE 1-continued
| Cmpd no. | Structure |
|---|---|
| 40 | 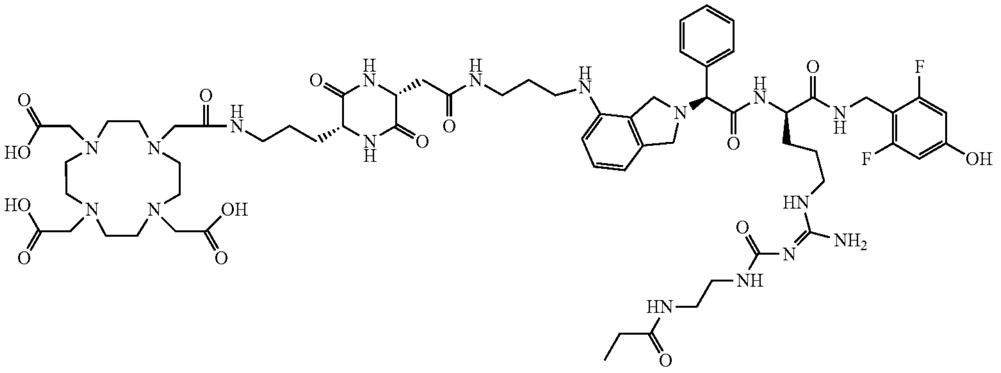 [SMILES: CCC(=O)NCCNC(=O)/N=C(/N)NCCC[C@@H](NC(=O)[C@H](c1ccccc1)N1Cc2cccc(NCCCNC(=O)C[C@H]3NC(=O)[C@@H](CCCNC(=O)CN4CCN(CC(=O)O)CCN(CC(=O)O)CCN(CC(=O)O)CC4)NC3=O)c2C1)C(=O)NCc1c(F)cc(O)cc1F] |
| 41 | 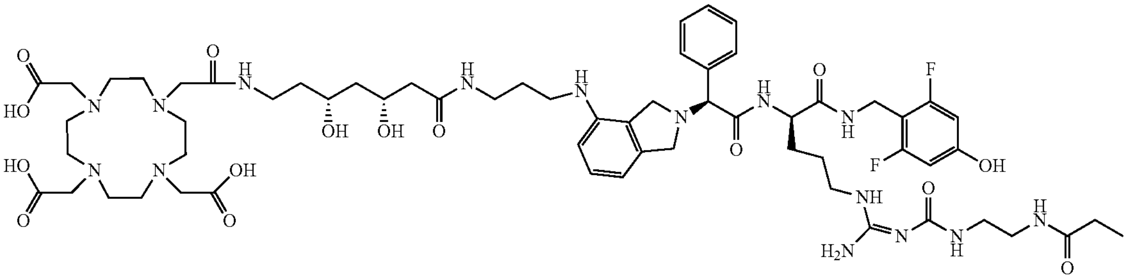 [SMILES: CCC(=O)NCCNC(=O)/N=C(/N)NCCC[C@@H](NC(=O)[C@H](c1ccccc1)N1Cc2cccc(NCCCNC(=O)C[C@H](O)C[C@H](O)CCNC(=O)CN3CCN(CC(=O)O)CCN(CC(=O)O)CCN(CC(=O)O)CC3)c2C1)C(=O)NCc1c(F)cc(O)cc1F] |
| 42 | 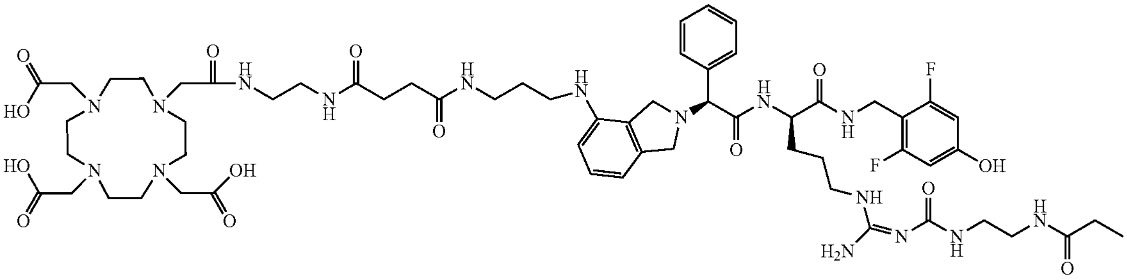 [SMILES: CCC(=O)NCCNC(=O)/N=C(/N)NCCC[C@@H](NC(=O)[C@H](c1ccccc1)N1Cc2cccc(NCCCNC(=O)CCC(=O)NCCNC(=O)CN3CCN(CC(=O)O)CCN(CC(=O)O)CCN(CC(=O)O)CC3)c2C1)C(=O)NCc1c(F)cc(O)cc1F] |
| 43 | 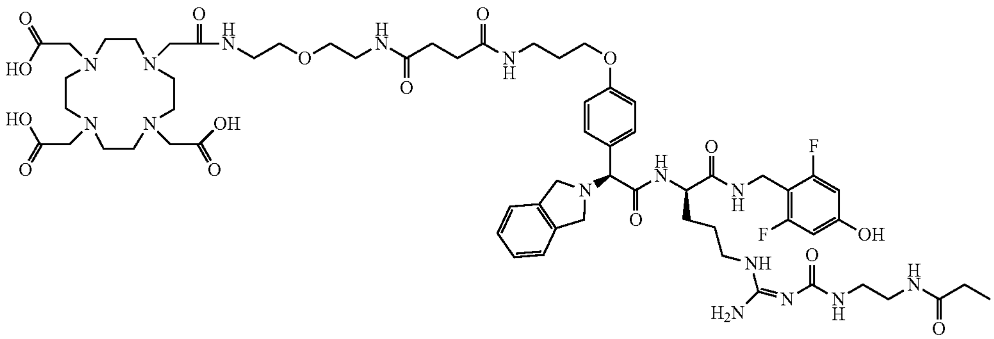 [SMILES: CCC(=O)NCCNC(=O)/N=C(/N)NCCC[C@@H](NC(=O)[C@H](c1ccc(OCCCNC(=O)CCC(=O)NCCOCCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |

TABLE 1-continued
| Cmpd no. | Structure |
|---|---|
| 44 | 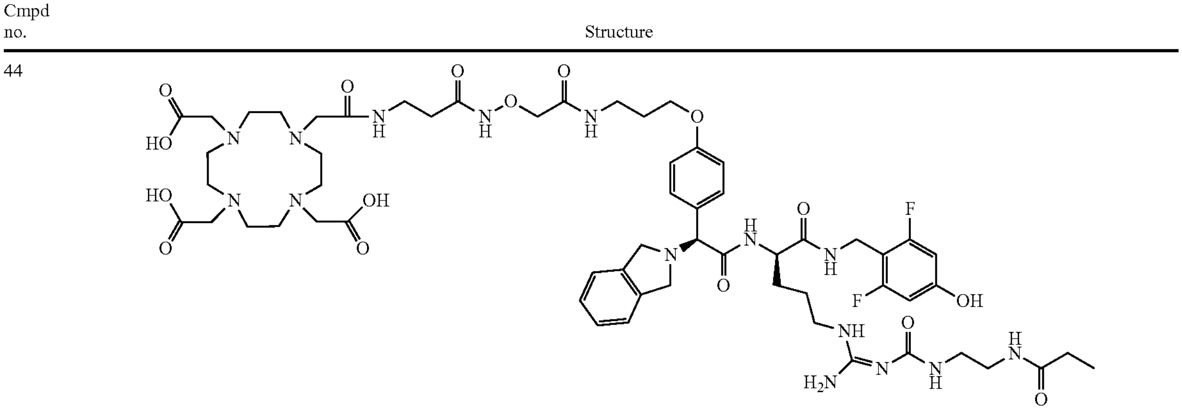 |
| 45 | 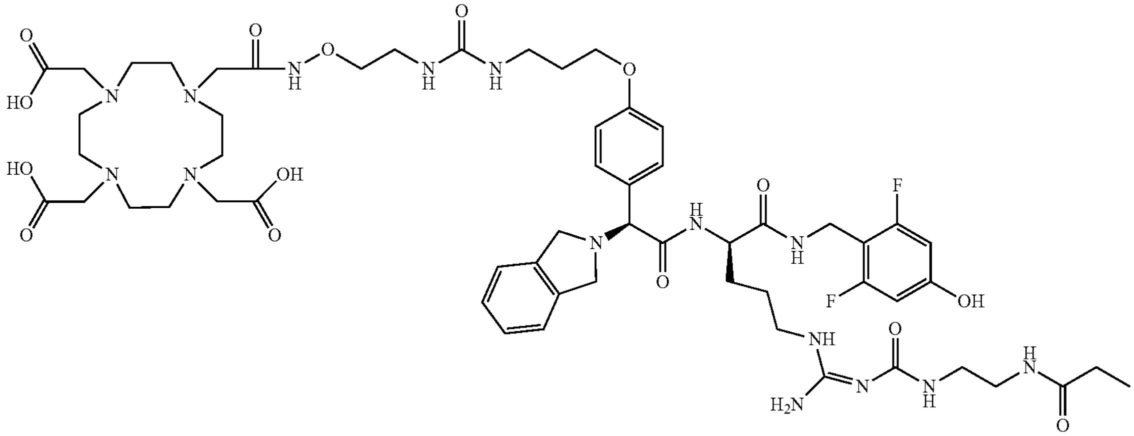 [SMILES: CCC(=O)NCCNC(=O)/N=C(/N)NCCC[C@@H](NC(=O)[C@H](c1ccc(OCCCNC(=O)NCCONC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |
| 46 | 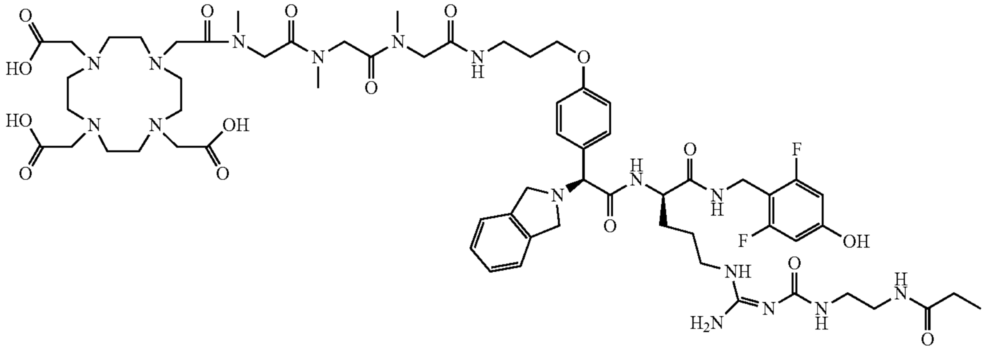 [SMILES: CCC(=O)NCCNC(=O)/N=C(/N)NCCC[C@@H](NC(=O)[C@H](c1ccc(OCCCNC(=O)CN(C)C(=O)CN(C)C(=O)CN(C)C(=O)CN2CCN(CC(=O)O)CCN(CC(=O)O)CCN(CC(=O)O)CC2)cc1)N1Cc2ccccc2C1)C(=O)NCc1c(F)cc(O)cc1F] |
| 47 | 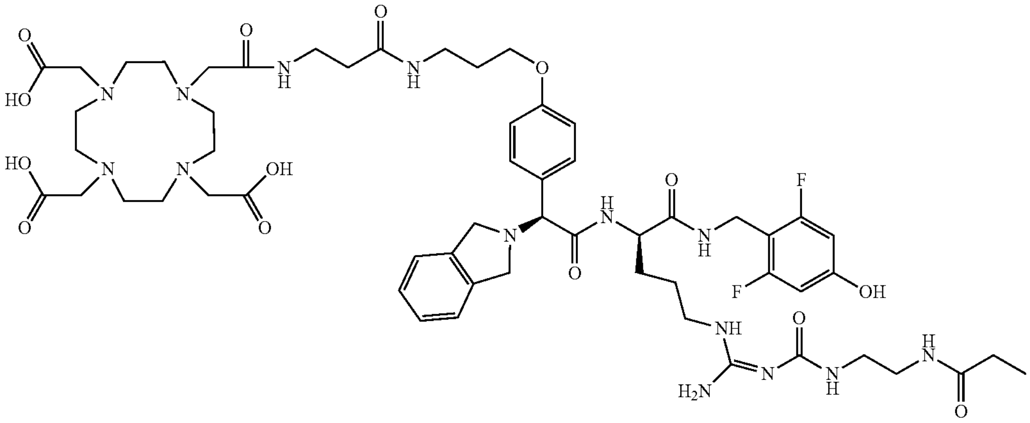 [SMILES: CCC(=O)NCCNC(=O)/N=C(/N)NCCC[C@@H](NC(=O)[C@H](c1ccc(OCCCNC(=O)CCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |

TABLE 1-continued
| Cmpd no. | Structure |
| --- | --- |
| 48 | 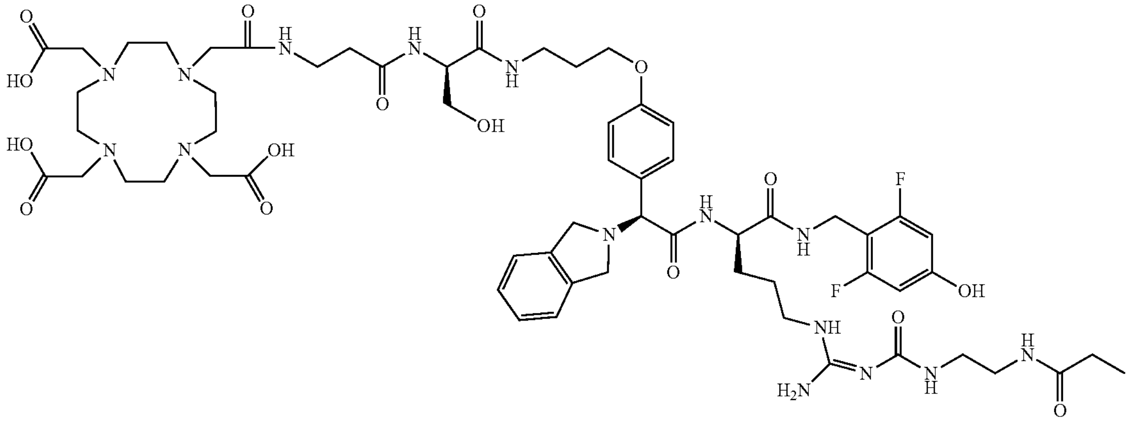 [SMILES: CCC(=O)NCCNC(=O)/N=C(/N)NCCC[C@@H](NC(=O)[C@H](c1ccc(OCCCNC(=O)[C@@H](CO)NC(=O)CCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |
| 49 | 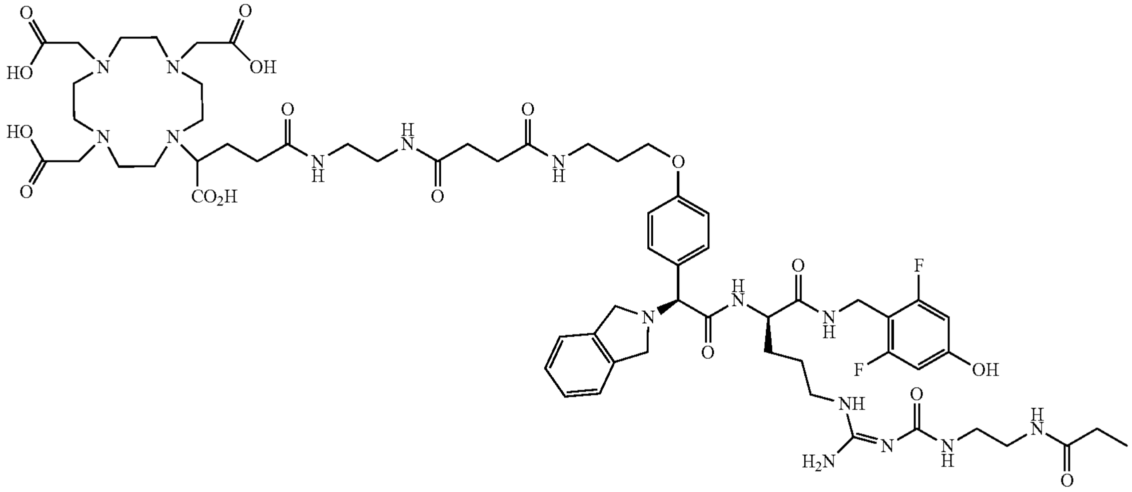 [SMILES: CCC(=O)NCCNC(=O)/N=C(/N)NCCC[C@@H](NC(=O)[C@H](c1ccc(OCCCNC(=O)CCC(=O)NCCNC(=O)CCC(C(=O)O)N2CCN(CC(=O)O)CCN(CC(=O)O)CCN(CC(=O)O)CC2)cc1)N1Cc2ccccc2C1)C(=O)NCc1c(F)cc(O)cc1F] |
| 50 | 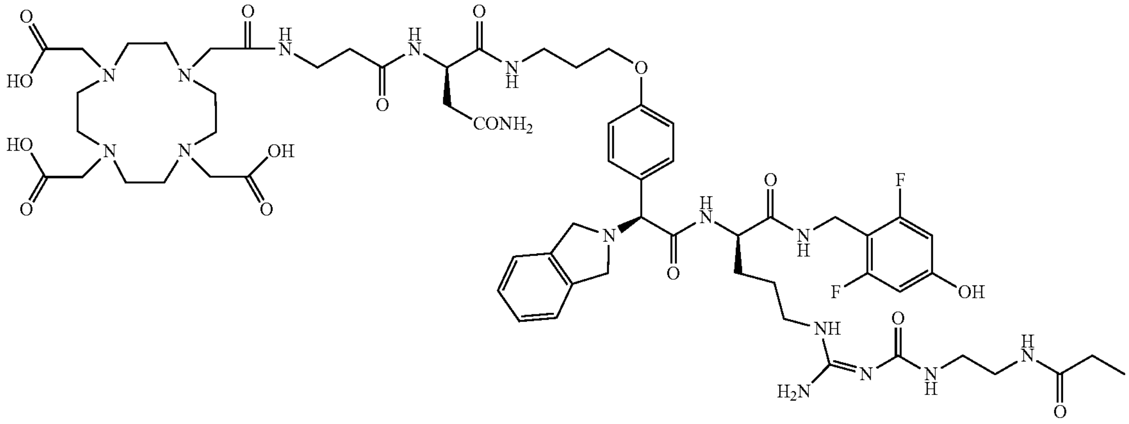 [SMILES: CCC(=O)NCCNC(=O)/N=C(/N)NCCC[C@@H](NC(=O)[C@H](c1ccc(OCCCNC(=O)[C@@H](CC(N)=O)NC(=O)CCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |

TABLE 1-continued
| Cmpd no. | Structure |
| --- | --- |
| 51 | 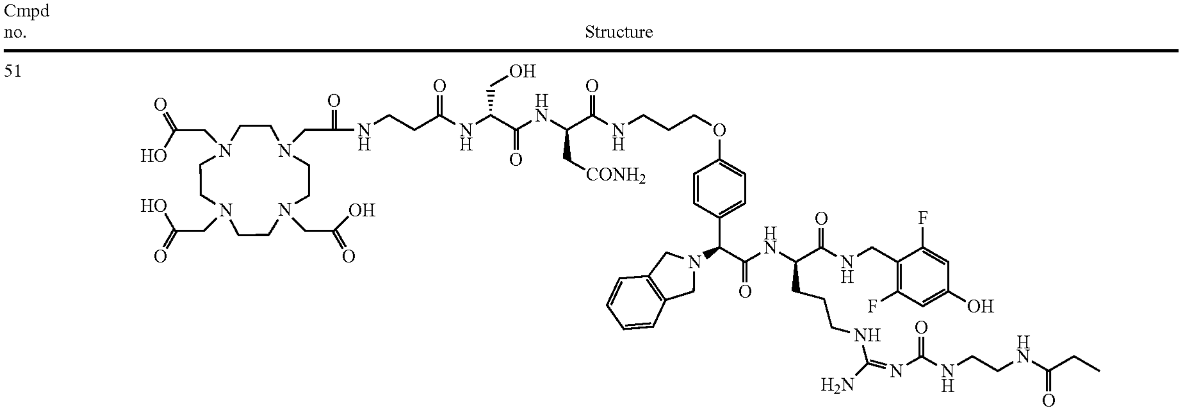 |
| 52 | 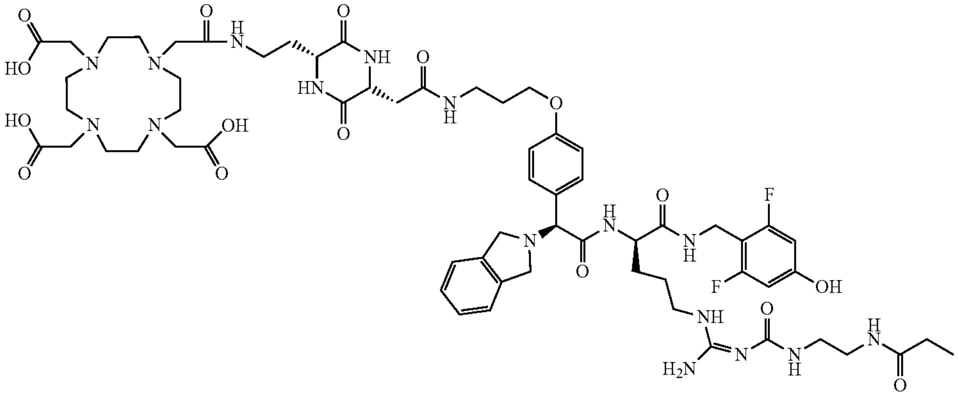 |
| 53 | 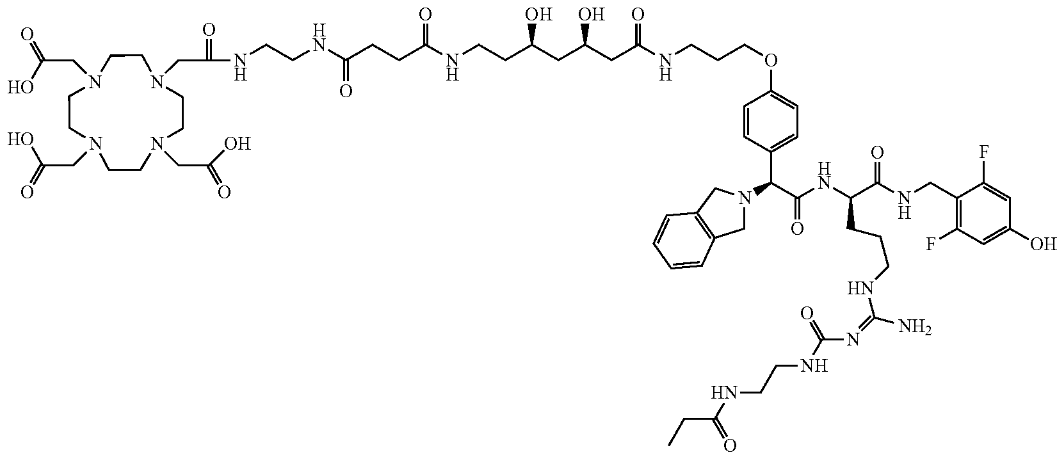 [SMILES: CCC(=O)NCCNC(=O)/N=C(/N)NCCC[C@@H](NC(=O)[C@H](c1ccc(OCCCNC(=O)C[C@H](O)C[C@H](O)CCNC(=O)CCC(=O)NCCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |
| 54 | 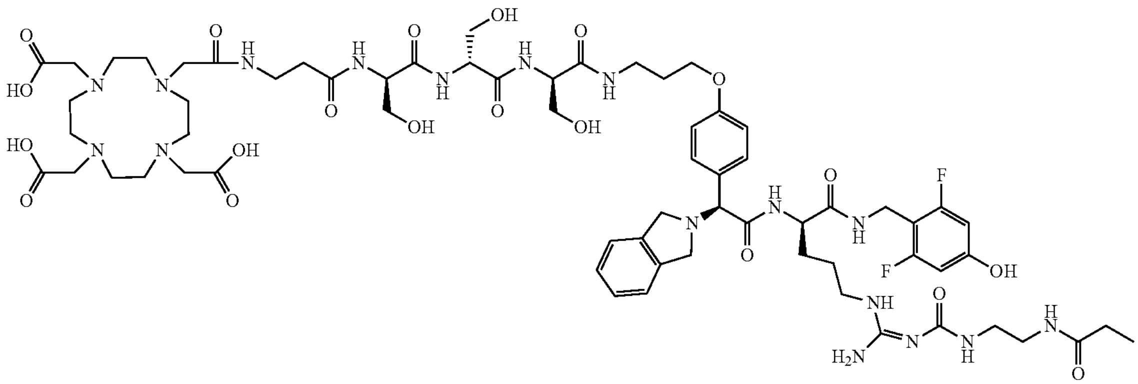 [SMILES: CCC(=O)NCCNC(=O)/N=C(/N)NCCC[C@@H](NC(=O)[C@H](c1ccc(OCCCNC(=O)[C@@H](CO)NC(=O)[C@@H](CO)NC(=O)[C@@H](CO)NC(=O)CCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |

TABLE 1-continued
| Cmpd no. | Structure |
| --- | --- |
| 55 | 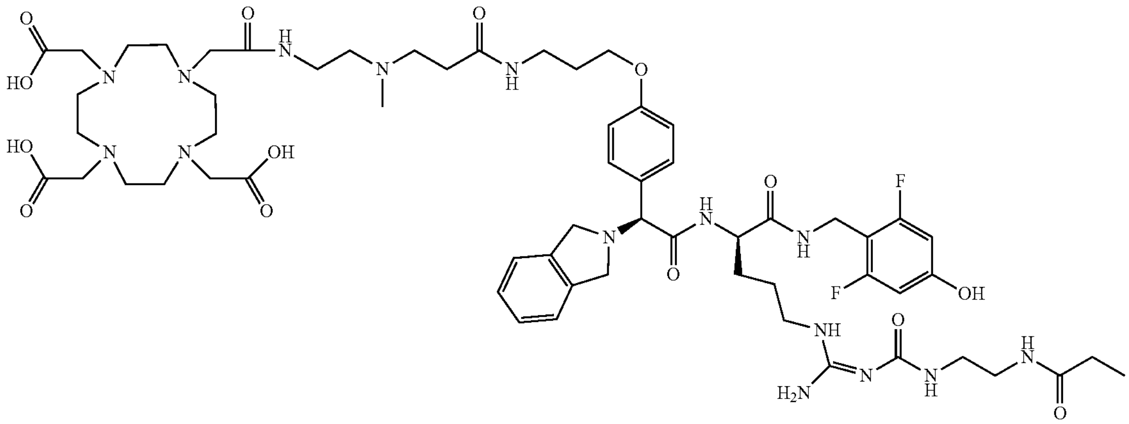 [SMILES: CCC(=O)NCCNC(=O)/N=C(/N)NCCC[C@@H](NC(=O)[C@H](c1ccc(OCCCNC(=O)CCN(C)CCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |
| 56 | 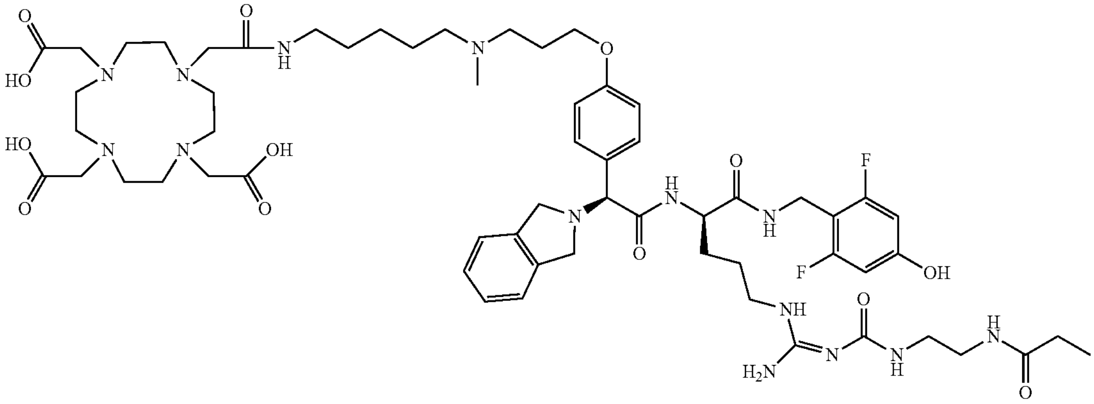 [SMILES: CCC(=O)NCCNC(=O)/N=C(/N)NCCC[C@@H](NC(=O)[C@H](c1ccc(OCCCN(C)CCCCCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F] |
| 57 | 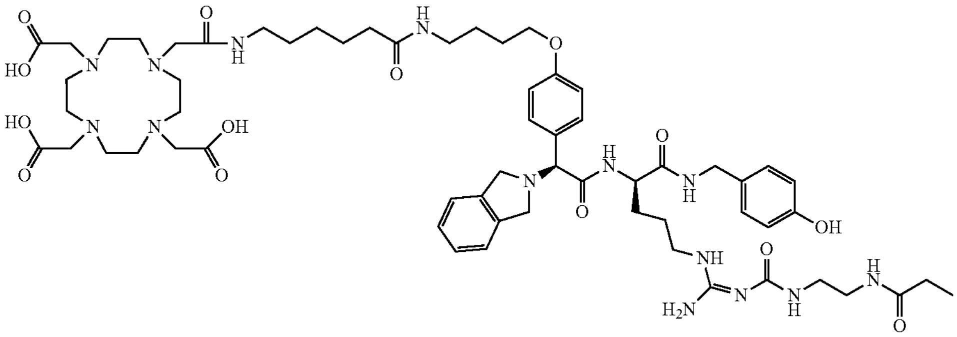 |
| 58 | 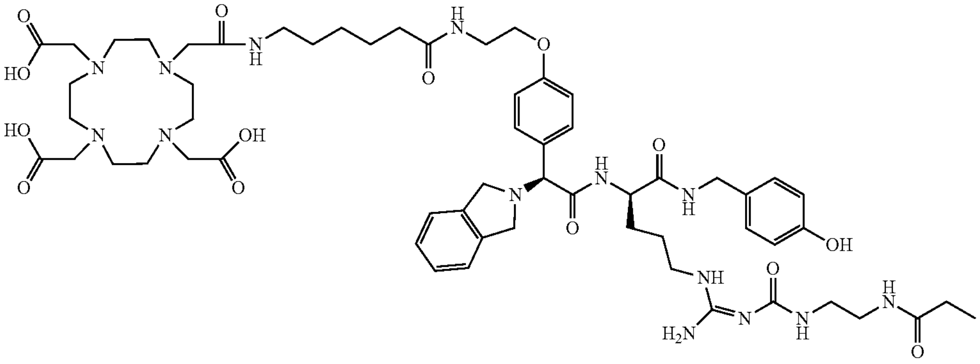 |

TABLE 1-continued

| Cmpd no. | Structure |
| --- | --- |
| 59 | 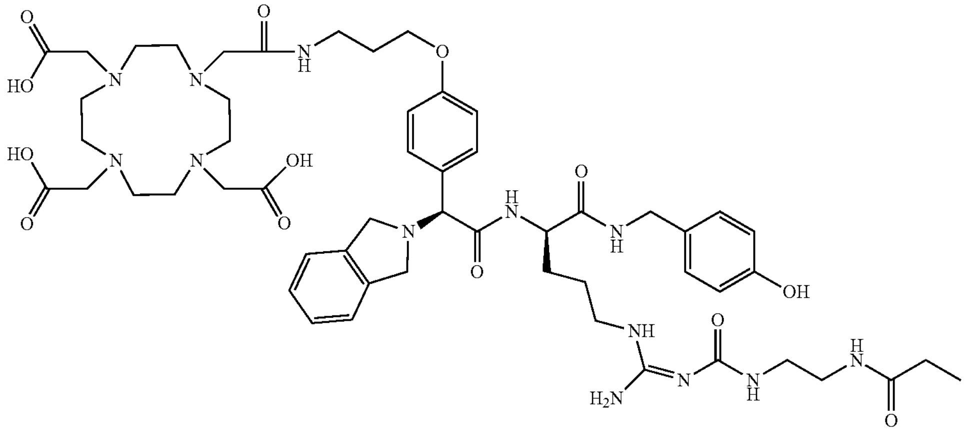 |

In some embodiments, the compound of Formula (I) is compound 1A, a pharmaceutically acceptable salt thereof, or radionuclide complex thereof; compound 1A-In, a pharmaceutically acceptable salt thereof; compound 1A-Lu, a pharmaceutically acceptable salt thereof; compound 1A-Ga, a pharmaceutically acceptable salt thereof; compound 2, a pharmaceutically acceptable salt thereof, or a radionuclide complex thereof; compound 3A, a pharmaceutically acceptable salt thereof, or a radionuclide complex thereof; 4, a pharmaceutically acceptable salt thereof, or a radionuclide complex thereof; compound 5, a pharmaceutically acceptable salt thereof, or a radionuclide complex thereof; compound 6, a pharmaceutically acceptable salt thereof, or a radionuclide complex thereof; compound 7, a pharmaceutically acceptable salt thereof, or a radionuclide complex thereof; compound 8A, a pharmaceutically acceptable salt thereof, or a radionuclide complex thereof; compound 9, a pharmaceutically acceptable salt thereof, or a radionuclide complex thereof; compound 10, a pharmaceutically acceptable salt thereof, or a radionuclide complex thereof; compound 11, a pharmaceutically acceptable salt thereof, or a radionuclide complex thereof; compound 12, a pharmaceutically acceptable salt thereof, or a radionuclide complex thereof; compound 13, a pharmaceutically acceptable salt thereof, or a radionuclide complex thereof; compound 14, a pharmaceutically acceptable salt thereof, or a radionuclide complex thereof; compound 15, a pharmaceutically acceptable salt thereof, or a radionuclide complex thereof; compound 16, a pharmaceutically acceptable salt thereof, or a radionuclide complex thereof; compound 17, a pharmaceutically acceptable salt thereof, or a radionuclide complex thereof; compound 18, a pharmaceutically acceptable salt thereof, or a radionuclide complex thereof; compound 19, a pharmaceutically acceptable salt thereof, or a radionuclide complex thereof; compound 20, a pharmaceutically acceptable salt thereof, or a radionuclide complex thereof, compound 21, a pharmaceutically acceptable salt thereof, or a radionuclide complex thereof, compound 22, a pharmaceutically acceptable salt thereof, or a radionuclide complex thereof, compound 23, a pharmaceutically acceptable salt thereof, or a radionuclide complex thereof, compound 25, a pharmaceutically acceptable salt thereof, or a radionuclide complex thereof, compound 26, a pharmaceutically acceptable salt thereof, or a radionuclide complex thereof, compound 27, a pharmaceutically acceptable salt thereof, or a radionuclide complex thereof, compound 28, a pharmaceutically acceptable salt thereof, or a radionuclide complex thereof, compound 29, a pharmaceutically acceptable salt thereof, or a radionuclide complex thereof, compound 30, a pharmaceutically acceptable salt thereof, or a radionuclide complex thereof, compound 31A, a pharmaceutically acceptable salt thereof, or a radionuclide complex thereof, compound 32A, a pharmaceutically acceptable salt thereof, or a radionuclide complex thereof, compound 33, a pharmaceutically acceptable salt thereof, or a radionuclide complex thereof, compound 34, a pharmaceutically acceptable salt thereof, or a radionuclide complex thereof, compound 35, a pharmaceutically acceptable salt thereof, or a radionuclide complex thereof, compound 36, a pharmaceutically acceptable salt thereof, or a radionuclide complex thereof, compound 37, a pharmaceutically acceptable salt thereof, or a radionuclide complex thereof, compound 38, a pharmaceutically acceptable salt thereof, or a radionuclide complex thereof, compound 39, a pharmaceutically acceptable salt thereof, or a radionuclide complex thereof, compound 40, a pharmaceutically acceptable salt thereof, or a radionuclide complex thereof, compound 41, a pharmaceutically acceptable salt thereof, or a radionuclide complex thereof, compound 42, a pharmaceutically acceptable salt thereof, or a radionuclide complex thereof, compound 43, a pharmaceutically acceptable salt thereof, or a radionuclide complex thereof, compound 44, a pharmaceutically acceptable salt thereof, or a radionuclide complex thereof, compound 45, a pharmaceutically acceptable salt thereof, or a radionuclide complex thereof, compound 46, a pharmaceutically acceptable salt thereof, or a radionuclide complex thereof, compound 47, a pharmaceutically acceptable salt thereof, or a radionuclide complex thereof, compound 48, a pharmaceutically acceptable salt thereof, or a radionuclide complex thereof, compound 49, a pharmaceutically acceptable salt thereof, or a radionuclide complex thereof, compound 50, a pharmaceutically acceptable salt thereof, or a radionuclide complex thereof, compound 51, a pharmaceutically acceptable salt thereof, or a radionuclide complex thereof, compound 52, a pharmaceutically acceptable salt thereof, or a radionuclide complex thereof, compound 53, a pharmaceutically acceptable salt thereof, or a radionuclide complex thereof, compound 54, a pharmaceutically acceptable salt thereof, or a radionuclide complex thereof, compound 55, a pharmaceutically acceptable salt thereof, or a radionuclide complex thereof, compound 56, a pharmaceutically acceptable salt thereof, or a radionuclide complex thereof, compound 57, a pharmaceutically acceptable salt thereof, or a radionuclide complex thereof, compound 58, a pharmaceutically acceptable salt thereof, or a radionuclide complex thereof, compound 59, a pharmaceutically acceptable salt thereof, or a radionuclide complex thereof.

In some embodiments, the compound of Formula (I) is compound 1B, a pharmaceutically acceptable salt thereof, or radionuclide complex thereof, compound 2B, a pharmaceutically acceptable salt thereof, or radionuclide complex thereof, compound 3B, a pharmaceutically acceptable salt thereof, or a radionuclide complex thereof, compound 4B, a pharmaceutically acceptable salt thereof, or radionuclide complex thereof, compound 6B, a pharmaceutically acceptable salt thereof, or radionuclide complex thereof, compound 7B, a pharmaceutically acceptable salt thereof, or radionuclide complex thereof, compound 8B, a pharmaceutically acceptable salt thereof, or a radionuclide complex thereof, compound 31B, a pharmaceutically acceptable salt thereof, or a radionuclide complex thereof, compound 32B, a pharmaceutically acceptable salt thereof, or a radionuclide complex thereof.

In some embodiments, the compound of Formula (I) is compound 1A, a pharmaceutically acceptable salt thereof, or radionuclide complex thereof. In some embodiments, the compound of Formula (I) is compound 1A-In, a pharmaceutically acceptable salt thereof. In some embodiments, the compound of Formula (I) is compound 1A-Lu, a pharmaceutically acceptable salt thereof. In some embodiments, the compound of Formula (I) is compound 1A-Ga, a pharmaceutically acceptable salt thereof. In some embodiments, the compound of Formula (I) is compound 1B, a pharmaceutically acceptable salt thereof, or a radionuclide complex thereof. In some embodiments, the compound of Formula (I) is compound 2, a pharmaceutically acceptable salt thereof, or a radionuclide complex thereof. In some embodiments, the compound of Formula (I) is compound 3, a pharmaceutically acceptable salt thereof, or a radionuclide complex thereof. In some embodiments, the compound of Formula (I) is compound 3A, a pharmaceutically acceptable salt thereof, or a radionuclide complex thereof. In some embodiments, the compound of Formula (I) is compound 3B, a pharmaceutically acceptable salt thereof, or a radionuclide complex thereof. In some embodiments, the compound of Formula (I) is compound 4, a pharmaceutically acceptable salt thereof, or a radionuclide complex thereof. In some embodiments, the compound of Formula (I) is compound 5, a pharmaceutically acceptable salt thereof, or a radionuclide complex thereof. In some embodiments, the compound of Formula (I) is compound 6, a pharmaceutically acceptable salt thereof, or a radionuclide complex thereof. In some embodiments, the compound of Formula (I) is compound 7, a pharmaceutically acceptable salt thereof, or a radionuclide complex thereof. In some embodiments, the compound of Formula (I) is compound 8A, a pharmaceutically acceptable salt thereof, or a radionuclide complex thereof. In some embodiments, the compound of Formula (I) is compound 8B, a pharmaceutically acceptable salt thereof, or a radionuclide complex thereof. In some embodiments, the compound of Formula (I) is compound 9, a pharmaceutically acceptable salt thereof, or a radionuclide complex thereof. In some embodiments, the compound of Formula (I) is compound 10, a pharmaceutically acceptable salt thereof, or a radionuclide complex thereof. In some embodiments, the compound of Formula (I) is compound 11, a pharmaceutically acceptable salt thereof, or a radionuclide complex thereof. In some embodiments, the compound of Formula (I) is compound 12, a pharmaceutically acceptable salt thereof, or a radionuclide complex thereof. In some embodiments, the compound of Formula (I) is compound 13, a pharmaceutically acceptable salt thereof, or a radionuclide complex thereof. In some embodiments, the compound of Formula (I) is compound 14, a pharmaceutically acceptable salt thereof, or a radionuclide complex thereof. In some embodiments, the compound of Formula (I) is compound 15, a pharmaceutically acceptable salt thereof, or a radionuclide complex thereof. In some embodiments, the compound of Formula (I) is compound 16, a pharmaceutically acceptable salt thereof, or a radionuclide complex thereof. In some embodiments, the compound of Formula (I) is compound 17, a pharmaceutically acceptable salt thereof, or a radionuclide complex thereof. In some embodiments, the compound of Formula (I) is compound 18, a pharmaceutically acceptable salt thereof, or a radionuclide complex thereof. In some embodiments, the compound of Formula (I) is compound 19, a pharmaceutically acceptable salt thereof, or a radionuclide complex thereof. In some embodiments, the compound of Formula (I) is compound 20, a pharmaceutically acceptable salt thereof, or a radionuclide complex thereof. In some embodiments, the compound of Formula (I) is compound 21, a pharmaceutically acceptable salt thereof, or a radionuclide complex thereof. In some embodiments, the compound of Formula (I) is compound 22, a pharmaceutically acceptable salt thereof, or a radionuclide complex thereof. In some embodiments, the compound of Formula (I) is compound 23, a pharmaceutically acceptable salt thereof, or a radionuclide complex thereof. In some embodiments, the compound of Formula (I) is compound 25, a pharmaceutically acceptable salt thereof, or a radionuclide complex thereof. In some embodiments, the compound of Formula (I) is compound 26, a pharmaceutically acceptable salt thereof, or a radionuclide complex thereof. In some embodiments, the compound of Formula (I) is compound 27, a pharmaceutically acceptable salt thereof, or a radionuclide complex thereof. In some embodiments, the compound of Formula (I) is compound 28, a pharmaceutically acceptable salt thereof, or a radionuclide complex thereof. In some embodiments, the compound of Formula (I) is compound 29, a pharmaceutically acceptable salt thereof, or a radionuclide complex thereof. In some embodiments, the compound of Formula (I) is compound 30, a pharmaceutically acceptable salt thereof, or a radionuclide complex thereof. In some embodiments, the compound of Formula (I) is compound 31A, a pharmaceutically acceptable salt thereof, or a radionuclide complex thereof. In some embodiments, the compound of Formula (I) is compound 31B, a pharmaceutically acceptable salt thereof, or a radionuclide complex thereof. In some embodiments, the compound of Formula (I) is compound 32A, a pharmaceutically acceptable salt thereof, or a radionuclide complex thereof. In some embodiments, the compound of Formula (I) is compound 33, a pharmaceutically acceptable salt thereof, or a radionuclide complex thereof. In some embodiments, the compound of Formula (I) is compound 34, a pharmaceutically acceptable salt thereof, or a radionuclide complex thereof. In some embodiments, the compound of Formula (I) is compound 35, a pharmaceutically acceptable salt thereof, or a radionuclide complex thereof. In some embodiments, the compound of Formula (I) is compound 36, a pharmaceutically acceptable salt thereof, or a radionuclide complex thereof. In some embodiments, the compound of Formula (I) is compound 37, a pharmaceutically acceptable salt thereof, or a radionuclide complex thereof. In some embodiments, the compound of Formula (I) is compound 38, a pharmaceutically acceptable salt thereof, or a radionuclide complex thereof. In some embodiments, the compound of Formula (I) is compound 39, a pharmaceutically acceptable salt thereof, or a radionuclide complex thereof. In some embodiments, the compound of Formula (I) is compound 40, a pharmaceutically acceptable salt thereof, or a radionuclide complex thereof. In some embodiments, the compound of Formula (I) is compound 41, a pharmaceutically acceptable salt thereof, or a radionuclide complex thereof. In some embodiments, the compound of Formula (I) is compound 42, a pharmaceutically acceptable salt thereof, or a radionuclide complex thereof. In some embodiments, the compound of Formula (I) is compound 43, a pharmaceutically acceptable salt thereof, or a radionuclide complex thereof. In some embodiments, the compound of Formula (I) is compound 44, a pharmaceutically acceptable salt thereof, or a radionuclide complex thereof. In some embodiments, the compound of Formula (I) is compound 45, a pharmaceutically acceptable salt thereof, or a radionuclide complex thereof. In some embodiments, the compound of Formula (I) is compound 46, a pharmaceutically acceptable salt thereof, or a radionuclide complex thereof. In some embodiments, the compound of Formula (I) is compound 47, a pharmaceutically acceptable salt thereof, or a radionuclide complex thereof. In some embodiments, the compound of Formula (I) is compound 48, a pharmaceutically acceptable salt thereof, or a radionuclide complex thereof. In some embodiments, the compound of Formula (I) is compound 49, a pharmaceutically acceptable salt thereof, or a radionuclide complex thereof. In some embodiments, the compound of Formula (I) is compound 50, a pharmaceutically acceptable salt thereof, or a radionuclide complex thereof. In some embodiments, the compound of Formula (I) is compound 51, a pharmaceutically acceptable salt thereof, or a radionuclide complex thereof. In some embodiments, the compound of Formula (I) is compound 52, a pharmaceutically acceptable salt thereof, or a radionuclide complex thereof. In some embodiments, the compound of Formula (I) is compound 53, a pharmaceutically acceptable salt thereof, or a radionuclide complex thereof. In some embodiments, the compound of Formula (I) is compound 54, a pharmaceutically acceptable salt thereof, or a radionuclide complex thereof. In some embodiments, the compound of Formula (I) is compound 55, a pharmaceutically acceptable salt thereof, or a radionuclide complex thereof. In some embodiments, the compound of Formula (I) is compound 56, a pharmaceutically acceptable salt thereof, or a radionuclide complex thereof. In some embodiments, the compound of Formula (I) is compound 57, a pharmaceutically acceptable salt thereof, or a radionuclide complex thereof. In some embodiments, the compound of Formula (I) is compound 58, a pharmaceutically acceptable salt thereof, or a radionuclide complex thereof. In some embodiments, the compound of Formula (I) is compound 59, a pharmaceutically acceptable salt thereof, or a radionuclide complex thereof.

Representative Neuropeptide Y Receptor ($NPY_1R$) Ligands

In one aspect, the $NPY_1R$ ligand described herein has the structure of Formula (III), or a pharmaceutically acceptable salt thereof. In some embodiments, described herein is a compound of Formula (III), or a pharmaceutically acceptable salt thereof:

Formula (III)

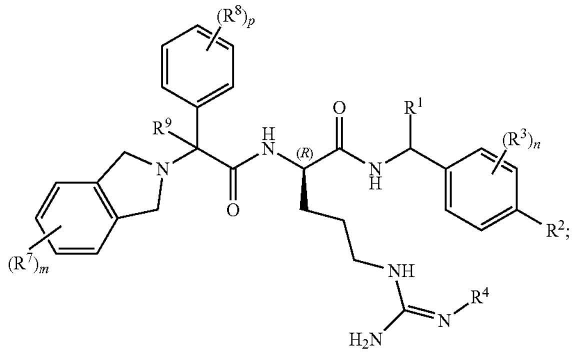

wherein:

$R^1$ is H, —$C_1$-$C_6$ alkyl, or —C(=O)$NH_2$;

$R^2$ is —OH, —$NH_2$, —C(=O)$NH_2$, or —$CH_2$NHC(=O)$NH_2$;

each $R^3$ is independently selected from the group consisting of $R^{3a}$, $R^{3b}$, $R^{3c}$, and $R^{3d}$;

$R^{3a}$, $R^{3b}$, $R^{3c}$, and $R^{3d}$ are each independently selected from the group consisting of H, F, Cl, Br, I, —CN, substituted or unsubstituted —$C_1$-$C_6$ alkyl, and substituted or unsubstituted —$C_1$-$C_6$ alkoxy;

$R^4$ is H, —C(=O)$R^{10}$, —C(=O)NH$R^{10}$, or —C(=O)N($CH_3$)$R^{10}$;

$R^{10}$ is substituted or unsubstituted —$C_1$-$C_6$ alkyl, substituted or unsubstituted 2 to 6-membered heteroalkyl, —$(CH_2)_t$—$NH_2$, —$(CH_2)_t$C(=O)O$(CH_2)_u$$CH_3$, —$(CH_2)_t$NHC(=O)$(CH_2)_u$$CH_3$, or —$(CH_2)_t$-substituted or unsubstituted 5 to 6 membered heteroaryl ring;

t is 1, 2, 3, 4, 5, or 6;

u is 1, 2, 3, or 4;

each $R^7$ is independently selected from the group consisting of F, Cl, Br, I, —CN, —OH, substituted or unsubstituted —$C_1$-$C_6$ alkyl, substituted or unsubstituted —$C_1$-$C_6$ alkoxy, and substituted or unsubstituted —NH—$C_1$-$C_6$ alkyl;

each $R^8$ is independently selected from the group consisting of F, Cl, Br, I, —CN, —OH, substituted or unsubstituted —$C_1$-$C_6$ alkyl, substituted or unsubstituted —$C_1$-$C_6$ alkoxy, and substituted or unsubstituted —NH—$C_1$-$C_6$ alkyl;

$R^9$ is H, substituted or unsubstituted —$C_1$-$C_4$ alkyl, or substituted or unsubstituted —$C_1$-$C_6$ alkoxy;

n is 0, 1, 2, 3, or 4;

m is 0, 1, 2, or 3; and p is 0, 1, 2, or 3.

In some embodiments, the compound has the following structure, or a pharmaceutically acceptable salt thereof:

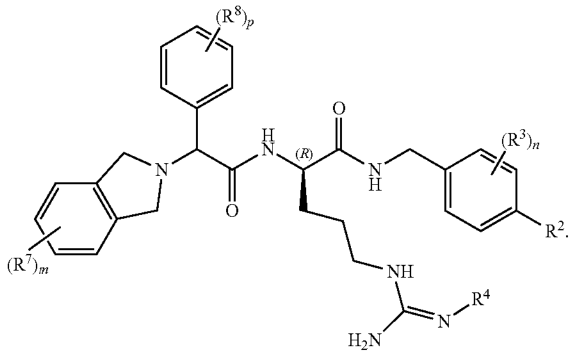

In some embodiments, the compound has the following structure, or a pharmaceutically acceptable salt thereof:

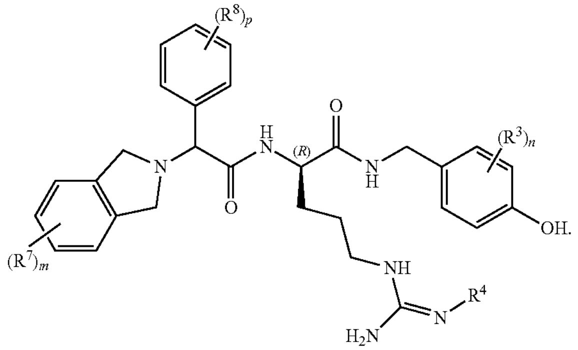

In some embodiments the compound has the following structure, or a pharmaceutically acceptable salt thereof:

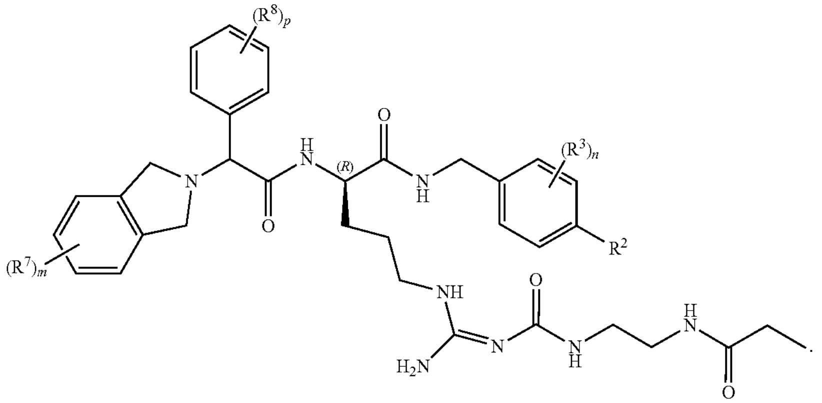

In some embodiments, the compound has the following structure, or a pharmaceutically acceptable salt thereof:

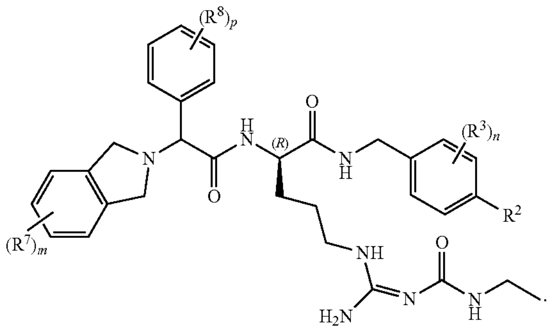

In some embodiments, the compound has the following structure, or a pharmaceutically acceptable salt thereof:

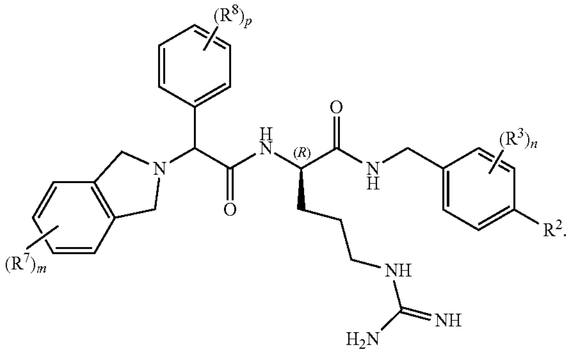

In some embodiments, the compound has the following structure, or a pharmaceutically acceptable salt thereof:

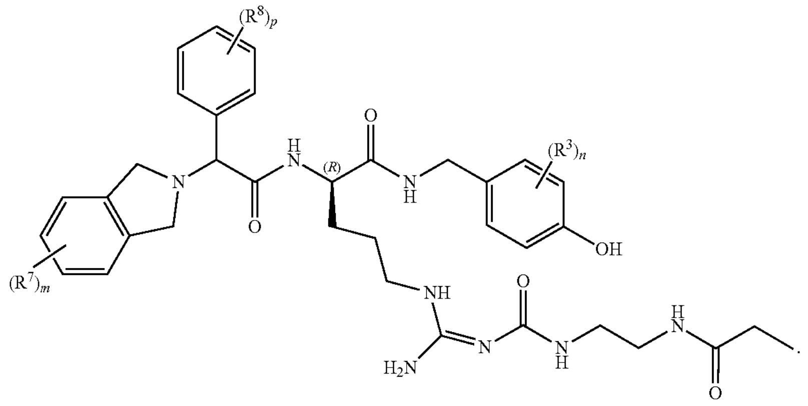

In some embodiments, the compound has the following structure, or a pharmaceutically acceptable salt thereof:

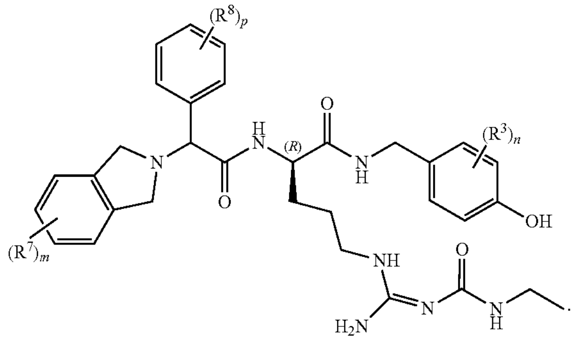

In some embodiments, the compound has the following structure, or a pharmaceutically acceptable salt thereof:

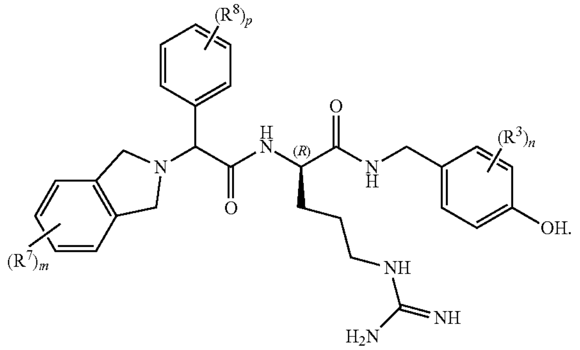

In some embodiments, $R^1$ is H.

In some embodiments, $R^2$ is —OH.

In some embodiments, n is 0. In some embodiments, n is 1. In some embodiments, n is 2. In some embodiments, n is 3.

In some embodiments, each $R^3$ is independently selected from the group consisting of $R^{3a}$, $R^{3b}$, $R^{3c}$, and $R^{3d}$; and $R^{3a}$, $R^{3b}$, $R^{3c}$, and $R^{3d}$ are each independently selected from the group consisting of H, F, Cl, Br, I, —CN, —$CH_3$, —$CF_3$, and —$OCH_3$.

In some embodiments, each $R^{3a}$, $R^{3b}$, $R^{3c}$ and $R^{3d}$ is independently selected from the group consisting of H, F, Cl, Br, I, —CN, —$CH_3$, —$CF_3$, and —$OCH_3$.

In some embodiments, $R^{3a}$ and $R^{3d}$ are F or Cl and $R^{3b}$ and $R^{3c}$ are H.

In some embodiments, $R^4$ is H. In some embodiments, $R^4$ is —C(═O)NHR$^{10}$. In some embodiments, $R^4$ is —C(═O)NH$(CH_2)_tCH_3$. In some embodiments, $R^4$ is —C(═O)NH$(CH_2)_t$NHC(═O)$(CH_2)_uCH_3$.

In some embodiments, $R^{10}$ is unsubstituted —$C_1$-$C_6$ alkyl or —$(CH_2)_t$NHC(═O)$(CH_2)_uCH_3$; t is 1, 2, 3, or 4; and u is 1 or 2. In some embodiments, $R^{10}$ is —$CH_2CH_3$. In some embodiments, $R^{10}$ is —$(CH_2)_2$NHC(═O)$(CH_2)CH_3$.

In some embodiments, m is 0. In some embodiments, m is 1. In some embodiments, m is 2. In some embodiments, m is 3.

In some embodiments, p is 0. In some embodiments, p is 1. In some embodiments, p is 2. In some embodiments, p is 3.

In some embodiments, $R^7$ is F, Cl, Br, I, —CN, or —OH, —$CH_3$, or —$CH_2CH_3$. In some embodiments, $R^7$ is —$C_1$-$C_6$ alkyl optionally substituted with F, Cl, Br, I, —CN, —OH, —$NH_2$, —O—$C_1$-$C_3$ alkyl, or —NH—$C_1$-$C_3$ alkyl. In some embodiments, $R^7$ is substituted or unsubstituted —$C_1$-$C_6$ alkoxy or substituted or unsubstituted —NH—$C_1$-$C_6$ alkyl. In some embodiments, $R^7$ is substituted or unsubstituted —O—$C_1$-$C_6$ alkyl. In some embodiments, $R^7$ is —$OCH_3$. In some embodiments, $R^7$ is —$OCH_2CH_3$. In some embodiments, $R^7$ is —$OCH_2CH_2CH_3$. In some embodiments, $R^7$ is substituted or unsubstituted —NH—$C_1$-$C_6$ alkyl. In some embodiments, $R^7$ is —$NHCH_3$. In some embodiments, $R^7$ is —$NHCH_2CH_3$. In some embodiments, $R^7$ is —$NHCH_2CH_2CH_3$. In some embodiments, $R^7$ is —$OCH_2OH$, —$OCH_2CH_2OH$, or —$OCH_2CH_2CH_2OH$. In some embodiments, $R^7$ is —$OCH_2NH_2$, —$OCH_2CH_2NH_2$, or —$OCH_2CH_2CH_2NH_2$. In some embodiments, $R^7$ is —$NHCH_2OH$, —$NHCH_2CH_2OH$, or —$NHCH_2CH_2CH_2OH$. In some embodiments, $R^7$ is —$NHCH_2NH_2$, —$NHCH_2CH_2NH_2$, or —$NHCH_2CH_2CH_2NH_2$.

In some embodiments, $R^7$ is F, Cl, Br, I, —CN, —OH, —$CH_3$, —$CH_2CH_3$, —$OCH_3$, —$OCH_2CH_3$, —$OCH_2CH_2CH_3$, —$NHCH_3$, —$NHCH_2CH_3$, —$NHCH_2CH_2CH_3$, —$OCH_2OH$, —$OCH_2CH_2OH$, —$OCH_2CH_2CH_2OH$, —$OCH_2NH_2$, —$OCH_2CH_2NH_2$, —$OCH_2CH_2CH_2NH_2$, —$NHCH_2OH$, —$NHCH_2CH_2OH$, —$NHCH_2CH_2CH_2OH$, —$NHCH_2NH_2$, —$NHCH_2CH_2NH_2$, or —$NHCH_2CH_2CH_2NH_2$.

In some embodiments, $R^8$ is F, Cl, Br, I, —CN, or —OH, —$CH_3$, or —$CH_2CH_3$. In some embodiments, $R^8$ is —$C_1$-$C_6$ alkyl optionally substituted with F, Cl, Br, I, —CN, —OH, —$NH_2$, —O—$C_1$-$C_3$ alkyl, or —NH—$C_1$-$C_3$ alkyl. In some embodiments, $R^8$ is substituted or unsubstituted —$C_1$-$C_6$ alkoxy or substituted or unsubstituted —NH—$C_1$-$C_6$ alkyl. In some embodiments, $R^8$ is substituted or unsubstituted —O—$C_1$-$C_6$ alkyl. In some embodiments, $R^8$ is —$OCH_3$. In some embodiments, $R^8$ is —$OCH_2CH_3$. In some embodiments, $R^8$ is —$OCH_2CH_2CH_3$. In some embodiments, $R^8$ is substituted or unsubstituted —NH—$C_1$-$C_6$ alkyl. In some embodiments, $R^8$ is —$NHCH_3$. In some embodiments, $R^8$ is —$NHCH_2CH_3$. In some embodiments, $R^8$ is —$NHCH_2CH_2CH_3$. In some embodiments, $R^8$ is —$OCH_2OH$, —$OCH_2CH_2OH$, or —$OCH_2CH_2CH_2OH$. In some embodiments, $R^8$ is —$OCH_2NH_2$, —$OCH_2CH_2NH_2$, or —$OCH_2CH_2CH_2NH_2$. In some embodiments, $R^8$ is —$NHCH_2OH$, —$NHCH_2CH_2OH$, or —$NHCH_2CH_2CH_2OH$. In some embodiments, $R^8$ is —$NHCH_2NH_2$, —$NHCH_2CH_2NH_2$, or —$NHCH_2CH_2CH_2NH_2$.

In some embodiments, $R^8$ is F, Cl, Br, I, —CN, —OH, —$CH_3$, —$CH_2CH_3$, —$OCH_3$, —$OCH_2CH_3$, —$OCH_2CH_2CH_3$, —$NHCH_3$, —$NHCH_2CH_3$, —$NHCH_2CH_2CH_3$, —$OCH_2OH$, —$OCH_2CH_2OH$, —$OCH_2CH_2CH_2OH$, —$OCH_2NH_2$, —$OCH_2CH_2NH_2$, —$OCH_2CH_2CH_2NH_2$, —$NHCH_2OH$, —$NHCH_2CH_2OH$, —$NHCH_2CH_2CH_2OH$, —$NHCH_2NH_2$, —$NHCH_2CH_2NH_2$, or —$NHCH_2CH_2CH_2NH_2$.

In some embodiments, $R^9$ is H.

In some embodiments, the compound has the following structure, or a pharmaceutically acceptable salt thereof:

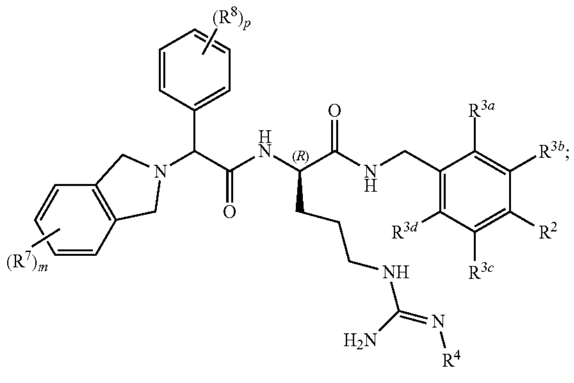

wherein each $R^{3a}$, $R^{3b}$, $R^{3c}$ and $R^{3d}$ is independently selected from the group consisting of H, F, Cl, Br, I, —CN, substituted or unsubstituted —$C_1$-$C_6$ alkyl, and substituted or unsubstituted —$C_1$-$C_6$ alkoxy.

In some embodiments, the compound has the following structure, or a pharmaceutically acceptable salt thereof:

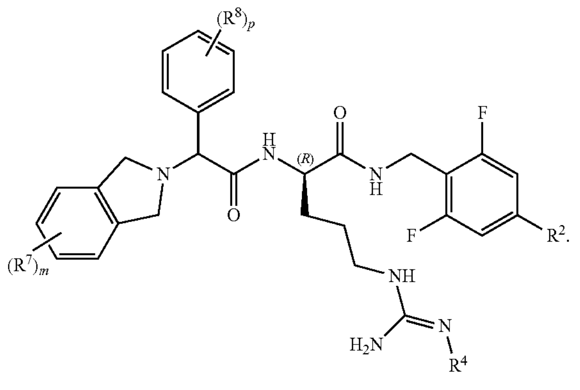

In some embodiments, the compound has the following structure, or a pharmaceutically acceptable salt thereof:

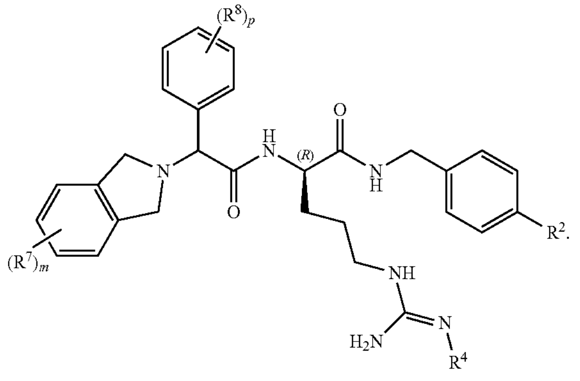

In some embodiments, the compound has the following structure, or a pharmaceutically acceptable salt thereof:

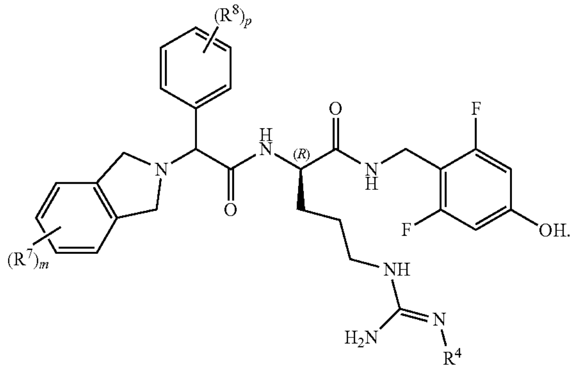

In some embodiments, the compound has the following structure, or a pharmaceutically acceptable salt thereof:

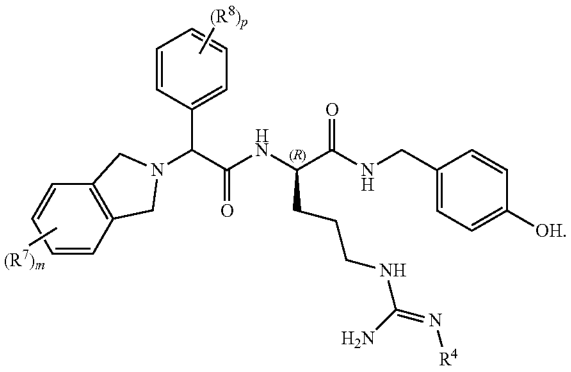
Representative Ligand Compounds
In some embodiments, the compound of Formula (III) has the following structure, or a
| Cmpd no. | Structure |
| --- | --- |
| 60 | 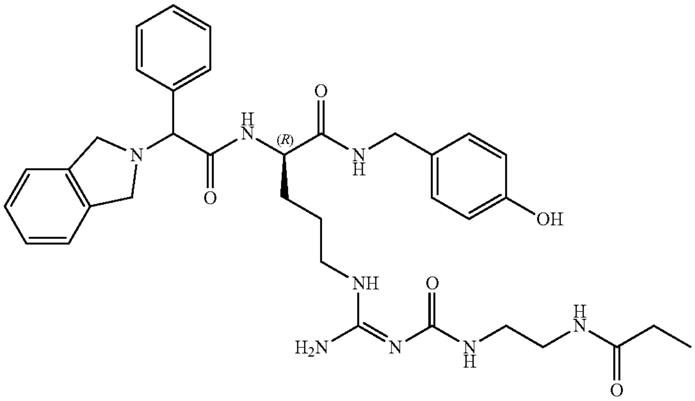 |
| 60A | 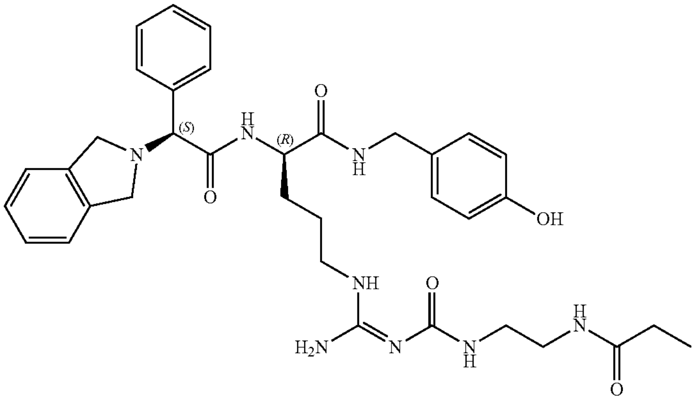 |

-continued
| Cmpd no. | Structure |
| --- | --- |
| 60B | 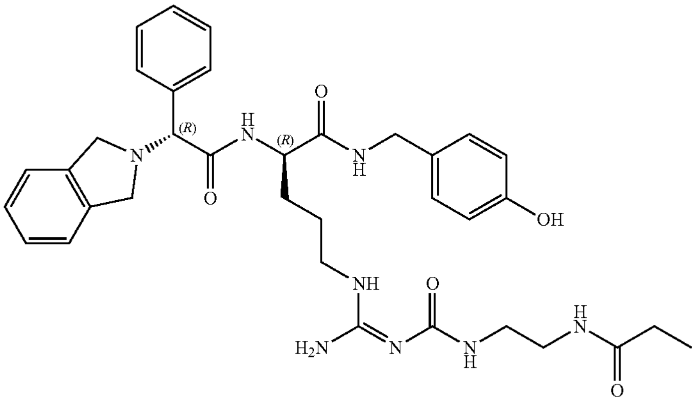 |
| 61A | 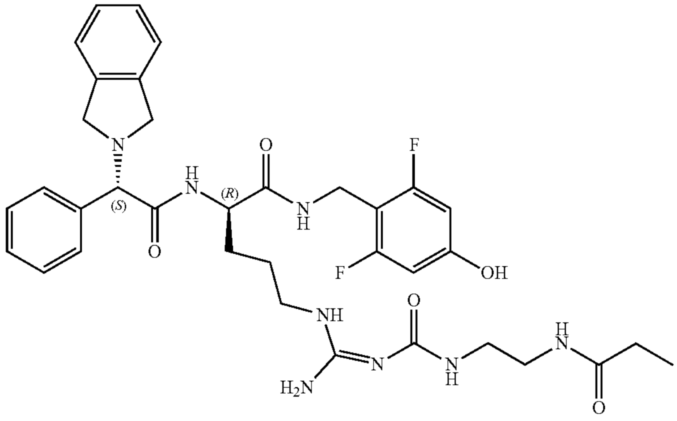 |
| 61B | 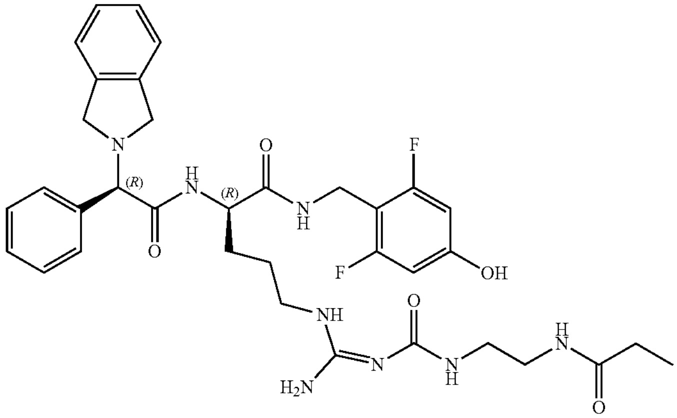 |

-continued
| Cmpd no. | Structure |
|---|---|
| 62 | 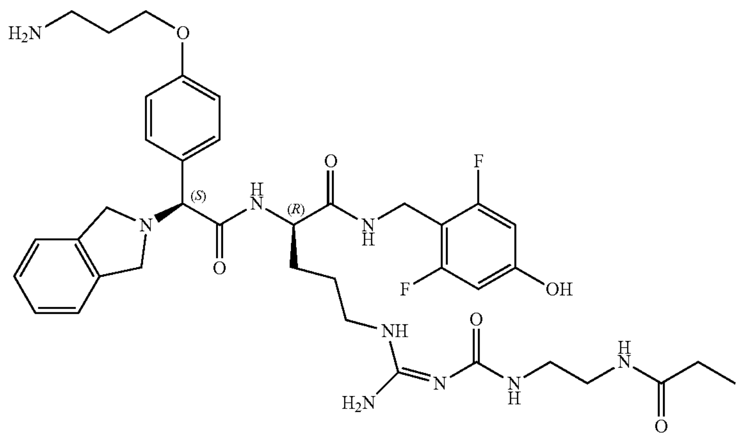 |
| 63 | 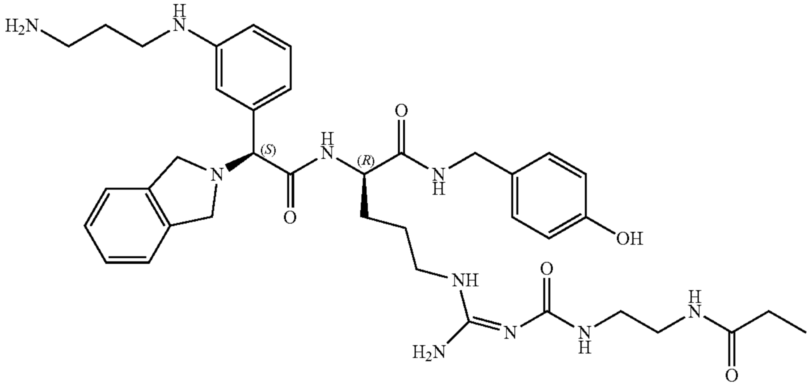 |
| 64A | 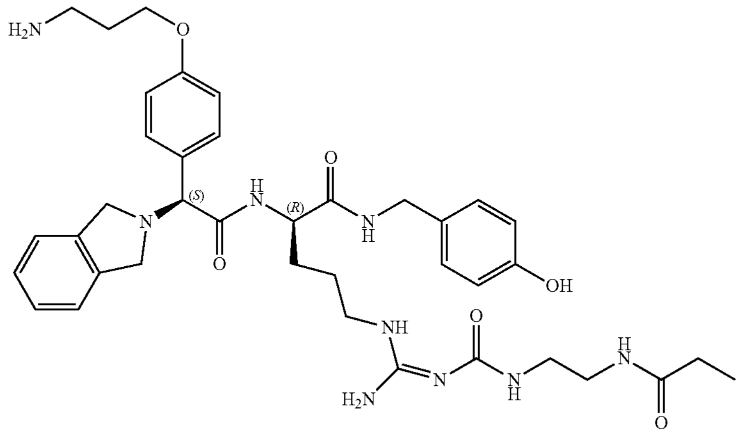 |

-continued
| Cmpd no. | Structure |
|---|---|
| 64B | 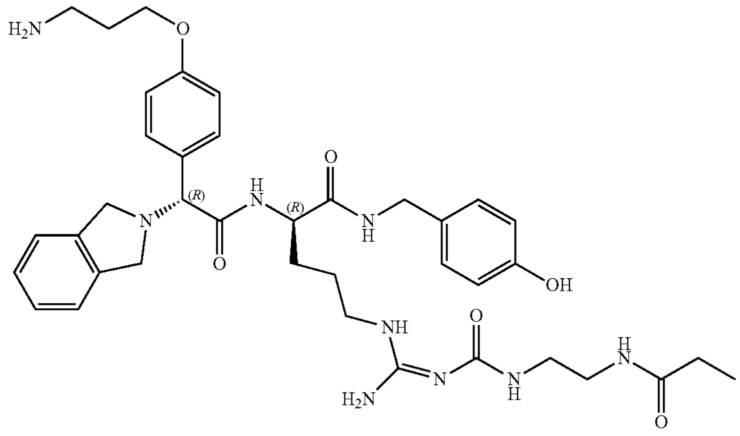 |
| 65 | 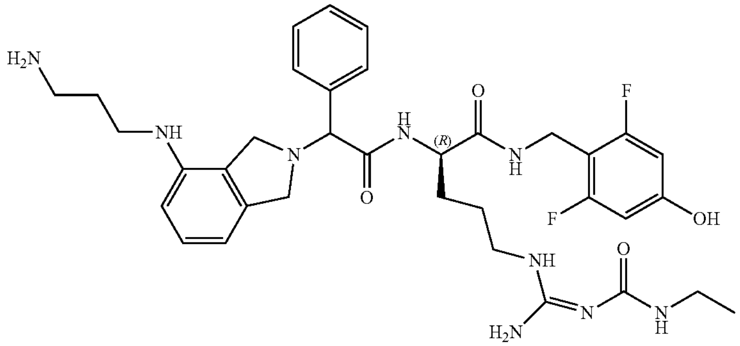 |
| 65A | 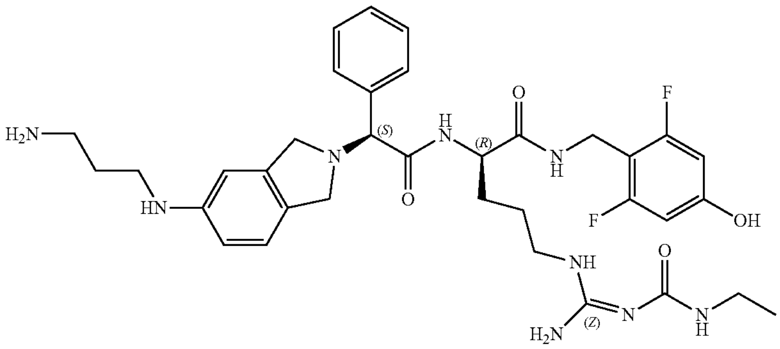 |
| 66A | 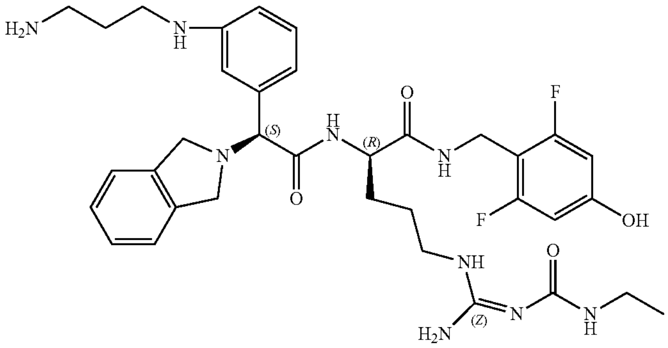 |

-continued
| Cmpd no. | Structure |
|---|---|
| 66B | 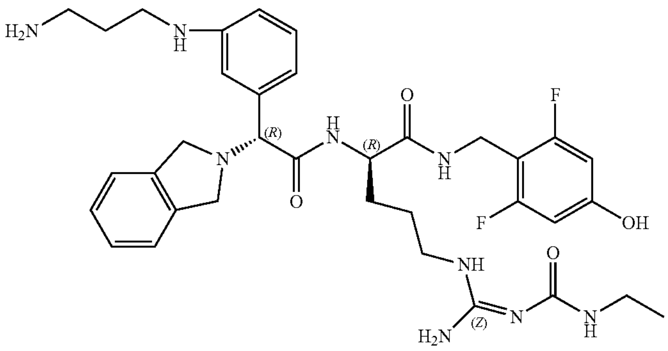 |
| 67 | 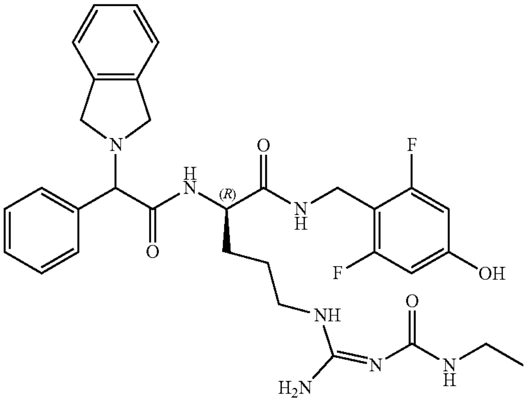 |
| 68 | 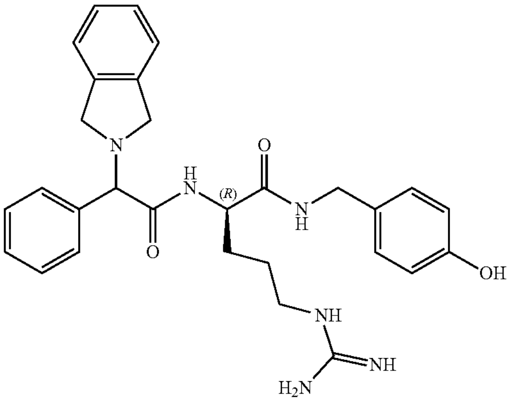 |
| 69 | 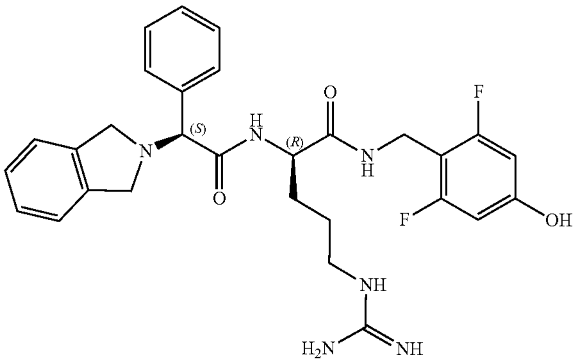 |

-continued
| Cmpd no. | Structure |
| --- | --- |
| 70 | 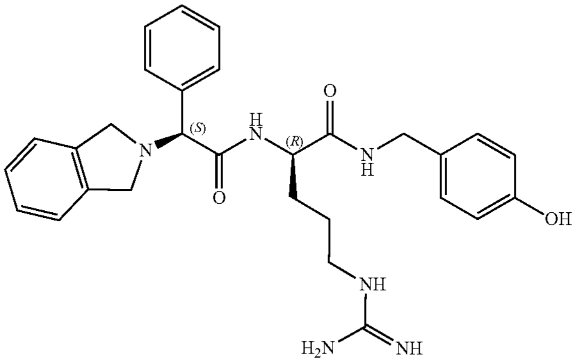 |
| 71A | 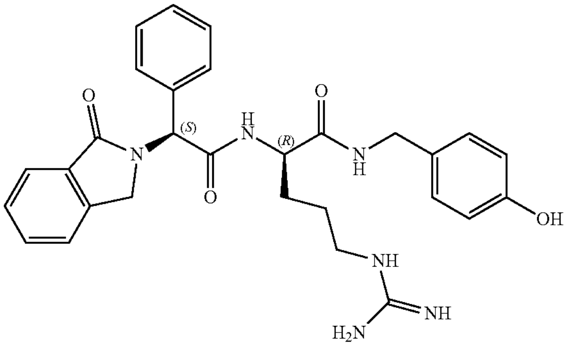 |
| 71B | 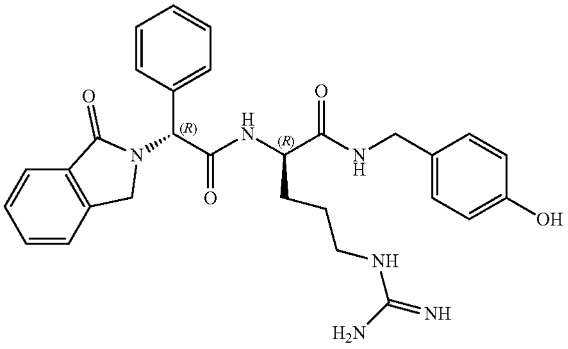 |
| 72 | 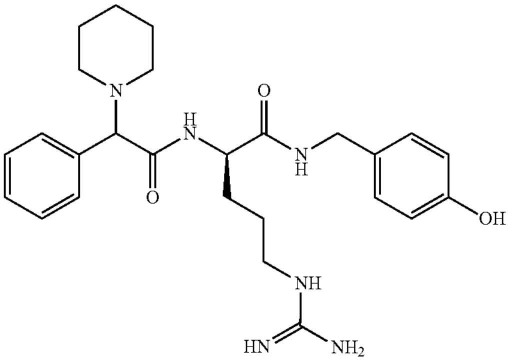 [SMILES: N=C(N)NCCC[C@@H](NC(=O)C(c1ccccc1)N1CCCCC1)C(=O)NCc1ccc(O)cc1] |

-continued
| Cmpd no. | Structure |
|---|---|
| 73 | 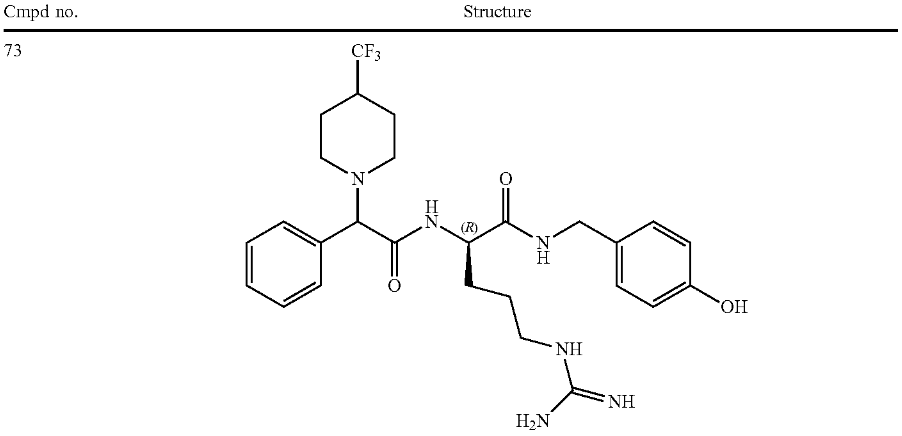 |
| 74 | 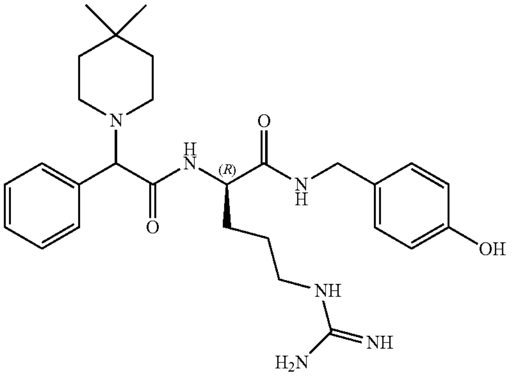 |
| 75 | 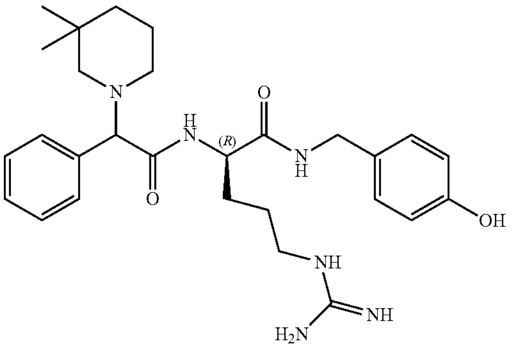 |
| 76 | 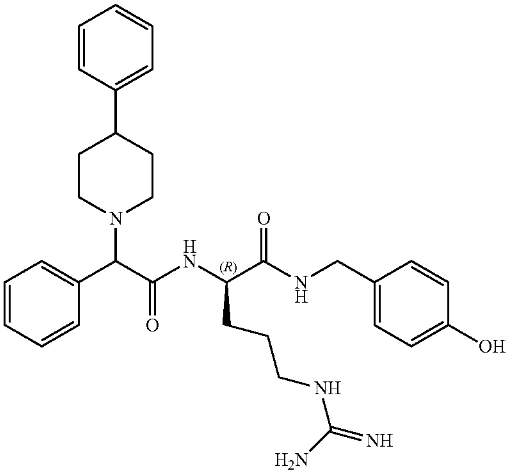 |

-continued
| Cmpd no. | Structure |
|---|---|
| 77 | 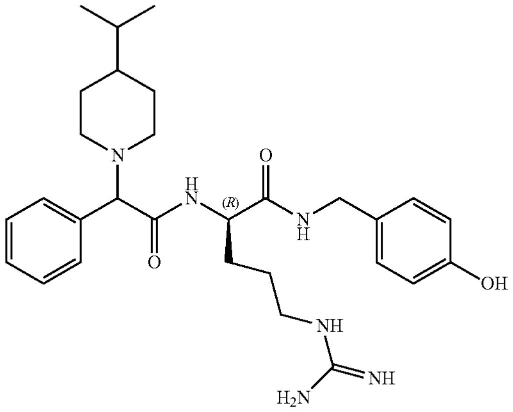 |
| 78 | 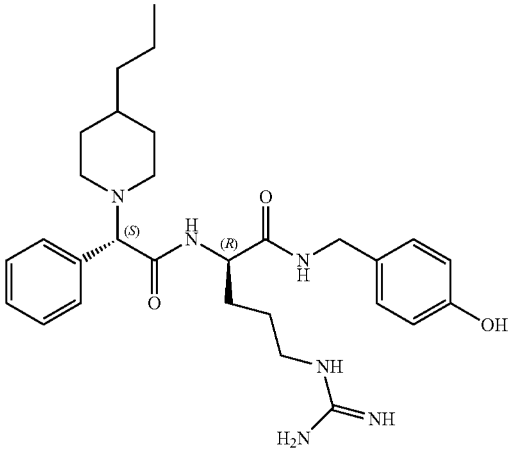 |
| 78A | 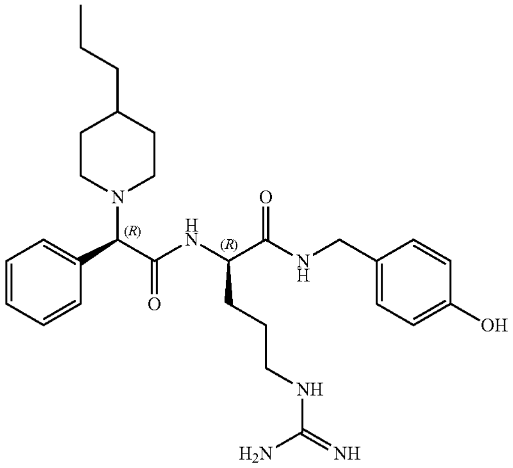 |

-continued
| Cmpd no. | Structure |
|---|---|
| 79 | 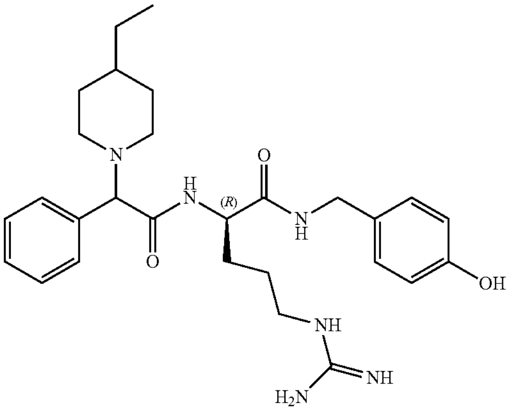 |
| 80 | 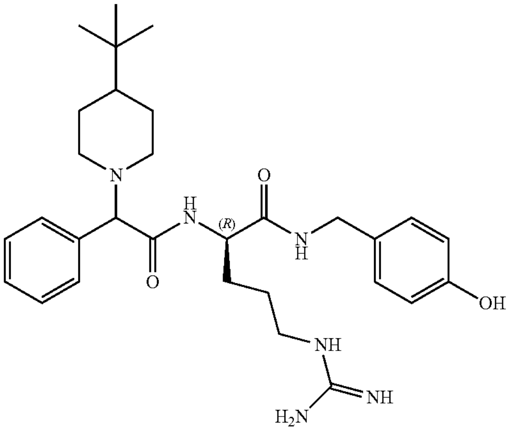 |
| 81 | 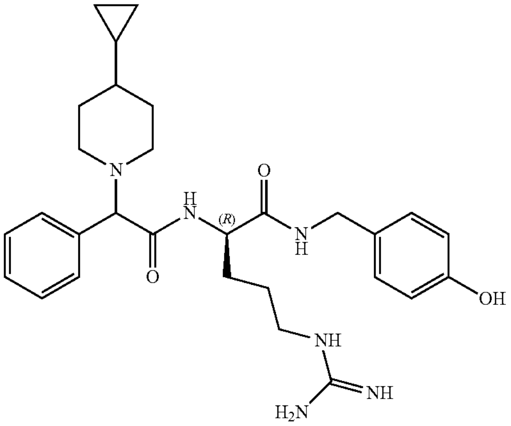 |

-continued
| Cmpd no. | Structure |
| --- | --- |
| 82 | 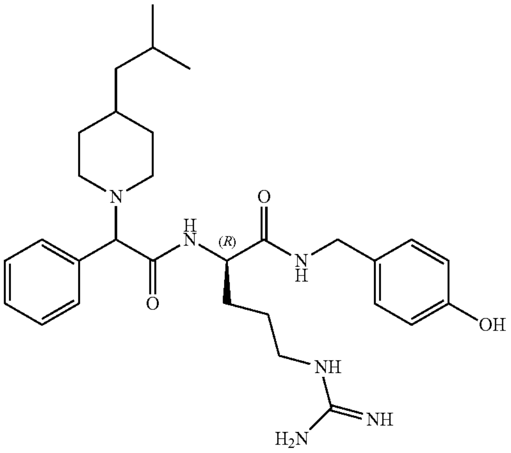 |
| 83 | 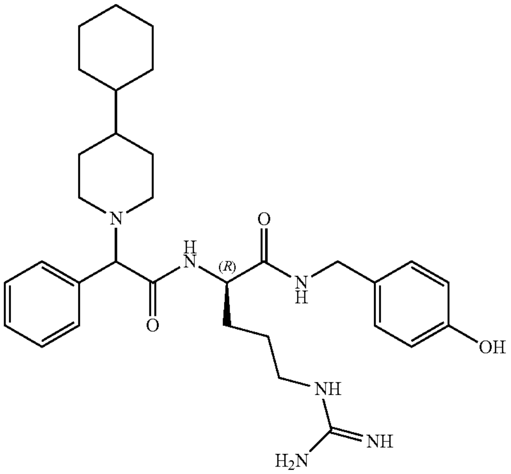 |
| 84 | 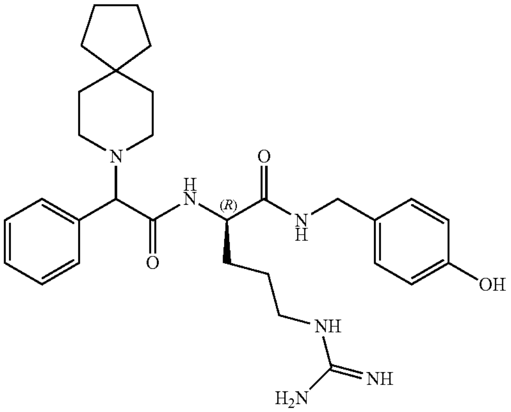 |

-continued
| Cmpd no. | Structure |
|---|---|
| 85 | 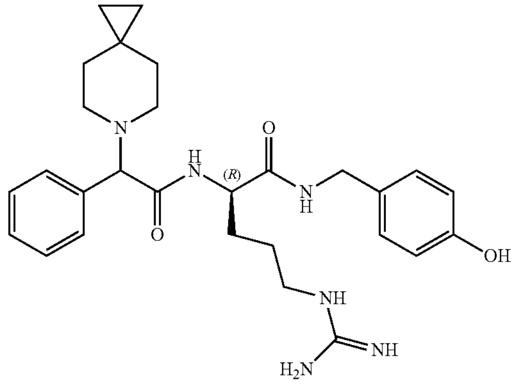 |
| 86 | 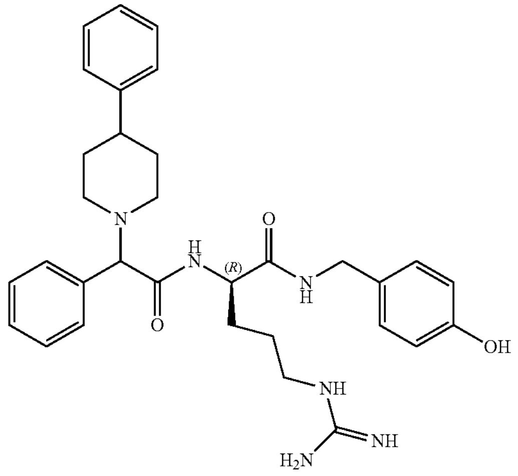 |
| 87 | 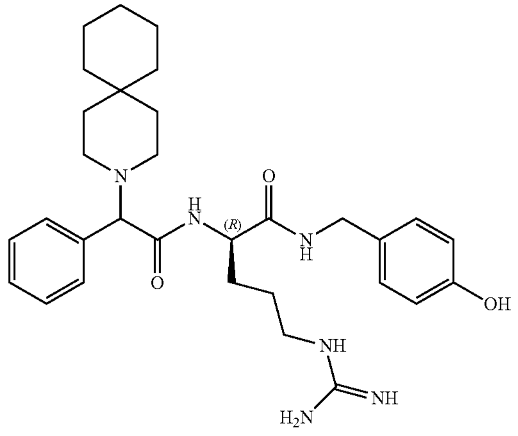 |

-continued
| Cmpd no. | Structure |
| --- | --- |
| 88A | 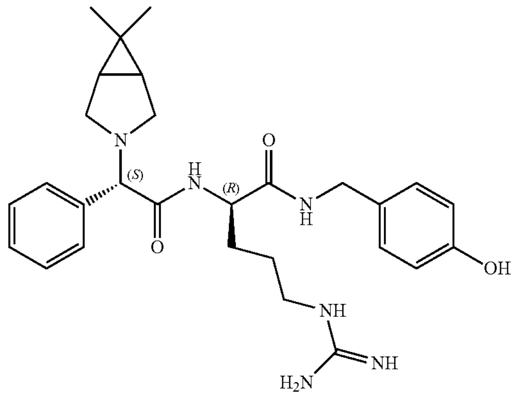 |
| 88B | 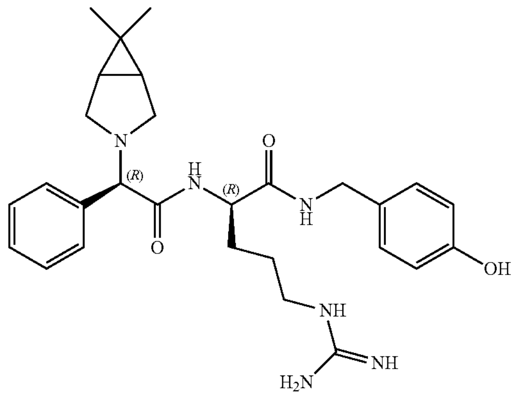 |
| 89 | 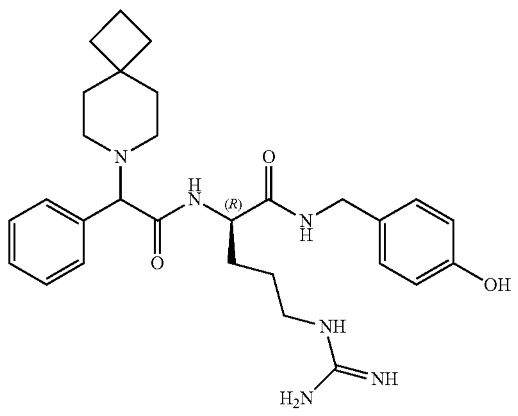 |

-continued

| Cmpd no. | Structure |
| --- | --- |
| 90 | 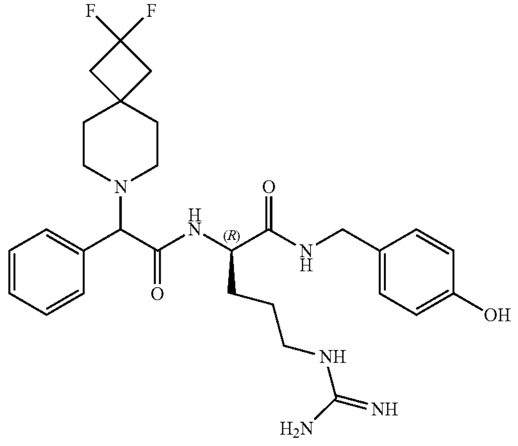 |
| 91 | 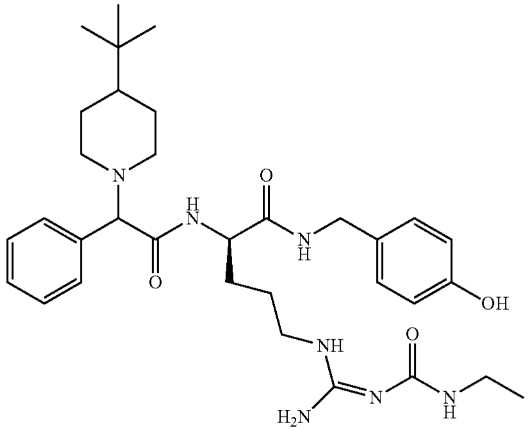 [SMILES: CCNC(=O)/N=C(/N)NCCC[C@@H](NC(=O)C(c1ccccc1)N1CCC(C(C)(C)C)CC1)C(=O)NCc1ccc(O)cc1] |
| 92 | 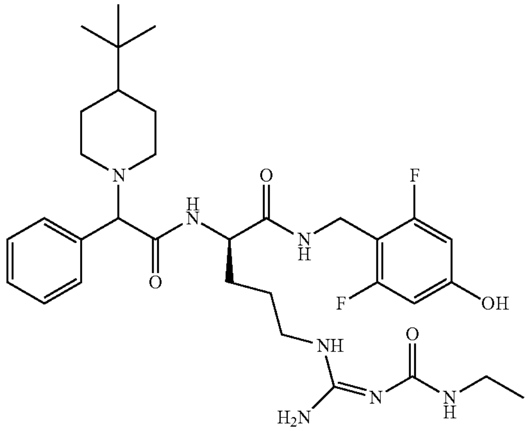 [SMILES: CCNC(=O)/N=C(/N)NCCC[C@@H](NC(=O)C(c1ccccc1)N1CCC(C(C)(C)C)CC1)C(=O)NCc1c(F)cc(O)cc1F] |

In some embodiments, the compound of Formula (III) is compound 60, or a pharmaceutically acceptable salt thereof. In some embodiments, the compound of Formula (III) is compound 60A, or a pharmaceutically acceptable salt thereof. In some embodiments, the compound of Formula (III) is compound 60B, or a pharmaceutically acceptable salt thereof. In some embodiments, the compound of Formula (III) is compound 61A, or a pharmaceutically acceptable salt thereof. In some embodiments, the compound of Formula (III) is compound 61B, or a pharmaceutically acceptable salt thereof. In some embodiments, the compound of Formula (III) is compound 62, or a pharmaceutically acceptable salt thereof. In some embodiments, the compound of Formula (III) is compound 63, or a pharmaceutically acceptable salt thereof. In some embodiments, the compound of Formula (III) is compound 64A, or a pharmaceutically acceptable salt thereof. In some embodiments, the compound of Formula (III) is compound 64B, or a pharmaceutically acceptable salt thereof. In some embodiments, the compound of Formula (III) is compound 65, or a pharmaceutically acceptable salt thereof. In some embodiments, the compound of Formula (III) is compound 65A, or a pharmaceutically acceptable salt thereof. In some embodiments, the compound of Formula (III) is compound 66A, or a pharmaceutically acceptable salt thereof. In some embodiments, the compound of Formula (III) is compound 66B, or a pharmaceutically acceptable salt thereof. In some embodiments, the compound of Formula (III) is compound 67, or a pharmaceutically acceptable salt thereof. In some embodiments, the compound of Formula (III) is compound 68, or a pharmaceutically acceptable salt thereof. In some embodiments, the compound of Formula (III) is compound 69, or a pharmaceutically acceptable salt thereof. In some embodiments, the compound of Formula (III) is compound 70, or a pharmaceutically acceptable salt thereof.

Any combination of the groups described above for the various variables is contemplated herein. Throughout the specification, groups and substituents thereof are chosen by one skilled in the field to provide stable moieties and compounds.

Synthesis of Compounds

Compounds described herein are synthesized using standard synthetic techniques or using methods known in the art in combination with methods described herein.

Unless otherwise indicated, conventional methods of mass spectroscopy, NMR, and HPLC are employed.

Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions.

In one aspect, compounds described herein are in the form of pharmaceutically acceptable salts. In addition, the compounds described herein can exist in unsolvated as well as solvated forms with pharmaceutically acceptable solvents such as water, ethanol, and the like. The solvated forms of the compounds presented herein are also considered to be disclosed herein.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible, and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound of Formula (I), with an acid. In some embodiments, the acid is an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (-L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (–L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I), is prepared as a chloride salt, sulfate salt, bromide salt, mesylate salt, maleate salt, citrate salt or phosphate salt.

In some embodiments, pharmaceutically acceptable salts are obtained by reacting a compound of Formula (I), with a base. In some cases, compounds described herein coordinate with an organic base, such as, but not limited to, ethanolamine, diethanolamine, triethanolamine, tromethamine, meglumine, N-methylglucamine, or dicyclohexylamine, tris (hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

In some embodiments, any one of the hydrogen atoms on the organic radicals (e.g., alkyl groups, aromatic rings) of compounds described herein are replaced with deuterium.

In some embodiments, the compounds of Formula (I), possess one or more stereocenters and each stereocenter exists independently in either the R or S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof. In some embodiments, the compound is a mixture of two diastereomers, wherein the diastereomeric ratio (the ratio of the percentage of one diastereoisomer in a mixture to the percentage of the other diastereomer in the mixture) is from about 99:1 to about 50:50. In some embodiments, the diastereomeric ratio is from about 99:1 to about 90:10. In some embodiments, the diastereomeric ratio is from about 95:5 to about 85:15. In some embodiments, the diastereomeric ratio is from about 90:10 to about 80:20. In some embodiments, the diastereomeric ratio is from about 85:15 to about 75:25. In some embodiments, the diastereomeric ratio is from about 80:20 to about 70:30. In some embodiments, the diastereomeric ratio is from about 75:25 to about 65:35. In some embodiments, the diastereomeric ratio is from about 70:30 to about 60:40. In some embodiments, the diastereomeric ratio is from about 65:35 to about 55:45. In some embodiments, the diastereomeric ratio is from about 60:40 to about 50:50. In some embodiments, the diastereomeric ratio is from about 55:45 to about 45:55.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. See for example Design of Prodrugs, Bundgaard, A. Ed., Elsevier, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference.

A "metabolite" of a compound disclosed herein is a derivative of that compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Metabolites of the compounds disclosed herein are optionally identified either by administration of compounds to a host and analysis of tissue samples from the host, or by incubation of compounds with hepatic cells in vitro and analysis of the resulting compounds.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be affected by any method that enables delivery of the compounds to the site of action. These methods include, though are not limited to, delivery via parenteral routes (including injection or infusion, and subcutaneous).

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and contain optional agents as excipients such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use.

Methods of Treatment

In some embodiments, the methods comprise administering to a subject a therapeutically effective amount of a compound of Formula (I), or a pharmaceutically acceptable salt or solvate thereof. In some embodiments, the compound of Formula (I), or pharmaceutically acceptable salt or solvate thereof is administered in a pharmaceutical composition. In some embodiments, the subject has cancer. In some embodiments, the cancer is a solid tumor. In some embodiments, the subject has a noncancerous tumor. In some embodiments, the subject has an adenoma. In some embodiments, the subject has been diagnosed with breast cancer, kidney cancer, ovarian cancer, melanoma, gastrointestinal stromal tumor (GIST), Ewing's sarcoma, nephroblastoma, or adrenal gland tumors. In some embodiments, the subject has been diagnosed with breast cancer.

In some embodiments, the treatment is sufficient to reduce or inhibit the growth of the subject's tumor, reduce the number or size of metastatic lesions, reduce tumor load, reduce primary tumor load, reduce invasiveness, prolong survival time, or maintain or improve the quality of life, or combinations thereof.

In some embodiments, provided herein are methods for killing a tumor cell comprising contacting the tumor cell with a compound of Formula (I), or a pharmaceutically acceptable salt or solvate thereof. In some embodiments, the compound of Formula (I), or pharmaceutically acceptable salt or solvate thereof releases a number of alpha particles by natural radioactive decay. In some embodiments, the released alpha particles are sufficient to kill the tumor cell. In some embodiments, the released alpha particles are sufficient to stop cell growth. In some embodiments, the tumor cell is a malignant tumor cell. In some embodiments, the tumor cell is a benign tumor cell. In some embodiments, the method comprises killing a tumor cell with a beta-particle emitting radionuclide. In some embodiments, the method comprises killing a tumor cell with an alpha-particle emitting radionuclide. In some embodiments, the method comprises killing a tumor cell with a gamma-particle emitting radionuclide.

In one aspect, provided herein are methods and compositions for treating cancers. In some embodiments, the cancer is breast cancer, kidney cancer, ovarian cancer, melanoma, gastrointestinal stromal tumor (GIST), Ewing's sarcoma, nephroblastoma, or adrenal gland tumors. In some embodiments, the cancer is breast cancer.

In one aspect, provided herein are methods and compositions for treating an adenoma.

In one aspect, provided herein are methods and compositions for treating a carcinoma.

In one aspect, provided herein is a method for identifying tissues or organs in a mammal that overexpress $NPY_1R$ comprising: (i) administering to the mammal a $NPY_1R$ radiopharmaceutical described herein, or a pharmaceutically acceptable salt thereof; and (ii) performing single-photon emission computerized tomography (SPECT) or positron emission tomography (PET) analysis on the mammal. In some embodiments, the method comprises: (i) administering to the mammal a $NPY_1R$ radiopharmaceutical described herein, or a pharmaceutically acceptable salt thereof; and (ii) performing positron emission tomography (PET) analysis on the mammal.

In some embodiments, the mammal was diagnosed with cancer. In some embodiments, the tissues in the mammal that overexpress $NPY_1R$ are tumors.

In some embodiments, $NPY_1R$ radiopharmaceutical described herein, or a pharmaceutically acceptable salt thereof are used in a method for in vivo imaging of a subject. In some embodiments, the method includes the steps of:

(i) administering to the mammal a $NPY_1R$ radiopharmaceutical described herein, or a pharmaceutically acceptable salt thereof;
(ii) waiting a sufficient amount of time to allow the $NPY_1R$ radiopharmaceutical, to accumulate at a tissue or cell site to be imaged; and
(iii) imaging the cells or tissues with a non-invasive imaging technique.

In some embodiments, the non-invasive imaging technique is single-photon emission computerized tomography (SPECT) or positron emission tomography (PET) analysis. In some embodiments, the non-invasive imaging technique is single-photon emission computerized tomography (SPECT). In some embodiments, the non-invasive imaging technique is selected from positron emission tomography imaging, or positron emission tomography with computed tomography imaging, and positron emission tomography with magnetic resonance imaging.

In some embodiments, the methods comprise administering to a subject a therapeutically effective amount of a compound of Formula (III), or a pharmaceutically acceptable salt or solvate thereof. In some embodiments, the compound of Formula (III), or pharmaceutically acceptable salt or solvate thereof is administered in a pharmaceutical composition. In some embodiments, the pharmaceutical composition is formulated for administration to a mammal by oral administration. In some embodiments, the subject has cancer. In some embodiments, the cancer is breast cancer. In some embodiments, the subject has obesity. In some embodiments, the subject has pain. In some embodiments, the subject has osteoporosis.

In one aspect, provided herein are methods and compositions for treating obesity.

In one aspect, provided herein are methods and compositions for treating pain.

In one aspect, provided herein are methods and compositions for treating osteoporosis.

Methods of Dosing and Treatment Regimens

In one embodiment, the $NPY_1R$ radiopharmaceutical described herein, or a pharmaceutically acceptable salt thereof, are used in the preparation of medicaments for the treatment of tumors in a mammal. Methods for treating any of the diseases or conditions described herein in a mammal in need of such treatment, involves administration of pharmaceutical compositions that include at least one compound of Formula (I), or a pharmaceutically acceptable salt thereof, in therapeutically effective amounts to said mammal.

In certain embodiments, the compositions containing the compound(s) described herein are administered for diagnostic and/or therapeutic treatments.

The amount of a given agent that corresponds to such an amount varies depending upon factors such as the particular conjugate, specific cancer or tumor to be treated (and its severity), the identity (e.g., weight, sex) of the subject or host in need of treatment, but nevertheless is determined according to the particular circumstances surrounding the case, including, e.g., the specific conjugate being administered, the route of administration, the condition being treated, and the subject or host being treated. Optimal doses are generally determined using experimental models and/or clinical trials. The optimal dose depends upon the body mass, weight, or blood volume of the subject.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans.

The amount of a compound of Formula (I), or pharmaceutically acceptable salts thereof that are administered are sufficient to deliver a therapeutically effective dose to the particular subject. In some embodiments, dosages of a compound of Formula (I), are between about 0.1 pg and about 50 mg per kilogram of body weight, 1 μg and about 50 mg per kilogram of body weight, or between about 0.1 and about 10 mg/kg of body weight. Therapeutically effective dosages can also be determined at the discretion of a physician. By way of example only, the dose of a compound of Formula (I), or a pharmaceutically acceptable salt thereof described herein for methods of treating a disease as described herein is about 0.001 mg/kg to about 1 mg/kg body weight of the subject per dose. In some embodiments, the dose is about 0.001 mg to about 1000 mg per dose for the subject being treated. In some embodiments, a compound of Formula (I), or a pharmaceutically acceptable salt thereof, described herein is administered to a subject at a dosage of from about 0.01 mg to about 500 mg, from about 0.01 mg to about 100 mg, or from about 0.01 mg to about 50 mg.

In some embodiments, a compound of Formula (I), or a pharmaceutically acceptable salt thereof described herein is administered to a subject at a dosage of about 0.01 picomole to about 1 mole, about 0.1 picomole to about 0.1 mole, about 1 nanomole to about 0.1 mole, or about 0.01 micromole to about 0.1 millimole.

In some embodiments, a compound of Formula (I), or a pharmaceutically acceptable salt thereof described herein is administered to a subject at a dosage of about 0.01 Gbq to about 1000 Gbq, about 0.5 Gbq to about 100 Gbq, or about 1 Gbq to about 50 Gbq.

In some embodiments, the dose is administered once a day, 1 to 3 times a week, 1 to 4 times a month, or 1 to 12 times a year.

In any of the aforementioned aspects are further embodiments in which the effective amount of the $NPY_1R$ radiopharmaceutical described herein, or a pharmaceutically acceptable salt thereof, is: (a) systemically administered to the mammal; and/or (b) intravenously administered to the mammal; and/or (c) administered by injection to the mammal.

In certain instances, it is appropriate to administer at least one $NPY_1R$ radiopharmaceutical described herein, or a pharmaceutically acceptable salt thereof, in combination with one or more other therapeutic agents.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, $C_1$-$C_x$ includes $C_1$-$C_2$, $C_1$-$C_3$ . . . $C_1$-$C_x$. By way of example only, a group designated as "$C_1$-$C_6$" indicates that there are one to six carbon atoms in the moiety, i.e., groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e., a $C_1$-$C_{10}$ alkyl. Whenever it appears herein, a numerical range such as "1 to 10" refers to each integer in the given range; e.g., "1 to 10 carbon atoms" means that the alkyl group consists of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a —$C_1$-$C_6$ alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl. In some embodiments, the alkyl group is an "alkenyl" or "alkynyl" group.

An "alkylene" group refers to a divalent alkyl radical. Any of the above-mentioned monovalent alkyl groups may be an alkylene by abstraction of a second hydrogen atom from the alkyl. In some embodiments, an alkylene is a —$C_1$-$C_6$ alkylene-. In other embodiments, an alkylene is a $C_1$-$C_4$ alkylene. Typical alkylene groups include, but are not limited to, —$CH_2$—, —$CH_2CH_2$—, —$CH_2CH_2CH_2$—, —$CH_2CH_2CH_2CH_2$—, and the like. In some embodiments, an alkylene is —$CH_2$—. In some embodiments, an alkylene is —$CH_2CH_2$—.

An "alkoxy" group refers to an (alkyl)O— group, where alkyl is as defined herein.

The term "alkenyl" refers to a type of alkyl group in which at least one carbon-carbon double bond is present. In one embodiment, an alkenyl group has the formula: —C(R)═$CR_2$, wherein R refers to the remaining portions of the alkenyl group, which may be the same or different. In some embodiments, each R is independently H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH═$CH_2$, —$C(CH_3)$═$CH_2$, —CH═$CHCH_3$, —$C(CH_3)$═$CHCH_3$, and —$CH_2CH$═$CH_2$.

The term "alkynyl" refers to a type of alkyl group in which at least one carbon-carbon triple bond is present. In one embodiment, an alkenyl group has the formula —C≡C—R, wherein R refers to the remaining portion of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡$CCH_3$, —C≡$CCH_2CH_3$, or —$CH_2C$≡CH.

The term "heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. In some embodiments, the "heteroalkyl" group has 2 to 10 atoms in the backbone, which include a combination of carbon atoms and heteroatoms (e.g. N, O, S), i.e., a 2 to 10-membered heteroalkyl. In some embodiments, the heteroalkyl is attached to the rest of the molecule at a carbon atom of the heteroalkyl. In one embodiment, a heteroalkyl is a 2 to 8 membered heteroalkyl.

A "heteroalkylene" group refers to a divalent alkyl radical derived from heteroalkyl, as exemplified, but not limited by, $-CH_2-CH_2-O-CH_2-CH_2-$ and $-CH_2-O-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(=O)O-$ represents both $-C(=O)O-$ and $-OC(=O)-$. Additionally, the formula $-C(=O)NH$-represents both $-C(=O)NH-$ and $-NHC(=O)-$.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahydronaphthyl. In some embodiments, an aryl is a $C_6$-$C_{10}$ aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e., skeletal atoms) is a carbon atom. In some embodiments, cycloalkyls are spirocyclic or bridged cycloalkyls. In some embodiments, cycloalkyls are optionally fused with an aromatic ring, and the point of attachment is at a carbon that is not an aromatic ring carbon atom. In some embodiments, cycloalkyl is a monocyclic cycloalkyl. In some embodiments, cycloalkyl is a bicyclic cycloalkyl. Cycloalkyl groups include rings having from 3 to 12 ring atoms. In some embodiments, cycloalkyl groups include rings having from 3 to 8 ring atoms. In some embodiments, cycloalkyl groups include rings having from 3 to 6 ring atoms. In some embodiments, cycloalkyl groups are selected from cyclopropyl, cyclobutyl, cyclopentyl, cyclohexyl, cycloheptyl, cyclooctyl, spiro[2.2]pentyl, norbornyl and bicyclo[1.1.1]pentyl. In some embodiments, a cycloalkyl is a $C_3$-$C_6$ cycloalkyl. In some embodiments, a cycloalkyl is a $C_3$-$C_4$ cycloalkyl. In some embodiments, a cycloalkyl is a $C_5$-$C_6$ cycloalkyl.

The term "cycloalkenyl" refers to a type of non-aromatic cycloalkyl in which at least one carbon-carbon double bond is present. In some embodiments, cycloalkenyl is a monocyclic cycloalkenyl or polycyclic cycloalkenyl. In some embodiments, cycloalkenyl is a monocyclic cycloalkenyl. In some embodiments, cycloalkenyls are spirocyclic or bridged cycloalkenyls. In some embodiments, cycloalkenyls are optionally fused with an aromatic ring, and the point of attachment is at a carbon that is not an aromatic ring carbon atom. Cycloalkenyl groups include groups having from 4 to 12 ring atoms. In some embodiments, cycloalkenyl groups include rings having from 4 to 8 ring atoms. In some embodiments, cycloalkenyl groups include rings having from 4 to 6 ring atoms. In some embodiments, cycloalkenyl groups are selected from cyclobutenyl, cyclopentenyl, cyclohexenyl, cycloheptenyl, and cyclooctenyl. In some embodiments, a cycloalkenyl is a $C_4$-$C_6$ cycloalkenyl. In some embodiments, a cycloalkenyl is a $C_4$-$C_8$ cycloalkenyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a $-C_1$-$C_6$ fluoroalkyl.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 12 atoms in its ring system, and with the proviso that any ring does not contain two adjacent O or S atoms. Non-aromatic heterocyclic groups (also known as heterocycloalkyls) include rings having 3 to 12 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The term "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, a heteroaryl contains 1 O atom. In some embodiments, a heteroaryl contains 1 S atom in the ring. In some embodiments, heteroaryl is a 5 to 10-membered heteroaryl. In some embodiments, a monocyclic heteroaryl is a 5 to 6 membered heteroaryl. In some embodiments, a monocyclic heteroaryl is a 5-membered heteroaryl. In some embodiments, a monocyclic heteroaryl is a 6-membered heteroaryl. In some embodiments, a bicyclic heteroaryl is a 10-membered heteroaryl.

A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. In one aspect, a heterocycloalkyl is a 3 to 12-membered heterocycloalkyl. In another aspect, a heterocycloalkyl is a 5 to 10-membered heterocycloalkyl. In some embodiments, a heterocycloalkyl is a 5-membered heterocycloalkyl. In some embodiments, a heterocycloalkyl is a 6-membered heterocycloalkyl. In some embodiments, a heterocycloalkyl is monocyclic or bicyclic. In some embodiments, a heterocycloalkyl is monocyclic and is a 3, 4, 5, 6, 7, or 8-membered ring. In some embodiments, a heterocycloalkyl is monocyclic and is a 3, 4, 5, or 6-membered ring. In some embodiments, a heterocycloalkyl is monocyclic and is a 3 or 4-membered ring. In some embodiments, a heterocycloalkyl contains 1-4 nitrogen (N) atoms in the ring. In some embodiments, a heterocycloalkyl contains 0-2 N atoms, 0-2 oxygen (O) atoms and 0-1 sulfur (S) atoms in the ring.

The term "bond" or "single bond" refers to a chemical bond between two atoms, or two moieties when the atoms joined by the bond are considered to be part of a larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, $—NH_2$, —NH(alkyl), $—N(alkyl)_2$, —OH, —C(═O)OH, —C(═O)O-alkyl, $—C(═O)NH_2$, —C(═O)NH(alkyl), $—C(═O)N(alkyl)_2$, $—S(═O)_2NH_2$, $—S(═O)_2NH(alkyl)$, $—S(═O)_2N(alkyl)_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, $—NH_2$, $—NH(CH_3)$, $—N(CH_3)_2$, —OH, —C(═O)OH, $—C(═O)O(C_1-C_4$ alkyl), $—C(═O)NH_2$, $—C(═O)NH(C_1-C_4$ alkyl), $—C(═O)N(C_1-C_4$ alkyl$)_2$, $—S(═O)_2NH_2$, $—S(═O)_2NH(C_1-C_4$alkyl), $—S(═O)_2N(C_1-C_4$ alkyl$)_2$, $C_1-C_4$ alkyl, $C_3-C_6$ cycloalkyl, $C_1-C_4$ fluoroalkyl, $C_1-C_4$heteroalkyl, $C_1-C_4$ alkoxy, $C_1-C_4$ fluoroalkoxy, $—SC_1-C_4$ alkyl, $—S(═O)C_1-C_4$ alkyl, and $—S(═O)_2C_1-C_4$ alkyl. In some embodiments, optional substituents are independently selected from halogen, —CN, $—NH_2$, —OH, $—NH(CH_3)$, $—N(CH_3)_2$, $—CH_3$, $—CH_2CH_3$, $—CHF_2$, $—CF_3$, $—OCH_3$, $—OCHF_2$, and $—OCF_3$. In some embodiments, substituted groups are substituted with one or two of the preceding groups. In some embodiments, an optional substituent on an aliphatic carbon atom (acyclic or cyclic) includes oxo (═O).

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion). Those of skill in the art are familiar with administration techniques that can be employed with the compounds and methods described herein.

The terms "co-administration" or the like, as used herein, are meant to encompass administration of the selected therapeutic agents to a single patient and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, and swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition.

NUMBERED EMBODIMENTS

Embodiment 1. A compound of Formula (I), or a pharmaceutically acceptable salt thereof:

Formula (I)

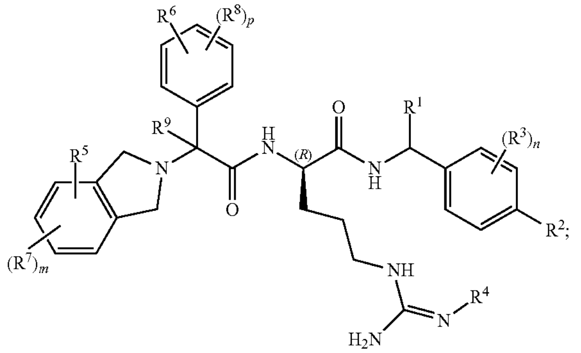

wherein:

$R^1$ is H, $-C_1$-$C_6$ alkyl, or $-C(=O)NH_2$;

$R^2$ is $-OH$, $-NH_2$, $-C(=O)NH_2$, or $-CH_2NHC(=O)NH_2$;

each $R^3$ is independently selected from the group consisting of $R^{3a}$, $R^{3b}$, $R^{3c}$, and $R^{3d}$;

$R^{3a}$, $R^{3b}$, $R^{3c}$, and $R^{3d}$ are each independently selected from the group consisting of H, F, Cl, Br, I, $-CN$, substituted or unsubstituted $-C_1$-$C_6$ alkyl, and substituted or unsubstituted $-C_1$-$C_6$ alkoxy;

$R^4$ is H, $-C(=O)R^{10}$, $-C(=O)NHR^{10}$, or $-C(=O)N(CH_3)R^{10}$;

$R^{10}$ is substituted or unsubstituted $-C_1$-$C_6$ alkyl, substituted or unsubstituted 2 to 6-membered heteroalkyl, $-(CH_2)_t-NH_2$, $-(CH_2)_tC(=O)O(CH_2)_uCH_3$, $-(CH_2)_tNHC(=O)(CH_2)_uCH_3$, or $-(CH_2)_t$-substituted or unsubstituted 5 to 6 membered heteroaryl ring;

t is 1, 2, 3, 4, 5, or 6;

u is 1, 2, 3, or 4;

$R^5$ is absent or $-Z^B$-$L^B$-$R^B$;

$Z^B$ is absent, $-C_1$-$C_6$ alkylene-, $-C_1$-$C_6$ alkylene-O—, $-O-C_1$-$C_6$ alkylene-, $-C(=O)NR^{11}-$, $-NR^{11}C(=O)-$, —O—, $-NR^{11}-$, —S—, $-S(=O)-$, $-SO_2-$, or $-NHC(=O)NH-$;

$L^B$ is a linker;

$R^B$ is a chelating moiety or a radionuclide complex thereof, $R^6$ is absent or $-Z^A$-$L^A$-$R^A$;

$Z^A$ is absent, $-C_1$-$C_6$ alkylene-, $-C_1$-$C_6$ alkylene-O—, $-O-C_1$-$C_6$ alkylene-, $-C(=O)NR^{12}-$, $-NR^{12}C(=O)-$, —O—, $-NR^{12}-$, —S—, $-S(=O)-$, $-SO_2-$, or $-NHC(=O)NH-$;

$L^A$ is a linker;

$R^A$ is a chelating moiety or a radionuclide complex thereof;

each $R^7$ is independently selected from the group consisting of F, Cl, Br, I, —CN, —OH, substituted or unsubstituted $-C_1$-$C_6$ alkyl, substituted or unsubstituted $-C_1$-$C_6$ alkoxy, and substituted or unsubstituted $-NH-C_1$-$C_6$ alkyl;

each $R^8$ is independently selected from the group consisting of F, Cl, Br, I, —CN, —OH, substituted or unsubstituted $-C_1$-$C_6$ alkyl, substituted or unsubstituted $-C_1$-$C_6$ alkoxy, and substituted or unsubstituted $-NH-C_1$-$C_6$ alkyl;

$R^9$ is H, substituted or unsubstituted $-C_1$-$C_4$ alkyl, or substituted or unsubstituted $-C_1$-$C_6$ alkoxy;

each $R^{11}$ is independently H or unsubstituted $-C_1$-$C_4$ alkyl;

each $R^{12}$ is independently H or unsubstituted $-C_1$-$C_4$ alkyl;

n is 0, 1, 2, 3, or 4;

m is 0, 1, 2, or 3; and p is 0, 1, 2, or 3;

wherein $R^8$ is $-Z^B$-$L^B$-$R^B$ when $R^6$ is absent; or $R^6$ is $-Z^A$-$L^A$-$R^A$ when $R^8$ is absent.

Embodiment 2. The compound of embodiment 1, or a pharmaceutically acceptable salt thereof, wherein:

$R^1$ is H;

$R^2$ is $-OH$, $-NH_2$, $-C(=O)NH_2$ or $-CH_2NHC(=O)NH_2$;

each $R^3$ is independently selected from the group consisting of $R^{3a}$, $R^{3b}$, $R^{3c}$, and $R^{3d}$;

$R^{3a}$, $R^{3b}$, $R^{3c}$, and $R^{3d}$ are each independently selected from the group consisting of H, F, Cl, Br, I, —CN, substituted or unsubstituted $-C_1$-$C_6$ alkyl, and substituted or unsubstituted $-C_1$-$C_6$ alkoxy;

$R^4$ is H, $-C(=O)R^{10}$, $-C(=O)NHR^{10}$ or $-C(=O)N(CH_3)R^{10}$;

$R^{10}$ is substituted or unsubstituted $-C_1$-$C_6$ alkyl, substituted or unsubstituted 2 to 6-membered heteroalkyl, or $-(CH_2)_tNHC(=O)(CH_2)_uCH_3$;

t is 1, 2, 3, 4, 5, or 6;

u is 1, 2, 3, or 4;

$R^5$ is absent or $-Z^B$-$L^B$-$R^B$;

$Z^B$ is absent, $-C_1$-$C_6$ alkylene-, $-C_1$-$C_6$ alkylene-O—, $-O-C_1$-$C_6$ alkylene-, $-C(=O)NR^{11}-$, $-NR^{11}C(=O)-$, —O—, or $-NR^{11}-$;

$L^B$ is a linker;

$R^B$ is a chelating moiety or a radionuclide complex thereof, $R^6$ is absent or $-Z^A$-$L^A$-$R^A$;

$Z^A$ is absent, $-C_1$-$C_6$ alkylene-, $-C_1$-$C_6$ alkylene-O—, $-O-C_1$-$C_6$ alkylene-, $-C(=O)NR^{12}-$, $-NR^{12}C(=O)-$, —O—, or $-NR^{12}$_.

$L^A$ is a linker;

$R^A$ is a chelating moiety or a radionuclide complex thereof;

$R^9$ is H;

each $R^{11}$ is independently H or unsubstituted $—C_1-C_4$ alkyl;

each $R^{12}$ is independently H or unsubstituted $—C_1-C_4$ alkyl;

n is 0, 1, 2, 3, or 4;

m is 0; and p is 0;

wherein $R^5$ is $—Z^B-L^B-R^B$ when $R^6$ is absent; or $R^6$ is $—Z^A-L^A-R^A$ when $R^5$ is absent.

Embodiment 3. The compound of embodiment 1 or 2, or a pharmaceutically acceptable salt thereof, wherein $R^5$ is $—Z^B-L^B-R^B$ and $R^6$ is absent; or $R^6$ is $—Z^A-L^A-R^A$ and $R^5$ is absent; $Z^A$ is $C_1-C_6$ alkylene, —O—, —NH—, $—N(—CH_3)—$, or —NHC(═O); and $Z^B$ is $C_1-C_6$ alkylene, —O—, —NH—, $—N(—CH_3)—$, or —NHC(═O)—.

Embodiment 4. The compound of any one of embodiments 1-3, or a pharmaceutically acceptable salt thereof, wherein each $R^3$ is independently selected from the group consisting of $R^{3a}$, $R^{3b}$, $R^{3c}$, and $R^{3d}$;

$R^{3a}$, $R^{3b}$, $R^{3c}$, and $R^{3d}$ are each independently selected from the group consisting of H, F, Cl, Br, I, —CN, $—CH_3$, $—CF_3$, and $—OCH_3$;

$R^5$ is $—Z^B-L^B-R^B$ and $R^6$ is absent; or $R^6$ is $—Z^A-L^A-R^A$ and $R^5$ is absent;

$Z^A$ is $—CH_2—$, —O—, —NH—, $—N(—CH_3)—$, or —NHC(═O)—;

$Z^B$ is $—CH_2—$, —O—, —NH—, $—N(—CH_3)—$, or —NHC(═O)—; and n is 0 or2.

Embodiment 5. The compound of any one of embodiments 1-3, or a pharmaceutically acceptable salt thereof, wherein the compound has the structure of Formula (If) or Formula (Ig), or a pharmaceutically acceptable salt thereof:

(If)

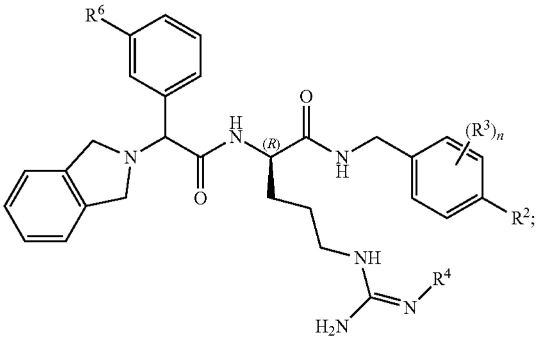

or

-continued (Ig)

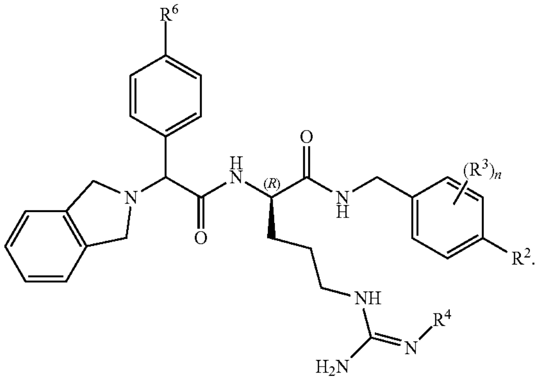

Embodiment 5a. The compound of any one of embodiments 1-3, or a pharmaceutically acceptable salt thereof, wherein the compound has the structure of Formula (IIf) or Formula (IIg), or a pharmaceutically acceptable salt thereof:

(IIf)

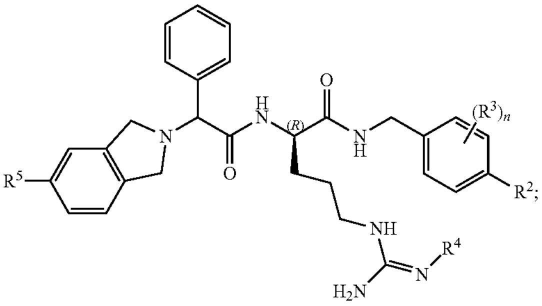

or (IIg)

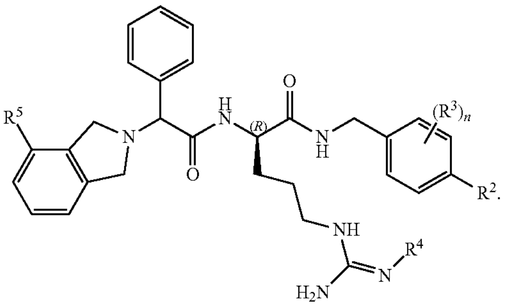

Embodiment 6. The compound of any one of embodiments 1-3, or a pharmaceutically acceptable salt thereof, wherein the compound has the following structure, or a pharmaceutically acceptable salt thereof:

(Iw)

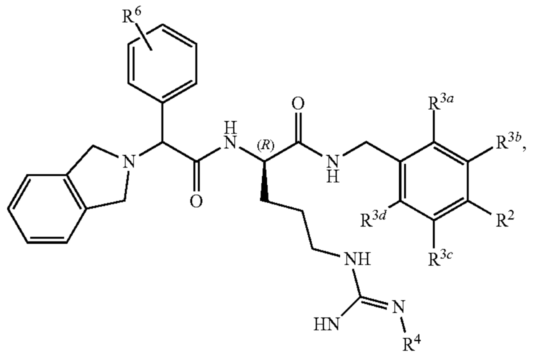

or (IIw)

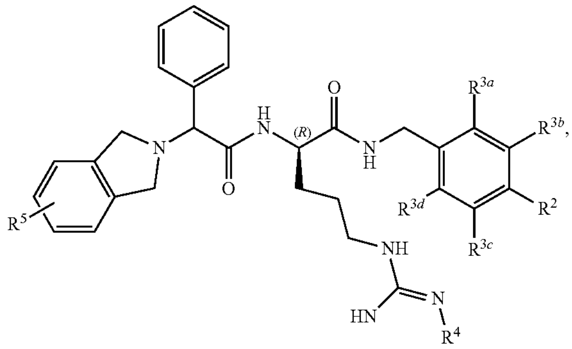

wherein each $R^{3a}$, $R^{3b}$, $R^{3c}$ and $R^{3d}$ is independently selected from the group consisting of H, F, Cl, Br, I, —CN, substituted or unsubstituted —$C_1$-$C_6$ alkyl, and substituted or unsubstituted —$C_1$-$C_6$ alkoxy.

Embodiment 6a. The compound of any one of embodiments 1-3, or a pharmaceutically acceptable salt thereof, wherein the compound has the following structure, or a pharmaceutically acceptable salt thereof.

pharmaceutically acceptable salt thereof:

(Iw-1S)

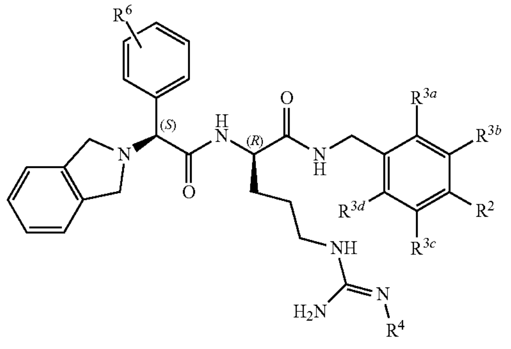

or

-continued (IIw-1S)

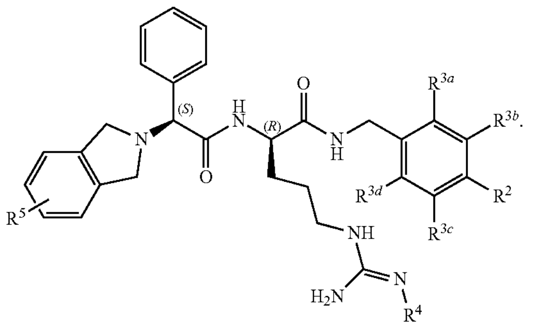

Embodiment 7. The compound of any one of embodiments 1-5, 5a, 6, or 6a, or a pharmaceutically acceptable salt thereof, wherein $R^2$ is —OH;

each $R^{3a}$, $R^{3b}$, $R^{3c}$ and $R^{3d}$ is independently selected from the group consisting of H, F, Cl, Br, I, —CN, —$CH_3$, —$CF_3$, and —$OCH_3$;

$R^4$ is —C(=O)NHR$^{10}$; $R^{10}$ is unsubstituted —$C_1$-$C_6$ alkyl or —$(CH_2)_t$NHC(=O)$(CH_2)_u$$CH_3$;

t is 1, 2, 3, or 4; and u is 1 or 2.

Embodiment 8. The compound of any one of embodiments 1-5, 5a, 6, 6a, or 7, or a pharmaceutically acceptable salt thereof, wherein, or a pharmaceutically acceptable salt thereof, wherein $R^2$ is —OH; $R^3$ and $R^{3d}$ are F or Cl and $R^{3b}$ and $R^{3c}$ are H; $R^4$ is —C(=O)NHR$^{10}$; $R^{10}$ is unsubstituted —$C_1$-$C_6$ alkyl or —$(CH_2)_t$NHC(=O)$(CH_2)_u$$CH_3$;

t is 1, 2, 3, or 4; and u is 1 or 2.

Embodiment 9. The compound of any one of embodiments 1-5, 5a, 6, 6a, 7, or 8, or a pharmaceutically acceptable salt thereof, wherein $R^A$ and $R^B$, whichever is present, are independently selected from the group consisting of:

1,4,7,10-tetraazacyclododecane-1,4,7,10-tetraacetic acid (DOTA);

2,2',2"-(10-(2-amino-2-oxoethyl)-1,4,7,10-tetraazacyclododecane-1,4,7-triyl)triacetic acid (PSC);

1,4,7,10-tetraazacyclododecane-1,4,7-triacetic acid (DO3A);

1,4,7,10-tetraazacyclododecane-1,7-diacetic acid (DO2A);

α,α',α",α'"-tetramethyl-1,4,7,10-tetraazacyclododecane-1,4,7,10-tetraacetic acid (DOTMA);

1,4,7,10-tetrakis(carbamoylmethyl)-1,4,7,10-tetraazacyclododecane (DOTAM);

1,4,7,10-tetraazacyclododecane-1,4,7,10-tetrapropionic acid (DOTPA);

2,2',2"-(10-(2-amino-2-oxoethyl)-1,4,7,10-tetraazacyclododecane-1,4,7-triyl)triacetic acid;

benzyl-1,4,7,10-tetraazacyclododecane-1,4,7,10-tetraacetic acid (Bn-DOTA);

p-hydroxy-benzyl-1,4,7,10-tetraazacyclododecane-1,4,7,10-tetraacetic acid (p-OH-Bn-DOTA);

6,6'-(((pyridine-2,6-diylbis(methylene))bis((carboxymethyl)azanediyl))bis(methylene))dipicolinic acid ($H_4$pypa);

$H_4$pypa-benzyl;

6,6',6",6'"-(((pyridine-2,6-diylbis(methylene))bis(azanetriyl))tetrakis(methylene))-tetrapicolinic acid ($H_4$py4pa);

$H_4$py4pa-benzyl;

2,2',2"-(1,4,7-triazacyclononane-1,4,7-triyl)triacetic acid (NOTA);

6,6'-((1,4,10,13-tetraoxa-7,16-diazacyclooctadecane-7,16-diyl)bis(methylene))dipicolinic acid (macropa);

2,2',2",2'"-(1,10-dioxa-4,7,13,16-tetraazacyclooctadecane-4,7,13,16-tetrayl)tetraacetic acid (crown);

6,6'-((ethane-1,2-diylbis((carboxymethyl)azanediyl))bis(methylene))dipicolinic acid ($H_4$octapa);

$H_4$octapa-benzyl; and 3,6,9,12-tetrakis(carboxymethyl)-3,6,9,12-tetraazatetradecanedioic acid (TTHA);

or a radionuclide complex thereof.

Embodiment 10. The compound of any one of embodiments 1-5, 5a, 6, 6a, 7, 8, or 9, or a pharmaceutically acceptable salt thereof, wherein $R^A$ and $R^B$, if present, are

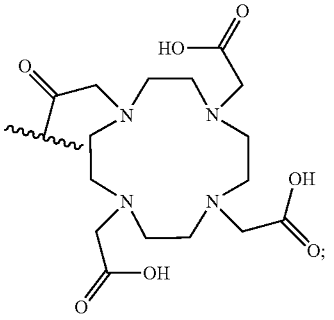 [SMILES: *C(=O)CN1CCN(CC(=O)O)CCN(CC(=O)O)CCN(CC(=O)O)CC1]

or a radionuclide complex thereof.

Embodiment 11. The compound of any one of embodiments 1-10, or a pharmaceutically acceptable salt thereof, wherein each of $L^A$ and $L^B$, whichever is present, are independently selected from -$L^2$-, -$L^3$-, -$L^4$-, -$L^5$-, -$L^6$-, -$L^7$-, -$L^2$-$L^3$-, -$L^2$-$L^7$-, -$L^4$-$L^7$-, -$L^2$-$L^4$-$L^7$-, -$L^2$-$L^6$-$L^7$-, -$L^2$-$L^3$-$L^4$-$L^7$-, -$L^2$-$L^4$-$L^5$-$L^7$-, -$L^2$-$L^4$-$L^6$-$L^7$-, or -$L^2$-$L^4$-$L^5$-$L^6$-$L^7$ $L^2$ is absent, substituted or unsubstituted —$C_1$-$C_{20}$ alkylene-$NR^{16}$—, substituted or unsubstituted —$C_1$-$C_{20}$ alkylene-$NR^{16}C$(═O)—, or —$(CH_2CH_2O)_w$—$CH_2CH_2$—; each $R^{16}$ is independently selected from H and $C_1$-$C_4$ alkyl;

w is 1, 2, 3, 4, 5, or 6;

$L^3$ is absent or a natural or unnatural amino acid or peptide that is formed from two or more independently selected natural and unnatural amino acids, wherein when two or more amino acids are present then the N atom of the amide linking the amino acids is optionally substituted with —$C_1$-$C_6$ alkyl;

$L^4$ is absent, substituted or unsubstituted 2 to 10-membered heteroalkylene, —$(CH_2)_v$—, —$(CH_2CH_2O)_v$—$CH_2CH_2$—, —C(═O)$CH_2CH_2$—, —$(CH_2)_v$—$NR^{17}$C(═O)—, —$CH_2CH_2$C(═O)$NHCH_2CH_2$—, —$CH_2CH_2$—C(═O)NH—$(CH_2CH_2O)_vCH_2CH_2$—, —$(CH_2)_x$—$NR^{17}$—$(CH_2)_v$—, —NHC(═O)NH—O—$(CH_2)_v$—, —NHC(═O)NH—$(CH_2)_v$—, —$(CH_2)_x$—NHC(═O)NH—$(CH_2)_v$—, —$(CH_2)_x$—NHC(═O)—$(CH_2)_v$—, —$(CH_2)_x$—C(═O)NH—$(CH_2)_v$—, —$CH_2$C(—OH)$CH_2$—C(OH)—$CH_2CH_2$—, —$CH_2$C(—OH)$CH_2$—C(OH)—$CH_2CH_2$—NHC(═O)$CH_2CH_2$C(═O)—$NHCH_2CH_2$—, or —NHC(═O)$CH_2$—O—NH—C(═O)$(CH_2)_v$—;

each $R^{17}$ is H or —$C_1$-$C_6$ alkyl;

each x is independently 1, 2, 3, 4, 5, or 6;

each v is independently 1, 2, 3, 4, 5, 6, 7, 8, 9, or 10;

$L^5$ is absent, —O—, or —$NR^{13}$C(═O); $R^{13}$ is H or —$C_1$-$C_4$ alkyl;

$L^6$ is absent or -$L^8$-$L^9$-$L^{10}$-;

$L^8$ is absent, —$(CH_2)_r$—, —$(CH_2)_r$—$NR^{14}$—, or substituted or unsubstituted heterocycloalkylene;

r is 0, 1, 2, or 3;

$L^9$ is substituted or unsubstituted cycloalkylene, substituted or unsubstituted cycloalkenylene, substituted or unsubstituted heterocycloalkylene, or substituted or unsubstituted arylene;

$L^{10}$ is absent, —$(CH_2)_q$—, —$NR^{15}$—$(CH_2)_q$—, or —C(═O)—$(CH_2)_q$—; q is 1, 2, 3, 4, 5 or 6;

$R^{14}$ and $R^{15}$ are each independently selected from H or —$C_1$-$C_6$ alkyl; and $L^7$ is —NH—.

Embodiment 12. The compound of embodiment 11, or a pharmaceutically acceptable salt thereof, wherein $L^2$ is substituted or unsubstituted —$C_1$-$C_{20}$ alkylene-NH— or substituted or unsubstituted —$C_1$-$C_{20}$ alkylene-NHC(═O)—;

$L^3$ is absent or $L^3$ is a natural amino acid, an unnatural amino acid, or peptide that is formed from two or more independently selected amino acids selected from the group consisting of alanine (Ala), 3-(2-Naphthyl)-alanine (2-Nal), arginine (Arg), asparagine (Asn), aspartate (Asp), cysteine (Cys), cysteic acid, glutamine (Gln), glutamate (Glu), gamma-Carboxyglutamate (Gla), glycine (Gly), histidine (His), isoleucine (Ile), leucine (Leu), lysine (Lys), hydroxylysine (Hyl), ornithine (Orn), methionine (Met), phenylalanine (Phe), p-phenyl phenylalanine (Bop), proline (Pro), hydroxyproline (Hyp), serine (Ser), homoserine (Hse), sarcosine (Sar), threonine (Thr), tryptophan (Trp), tyrosine (Tyr), and valine (Val), wherein when two or more amino acids are present then the N atom of the amide linking the amino acids is optionally substituted with —$CH_3$; $L^4$ is —$(CH_2)_v$—, —$(CH_2CH_2O)_v$—$CH_2CH_2$—, —$(CH_2)_v$—$NR^{17}$C(═O)—, —$CH_2CH_2$C(═O)$NHCH_2CH_2$—, —$CH_2CH_2$—C(═O)NH—$(CH_2CH_2O)_vCH_2CH_2$—, —$(CH_2)_v$—$NR^{17}$—$(CH_2)_v$—, —NH(C═O)NH—O—$(CH_2)_v$—, —NHC(═O)NH—$(CH_2)_v$—, —$(CH_2)_x$—NHC(═O)NH—$(CH_2)_v$—, —$CH_2$C(OH)$CH_2$—C(OH)—$CH_2CH_2$—, —$CH_2$C(OH)$CH_2$—C(OH)—$CH_2CH_2$—NHC(═O)$CH_2CH_2$C(═O)—$NHCH_2CH_2$—, or —NHC(═O)$CH_2$—O—NH—C(═O)$(CH_2)_v$—;

v is 1, 2, 3, 4, 5, or 6;

$L^6$ is absent or -$L^8$-$L^9$-$L^{10}$-;

$L^8$ is absent, —$(CH_2)_r$—, or —$(CH_2)_r$—$NR^{14}$—;

r is 1 or 2;

$L^9$ is substituted or unsubstituted 4 to 6 membered heterocycloalkylene, an unsubstituted or substituted $C_4$-$C_8$ cycloalkylene, an unsubstituted or substituted $C_4$-$C_8$ cycloalkenylene, or unsubstituted phenylene; and $L^{10}$ is absent, —$(CH_2)_q$—, —NH—$(CH_2)_q$—, or —C(═O)—$(CH_2)_q$—.

Embodiment 13. The compound of embodiments 11 or 12, or a pharmaceutically acceptable salt thereof, wherein $L^9$ is azetidinylene, pyrrolidinylene, piperidinylene, piperazinylene, or

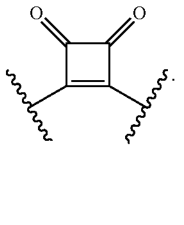 [SMILES: *c1c(*)c(=O)c1=O]

Embodiment 14. The compound of any one of embodiments 1-5, 5a, 6, 6a, or 7-10, or a pharmaceutically acceptable salt thereof, wherein:

$R^6$ is $—Z^A$-$L^A$-$R^A$ and $L_A$-$R^A$ is -$L^2$-$L^3$-$R^A$; or $R^5$ is $—Z^B$-$L^B$-$R^B$ and $L^B$-$R^B$ is -$L^2$-$L^3$-$R^B$;

$L^2$ is unsubstituted $—C_1$-$C_6$ alkylene-NH—; and $L^3$ is a natural or unnatural amino acid, wherein the N atom of the amide linking the amino acids is optionally substituted with $—CH_3$.

Embodiment 15. The compound of any one of embodiments 1-5, 5a, 6, 6a, or 7-10, or a pharmaceutically acceptable salt thereof, wherein: $L^A$-$R^A$ is -$L^2$-$L^7$-$R^A$; or $L^B$-$R^B$ is -$L^2$-$L^7$-$R^B$; $L^2$ is $—(CH_2CH_2O)_w—CH_2CH_2—$; and $L^7$ is —NH—.

Embodiment 16. The compound of any one of embodiments 1-10, or a pharmaceutically acceptable salt thereof, wherein:

$R^6$ is $—Z^A$-$L^A$-$R^A$ and $L^A$-$R^A$ is -$L^2$-$L^4$-$L^7$-$R^A$; or $R^5$ is $—Z^B$-$L^B$-$R^B$ and $L^B$-$R^B$ is -$L^2$-$L^4$-$L^7$-$R^B$;

$L^2$ is unsubstituted $—C_1$-$C_6$ alkylene- or unsubstituted $—C_1$-$C_6$ alkylene-NHC(═O)—;

$L^4$ is $—(CH_2)_v—$, $—(CH_2CH_2O)_v—CH_2CH_2—$, $—(CH_2)_v—NR^{17}—(CH_2)_v$, —NHC(═O)NH—O—$(CH_2)_v$— NHC(═O)$CH_2$—O—NH—C(═O)$(CH_2)_v$, $—CH_2C(—OH)CH_2—C(OH)—CH_2CH_2—$, $—CH_2CH_2C(═O)NHCH_2CH_2—$, $—CH_2CH_2—C(═O)NH—(CH_2CH_2O)_vCH_2CH_2—$, or $—CH_2C(—OH)CH_2—C(OH)—CH_2CH_2—NHC(═O)CH_2CH_2C(═O)—NHCH_2CH_2$; and $L^7$ is —NH—.

Embodiment 17. The compound of any one of any one of embodiments 1-5, 5a, 6, 6a, or 7-10, or a pharmaceutically acceptable salt thereof, wherein:

$R^6$ is $—Z^A$-$L^A$-$R^A$ and $L^A$-$R^A$ is -$L^2$-$L^6$-$L^7$-$R^A$; or $R^5$ is $—Z^B$-$L^B$-$R^B$ and $L^B$-$R^B$ is -$L^2$-$L^6$-$L^7$-$R^B$;

$L^2$ is unsubstituted $—C_1$-$C_6$ alkylene-, unsubstituted $—C_1$-$C_6$ alkylene-NH—, or unsubstituted $—C_1$-$C_6$ alkylene-NHC(═O)—;

$L^6$ is -$L^8$-$L^9$-$L^{10}$-; and $L^7$ is —NH—.

Embodiment 18. The compound of any one of embodiments 1-5, 5a, 6, 6a, or 7-10, or a pharmaceutically acceptable salt thereof, wherein each of $L^A$ and $L^B$, whichever is present, are each independently:

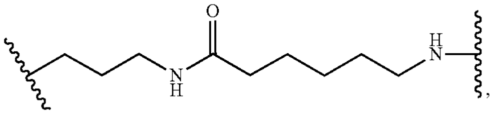
,
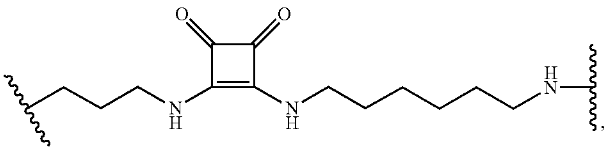
,
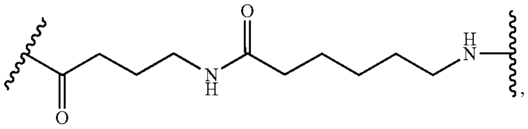
,
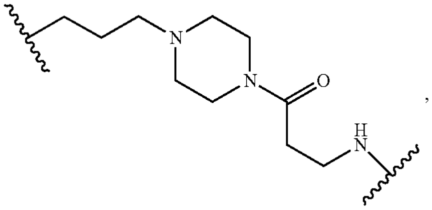
,
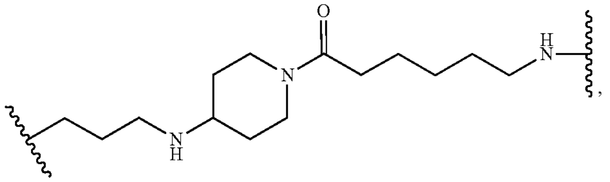
,
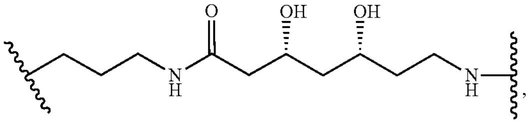
,
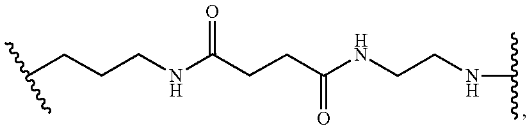
,
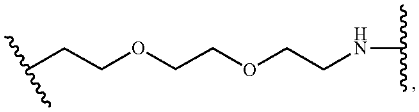
,
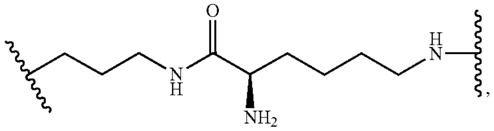
,
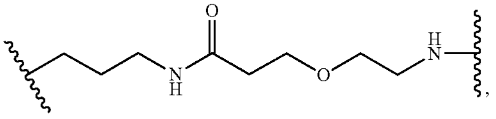
,
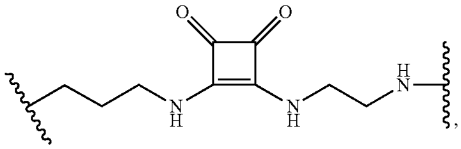
,
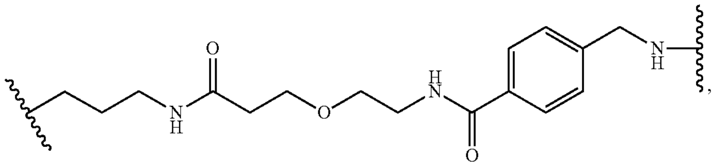
, -continued
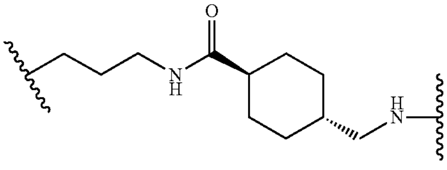,
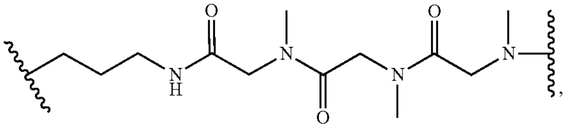,
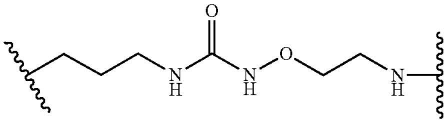,
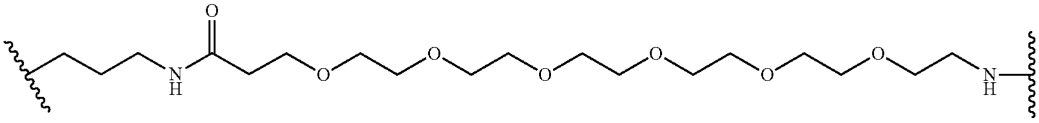,
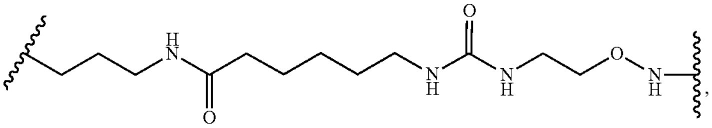,
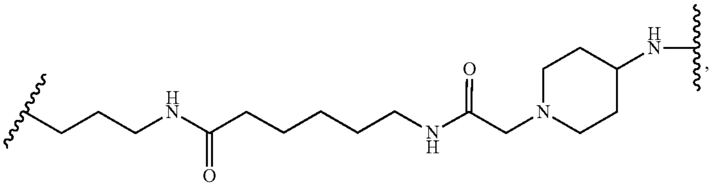,
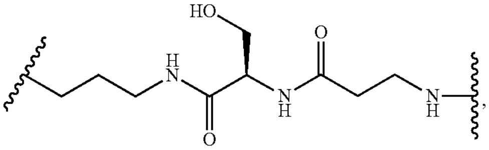,
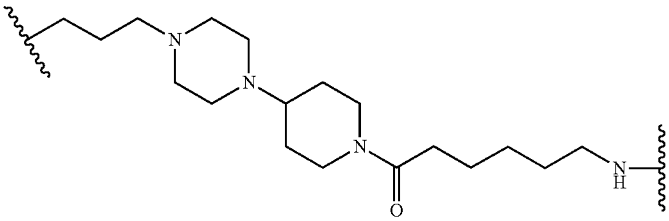,
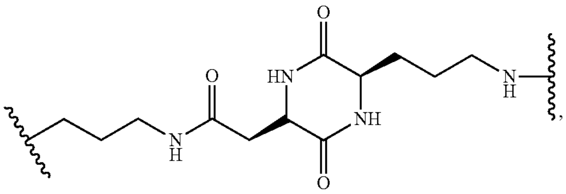,
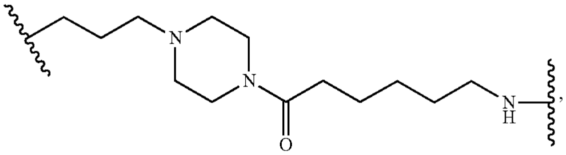,
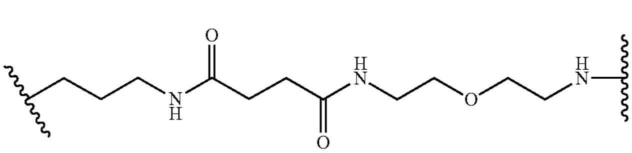,
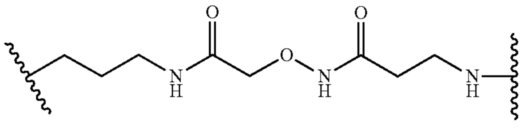,
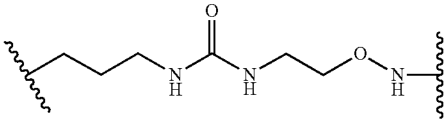,
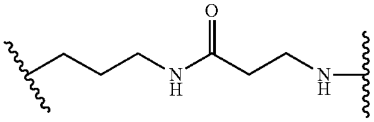,
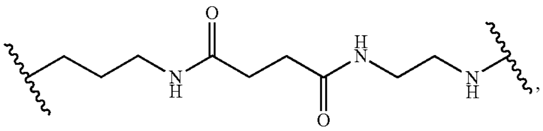,
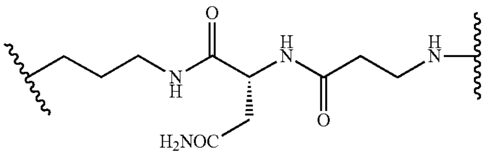, -continued

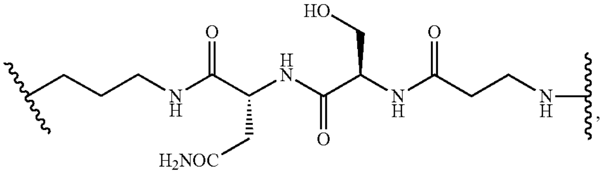,

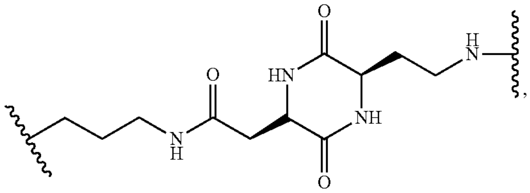,

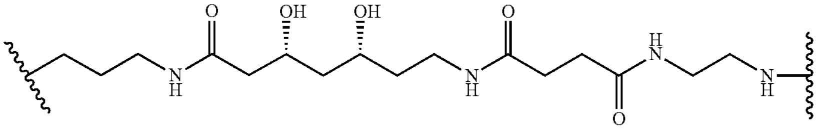,

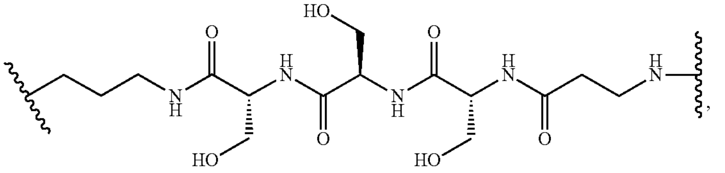,

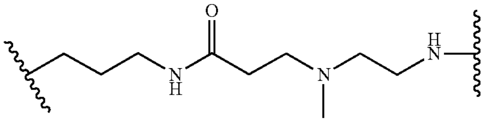,

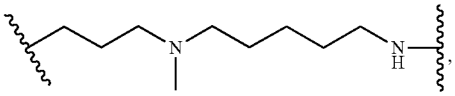,

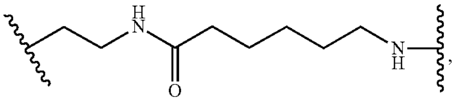, or

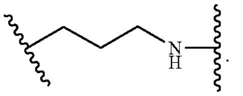.

Embodiment 19. The compound of any one of embodiments 1-5, 5a, 6, 6a, or 7-17, or a pharmaceutically acceptable salt thereof, wherein:

$R^1$ is H; $R^2$ is —OH;

each $R^3$ is independently selected from the group consisting of $R^{3a}$, $R^{3b}$, $R^{3c}$, and $R^{3d}$;

$R^{3a}$, $R^{3b}$, $R^{3c}$ and $R^{3d}$ is independently selected from the group consisting of H, F, Cl, Br, I, —CN, —$CH_3$, —$CF_3$, and —$OCH_3$;

$R^4$ is —C(═O)$NHR^{10}$;

$R^{10}$ is unsubstituted —$C_1$-$C_6$ alkyl or —$(CH_2)_t$NHC(═O)$(CH_2)_u$$CH_3$;

t is 1, 2, 3, or 4; u is 1 or 2;

$R^5$ is —$Z^B$-$L^B$-$R^B$ and $R^6$ is absent; or $R^6$ is —$Z^A$-$L^A$-$R^A$ and $R^5$ is absent;

$Z^B$ is —O—, —NH—, —N(—$CH_3$)—, —NHC(═O)— or —$CH_2$—; and $Z^A$ is —O—, —NH—, —N(—$CH_3$)—, —NHC(═O)— or —$CH_2$—.

Embodiment 20. The compound of any one of any one of embodiments 1-5, 5a, 6, 6a, 7, or 8, or a pharmaceutically acceptable salt thereof, wherein $L^A$-$R^A$ or $L^B$-$R^B$, whichever is present, is:

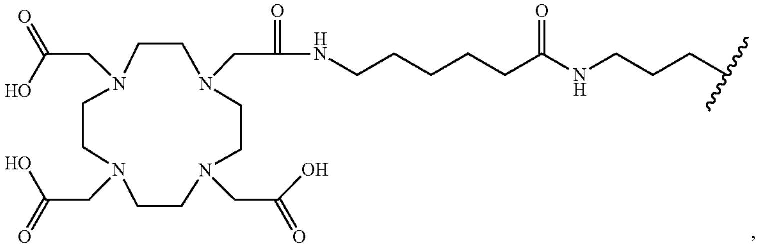,

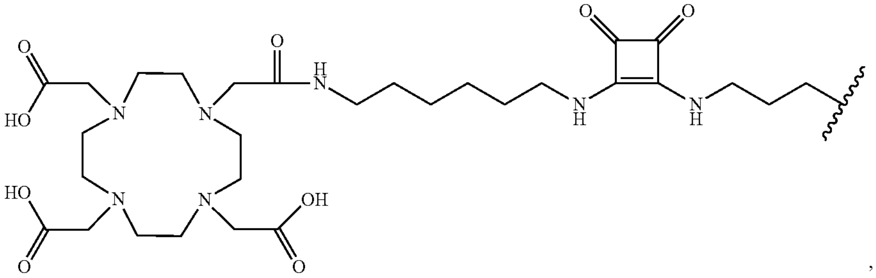,

-continued
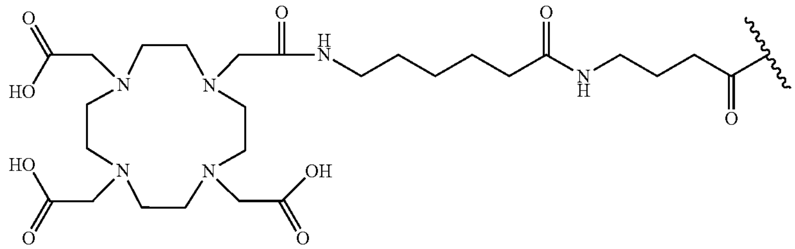
,
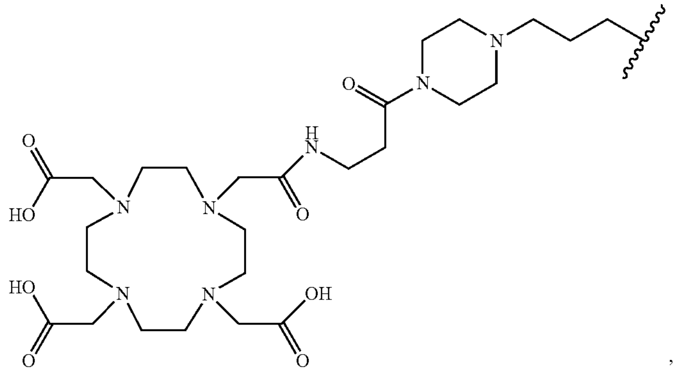
,
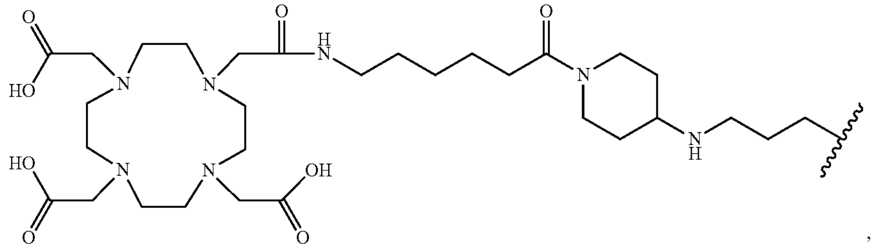
,
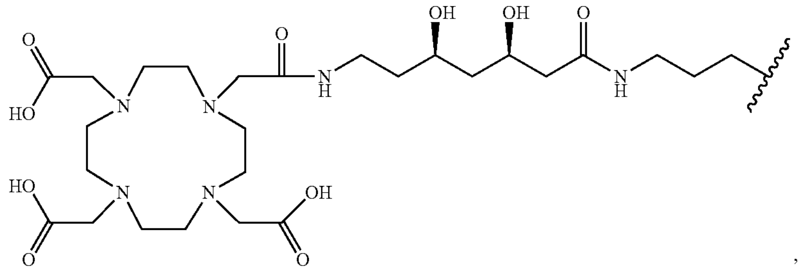
,
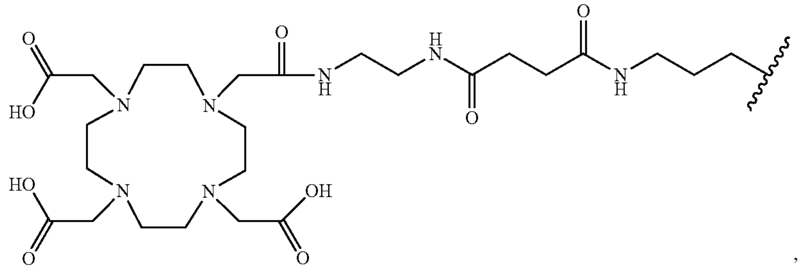
,
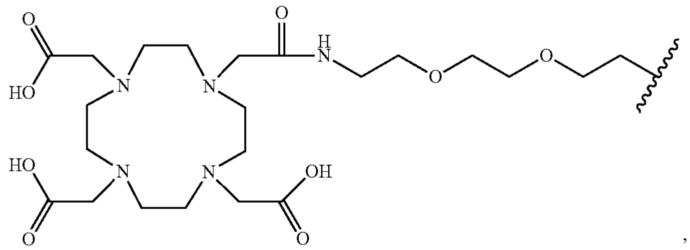
, -continued
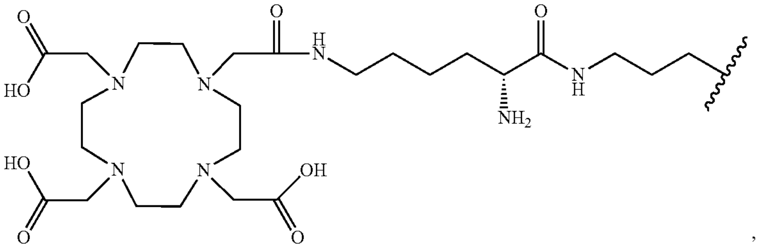
,
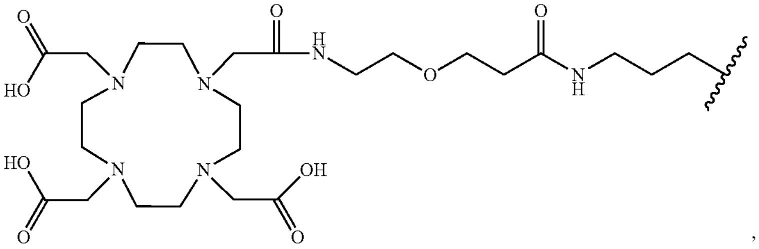
,
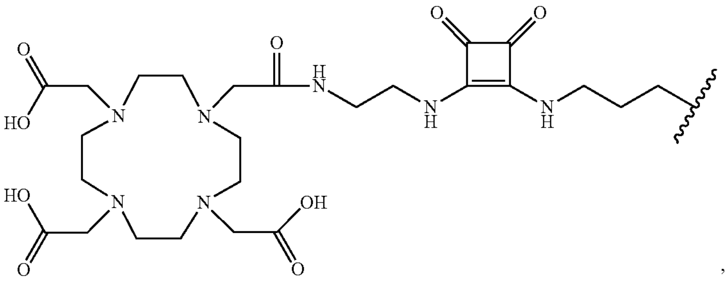
,
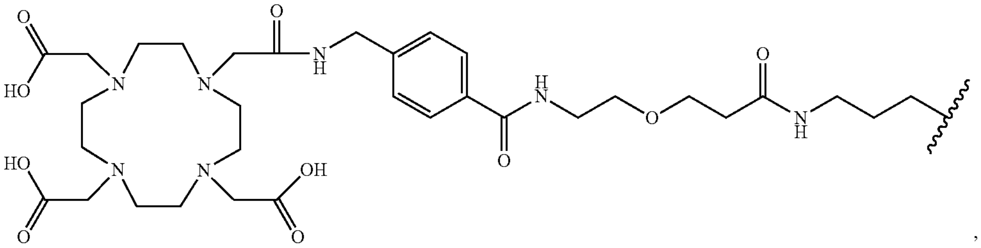
,
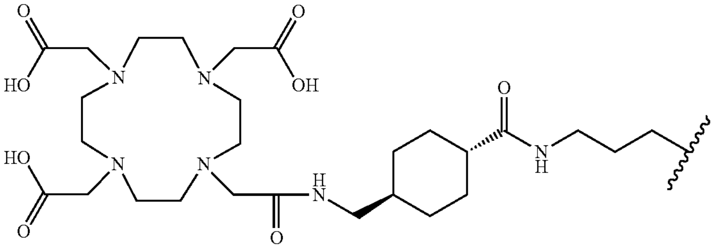
,
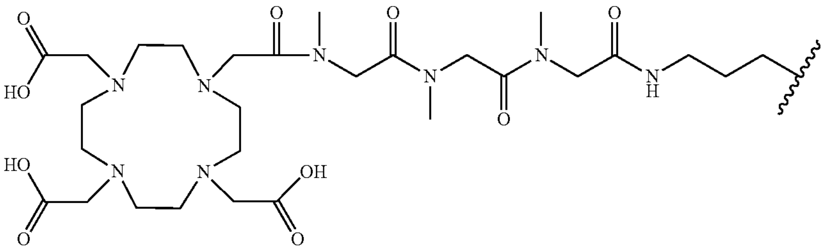
, -continued
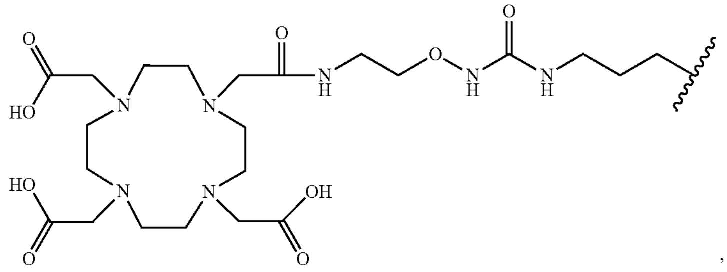
,
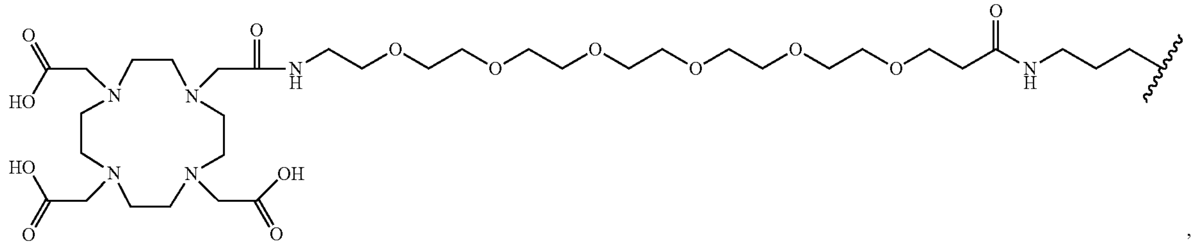
,
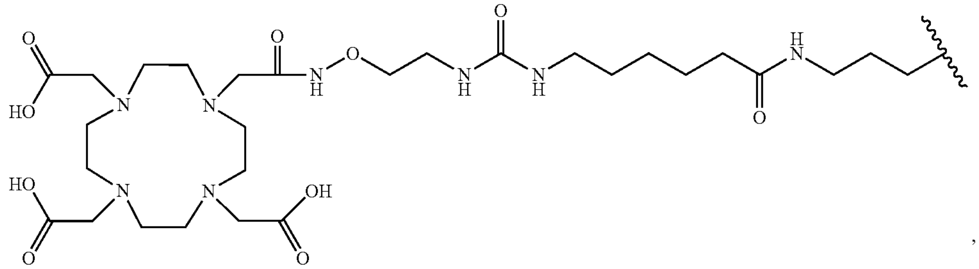
,
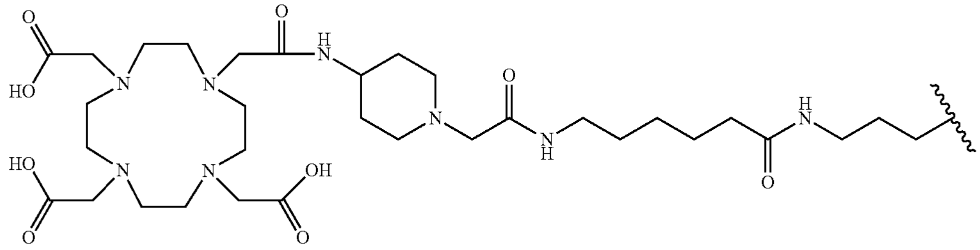
,
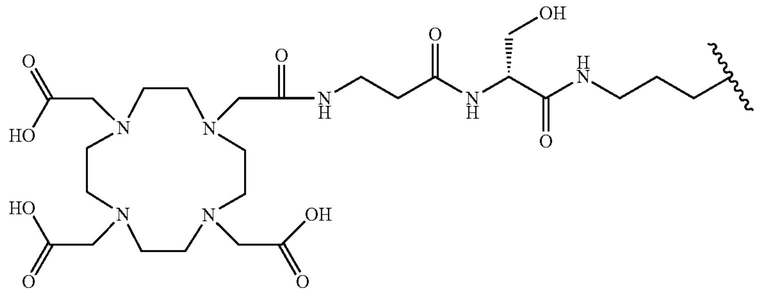
,
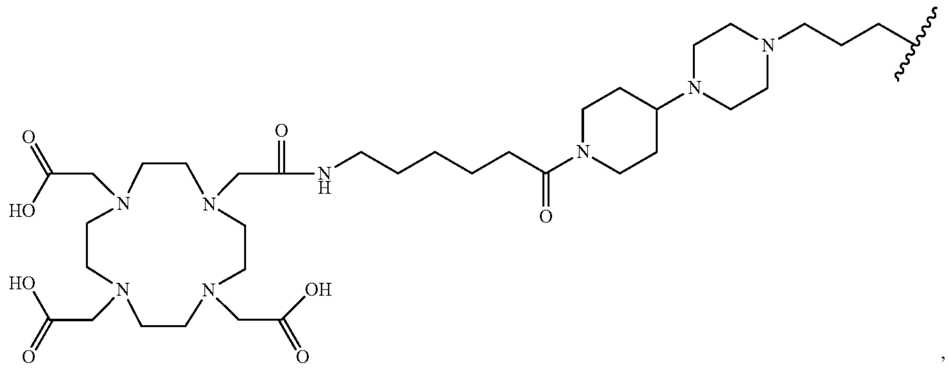
, -continued
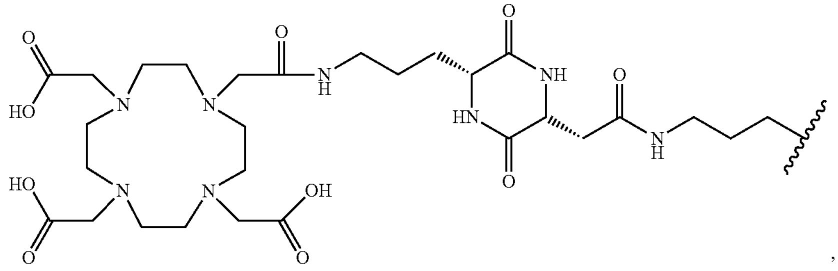
,
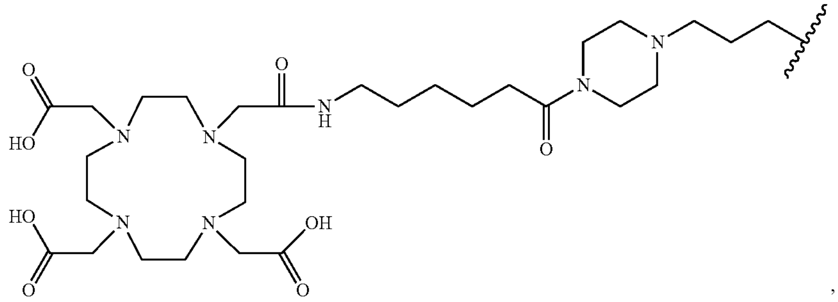
,
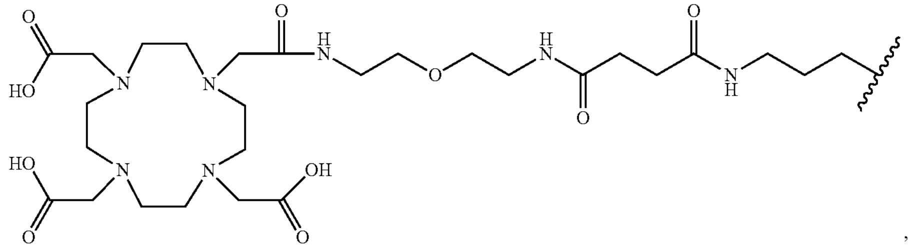
,
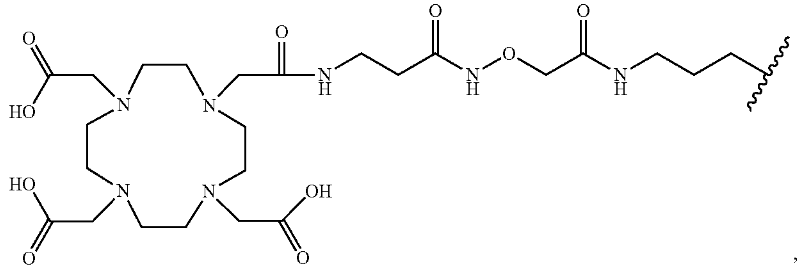
,
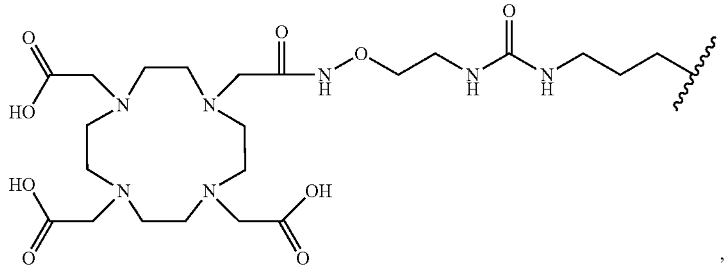
,
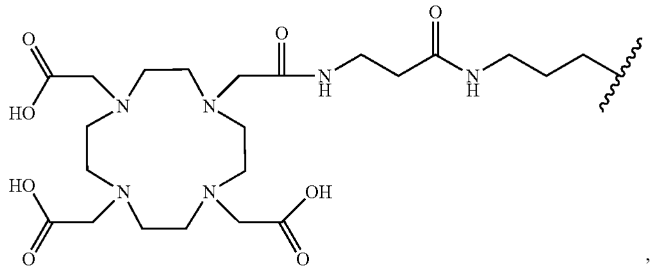
, -continued
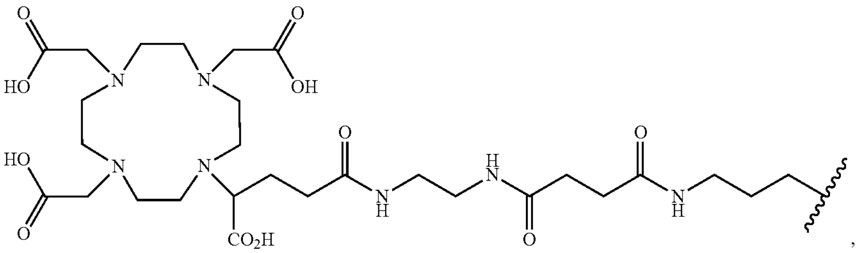
,
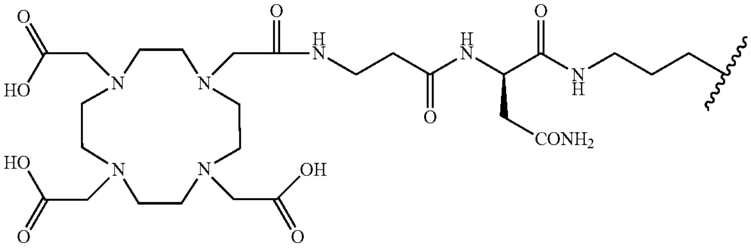
,
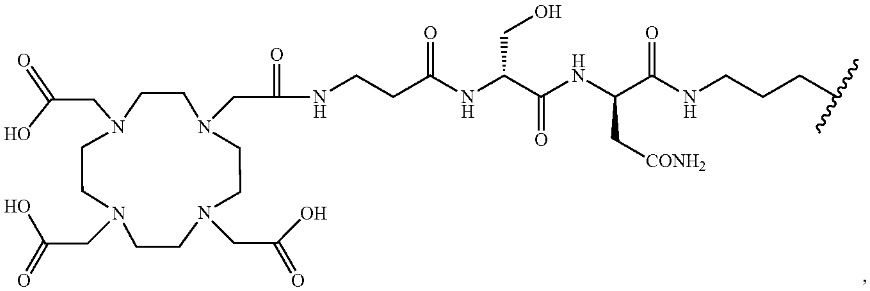
,
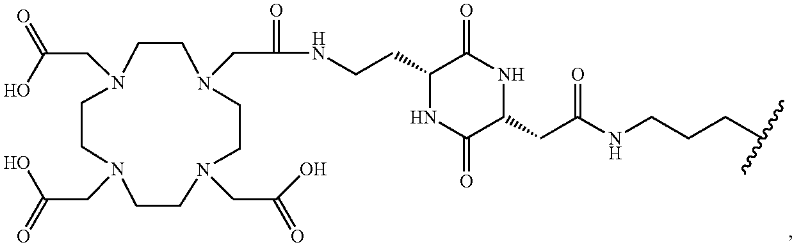
,
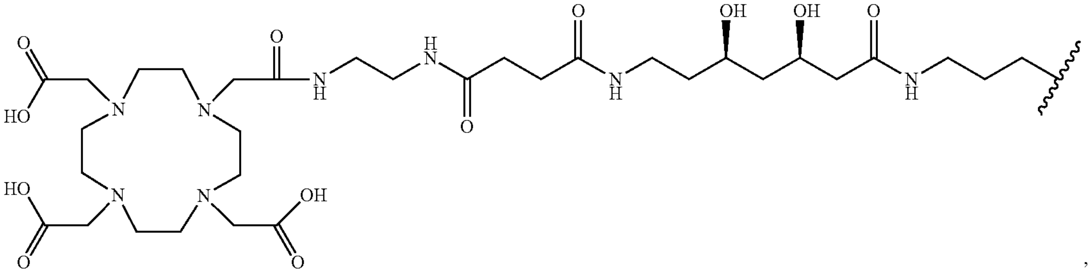
,
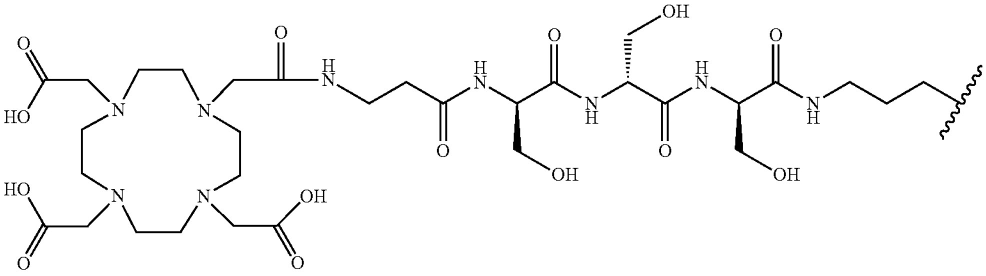
, -continued

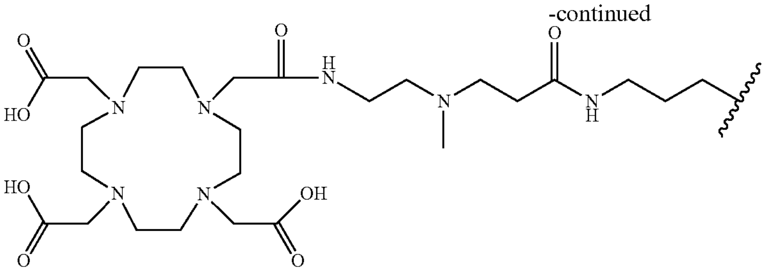

,

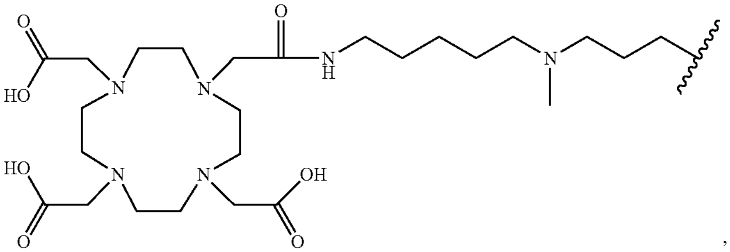

,

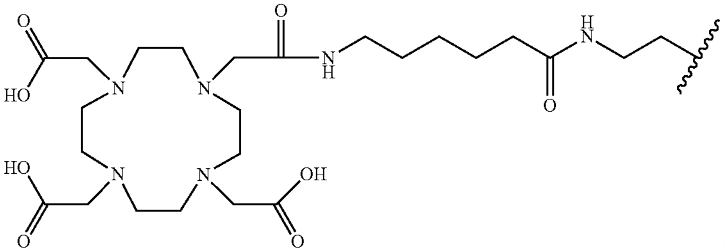

, or

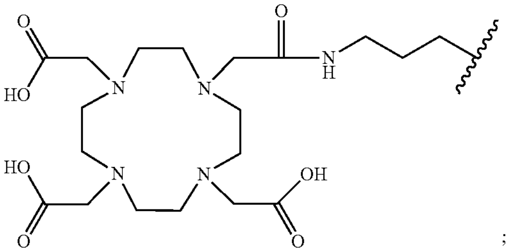 [SMILES: *CCCNC(=O)CN1CCN(CC(=O)O)CCN(CC(=O)O)CCN(CC(=O)O)CC1]

;

or a radionuclide complex thereof.

Embodiment 21. The compound of embodiment 1, or a pharmaceutically acceptable salt thereof, wherein the compound is a compound recited in Table 1, or a radionuclide complex thereof.

Embodiment 22. The compound of embodiment 1, or a pharmaceutically acceptable salt thereof, wherein the compound of Formula (I) has one of the following structures, or a

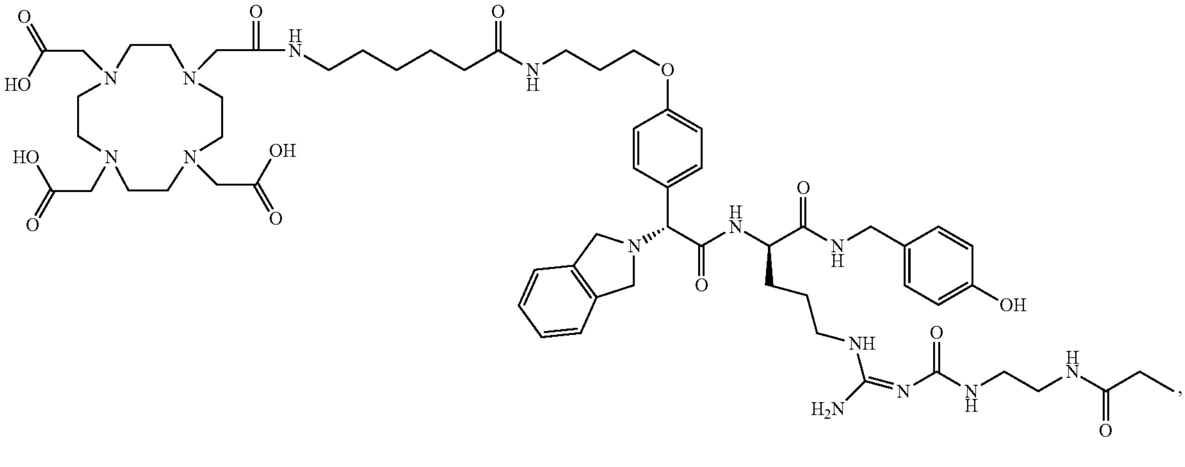

,

-continued
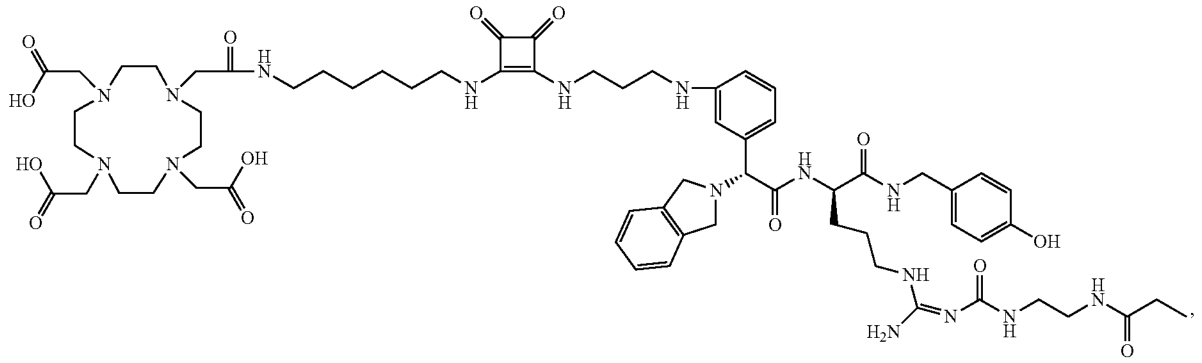
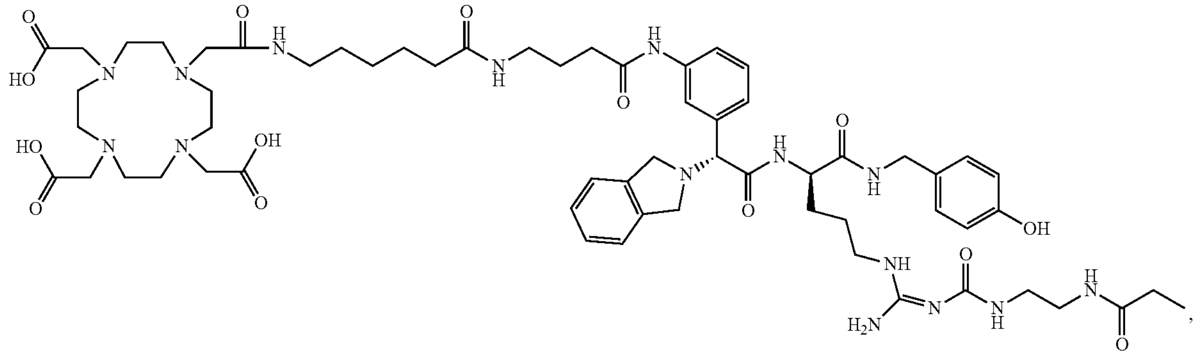
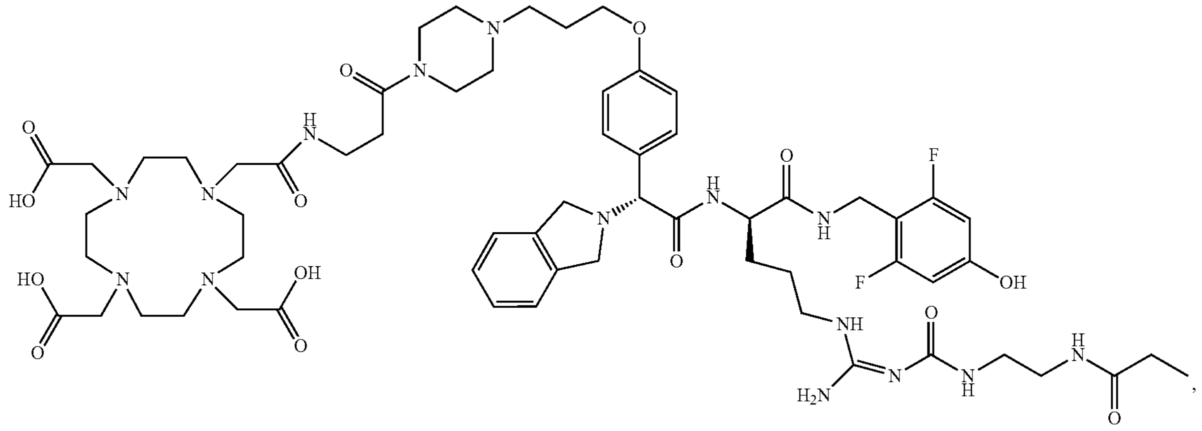
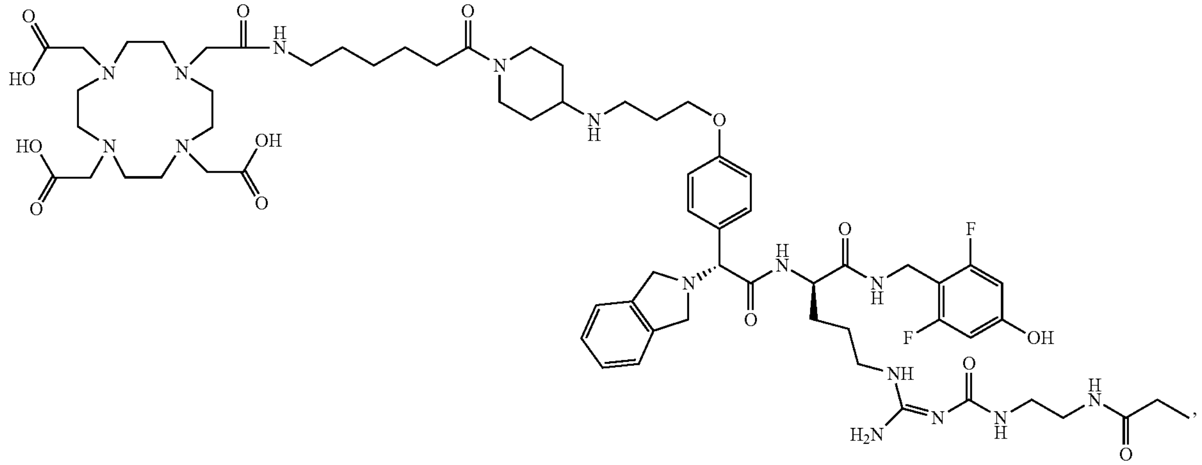

-continued
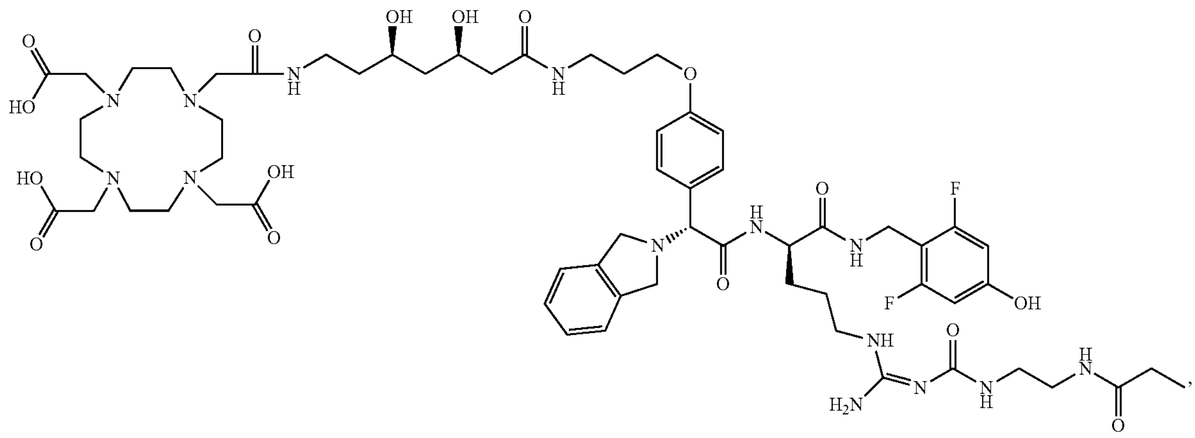
,
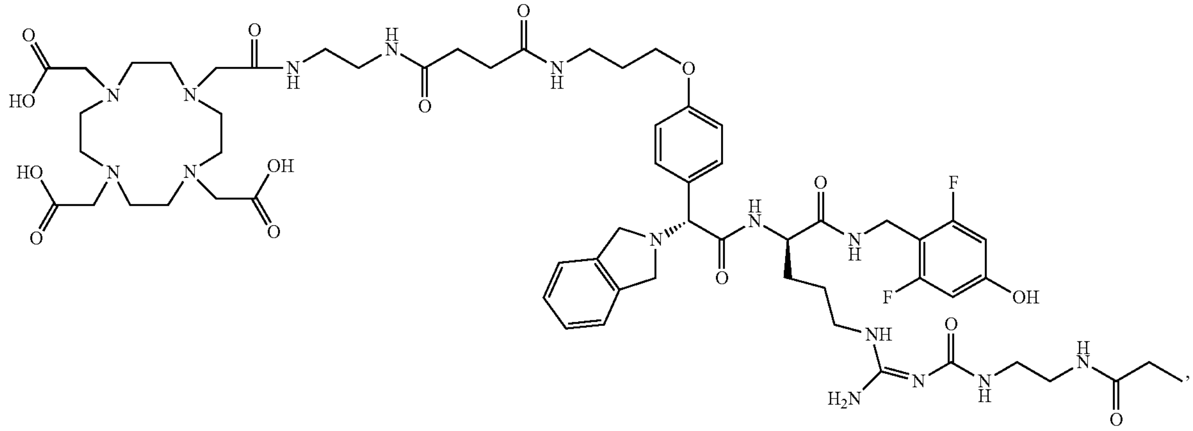
,
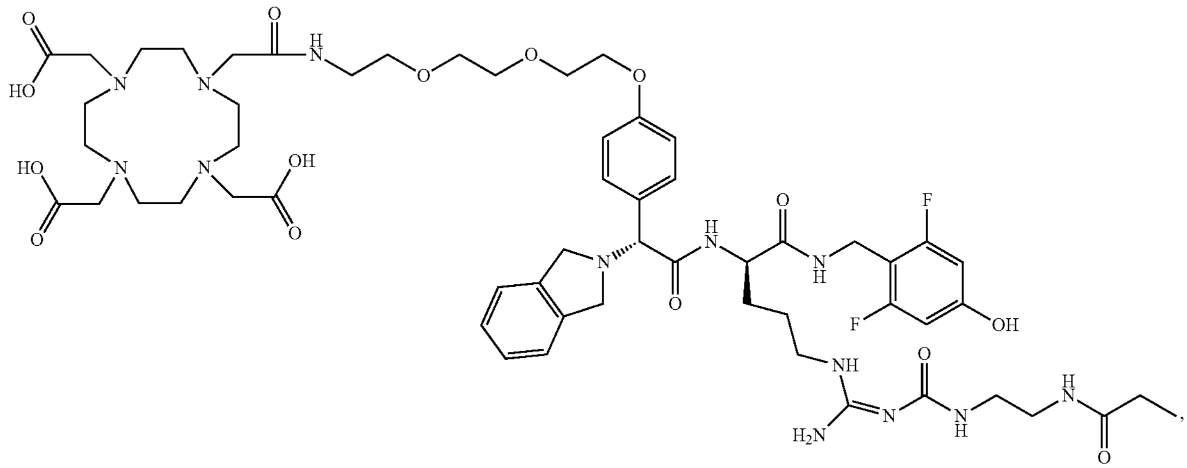
,
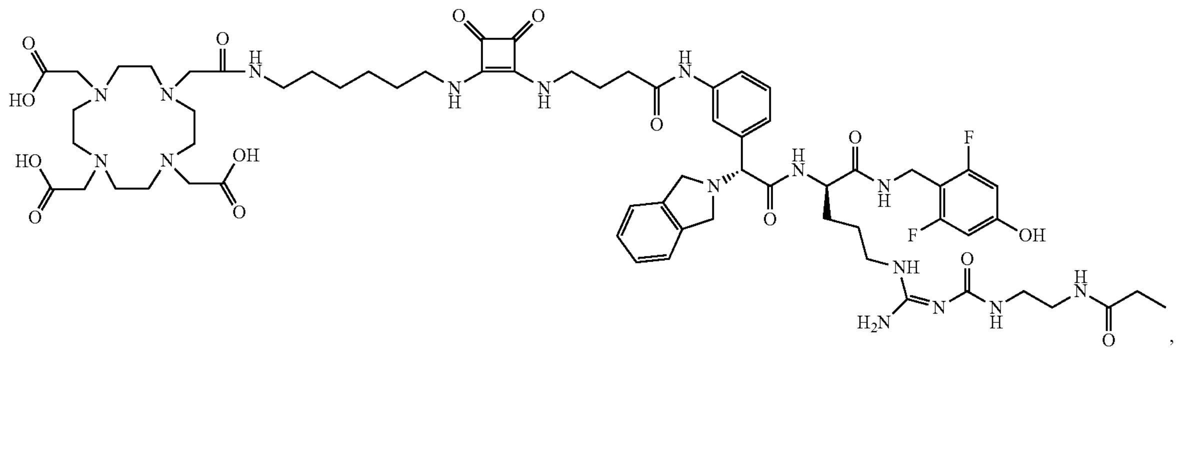
, or

-continued

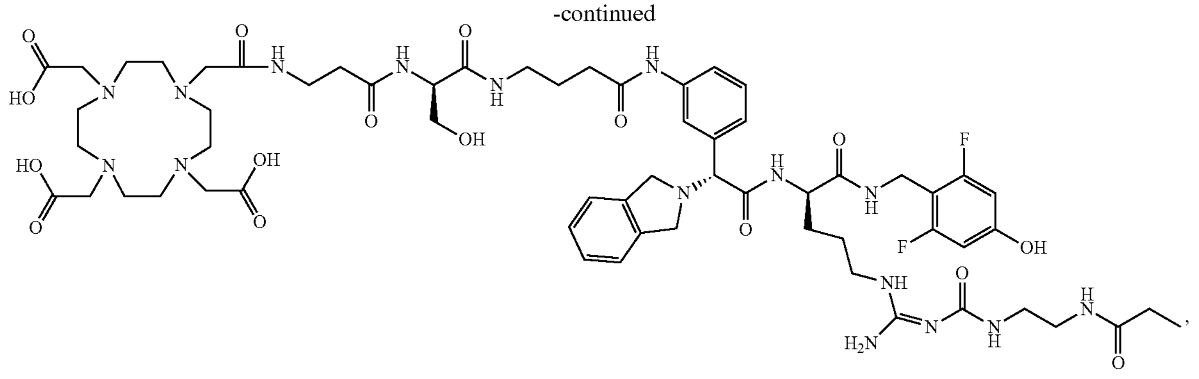

or a radionuclide complex thereof.

Embodiment 23. The compound of any one of embodiments of any one of embodiments 1-5, 5a, 6, 6a, or 7-22, or a pharmaceutically acceptable salt thereof, wherein the compound is a radionuclide complex and the radionuclide of the radionuclide complex is: an Auger electron-emitting radionuclide that is 111-indium ($^{111}In$), 67-gallium ($^{67}Ga$), 68-gallium ($^{68}Ga$), 99m-technetium ($^{99m}Tc$), or 195m-platinum ($^{195m}Pt$); or an α-emitting radionuclide that is 225-actinium ($^{225}Ac$), 213-bismuth ($^{213}Bi$), 223-radium ($^{223}Ra$), or 212-lead ($^{212}Pb$); or a β-emitting radionuclide that is 90-yttrium ($^{90}Y$), 177-lutetium ($^{177}Lu$), 186-rhenium ($^{186}Re$), 188-rhenium ($^{188}Re$), 64-copper ($^{64}Cu$), 67-copper ($^{67}Cu$), 153-samarium ($^{153}Sm$), 89-strontium ($^{89}Sr$), 198-gold ($^{198}Au$), 169-Erbium ($^{169}Er$), 165-dysprosium ($^{165}Dy$), 99m-technetium ($^{99m}Tc$), 89-zirconium ($^{89}Zr$), or 52-manganese ($^{52}Mn$); or a 7-emitting radionuclide that is 60-cobalt ($^{60}Co$), 103-palldium ($^{103}Pd$), 137-cesium ($^{137}Cs$), 169-ytterbium ($^{169}Yb$) 192-iridium ($^{192}Ir$), or 226-radium ($^{226}Ra$).

Embodiment 24. The compound of any one of embodiments 1-5, 5a, 6, 6a, or 7-22, or a pharmaceutically acceptable salt thereof, wherein: the compound is a radionuclide complex and the radionuclide of the radionuclide complex is 111-indium ($^{111}n$), 115-indium ($^{115}In$), 67-gallium ($^{67}Ga$), 68-gallium ($^{68}Ga$), 69-gallium ($^{69}Ga$), 71-gallium ($^{71}Ga$), 225-actinium ($^{225}Ac$), 175-lutetium ($^{175}Lu$), 177-lutetium ($^{177}Lu$), 204-lead ($^{204}Pb$), 206-lead ($^{206}Pb$), 207-lead ($^{207}Pb$), 208-lead ($^{208}Pb$), 212-lead ($^{212}Pb$), 63-copper ($^{63}Cu$), 64-copper ($^{64}Cu$), 65-copper ($^{65}Cu$), or 67-copper ($^{67}Cu$).

Embodiment 25. The compound of any one of embodiments 1-5, 5a, 6, 6a, or 7-22, or a pharmaceutically acceptable salt thereof, wherein: the compound is a radionuclide complex and the radionuclide of the radionuclide complex is 111-indium ($^{111}In$), 115-indium ($^{115}In$), 67-gallium ($^{67}Ga$), 68-gallium ($^{68}Ga$), 225-actinium ($^{225}Ac$), 175-lutetium ($^{175}Lu$), or 177-lutetium ($^{177}Lu$).

Embodiment 26. A pharmaceutical composition comprising a compound of any one of embodiments 1-5, 5a, 6, 6a, or 7-25, or a pharmaceutically acceptable salt thereof, and at least one pharmaceutically acceptable excipient.

Embodiment 27. A method for the treatment of cancer comprising administering to a mammal with cancer an effective amount of a compound of any one of embodiments 1-5, 5a, 6, 6a, or 7-25, or a pharmaceutically acceptable salt thereof; wherein the compound is a radionuclide complex and the radionuclide of the radionuclide complex is: an α-emitting radionuclide that is 225-actinium ($^{225}Ac$), 213-bismuth ($^{213}Bi$), 223-radium ($^{223}Ra$), or 212-lead (212Pb); or a β-emitting radionuclide that is 90-yttrium ($^{90}Y$), 177-lutetium ($^{177}Lu$), 64-copper ($^{64}Cu$), 67-copper ($^{67}Cu$), or 153-samarium (153Sm).

Embodiment 27a. The method compound of embodiment 27, wherein the cancer comprises tumors and the tumors overexpress the neuropeptide $Y_1$ receptor ($NPY_1R$).

Embodiment 28. The method compound of embodiment 27 or 27a, wherein the cancer is breast cancer, kidney cancer, ovarian cancer, melanoma, gastrointestinal stromal tumor (GIST), Ewing's sarcoma, nephroblastoma, or adrenal gland tumors.

Embodiment 29. A method of killing tumors in a mammal that overexpress the neuropeptide $Y_1$ receptor ($NPY_1R$) comprising administering to the mammal a compound of any one of embodiments 1-5, 5a, 6, 6a, or 7-25, or a pharmaceutically acceptable salt thereof, wherein the compound is a radionuclide complex and the radionuclide of the radionuclide complex is: an α-emitting radionuclide that is 225-actinium ($^{225}Ac$), 213-bismuth ($^{213}Bi$), 223-radium ($^{223}Ra$), or 212-lead ($^{212}Pb$); or a β-emitting radionuclide that is 90-yttrium ($^{90}Y$), 177-lutetium ($^{177}Lu$), 64-copper ($^{64}Cu$), 67-copper ($^{67}Cu$), or 153-samarium ($^{153}Sm$).

Embodiment 30. The method of embodiment 29, wherein the mammal has been diagnosed with breast cancer, kidney cancer, ovarian cancer, melanoma, gastrointestinal stromal tumor (GIST), Ewing's sarcoma, nephroblastoma, or adrenal gland tumors.

Embodiment 31. A compound of Formula (I), or a pharmaceutically acceptable salt thereof:

Formula (I)

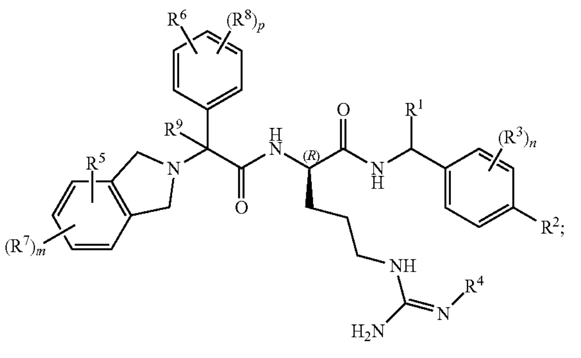

wherein:

$R^1$ is H, —$C_1$-$C_6$ alkyl, or —C(=O)$NH_2$;

$R^2$ is —OH, —$NH_2$, —C(=O)$NH_2$, or —$CH_2$NHC(=O)$NH_2$;

each $R^3$ is independently selected from the group consisting of $R^{3a}$, $R^{3b}$, $R^{3c}$, and $R^{3d}$;

$R^{3a}$, $R^{3b}$, $R^{3c}$, and $R^{3d}$ are each independently selected from the group consisting of H, F, Cl, Br, I, —CN, substituted or unsubstituted —$C_1$-$C_6$ alkyl, and substituted or unsubstituted —$C_1$-$C_6$ alkoxy;

$R^4$ is H, —C(═O)$R^{10}$, —C(═O)NH$R^{10}$, or —C(═O)N($CH_3$)$R^{10}$;

$R^{10}$ is substituted or unsubstituted —$C_1$-$C_6$ alkyl, substituted or unsubstituted 2 to 6-membered heteroalkyl, —$(CH_2)_t$—$NH_2$, —$(CH_2)_t$C(═O)O$(CH_2)_u$$CH_3$, —$(CH_2)_t$NHC(═O)$(CH_2)_u$$CH_3$, or —$(CH_2)_t$-substituted or unsubstituted 5 to 6 membered heteroaryl ring;

t is 1, 2, 3, 4, 5, or 6;

u is 1, 2, 3, or 4;

$R^5$ is absent or —$Z^B$-$L^B$-$R^B$;

$Z^B$ is absent, —$C_1$-$C_6$ alkylene-, —$C_1$-$C_6$ alkylene-O—, —O—$C_1$-$C_6$ alkylene-, —C(═O)$NR^{11}$— $NR^{11}$C(═O)—, —O—, —$NR^{11}$—, —S—, —S(═O)—, —$SO_2$—, or —NHC(═O)NH—;

$L^B$ is a linker;

$R^B$ is a chelating moiety or a radionuclide complex thereof, $R^6$ is absent or —$Z^A$-$L^A$-$R^A$;

$Z^A$ is absent, —$C_1$-$C_6$ alkylene-, —$C_1$-$C_6$ alkylene-O—, —O—$C_1$-$C_6$ alkylene-, —C(═O)$NR^{12}$—, —$NR^{12}$C(═O)—, —O—, —$NR^{12}$—, —S—, —S(═O)—, —$SO_2$—, or —NHC(═O)NH—;

$L^A$ is a linker;

$R^A$ is a chelating moiety or a radionuclide complex thereof;

each $R^7$ is independently selected from the group consisting of F, Cl, Br, I, —CN, —OH, substituted or unsubstituted —$C_1$-$C_6$ alkyl, and substituted or unsubstituted —$C_1$-$C_6$ alkoxy;

each $R^8$ is independently selected from the group consisting of F, Cl, Br, I, —CN, —OH, substituted or unsubstituted —$C_1$-$C_6$ alkyl, and substituted or unsubstituted —$C_1$-$C_6$ alkoxy;

$R^9$ is H, substituted or unsubstituted —$C_1$-$C_4$ alkyl, or substituted or unsubstituted —$C_1$-$C_6$ alkoxy;

each $R^{11}$ is independently H or unsubstituted —$C_1$-$C_4$ alkyl;

each $R^{12}$ is independently H or unsubstituted —$C_1$-$C_4$ alkyl;

n is 0, 1, 2, 3, or 4;

m is 0, 1, 2, or 3;

p is 0, 1, 2, or 3; and wherein $R^5$ is —$Z^B$-$L^B$-$R^B$ when $R^6$ is absent; or $R^6$ is —$Z^A$-$L^A$-$R^A$ when $R^5$ is absent.

Embodiment 32. The compound of embodiment 31, wherein:

$R^1$ is H;

$R^2$ is —OH, —$NH_2$, —C(═O)$NH_2$ or —$CH_2$NHC(═O)$NH_2$;

each $R^3$ is independently selected from the group consisting of $R^{3a}$, $R^{3b}$, $R^{3c}$, and $R^{3d}$;

$R^{3a}$, $R^{3b}$, $R^{3c}$, and $R^{3d}$ are each independently selected from the group consisting of H, F, Cl, Br, I, —CN, substituted or unsubstituted —$C_1$-$C_6$ alkyl, and substituted or unsubstituted —$C_1$-$C_6$ alkoxy;

$R^4$ is H, —C(═O)$R^{10}$, —C(═O)NH$R^{10}$ or —C(═O)N($CH_3$)$R^{10}$;

$R^{10}$ is substituted or unsubstituted —$C_1$-$C_6$ alkyl, substituted or unsubstituted 2 to 6-membered heteroalkyl, or —$(CH_2)_t$NHC(═O)$(CH_2)_u$$CH_3$;

t is 1, 2, 3, 4, 5, or 6;

u is 1, 2, 3, or 4;

$R^5$ is absent or —$Z^B$-$L^B$-$R^B$;

$Z^B$ is absent, —$C_1$-$C_6$ alkylene-, —$C_1$-$C_6$ alkylene-O—, —O—$C_1$-$C_6$ alkylene-, —C(═O)$NR^{11}$—, —$NR^{11}$C(═O)—, —O—, or —$NR^{11}$—;

$L^B$ is a linker;

$R^B$ is a chelating moiety or a radionuclide complex thereof, $R^6$ is absent or —$Z^A$-$L^A$-$R^A$;

$Z^A$ is absent, —$C_1$-$C_6$ alkylene-, —$C_1$-$C_6$ alkylene-O—, —O—$C_1$-$C_6$ alkylene-, —C(═O)$NR_{12}$—, —$NR^{12}$C(═O)—, —O—, or —$NR_{12}$—;

$L^A$ is a linker;

$R^A$ is a chelating moiety or a radionuclide complex thereof;

$R^9$ is H;

each $R^{11}$ is independently H or unsubstituted —$C_1$-$C_4$ alkyl;

each $R^{12}$ is independently H or unsubstituted —$C_1$-$C_4$ alkyl;

n is 0, 1, 2, 3, or 4;

m is 0;

p is 0; and wherein $R^5$ is —$Z^B$-$L^B$-$R^B$ when $R^6$ is absent; or $R^6$ is —$Z^A$-$L^A$-$R^A$ when $R^5$ is absent.

Embodiment 33. The compound of embodiment 31 or 32, wherein the compound has the structure of Formula (Ia), or a pharmaceutically acceptable salt thereof:

Formula (Ia)

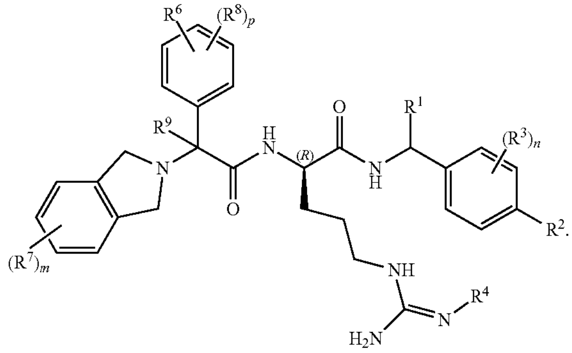

Embodiment 34. The compound of embodiment 31 or 32, wherein the compound has the structure of Formula (Id), or a pharmaceutically acceptable salt thereof:

Formula (Id)

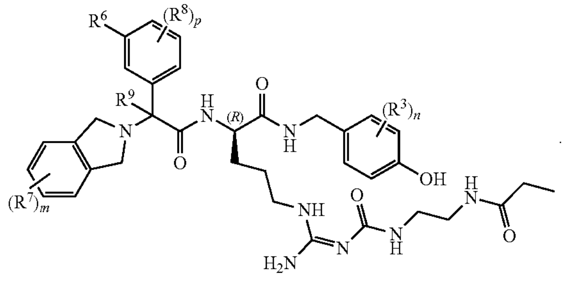

Embodiment 35. The compound of embodiment 31 or 32, wherein the compound has the structure of Formula (Ie), or a pharmaceutically acceptable salt thereof:

Formula (Ie)

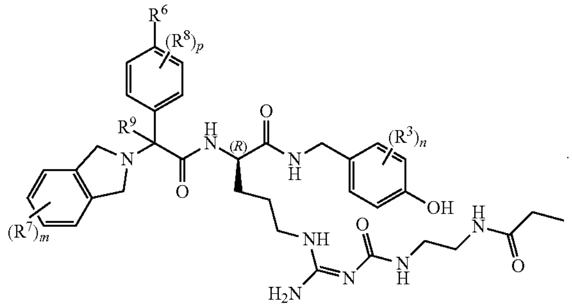

Embodiment 36. The compound of embodiment 31 or 32, wherein the compound has the structure of Formula (If), or a pharmaceutically acceptable salt thereof:

Formula (If)

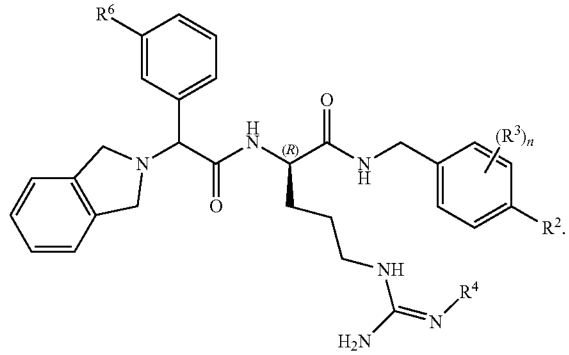

Embodiment 37. The compound of embodiment 31 or 32, wherein the compound has the structure of Formula (Ig), or a pharmaceutically acceptable salt thereof:

Formula (Ig)

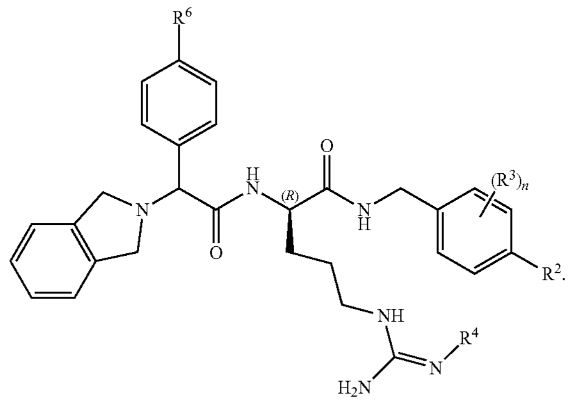

Embodiment 38. The compound of embodiment 31 or 32, or a pharmaceutically acceptable salt thereof, wherein $R^5$ is absent.

Embodiment 39. The compound of embodiment 31 or 32, or a pharmaceutically acceptable salt thereof, wherein $R^5$ is —$Z^B$-$L^B$-$R^B$.

Embodiment 40. The compound of any one of embodiments 31, 32, or 39, or a pharmaceutically acceptable salt thereof, wherein $Z^B$ is —$C_1$-$C_6$ alkylene-, —O—, —NH—, or —NMe-.

Embodiment 41. The compound of any one of embodiments 31-40, or a pharmaceutically acceptable salt thereof, wherein $R^1$ is H.

Embodiment 42. The compound of any one of embodiments 31-41, or a pharmaceutically acceptable salt thereof, wherein n is 0.

Embodiment 43. The compound of any one of embodiments 31-41, or a pharmaceutically acceptable salt thereof, wherein n is 2.

Embodiment 44. The compound of any one of embodiments 31-35 or 38-43, or a pharmaceutically acceptable salt thereof, wherein m is 0.

Embodiment 45. The compound of any one of embodiments 31-35 or 38-44, or a pharmaceutically acceptable salt thereof, wherein p is 0.

Embodiment 46. The compound of any one of embodiments 31-45, or a pharmaceutically acceptable salt thereof, wherein each $R^3$ is independently selected from the group consisting of $R^{3a}$, $R^{3b}$, $R^{3c}$, and $R^{3d}$; wherein $R^{3a}$, $R^{3b}$, $R^{3c}$, and $R^{3d}$ are each independently selected from the group consisting of H, F, Cl, Br, I, —CN, —$CH_3$, —$CF_3$, and —$OCH_3$.

Embodiment 47. The compound of embodiment 31, wherein the compound has the following structure, or a pharmaceutically acceptable salt thereof:

(Iw)

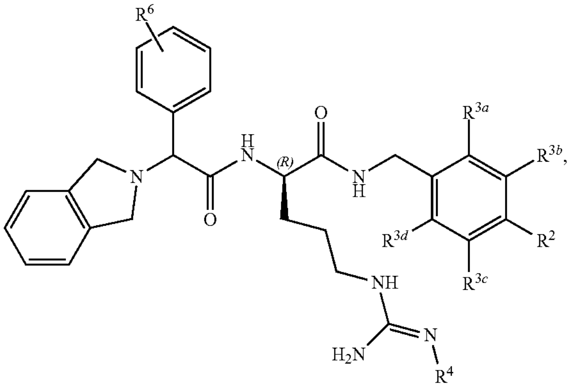

wherein each $R^{3a}$, $R^{3b}$, $R^{3c}$ and $R^{3d}$ is independently selected from the group consisting of H, F, Cl, Br, I, —CN, substituted or unsubstituted —$C_1$-$C_6$ alkyl, and substituted or unsubstituted —$C_1$-$C_6$ alkoxy.

Embodiment 48. The compound of embodiment 47, wherein each $R^{3a}$, $R^{3b}$, $R^{3c}$ and $R^{3d}$ is independently selected from the group consisting of H, F, Cl, Br, I, —CN, —$CH_3$, —$CF_3$, and —$OCH_3$.

Embodiment 49. The compound of embodiment 47, wherein $R^{3a}$ and $R^{3d}$ are F or Cl and $R^{3b}$ and $R^{3c}$ are H.

Embodiment 50. The compound of any one of embodiments 31-49, or a pharmaceutically acceptable salt thereof, wherein $R^2$ is —OH.

Embodiment 51. The compound of any one of embodiments 31-50, or a pharmaceutically acceptable salt thereof, wherein $R^4$ is —C(═O)$NHR^{10}$.

Embodiment 52. The compound of any one of embodiments 31-50, or a pharmaceutically acceptable salt thereof, wherein $R^4$ is $—C(=O)NH(CH_2)_tNHC(=O)(CH_2)_uCH_3$.

Embodiment 53. The compound of any one of embodiments 31-50, or a pharmaceutically acceptable salt thereof, wherein $R^{10}$ is unsubstituted $—C_1$-$C_6$ alkyl or $—(CH_2)_tNHC(=O)(CH_2)_uCH_3$; t is 1, 2, 3, or 4; and u is 1 or 2.

Embodiment 54. The compound of embodiment 52 or 53, or a pharmaceutically acceptable salt thereof, wherein t is 2 and u is 1.

Embodiment 55. The compound of any one of embodiments 31-54, or a pharmaceutically acceptable salt thereof, wherein $Z^A$ is $C_1$-$C_6$ alkylene, —O—, —NH—, —N(—CH$_3$)—, or —NHC(=O)—.

Embodiment 56. The compound of any one of embodiments 31-54, or a pharmaceutically acceptable salt thereof, wherein $Z^A$ is —O—.

Embodiment 57. The compound of any one of embodiments 31-54, or a pharmaceutically acceptable salt thereof, wherein $Z^A$ is —NH—.

Embodiment 58. The compound of any one of embodiments 31-54, or a pharmaceutically acceptable salt thereof, wherein $Z^A$ is —N(—CH$_3$)—.

Embodiment 59. The compound of any one of embodiments 31-54, or a pharmaceutically acceptable salt thereof, wherein $Z^A$ is —NHC(=O)— or —CH$_2$—.

Embodiment 60. The compound of any one of embodiments 31-59, or a pharmaceutically acceptable salt thereof, wherein $R^A$ and $R^B$, if present, are independently selected from the group consisting of:

1,4,7,10-tetraazacyclododecane-1,4,7,10-tetraacetic acid (DOTA);

2,2',2"-(10-(2-amino-2-oxoethyl)-1,4,7,10-tetraazacyclododecane-1,4,7-triyl)triacetic acid (PSC);

1,4,7,10-tetraazacyclododecane-1,4,7-triacetic acid (DO3A);

1,4,7,10-tetraazacyclododecane-1,7-diacetic acid (DO2A);

α,α',α",α'"-tetramethyl-1,4,7,10-tetraazacyclododecane-1,4,7,10-tetraacetic acid (DOTMA);

1,4,7,10-tetrakis(carbamoylmethyl)-1,4,7,10-tetraazacyclododecane (DOTAM);

1,4,7,10-tetraazacyclododecane-1,4,7,10-tetrapropionic acid (DOTPA);

2,2',2"-(10-(2-amino-2-oxoethyl)-1,4,7,10-tetraazacyclododecane-1,4,7-triyl)triacetic acid;

benzyl-1,4,7,10-tetraazacyclododecane-1,4,7,10-tetraacetic acid (Bn-DOTA);

p-hydroxy-benzyl-1,4,7,10-tetraazacyclododecane-1,4,7,10-tetraacetic acid (p-OH-Bn-DOTA);

6,6'-(((pyridine-2,6-diylbis(methylene))bis((carboxymethyl)azanediyl))bis(methylene))dipicolinic acid ($H_4$pypa);

$H_4$pypa-benzyl;

6,6',6",6'θ-(((pyridine-2,6-diylbis(methylene))bis(azanetriyl))tetrakis(methylene))-tetrapicolinic acid ($H_4$py4pa);

$H_4$py4pa-benzyl;

2,2',2"-(1,4,7-triazacyclononane-1,4,7-triyl)triacetic acid (NOTA);

6,6'-((1,4,10,13-tetraoxa-7,16-diazacyclooctadecane-7,16-diyl)bis(methylene))dipicolinic acid (macropa);

2,2',2",2'"-(1,10-dioxa-4,7,13,16-tetraazacyclooctadecane-4,7,13,16-tetrayl)tetraacetic acid (crown);

6,6'-((ethane-1,2-diylbis((carboxymethyl)azanediyl))bis(methylene))dipicolinic acid ($H_4$octapa);

$H_4$octapa-benzyl; and 3,6,9,12-tetrakis(carboxymethyl)-3,6,9,12-tetraazatetradecanedioic acid (TTHA); or a radionuclide complex thereof.

Embodiment 61. The compound of any one of embodiments 31-59, or a pharmaceutically acceptable salt thereof, wherein $R^A$ and $R^B$, if present, are independently selected from the group consisting of:

1,4,7,10-tetraazacyclododecane-1,4,7,10-tetraacetic acid (DOTA), 1,4,7,10-tetraazacyclododecane-1,4,7-triacetic acid (DO3A), and 2-(4,7,10-tris(carboxymethyl)-1,4,7,10-tetraazacyclododecan-1-yl)pentanedioic acid (DOTAGA); or a radionuclide complex thereof.

Embodiment 62. The compound of any one of embodiments 31-59, or a pharmaceutically acceptable salt thereof, wherein $R^A$ and $R^B$, if present, are independently selected from the group consisting of:

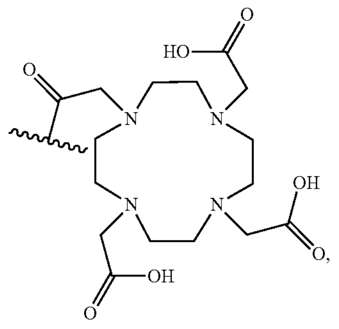

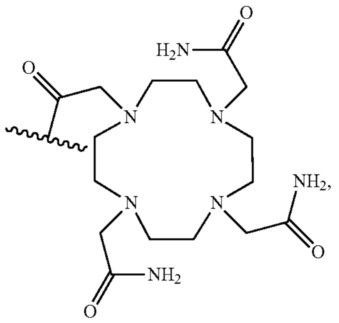

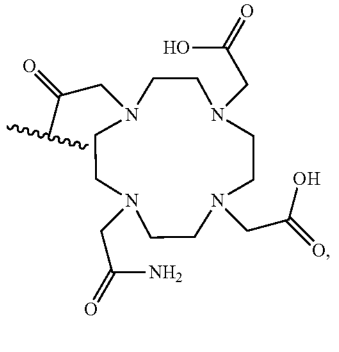

-continued

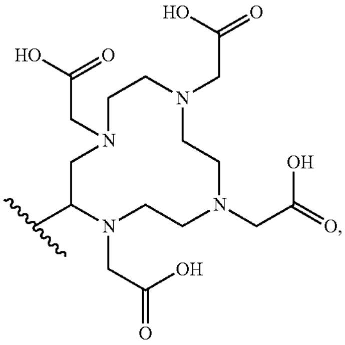

and

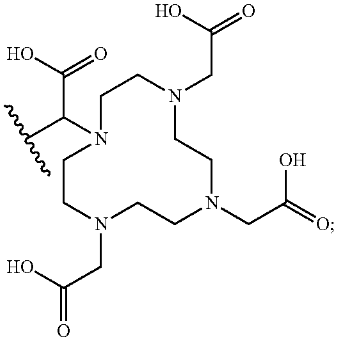

;

or a radionuclide complex thereof.

Embodiment 63. The compound of any one of embodiments 31-59, or a pharmaceutically acceptable salt thereof, wherein $R^A$ and $R^B$, if present, are

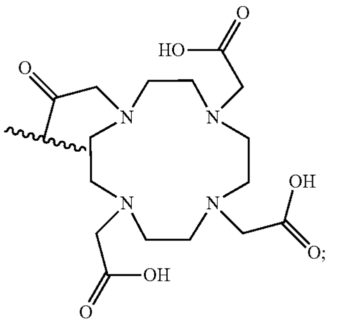 [SMILES: *C(=O)CN1CCN(CC(=O)O)CCN(CC(=O)O)CCN(CC(=O)O)CC1]

;

or a radionuclide complex thereof.

Embodiment 64. The compound of any one of embodiments 31-59, or a pharmaceutically acceptable salt thereof, wherein $R^A$ and $R^B$, if present, are independently selected from:

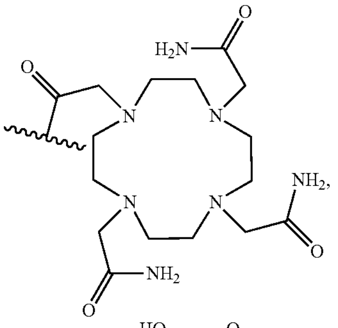

,

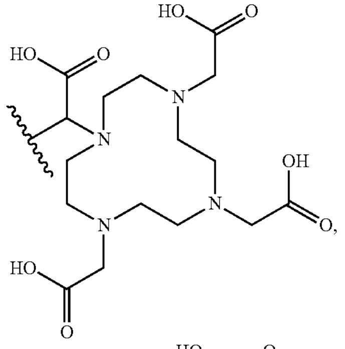

, or

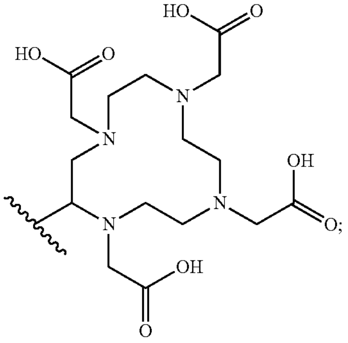

;

or a radionuclide complex thereof.

Embodiment 65. The compound of any one of embodiments 31-59, or a pharmaceutically acceptable salt thereof, wherein $R^A$ and $R^B$, if present, are

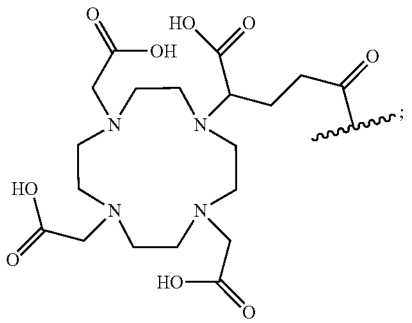 [SMILES: *C(=O)CCC(C(=O)O)N1CCN(CC(=O)O)CCN(CC(=O)O)CCN(CC(=O)O)CC1]

;

or a radionuclide complex thereof.

Embodiment 66. The compound of any one of embodiments 31-65, or a pharmaceutically acceptable salt thereof, wherein $L^A$ and $L^B$, if present, are independently selected from: $-L^2-$, $-L^3-$, $-L^4-$, $-L^5-$, $-L^6-$, $-L^7-$, $-L^2-L^3-$, $-L^2-L^4-$, $-L^2-L^6-$, $-L^2-L^7-$, $-L^4-L^6-$, $-L^4-L^7-$, $-L^6-L^7-$, $-L^2-L^3-L^7-$, $-L^2-L^4-L^7-$, $-L^2-L^5-L^7-$, $-L^2-L^6-L^7-$, $-L^3-L^4-L^7-$, $-L^4-L^5-L^7-$, $-L^2-$ $L^3$-$L^4$-$L^7$-, -$L^2$-$L^4$-$L^5$-$L^7$-, -$L^2$-$L^4$-$L^6$-$L^7$-, -$L^4$-$L^5$-$L^6$-$L^7$-, -$L^2$-$L^4$-$L^5$-$L^6$-$L^7$-, or -$L^2$-$L^3$-$L^4$-$L^5$-$L^6$-$L^7$-;

$L^2$ is absent, substituted or unsubstituted —$C_1$-$C_{20}$ alkylene, substituted or unsubstituted —$C_1$-$C_{20}$ alkylene-$NR^{16}$—, substituted or unsubstituted —$C_1$-$C_{20}$ alkylene-C(═O)—, substituted or unsubstituted —$C_1$-$C_{20}$ alkylene-C(═O)$NR^{16}$—, substituted or unsubstituted —$C_1$-$C_{20}$ alkylene-$NR^{16}$C(═O)—, substituted or unsubstituted 2 to 20 membered heteroalkylene, —$(CH_2CH_2O)_w$—, —$(OCH_2CH_2)_w$—, or —$(CH_2CH_2O)_w$—$CH_2CH_2$—;

each $R^{16}$ is independently selected from H and $C_1$-$C_4$ alkyl;

w is 1, 2, 3, 4, 5, or 6;

$L^3$ is absent or a natural or unnatural amino acid or peptide that is formed from two or more independently selected natural and unnatural amino acids, wherein when two or more amino acids are present then the N atom of the amide linking the amino acids is optionally substituted with —$C_1$-$C_6$ alkyl;

$L^4$ is absent, substituted or unsubstituted 2 to 10-membered heteroalkylene, —$(CH_2)_v$—, —$CH_2$—$(OCH_2CH_2)_v$—, —$(CH_2CH_2O)_v$—$CH_2CH_2$—, —C(═O)$CH_2CH_2$—, —$CH_2CH_2$C(═O)—, —$(CH_2)_v$—$NR^{17}$C(═O)—, —$CH_2CH_2$C(═O)$NHCH_2CH_2$—, —$CH_2CH_2$—C(═O)NH—$(CH_2CH_2O)_vCH_2CH_2$—, —$(CH_2)_x$—$NR^{17}$—$(CH_2)_v$, —NHC(═O)NH—O—$(CH_2)_v$—, —NHC(═O)NH—$(CH_2)_v$—, —$(CH_2)_x$—NHC(═O)NH—$(CH_2)_v$—, —$(CH_2)_x$—NHC(═O)—$(CH_2)_v$—, —$(CH_2)_x$—C(═O)NH—$(CH_2)_v$—, —$CH_2$C(—OH)$CH_2$—C(OH)—$CH_2CH_2$—, —$CH_2$C(—OH)$CH_2$—C(OH)—$CH_2CH_2$—NHC(═O)$CH_2CH_2$C(═O)—$NHCH_2CH_2$—, or —NHC(═O)$CH_2$—O—NH—C(═O)$(CH_2)_v$—;

each $R^{17}$ is independently H or —$C_1$-$C_6$ alkyl;

each x is independently 1, 2, 3, 4, 5 or 6;

v is independently 1, 2, 3, 4, 5, 6, 7, 8, 9, or 10;

$L^5$ is absent, —O—, —$NR^{13}$—, —C(═O)—, —C(═O)$NR^{13}$—, —$NR^{13}$C(═O), —$NR^{13}$C(═O)O—, —$NR^{13}$C(═O)$NR^{13}$—, or —OC(═O)$NR^{13}$—;

each $R^{13}$ is independently selected from H and —$C_1$-$C_4$ alkyl;

$L^6$ is absent or -$L^8$-$L^9$-$L^{10}$-;

$L^8$ is absent, —$(CH_2)_r$—, —$(CH_2)_r$—C(═O)—, —$(CH_2)_r$—$NR^{14}$—, —$(CH_2)_r$—$NR^{14}$C(═O)—, —$(CH_2)_r$—C(═O)$NR^{14}$—, or substituted or unsubstituted heterocycloalkylene;

r is 0, 1, 2, or 3;

$L^9$ is substituted or unsubstituted cycloalkylene, substituted or unsubstituted heterocycloalkylene, substituted or unsubstituted arylene, or substituted or unsubstituted heteroarylene;

$L^{10}$ is absent, —$(CH_2)_q$—, —$NR^{15}$—, —$NR^{15}$—$(CH_2)_q$—, —$(CH_2)_q$—C(═O)—, —C(═O)—$(CH_2)_q$—, —$(CH_2)_q$—$NR^{15}$—, —$(CH_2)_q$—$NR^{15}$C(═O)—, —$(CH_2)_q$—C(═O)$NR^{15}$, —$NR^{15}$C(═O)—$(CH_2)_q$—, or —C(═O)$NR^{15}$—$(CH_2)_q$—;

q is 1, 2, 3, 4, 5 or 6;

$R^{14}$ and $R^{15}$ are each independently selected from H or —$C_1$-$C_6$ alkyl;

p is 1, 2, 3, 4, 5, or 6; and $L^7$ is absent, —NH—, or —$N(CH_3)$—.

Embodiment 67. The compound of any one of embodiments 31-66, or a pharmaceutically acceptable salt thereof, wherein $L^A$ and $L^B$, if present, are independently selected from -$L^2$-, -$L^3$-, -$L^4$-, -$L^5$-, -$L^6$-, -$L^7$-, -$L^2$-$L^3$-, -$L^2$-$L^7$-, -$L^4$-$L^7$-, -$L^2$-$L^4$-$L^7$-, -$L^2$-$L^6$-$L^7$-, - $L^2$-$L^3$-$L^4$-$L^7$-, -$L^2$-$L^4$-$L^5$-$L^7$-, -$L^2$-$L^4$-$L^6$-$L^7$-, or -$L^2$-$L^4$-$L^5$-$L^6$-$L^7$ $L^2$ is absent, substituted or unsubstituted —$C_1$-$C_{20}$ alkylene-$NR^{16}$—, substituted or unsubstituted —$C_1$-$C_{20}$ alkylene-$NR^{16}$C(═O)—, or —$(CH_2CH_2O)_w$—$CH_2CH_2$—; each $R^{16}$ is independently selected from H and $C_1$-$C_4$ alkyl;

w is 1, 2, 3, 4, 5, or 6;

$L^3$ is a natural or unnatural amino acid or peptide that is formed from two or more independently selected natural and unnatural amino acids, wherein when two or more amino acids are present then the N atom of the amide linking the amino acids is optionally substituted with —$C_1$-$C_6$ alkyl;

$L^4$ is absent, substituted or unsubstituted 2 to 10-membered heteroalkylene, —$(CH_2)_v$—, —$(CH_2CH_2O)_v$—$CH_2CH_2$—, —C(═O)$CH_2CH_2$—, —$(CH_2)_v$—$NR^{17}$C(═O)—, —$CH_2CH_2$C(═O)$NHCH_2CH_2$—, —$CH_2CH_2$—C(═O)NH—$(CH_2CH_2O)_vCH_2CH_2$—, —$(CH_2)_x$—$NR^{17}$—$(CH_2)_v$—, —NHC(═O)NH—O—$(CH_2)_v$—, —NHC(═O)NH—$(CH_2)_v$—, —$(CH_2)_x$—NHC(═O)NH—$(CH_2)_v$—, —$(CH_2)_x$—NHC(═O)—$(CH_2)_v$—, —$(CH_2)_x$—C(═O)NH—$(CH_2)_v$—, —$CH_2$C(—OH)$CH_2$—C(OH)—$CH_2CH_2$—, —$CH_2$C(—OH)$CH_2$—C(OH)—$CH_2CH_2$—NHC(═O)$CH_2CH_2$C(═O)—$NHCH_2CH_2$—, or —NHC(═O)$CH_2$—O—NH—C(═O)$(CH_2)_v$—;

each $R^{17}$ is H or —$C_1$-$C_6$ alkyl;

each x is independently 1, 2, 3, 4, 5, or 6;

each v is independently 1, 2, 3, 4, 5, 6, 7, 8, 9, or 10;

$L^5$ is absent, —O—, or —$NR^{13}$C(═O); $R^{13}$ is H or —$C_1$-$C_4$ alkyl;

$L^6$ is -$L^8$-$L^9$-$L^{10}$-;

$L^8$ is absent, —$(CH_2)_r$— or substituted or unsubstituted heterocycloalkylene;

r is 0, 1, 2, or 3;

$L^9$ is substituted or unsubstituted cycloalkylene, substituted or unsubstituted heterocycloalkylene, or substituted or unsubstituted arylene;

$L^{10}$ is absent, —$(CH_2)_q$—, —$NR^{15}$—$(CH_2)_q$—, or —C(═O)—$(CH_2)_q$—; q is 1, 2, 3, 4, 5 or 6;

$R^{14}$ and $R^{15}$ are each independently selected from H or —$C_1$-$C_6$ alkyl; and $L^7$ is —NH—.

Embodiment 68. The compound of embodiment 66 or 67, or a pharmaceutically acceptable salt thereof, wherein $L^A$ and $L^B$ are independently selected from -$L^2$-$L^3$-, -$L^2$-$L^7$-, -$L^4$-$L^7$-, -$L^2$-$L^4$-$L^7$-, -$L^2$-$L^6$-$L^7$-, -$L^2$-$L^3$-$L^4$-$L^7$-, -$L^2$-$L^4$-$L^5$-$L^7$-, -$L^2$-$L^4$-$L^6$-$L^7$-, or -$L^2$-$L^4$-$L^5$-$L^6$-$L^7$-.

Embodiment 69. The compound of any one of embodiments 66-68, or a pharmaceutically acceptable salt thereof, wherein $L^2$ is substituted or unsubstituted —$C_1$-$C_{20}$ alkylene-NH— or substituted or unsubstituted —$C_1$-$C_{20}$ alkylene-NHC(═O)—.

Embodiment 70. The compound of any one of embodiments 66-69, or a pharmaceutically acceptable salt thereof, wherein $L^2$ is —$(CH_2CH_2O)_w$—$CH_2CH_2$—.

Embodiment 71. The compound of any one of embodiments 66-70, or a pharmaceutically acceptable salt thereof, wherein w is 2.

Embodiment 72. The compound of any one of embodiments 66-71, or a pharmaceutically acceptable salt thereof, wherein $L^3$ is absent.

Embodiment 73. The compound of any one of embodiments 66-71, or a pharmaceutically acceptable salt thereof, wherein $L^3$ is a natural amino acid, an unnatural amino acid, or peptide that is formed from two or more independently selected amino acids selected from the group consisting of alanine (Ala), 3-(2-Naphthyl)-alanine (2-Nal), arginine (Arg), asparagine (Asn), aspartate (Asp), cysteine (Cys), cysteic acid, glutamine (Gln), glutamate (Glu), gamma-Carboxyglutamate (Gla), glycine (Gly), histidine (His), isoleucine (Ile), leucine (Leu), lysine (Lys), hydroxylysine (Hyl), ornithine (Orn), methionine (Met), phenylalanine (Phe), p-phenyl phenylalanine (Bip), proline (Pro), hydroxyproline (Hyp), serine (Ser), homoserine (Hse), sarcosine (Sar), threonine (Thr), tryptophan (Trp), tyrosine (Tyr), and valine (Val), wherein when two or more amino acids are present then the N atom of the amide linking the amino acids is optionally substituted with —$CH_3$.

Embodiment 74. The compound of any one of embodiments 66-73, or a pharmaceutically acceptable salt thereof, wherein $L^4$ is absent.

Embodiment 75. The compound of any one of embodiments 66-73, or a pharmaceutically acceptable salt thereof, wherein $L^4$ is —$(CH_2)_v$—.

Embodiment 76. The compound of any one of embodiments 66-73, or a pharmaceutically acceptable salt thereof, wherein $L^4$ is —C(═O)$CH_2CH_2$—.

Embodiment 77. The compound of any one of embodiments 66-73, or a pharmaceutically acceptable salt thereof, wherein $L^4$ is —$(CH_2CH_2O)_v$—$CH_2CH_2$—.

Embodiment 78. The compound of any one of embodiments 66-73, or a pharmaceutically acceptable salt thereof, wherein $L^4$ is —$(CH_2)_v$—$NR^{17}$C(═O)—, —$CH_2CH_2$C(═O)NH$CH_2CH_2$—, —$CH_2CH_2$—C(═O)NH—$(CH_2CH_2O)_v$$CH_2CH_2$—, or —$(CH_2)_v$—$NR^{17}$—$(CH_2)_v$—.

Embodiment 79. The compound of any one of embodiments 66-73, or a pharmaceutically acceptable salt thereof, wherein $L^4$ is —NH(C═O)NH—O—$(CH_2)_v$—, —NHC(═O)NH—$(CH_2)_v$—, —$(CH_2)_x$—NHC(═O)NH—$(CH_2)_v$—, —$CH_2$C(—OH)$CH_2$—C(OH)—$CH_2CH_2$—, —$CH_2$C(—OH)$CH_2$—C(OH)—$CH_2CH_2$—NHC(═O)$CH_2CH_2$C(═O)—NH$CH_2CH_2$—, or —NHC(═O)$CH_2$—O—NH—C(═O)$(CH_2)_v$—.

Embodiment 80. The compound of any one of embodiments 66-79, or a pharmaceutically acceptable salt thereof, wherein v is 1, 2, 3, 4, 5, or 6.

Embodiment 81. The compound of any one of embodiments 66-80, or a pharmaceutically acceptable salt thereof, wherein $L^5$ is —O—.

Embodiment 82. The compound of any one of embodiments 66-80, or a pharmaceutically acceptable salt thereof, wherein $L^5$ is —NHC(═O)—.

Embodiment 83. The compound of any one of embodiments 66-82, or a pharmaceutically acceptable salt thereof, wherein $L^6$ is -$L^8$-$L^9$-$L^{10}$-.

Embodiment 84. The compound of any one of embodiments 66-82, or a pharmaceutically acceptable salt thereof, wherein $L^6$ is absent.

Embodiment 85. The compound of any one of embodiments 66-83, or a pharmaceutically acceptable salt thereof, wherein $L^8$ is absent.

Embodiment 86. The compound of any one of embodiments 66-83, or a pharmaceutically acceptable salt thereof, wherein $L^8$ is —$(CH_2)_r$—.

Embodiment 87. The compound of any one of embodiments 66-83, or a pharmaceutically acceptable salt thereof, wherein $L^9$ is substituted or unsubstituted heterocycloalkylene.

Embodiment 88. The compound of any one of embodiments 66-86, or a pharmaceutically acceptable salt thereof, wherein r is 1 or 2.

Embodiment 89. The compound of any one of embodiments 66-88, or a pharmaceutically acceptable salt thereof, wherein $L^9$ is substituted or unsubstituted 4 to 6 membered heterocycloalkylene.

Embodiment 90. The compound of any one of embodiments 66-88, or a pharmaceutically acceptable salt thereof, wherein $L^9$ is azetidinylene, pyrrolidinylene, piperidinylene or piperazinylene.

Embodiment 91. The compound of any one of embodiments 66-88, or a pharmaceutically acceptable salt thereof, wherein $L^9$ is an unsubstituted or substituted $C_4$-$C_8$ cycloalkylene.

Embodiment 92. The compound of any one of embodiments 66-88, or a pharmaceutically acceptable salt thereof, wherein $L^9$ is

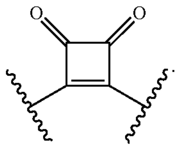 [SMILES: *c1c(*)c(=O)c1=O]

Embodiment 93. The compound of any one of embodiments 66-88, or a pharmaceutically acceptable salt thereof, wherein $L^9$ is unsubstituted phenylene.

Embodiment 94. The compound of any one of embodiments 66-93, or a pharmaceutically acceptable salt thereof, wherein $L^{10}$ is absent.

Embodiment 95. The compound of any one of embodiments 66-93, or a pharmaceutically acceptable salt thereof, wherein $L^{10}$ is —$(CH_2)_q$—.

Embodiment 96. The compound of any one of embodiments 66-93, or a pharmaceutically acceptable salt thereof, wherein $L^{10}$ is —NH—$(CH_2)_q$—.

Embodiment 97. The compound of any one of embodiments 66-93, or a pharmaceutically acceptable salt thereof, wherein $L^{10}$ is —C(═O)—$(CH_2)_q$—.

Embodiment 98. The compound of any one of embodiments 66-93 or 95-97, or a pharmaceutically acceptable salt thereof, wherein q is 1, 2 or 3.

Embodiment 99. The compound of any one of embodiments 66-93 or 95-97, or a pharmaceutically acceptable salt thereof, wherein q is 4, 5 or 6.

Embodiment 100. The compound of any one of embodiments 31-99, or a pharmaceutically acceptable salt thereof, wherein $L^7$ is —NH—.

Embodiment 101. The compound of any one of embodiments 31-100, or a pharmaceutically acceptable salt thereof, wherein $L^A$-$R^A$ is -$L^2$-$L^3$-$R^A$ or $L^B$-$R^B$ is -$L^2$-$L^3$-$R^B$; $L^2$ is unsubstituted —$C_1$-$C_6$ alkylene-NH—; and $L^3$ is a natural or unnatural amino acid, wherein the N atom of the amide linking the amino acids is optionally substituted with —$CH_3$.

Embodiment 102. The compound of any one of embodiments 31-100, or a pharmaceutically acceptable salt thereof, wherein $L^A$-$R^A$ is -$L^2$-$L^7$-$R^A$ or $L^B$-$R^B$ is -$L^2$-$L^7$-$R^B$; $L^2$ is —$(CH_2CH_2O)_w$—$CH_2CH_2$—; and $L^7$ is —NH—.

Embodiment 103. The compound of any one of embodiments 31-100, or a pharmaceutically acceptable salt thereof, wherein $L^A$-$R^A$ is -$L^2$-$L^4$-$L^7$-$R^A$ or $L^B$-$R^B$ is -$L^2$-$L^4$-$L^7$-$R^B$;

$L^2$ is unsubstituted —$C_1$-$C_6$ alkylene- or unsubstituted —$C_1$-$C_6$ alkylene-NHC(═O)—;

$L^4$ is —$(CH_2)_v$—, —$(CH_2CH_2O)_v$—$CH_2CH_2$—, —$(CH_2)_v$—$NR^{17}$—$(CH_2)_v$, —NHC(═O)NH—O—$(CH_2)_v$—NHC(═O)$CH_2$—O—NH—C(═O)$(CH_2)_v$,

—$CH_2C$(—OH)$CH_2$—C(OH)—$CH_2CH_2$—, —$CH_2CH_2C$(═O)$NHCH_2CH_2$—, —$CH_2CH_2$—C(═O)NH—$(CH_2CH_2O)_v CH_2CH_2$—, or —$CH_2C$(—OH)$CH_2$—C(OH)—$CH_2CH_2$—NHC(═O)$CH_2CH_2C$(═O)—$NHCH_2CH_2$; and $L^7$ is —NH—.

Embodiment 104. The compound of any one of embodiments 31-100, or a pharmaceutically acceptable salt thereof, wherein $L^A$-$R^A$ is -$L^2$-$L^6$-$L^7$-$R^A$ or $L^B$-$R^B$ is -$L^2$-$L^6$-$L^7$-$R^B$;

$L^2$ is unsubstituted —$C_1$-$C_6$ alkylene-, unsubstituted —$C_1$-$C_6$ alkylene-NH—, or unsubstituted —$C_1$-$C_6$ alkylene-NHC(═O)—;

$L^6$ is -$L^8$-$L^9$-$L^{10}$-; and $L^7$ is —NH—.

Embodiment 105. The compound of any one of embodiments 31-100, or a pharmaceutically acceptable salt thereof, wherein -$L^A$- and -$L^B$-, if present, are each independently a structure of embodiment 18.

Embodiment 106. The compound of any one of embodiments 31-100, or a pharmaceutically acceptable salt thereof, wherein $L^A$-$R^A$ and $L^B$-$R^B$, if present, are each independently a structure of embodiment 20.

Embodiment 107. The compound of embodiment 31, or a pharmaceutically acceptable salt thereof, wherein the compound of Formula (I) is a compound of Table 1, or a pharmaceutically acceptable salt thereof, or a radionuclide complex thereof.

Embodiment 108. The compound of embodiment 31, or a pharmaceutically acceptable salt thereof, wherein the compound of Formula (I) is a compound of embodiment 22, or a pharmaceutically acceptable salt thereof, or a radionuclide complex thereof.

Embodiment 109. The compound of any one of embodiments 31-108, or a pharmaceutically acceptable salt thereof, wherein: the radionuclide of the radionuclide complex is a lanthanide or an actinide.

Embodiment 110. The compound of any one of embodiments 31-108, or a pharmaceutically acceptable salt thereof, wherein: the radionuclide of the radionuclide complex is actinium, bismuth, cesium, cobalt, copper, dysprosium, erbium, gold, indium, iridium, gallium, lead, lutetium, manganese, palladium, platinum, radium, rhenium, samarium, strontium, technetium, ytterbium, yttrium, or zirconium.

Embodiment 111. The compound of any one of embodiments 31-108, or a pharmaceutically acceptable salt thereof, wherein: the radionuclide of the radionuclide complex is a diagnostic or therapeutic radionuclide.

Embodiment 112. The compound of any one of embodiments 31-108, or a pharmaceutically acceptable salt thereof, wherein: the radionuclide of the radionuclide complex is an Auger electron-emitting radionuclide, α-emitting radionuclide, β-emitting radionuclide, or γ-emitting radionuclide.

Embodiment 113. The compound of any one of embodiments 31-108, or a pharmaceutically acceptable salt thereof, wherein the radionuclide of the radionuclide complex is:

an Auger electron-emitting radionuclide that is 111-indium ($^{111}$In), 67-gallium ($^{67}$Ga), 68-gallium ($^{68}$Ga), 99m-technetium ($^{99m}$Tc), or 195m-platinum ($^{195m}$Pt); or an α-emitting radionuclide that is 225-actinium ($^{225}$Ac), 213-bismuth ($^{213}$Bi), 223-Radium (223Ra), or 212-lead ($^{212}$Pb); or a β-emitting radionuclide that is 90-yttrium ($^{90}$Y), 177-lutetium ($^{177}$Lu), 186-rhenium ($^{186}$Re), 188-rhenium ($^{188}$Re), 64-copper ($^{64}$Cu), 67-copper ($^{67}$Cu), 153-samarium ($^{153}$Sm), 89-strontium ($^{89}$Sr), 198-gold ($^{198}$Au), 169-Erbium ($^{169}$Er), 165-dysprosium ($^{165}$Dy), 99m-technetium ($^{99m}$Tc), 89-zirconium ($^{89}$Zr), or 52-manganese ($^{52}$Mn); or a γ-emitting radionuclide that is 60-cobalt ($^{60}$Co), 103-palldium ($^{103}$Pd), 137-cesium ($^{137}$Cs), 169-ytterbium ($^{169}$Yb) 192-iridium ($^{192}$Ir), or 226-radium ($^{226}$Ra).

Embodiment 114. The compound of any one of embodiments 31-108, or a pharmaceutically acceptable salt thereof, wherein: the radionuclide of the radionuclide complex is 111-indium ($^{111}$In), 115-indium ($^{115}$In), 67-gallium ($^{67}$Ga), 68-gallium ($^{68}$Ga), 69-gallium ($^{69}$Ga), 71-gallium ($^{71}$Ga), 225-actinium ($^{225}$Ac), 175-lutetium ($^{175}$Lu), 177-lutetium ($^{177}$Lu), 204-lead ($^{204}$Pb), 206-lead ($^{206}$Pb), 207-lead ($^{207}$Pb), 208-lead ($^{208}$Pb), 212-lead ($^{212}$Pb), 63-copper ($^{63}$Cu), 64-copper ($^{64}$Cu), 65-copper ($^{65}$Cu), or 67-copper ($^{67}$Cu).

Embodiment 115. The compound of any one of embodiments 31-108, or a pharmaceutically acceptable salt thereof, wherein: the radionuclide of the radionuclide complex is 111-indium ($^{111}$In), 115-indium ($^{115}$In), 67-gallium ($^{67}$Ga), 68-gallium ($^{68}$Ga), 225-actinium ($^{225}$Ac), 175-lutetium ($^{175}$Lu), or 177-lutetium ($^{177}$Lu).

Embodiment 116. A pharmaceutical composition comprising a compound of any one of embodiments 31-115, or a pharmaceutically acceptable salt thereof, and at least one pharmaceutically acceptable excipient.

Embodiment 117. The pharmaceutical composition of embodiment 116, wherein the pharmaceutical composition is formulated for administration to a mammal by intravenous administration.

Embodiment 118. A method for the treatment of cancer comprising administering to a mammal with cancer an effective amount of a compound of any one of embodiments 31-115, or a pharmaceutically acceptable salt thereof.

Embodiment 119. The method of embodiment 118, wherein the cancer comprises tumors and the tumor overexpress the neuropeptide $Y_1$ receptor ($NPY_1R$).

Embodiment 120. The method of embodiment 118 or embodiment 119, wherein the cancer is breast cancer, kidney cancer, ovarian cancer, melanoma, gastrointestinal stromal tumor (GIST), Ewing's sarcoma, nephroblastoma, or adrenal gland tumors.

Embodiment 121. The method of embodiment 118 or embodiment 119, wherein the cancer is breast cancer.

Embodiment 122. A method of killing tumors in a mammal that overexpress the neuropeptide $Y_1$ receptor ($NPY_1R$) comprising administering to the mammal a compound of any one of embodiments 31-115, or a pharmaceutically acceptable salt thereof, wherein the compound of any one of embodiments 31-115, or a pharmaceutically acceptable salt thereof, comprises a therapeutic radionuclide.

Embodiment 123. The method of embodiment 122, wherein the mammal has been diagnosed with breast cancer, kidney cancer, ovarian cancer, melanoma, gastrointestinal stromal tumor (GIST), Ewing's sarcoma, nephroblastoma, or adrenal gland tumors.

Embodiment 124. The method of embodiment 122, wherein the mammal has been diagnosed with breast cancer.

Embodiment 125. A method for identifying tumors expressing the neuropeptide $Y_1$ receptor ($NPY_1R$) in a mammal comprising administering to the mammal a compound of any one of embodiments 31-115, or a pharmaceutically acceptable salt thereof, and performing positron emission tomography (PET) analysis, single-photon emission computerized tomography (SPECT), or magnetic resonance imaging (MRI); wherein the compound of any one of embodiments 31-115, or a pharmaceutically acceptable salt thereof, comprises a diagnostic radionuclide.

Embodiment 126. A method for the in vivo imaging of tissues or organs in a mammal with tumors expressing the neuropeptide Y1 receptor (NPY1R) comprising administering to the mammal a compound of any one of embodiments 31-115, or a pharmaceutically acceptable salt thereof, and performing positron emission tomography (PET) analysis, single-photon emission computerized tomography (SPECT), or magnetic resonance imaging (MRI); wherein the compound of any one of embodiments 31-115, or a pharmaceutically acceptable salt thereof, comprises a diagnostic radionuclide.

Embodiment 127. A compound of Formula (III), or a pharmaceutically acceptable salt thereof:

Formula (III)

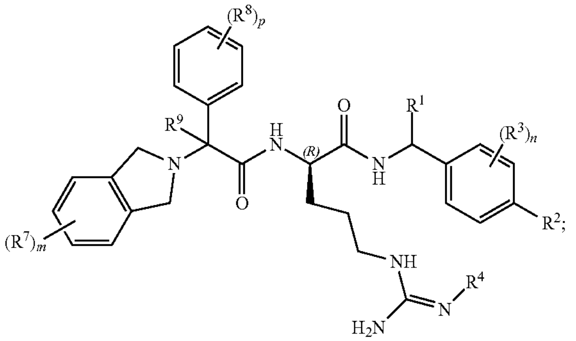

wherein:

$R^1$ is H, —$C_1$-$C_6$ alkyl, or —C(═O)$NH_2$;

$R^2$ is —OH, —$NH_2$, —C(═O)$NH_2$, or —$CH_2$NHC(═O)$NH_2$;

each $R^3$ is independently selected from the group consisting of $R^{3a}$, $R^{3b}$, $R^{3c}$, and $R^{3d}$;

$R^{3a}$, $R^{3b}$, $R^{3c}$, and $R^{3d}$ are each independently selected from the group consisting of H, F, Cl, Br, I, —CN, substituted or unsubstituted —$C_1$-$C_6$ alkyl, and substituted or unsubstituted —$C_1$-$C_6$ alkoxy;

$R^4$ is H, —C(═O)$R^{10}$, —C(═O)NH$R^{10}$, or —C(═O)N($CH_3$)$R^{10}$;

$R^{10}$ is substituted or unsubstituted —$C_1$-$C_6$ alkyl, substituted or unsubstituted 2 to 6-membered heteroalkyl, —$(CH_2)_t$—$NH_2$, —$(CH_2)_t$C(═O)O$(CH_2)_u$$CH_3$, —$(CH_2)_t$NHC(═O)$(CH_2)_u$$CH_3$, or —$(CH_2)_t$-substituted or unsubstituted 5 to 6 membered heteroaryl ring;

t is 1, 2, 3, 4, 5, or 6;

u is 1, 2, 3, or 4;

each $R^7$ is independently selected from the group consisting of F, Cl, Br, I, —CN, —OH, substituted or unsubstituted —$C_1$-$C_6$ alkyl, substituted or unsubstituted —$C_1$-$C_6$ alkoxy, and substituted or unsubstituted —NH—$C_1$-$C_6$ alkyl;

each $R^8$ is independently selected from the group consisting of F, Cl, Br, I, —CN, —OH, substituted or unsubstituted —$C_1$-$C_6$ alkyl, substituted or unsubstituted —$C_1$-$C_6$ alkoxy, and substituted or unsubstituted —NH—$C_1$-$C_6$ alkyl;

$R^9$ is H, substituted or unsubstituted —$C_1$-$C_4$ alkyl, or substituted or unsubstituted —$C_1$-$C_6$ alkoxy;

n is 0, 1, 2, 3, or 4;

m is 0, 1, 2, or 3; and p is 0, 1, 2, or 3.

Embodiment 128. The compound of embodiment 127, or a pharmaceutically acceptable salt thereof, wherein $R^1$ is H.

Embodiment 129. The compound of embodiment 127 or 128, or a pharmaceutically acceptable salt thereof, wherein $R^2$ is —OH.

Embodiment 130. The compound of any one of embodiments 127-129, or a pharmaceutically acceptable salt thereof, wherein n is 0.

Embodiment 131. The compound of any one of embodiments 127-129, or a pharmaceutically acceptable salt thereof, wherein n is 2.

Embodiment 132. The compound of any one of embodiments 127-131, or a pharmaceutically acceptable salt thereof, wherein each $R^3$ is independently selected from the group consisting of $R^{3a}$, $R^{3b}$, $R^{3c}$, and $R^{3d}$; and wherein $R^{3a}$, $R^{3b}$, $R^{3c}$, and $R^{3d}$ are each independently selected from the group consisting of H, F, Cl, Br, I, —CN, —$CH_3$, —$CF_3$, and —$OCH_3$.

Embodiment 133. The compound of embodiment 132, wherein each $R^{3a}$, $R^{3b}$, $R^{3c}$ and $R^{3d}$ is independently selected from the group consisting of H, F, Cl, Br, I, —CN, —$CH_3$, —$CF_3$, and —$OCH_3$.

Embodiment 134. The compound of embodiment 132, wherein $R^{3a}$ and $R^{3d}$ are F or Cl and $R^{3b}$ and $R^{3c}$ are H.

Embodiment 135. The compound of any one of embodiments 127-134, or a pharmaceutically acceptable salt thereof, wherein $R^4$ is —C(═O)NH$R^{10}$.

Embodiment 136. The compound of any one of embodiments 127-134, or a pharmaceutically acceptable salt thereof, wherein $R^4$ is —C(═O)NH$(CH_2)_t$NHC(═O)$(CH_2)_u$$CH_3$.

Embodiment 137. The compound of any one of embodiments 127-135, or a pharmaceutically acceptable salt thereof, wherein $R^{10}$ is unsubstituted —$C_1$-$C_6$ alkyl or —$(CH_2)_t$NHC(═O)$(CH_2)_u$$CH_3$; t is 1, 2, 3, or 4; and u is 1 or 2.

Embodiment 138. The compound of any one of embodiments 127-137, or a pharmaceutically acceptable salt thereof, wherein m is 0.

Embodiment 139. The compound of any one of embodiments 127-138, or a pharmaceutically acceptable salt thereof, wherein p is 0.

Embodiment 140. The compound of any one of embodiments 127-139, or a pharmaceutically acceptable salt thereof, wherein $R^9$ is H.

Embodiment 141. The compound of embodiment 127, wherein the compound has the following structure, or a pharmaceutically acceptable salt thereof.

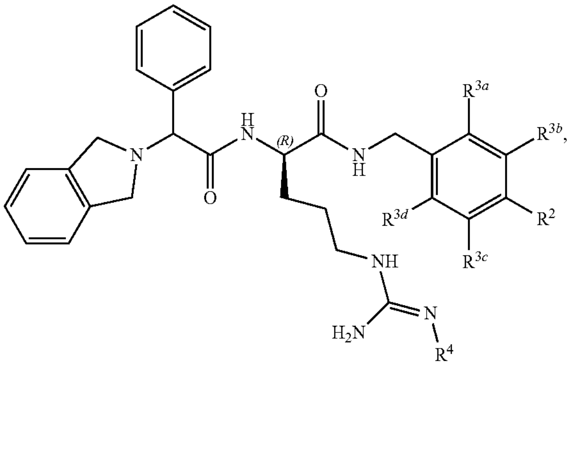

wherein each $R^{3a}$, $R^{3b}$, $R^{3c}$ and $R^{3d}$ is independently selected from the group consisting of H, F, Cl, Br, I, —CN, substituted or unsubstituted —$C_1$-$C_6$ alkyl, and substituted or unsubstituted —$C_1$-$C_6$ alkoxy.

Embodiment 142. The compound of embodiment 127, or a pharmaceutically acceptable salt thereof, wherein the compound of Formula (III) has one of the following structures, or a pharmaceutically acceptable salt thereof.

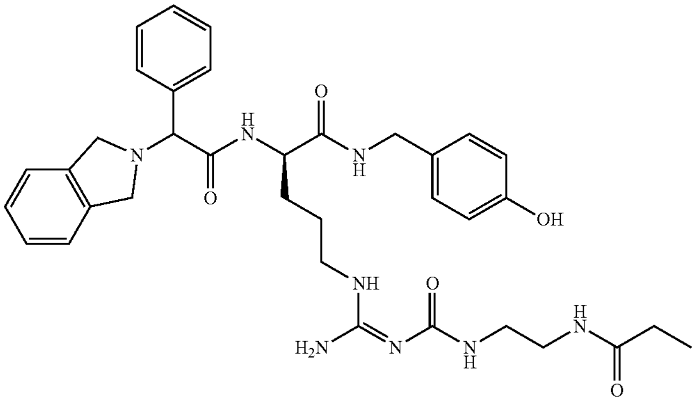

,

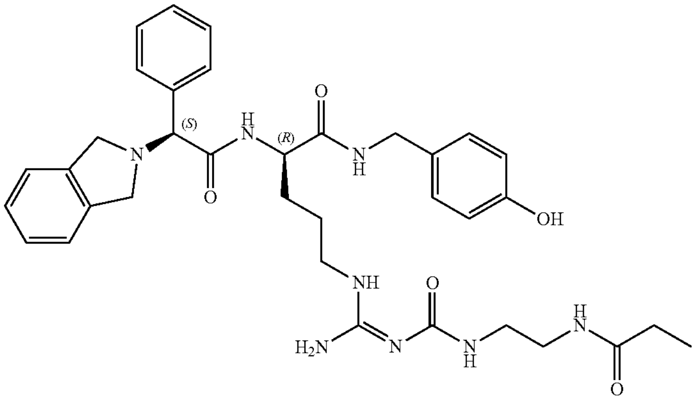

,

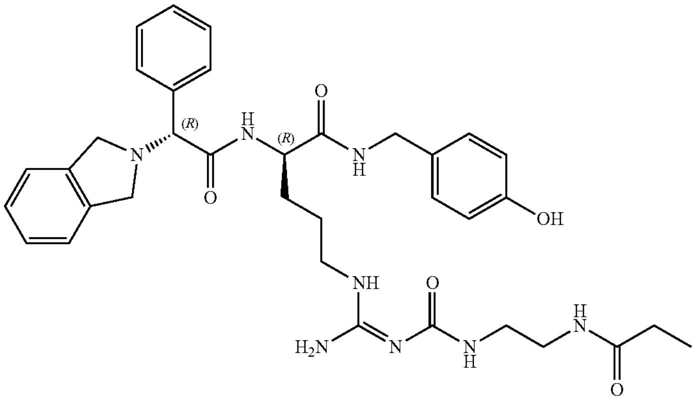

,

-continued
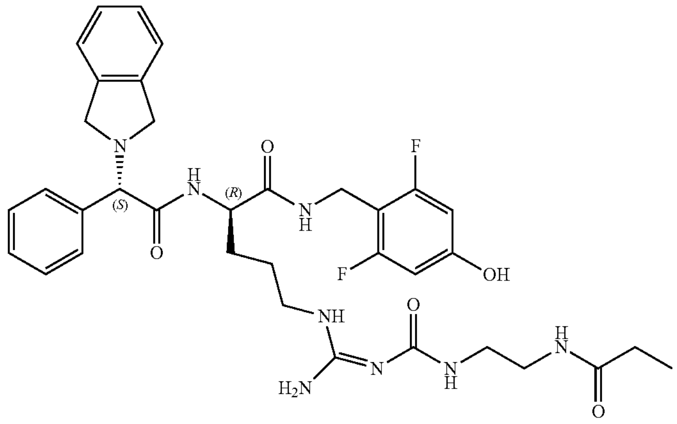
,
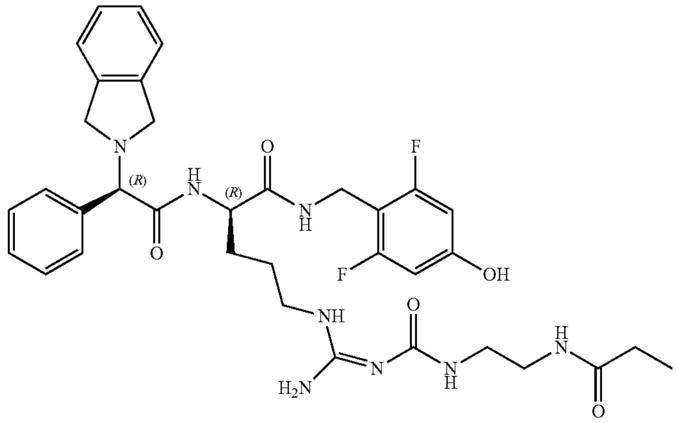
,
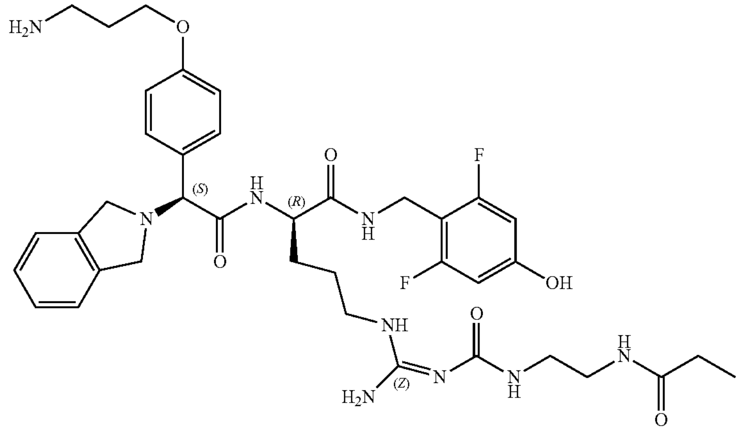
,
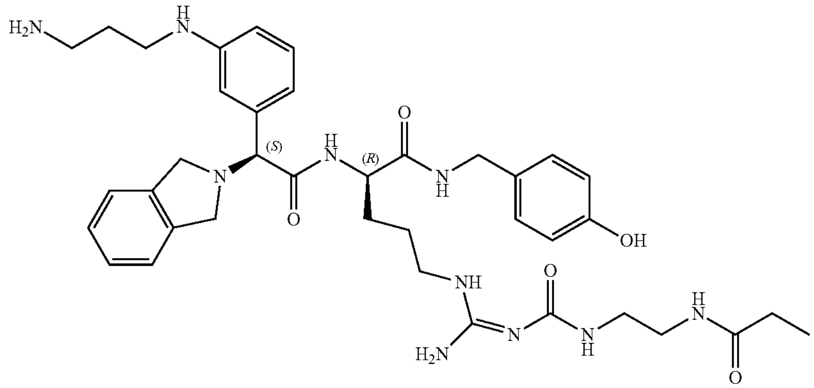
,

-continued
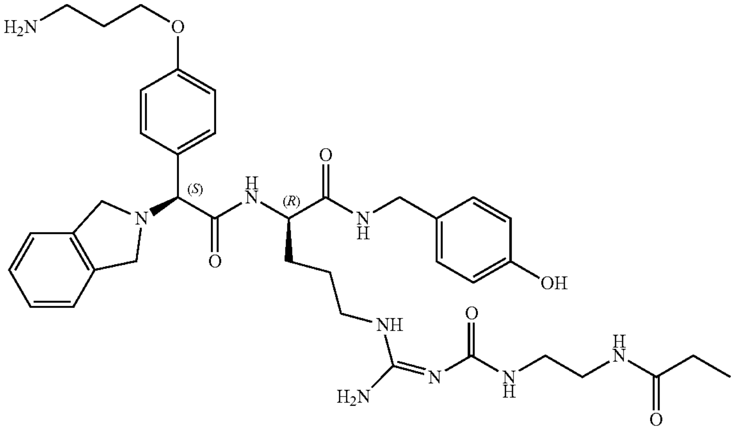
,
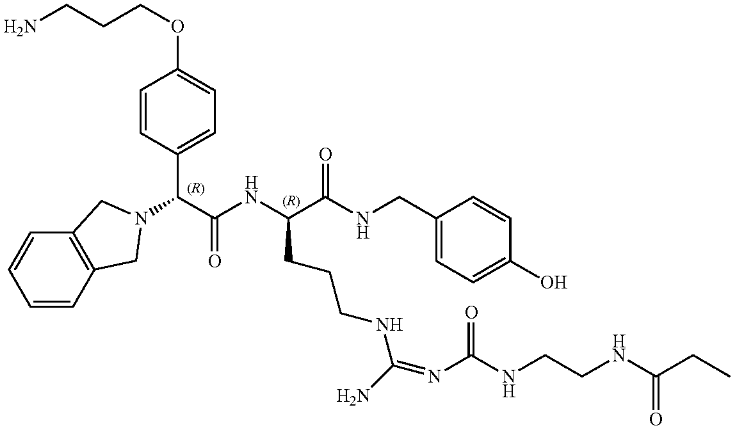
,
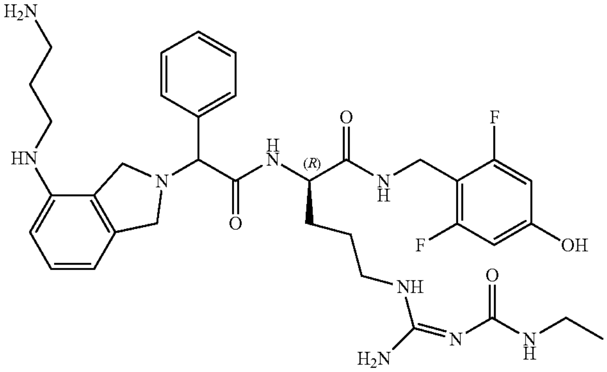
,
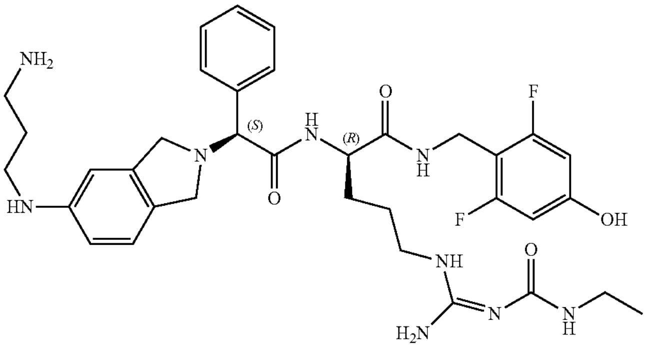
,

-continued
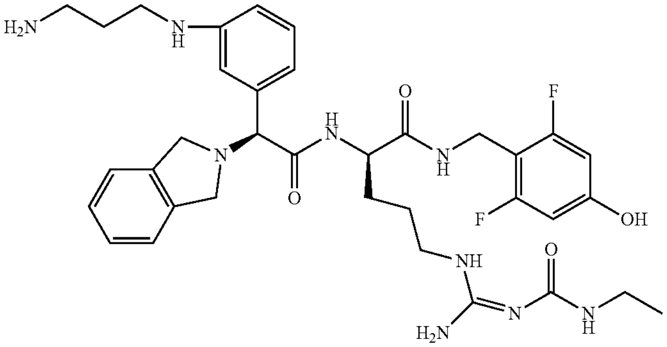
,
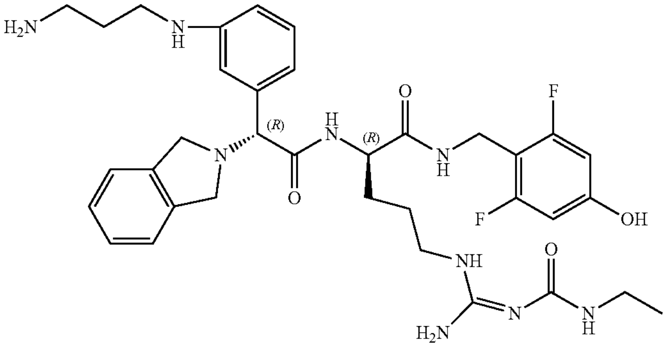
,
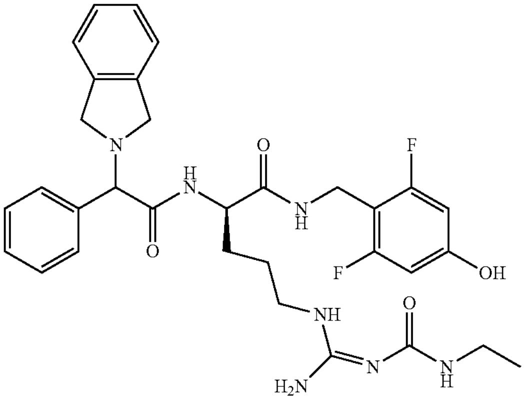
,
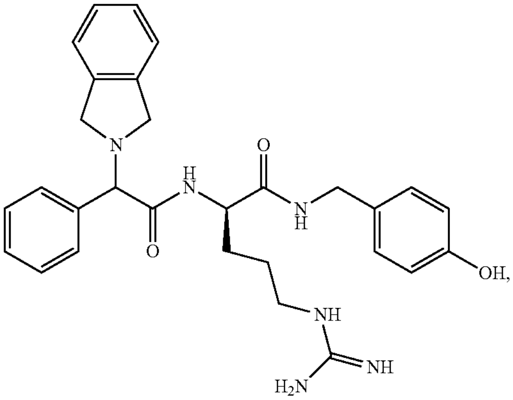
OH,
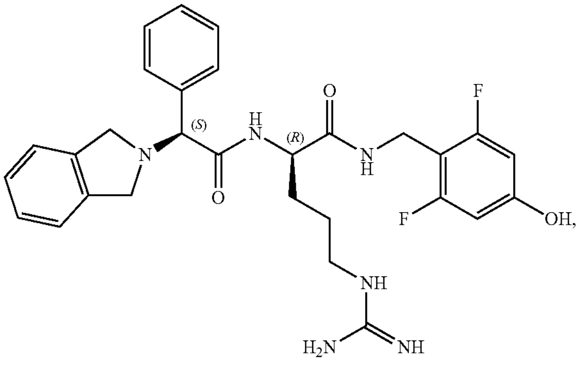
OH, or -continued

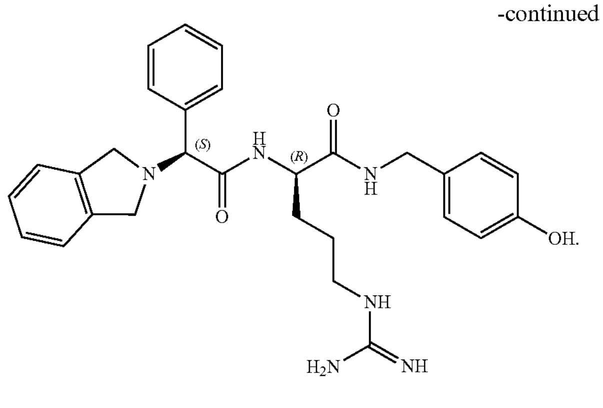

Embodiment 143. A pharmaceutical composition comprising a compound of any one of embodiments 127-142, or a pharmaceutically acceptable salt thereof, and at least one pharmaceutically acceptable excipient.

Embodiment 144. The pharmaceutical composition of embodiment 143, wherein the pharmaceutical composition is formulated for administration to a mammal by oral administration.

Embodiment 145. A method for the treatment of a metabolic disease comprising administering to a mammal an effective amount of a compound of any one of embodiments 127-142, or a pharmaceutically acceptable salt thereof.

Embodiment 146. The method of embodiment 145, wherein the metabolic disease is obesity, pain, or osteoporosis.

Embodiment 147. A method for the treatment of cancer comprising administering to a mammal an effective amount of a compound of any one of embodiments 127-142, or a pharmaceutically acceptable salt thereof.

Embodiment 148. The method of embodiment 147, wherein the cancer is breast cancer.

EXAMPLES

The following examples are provided for illustrative purposes only and not to limit the scope of the claims provided herein.

Abbreviations

ACN or MeCN or $CH_3CN$: acetonitrile; DCM: dichloromethane; DMF: dimethylformamide; EtOAc or EA: ethyl acetate; DMSO: dimethyl sulfoxide; $H_2O$: water; MeOH: methanol; IPA: i-PrOH or isopropanol; PE: petroleum ether; THF: tetrahydrofuran; AcOH: acetic acid; FA: formic acid; HCl: hydrochloric acid or hydrochloride; TFA: trifluoroacetic acid; $HNO_3$: nitric acid: $H_2SO_4$: sulfuric acid; PA: phosphoric acid; AIBN: 2,2'-azobis(2-methylpropionitrile); brine: saturated NaCl solution; NaCl: sodium chloride; $BBr_3$: boron tribromide; $CaCl_2$): calcium chloride; CuI: copper(I) iodide; $HgCl_2$: mercury(II) chloride or mercuric chloride; $MgCl_2$: magnesium chloride; $ZnCl_2$: zinc chloride; BSA: bovine serum albumin; FBS: fetal bovine serum; CDI: 1,1'-carbonyldiimidazole; DCC: N,N'-dicyclohexylcarbodiimide; DEAD: diethyl azodicarboxylate; EDC or EDCI: (1-ethyl-3-(3-dimethylaminopropyl)carbodiimide hydrochloride) or 1-(3-dimethylaminopropyl)-3-ethylcarbodiimide hydrochloride; HATU: 1-[bis(dimethylamino)methylene]-1H-1,2,3-triazolo[4,5-b]pyridinium 3-oxide hexafluorophosphate; HBTU: hexafluorophosphate benzotriazole tetramethyl uranium; HOBt: hydroxybenzotriazole; HOPO: 2-hydroxypyridine 1-oxide; HOTU: 0-[(Ethoxycarbonyl)cyanomethylenamino]-N,N,N',N'-tetramethyluronium hexafluorophosphate; $SOCl_2$: thionyl chloride; NHS: N-hydroxysuccinimide; TBTU: 2-(1H-Benzotriazole-1-yl)-1,1,3,3-tetramethylaminium tetrafluoroborate; TCFH: chloro-N,N,N',N'-tetramethylformamidinium hexafluorophosphate; TOTU: O—[(Ethoxycarbonyl)cyanomethyleneamino]-N,N,N'N'-tetramethyluronium tetrafluoroborate; $Cs_2CO_3$: cesium carbonate; DIEA or DIPEA: N,N-diisopropylethylamine; DMAP: 4-dimethylaminopyridine; DBU: 1,8-diazabicyclo[5.4.0]undec-7-ene; $K_2CO_3$: potassium carbonate; $KHCO_3$: sodium bicarbonate; LiOH: lithium hydroxide; $Na_2SO_4$: sodium sulfate; TEA or $Et_3N$: triethylamine; DOTA: 2,2',2",2'"-(1,4,7,10-tetraazacyclododecane-1,4,7,10-tetrayl)tetraacetic acid; DOTA-tris(t-Bu)ester NHS ester: 2,2',2"-(10-(2-((2,5-dioxopyrrolidin-1-yl)oxy)-2-oxoethyl)-1,4,7,10-tetraazacyclododecane-1,4,7-triyl)triacetic acid; EGTA: ethylene glycol-bis(2-aminoethylether)-N,N,N',N'-tetraacetic acid; HEPES: N-2-hydroxyethylpiperazine-N-2-ethane sulfonic acid; $InCl_3$: indium trichloride; $LuCl_3$: lutetium (III) chloride; LCMS: liquid chromatography-mass spectrometry; MPLC: medium pressure liquid chromatography; MS: mass spectrometry; Prep-HPLC: preparative high-performance liquid chromatography; UV: ultraviolet; $Me_3SnOH$: trimethyltin hydroxide; $NH_4OH$: ammonium hydroxide; $NaBH_3CN$: sodium cyanoborohydride; NaI: sodium iodide; $NaNO_2$. sodium nitrite; NBS: N-bromosuccinimide; Pd/C: palladium on activated charcoal; $Pd(PPh_3)_4$: tetrakis(triphenylphosphine)palladium(0); $PPh_3$: triphenylphosphine; $PtO_2$: platinum(IV) oxide; PyClU: chlorodipyrrolidinocarbenium hexafluorophosphate; rt: room temperature; min: minute; h or hr: hour; hrs: hours; mg: milligrams; kg: kilograms; mL or ml: milliliter; Eq: equivalents; mol: moles; mmol: millimole.

General Analytical Methods:

Prep-HPLC with DAC: The crude product was purified by DAC-HPLC: Column, YMC-C18, 150-250 nm, 10 um; Mobile phase, Water (0.05% TFA) and ACN (25% ACN up to 65% in 8 min); Total flow rate, 120 mL/min; Detector, UV 220 nm.

LC-MS analyses were carried out on a Shimadzu LCMS-2020 series equipped with a binary pump LC-20ADXR, micro vacuum degasser, standard auto sampler SIL-20AC XR, thermostatted column compartment CTO-20AC, variable wavelength detector SPD-M20A, and data were analyzed by Shimadzu LabSolutions standalone workstation software. HPLC solvents consisted of $H_2O$ containing 0.05% ammonia (mobile phase A) and acetonitrile (mobile phase B). Conditions: An Ascentis Express C18 (2.6 μm, 3.0×50 mm) column was used with a flow rate of 1.2 mL/min.

$^{1}H$ NMR spectra were recorded using a AVANCE III HD 300 MHz. Chemical shifts are reported in δ (ppm) relative to $TMS_4Si$ (in DMSO-$d_6$) as internal standard using Instrument model (Bruker TopSpin) unless otherwise noted.

Solid phase peptide synthesis (SPPS) was carried out with a Syro II (Biotage) and/or manual shaker using Fmoc chemistry unless otherwise noted. 2-Chlorotrityl chloride resin was purchased from Novabiochem. Fmoc-D-Arg(Pbf)-OH was purchased from NJ Peptide Ltd. (Nanjing, China). Solvents and reagents were obtained from commercial suppliers and used without further purification unless otherwise noted.

RP-HPLC purifications were performed on a Waters PrepLC system equipped with a Waters 2545 pump, a Waters 2489 UV/Vis detector, a Waters 2767 Sample Manager and an XSelect CSH C18 OBD Prep Column (130 Å, 5 mm, 30×150 mm) at room temperature. HPLC solvents consisted of $H_2O$ containing 0.05% trifluoroacetic acid (mobile phase A) and acetonitrile (mobile phase B) unless otherwise noted.

HPLC analyses were performed on a Shimadzu LCMS-2020 system equipped with a binary pump LC-20AD, a micro vacuum degasser, a standard auto sampler SIL-20AC HT, a thermostatted column compartment CTO-20A, a variable wavelength detector SPD-M20A, and a Kinetex EVO column (100 Å, 2.6 μm, 4.6×100 mm). Data were analyzed by Lab Solutions network workstation software from Shimadzu LCMS-2020. HPLC solvents consisted of $H_2O$ containing 0.05% trifluoroacetic acid (mobile phase A) and acetonitrile (mobile phase B) unless otherwise noted.

Synthesis of Compounds

Example 1: 2,2',2"-(10-(2-((6-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)amino)-2-oxoethyl)-1,4,7,10-tetraazacyclododecane-1,4,7-triyl)triacetic acid (Compound 1A)

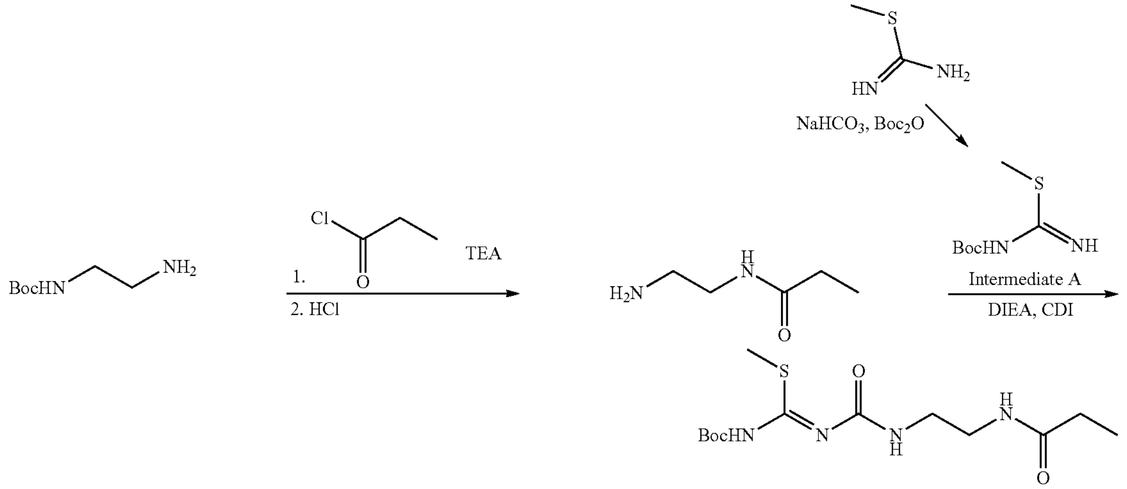

Intermediate B

Synthesis of Intermediate B

Step 1: Into a 1 L round bottom flask, was placed a mixture of methyl carbamimidothioate (30.0 g, 1 Eq, 333 mmol), sodium bicarbonate (41 g, 19 mL, 1.5 Eq, 0.49 mol), THE (300 mL), and $H_2O$ (300 mL), to which was added a solution of di-tert-butyl dicarbonate (87 g, 1.2 Eq, 0.40 μmol) in THE (100 mL) dropwise at 0° C. The reaction mixture was stirred at 25° C. for 4 hours. The mixture was quenched with water (300 mL), extracted with DCM (500 mL×2), the combined organic layers were washed with brine (300 mL), dried over anhydrous $Na_2SO_4$, and concentrated under reduced pressure to afford Intermediate A (30.6 g, 161 mmol, 48.3%) as a white solid, which was used directly for the next step without any purification. MS: Calc'd for $C_7H_{14}N_2O_2S$: 190.08, found $[M+H]^+$: 191.1.

Step 2: Into a 500-mL round bottom flask, was placed a mixture of tert-butyl (2-aminoethyl)carbamate (20.0 g, 1 Eq, 125 mmol), TEA (37.9 g, 52.2 mL, 3.00 Eq, 375 mmol) and THE (300 mL), to which was added propionyl chloride (13.9 g, 1.20 Eq, 150 mmol) dropwise at 0° C. The reaction mixture was stirred at 25° C. for 1 hour. The mixture was quenched with water (100 mL), extracted with DCM (300 mL×2), the combined organic layers were washed with brine (300 mL), dried over anhydrous $Na_2SO_4$, then concentrated under reduced pressure to afford tert-butyl (2-propionamidoethyl)carbamate (27.6 g, 0.11 μmol, 92%) as a light yellow solid, which was used directly for the next step without any purification. MS: Calc'd for $C_{10}H_{20}MN_2O_3$: 216.15, found $[M+H]^+$: 217.3.

Step 3: Into a 500-mL round bottom flask, was placed a mixture of tert-butyl (2-propionamidoethyl)carbamate (27.6 g, 1 Eq, 128 mmol) and 4M HCl in dioxane (14.0 g, 96.0 mL, 4 molar, 3.01 Eq, 384 mmol), to which was added MeOH (100 mL). The reaction mixture was stirred at 25° C. for 4 hours. The mixture was concentrated under reduced pressure to provide N-(2-aminoethyl)propionamide (22 g, 0.13 μmol, 100%) as a yellow solid, which was stored at −78° C. MS: Calc'd for $C_5H_{12}N_2O$: 116.09, found $[M+H]^+$: 117.2.

Step 4: Into a 500-mL round bottom flask, was placed a mixture of Intermediate A (from Step 1, 30.6 g, 1 Eq, 161 mmol), DIEA (104 g, 140 mL, 5.00 Eq, 805 mmol), CDI (53 g, 2.0 Eq, 0.33 μmol) and THE (300 mL). The reaction mixture was stirred at 0° C. for 1 hour, then N-(2-aminoethyl)propionamide (28 g, 1.5 Eq, 0.24 μmol), was added and the reaction mixture was stirred at 25° C. for an additional 2 hours. The mixture was diluted with water (100 mL), then extracted with EtOAc (100 mL×3). The combined organic layers were washed with water (100 mL×2) and brine (100 mL), dried over anhydrous $Na_2SO_4$ and concentrated under reduced pressure. The crude product was purified by MPLC to provide Intermediate B (25 g, 75 mmol, 47%) as a white solid. MS: Calc'd for $C_{13}H_{24}N_4O_4S$: 332.15, found $[M+H]^+$: 333.1.

Eq, 8.0 mmol) were added in additional THE (2 mL):$H_2O$ (1.9 mL) and the reaction mixture was stirred for an additional 10 min. Then the reaction solution was mixed and the reaction stirred at 30° C. for 1 hour. The mixture was directly purified by MPLC to provide benzyl tert-butyl (5-((4-(tert-butoxy)benzyl)amino)-5-oxopentane-1,4-diyl)(R)-dicarbamate (4.1 g, 7.8 mmol, 60%) as a yellow oil. MS: Calc'd for $C_{29}H_{41}N_3O_6$: 527.30, found $[M+H]^+$: 528.3.

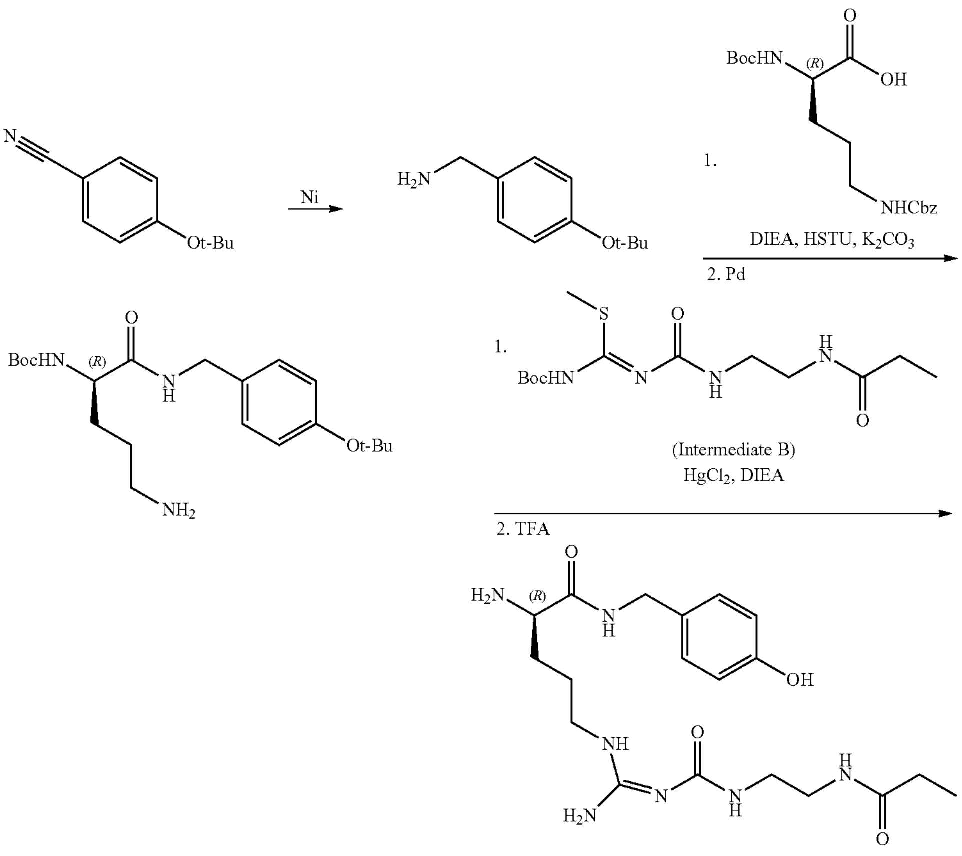

Intermediate C

Synthesis of Intermediate C

Step 1: Into a 500-mL round-bottom flask, purged and maintained with an inert atmosphere of nitrogen, was placed 4-(tert-butoxy)benzonitrile (23 g, 1 Eq, 0.13 μmol), IPA (400 mL) and $NH_3 \cdot H_2O$ (15 mL), to which was carefully added Nickel (15 g, 2.0 mL, 1.9 Eq, 0.26 mol). The flask was evacuated and flushed with hydrogen three times. The mixture was stirred at 25° C. for 3 hours under $H_2$. The reaction mixture was filtered through a pad of celite, then the filtrate was concentrated to provide (4-(tert-butoxy)phenyl) methanamine (20 g, 0.11 μmol, 85%) as a white solid.

Step 2: Into a 40-mL vial, was placed a mixture of (R)-5-(((benzyloxy)carbonyl)-amino)-2-((tert-butoxycarbonyl)amino)pentanoic acid (5 g, 1 Eq, 0.01 μmol), 2-(2,5-dioxopyrrolidin-1-yl)-1,1,3,3-tetramethyluronium hexafluorophosphate(V) (6 g, 1 Eq, 0.02 mol), DIEA (5 g, 7 mL, 3 Eq, 0.04 μmol) and THE (2 mL). The reaction mixture was stirred at 30° C. for 1 hour, then (4-(tert-butoxy)phenyl) methanamine (3.3 g, 1 Eq, 18 mmol) and $K_2CO_3$ (1.1 g, 2.9

Step 3. Into a 500-mL round-bottom flask, purged and maintained under an inert atmosphere of nitrogen, was placed benzyl tert-butyl (5-((4-(tert-butoxy)benzyl)amino)-5-oxopentane-1,4-diyl)(R)-dicarbamate (4.1 g, 1 Eq, 7.8 mmol) and $CF_3CH_2OH$ (300 mL), to which was carefully added Pd/C (4.1 g, 5.0 Eq, 39 mmol). The flask was evacuated and flushed with hydrogen three times. The mixture was stirred for 1 hour at 30° C. under $H_2$. The reaction mixture was filtered through a pad of celite. The collected fractions were concentrated under reduced pressure and dried to provide tert-butyl (R)-(5-amino-1-((4-(tert-butoxy)benzyl)amino)-1-oxopentan-2-yl)carbamate (3.1 g, 7.9 mmol, 100%) as a liquid. MS: Calc'd for $C_{21}H_{35}N_3O_4$: 393.26, found $[M+H]^+$: 394.2.

Step 4. Into a 40 mL vial, was placed a mixture of tert-butyl (R)-(5-amino-1-((4-(tert-butoxy)benzyl)amino)-1-oxopentan-2-yl)carbamate (360 mg, 70% Wt, 1 Eq, 640 μmol), $HgCl_2$ (273 mg, 1.57 Eq, 1.01 mmol), DIEA (355 mg, 4.29 Eq, 2.75 mmol) and DCM (4 mL). The mixture was cooled to 0° C., then a solution of Intermediate B (335 mg, 1.57 Eq, 1.01 mmol) in DCM (1 mL) was added dropwise. The reaction mixture was stirred at 20° C. for 2 hours. The mixture was concentrated and the crude product was purified by MPLC to afford the product (350 mg, 516 μmol, 80.6%) as a yellow oil. MS: Calc'd for $C_{33}H_{55}N_7O_8$: 677.41, found $[M+H]^+$: 678.4.

Step 5. Into an 8-mL vial, was placed a mixture of the product from Step 4 (350 mg, 1 Eq, 516 μmol) and DCM (3 mL), to which was added TFA (1 mL). The reaction mixture was stirred at 20° C. for 1 hour. The mixture was concentrated under reduced pressure. The crude product (R,Z)-2-amino-N-(4-hydroxybenzyl)-5-(2-((2-propionamidoethyl) carbamoyl)guanidino)-pentanamide (Intermediate C, 350 mg, 0.46 mmol, 88%) was used directly in the next step without purification. MS: Calc'd for $C_{19}H_{31}N_7O_4$: 421.24, found $[M+H]^+$: 422.2.

Synthesis of Intermediate D

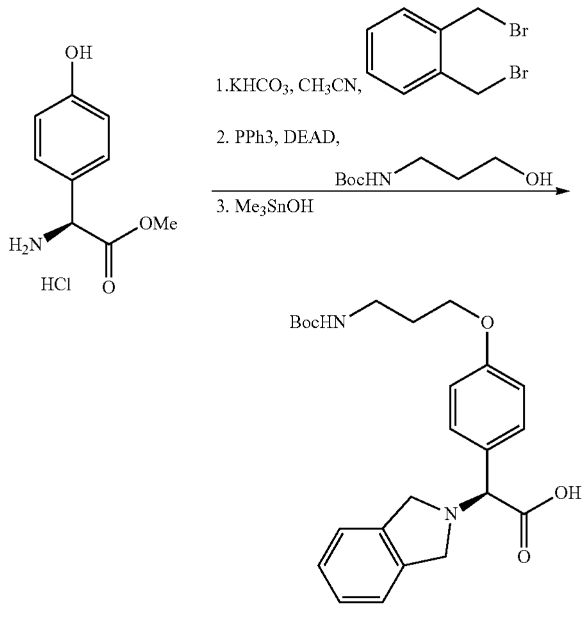

Intermediate D

Step 1. Into a 500-mL round bottom flask, was placed a mixture of methyl (S)-2-amino-2-(4-hydroxyphenyl)acetate hydrochloride (9.1 g, 1.1 Eq, 42 mmol), 1,2-bis(bromomethyl)benzene (10.0 g, 1 Eq, 37.9 mmol), potassium bicarbonate (11.4 g, 5.25 mL, 3.01 Eq, 114 mmol) and MeCN (200 mL). The reaction mixture was stirred at 30° C. for 48 hours. The mixture was filtered, concentrated under reduced pressure and dried to afford methyl (S)-2-(4-hydroxyphenyl)-2-(isoindolin-2-yl)acetate (12.5 g, 38 mmol, 99%) as a yellow solid, which was used directly in the next step without any purification. $[M+H]^+$=284.0.

Step 2. Into a 250-mL round bottom flask, was placed a mixture of methyl (S)-2-(4-hydroxyphenyl)-2-(isoindolin-2-yl)acetate (6.5 g, 1 Eq, 23 mmol), tert-butyl (3-hydroxypropyl)carbamate (8.0 g, 2.0 Eq, 46 mmol), triphenylphosphine (13 g, 11 mL, 2.2 Eq, 50 mmol) and THE (120 mL). The reaction mixture was stirred at 0° C. for 10 minutes, then DEAD (8.8 g, 7.9 mL, 2.2 Eq, 51 mmol) was added and the reaction mixture was stirred at 25° C. for an additional 1 hour. The crude product was purified by MPLC to provide methyl (S)-2-(4-(3-((tert-butoxycarbonyl)amino)propoxy) phenyl)-2-(isoindolin-2-yl)acetate (9.6 g, 20 mmol, 85%) as a yellow solid. $[M+H]^+$=441.2.

Step 3. Into a 500-mL round bottom flask, was placed a mixture of methyl (S)-2-(4-(3-((tert-butoxycarbonyl)amino) propoxy)phenyl)-2-(isoindolin-2-yl)acetate (9.5 g, 1 Eq, 22 mmol) and DCE (200 mL), to which was added trimethyltinhydroxide (12 g, 3.1 Eq, 66 mmol). The reaction mixture was stirred at 90° C. for 18 hours. The mixture was filtered, concentrated under reduced pressure, then purified by MPLC to afford Intermediate D (4.0 g, 9.4 mmol, 43%) as a white solid. LCMS: (ESI, m/z): $[M+H]^+$=427.3.

Synthesis of Compound 1A

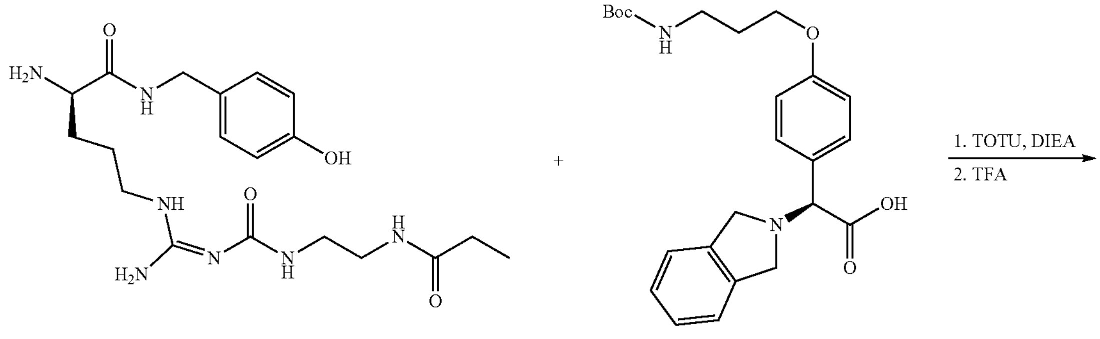

Intermediate C Intermediate D

-continued

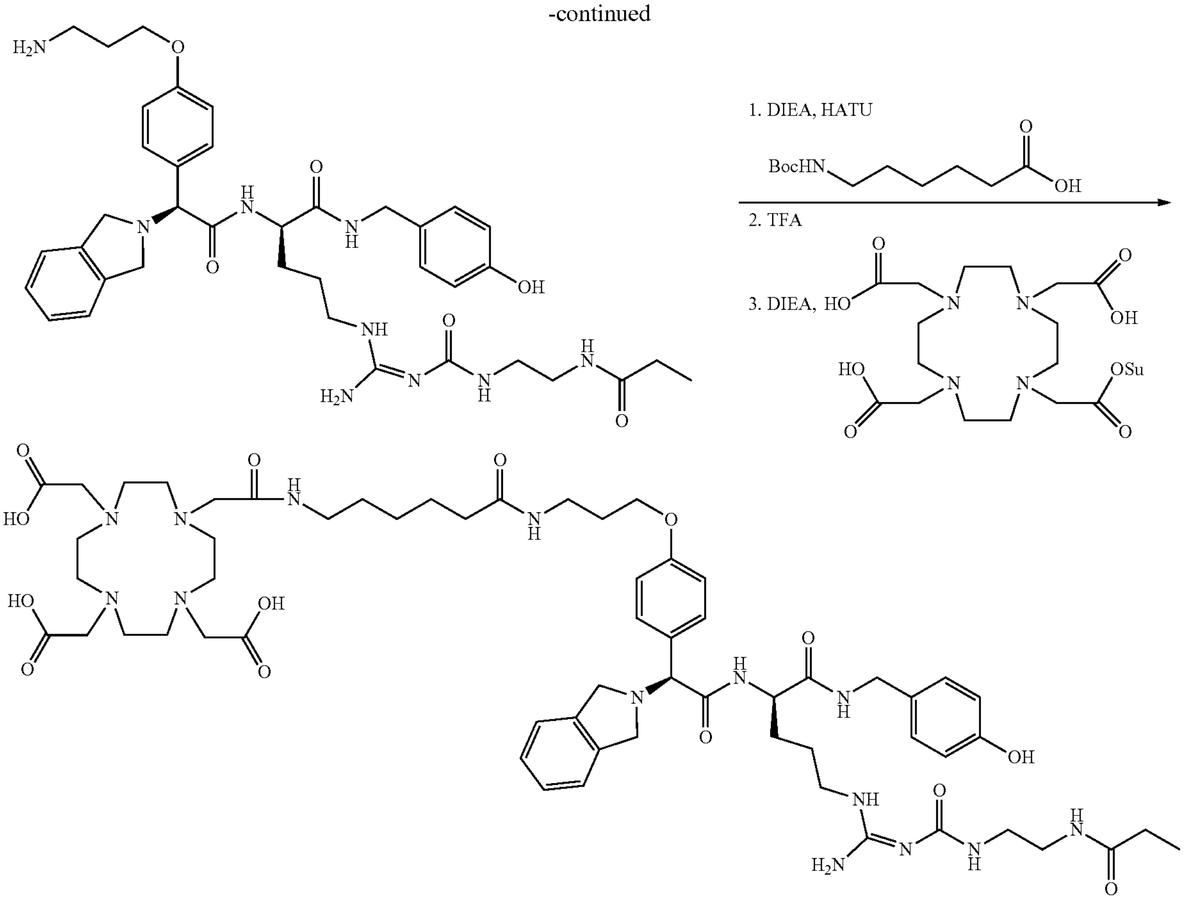

Step 1: Into a 40-mL vial, was placed a mixture of (S)-2-(4-(3-((tert-butoxycarbonyl)amino)propoxy)phenyl)-2-(isoindolin-2-yl)acetic acid (200 mg, 1 Eq, 469 mol), TOTU (154 mg, 1.00 Eq, 469 μmol), DIEA (182 mg, 245 μL, 3.00 Eq, 1.41 mmol) and DMF (4 mL). The reaction mixture was stirred at 20° C. for 10 minutes, then (R,Z)-2-amino-N-(4-hydroxybenzyl)-5-(2-((2-propionamidoethyl) carbamoyl)guanidino)pentanamide (400 mg, 60% Wt, 1.21 Eq, 569 μmol) was added and the reaction mixture was stirred at 25° C. for an additional 2 hours. The mixture was directly purified by MPLC to provide tert-butyl (3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)carbamate (250 mg, 301 μmol, 64.2%) as a yellow oil. $[M+H]^+$=830.3.

Step 2: Into an 8-mL vial was placed a mixture of tert-butyl (3-(4-((1S,4R,Z)-9-amino-4-((4-hydroxybenzyl) carbamoyl)-1-(isoindolin-2-yl)-2,11,16-trioxo-3,8,10,12,15-pentaazaoctadec-9-en-1-yl)phenoxy)propyl)carbamate (250 mg, 1 Eq, 301 μmol) and DCM (2.5 mL), to which was added TFA (0.5 mL). The reaction mixture was stirred at 25° C. for 30 min. The mixture was concentrated under reduced pressure to provide (R)-2-((S)-2-(4-(3-aminopropoxy)phenyl)-2-(isoindolin-2-yl)acetamido)-N-(4-hydroxybenzyl)-5-((Z)-2-((2-propionamidoethyl)carbamoyl)guanidino)pentanamide (300 mg, 0.27 mmol, 89%) as a yellow oil. $[M+H]^+$=730.6.

Step 3: Into a 8-mL vial, was placed a mixture of 6-((tert-butoxycarbonyl)amino)hexanoic acid (55.6 mg, 0.900 Eq, 240 μmol), HATU (102 mg, 1.00 Eq, 268 μmol), DIEA (104 mg, 140 μL, 3.01 Eq, 805 μmol) and DMF (3 mL). The reaction mixture was stirred at 20° C. for 10 minutes, then (R)-2-((S)-2-(4-(3-aminopropoxy)phenyl)-2-(isoindolin-2-yl)acetamido)-N-(4-hydroxybenzyl)-5-((Z)-2-((2-propionamidoethyl)carbamoyl)guanidino)-pentanamide (300 mg, 65% Wt, 1 Eq, 267 μmol) was added and the reaction mixture was stirred at 25° C. for an additional 2 hours. The mixture was directly purified by MPLC to provide tert-butyl (6-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)carbamate (190 mg, 201 μmol, 75.4%) as a white solid. $[M+H]^+$=943.7.

Step 4: Into an 8-mL vial, was placed a mixture of tert-butyl (6-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)carbamate (190 mg, 1 Eq, 201 mol) and DCM (2 mL), to which was added TFA (0.4 mL). The reaction mixture was stirred at 25° C. for 30 min. The mixture was concentrated under reduced pressure to provide 6-amino-N-(3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)hexanamide (200 mg, 0.19 mmol, 94%) as a yellow oil. $[M+H]^+$=843.7.

Step 5: Into an 8-mL vial, was placed a mixture of 6-amino-N-(3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)hexanamide (200 mg, 80% Wt, 1 Eq, 190 mol), DIEA (73 mg, 98

μL, 3.0 Eq, 0.56 mmol) and DMF (1 mL), to which was added 2,2',2"-(10-(2-((2,5-dioxopyrrolidin-1-yl)oxy)-2-oxoethyl)-1,4,7,10-tetraazacyclododecane-1,4,7-triyl)triacetic acid (286 mg, 3.00 Eq, 570 μmol). The reaction mixture was stirred at 25° C. for 2 hours. The mixture was directly purified by Prep-HPLC to provide the trifluoroacetic acid salt of 2,2',2"-(10-(2-((6-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)amino)-2-oxoethyl)-1,4,7,10-tetraazacyclododecane-1,4,7-triyl)triacetic acid (148 mg, 110 μmol, 58.0%) as a white solid. MS: Calc'd for $C_{60}H_{88}N_{14}O_{14}$: 1228.66, found 1229.5. $^1$H-NMR (300 MHz, Methanol-$d_4$) δ 7.57-7.54 (m, 2H), 7.45-7.36 (m, 2H), 7.35-7.26 (m, 2H), 7.20-7.18 (m, 2H), 7.08-7.05 (m, 2H), 6.78-6.74 (m, 2H), 5.22 (s, 1H), 4.70-4.60 (m, 2H), 4.42-4.24 (m, 5H), 4.10-4.05 (m, 2H), 3.84-3.56 (m, 7H), 3.50-3.32 (m, 13H), 3.30-3.02 (m, 14H), 2.22-2.15 (m, 4H), 2.04-1.94 (m, 2H), 1.81-1.37 (m, 7H), 1.36-1.24 (m, 2H), 1.12-1.08 (m, 3H).

Example 2: 2,2',2"-(10-(2-((6-((3-(4-((1R,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)-amino)-6-oxohexyl)amino)-2-oxoethyl)-1,4,7,10-tetraazacyclododecane-1,4,7-triyl)triacetic acid-2,2,2-trifluoroacetic acid (1/1) (Compound 1B)

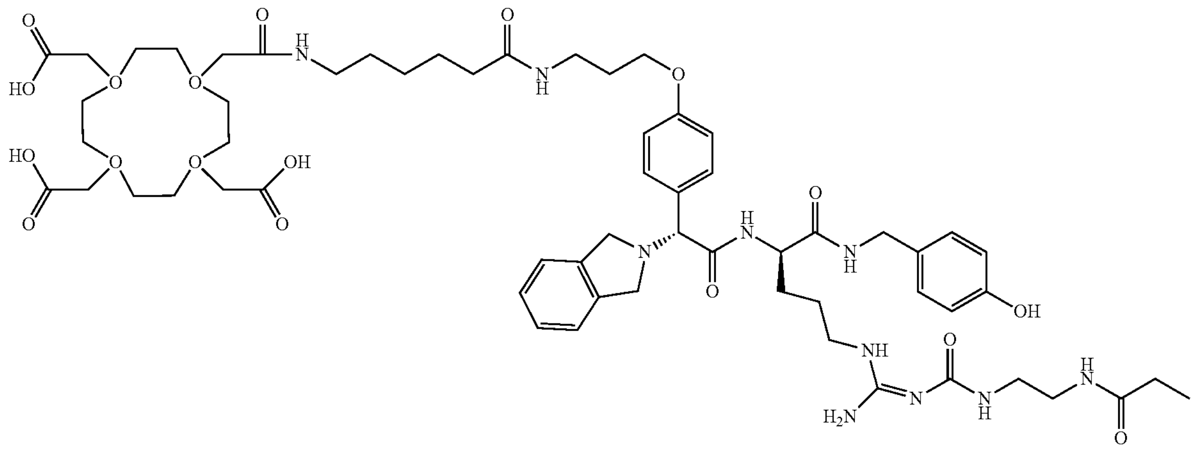

Step 1. Into a 8-mL round-bottom flask, was placed a mixture of (R)-2-(4-(3-((tert-butoxycarbonyl)amino)propoxy)phenyl)-2-(isoindolin-2-yl)acetic acid (200 mg, 1 Eq, 469 μmol) and N-Hydroxysuccinimide (81.0 mg, 1.50 Eq, 704 μmol) in THE (2 mL), to which was added DCC (145 mg, 1.50 Eq, 703 μmol) in THE (2 mL) at 0° C. under $N_2$. The reaction mixture was stirred at 25° C. for 1 hour. The crude product was used in the next step without purification. Into a 8-mL vial, was placed a mixture of (R,Z)-2-amino-N-(4-hydroxybenzyl)-5-(2-((2-propionamidoethyl)carbamoyl)guanidino)pentanamide (296 mg, 1.50 Eq, 702 mol) and DIEA (182 mg, 245 μL, 3.00 Eq, 1.41 mmol) in THE (2 mL), to which was added the crude mixture from the first step. The resulting reaction mixture was stirred at 50° C. for 1 hour. The mixture was directly purified by MPLC to provide the product (110 mg, 133 μmol, 28.3%) as a light yellow solid. [M+H]=830.3.

Steps 2-5. 2,2',2''-(10-(2-((6-((3-(4-((1R,4R,Z)-9-amino-4-((4-hydroxybenzyl)-carbamoyl)-1-(isoindolin-2-yl)-2,11,16-trioxo-3,8,10,12,15-pentaazaoctadec-9-en-1-yl)phenoxy)propyl)amino)-6-oxohexyl)amino)-2-oxoethyl)-1,4,7,10-tetraazacyclododecane-1,4,7-triyl)triacetic acid-2,2,2-trifluoroacetic acid (1/1) was prepared from tert-butyl (3-(4-((1R,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)carbamate in a manner similar to Example 1, Steps 2-5 to provide the product as a white solid. MS: Calc'd for $C_{62}H_{89}F_3N_{14}O_{16}$: 1342.6, found $[M+H-TFA]^+$: 1229.5.

Example 3: Indium (III) 2,2',2''-(10-(2-((6-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)amino)-2-oxoethyl)-1,4,7,10-tetraazacyclododecane-1,4,7-triyl)triacetate (Compound 1A-In)

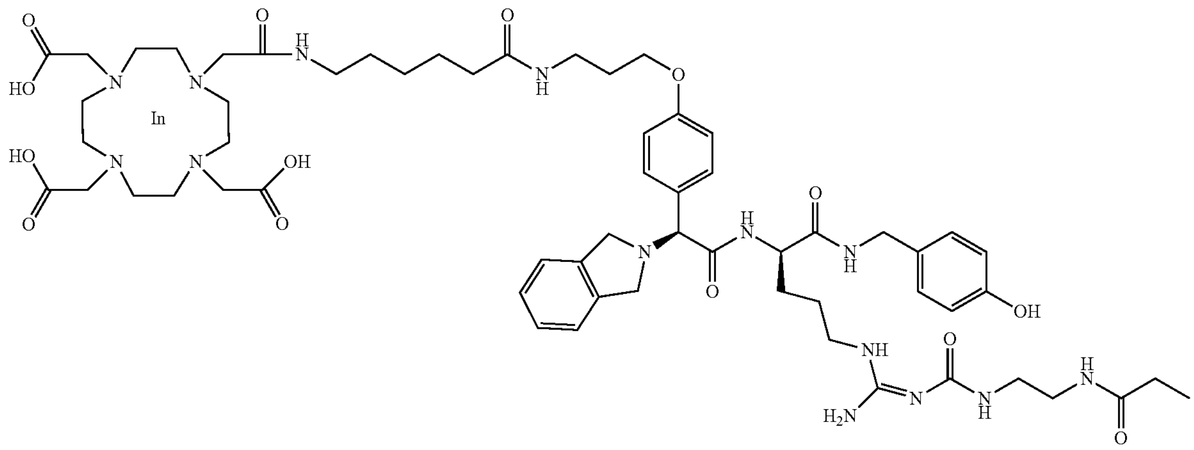

Into an 8-mL vial, was placed a mixture of 2,2',2''-(10-(2-((6-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)amino)-2-oxoethyl)-1,4,7,10-tetraazacyclododecane-1,4,7-triyl)triacetic acid (60 mg, 1 Eq, 49 μmol) and AcONa—AcOH (0.8 mL), to which was added indium trichloride (43 mg, 13 μL, 4.0 Eq, 0.19 mmol). The reaction mixture was stirred at 80° C. for 0.5 hours. The crude product was purified by Prep-HPLC to provide the title compound (35.7 mg, 24.5 μmol) as a white solid. MS: Calc'd for $C_{60}H_{85}InN_{14}O_{14}$: 1340.54, found $[M+H]^+$: 1341.4.

Example 4: Lutetium (III) 2,2',2"-(10-(2-((6-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)amino)-2-oxoethyl)-1,4,7,10-tetraazacyclododecane-1,4,7-triyl)triacetate (Compound 1A-Lu)

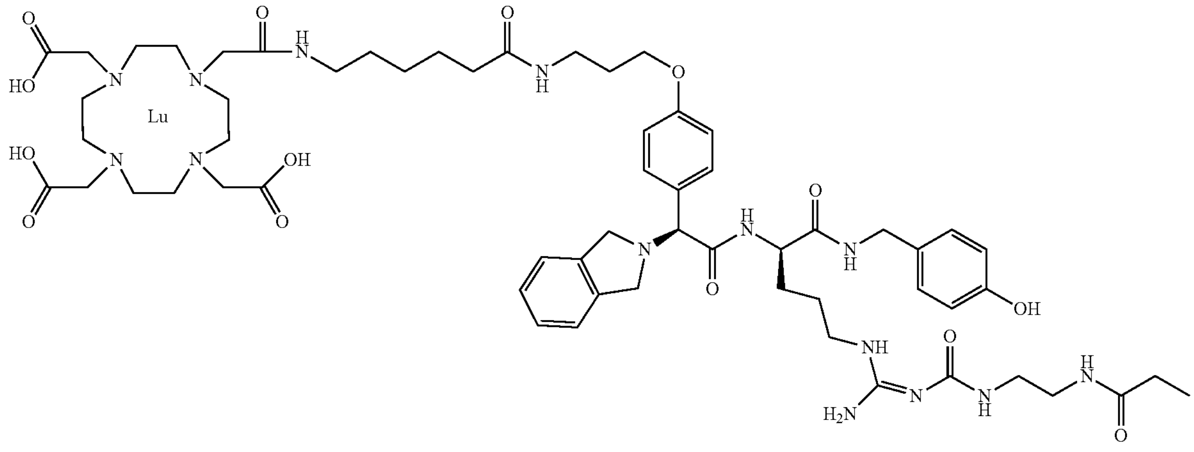

Into an 8-mL vial, was placed a mixture of 2,2',2"-(10-(2-((6-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)p-pyl)amino)-6-oxohexyl)amino-2-oxoethyl)-1,4,7,10-tetraazacyclododecane-1,4,7-triyl)triacetic acid-2,2,2-trifluoroacetic acid (1/1) (40 mg, 1 Eq, 30 mol), lutetium (III) chloride (27 mg, 6.8 μL, 3.2 Eq, 96 μmol) and AcOH/AcONa Buffer (1 mL). The reaction mixture was stirred at 60° C. for 1 hour. The mixture was directly purified by Prep-HPLC to provide the title compound (26.0 mg, 17.2 μmol, 58%) as a white solid. MS: Calc'd for $C_{60}H_{85}LuN_{14}O_{14}$: 1400.58, found $[M+H]^+$: 1401.4.

Example 5: Gallium (III) 2,2',2"-(10-(2-((6-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)amino)-2-oxoethyl)-1,4,7,10-tetraazacyclododecane-1,4,7-triyl)triacetate (Compound 1A-Ga)

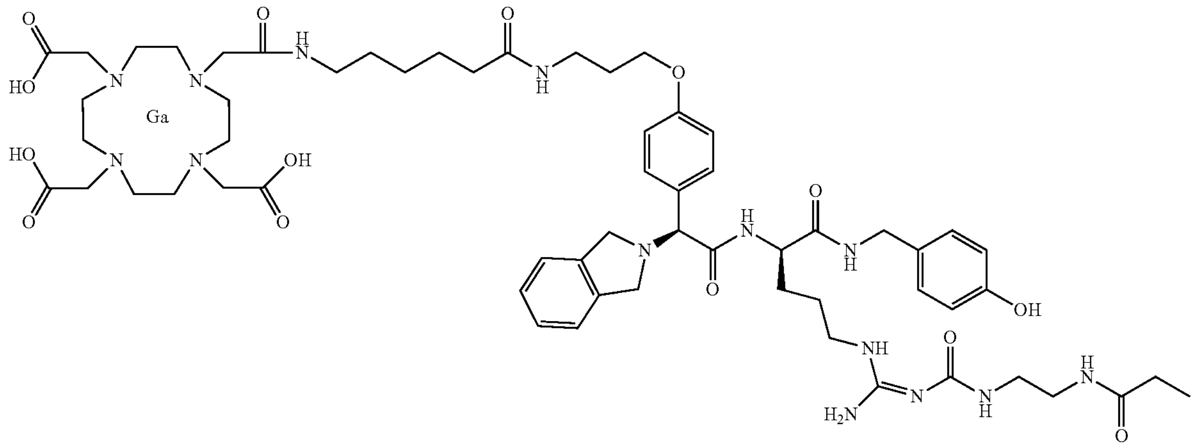

Into an 8-mL vial, was placed a mixture of 2,2',2"-(10-(2-((6-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)p-pyl)amino)-6-oxohexyl)amino-2-oxoethyl)-1,4,7,10-tetraazacyclododecane-1,4,7-triyl)triacetic acid-2,2,2-trifluoroacetic acid (1/1) (40 mg, 1 Eq, 30 mol), gallium(III) chloride (17 mg, 3.2 Eq, 97 μmol) and AcOH/AcONa Buffer (1 mL). The reaction mixture was stirred at 60° C. for 1 hour. The mixture was directly purified by Prep-HPLC to provide the title compound (27.1 mg, 19.2 μmol, 59%) as a white solid. MS: Calc'd for $C_{62}H_{85}GaN_{14}O_{14}$: 1294.56, found $[M+H]^+$: 1295.4.

Example 6: 2,2',2"-(10-(2-((6-((2-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-3,4-dioxocyclobut-1-en-1-yl)amino)hexyl)amino)-2-oxoethyl)-1,4,7,10-tetraazacyclododecane-1,4,7-triyl)triacetic acid-formic acid (1/1) (Compound 2)

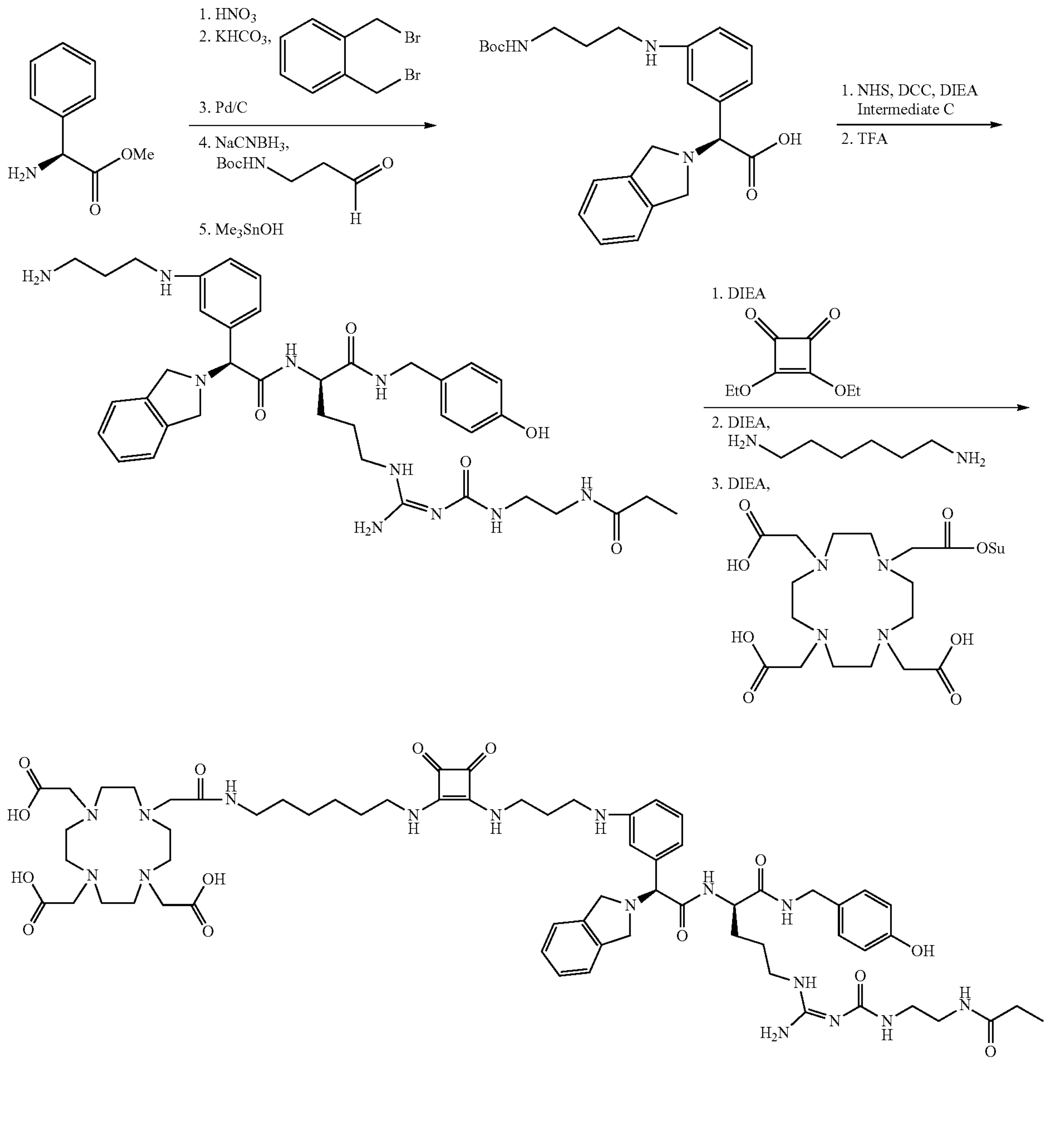

Step 1. Into a 250-mL round bottom flask, was placed a mixture of methyl (S)-2-amino-2-phenylacetate (10.5 g, 1 Eq, 63.6 mmol) and $H_2SO_4$ (30 mL), to which was added nitric acid (8.01 g, 2.00 Eq, 127 mmol) dropwise at 0° C. The reaction mixture was stirred at 0° C. for 30 min. The mixture was quenched with ice-water (500 g) and purified by MPLC to provide methyl (S)-2-amino-2-(3-nitrophenyl) acetate (10.3 g, 49.0 mmol, 77.1%) as a yellow oil. $[M+H]^+$=211.1.

Step 2. Into a 2 L round bottom flask, was placed a mixture of methyl (S)-2-amino-2-(3-nitrophenyl)acetate (10.3 g, 1 Eq, 49.0 mmol), 1,2-bis(bromomethyl)benzene (15.5 g, 1.20 Eq, 58.7 mmol), $KHCO_3$ (14.7 g, 3.00 Eq, 147 mmol) and ACN (1 L) The reaction mixture was stirred at 80° C. for 16 hours. The reaction mixture was filtered through a pad of celite, then the filtrate was concentrated and purified by MPLC to provide methyl (S)-2-(isoindolin-2-yl)-2-(3-nitrophenyl)acetate (10.3 g, 33.0 mmol, 67.3%) as a yellow oil. $[M+H]^+$=312.9.

Step 3. Into a 250-mL round-bottom flask, purged and maintained under an inert atmosphere of nitrogen, was placed methyl (S)-2-(isoindolin-2-yl)-2-(3-nitrophenyl)acetate (5 g, 1 Eq, 0.02 μmol) and i-PrOH (50 mL), to which was carefully added Pd/C (0.5 g, 0.3 Eq, 5 mmol). The flask was evacuated and flushed with hydrogen three times. The mixture was stirred at 25° C. for 4 hours under $H_2$. The crude product was purified by MPLC to provide methyl (S)-2-(3-aminophenyl)-2-(isoindolin-2-yl)acetate as a yellow oil. $[M+H]^+$=283.1.

Step 4. Into a 100-mL round bottom flask, was placed a mixture of methyl (S)-2-(3-aminophenyl)-2-(isoindolin-2-yl)acetate (1.5 g, 1 Eq, 5.3 mmol), tert-butyl (3-oxopropyl) carbamate (1.0 g, 1.1 Eq, 5.8 mmol), $NaBH_3CN$ (1.0 g, 3.0 Eq, 16 mmol) and MeOH (15 mL). The reaction mixture was stirred at 25° C. for 2 hours. The mixture was directly purified by MPLC to provide methyl (S)-2-(3-((3-((tert-butoxycarbonyl)amino)propyl)amino)phenyl)-2-(isoindolin-2-yl)acetate (850 mg, 1.93 mmol, 36%) as a yellow oil. $[M+H]^+$=440.2.

Step 5. Into a 40 mL vial, was placed a mixture of methyl (S)-2-(3-((3-((tert-butoxycarbonyl)amino)propyl)amino) phenyl)-2-(isoindolin-2-yl)acetate (850 mg, 1 Eq, 1.93 mmol), $Me_3SnOH$ (3.50 g, 10.0 Eq, 19.4 mmol) and DCE (10 mL). The reaction mixture was stirred at 90° C. for 30 hours. The mixture was directly purified by MPLC to provide (S)-2-(3-((3-((tert-butoxycarbonyl)amino)propyl) amino)phenyl)-2-(isoindolin-2-yl)acetic acid (600 mg, 1.41 mmol, 72.9%) as a brown solid. $[M+H]^+$=426.2.

Step 6. Into a 40-mL vial, was placed (S)-2-(3-((3-((tert-butoxycarbonyl)amino)propyl)amino)phenyl)-2-(isoindolin-2-yl)acetic acid (580 mg, 1 Eq, 1.36 mmol), 1-hydroxypyrrolidine-2,5-dione (235 mg, 1.50 Eq, 2.04 mmol) and THE (6 mL). To the mixture was added dicyclohexylmethanediimine (422 mg, 1.50 Eq, 2.05 mmol) under $N_2$. The reaction mixture was stirred at 25° C. for 2 hours. The reaction mixture was filtered and the resulting solid was washed with THF. The filtrate was concentrated below 35° C. to provide a crude white oil (660 mg). Into a 8-mL vial, was placed a mixture of (R,Z)-2-amino-N-(4-hydroxybenzyl)-5-(2-((2-propionamidoethyl)carbamoyl)guanidino)pentanamide (1.15 g, 2.00 Eq, 2.73 mmol), N-ethyl-N-isopropylpropan-2-amine (529 mg, 3.00 Eq, 4.09 mmol) and THE (6 mL). A solution of the crude white oil product in THE (0.5 mL) was added dropwise into the mixture at 25° C. The reaction mixture was stirred at 50° C. for 4 hours. The reaction mixture was directly purified by Prep-HPLC to afford tert-butyl (3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl) carbamate (500 mg, 603 μmol, 44.2%) (S,R-isomer) as a white solid. $[M+H]^+$=829.2.

Step 7. Into a 40-mL vial, was placed a mixture of tert-butyl (3-((3-((1S,4R,Z)-9-amino-4-((4-hydroxybenzyl) carbamoyl)-1-(isoindolin-2-yl)-2,11,16-trioxo-3,8,10,12,15-pentaazaoctadec-9-en-1-yl)phenyl)amino)propyl)carbamate (500 mg, 1 Eq, 603 μmol) and DCM (5 mL), to which was added TFA (1 mL). The reaction mixture was stirred at 25° C. for 1 hour. The mixture was concentrated under reduced pressure. The crude product was purified by Prep-HPLC to provide (R)-2-((S)-2-(3-((3-aminopropyl) amino)phenyl)-2-(isoindolin-2-yl)acetamido)-N-(4-hydroxybenzyl)-5-((Z)-2-((2-propionamidoethyl)carbamoyl) guanidino)pentanamide 2,2,2-trifluoroacetate (290 mg, 344 μmol, 57.0%) as a white solid. $[M+H-TFA]^+$=729.5.

Step 8. Into an 8-mL vial, was placed a mixture of (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide (50 mg, 1 Eq, 69 μmol), DIEA (27 mg, 36 μL, 3.0 Eq, 0.21 mmol), 3,4-diethoxycyclobut-3-ene-1,2-dione (23 mg, 2.0 Eq, 0.14 mmol) and DMF (0.5 mL). The reaction mixture was stirred at 25° C. for 2 hours. The reaction mixture was used directly in the next step without any purification. $[M+H]^+$=853.6.

Step 9. In the 8-mL vial, hexane-1,6-diamine (16 mg, 1 Eq, 0.14 mmol) was added to the reaction solution from the previous step. The reaction mixture was stirred at 25° C. for 2 hours. The mixture was directly purified by MPLC to provide (R)-2-((S)-2-(3-((3-((2-((6-aminohexyl)amino)-3,4-dioxocyclobut-1-en-1-yl)amino)propyl)amino)phenyl)-2-(isoindolin-2-yl)acetamido)-N-(4-hydroxybenzyl)-5-((Z)-2-((2-propionamidoethyl)carbamoyl)guanidino)pentanamide (28 mg, 30 μmol) as a white solid. $[M+H]^+$=923.6.

Step 10. (R)-2-((S)-2-(3-((3-((2-((6-aminohexyl)amino)-3,4-dioxocyclobut-1-en-1-yl)amino)propyl)amino)phenyl)-2-(isoindolin-2-yl)acetamido)-N-(4-hydroxybenzyl)-5-((Z)-2-((2-propionamidoethyl)carbamoyl)guanidino) pentanamide was treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide 2,2',2''-(10-(2-((6-((2-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl) amino)-3,4-dioxocyclobut-1-en-1-yl)amino)hexyl)amino)-2-oxoethyl)-1,4,7,10-tetraazacyclododecane-1,4,7-triyl) triacetic acid-formic acid (1/1) (12.7 mg, 9.37 μmol, 31%) as a white solid. MS: Calc'd for $C_{65}H_{94}N_{16}O_{16}$: 1308.7, found $[M+H]^+$: 1309.5.

Example 7: 2,2',2"-(10-(2-((6-((4-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-6-oxohexyl)amino)-2-oxoethyl)-1,4,7,10-tetraazacyclododecane-1,4,7-triyl)triacetic acid-2,2,2-trifluoroacetic acid (1/1) (Compound 3A)

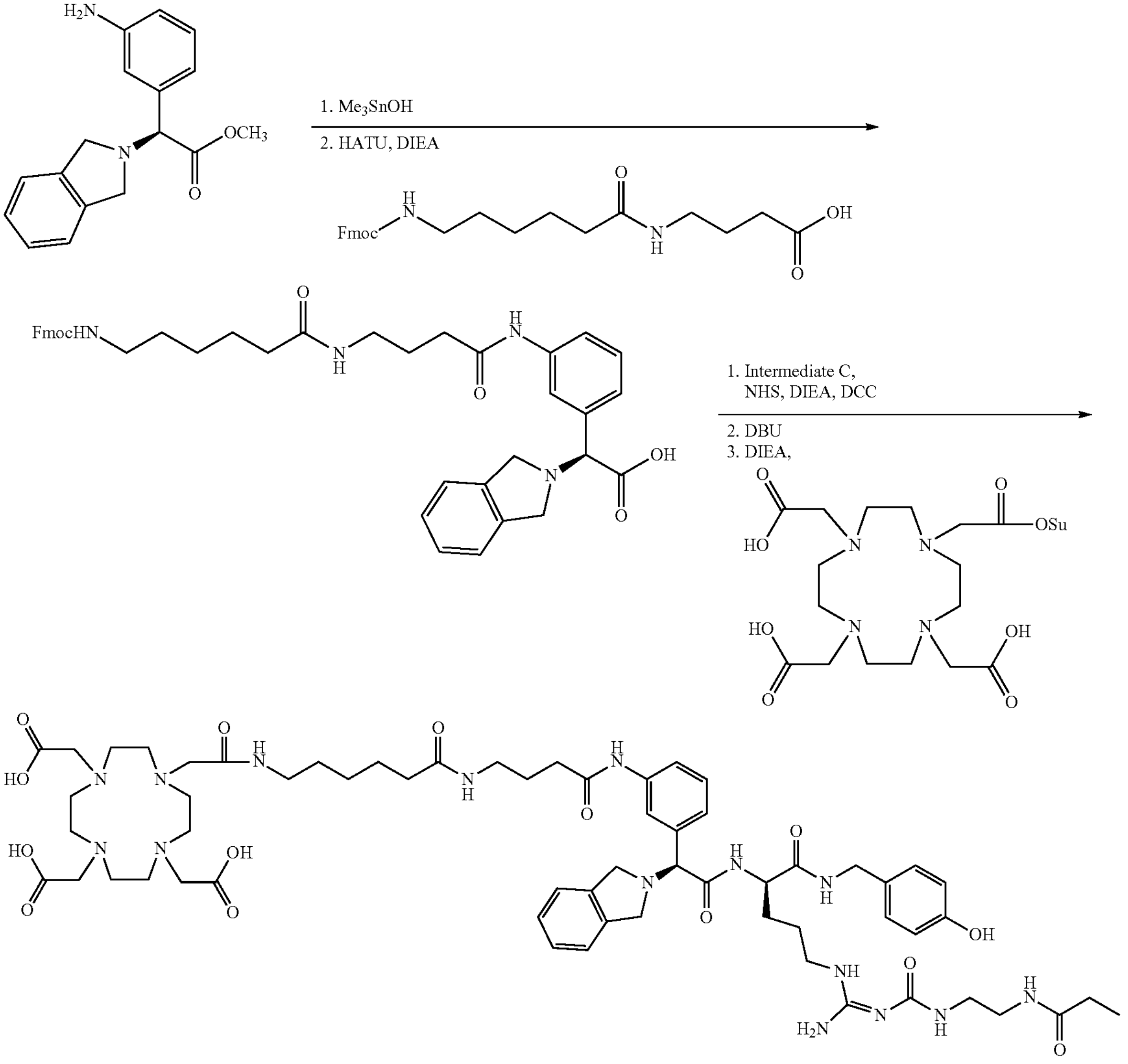

Step 1. Into an 8-mL vial, was placed a mixture of methyl (S)-2-(3-aminophenyl)-2-(isoindolin-2-yl)acetate (350 mg, 1 Eq, 1.24 mmol), trimethyltinhydroxide (700 mg, 3.12 Eq, 3.87 mmol), and DCE (5 mL). The reaction mixture was stirred at 90° C. for 16 h. The mixture was directly purified by MPLC to provide (S)-2-(3-aminophenyl)-2-(isoindolin-2-yl)acetic acid (230 mg, 857 μmol, 69.1%) as a yellow oil. $[M+H]^+$=269.0.

Step 2. (S)-2-(3-aminophenyl)-2-(isoindolin-2-yl)acetic acid was treated with 4-(6-((((9H-fluoren-9-yl)methoxy)carbonyl)amino)hexanamido)butanoic acid, HATU and DIEA in a manner similar to Step 3 of the synthesis of Compound 1, to provide (S)-2-(3-(4-(6-((((9H-fluoren-9-yl)methoxy)carbonyl)amino)hexanamido)butanamido)phenyl)-2-(isoindolin-2-yl)acetic acid as a yellow oil. $[M+H]^+$=689.4.

Step 3. Into an 8-mL vial, was placed a mixture of (S)-2-(3-(4-(6-((((9H-fluoren-9-yl)methoxy)carbonyl)amino)hexanamido)butanamido)phenyl)-2-(isoindolin-2-yl)acetic acid (100 mg, 1 Eq, 145 μmol), N-hydroxysuccinimide (30 mg, 1.8 Eq, 0.26 mmol), dicyclohexylcarbodiimide (50 mg, 43 L, 1.7 Eq, 0.24 mmol) and THE (3 mL). The reaction mixture was stirred at 25° C. for 2 h, then (R,Z)-2-amino-N-(4-hydroxybenzyl)-5-(2-((2-propionamidoethyl)carbamoyl)guanidino)pentanamide (65 mg, 1.1 Eq, 0.15 mmol) and DIEA (60 mg, 81 μL, 3.2 Eq, 0.46 mmol) were added and the reaction mixture was stirred at 50° C. for an additional 4 hours. The mixture was directly purified by MPLC to provide (9H-fluoren-9-yl)methyl (6-((4-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9- en-1-yl)phenyl)amino)-4-oxobutyl)amino)-6-oxohexyl) carbamate (70 mg, 64 μmol, 44%) as a white solid. $[M+H]^+$=1092.6.

Step 4. Into an 8-mL vial, was placed a mixture of (9H-fluoren-9-yl)methyl (6-((4-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl) amino)-4-oxobutyl)amino)-6-oxohexyl)carbamate (70 mg, 1 Eq, 64 μmol), DBU (15 mg, 15 L, 1.5 Eq, 99 μmol) and DMF (1 mL). The reaction mixture was stirred at 25° C. for 30 minutes. The reaction mixture was used directly in the next step without any purification. $[M+H]^+$=870.5.

Step 5. 6-amino-N-(4-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl) amino)-4-oxobutyl)hexanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Step 5 in the synthesis of Compound 1 to provide 2,2',2"-(10-(2-((6-((4-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-6-oxohexyl)amino)-2-oxoethyl)-1,4,7,10-tetraazacyclododecane-1,4,7-triyl) triacetic acid-2,2,2-trifluoroacetic acid (1/1) (3 mg, 2 mol, 3%) as a white solid. MS: Calc'd for $C_{61}H_{89}N_{15}O_{14}$: 1255.67, found $[M+H]^+$: 1256.6.

Example 8: 2,2',2"-(10-(2-((6-((4-((3-((1R,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-6-oxohexyl)amino)-2-oxoethyl)-1,4,7,10-tetraazacyclododecane-1,4,7-triyl)triacetic acid (Compound 3B)

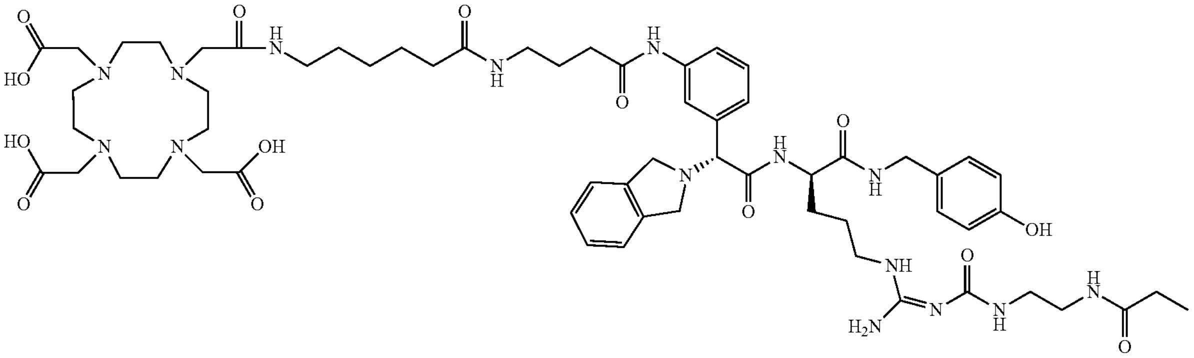 [SMILES: CCC(=O)NCCNC(=O)/N=C(/N)NCCC[C@@H](NC(=O)[C@@H](c1cccc(NC(=O)CCCNC(=O)CCCCCNC(=O)CN2CCN(CC(=O)O)CCN(CC(=O)O)CCN(CC(=O)O)CC2)c1)N1Cc2ccccc2C1)C(=O)NCc1ccc(O)cc1]

Step 1. 6-amino-N-(4-((3-((1R,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl) amino)-4-oxobutyl)hexanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Step 5 in the synthesis of Compound 1 to provide 2,2',2"-(10-(2-((6-((4-((3-((1R,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-6-oxohexyl)amino)-2-oxoethyl)-1,4,7,10-tetraazacyclododecane-1,4,7-triyl) triacetic acid (17.1 mg, 13.6 μmol, 20%) as a white solid. MS: Calc'd for $C_{61}H_{89}N_{15}O_{14}$: 1255.67, found $[M+H]^+$: 1256.6.

Example 9: 2,2',2"-(10-(2-((3-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl) piperazin-1-yl)-3-oxopropyl)amino)-2-oxoethyl)-1,4,7,10-tetraazacyclododecane-1,4,7-triyl)triacetic acid-2,2,2-trifluoroacetic acid (1/1) (Compound 4)

Synthesis of Intermediate E

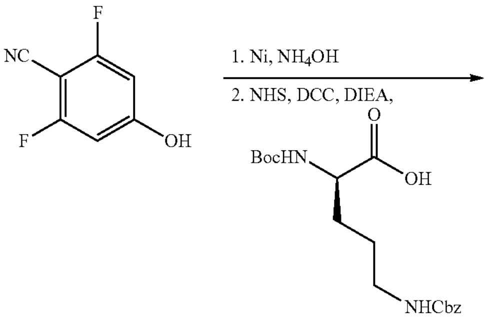

-continued

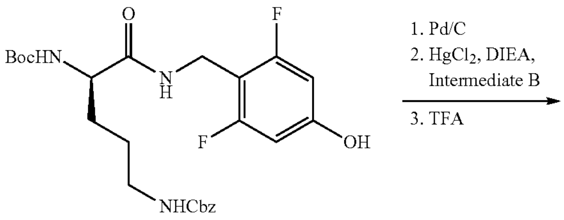

-continued

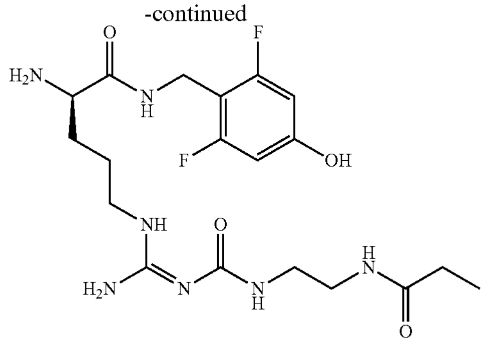

Intermediate E

Step 1. Into a 1-L round-bottom flask, purged and maintained under an inert atmosphere of nitrogen, was placed 2,6-difluoro-4-hydroxybenzonitrile (50 g, 1 Eq, 0.32 mol), ammonia water (11 g, 12 mL, 0.96 Eq, 0.31 μmol) and IPA (500 mL), to which was carefully added nickel (10 g, 1.1 mL, 0.53 Eq, 0.17 μmol). The flask was evacuated and flushed with hydrogen three times. The mixture was stirred at 25° C. for 4 hour under $H_2$. The reaction mixture was filtered through a pad of celite and the filtrate was concentrated to provide 4-(aminomethyl)-3,5-difluorophenol (32 g, 0.17 μmol, 54%) as a light blue solid.

Step 2. Into a 250-mL round bottom flask, was placed (R)-5-(((benzyloxy)carbonyl)amino)-2-((tert-butoxycarbonyl)amino)pentanoic acid (12.5 g, 1.1 Eq, 34.1 mmol), N-hydroxysuccinimide (5.4 g, 1.5 Eq, 47 mmol) and THE (50 mL). To the mixture was added DCC (9.6 g, 1.5 Eq, 47 mmol) under $N_2$. The reaction mixture was stirred at 25° C. for 1 hour. Into another 250-mL round bottom flask, was placed a mixture of 4-(aminomethyl)-3,5-difluorophenol (5.0 g, 1 Eq, 31 mmol), DIEA (13 g, 18 mL, 3.2 Eq, 0.10 mol) and THE (50 mL). The initial reaction mixture was transferred dropwise into the second mixture at 25° C. The resulting reaction mixture was stirred at 25° C. for 2 hours. The mixture was diluted with water (100 mL), extracted with EtOAc (100 mL×3), then the combined organic layers were washed with water (100 mL×2) and brine (100 mL), dried over anhydrous $Na_2SO_4$ and concentrated under reduced pressure. The crude product was purified by MPLC to provide benzyl tert-butyl (5-((2,6-difluoro-4-hydroxybenzyl)amino)-5-oxopentane-1,4-diyl)(R)-dicarbamate (11 g, 17 mmol, 55%) as a white solid. $[M+H]^+$=508.3.

Step 3. Into a 250-mL round-bottom flask, purged and maintained with an inert atmosphere of nitrogen, was placed benzyl tert-butyl (5-((2,6-difluoro-4-hydroxybenzyl) amino)-5-oxopentane-1,4-diyl)(R)-dicarbamate (11 g, 1 Eq, 22 mmol), 2,2,2-trifluoroethanol (110 mL), to which was carefully added Pd/C (0.7 g, 0.3 Eq, 7 mmol)(wet, 10%). The flask was evacuated and flushed with hydrogen three times. The mixture was stirred at 25° C. for 4 hours under $H_2$. The reaction mixture was filtered through a pad of celite, then the filtrate was concentrated. The collected fractions were concentrated under reduced pressure and dried to provide tert-butyl (R)-(5-amino-1-((2,6-difluoro-4-hydroxybenzyl)amino)-1-oxopentan-2-yl)carbamate (9 g, 0.02 μmol, 90%) as an off-white solid. $[M+H]^+$=374.3.

Step 4. Into a 250 mL round bottom flask, purged and maintained with an inert atmosphere of nitrogen, was placed a mixture of tert-butyl (R)-(5-amino-1-((2,6-difluoro-4-hydroxybenzyl)amino)-1-oxopentan-2-yl)carbamate (9.0 g, 1 Eq, 24 mmol), mercuric chloride (5 g, 1 mL, 0.8 Eq, 0.02 μmol), DIEA (9.5 g, 13 mL, 3.0 Eq, 74 mmol) and DCM (100 mL), to which was dropwise added Intermediate B (9.2 g, 1.1 Eq, 28 mmol). The reaction mixture was stirred at 25° C. for 2 hours. The mixture was filtrated directly and concentrated. The crude product was diluted with 250 mL of water, extracted with EtOAc (100 mL×3), the combined organic layers were washed with water (250 mL×2) and brine (250 mL), dried over anhydrous $Na_2SO_4$ and concentrated under reduced pressure to provide the crude product (8.5 g, 10 mmol, 43%) as an off-white semi solid. $[M+H]^+$=658.7.

Step 5. Into a 8-mL vial, was placed a mixture of product from Step 4 (135 mg, 1 Eq, 205 μmol) and DCM (2.5 mL), to which was added TFA (0.5 mL). The reaction mixture was stirred at 25° C. for 1 hour. The mixture was concentrated under reduced pressure to provide (R,Z)-2-amino-N-(2,6-difluoro-4-hydroxybenzyl)-5-(2-((2-propionamidoethyl) carbamoyl)guanidino)pentanamide (140 mg, 0.18 mmol, 89%) as a white solid, which was used directly in the next step without any purification. $[M+H]^+$=458.2.

Synthesis of Intermediate F

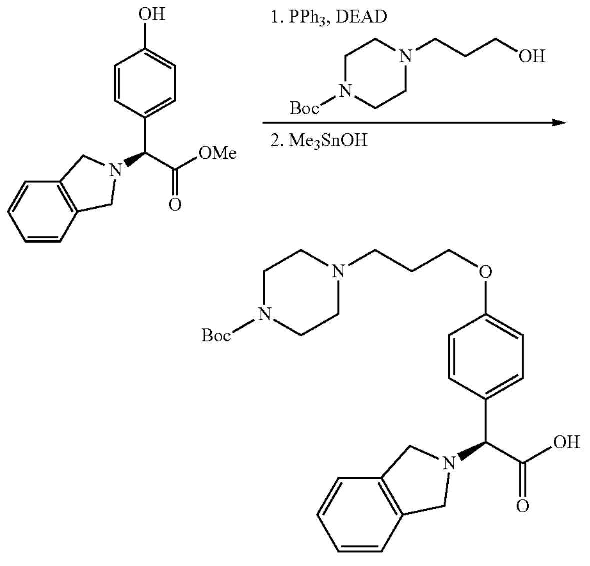

Intermediate F

Step 1. Into a 250-mL round bottom flask, was placed a mixture of methyl (S)-2-(4-hydroxyphenyl)-2-(isoindolin-2-yl)acetate (3.0 g, 1 Eq, 11 mmol), tert-butyl 4-(3-hydroxypropyl)piperazine-1-carboxylate (5.2 g, 2.0 Eq, 21 mmol), and THE (60 mL). The reaction mixture was stirred at 0° C. for 10 minutes, then DEAD (4.1 g, 3.7 mL, 2.2 Eq, 24 mmol) was added and the reaction mixture was stirred at 25° C. for an additional 2 hours. The crude product was purified by MPLC to provide tert-butyl (S)-4-(3-(4-(1-(isoindolin-2-yl)-2-methoxy-2-oxoethyl)phenoxy)propyl)piperazine-1-carboxylate (4.5 g, 8.8 mmol, 83%) as a white solid. $[M+H]^+$=510.3.

Step 2. Into a 100-mL round bottom flask, was placed a mixture of tert-butyl (S)-4-(3-(4-(1-(isoindolin-2-yl)-2-methoxy-2-oxoethyl)phenoxy)propyl)piperazine-1-carboxylate (3.0 g, 1 Eq, 5.9 mmol) and DCE (60 mL), to which was added trimethyltinhydroxide (4.2 g, 3.9 Eq, 23 mmol). The reaction mixture was stirred at 90° C. for 16 hours. The mixture was concentrated under reduced pressure. The crude product was purified by Prep-HPLC to provide (S)-2-(4-(3-(4-(tert-butoxycarbonyl)piperazin-1-yl)propoxy)phenyl)-2-(isoindolin-2-yl)acetic acid (2.3 g, 4.6 mmol, 79%) as a white solid. $[M+H]^+$=496.2.

Synthesis of Compound 4

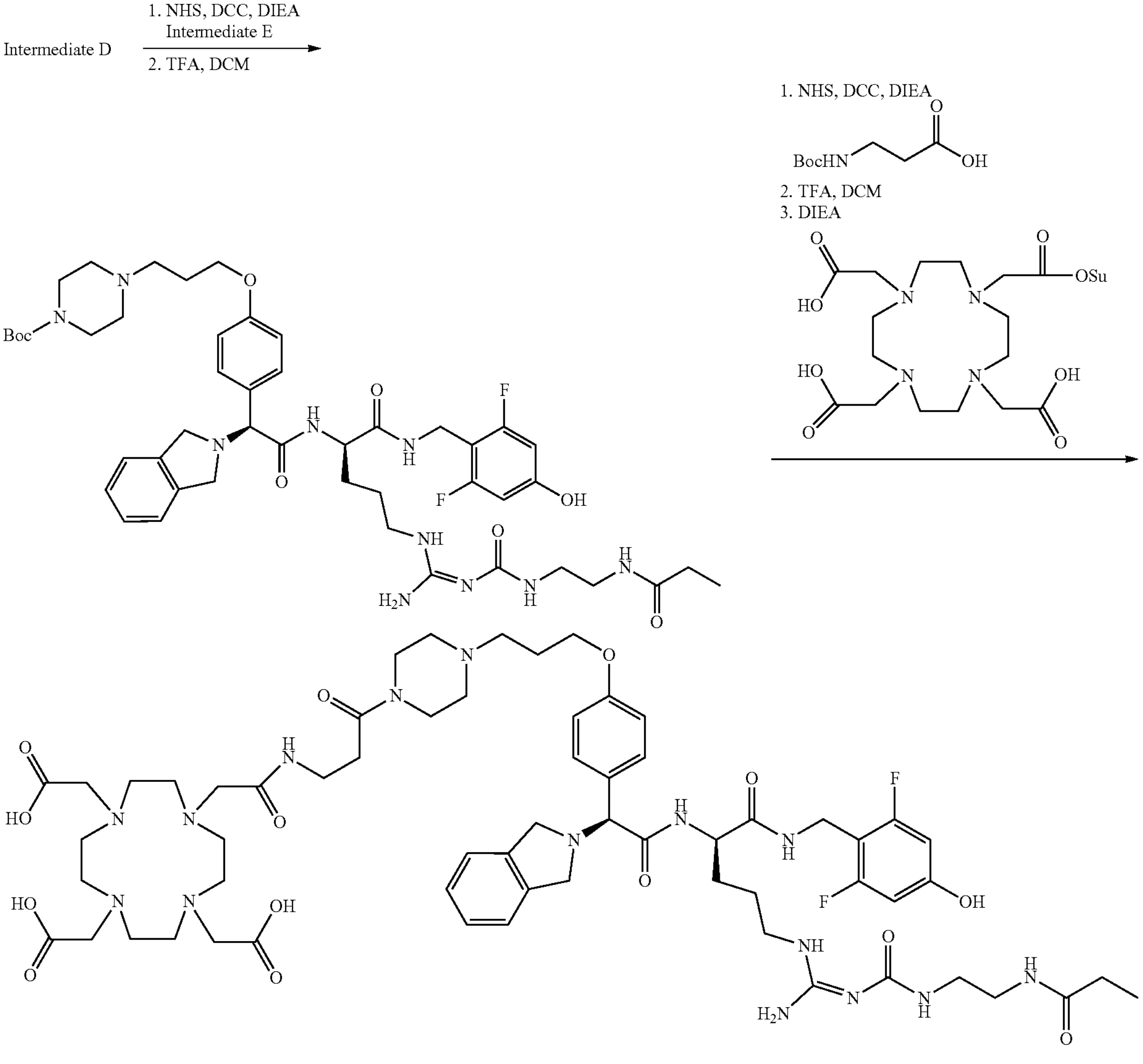

Step 1. (R,Z)-2-amino-N-(2,6-difluoro-4-hydroxybenzyl)-5-(2-((2-propionamidoethyl)carbamoyl)guanidino)pentanamide was treated with NHS and DCC in a manner similar to Example 7, Step 3 to provide tert-butyl 4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazine-1-carboxylate (114 mg, 122 μmol, 46.5%) as a yellow oil. $[M+H]^+=935.7$.

Step 2. tert-Butyl 4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazine-1-carboxylate was treated with TFA in a manner similar to Step 2 in the synthesis of Compound 1 to provide (R)—N-(2,6-difluoro-4-hydroxybenzyl)-2-((S)-2-(isoindolin-2-yl)-2-(4-(3-(piperazin-1-yl)propoxy)phenyl)acetamido)-5-((Z)-2-((2-propionamidoethyl)carbamoyl)guanidino)pentanamide (70 mg, 84 μmol, 69%) as a light yellow solid, which was used directly in the next step without any purification. $[M+H]^+=835.6$.

Step 3. (R)—N-(2,6-difluoro-4-hydroxybenzyl)-2-((S)-2-(isoindolin-2-yl)-2-(4-(3-(piperazin-1-yl)propoxy)phenyl)acetamido)-5-((Z)-2-((2-propionamidoethyl)carbamoyl)guanidino)pentanamide was treated with HATU, DIEA, and 3-((tert-butoxycarbonyl)amino)propanoic acid in a manner similar to Step 3 of the synthesis of Compound 1, to provide tert-butyl (3-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazin-1-yl)-3-oxopropyl)carbamate (60 mg, 60 μmol, 62%) as a yellow oil. $[M+H]^+=1006.7$.

Step 4. tert-butyl (3-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazin-1-yl)-3-oxopropyl)carbamate was treated with TFA in a manner similar to Step 2 in the synthesis of Compound 1 to provide (R)-2-((S)-2-(4-(3-(4-(3-aminopropanoyl)piperazin-1-yl)propoxy)phenyl)-2-(isoindolin-2-yl)acetamido)-N-(2,6-difluoro-4-hydroxybenzyl)-5-((Z)-2-((2-propionamidoethyl)carbamoyl)guanidino)

pentanamide (35 mg, 31 μmol, 78%) as a light yellow solid, which was used directly for the next step without any purification. [M+H]$^+$=906.3.

Step 5. (R)-2-((S)-2-(4-(3-(4-(3-aminopropanoyl)piperazin-1-yl)propoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Step 5 in the synthesis of Compound 1 to provide 2,2',2"-(10-(2-((3-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazin-1-yl)-3-oxopropyl)amino)-2-oxoethyl)-1,4,7,10-tetraazacyclododecane-1,4,7-triyl)triacetic acid-2,2,2-trifluoroacetic acid (1/1) (15.2 mg, 10.8 μmol, 28%) as a white solid. MS: Calc'd for $C_{61}H_{87}F_2N_{15}O_{14}$: 1255.67, found [M+H]$^+$: 1292.5

Example 10: 2,2',2"-(10-(2-((6-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)piperidin-1-yl)-6-oxohexyl)amino)-2-oxoethyl)-1,4,7,10-tetraazacyclododecane-1,4,7-triyl)triacetic acid-2,2,2-trifluoroacetic acid (1/1) (Compound 5)

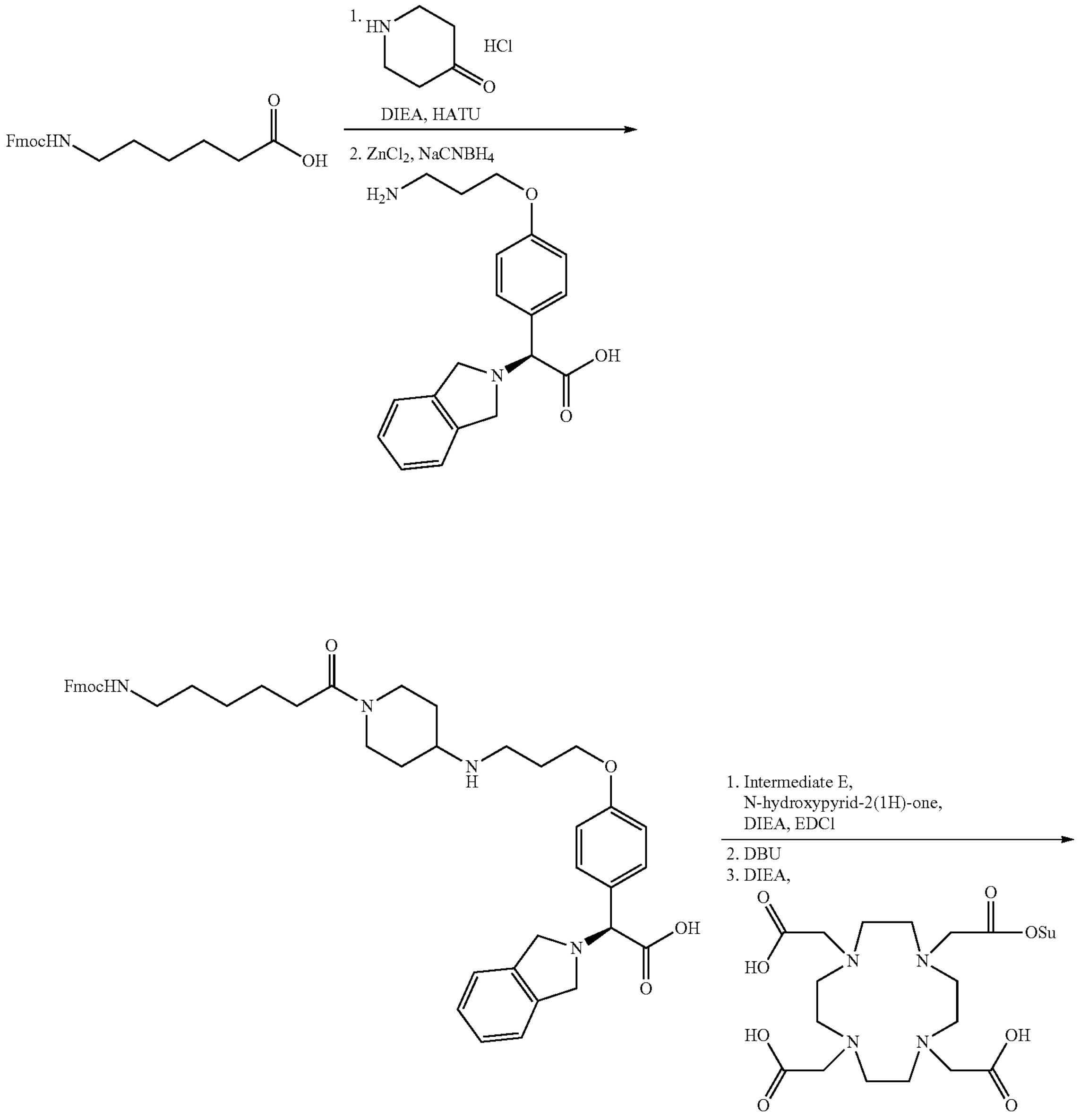

-continued

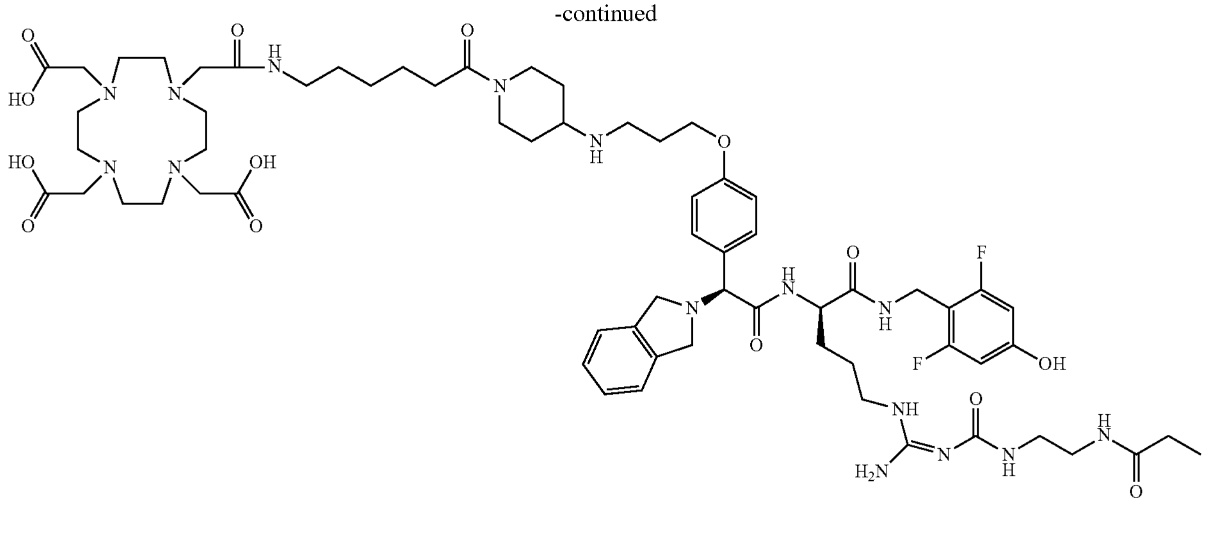

Step 1. Into a 40-mL vial, was placed a mixture of 6-((((9H-fluoren-9-yl)methoxy)carbonyl)amino)hexanoic acid (3.3 g, 1.0 Eq, 9.3 mmol), HATU (4.2 g, 1.2 Eq, 11 mmol), DIPEA (3.6 g, 4.9 mL, 3.0 Eq, 28 mmol) and DMF (20 mL). The reaction mixture was stirred at 20° C. for 10 minutes, then piperidin-4-one hydrochloride (1.5 g, 1.2 Eq, 11 mmol) was added and the reaction mixture was stirred at 25° C. for an additional 1 hour. The mixture was directly purified by MPLC to provide (9H-fluoren-9-yl)methyl (6-oxo-6-(4-oxopiperidin-1-yl)hexyl)carbamate (4.1 g, 8.5 mmol, 92%) as a yellow oil. $[M+H]^+$=434.5.

Step 2. Into an 8-mL vial, was placed a mixture of (S)-2-(4-(3-aminopropoxy)phenyl)-2-(isoindolin-2-yl)acetic acid (220 mg, 70% Wt, 1 Eq, 472 μmol), (9H-fluoren-9-yl)methyl (6-oxo-6-(4-oxopiperidin-1-yl)hexyl)carbamate (246 mg, 1.20 Eq, 566 μmol), zinc chloride (193 mg, 91.0 μL, 3.00 Eq, 1.42 mmol) and MeOH (2 mL), to which was added $NaCNBH_4$ (89 mg, 3.0 Eq, 1.4 mmol) dropwise at 0° C. over 2 min. The reaction mixture was stirred at 25° C. for 2 hours. The mixture was concentrated under reduced pressure then purified by Prep-HPLC to provide (S)-2-(4-(3-((1-(6-((((9H-fluoren-9-yl)methoxy)carbonyl)amino)hexanoyl)piperidin-4-yl)amino)propoxy)phenyl)-2-(isoindolin-2-yl)acetic acid (210 mg, 282 μmol, 59.7%) as a white solid. $[M+H]^+$=745.3.

Step 3. Into an 8-mL vial, was placed a mixture of (S)-2-(4-(3-((1-(6-((((9H-fluoren-9-yl)methoxy)carbonyl)amino)hexanoyl)piperidin-4-yl)amino)propoxy)phenyl)-2-(isoindolin-2-yl)acetic acid (70 mg, 1 Eq, 94 μmol), N-hydroxypyrid-2(1H)-one (16 mg, 1.5 Eq, 0.14 mmol), 1-(3-dimethylaminopropyl)-3-ethylcarbodiimide hydrochloride (EDCI) (27 mg, 1.5 Eq, 0.14 mmol), DIPEA (36 mg, 49 μL, 3.0 Eq, 0.28 mmol), and DMF (1 mL). The reaction mixture was stirred at 20° C. for 10 minutes, then (R,Z)-2-amino-N-(2,6-difluoro-4-hydroxybenzyl)-5-(2-((2-propionamidoethyl)carbamoyl)guanidino)pentanamide (64 mg, 1.5 Eq, 0.14 mmol) was added and the reaction mixture was stirred at 25° C. for an additional 1 hour. The mixture was directly purified by MPLC to provide (9H-fluoren-9-yl)methyl (6-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)piperidin-1-yl)-6-oxohexyl)carbamate (25 mg, 21 μmol, 22%) as a yellow oil. $[M+H]^+$=1184.7.

Step 4. (9H-fluoren-9-yl)methyl (6-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)piperidin-1-yl)-6-oxohexyl)carbamate was treated with DBU in a manner similar to Example 7, Step 4 to provide (R)-2-((S)-2-(4-(3-((1-(6-aminohexanoyl)piperidin-4-yl)amino)propoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (22 mg, 21 μmol, 97%) as a light yellow oil, which was used directly in the next step without any purification. $[M+H]^+$=962.2.

Step 5. (R)-2-((S)-2-(4-(3-((1-(6-aminohexanoyl)piperidin-4-yl)amino)propoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Step 5 in the synthesis of Compound 1 to provide 2,2',2"-(10-(2-((6-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)piperidin-1-yl)-6-oxohexyl)amino)-2-oxoethyl)-1,4,7,10-tetraazacyclododecane-1,4,7-triyl)triacetic acid-2,2,2-trifluoroacetic acid (1/1) (16 mg, 11 μmol, 48%) as a white solid. MS: Calc'd for $C_{67}H_{96}F_5N_{15}O_{16}$: 1461.6, found $[M+H-TFA]^+$: 1348.5.

Example 11: 2,2',2"-(10-(2-(((3R,5R)-7-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3,5-dihydroxy-7-oxoheptyl)amino)-2-oxoethyl)-1,4,7,10-tetraazacyclododecane-1,4,7-triyl)triacetic acid-2,2,2-trifluoroacetic acid (1/1) (Compound 6)

Synthesis of Intermediate G

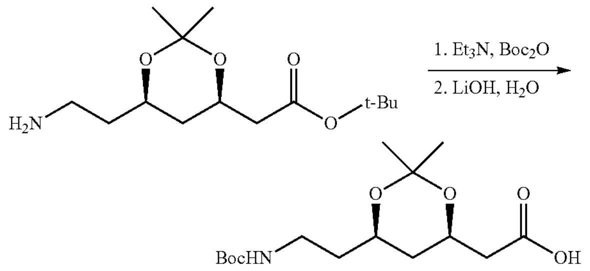

Intermediate G

Step 1. Into a 100-mL round bottom flask, was placed a mixture of tert-butyl 2-((4R,6R)-6-(2-aminoethyl)-2,2-dimethyl-1,3-dioxan-4-yl)acetate (2 g, 1 Eq, 7 mmol), TEA (2 g, 3 mL, 3 Eq, 0.02 μmol), $Boc_2O$ (2 g, 2 mL, 1 Eq, 9 mmol) and DCM (20 mL). The reaction mixture was stirred at 25° C. for 1 hour. The mixture was purified by MPLC to provide tert-butyl 2-((4R,6R)-6-(2-((tert-butoxycarbonyl)amino)ethyl)-2,2-dimethyl-1,3-dioxan-4-yl)acetate (2.34 g, 6.27 mmol, 90%) as a yellow oil. [M+H]=374.2.

Step 2. Into a 40-mL round bottom flask, was placed a mixture of tert-butyl 2-((4R,6R)-6-(2-((tert-butoxycarbonyl)amino)ethyl)-2,2-dimethyl-1,3-dioxan-4-yl)acetate (2.34 g, 1 Eq, 6.27 mmol), LiOH (3.0 g, 20 Eq, 0.13 μmol), $H_2O$ (2 g, 2 mL, 2e+1 Eq, 0.1 μmol) and MeOH (6 mL). The reaction mixture was stirred at 25° C. for 16 hours. The mixture was diluted with water (100 mL), extracted with EtOAc (50 mL×3), the combined organic layers were washed with water (50 mL×2), brine (50 mL), dried over anhydrous $Na_2SO_4$ and concentrated under reduced pressure to provide 2-((4R,6R)-6-(2-((tert-butoxycarbonyl)amino)ethyl)-2,2-dimethyl-1,3-dioxan-4-yl)acetic acid (1.37 g, 4.32 mmol, 68.9%) as a yellow oil. [M+H]=318.2.

Synthesis of Compound 6

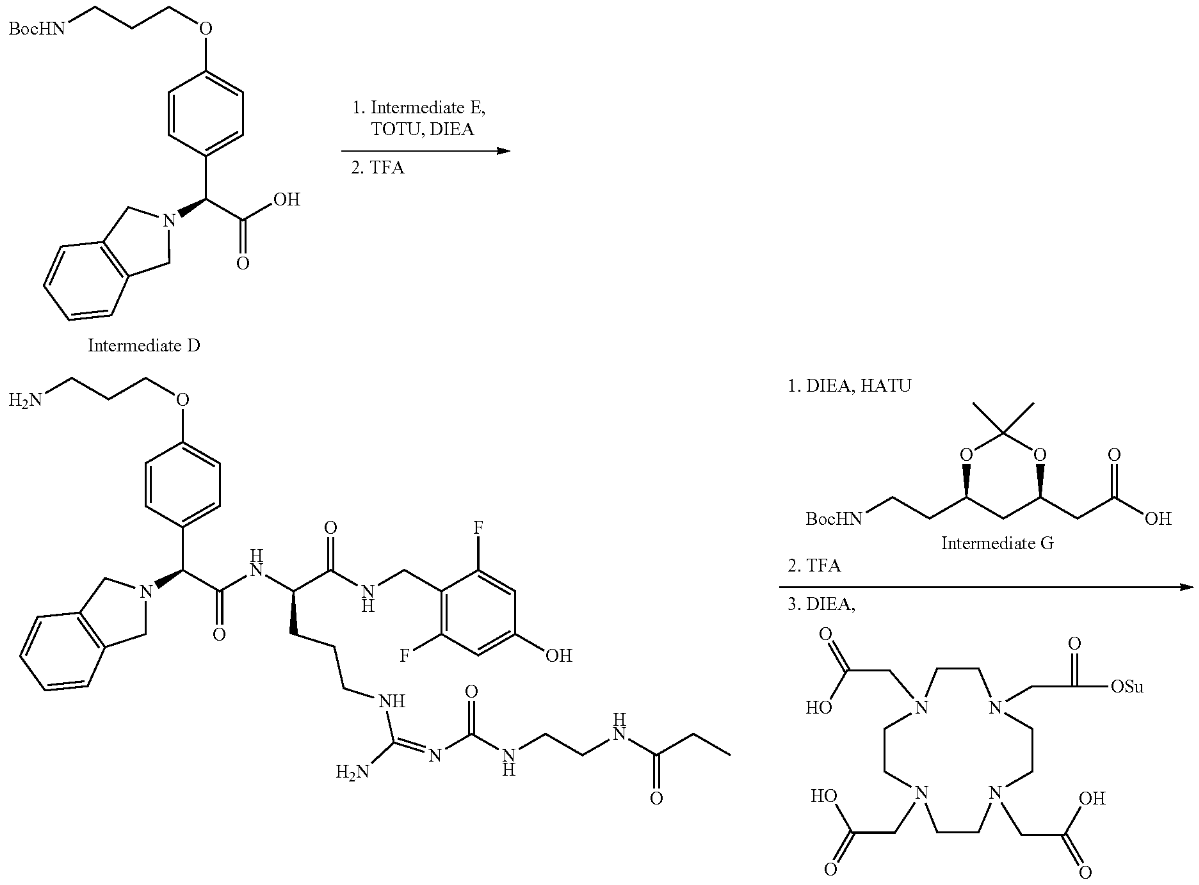

-continued

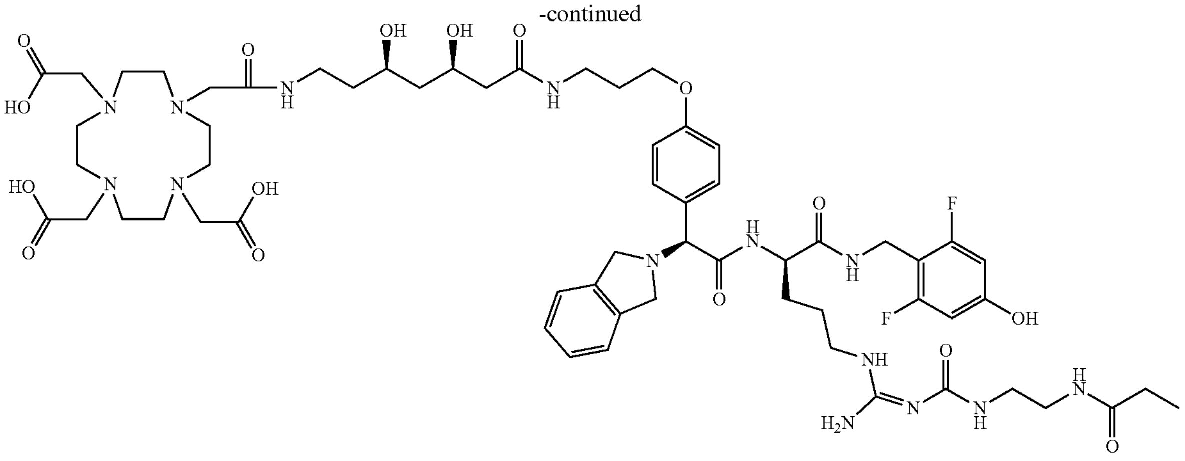

Step 1. Into a 40-mL vial, was placed a mixture of (S)-2-(4-(3-((tert-butoxycarbonyl)amino)propoxy)phenyl)-2-(isoindolin-2-yl)acetic acid (0.84 g, 0.90 Eq, 2.0 mmol), TOTU (0.65 g, 0.91 Eq, 2.0 mmol), DIEA (0.85 g, 1.1 mL, 3.0 Eq, 6.6 mmol) and DMF (10 mL). The reaction mixture was stirred at 20° C. for 10 minutes, then (R,Z)-2-amino-N-(2,6-difluoro-4-hydroxybenzyl)-5-(2-((2-propionamido-ethyl)carbamoyl)guanidino)pentanamide (1.0 g, 1 Eq, 2.2 mmol) was added and the reaction mixture was stirred at 25° C. for an additional 1 hour. The mixture was directly purified by MPLC to provide tert-butyl (3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)carbamate (1.1 g, 1.3 mmol, 58%) as a yellow oil. $[M+H]^+$=866.5.

Step 2. Into a 40-mL vial, was placed a mixture of tert-butyl (3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)carbamate (1.2 g, 1 Eq, 1.4 mmol) and DCM (10 mL), to which was added TFA (2 mL). The reaction mixture was stirred at 25° C. for 30 min. The mixture was concentrated under reduced pressure then ACN (20 mL) and $H_2O$ (100 mL) were added into the crude product and the mixture was dried by lyophilization to provide (R)-2-((S)-2-(4-(3-amino-propoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (1.1 g, 1.4 mmol, 100%) as a brown solid. $[M+H]^+$=766.2.

Step 3. Into an 8-mL vial, was placed a mixture of 2-((4R,6R)-6-(2-((tert-butoxycarbonyl)amino)ethyl)-2,2-dimethyl-1,3-dioxan-4-yl)acetic acid (Intermediate G) (23 mg, 1.0 Eq, 72 μmol), DIEA (20 mg, 27 L, 2.2 Eq, 0.15 mmol), HATU (30 mg, 1.1 Eq, 79 mol) and DMF (1 mL). The reaction mixture was stirred at 20° C. for 10 minutes, then added the mixture to (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (55 mg, 1 Eq, 72 μmol) in batches. The mixture was stirred at 25° C. for an additional 1 hour. The mixture was directly purified by MPLC to provide tert-butyl (2-((4R,6R)-6-(2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-2,2-dimethyl-1,3-dioxan-4-yl)ethyl)carbamate (33 mg, 31 μmol, 43%) as a yellow oil. $[M+Na]^+$=1087.6.

Step 4. tert-butyl (2-((4R,6R)-6-(2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-2,2-dimethyl-1,3-dioxan-4-yl)ethyl)carbamate was treated with TFA in a manner similar to Step 2 in the synthesis of Compound 1 to provide (3R,5R)-7-amino-N-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)-3,5-dihydroxyheptanamide (30 mg, 32 μmol, 100%) as a yellow oil. $[M+H]^+$=925.6.

Step 5. (3R,5R)-7-amino-N-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)-3,5-dihydroxyheptanamide was treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Step 5 in the synthesis of Compound 1 to provide 2,2',2''-(10-(2-(((3R,5R)-7-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3,5-dihydroxy-7-oxoheptyl)amino)-2-oxoethyl)-1,4,7,10-tetraazacyclododecane-1,4,7-triyl)triacetic acid-2,2,2-trifluoroacetic acid (1/1) as a white solid. MS: Calc'd for $C_{61}H_{88}F_2N_{14}O_{16}$: 1310.6, found $[M+H]^+$: =1311.6.

Example 12: 2,2',2"-(10-(2-((2-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-4-oxobutanamido)ethyl)amino)-2-oxoethyl)-1,4,7,10-tetraazacyclododecane-1,4,7-triyl)triacetic acid-2,2,2-trifluoroacetic acid (1/1) (Compound 7)

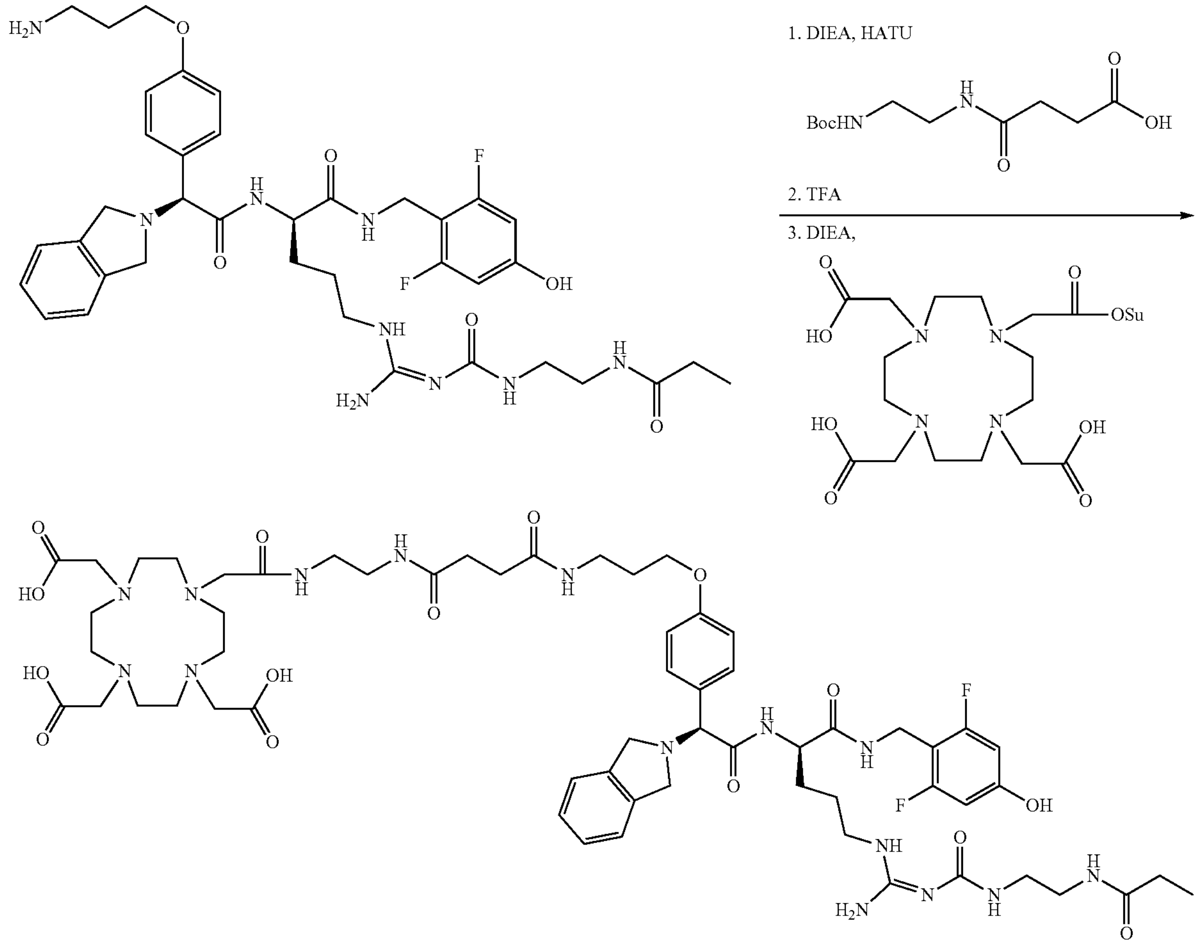

Step 1. (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino) pentanamide was treated with DIEA, HATU, and 4-((2-((tert-butoxycarbonyl)amino)ethyl)amino)-4-oxobutanoic acid in a manner similar to Example 11, Step 2 to provide tert-butyl (2-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy) propyl)amino)-4-oxobutanamido)ethyl)carbamate (120 mg, 119 μmol, 45.6%) as a yellow oil. $[M+H]^+$=1008.5.

Step 2. tert-butyl (2-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl) phenoxy)propyl)amino)-4-oxobutanamido)ethyl)carbamate was treated with TFA in a manner similar to Step 2 in the synthesis of Compound 1 to provide N1-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)-N4-(2-aminoethyl) succinamide (35 mg, 35 μmol, 87%) as a yellow oil, which was used directly in the next step without any purification. $[M+H]^+$=908.7.

Step 3. N1-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)-N4-(2-aminoethyl)succinamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Step 5 in the synthesis of Compound 1 to provide 2,2',2"-(10-(2-((2-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-4-oxobutanamido)ethyl)amino)-2-oxoethyl)-1,4,7,10-tetraazacyclododecane-1,4,7-triyl)triacetic acid-2,2,2-trifluoroacetic acid (1/1) (31.4 mg, 22.3 μmol, 58%) as a white solid. MS: Calc'd for $C_{62}H_{86}F_5N_{15}O_{17}$: 1407.45, found $[M+H-TFA]^+$: 1294.5.

Example 13: A single isomer of 2,2',2"-(10-(2-((2-(2-(3-(4-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)propoxy)ethoxy)ethyl)amino)-2-oxoethyl)-1,4,7,10-tetraazacyclododecane-1,4,7-triyl)triacetic acid (Compound 8A)
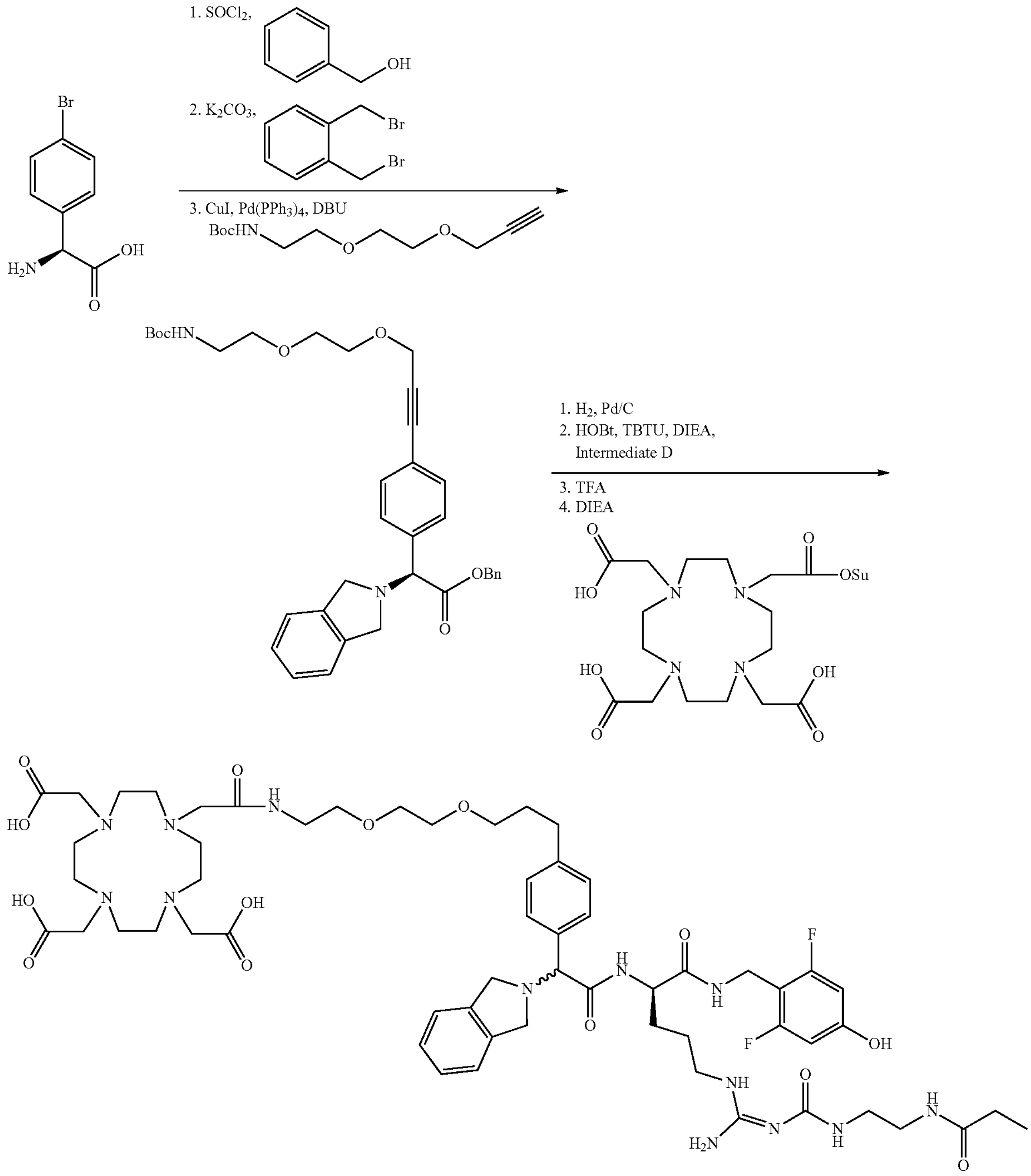

Step 1. Into a 100-mL three-neck flask, was placed a mixture of (S)-2-amino-2-(4-bromophenyl)acetic acid (1.0 g, 1 Eq, 4.3 mmol) and phenylmethanol (0.47 g, 20 mL, 1 Eq, 4.3 mmol). The reaction mixture was stirred at 0° C., then $SOCl_2$ (6.2 g, 3.8 mL, 12 Eq, 52 mmol) was added dropwise. The reaction mixture was stirred at 25° C. for 16 hours, then cold ether (100 mL) was added, and the solid precipitates were collected by centrifugation. The solid was concentrated under reduced pressure to provide benzyl (S)-2-amino-2-(4-bromophenyl)acetate hydrochloride (800 mg, 2.24 mmol, 52%) as a white solid. $[M+H-HCl]^+$=320.9, 321.9.

Step 2. Into a 40 mL vial was placed benzyl (S)-2-amino-2-(4-bromophenyl)acetate (800 mg, 1 Eq, 2.50 mmol), 1,2-bis(bromomethyl)benzene (660 mg, 1.00 Eq, 2.50 mmol) and potassium bicarbonate (750 mg, 346 L, 3.00 Eq, 7.49 mmol) in MeCN (15 mL). The reaction mixture was stirred at 25° C. for 16 hours. The reaction mixture was filtered and the filtrate concentrated and purified by MPLC to provide benzyl (S)-2-(4-bromophenyl)-2-(isoindolin-2-yl)acetate (650 mg, 1.54 mmol, 61.6%) as a light brown oil. $[M+H]^+$=421.9, 423.9.

Step 3. Into an 8-mL vial, was placed a mixture of benzyl (S)-2-(4-bromophenyl)-2-(isoindolin-2-yl)acetate (150 mg, 1 Eq, 355 μmol), tert-butyl (2-(2-(prop-2-yn-1-yloxy) ethoxy)ethyl)carbamate (860 mg, 9.95 Eq, 3.53 mmol), CuI (68 mg, 1.0 Eq, 0.36 mmol), DBU (162 mg, 160 μL, 3.00 Eq, 1.06 mmol) and $Pd(Ph_3P)_4$ (41 mg, 0.10 Eq, 35 mol) in THE (2 mL) under Ar gas. The reaction mixture was stirred at 70° C. for 16 hours. The crude product was purified by Prep-HPLC to provide benzyl (S)-2-(4-(2,2-dimethyl-4-oxo-3,8,11-trioxa-5-azatetradec-13-yn-14-yl)phenyl)-2-(isoindolin-2-yl)acetate (100 mg, 91 μmol, 26%) as a light yellow solid. $[M+H]^+$=585.2.

Step 4. Into a 50-mL round-bottom flask, purged and maintained under an inert atmosphere of nitrogen, was placed benzyl (S)-2-(4-(2,2-dimethyl-4-oxo-3,8,11-trioxa-5-azatetradec-13-yn-14-yl)phenyl)-2-(isoindolin-2-yl)acetate (100 mg, 1 Eq, 171 μmol) in MeOH (10 mL), to which was carefully added Pd/C (20 mg, 1.1 Eq, 0.19 mmol). The flask was evacuated and flushed with hydrogen three times. The mixture was stirred at 25° C. for 2 hour under $H_2$. The reaction mixture was filtered through a pad of celite and the filtrate was concentrated to provide (S)-2-(4-(2,2-dimethyl-4-oxo-3,8,11-trioxa-5-azatetradecan-14-yl)phenyl)-2-(isoindolin-2-yl)acetic acid (88 mg, 0.11 mmol, 65%) as a light yellow oil. $[M+H]^+$=499.5.

Step 5. Into a 8-mL vial, was placed a mixture of (S)-2-(4-(2,2-dimethyl-4-oxo-3,8,11-trioxa-5-azatetradecan-14-yl)phenyl)-2-(isoindolin-2-yl)acetic acid (88 mg, 1 Eq, 0.18 mmol), 0-(benzotriazol-1-yl)-N,N,N',N'-tetramethyluroniumtetrafluoroborate (TBTU) (57 mg, 1.0 Eq, 0.18 mmol), HOBt (54 mg, 2.0 Eq, 0.35 mmol) and DIEA (68 mg, 92 μL, 3.0 Eq, 0.53 mmol) in DMF (1 mL). The reaction mixture was stirred at 25° C. for 10 minutes, then (R,Z)-2-amino-N-(2,6-difluoro-4-hydroxybenzyl)-5-(2-((2-propionamidoethyl)carbamoyl)guanidino)pentanamide (90 mg, 1.1 Eq, 0.20 mmol) was added and the reaction mixture was stirred at 25° C. for an additional 2 hours. The mixture was directly purified by MPLC to provide two isomers isolated from two peaks. The front peak fractions were collected to afford a single isomer of tert-butyl (2-(2-(3-(4-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)propoxy)ethoxy)ethyl)carbamate (front peak fractions) (18 mg, 19 μmol, 11%) as a white solid. $[M+Na]^+$=960.4. The back fractions were collected and dried by lyophilization to provide the other single isomer of tert-butyl (2-(2-(3-(4-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)propoxy)ethoxy)ethyl)carbamate (20 mg, 21 mol, 12%) as a white solid. $[M+H]^+$=938.3.

Step 6. Into a 8-mL vial, was placed a mixture of tert-butyl (2-(2-(3-(4-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)propoxy) ethoxy)ethyl)carbamate (18 mg, 1 Eq, 19 μmol) and TFA (0.2 mL), to which was added DCM (1 mL). The reaction mixture was stirred at 25° C. for 1 hour. The mixture was concentrated under reduced pressure to afford (2R)-2-(2-(4-(3-(2-(2-aminoethoxy)ethoxy)propyl)phenyl)-2-(isoindolin-2-yl)acetamido)-N-(2,6-difluoro-4-hydroxybenzyl)-5-((Z)-2-((2-propionamidoethyl)carbamoyl)guanidino) pentanamide (16 mg, 19 mol, 100%) as a light yellow oil, which was used directly in the next step without any purification. $[M+H]^+$=838.4.

Step 7. (2R)-2-(2-(4-(3-(2-(2-aminoethoxy)ethoxy)propyl)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the TFA salt of 2,2',2"-(10-(2-((2-(2-(3-(4-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl) phenyl)propoxy)ethoxy)ethyl)amino)-2-oxoethyl)-1,4,7,10-tetraazacyclododecane-1,4,7-triyl)triacetic acid (5.9 mg, 4.4 μmol, 23%) as a white solid. MS: Calc'd for $C_{57}H_{83}F_5N_{13}O_{16}$: 1337.40, found $[M+H-TFA]^+$: 1224.5.

Example 14: A single isomer of 2,2',2"-(10-(2-((2-(2-(3-(4-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)propoxy)ethoxy)ethyl)amino)-2-oxoethyl)-1,4,7,10-tetraazacyclododecane-1,4,7-triyl)triacetic acid (Compound 8B)

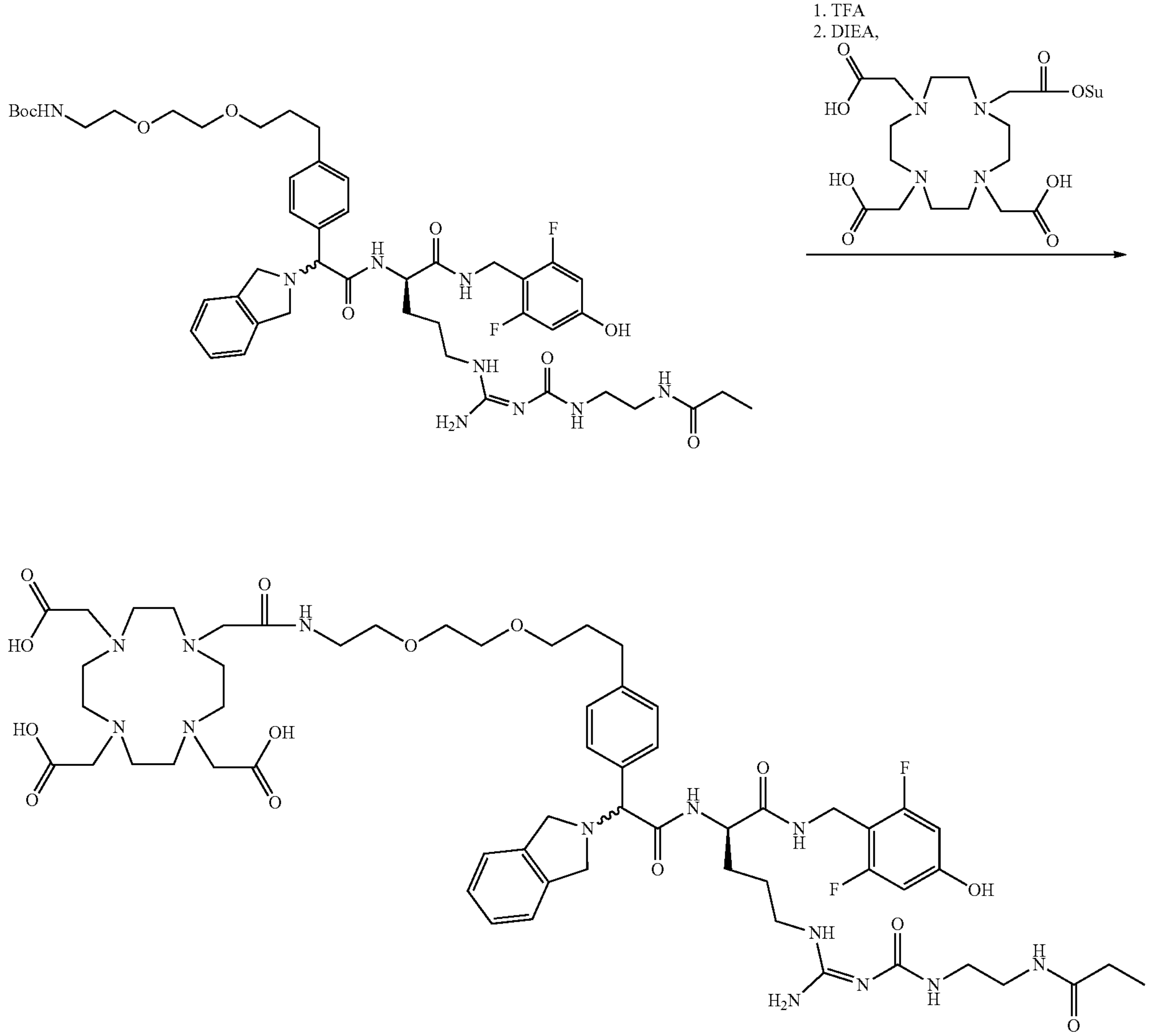

The other isomer of 2,2',2"-(10-(2-((2-(2-(3-(4-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)propoxy)ethoxy)ethyl)amino)-2-oxoethyl)-1,4,7,10-tetraazacyclododecane-1,4,7-triyl)triacetic acid was synthesized from tert-butyl (2-(2-(3-(4-((1R,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)propoxy)ethoxy)ethyl)carbamate (back peak fractions from Example 13, Step 5) in a manner similar to Example 13 to provide the TFA salt of the product (10.4 mg, 7.77 μmol, 36%) as a white solid. MS: Calc'd for $C_{60}H_{84}F_5N_{13}O_{16}$: 1337.40, found $[M+H-TFA]^+$: 1224.4.

Example 15: 2,2',2"-(10-(2-((6-((4-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)-4-oxobutyl)amino)-6-oxohexyl)amino)-2-oxoethyl)-1,4,7,10-tetraazacyclododecane-1,4,7-triyl)triacetic acid (Compound 9)

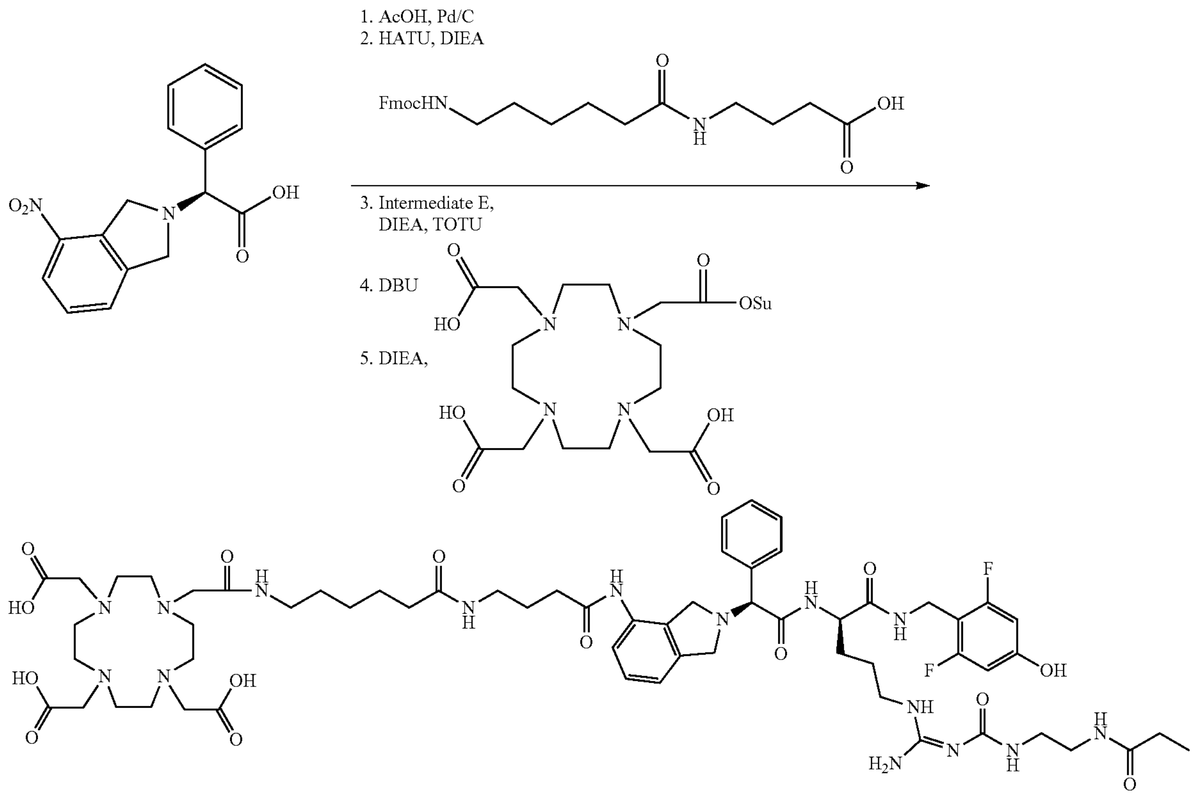

Step 1. Into a 25-mL round-bottom flask, purged and maintained under an inert atmosphere of nitrogen, was placed (S)-2-(4-nitroisoindolin-2-yl)-2-phenylacetic acid (150 mg, 1 Eq, 503 μmol), AcOH (90 mg, 86 μL, 3.0 Eq, 1.5 mmol) and i-PrOH (3 mL), to which was carefully added Pd/C (11 mg, 0.21 Eq, 0.10 mmol). The flask was evacuated and flushed with hydrogen three times. The mixture was stirred at 25° C. for 3 hours under $H_2$. The reaction mixture was filtered through a pad of celite, the filtrate was concentrated and purified by MPLC to provide (S)-2-(4-aminoisoindolin-2-yl)-2-phenylacetic acid (60 mg, 0.22 mmol, 44%) as a white solid. $[M+H]^+$=269.1.

Step 2. 4-(6-((((9H-fluoren-9-yl)methoxy)carbonyl)amino)hexanamido)butanoic acid was treated with (S)-2-(4-aminoisoindolin-2-yl)-2-phenylacetic acid, HATU and DIEA in a manner similar to Step 3 of the synthesis of Compound 1, to provide (S)-2-(4-(4-(6-((((9H-fluoren-9-yl)methoxy)carbonyl)amino)hexanamido)butanamido)isoindolin-2-yl)-2-phenylacetic acid (55 mg, 80 μmol, 36%) as a white solid. $[M+H]^+$=689.2.

Step 3. (S)-2-(4-(4-(6-((((9H-fluoren-9-yl)methoxy)carbonyl)amino)hexanamido)butanamido)isoindolin-2-yl)-2-phenylacetic acid was treated with Intermediate E, DIEA and TOTU in a manner similar to Step 1 of the synthesis of Compound 1 to provide (9H-fluoren-9-yl)methyl (6-((4-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)-4-oxobutyl)amino)-6-oxohexyl)carbamate (45 mg, 40 μmol, 50%) as a white solid. $[M+H]^+$=1128.3.

Step 4. (9H-fluoren-9-yl)methyl (6-((4-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)-4-oxobutyl)amino)-6-oxohexyl)carbamate was treated with DBU in a manner similar to Example 7, Step 4 to provide 6-amino-N-(4-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)-4-oxobutyl)hexanamide (30 mg, 33 μmol, 83%) as a white solid. $[M+H]^+$=906.3.

Step 5. 6-Amino-N-(4-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)-4-oxobutyl)hexanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the TFA salt of 2,2',2"-(10-(2-((6-((4-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)-4-oxobutyl)amino)-6-oxohexyl)amino)-2-oxoethyl)-1,4,7,10-tetraazacyclododecane-1,4,7-triyl)triacetic acid (32.5 mg, 23.1 μmol, 70%) as a white solid. MS: Calc'd for $C_{63}H_{88}F_5N_{15}O_{16}$: 1405.5, found $[M+H-TFA]^+$: 1292.4.

Example 16: 2,2',2"-(10-(9-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)oxy)propyl)amino)-2,9-dioxononyl)-1,4,7,10-tetraazacyclododecane-1,4,7-triyl)triacetic acid (Compound 10)

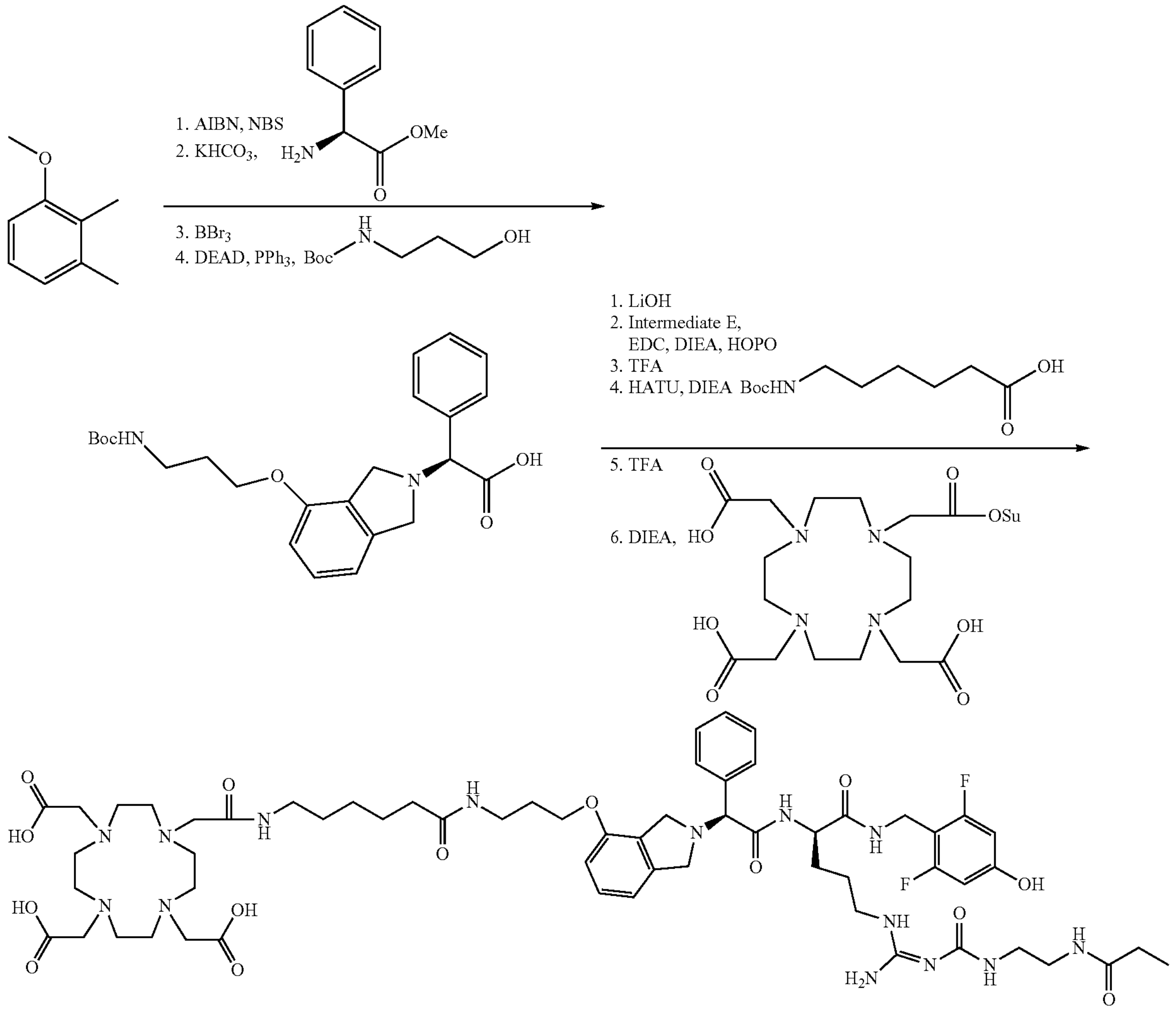

Step 1. Into a 250-mL round bottom flask, was placed a mixture of 1-methoxy-2,3-dimethylbenzene (5 g, 1 Eq, 0.04 μmol), AIBN (1.0 g, 0.2 Eq, 6.1 mmol), NBS (20 g, 3 Eq, 0.11 mol) and $CCl_4$ (50 mL). The reaction mixture was stirred at 75° C. for 16 hours. The mixture was diluted with water (100 mL), extracted with EtOAc (50 mL×3), then the combined organic layers were washed with water (50 mL×2), brine (50 mL), dried over anhydrous $Na_2SO_4$ and concentrated under reduced pressure. The crude product was purified by MPLC to provide 1,2-bis(bromomethyl)-3-methoxybenzene (6 g, 0.02 μmol, 60%) as an off-white solid.

Step 2. 1,2-bis(bromomethyl)-3-methoxybenzene was treated with methyl (S)-2-amino-2-phenylacetate and $KHCO_3$ in a manner similar to Step 2 of Example 6 to provide methyl (S)-2-(4-methoxyisoindolin-2-yl)-2-phenylacetate (1.6 g, 5.4 mmol, 80%) as a white solid. $[M+H]^+$=298.0.

Step 3. Into a 20-mL vial, was placed a mixture of methyl (S)-2-(4-methoxyisoindolin-2-yl)-2-phenylacetate (1.6 g, 1 Eq, 5.4 mmol) and DCM (3 mL), to which was added boron tribromide (13 g, 6.2 mL, 9.6 Eq, 52 mmol) at 0° C. over 20 min. The reaction mixture was stirred at 25° C. for 2 hours. The mixture was quenched with an aqueous solution of $NH_4Cl$ (10 mL), extracted with DCM (30 mL×3), then the mixture was concentrated under reduced pressure. The crude product was purified by Prep-HPLC to provide methyl (S)-2-(4-hydroxyisoindolin-2-yl)-2-phenylacetate (230 mg, 812 μmol, 15%) as a brown oil. $[M+H]^+$=284.0.

Step 4. Methyl (S)-2-(4-hydroxyisoindolin-2-yl)-2-phenylacetate was treated with tert-butyl (3-hydroxypropyl) carbamate, DEAD, $PhP_3$ in a manner similar to Step 2 of Intermediate D (Example 1) to provide methyl (S)-2-(4-(3-((tert-butoxycarbonyl)amino)propoxy)isoindolin-2-yl)-2-phenylacetate (280 mg, 636 μmol, 78.3%) as a white solid. $[M+H]^+$=441.2.

Step 5. Into a 20-mL vial, was placed a mixture of methyl (S)-2-(4-(3-((tert-butoxycarbonyl)amino)propoxy)isoindolin-2-yl)-2-phenylacetate (200 mg, 1 Eq, 454 mol), LiOH (44 mg, 4.0 Eq, 1.8 mmol), MeOH (1 mL) and $H_2O$ (0.4 mL). The reaction mixture was stirred at 25° C. for 4 hours. The mixture was directly purified by MPLC to provide (S)-2-(4-(3-((tert-butoxycarbonyl)amino)propoxy)isoindolin-2-yl)-2-phenylacetic acid (190 mg, 445 mol, 98.1%) as a yellow oil. $[M+H]^+=427.4$.

Step 6. Into an 8-mL vial, was placed a mixture of (S)-2-(4-(3-((tert-butoxycarbonyl)amino)propoxy)isoindolin-2-yl)-2-phenylacetic acid (190 mg, 1 Eq, 445 mol), (R,Z)-2-amino-N-(2,6-difluoro-4-hydroxybenzyl)-5-(2-((2-propionamidoethyl)carbamoyl)guanidino)pentanamide (306 mg, 1.50 Eq, 669 μmol), HOPO (99 mg, 2.0 Eq, 0.89 mmol), EDC (171 mg, 2.00 Eq, 892 μmol), DIEA (115 mg, 155 μL, 2.00 Eq, 890 μmol) and DMF (2 mL). The reaction mixture was stirred at 25° C. for 3 hours. The crude product was purified by Prep-HPLC to provide tert-butyl (3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)oxy)propyl)carbamate (120 mg, 139 μmol, 31.1%) as a white solid. $[M+H]^+=866.6$.

Steps 7-8. tert-butyl (3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)oxy)propyl)carbamate was treated with TFA in a manner similar to Step 2 in the synthesis of Compound 1, then 6-((tert-butoxycarbonyl)amino)hexanoic acid, HATU and DIEA in a manner similar to Step 3 of the synthesis of Compound 1, to provide tert-butyl (6-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)oxy)propyl)amino)-6-oxohexyl) carbamate (100 mg, 102 μmol, 65.2%) as a white solid. $[M+H]^+=979.3$.

Step 9. tert-Butyl (6-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)oxy)propyl)amino)-6-oxohexyl)carbamate was treated with TFA in a manner similar to Step 2 in the synthesis of Compound 1, then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Step 5 in the synthesis of Compound 1 to provide the trifluoroacetic acid salt of 2,2',2"-(10-(9-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)oxy)propyl)amino)-2,9-dioxononyl)-1,4,7,10-tetraazacyclododecane-1,4,7-triyl) triacetic acid (63.2 mg, 45.8 μmol, 50%) as a white solid. MS: Calc'd for $C_{61}H_{87}F_3N_{13}O_{14}$: 1264.64, found $[M+H]^+$: 1265.5.

Example 17: 2,2',2"-(10-(2-((6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)(methyl)amino)propyl)amino)-6-oxohexyl)amino)-2-oxoethyl)-1,4,7,10-tetraazacyclododecane-1,4,7-triyl)triacetic acid (Compound 11)

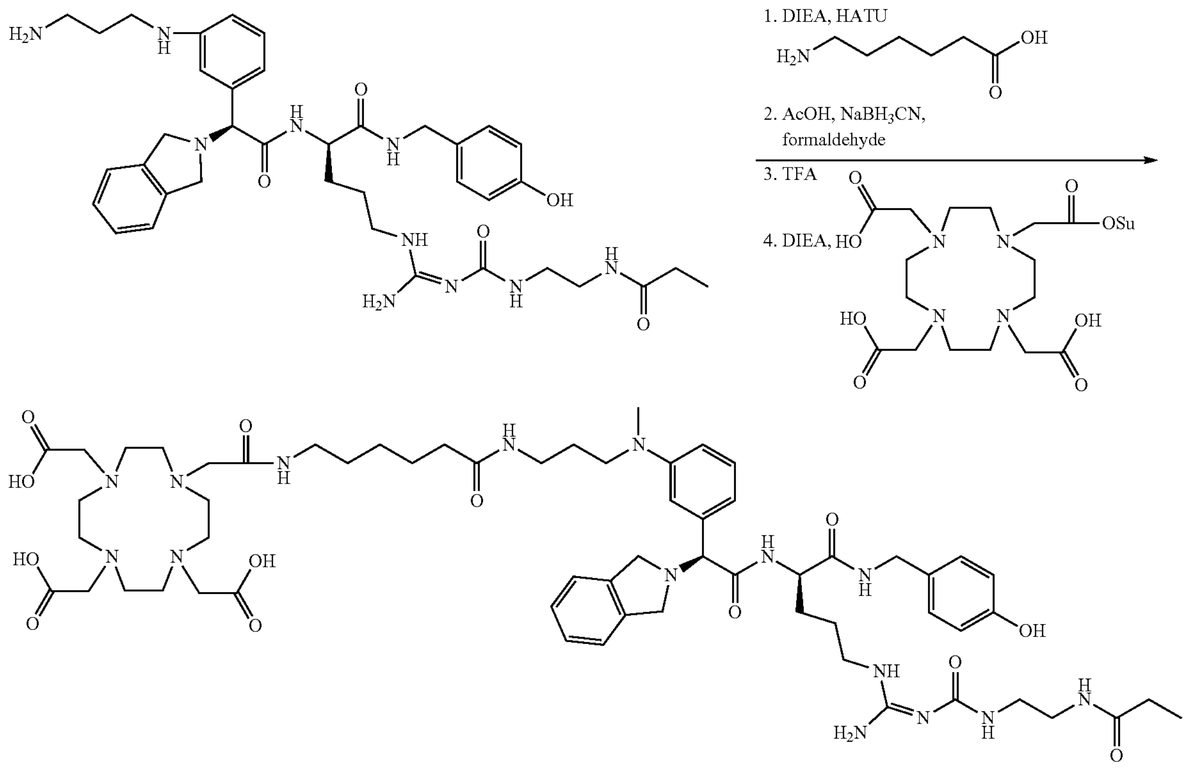

Step 1. (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide was treated with 6-((tert-butoxycarbonyl)amino) hexanoic acid, DIEA and HATU in a manner similar to Step 3 of the synthesis of Compound 1, to provide tert-butyl (6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)carbamate (50 mg, 53 μmol, 48%) as a white solid. $[M+Na]^+$=964.5.

Step 2. tert-Butyl (6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino) propyl)amino)-6-oxohexyl)carbamate was treated in a manner similar to Step 4 of Example 6 to provide tert-butyl (6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)(methyl)amino)propyl) amino)-6-oxohexyl)carbamate (12 mg, 13 μmol, 59%) as a white solid. $[M+Na]^+$=978.5.

Steps 3-4. tert-Butyl (6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl) (methyl)amino)propyl)amino)-6-oxohexyl)carbamate was treated with TFA in a manner similar to Step 2 in the synthesis of Compound 1, then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Step 5 in the synthesis of Compound 1 to provide the trifluoroacetic acid salt of 2,2',2"-(10-(2-((6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)(methyl)amino)propyl)amino)-6-oxohexyl)amino)-2-oxoethyl)-1,4,7,10-tetraazacyclododecane-1,4,7-triyl)triacetic acid. MS: Calc'd for $C_{61}H_{91}N_{15}O_{13}$: 1241.69, found $[M+H]^+$: 1242.5.

Example 18: 2,2',2"-(10-(2-((6-((3-(3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl) amino)-2-oxoethyl)-1,4,7,10-tetraazacyclododecane-1,4,7-triyl)triacetic acid (Compound 12)

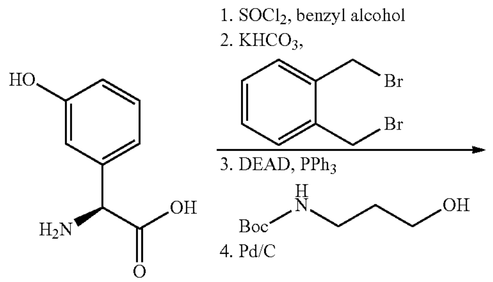

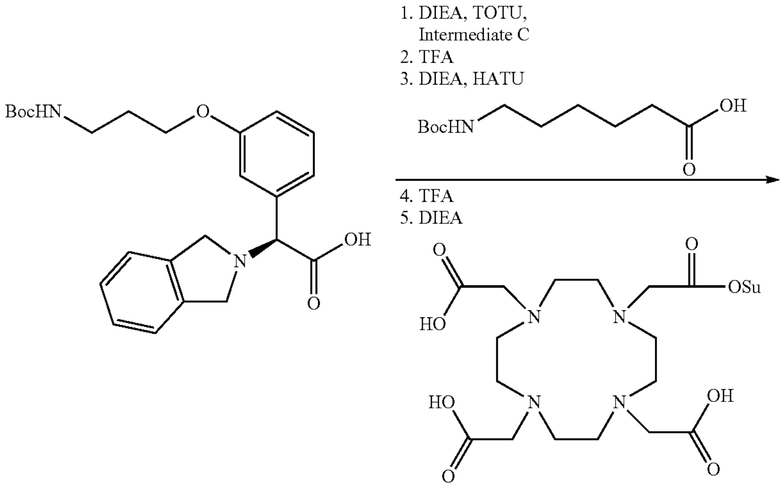

-continued

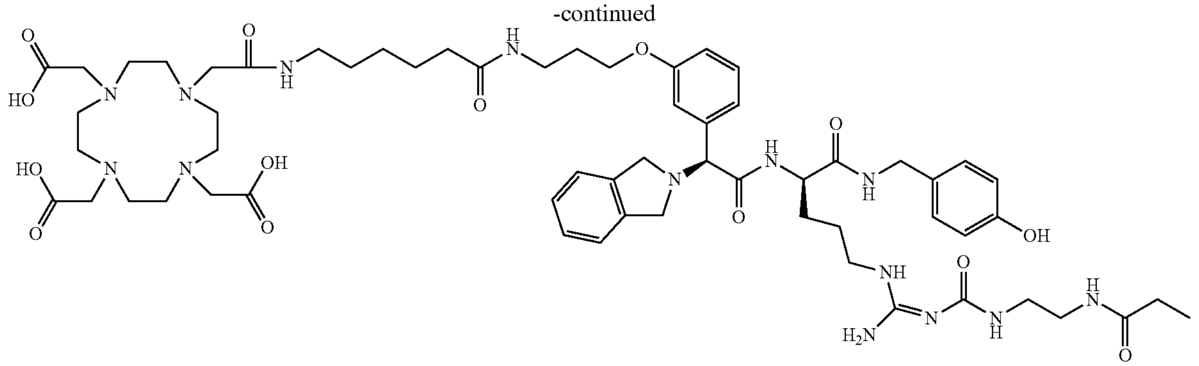

Step 1. Into a 250-mL three-necked round bottom, flask purged and maintained under an inert atmosphere of argon, was placed a mixture of (S)-2-amino-2-(3-hydroxyphenyl) acetic acid (1.0 g, 1 Eq, 6.0 mmol) and benzyl alcohol (50 mL), to which was added sulfurous dichloride (9.2 g, 13 Eq, 77 mmol) dropwise at 0° C. over 30 min. The reaction mixture was stirred at 25° C. for 2 hours. The mixture was concentrated under reduced pressure. The crude product was washed with cold ethyl ether, filtered and dried to afford benzyl (S)-2-amino-2-(3-hydroxyphenyl)acetate hydrochloride (800 mg, 2.72 mmol, 46%) as a brown solid. $[M+H]^+$=258.1.

Step 2. benzyl (S)-2-amino-2-(3-hydroxyphenyl)acetate hydrochloride was treated with 1,2-bis(bromomethyl)benzene and $KHCO_3$ in a manner similar to Example 13, Step 2 to provide benzyl (S)-2-(3-hydroxyphenyl)-2-(isoindolin-2-yl)acetate (410 mg, 1.14 mmol, 47.9%) as a yellow oil. $[M+H]^+$=360.1.

Step 3. Into a 50-mL three-necked round bottom flask, purged and maintained under an inert atmosphere of nitrogen, was placed a mixture of benzyl (S)-2-(3-hydroxyphenyl)-2-(isoindolin-2-yl)acetate (360 mg, 1 Eq, 1.00 mmol), tert-butyl (3-hydroxypropyl)carbamate (800 mg, 4.56 Eq, 4.57 mmol) and THE (5 mL), to which was added triphenylphosphane (550 mg, 2.09 Eq, 2.10 mmol) dropwise at 0° C. over 10 min. Then DEAD (350 mg, 315 μL, 2.01 Eq, 2.01 mmol) was added to the reaction mixture and the mixture was stirred at 0° C. for 15 min. The mixture was quenched with an aqueous solution of $NH_4Cl$ (50 mL), extracted with EtOAc (50 mL×3), then the combined organic layers were washed with brine (50 mL), dried over anhydrous $Na_2SO_4$ and concentrated under reduced pressure. The crude product was purified by MPLC to provide benzyl (S)-2-(3-(3-((tert-butoxycarbonyl)amino)propoxy)phenyl)-2-(isoindolin-2-yl) acetate (300 mg, 581 μmol, 58.0%) as a yellow oil.

Step 4. benzyl (S)-2-(3-(3-((tert-butoxycarbonyl)amino) propoxy)phenyl)-2-(isoindolin-2-yl)acetate was treated with Pd/C in MeOH in a manner similar to Example 13, Step 4 to provide (S)-2-(3-(3-((tert-butoxycarbonyl)amino) propoxy)phenyl)-2-(isoindolin-2-yl)acetic acid (170 mg, 399 μmol, 68.6%) as a white solid. $[M+H]^+$=427.2.

Step 5. (S)-2-(3-(3-((tert-butoxycarbonyl)amino) propoxy)phenyl)-2-(isoindolin-2-yl)acetic acid was treated with Intermediate C, DIEA and TOTU in a manner similar to Step 1 of the synthesis of Compound 1 to provide tert-butyl (3-(3-((1S,4R,Z)-9-amino-4-((4-hydroxybenzyl) carbamoyl)-1-(isoindolin-2-yl)-2,11,16-trioxo-3,8,10,12,15-pentaazaoctadec-9-en-1-yl)phenoxy)propyl)carbamate (70 mg, 84 μmol, 21%) as a white solid. $[M+H]^+$=830.6.

Step 6. tert-Butyl (3-(3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)carbamate was treated with TFA in a manner similar to Step 2 in the synthesis of Compound 1 to provide (R)-2-((S)-2-(3-(3-aminopropoxy)phenyl)-2-(isoindolin-2-yl)acetamido)-N-(4-hydroxybenzyl)-5-((Z)-2-((2-propionamidoethyl)carbamolguanidino)pentanamide (55 mg, 75 μmol, 89%). $[M+H]^+$=730.2.

Step 7. (R)-2-((S)-2-(3-(3-aminopropoxy)phenyl)-2-(isoindolin-2-yl)acetamido)-N-(4-hydroxybenzyl)-5-((Z)-2-((2-propionamidoethyl)carbamoyl)guanidino)pentanamide was treated with 6-((tert-butoxycarbonyl)amino)hexanoic acid, DIEA, and HATU in a manner similar to Step 3 of the synthesis of Compound 1, to provide tert-butyl (6-((3-(3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl) carbamate (60 mg, 64 μmol, 84%) as a white solid. $[M+H]^+$=943.8.

Step 8. tert-butyl (6-((3-(3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)carbamate was treated with TFA in a manner similar to Step 2 in the synthesis of Compound 1 to provide crude 6-amino-N-(3-(3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy) propyl)hexanamide (40 mg, 47 μmol, 75%) which was used directly in the next step without further purification. $[M+H]^+$=843.7.

Step 9. 6-Amino-N-(3-(3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)hexanamide was treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the TFA salt of 2,2',2''-(10-(2-((6-((3-(3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)amino)-2-oxoethyl)-1,4,7,10-tetraazacyclododecane-1,4,7-triyl)triacetic acid (32.3 mg, 24.0 μmol, 51%) as a white solid. MS: Calc'd $C_{60}H_{88}N_{14}O_{14}$: 1228.66, found $[M+H]^+$: 1229.5.

Example 19: 2,2',2"-(10-(2-(((R)-5-amino-6-((3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino)propyl)amino)-6-oxohexyl)amino)-2-oxoethyl)-1,4,7,10-tetraazacyclododecane-1,4,7-triyl)triacetic acid (Compound 13)

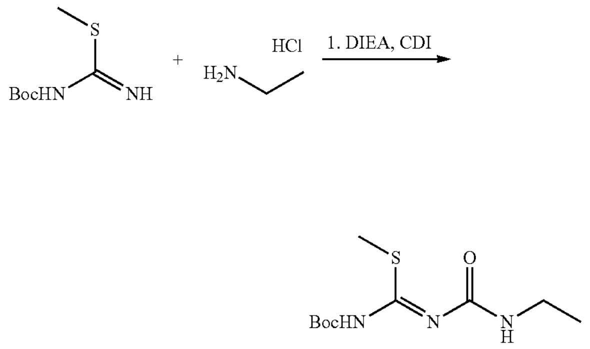

Synthesis of Boc protected methyl (Z)—N-(ethylcarbamoyl)-12-azanecarbimidothioate Step 1. Into a 250-mL round bottom, was placed a mixture of Intermediate A (6.0 g, 50% Wt, 1 Eq, 16 mmol), CDI (4.0 g, 1.6 Eq, 25 mmol), N-ethyl-N-isopropylpropan-2-amine (10.0 g, 4.9 Eq, 77.4 mmol) and THE (60 mL). The reaction mixture was stirred at 0° C. for 1 hour, then ethanamine hydrochloride (1.4 g, 1.1 Eq, 17 mmol) was added and the reaction mixture was stirred at 25° C. for an additional 8 hours. The mixture was diluted with 100 mL of water, extracted with EtOAc (100 mL×3), the combined organic layers were washed with water (100 mL×2) and brine (100 mL), dried over anhydrous $Na_2SO_4$ and concentrated under reduced pressure. The crude product was purified by MPLC to provide Boc protected methyl (Z)—N-(ethylcarbamoyl)-12-azanecarbimidothioate (2.6 g, 9.9 mmol, 63%) as a white solid. [M+H]=262.1.

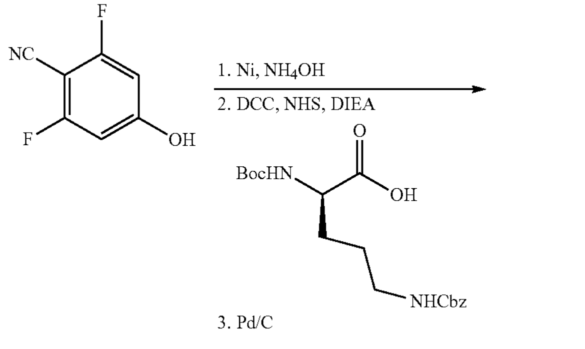

-continued

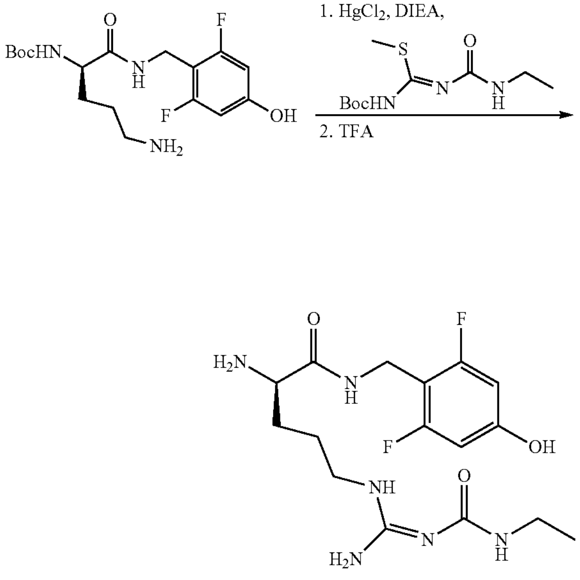

Intermediate H

Synthesis of Intermediate H

Step 1. 2,6-Difluoro-4-hydroxybenzonitrile was treated with $NH_3{\cdot}H_2O$ and Nickel in a manner similar to Step 1 in the synthesis of Intermediate C (Example 1) to provide 4-(aminomethyl)-3,5-difluorophenol (24.6 g, 0.14 μmol, 62%) as an off-white solid. [M−H]=158.1.

Step 2. (A) Into an 8-mL vial, was placed a mixture of (R)-5-(((benzyloxy)carbonyl)amino)-2-((tert-butoxycarbonyl)amino)pentanoic acid (9 g, 1 Eq, 0.02 mol), dicyclohexylcarbodiimide (7.8 g, 6.8 mL, 1.5 Eq, 38 mmol), N-hydroxysuccinimide (4.3 g, 1.5 Eq, 37 mmol) and THE (100 mL). The reaction mixture was stirred at 25° C. for 2 hours. The mixture was added to reaction (B), and transferred with THF. (B) Into another 8-mL vial, was placed a mixture of solution from step (A), 4-(aminomethyl)-3,5-difluorophenol (4.0 g, 1 Eq, 25 mmol), DIEA (9.7 g, 13 mL, 3.0 Eq, 75 mmol) and THE (100 mL). The reaction mixture was stirred at 25° C. for 2 hours. The mixture was concentrated and the crude product was purified by MPLC to provide benzyl tert-butyl (5-((2,6-difluoro-4-hydroxybenzyl)amino)-5-oxopentane-1,4-diyl)(R)-dicarbamate (11 g, 20 mmol, 78%) as a grey solid. [M+H]=508.4.

Steps 3-5. Benzyl tert-butyl (5-((2,6-difluoro-4-hydroxybenzyl)amino)-5-oxopentane-1,4-diyl)(R)-dicarbamate was treated with Pd/C in a manner similar to Step 3 in the synthesis of Intermediate C, then treated with $HgCl_2$, DIEA, and Boc protected methyl (Z)—N-(ethylcarbamoyl)-12-azanecarbimidothioate in a manner similar to Step 4 in the synthesis of Intermediate C, then treated with TFA in a manner similar to Step 5 in the synthesis of Intermediate C to provide the trifluoroacetic acid salt of (R,Z)-2-amino-N-(2,6-difluoro-4-hydroxybenzyl)-5-(2-(ethylcarbamoyl)guanidino)pentanamide (3.2 g, 5.8 mmol, 59%) as an off-white solid. MS: Calc'd for $C_{18}H_{25}F_2N_6O_5$: 500.18, found [M+H−TFA]$^+$: 387.2.

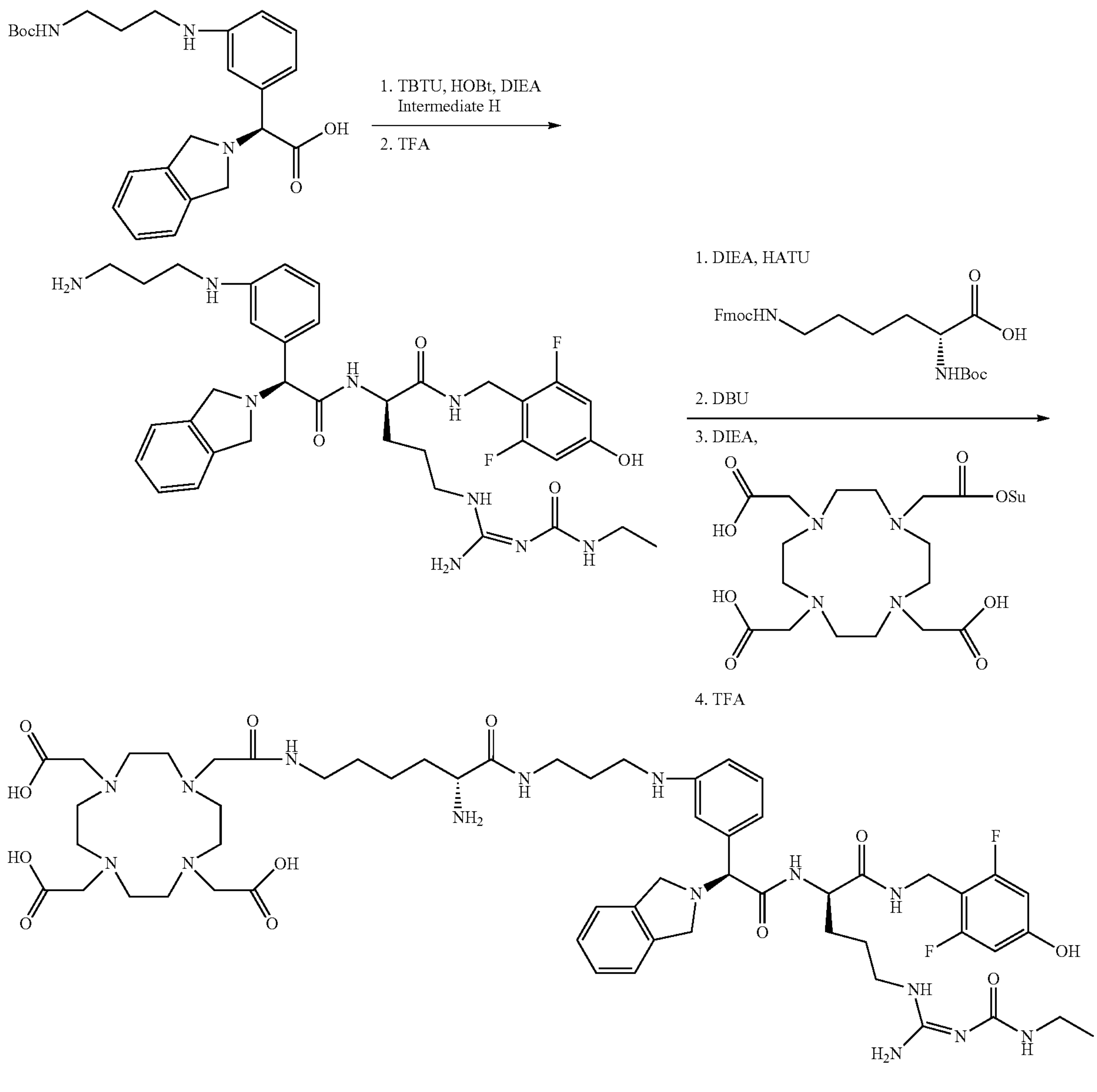

Step 1. (S)-2-(3-((3-((tert-butoxycarbonyl)amino)propyl)amino)phenyl)-2-(isoindolin-2-yl)acetic acid (from Step 5 of Example 6) was treated with TBTU, HOBt, DIEA and (R,Z)-2-amino-N-(2,6-difluoro-4-hydroxybenzyl)-5-(2-(ethylcarbamoyl)guanidino)pentanamide (Intermediate H) in a manner similar to Example 13, Step 5 to provide the front peak fractions as tert-butyl (3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino)propyl)carbamate (185 mg, 233 μmol, 16.5%) as a white solid. [M+H]=794.2.

Step 2. tert-butyl (3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino)propyl)carbamate was treated with TFA in a manner similar to Step 2 in the synthesis of Compound 1 to provide (R)-2-((S)-2-(3-((3-aminopropyl)amino)phenyl)-2-(isoindolin-2-yl)acetamido)-N-(2,6-difluoro-4-hydroxybenzyl)-5-((Z)-2-(ethylcarbamoyl)guanidino)pentanamide (110 mg, 0.14 mmol, 94%) as a white solid. [M+H]=694.5.

Step 3. (R)-2-((S)-2-(3-((3-aminopropyl)amino)phenyl)-2-(isoindolin-2-yl)acetamido)-N-(2,6-difluoro-4-hydroxybenzyl)-5-((Z)-2-(ethylcarbamoyl)guanidino)pentanamide was treated with $N_6$-(((9H-fluoren-9-yl)methoxy)carbonyl)-$N_2$-(tert-butoxycarbonyl)-D-lysine, HATU and DIEA in a manner similar to Step 3 of the Synthesis of Compound 1, to provide (9H-fluoren-9-yl)methyl tert-butyl ((R)-6-((3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino)propyl)amino)-6-oxohexane-1,5-diyl)dicarbamate (35 mg, 31 μmol, 39%) as a yellow oil. [M+H]=1144.5.

Step 4. (9H-fluoren-9-yl)methyl tert-butyl ((R)-6-((3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino)propyl)amino)-6-oxohexane-1,5-diyl)dicarbamate was treated with DBU in a manner similar to Example 7, Step 4 to provide tert-butyl ((R)-6-amino-1-((3-((3-((11R,14S,Z)-6-amino-11-((2,6-difluoro-4-hydroxybenzyl)carbamoyl)-14-(isoindolin-2-yl)-4, 13-dioxo-3,5,7,12-tetraazatetradec-5-en-14-yl)phenyl) amino)propyl)amino)-1-oxohexan-2-yl)carbamate (24 mg, 26 μmol, 85%) as a white solid. [M+H]=922.8.

Step 5. tert-butyl ((R)-6-amino-1-((3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino)propyl)amino)-1-oxohexan-2-yl) carbamate was treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide 2,2',2''-(10-(2-(((R)-6-((3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl) amino)propyl)amino)-5-((tert-butoxycarbonyl)amino)-6-oxohexyl)amino)-2-oxoethyl)-1,4,7,10-tetraazacyclododecane-1,4,7-triyl)triacetic acid (25 mg, 19 μmol, 70%) as a white solid. [M+H]=1308.9.

Step 6. 2,2',2''-(10-(2-(((R)-6-((3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino)propyl)amino)-5-((tert-butoxycarbonyl)amino)-6-oxohexyl)amino)-2-oxoethyl)-1,4,7,10-tetraazacyclododecane-1,4,7-triyl)triacetic acid was treated with TFA in a manner similar to Step 2 in the synthesis of Compound 1 to provide 2,2',2''-(10-(2-(((R)-5-amino-6-((3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino) propyl)amino)-6-oxohexyl)amino)-2-oxoethyl)-1,4,7,10-tetraazacyclododecane-1,4,7-triyl)triacetic acid (22.3 mg, 16.9 μmol, 88%) as a white solid. MS: Calc'd for $C_{59}H_{84}F_5N_{15}O_{14}$: 1321.62, found $[M+H-TFA]^+$: 1208.5.

Example 20: 2,2',2''-(10-(2-((2-(3-((3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino)propyl) amino)-3-oxopropoxy)ethyl)amino)-2-oxoethyl)-1,4,7,10-tetraazacyclododecane-1,4,7-triyl)triacetic acid (Compound 14)

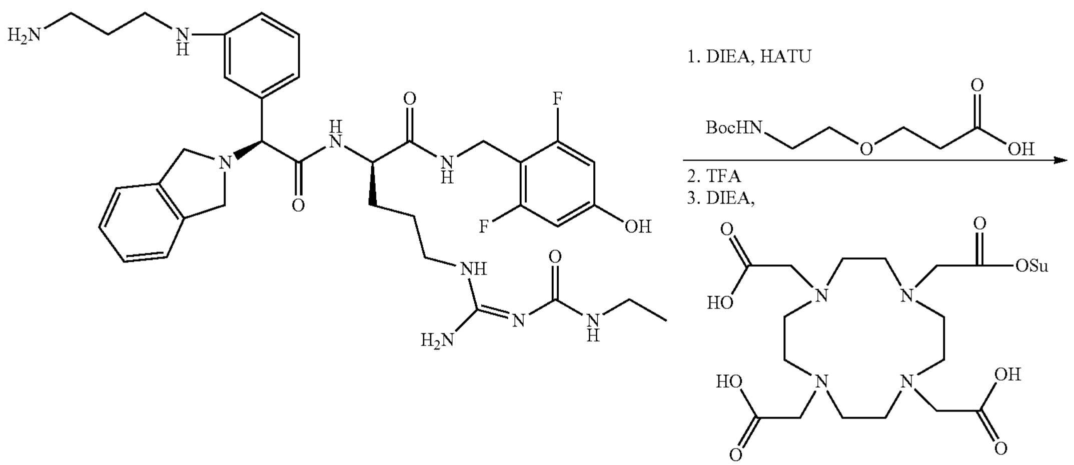

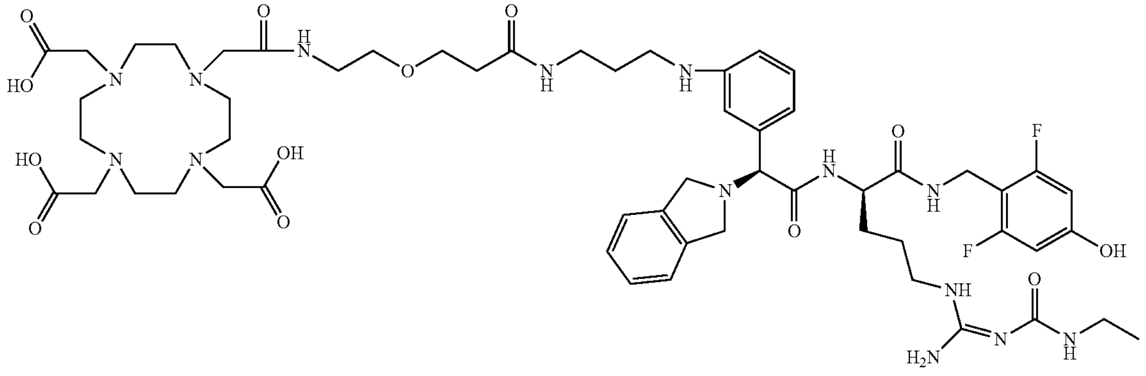

Step 1. (R)-2-((S)-2-(3-((3-aminopropyl)amino)phenyl)-2-(isoindolin-2-yl)acetamido)-N-(2,6-difluoro-4-hydroxybenzyl)-5-((Z)-2-(ethylcarbamoyl)guanidino)pentanamide was treated with 3-(2-((tert-butoxycarbonyl)amino)ethoxy) propanoic acid, HATU and DIEA in a manner similar to Step 3 of the synthesis of Compound 1, to provide tert-butyl (2-(3-((3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino)propyl) amino)-3-oxopropoxy)ethyl)carbamate (40 mg, 44 μmol, 56%) as a yellow oil. [M+H]=909.4.

Step 2. tert-Butyl (2-(3-((3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino)propyl)amino)-3-oxopropoxy)ethyl)carbamate was treated with TFA in a manner similar to Step 2 in the synthesis of Compound 1 to provide (R)-2-((S)-2-(3-((3-(3-(2-aminoethoxy)propanamido)propyl)amino)phenyl)-2-(isoindolin-2-yl)acetamido)-N-(2,6-difluoro-4-hydroxybenzyl)-5-((Z)-2-(ethylcarbamoyl)guanidino)pentanamide (35 mg, 43 μmol, 98%) as a yellow oil. [M+H]=809.6.

Step 3. (R)-2-((S)-2-(3-((3-(3-(2-aminoethoxy)propanamido)propyl)amino)phenyl)-2-(isoindolin-2-yl)acetamido)-N-(2,6-difluoro-4-hydroxybenzyl)-5-((Z)-2-(ethylcarbamoyl)guanidino)pentanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the TFA salt of 2,2',2"-(10-(2-((2-(3-((3-((3-((11R,14S,Z)-6-amino-11-((2,6-difluoro-4-hydroxybenzyl)carbamoyl)-14-(isoindolin-2-yl)-4,13-dioxo-3,5,7,12-tetraazatetradec-5-en-14-yl)phenyl)amino)propyl)amino)-3-oxopropoxy)ethyl) amino)-2-oxoethyl)-1,4,7,10-tetraazacyclododecane-1,4,7-triyl)triacetic acid (33.6 mg, 25.7 μmol, 61%) as a white solid. MS: Calc'd for $C_{58}H_{81}F_5N_{14}O_{15}$: 1308.59, found $[M+H-TFA]^+$: 1195.4.

Example 21: 2,2',2"-(10-(2-((2-(3-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropoxy)ethyl)amino)-2-oxoethyl)-1,4,7,10-tetraazacyclododecane-1,4,7-triyl)triacetic acid (Compound 15)

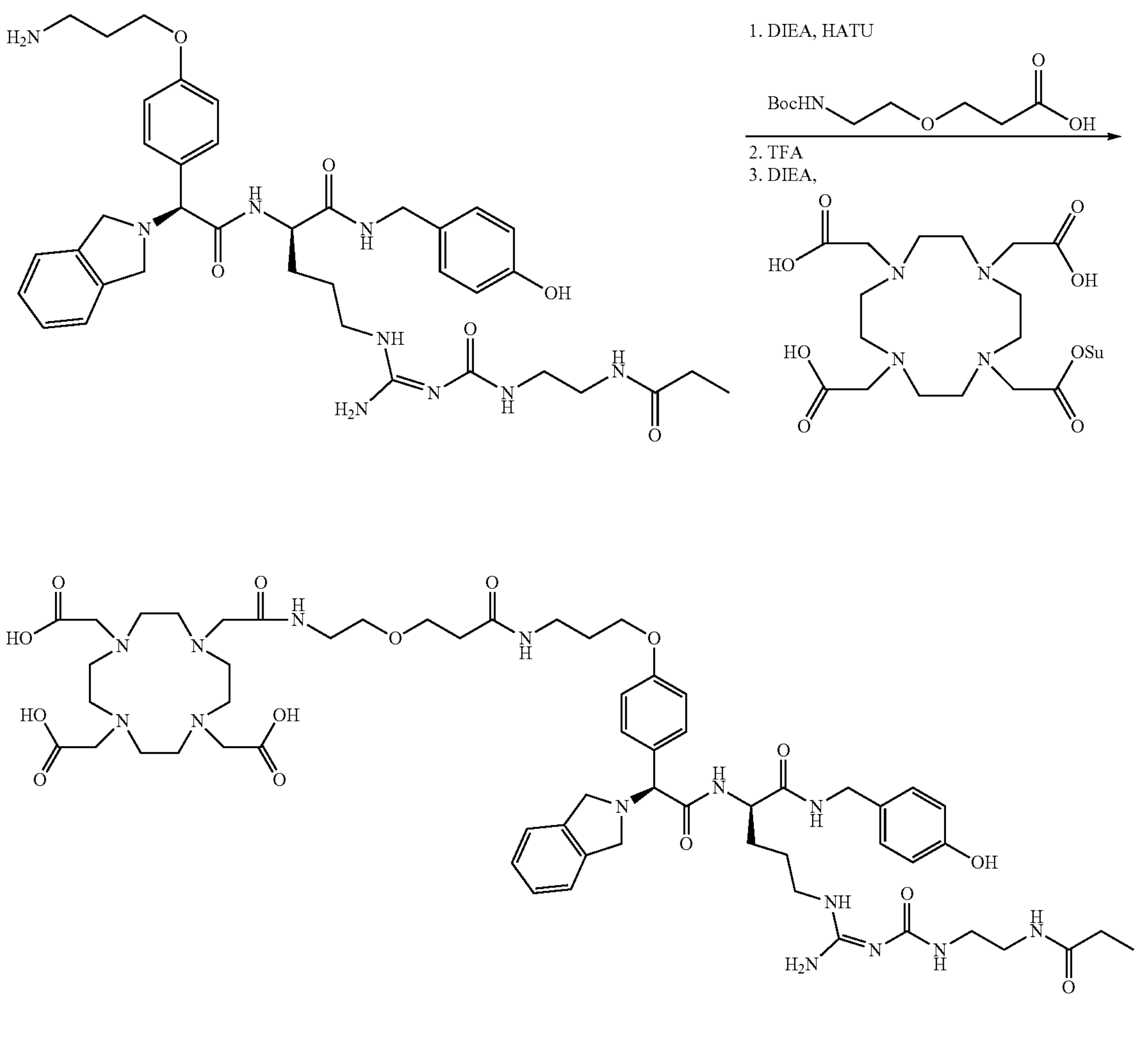

Steps 1-3. The TFA salt of 2,2',2"-(10-(2-((2-(3-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropoxy)ethyl)amino)-2-oxoethyl)-1,4,7,10-tetraazacyclododecane-1,4,7-triyl)triacetic acid was synthesized from (R)-2-((S)-2-(4-(3-aminopropoxy)phenyl)-2-(isoindolin-2-yl)acetamido)-N-(4-hydroxybenzyl)-5-((Z)-2-((2-propionamidoethyl)carbamoyl)guanidino)pentanamide and 3-(2-((tert-butoxycarbonyl)amino)ethoxy)propanoic acid in manner similar to Steps 3-5 in the synthesis of Compound 1A to provide the product (34.2 mg, 25.4 μmol, 74%) as a white solid. MS: Calc'd for $C_{61}H_{87}F_3N_{14}O_{17}$: 1344.63, found $[M+H-TFA]^+$: 1231.6.

Example 22: 2,2',2"-(10-(2-((2-((2-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3,4-dioxocyclobut-1-en-1-yl)amino)ethyl)amino)-2-oxoethyl)-1,4,7,10-tetraazacyclododecane-1,4,7-triyl)triacetic acid (Compound 16)

Step 1. (R)-2-((S)-2-(4-(3-aminopropoxy)phenyl)-2-(isoindolin-2-yl)acetamido)-N-(4-hydroxybenzyl)-5-((Z)-2-((2-propionamidoethyl)carbamoyl)guanidino)pentanamide (60 mg, 1 Eq, 82 μmol) is treated with 3,4-diethoxycyclobut-3-ene-1,2-dione and DIEA in a manner similar to Step 8 of Example 6 to provide crude (R)-2-((S)-2-(4-(3-((2-ethoxy-3,4-dioxocyclobut-1-en-1-yl)amino)propoxy)phenyl)-2-(isoindolin-2-yl)acetamido)-N-(4-hydroxybenzyl)-5-((Z)-2-((2-propionamidoethyl)carbamoyl)guanidino)pentanamide, which was used directly in the next step without purification. $[M+H]^+$=854.3.

Step 2. (R)-2-((S)-2-(4-(3-((2-ethoxy-3,4-dioxocyclobut-1-en-1-yl)amino)propoxy)phenyl)-2-(isoindolin-2-yl)acetamido)-N-(4-hydroxybenzyl)-5-((Z)-2-((2-propionamidoethyl)carbamoyl)guanidino)pentanamide was treated with ethylene-1,2-diamine in a manner similar to Step 9 of Example 6 to provide (R)-2-((S)-2-(4-(3-((2-((2-aminoethyl)amino)-3,4-dioxocyclobut-1-en-1-yl)amino)propoxy)phenyl)-2-(isoindolin-2-yl)acetamido)-N-(4-hydroxybenzyl)-5-((Z)-2-((2-propionamidoethyl)carbamoyl)guanidino)pentlmide (36 mg, 41 μmol, 57%) as a white solid. $[M+H]^+$=868.3.

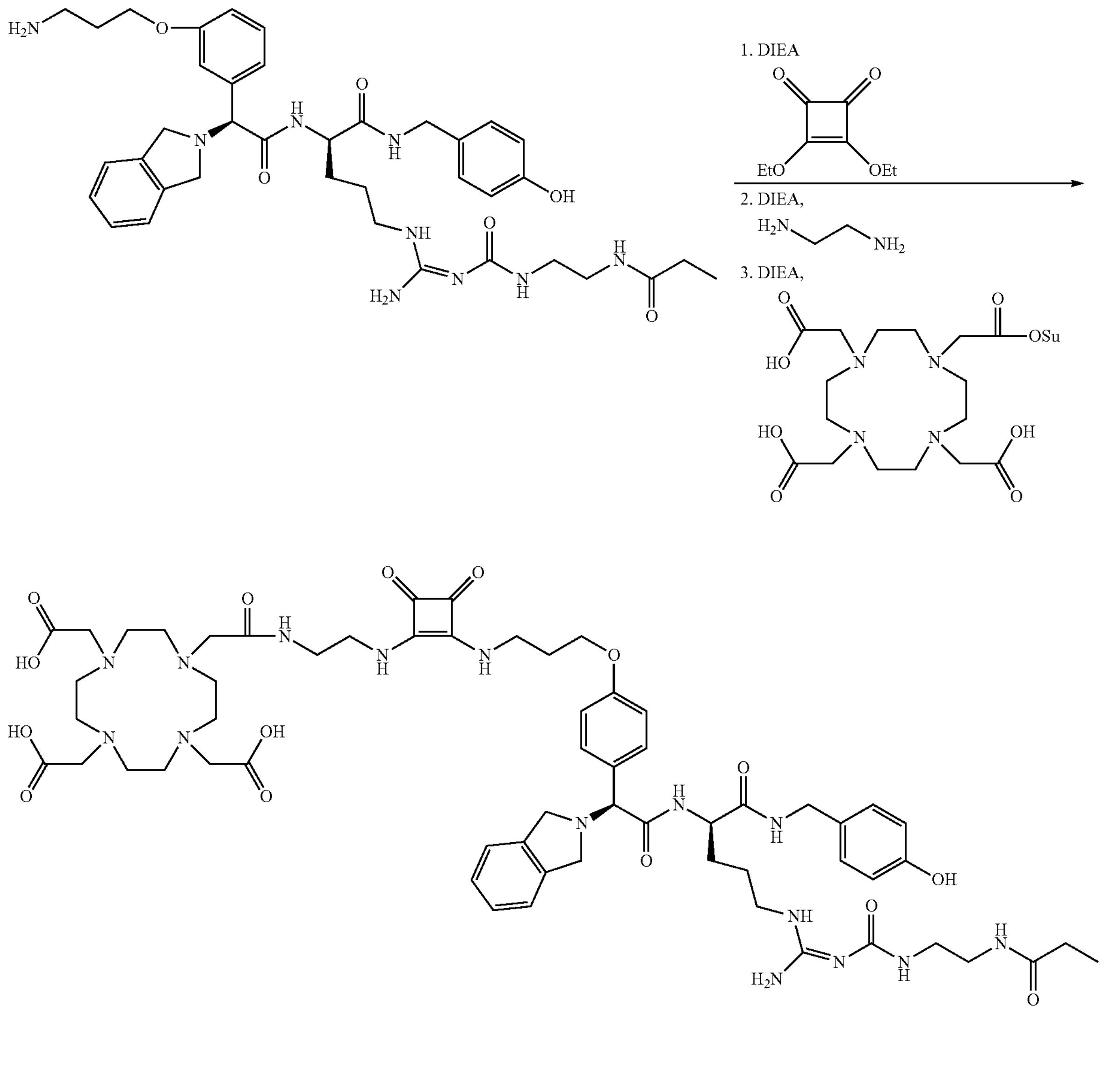

Step 3. (R)-2-((S)-2-(4-(3-((2-((2-aminoethyl)amino)-3,4-dioxocyclobut-1-en-1-yl)amino)propoxy)phenyl)-2-(isoindolin-2-yl)acetamido)-N-(4-hydroxybenzyl)-5-((Z)-2-((2-propionamidoethyl)carbamoyl)guanidino)pentanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-((2-((2-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3,4-dioxocyclobut-1-en-1-yl)amino)ethyl)amino)-2-oxoethyl)-1,4,7,10-tetraazacyclododecane-1,4,7-triyl)triacetic acid (20.0 mg, 14.6 μmol, 36%) as a white solid. $[M+H]^+=1254.5$.

Example 23: 2,2',2"-(10-(2-((4-((2-(3-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropoxy)ethyl)carbamoyl)benzyl)amino)-2-oxoethyl)-1,4,7,10-tetraazacyclododecane-1,4,7-triyl)triacetic acid (Compound 17)

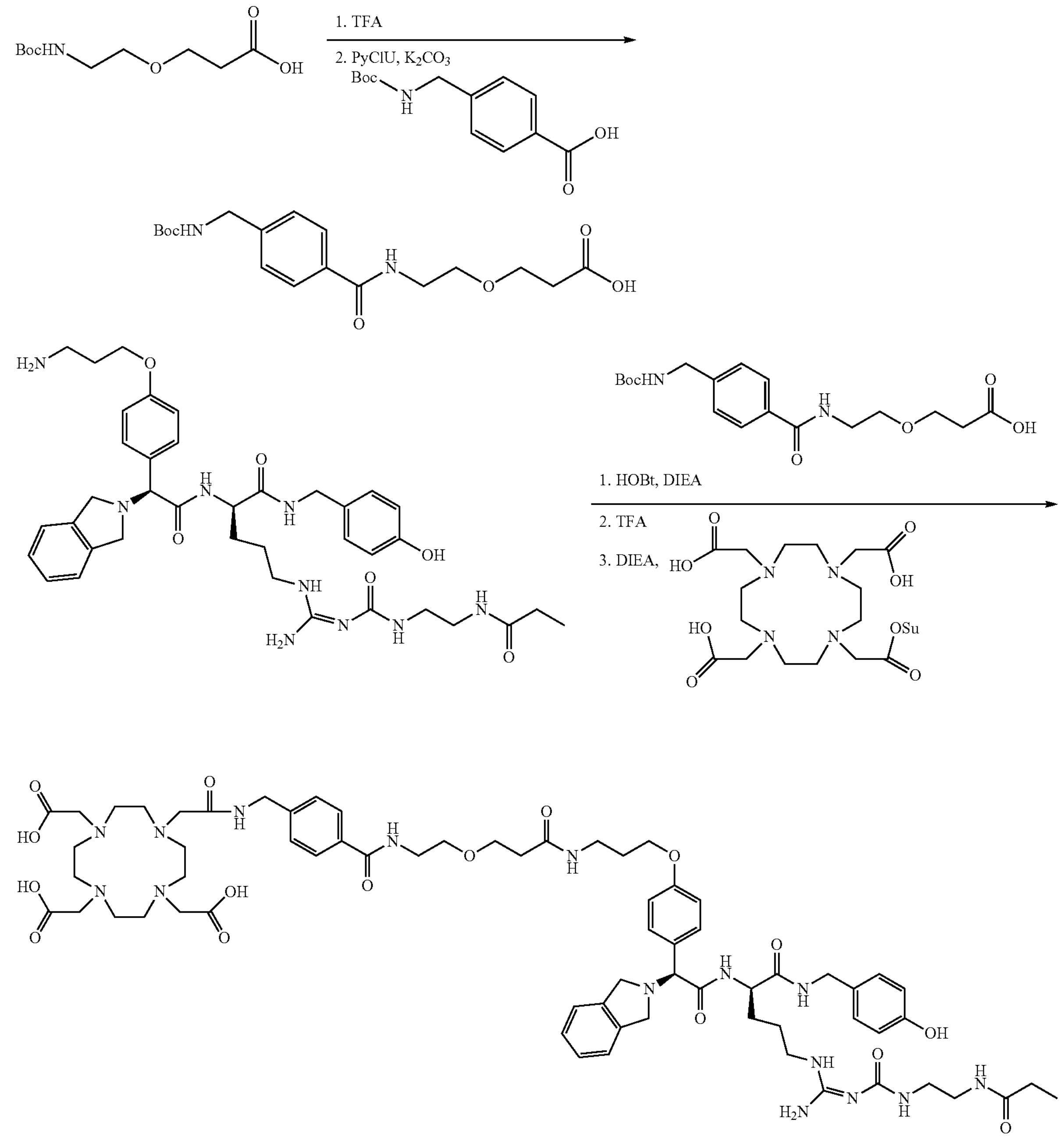

Step 1. Into a 40-mL vial, was placed a mixture of 3-(2-((tert-butoxycarbonyl)amino)ethoxy)propanoic acid (550 mg, 1 Eq, 2.36 mmol) and DCM (5 mL), to which was added TFA (1 mL). The reaction mixture was stirred at 20° C. for 1 hour. The mixture was concentrated under reduced pressure to provide 3-(2-aminoethoxy)propanoic acid (540 mg, 2.0 mmol, 86%) as a yellow oil.

Step 2. Into a 40-mL vial, was placed a mixture of 4-(((tert-butoxycarbonyl)amino)methyl)benzoic acid (510 mg, 1.00 Eq, 2.03 mmol), PyClU (675 mg, 1.00 Eq, 2.03 mmol) and DMF (5 mL). The reaction mixture was stirred at 20° C. for 30 minutes, then 3-(2-aminoethoxy)propanoic acid (540 mg, 50% Wt, 1 Eq, 2.03 mmol) and $K_2CO_3$ (1.12 g, 4.00 Eq, 8.10 mmol) was added and the reaction mixture was stirred at 20° C. for an additional 0.5 hour. The mixture was directly purified by MPLC to provide 3-(2-(4-(((tert-butoxycarbonyl)amino)methyl)benzamido)ethoxy)propanoic acid (130 mg, 355 μmol, 17.5%) as a yellow oil. $[M+H]^+$=367.1.

Step 3. Into an 8-mL vial, was placed a mixture of (R)-2-((S)-2-(4-(3-aminopropoxy)phenyl)-2-(isoindolin-2-yl)acetamido)-N-(4-hydroxybenzyl)-5-((Z)-2-((2-propionamidoethyl)carbamoyl)guanidino)pentanamide 2,2,2-trifluoroacetate (50 mg, 1 Eq, 59 mol) and DMF (1 mL), to which was added 3-(2-(4-(((tert-butoxycarbonyl)amino)methyl)benzamido)ethoxy)propanoic acid (25 mg, 1.2 Eq, 68 mol), HOBt (13 mg, 1.4 Eq, 85 μmol), EDCI (16 mg, 1.4 Eq, 83 μmol) and DIEA (27 mg, 36 L, 3.5 Eq, 0.21 mmol). The reaction mixture was stirred at 20° C. for 6 hours. The mixture was directly purified by MPLC to provide tert-butyl (4-((2-(3-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropoxy)ethyl)carbamoyl)benzyl)carbamate (40 mg, 37 mol, 63%) as a yellow oil. $[M+H]^+$=1078.7.

Step 4. tert-Butyl (4-((2-(3-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropoxy)ethyl)carbamoyl)benzyl)carbamate was treated with TFA in a manner similar to Step 2 in the synthesis of Compound 1 to provide N-(2-(3-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropoxy)ethyl)-4-(aminomethyl)benzamide (60 mg, 55 μmol, 94%) as a yellow oil. $[M+H]^+$=978.8.

Step 5. N-(2-(3-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropoxy)ethyl)-4-(aminomethyl)benzamide was treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2''-(10-(2-((4-((2-(3-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropoxy)ethyl)carbamoyl)benzyl)amino)-2-oxoethyl)-1,4,7,10-tetraazacyclododecane-1,4,7-triyl)triacetic acid (30.9 mg, 20.9 μmol, 38%) as a white solid. MS: Calc'd for $C_{69}H_{94}F_3N_{15}O_{18}$: 1477.69, found $[M+H-TFA]^+$: 1364.6.

Example 24: 2,2',2''-(10-(2-((((1S,4r)-4-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)carbamoyl)cyclohexyl)methyl)amino)-2-oxoethyl)-1,4,7,10-tetraazacyclododecane-1,4,7-triyl)triacetic acid (Compound 18)

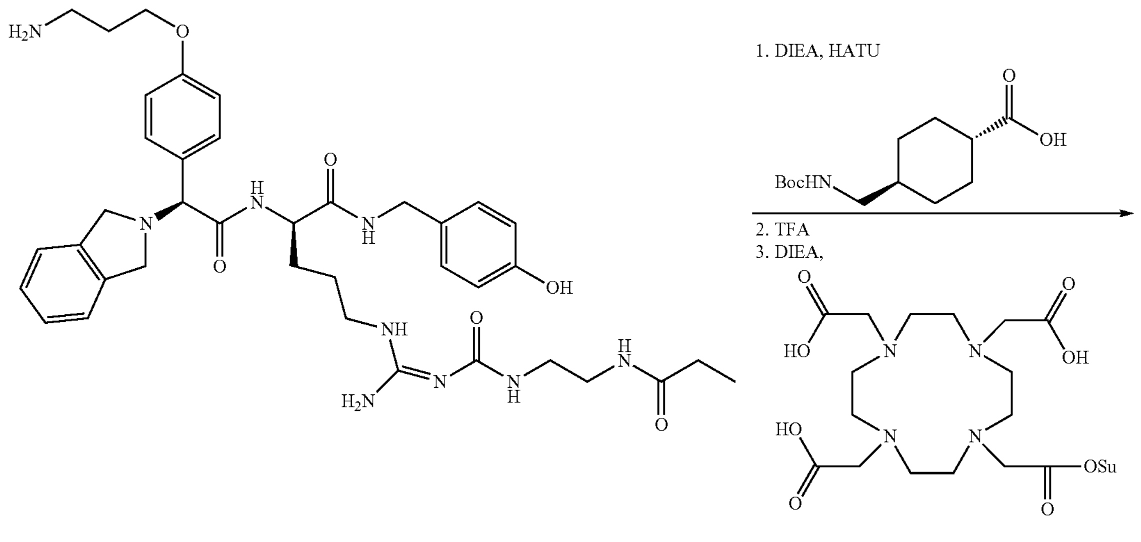

-continued

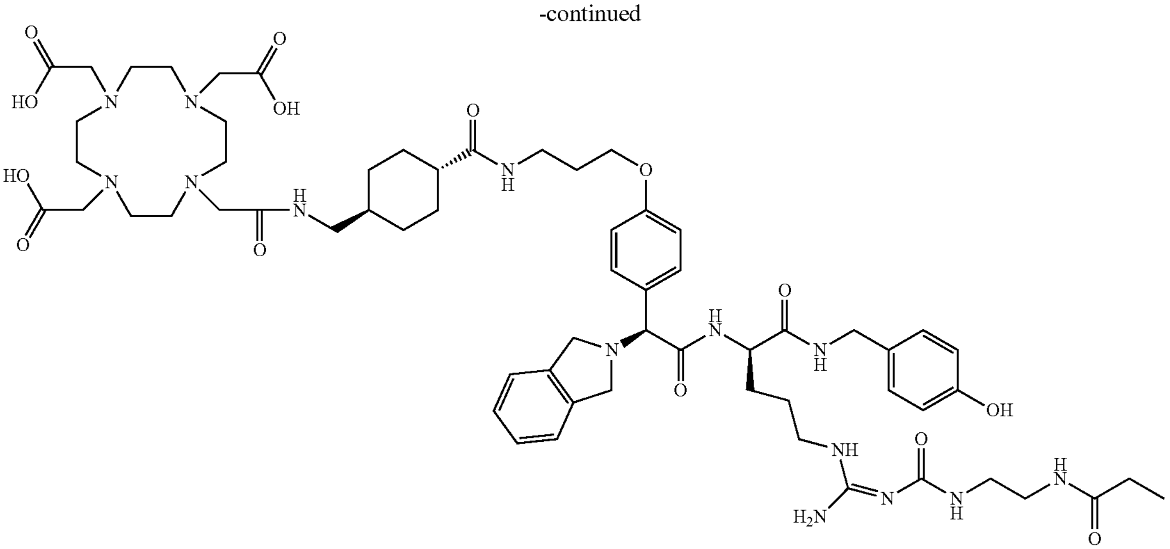

Step 1. (R)-2-((S)-2-(4-(3-aminopropoxy)phenyl)-2-(isoindolin-2-yl)acetamido)-N-(4-hydroxybenzyl)-5-((Z)-2-((2-propionamidoethyl)carbamoyl)guanidino)pentanamide 2,2,2-trifluoroacetate (50 mg, 1 Eq, 59 μmol) was treated with (1r,4r)-4-(((tert-butoxycarbonyl)amino)methyl)cyclohexane-1-carboxylic acid, HATU, and DIEA in a manner similar to Step 3 of the synthesis of Compound 1, to provide tert-butyl (((1S,4r)-4-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)carbamoyl)cyclohexyl)methyl)carbamate (16 mg, 15 μmol, 25%) as an off-white solid. $[M+H]^+$=969.6.

Step 2. tert-butyl (((1S,4r)-4-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)carbamoyl)cyclohexyl)methyl)carbamate (16 mg, 1 Eq, 17 μmol) was treated with TFA in a manner similar to Step 2 in the synthesis of Compound 1 to provide (1R,4S)—N-(3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)-4-(aminomethyl)cyclohexane-1-carboxamide 2,2,2-trifluoroacetate (9 mg, 8 μmol, 50%) as a brown oil, which was used directly in the next step without any purification. $[M+H]^+$=869.6.

Step 3. (1R,4S)—N-(3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)-4-(aminomethyl)cyclohexane-1-carboxamide 2,2,2-trifluoroacetate was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide 2,2',2"-(10-(2-((((1S,4r)-4-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy) propyl)carbamoyl)cyclohexyl)methyl)amino)-2-oxoethyl)-1,4,7,10-tetraazacyclododecane-1,4,7-triyl)triacetic acid (1.6 mg, 1.1 μmol, 10%) as an off-white solid. MS: Calc'd for $C_{62}H_{9}N_{14}O_{14}$: 1254.68, found $[M+H-TFA]^+$: 1255.6.

Example 25: 2,2',2"-(10-(2-((6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)amino)-2-oxoethyl)-1,4,7,10-tetraazacyclododecane-1,4,7-triyl)triacetic acid (Compound 19)

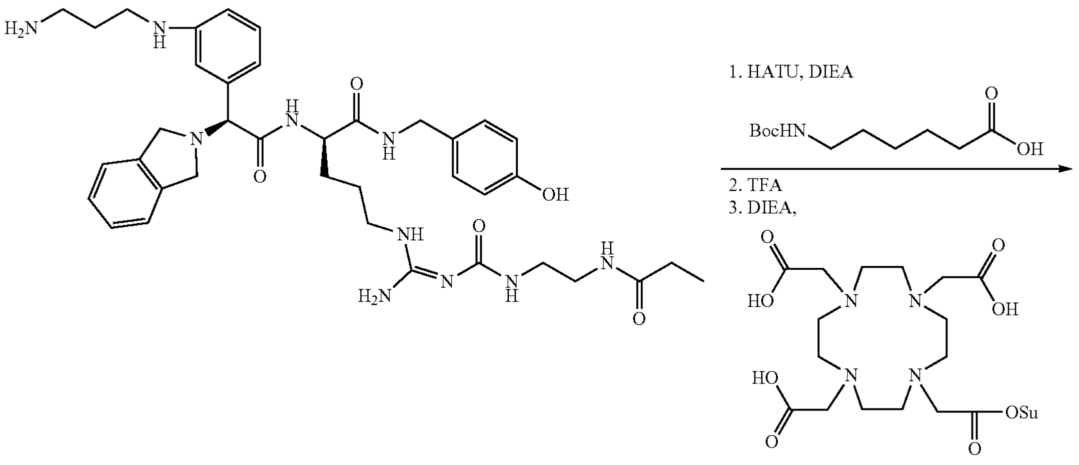

-continued

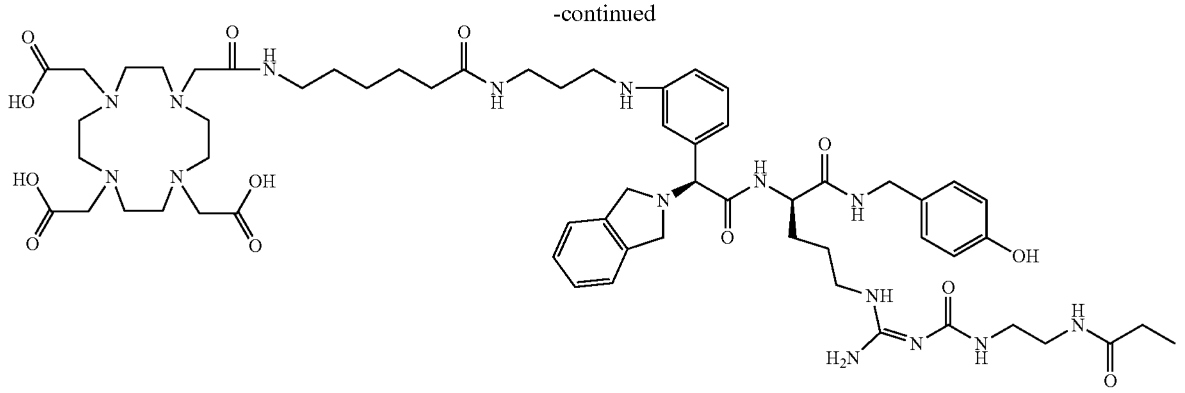

Step 1. Into an 8-mL vial, was placed a mixture of (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide 2,2,2-trifluoroacetate (50 mg, 50% wt, 1 Eq, 30 μmol) and DMF (1 mL), to which was added 6-((tert-butoxycarbonyl)amino) hexanoic acid (7 mg, 1 Eq, 0.03 mmol), HATU (12 mg, 1.1 Eq, 32 μmol) and DIEA (12 mg, 16 μL, 3.1 Eq, 93 μmol). The reaction mixture was stirred at 20° C. for 2 hours. The mixture was directly purified by MPLC to provide tert-butyl (6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)carbamate (16 mg, 17 μmol, 57%) as a yellow oil. $[M+H]^+=942.6$.

Step 2. tert-Butyl (6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino) propyl)amino)-6-oxohexyl)carbamate was treated with TFA in a manner similar to Step 2 in the synthesis of Compound 1 to provide 6-amino-N-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino) propyl)hexanamide (16 mg, 15 μmol, 90%) as a yellow oil. $[M+H]^+=842.5$.

Step 3. 6-Amino-N-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino) propyl)hexanamide was treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2''-(10-(2-((6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)amino)-2-oxoethyl)-1,4,7,10-tetraazacyclododecane-1,4,7-triyl) triacetic acid (4.6 mg, 3.3 μmol, 21%) as a yellow oil. MS: Calc'd for $C_{62}H_{90}F_3N_{15}O_{15}$: 1341.67, found $[M+H-TFA]^+$: 1228.6.

Example 26: 2,2',2''-(10-(2-((2-(3-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl) amino)-3-oxopropoxy)ethyl)amino)-2-oxoethyl)-1,4,7,10-tetraazacyclododecane-1,4,7-triyl)triacetic acid (Compound 20)

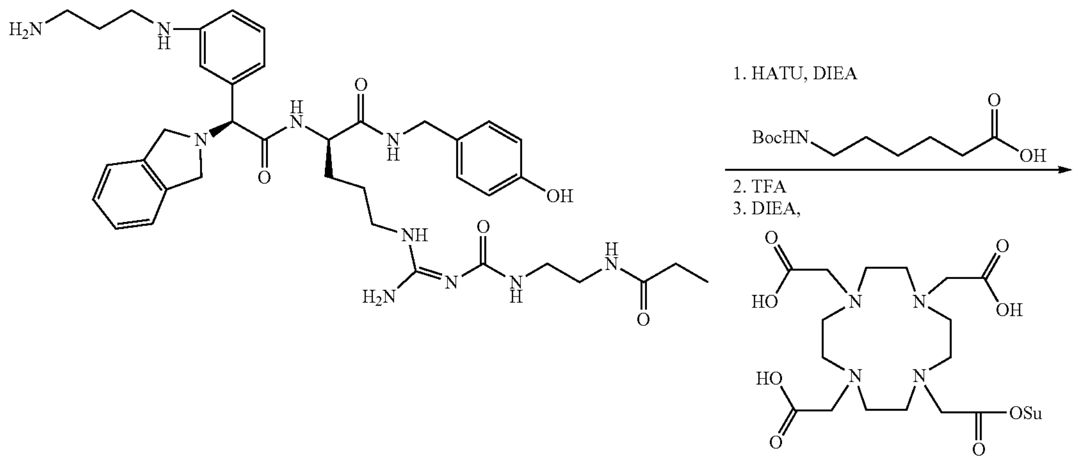

-continued

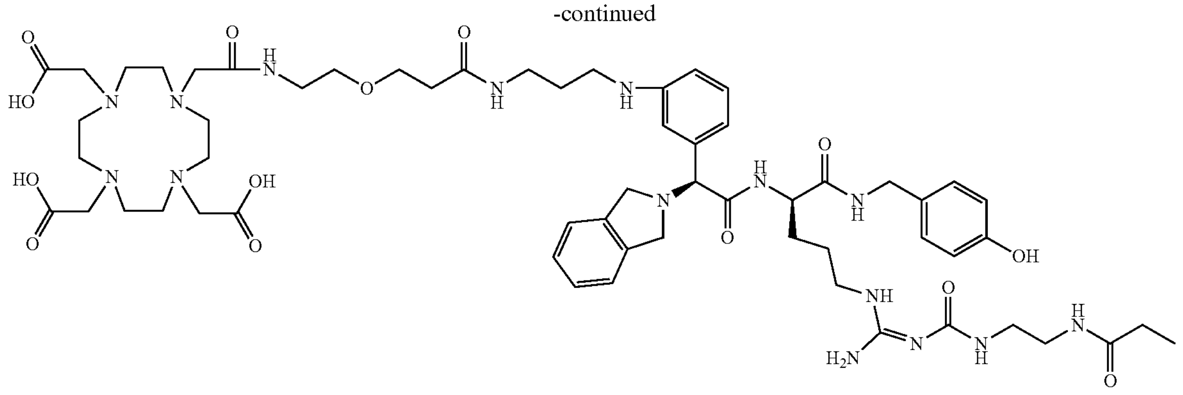

Step 1. Into an 8-mL vial, was placed a mixture of (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide 2,2,2-trifluoroacetate (50 mg, 1 Eq, 59 mol) and DMF (1 mL), to which was added 3-(2-((tert-butoxycarbonyl)amino)ethoxy) propanoic acid (7 mg, 0.5 Eq, 0.03 mmol), HATU (11 mg, 0.49 Eq, 29 μmol) and DIEA (23 mg, 31 μL, 3.0 Eq, 0.18 mmol). The reaction mixture was stirred at 20° C. for 2 hours. The mixture was directly purified by MPLC to provide tert-butyl (2-(3-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino) propyl)amino)-3-oxopropoxy)ethyl)carbamate (30 mg, 32 μmol, 54%) as a yellow oil. $[M+H]^+=944.6$.

Step 2. tert-Butyl (2-(3-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl) amino)propyl)amino)-3-oxopropoxy)ethyl)carbamate was treated with TFA in a manner similar to Step 2 in the synthesis of Compound 1 to provide (R)-2-((S)-2-(3-((3-(3-(2-aminoethoxy)propanamido)propyl)amino)phenyl)-2-(isoindolin-2-yl)acetamido)-N-(4-hydroxybenzyl)-5-((Z)-2-((2-propionamidoethyl)carbamoyl)guanidino)pentanamide (30 mg, 28 mol, 89%) as a yellow oil. $[(M+H)/2]^+=422.9$.

Step 3. (R)-2-((S)-2-(3-((3-(3-(2-aminoethoxy)propanamido)propyl)amino)phenyl)-2-(isoindolin-2-yl)acetamido)-N-(4-hydroxybenzyl)-5-((Z)-2-((2-propionamidoethyl)carbamoyl)guanidino)pentanamide was treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2''-(10-(2-((2-(3-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-3-oxopropoxy) ethyl)amino)-2-oxoethyl)-1,4,7,10-tetraazacyclododecane-1,4,7-triyl)triacetic acid (2.5 mg, 1.7 μmol, 4.7%) as a yellow oil. MS: Calc'd for $C_{61}H_{88}F_3N_{15}O_{16}$: 1343.65, found $[M+H-TFA]^+$: 1230.6.

Example 27: 2,2',2''-(10-(15-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-3,6,9-trimethyl-2,5,8,11-tetraoxo-3,6,9,12-tetraazapentadecyl)-1,4,7,10-tetraazacyclododecane-1,4,7-triyl)triacetic acid (Compound 21)

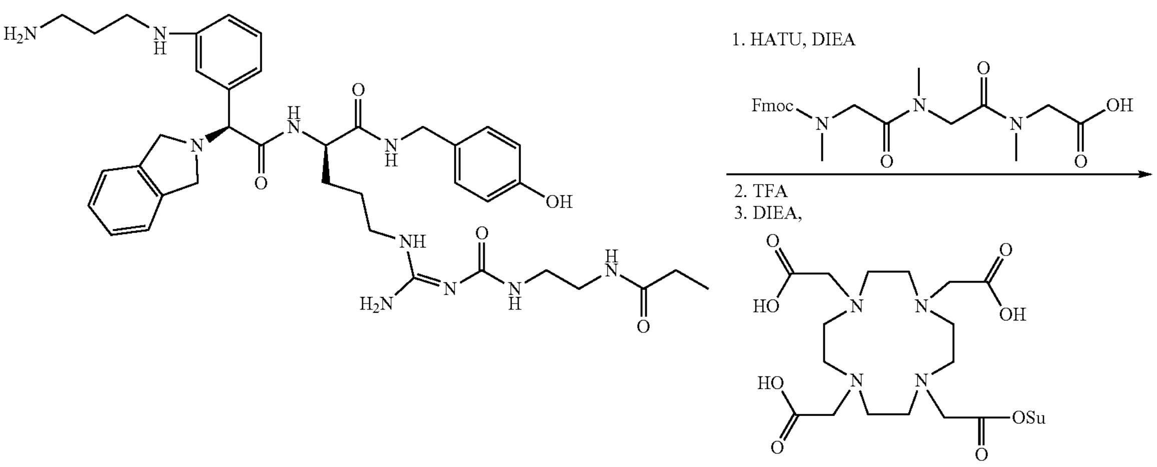

-continued

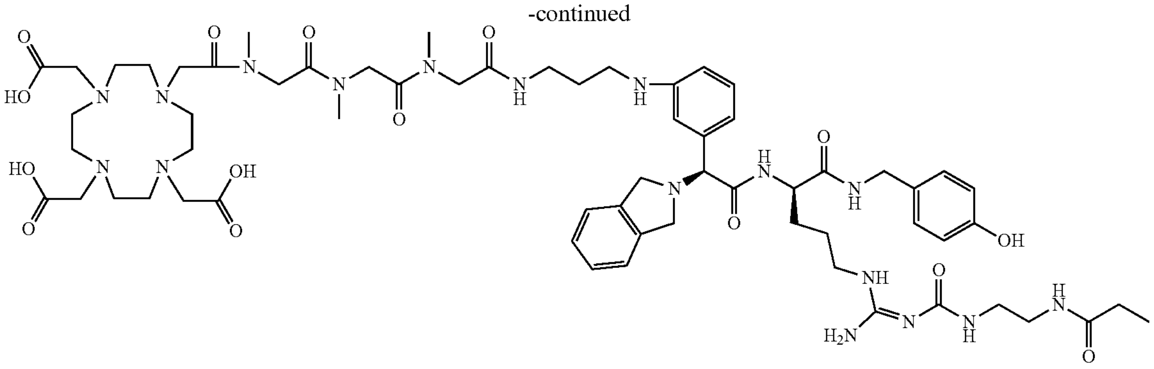

Step 1. Into an 8-mL vial, was placed a mixture of 1-(9H-fluoren-9-yl)-4,7,10-trimethyl-3,6,9-trioxo-2-oxa-4,7,10-triazadodecan-12-oic acid (34 mg, 1.1 Eq, 75 μmol), HATU (29 mg, 1.1 Eq, 76 μmol), DIEA (27 mg, 36 μL, 3.0 Eq, 0.21 mmol) and DMF (0.5 mL). The reaction mixture was stirred at 20° C. for 10 minutes, then (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide (50 mg, 1 Eq, 69 μmol) was added and the reaction mixture was stirred at 25° C. for an additional 2 hours. The mixture was directly purified by MPLC to provide (9H-fluoren-9-yl)methyl (2-((2-((2-((3-((3-((1S,4R,Z)-9-amino-4-((4-hydroxybenzyl) carbamoyl)-1-(isoindolin-2-yl)-2,11,16-trioxo-3,8,10,12,15-pentaazaoctadec-9-en-1-yl)phenyl)amino)propyl) amino)-2-oxoethyl)(methyl)amino)-2-oxoethyl)(methyl) amino)-2-oxoethyl)(methyl)carbamate (20 mg, 17 μmol, 25%) as a yellow oil. $[M+H]^+$=1164.7.

Step 2. (9H-fluoren-9-yl)methyl (2-((2-((2-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-2-oxoethyl)(methyl) amino)-2-oxoethyl)(methyl)amino)-2-oxoethyl)(methyl) carbamate was treated with TFA in a manner similar to Step 2 in the synthesis of Compound 1 to provide crude (R)-2-((S)-2-(3-((5,8-dimethyl-4,7,10-trioxo-2,5,8,11-tetraazatetradecan-14-yl)amino)phenyl)-2-(isoindolin-2-yl)acetamido)-N-(4-hydroxybenzyl)-5-((Z)-2-((2-propionamidoethyl)carbamoyl)guanidino)pentanamide, which was used in the next step without any purification. $[M+Na]^+$=965.6.

Step 3. (R)-2-((S)-2-(3-((5,8-dimethyl-4,7,10-trioxo-2,5,8,11-tetraazatetradecan-14-yl)amino)phenyl)-2-(isoindolin-2-yl)acetamido)-N-(4-hydroxybenzyl)-5-((Z)-2-((2-propionamidoethyl)carbamoyl)guanidino)pentanamide was treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2''-(10-(15-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-3,6,9-trimethyl-2,5,8,11-tetraoxo-3,6,9,12-tetraazapentadecyl)-1,4,7,10-tetraazacyclododecane-1,4,7-triyl)triacetic acid (8.7 mg, 6.0 μmol, 36%) as a white solid. MS: Calc'd for $C_{63}H_{93}N_{17}O_{15}$: 1327.7, found $[M+H-TFA]^+$: 1328.5.

Example 28: 2,2',2''-(10-(12-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-2,8-dioxo-6-oxa-3,7,9-triazadodecyl)-1,4,7,10-tetraazacyclododecane-1,4,7-triyl)triacetic acid (Compound 22)

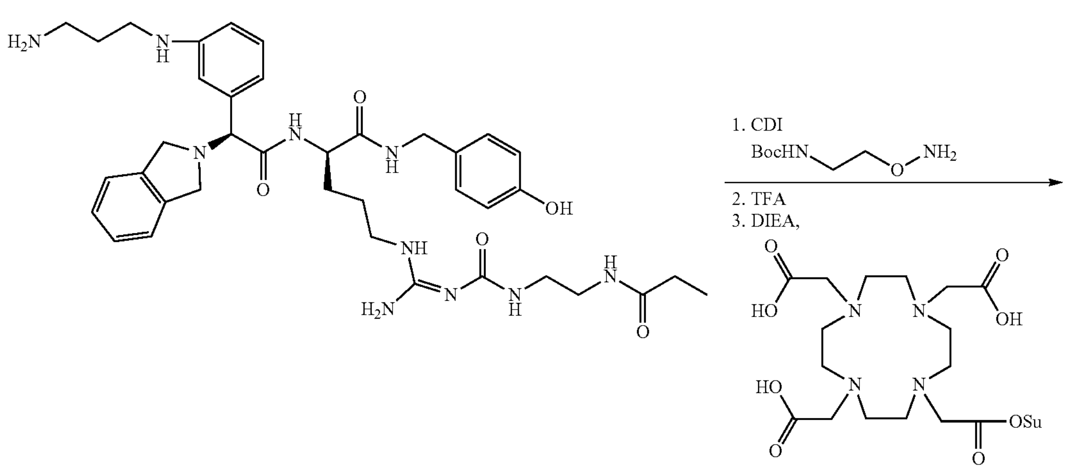

-continued

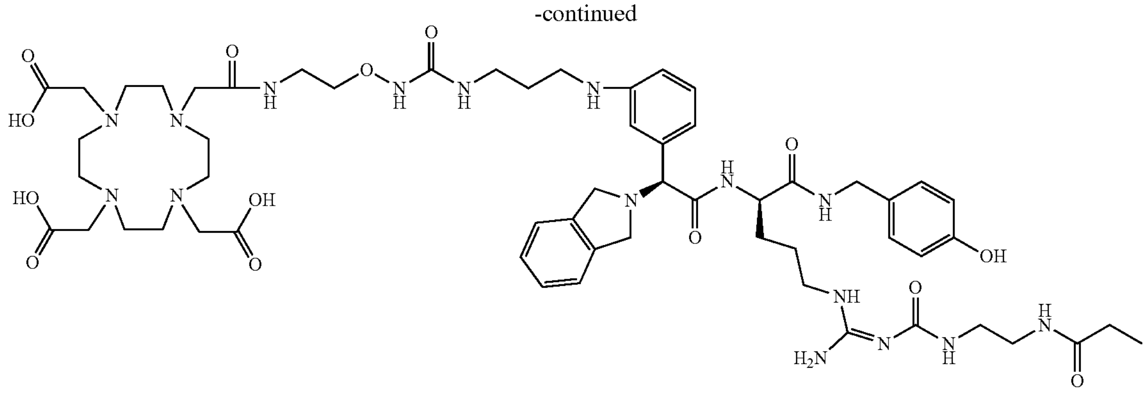

Step 1. Into an 8-mL vial, was placed a mixture of (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide (43 mg, 1 Eq, 59 μmol), CDI (9 mg, 0.9 Eq, 0.06 mmol) and ACN (1 mL). The reaction mixture was stirred at 70° C. for 30 minutes, then tert-butyl (2-(aminooxy)ethyl)carbamate (16 mg, 1.5 Eq, 91 μmol) was added and the reaction mixture was stirred at 70° C. for an additional 2 hours. The mixture was directly purified by MPLC to provide tert-butyl (2-((3-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)ureido)oxy)ethyl)carbamate (30 mg, 32 μmol, 55%) as a white solid. $[M+H]^+$=931.5.

Steps 2-3. tert-Butyl (2-((3-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)ureido)oxy)ethyl)carbamate was treated with TFA in a manner similar to Step 2 in the synthesis of Compound 1, then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(12-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-2,8-dioxo-6-oxa-3,7,9-triazadodecyl)-1,4,7,10-tetraazacyclododecane-1,4,7-triyl)triacetic acid (17.0 mg, 12.8 μmol, 35%) as a white solid. MS: Calc'd for $C_{57}H_{84}N_{16}O_{14}$: 1216.6, found $[M+H]^+$: 1217.4.

Example 29: 2,2',2"-(10-(28-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-2,24-dioxo-6,9,12,15,18,21-hexaoxa-3,25-diazaoctacosyl)-1,4,7,10-tetraazacyclododecane-1,4,7-triyl)triacetic acid (Compound 23)

Step 1. Into a 8-mL was placed a mixture of (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide 2,2,2-trifluoroacetate (43 mg, 1 Eq, 51 mol), 2,2-dimethyl-4-oxo-3,8,11,14,17,20,23-heptaoxa-5-azapentacosan-25-oic acid (26 mg, 1.2 Eq, 59 μmol), 1H-benzo[d][1,2,3]triazol-1-ol hydrate (14 mg, 1.8 Eq, 91 μmol), 3-(((ethylimino)methylene)amino)-N,N-dimethylpropan-1-amine hydrochloride (17 mg, 1.7 Eq, 89 mol), N-ethyl-N-isopropylpropan-2-amine (15 mg, 2.3 Eq, 0.12 mmol) and DMF (1 mL). The reaction mixture was stirred at 25° C. for 3 hours under $N_2$. The mixture was directly purified by MPLC to afford tert-butyl (25-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-21-oxo-3,6,9,12,15,18-hexaoxa-22-azapentacosyl)carbamate (50 mg, 43 μmol, 84%) as a yellow solid. $[M+H]^+$=1164.8.

Step 2. tert-butyl (25-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-21-oxo-3,6,9,12,15,18-hexaoxa-22-azapentacosyl)carbamate was treated with TFA in a manner similar to Step 2 in the synthesis of Compound 1 to provide 1-amino-N-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)-3,6,9,12,15,18-hexaoxahenicosan-21-amide (40 mg, 38 μmol, 88%) as colorless crude oil, which was used directly in the next step without purification. $[M+H]^+$=1064.4.

Step 3. 1-amino-N-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)-3,6,9,12,15,18-hexaoxahenicosan-21-amide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step

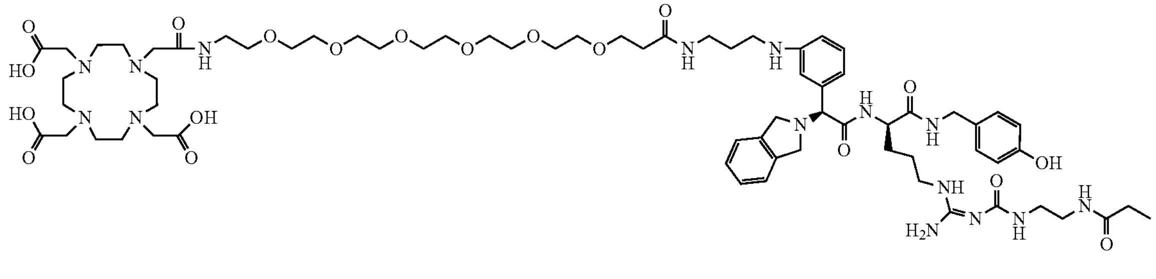 [SMILES: CCC(=O)NCCNC(=O)/N=C(/N)NCCC[C@@H](NC(=O)[C@H](c1cccc(NCCCNC(=O)CCOCCOCCOCCOCCOCCOCCNC(=O)CN2CCN(CC(=O)O)CCN(CC(=O)O)CCN(CC(=O)O)CC2)c1)N1Cc2ccccc2C1)C(=O)NCc1ccc(O)cc1]

5 to provide the trifluoroacetic acid salt of 2,2',2"-(10-(28-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-2,24-dioxo-6,9,12,15,18,21-hexaoxa-3,25-diazaoctacosyl)-1,4,7,10-tetraazacyclododecane-1,4,7-triyl)triacetic acid (19.4 mg, 12.4 μmol, 33%) as a white solid. MS: Calc'd for $C_{71}H_{108}F_3N_{15}O_{21}$: 1563.79, found $[M+H-TFA]^+$: 1450.6.

Example 30: 2,2',2"-(10-(2-(((R)-5-amino-6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)amino)-2-oxoethyl)-1,4,7,10-tetraazacyclododecane-1,4,7-triyl)triacetic acid (Compound 25)

Step 2. (9H-fluoren-9-yl)methyl tert-butyl ((R)-6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexane-1,5-diyl)dicarbamate was treated with DBU in a manner similar to Example 7, Step 4 to provide tert-butyl ((R)-6-amino-1-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-1-oxohexan-2-yl)carbamate (26 mg, 27 μmol, 71%). $[M+H]^+$=957.4.

Step 3. tert-butyl ((R)-6-amino-1-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-1-oxohexan-2-yl)carbamate was treated with 2,2',2"-(10-(2-((2,5-dioxopyrrolidin-1-yl)oxy)-2-oxoethyl)-1,4,7,10-tetraazacyclododecane-1,4,7-

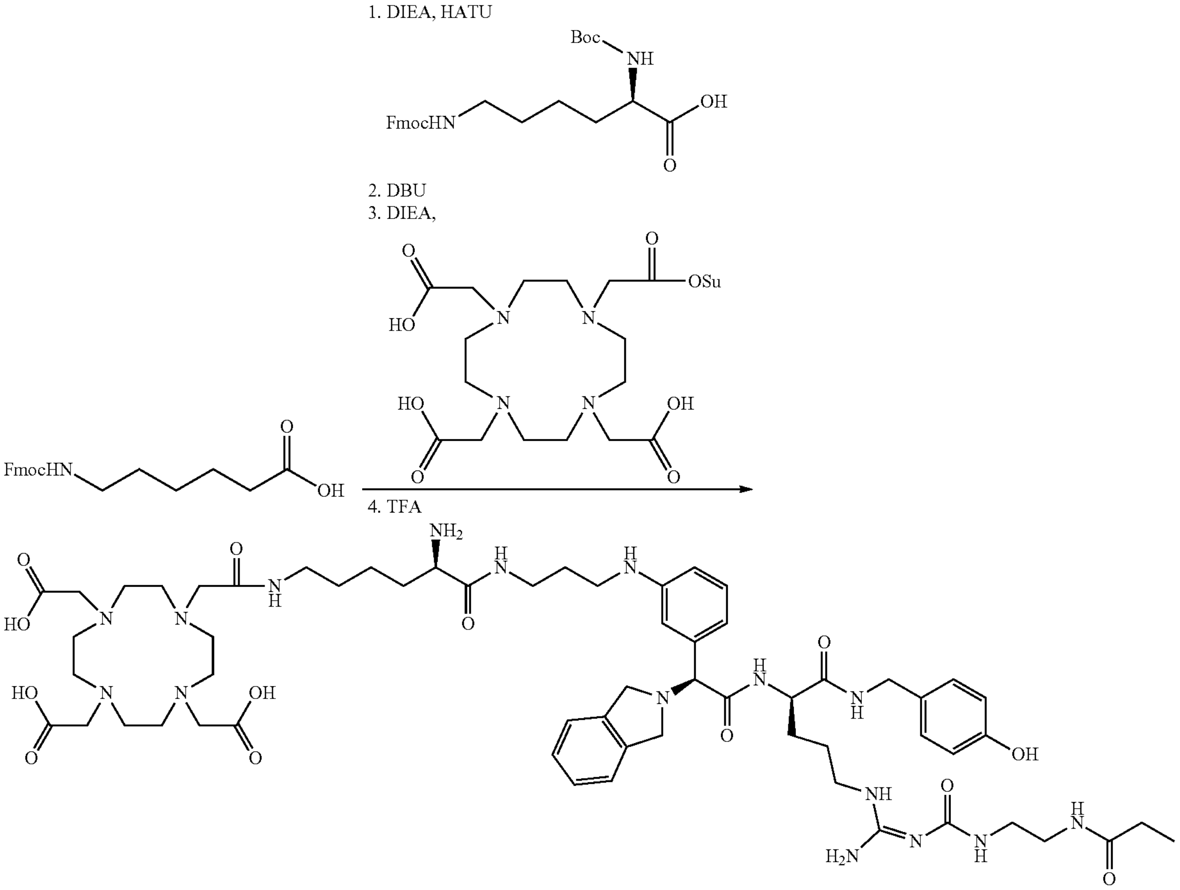

Step 1. (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide (100 mg, 1 Eq, 137 μmol) was treated with $N_6$-(((9H-fluoren-9-yl)methoxy)carbonyl)-$N_2$-(tert-butoxycarbonyl)-D-lysine, DIEA and HATU in a manner similar to Step 3 of the synthesis of Compound 1, to provide (9H-fluoren-9-yl)methyl tert-butyl ((R)-6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexane-1,5-diyl)dicarbamate (45 mg, 38 μmol, 28%) as a yellow oil. $[M+Na]^+$=1201.6.

triyl)triacetic acid and DIEA in a manner similar to Example 1, Step 5 to provide 2,2',2"-(10-(2-(((R)-6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-5-((tert-butoxycarbonyl)amino)-6-oxohexyl)amino)-2-oxoethyl)-1,4,7,10-tetraazacyclododecane-1,4,7-triyl)triacetic acid (15 mg, 11 μmol, 41%) as a white solid. $[M+Na]^+$=1365.7.

Step 4. 2,2',2"-(10-(2-(((R)-6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-5-((tert-butoxycarbonyl)amino)-6-oxohexyl)amino)-2-oxoethyl)-1,4,7,10- tetraazacyclododecane-1,4,7-triyl)triacetic acid was treated with TFA in a manner similar to Step 2 in the synthesis of Compound 1 to provide the trifluoroacetic acid salt of 2,2',2"-(10-(2-(((R)-5-amino-6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)amino)-2-oxoethyl)-1,4,7,10-tetraazacyclododecane-1,4,7-triyl)triacetic acid (10.3 mg, 7.59 μmol, 68%) as a white solid. MS: Calc'd for $C_{62}H_{91}F_3N_{16}O_{15}$: 1356.68, found $[M+H-TFA]^+$: 1243.6

Example 31: 2,2',2"-(10-(2-((2-(4-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-4-oxobutanamido)ethyl)amino)-2-oxoethyl)-1,4,7,10-tetraazacyclododecane-1,4,7-triyl)triacetic acid (Compound 26)

butoxycarbonyl)amino)ethyl)amino)-4-oxobutanoic acid (1.5 g, 5.8 mmol, 58%) as a white solid.

Step 2. (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide was treated with 4-((2-((tert-butoxycarbonyl)amino)ethyl)amino)-4-oxobutanoic acid, HATU, and DIEA in a manner similar to Step 3 of the synthesis of Compound 1, to provide tert-butyl (2-(4-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-4-oxobutanamido)ethyl)carbamate (40 mg, 41 μmol, 30%) as a white solid. $[M+H]^+$=972.7.

Step 3. tert-Butyl (2-(4-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)

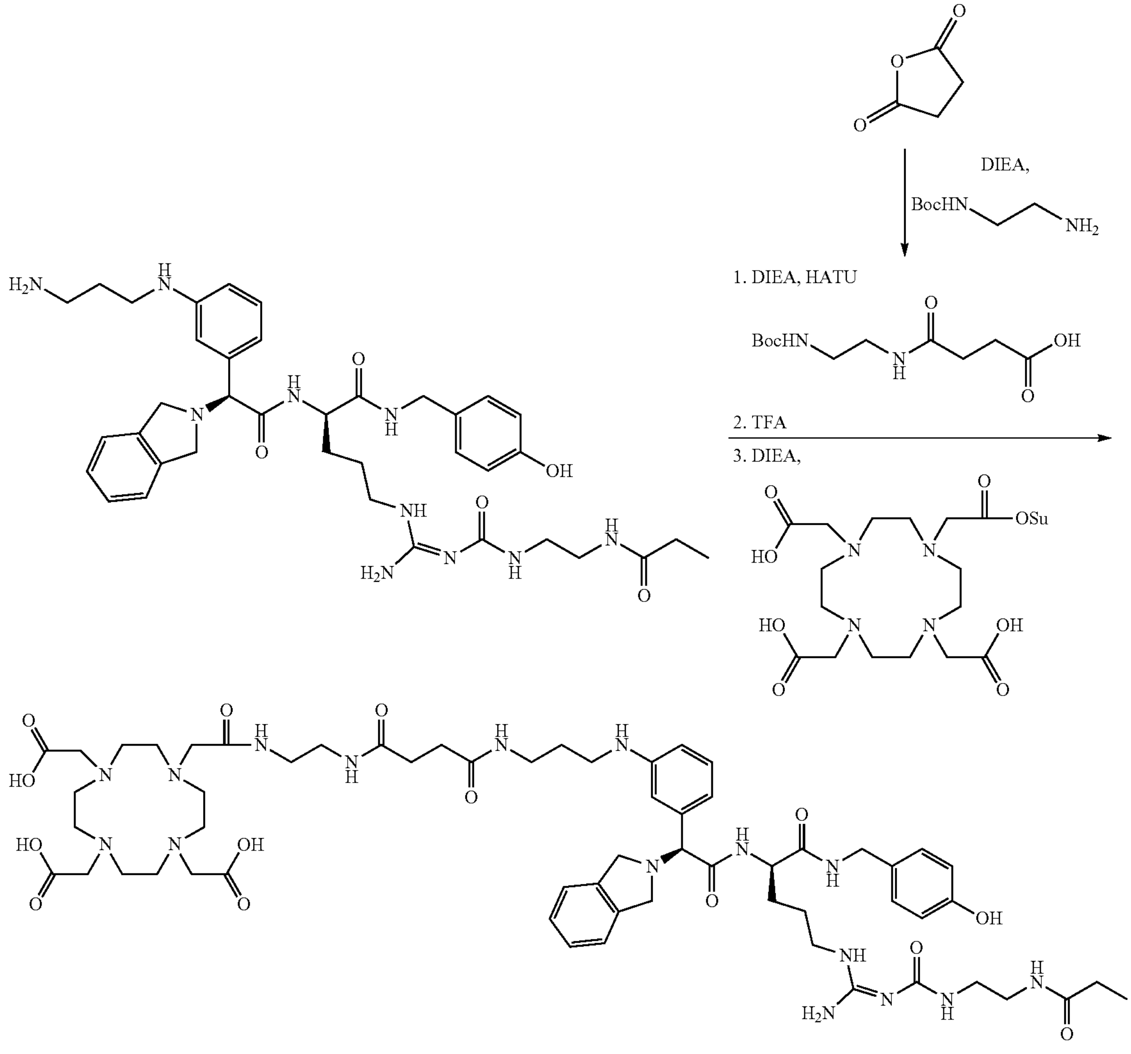

Step 1. Into a 40-mL vial, was placed a mixture of dihydrofuran-2,5-dione (1.0 g, 1 Eq, 10 mmol), DIEA (3.9 g, 5.3 mL, 3.0 Eq, 30 mmol), tert-butyl (2-aminoethyl) carbamate (1.8 g, 1.1 Eq, 11 mmol) and DCE (10 mL). The reaction mixture was stirred at 30° C. for 1 hour. The mixture was concentrated under reduced pressure. The crude product was purified by Prep-HPLC to provide 4-((2-((tertamino)propyl)amino)-4-oxobutanamido)ethyl)carbamate was treated with TFA in a manner similar to Step 2 in the synthesis of Compound 1 to provide N1-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)-N4-(2-aminoethyl)succinamide (29 mg, 33 mol, 81%) as a white solid. $[M+H]^+$=871.4.

Step 4. N1-(3-((3-((1S,4R,Z)-9-Amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)-$N_4$-(2-aminoethyl)succinimide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-((2-(4-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-4-oxobutanamido)ethyl)amino)-2-oxoethyl)-1,4,7,10-tetraazacyclododecane-1,4,7-triyl)triacetic acid (19.8 mg, 14.4 μmol, 43%) as a white solid. MS: Calc'd for $C_{62}H_{89}F_3N_{16}O_{16}$: 1370.66, found $[M+H-TFA]^+$: 1257.6.

Example 32: 2,2',2"-(10-(19-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-2,8,15-trioxo-4-oxa-3,7,9,16-tetraazanonadecyl)-1,4,7,10-tetraazacyclododecane-1,4,7-triyl)triacetic acid (Compound 27)

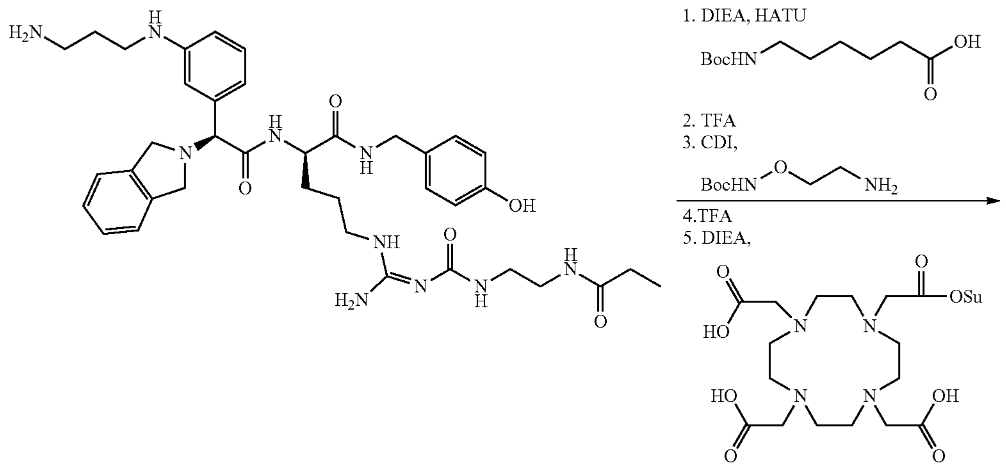

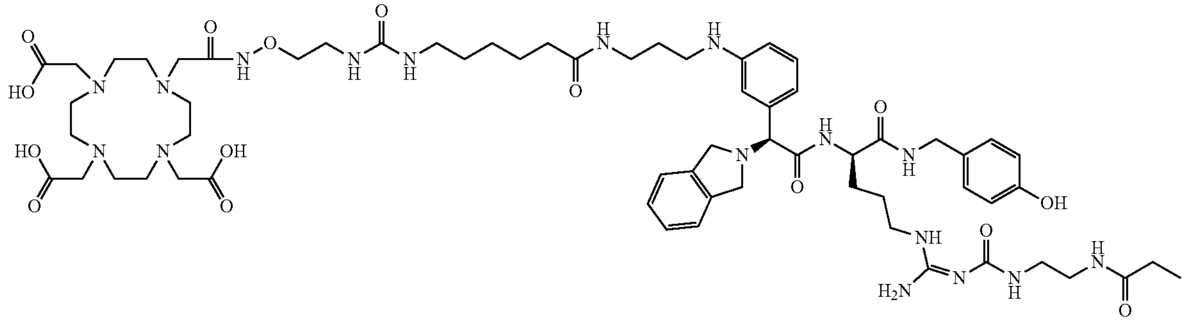

Step 1. (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide was treated with 6-((tert-butoxycarbonyl)amino)hexanoic acid, DIEA, and HATU in a manner similar to Step 3 of the synthesis of Compound 1, to provide tert-butyl (6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)carbamate (390 mg, 414 μmol, 67.0%) as a yellow oil. $[M+H]^+$=942.9.

Step 2. tert-Butyl (6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)carbamate was treated with TFA in a manner similar to Step 2 in the synthesis of Compound 1 to provide 6-amino-N-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)hexanamide (230 mg, 273 μmol, 88.7%) as a light yellow solid, which was used directly in the next step without any purification. $[M+Na]^+$=842.7.

Step 3. Into a 8-mL vial, was placed a mixture of tert-butyl (2-aminoethoxy)carbamate (25 mg, 1.3 Eq, 0.14 mmol), CDI (25 mg, 1.4 Eq, 0.15 mmol) and THE (2 mL). The reaction mixture was stirred at 25° C. for 10 minutes, then 6-amino-N-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)hexanamide (95 mg, 1 Eq, 0.11 mmol) was added and the reaction mixture was stirred at 25° C. for an additional 1 hour. The mixture was directly purified by MPLC to provide tert-butyl (2-(3-(6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)ureido)ethoxy)carbamate (60 mg, 57 μmol, 51%) as a yellow oil. $[M+H]^+$=1044.6.

Step 4. tert-Butyl (2-(3-(6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)ureido)ethoxy)carbamate was treated with TFA in a manner similar to Step 2 in the synthesis of Compound 1 to provide N-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)-6-(3-(2-(aminooxy)ethyl)ureido)hexanamide (50 mg, 37 μmol, 65%) as a light yellow solid, which was used directly in the next step without any purification. $[M+H]^+$=944.7.

Step 5. N-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)-6-(3-(2-(aminooxy)ethyl)ureido)hexanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the formic acid salt of 2,2',2"-(10-(19-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)-2,8,15-trioxo-4-oxa-3,7,9,16-tetraazanonadecyl)-1,4,7,10-tetraazacyclododecane-1,4,7-triyl)triacetic acid (7.5 mg, 5.4 μmol, 10%) as a white solid. MS: Calc'd for $C_{63}H_{95}N_{17}O_{15}$: 1329.7, found $[M+H]^+$: 1330.7.

Example 33: 2,2',2"-(10-(2-((1-(2-((6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)amino)-2-oxoethyl)piperidin-4-yl)amino)-2-oxoethyl)-1,4,7,10-tetraazacyclododecane-1,4,7-triyl)triacetic acid (Compound 28)

Step 1. Into a 8-mL vial, was placed a mixture of 2-(4-((((9H-fluoren-9-yl)methoxy)carbonyl)amino)piperidin-1-yl)acetic acid (45 mg, 1.1 Eq, 0.12 mmol), pentafluorophenyldiphenylphosphinate (45 mg, 1.1 Eq, 0.12 mmol), 4-methylmorpholine (33 mg, 36 μL, 3.1 Eq, 0.33 mmol) and DMF (2 mL). The reaction mixture was stirred at 25° C. for 10 minutes, then 6-amino-N-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)hexanamide (90 mg, 1 Eq, 0.11 mmol) was added and the reaction mixture was stirred at 25° C. for an additional 1 hour. The mixture was directly purified by MPLC to provide (9H-fluoren-9-yl)methyl (1-(2-((6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)amino)-2-oxoethyl)piperidin-4-yl)carbamate (60 mg, 50 μmol, 47%) as a yellow oil. $[M+H]^+$=1204.7.

Step 2. (9H-Fluoren-9-yl)methyl (1-(2-((6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)amino)-2-oxoethyl)piperidin-4-yl)carbamate was treated with DBU in a manner similar to Example 7, Step 4 to provide N-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)-6-(2-(4-aminopiperidin-1-yl)acetamido)hexanamide (40 mg, 41 μmol, 82%) which was used directly in the next step without any purification. $[M+H]^+$=982.9.

Step 3. N-(3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)-6-(2-(4-aminopiperidin-1-yl)acetamido)hexanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-((1-(2-((6-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-6-oxohexyl)amino)-2-oxoethyl)piperidin-4-yl)amino)-2-oxoethyl)-1,4,7,10-tetraazacyclododecane-1,4,7-triyl)triacetic acid as a white solid. $[M+H]^+$=1368.6.

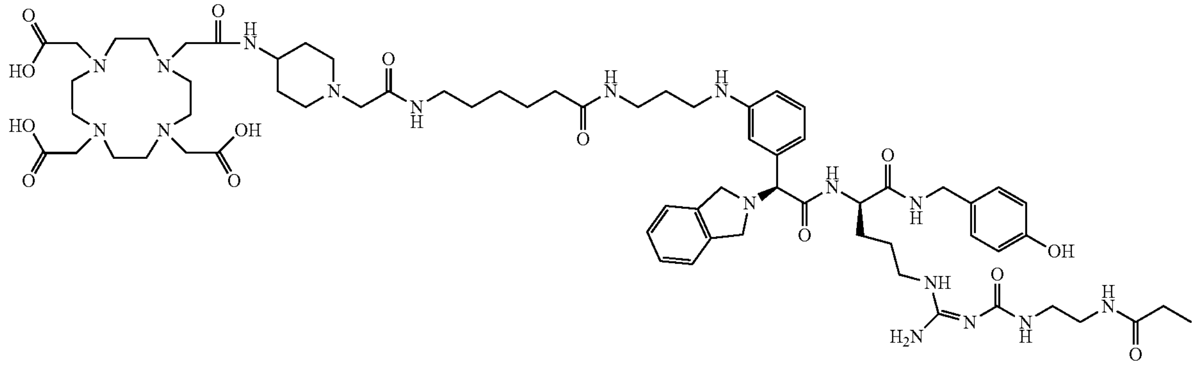 [SMILES: CCC(=O)NCCNC(=O)/N=C(/N)NCCC[C@@H](NC(=O)[C@H](c1cccc(NCCCNC(=O)CCCCCNC(=O)CN2CCC(NC(=O)CN3CCN(CC(=O)O)CCN(CC(=O)O)CCN(CC(=O)O)CC3)CC2)c1)N1Cc2ccccc2C1)C(=O)NCc1ccc(O)cc1]

Example 34: 2,2',2''-(10-(2-(((3R,5R)-7-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-3,5-dihydroxy-7-oxoheptyl)amino)-2-oxoethyl)-1,4,7,10-tetraazacyclododecane-1,4,7-triyl)triacetic acid (Compound 29)

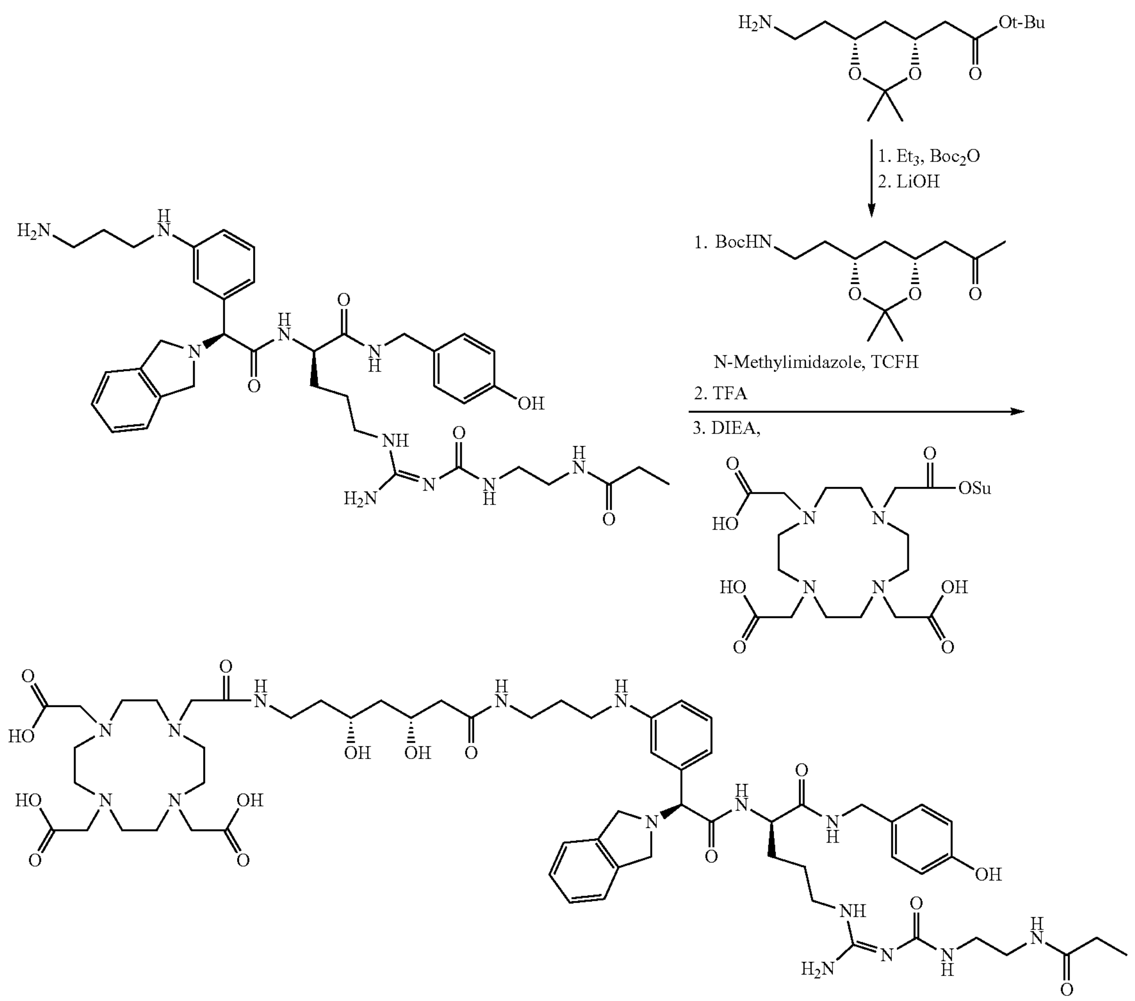

Step 1. Into a 100-mL round bottom flask, was placed a mixture of tert-butyl 2-((4R,6R)-6-(2-aminoethyl)-2,2-dimethyl-1,3-dioxan-4-yl)acetate (2.0 g, 1 Eq, 7.3 mmol), TEA (2.2 g, 3.0 mL, 3.0 Eq, 22 mmol), $Boc_2O$ (2.4 g, 2.5 mL, 1.5 Eq, 11 mmol) and DCM (20 mL). The reaction mixture was stirred at 25° C. for 1 hour. The mixture was concentrated under reduced pressure to provide tert-butyl 2-((4R,6R)-6-(2-((tert-butoxycarbonyl)amino)ethyl)-2,2-dimethyl-1,3-dioxan-4-yl)acetate (3 g, 6 mmol, 90%) as a yellow oil. [M+H]=374.2.

Step 2. Into a 100-mL round bottom flask, was placed a mixture of tert-butyl 2-((4R,6R)-6-(2-((tert-butoxycarbonyl)amino)ethyl)-2,2-dimethyl-1,3-dioxan-4-yl)acetate (3.0 g, 1 Eq, 8.0 mmol), LiOH (960 mg, 5.0 Eq, 40.1 mmol), water (7 mL) and MeOH (21 mL). The reaction mixture was stirred at 25° C. for 16 hours. The mixture was diluted with water (100 mL), extracted with EtOAc (50 mL×3), the aqueous layer was adjusted to pH=5-6 by adding a saturated aqueous solution of $Na_2HSO_4$, then extracted with EtOAc (50 mL×3), brine (50 mL), dried over anhydrous $Na_2SO_4$ and concentrated under reduced pressure. This resulted in 2-((4R,6R)-6-(2-((tert-butoxycarbonyl)amino)ethyl)-2,2-dimethyl-1,3-dioxan-4-yl)acetic acid (1.8 g, 5.7 mmol, 71%) as a yellow oil. [M+H]=318.1.

Step 3. Into a 8-mL vial, was placed a mixture of 2-((4R,6R)-6-(2-((tert-butoxycarbonyl)amino)ethyl)-2,2-dimethyl-1,3-dioxan-4-yl)acetic acid (44 mg, 1.0 Eq, 0.14 mmol), N-(chloro(dimethylamino)methylene)-N-methylmethanaminium hexafluorophosphate(V) (46 mg, 1.2 Eq, 0.16 mmol), 1-methyl-1H-imidazole (34 mg, 3.0 Eq, 0.41 mmol) and DMF (1 mL). The reaction mixture was stirred at 20° C. for 10 minutes, then (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide (100 mg, 1 Eq, 137 μmol) was added and the reaction mixture was stirred at 25° C. for 1 hour. The mixture was directly purified by Prep-HPLC to provide tert-butyl (2-((4R,6R)-6-(2-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-2-oxoethyl)-2,2-dimethyl-1,3-dioxan-4-yl)ethyl)carbamate (80 mg, 62 μmol, 45%) as a light yellow oil. $[M+H]^+$=1028.6.

Steps 4-5. tert-Butyl (2-((4R,6R)-6-(2-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-2-oxoethyl)-2,2-dimethyl-1,3-dioxan-4-yl)ethyl)carbamate was treated with TFA in a manner similar to Step 2 in the synthesis of Compound 1, then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-(((3R,5R)-7-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-3,5-dihydroxy-7-oxoheptyl)amino)-2-oxoethyl)-1,4,7,10-tetraazacyclododecane-1,4,7-triyl)triacetic acid (15.9 mg, 11.5 μmol, 16%) as a white solid. MS: Calc'd for $C_{61}H_{91}N_{15}O_{15}$: 1273.68, found $[M+H]^+$: 1274.6 Example 35: 2,2',2"-(10-(2-((3-(((R)-1-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-3-hydroxy-1-oxopropan-2-yl)amino)-3-oxopropyl)amino)-2-oxoethyl)-1,4,7,10-tetraazacyclododecane-1,4,7-triyl)triacetic acid (Compound 30)

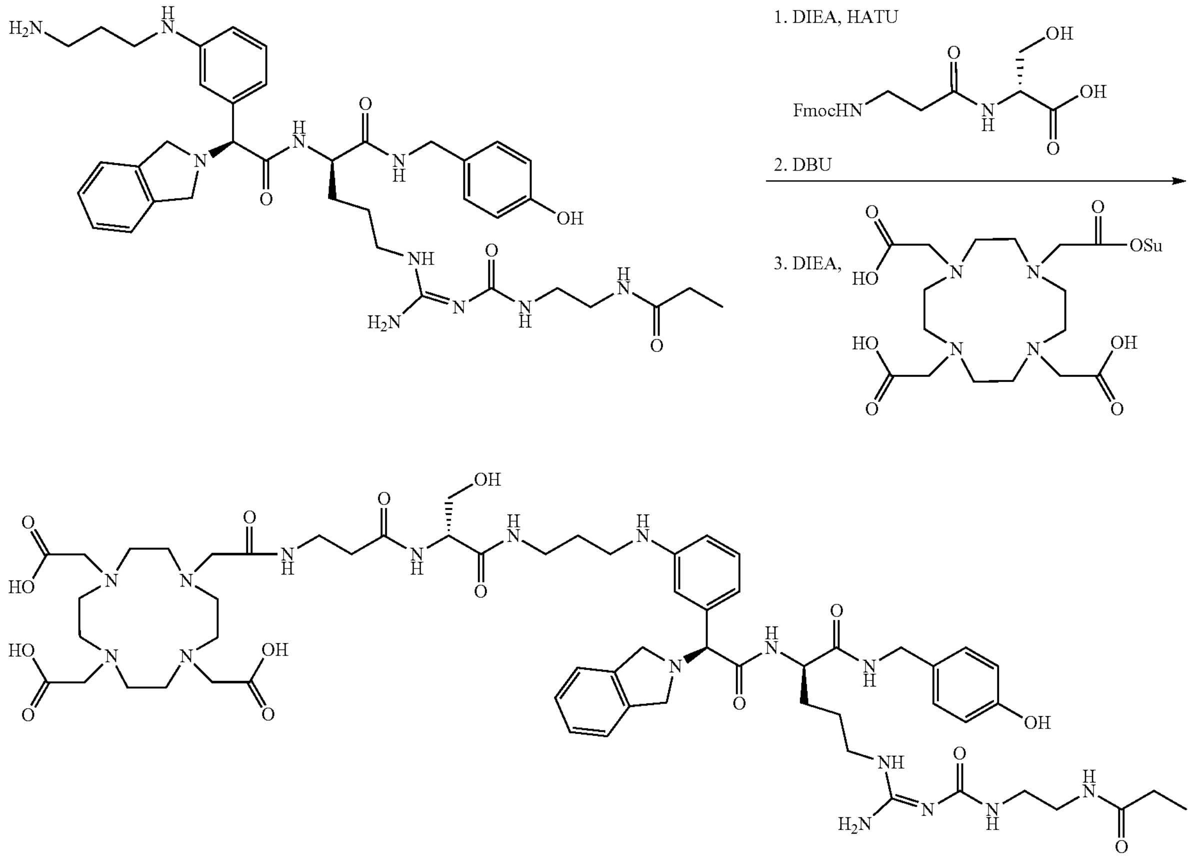

-

Steps 1-3. (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide was treated with DIEA, HATU and (3-((((9H-fluoren-9-yl)methoxy)carbonyl)amino)propanoyl)-D-serine in a manner similar to Step 3 of the synthesis of Compound 1, then treated with DBU in a manner similar to Example 7, Step 4 then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the TFA salt of 2,2',2"-(10-(2-((3-(((R)-1-((3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)amino)-3-hydroxy-1-oxopropan-2-yl)amino)-3-oxopropyl)amino)-2-oxoethyl)-1,4,7,10-tetraazacyclododecane-1,4,7-triyl)triacetic acid (20.2 mg, 14.6 μmol, 22%) as a white solid. MS: Calc'd $C_{60}H_{90}N_{16}O_{15}$: 1272.66, found $[M+H]^+$: 1273.5.

Example 36: A single isomer of 2,2',2"-(10-(2-((6-((2-((4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3,4-dioxocyclobut-1-en-1-yl)amino)hexyl)amino)-2-oxoethyl)-1,4,7,10-tetraazacyclododecane-1,4,7-triyl)triacetic acid (Compound 31A)

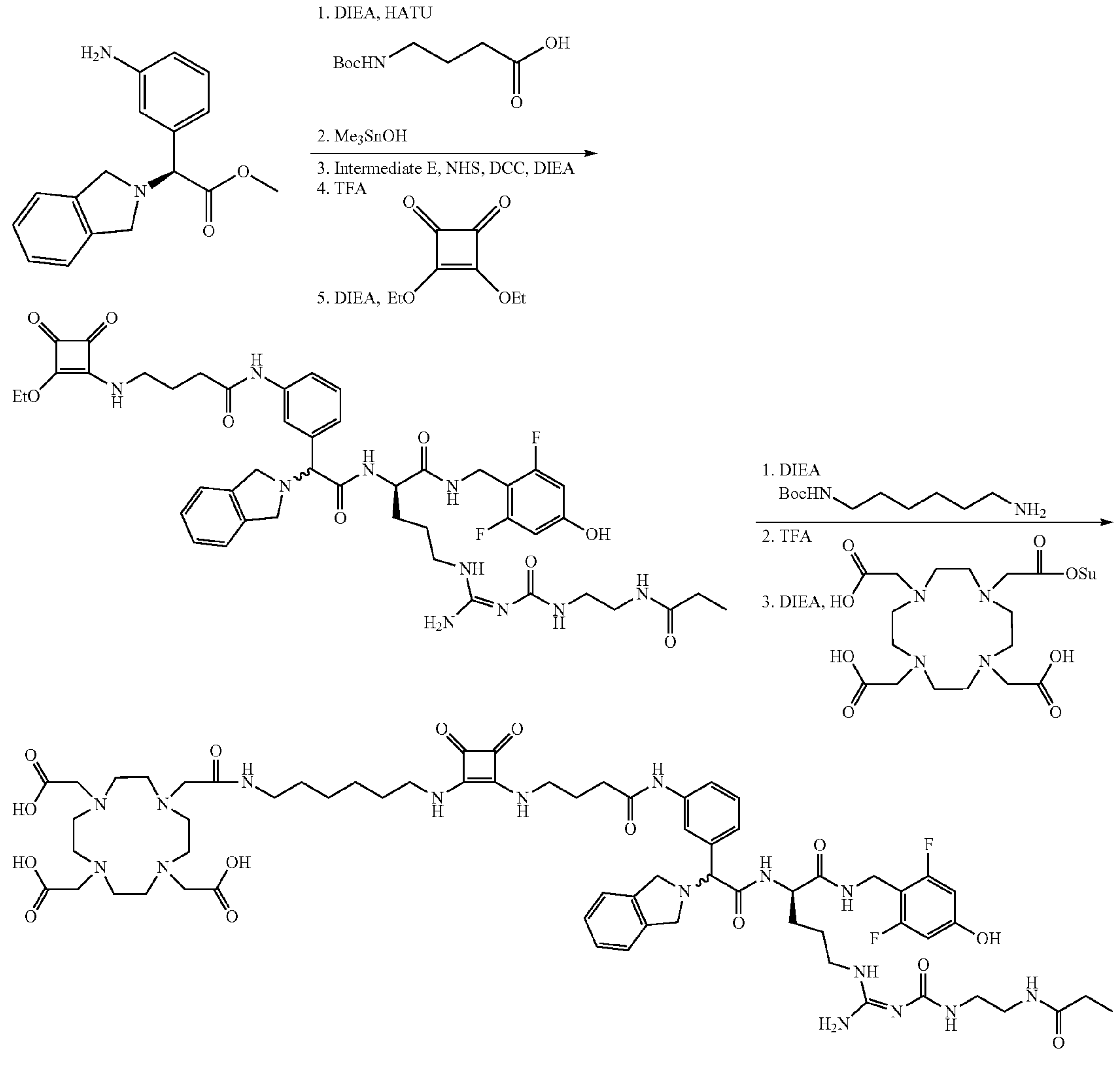

Step 1. 4-((tert-Butoxycarbonyl)amino)butanoic acid and methyl (S)-2-(3-aminophenyl)-2-(isoindolin-2-yl)acetate were treated with HATU and DIEA in a manner similar to Step 3 of the synthesis of Compound 1, to provide methyl (S)-2-(3-(4-((tert-butoxycarbonyl)amino)butanamido)phenyl)-2-(isoindolin-2-yl)acetate (850 mg, 1.82 mmol, 85.5%) as a yellow oil. $[M+H]^+$=468.4.

Step 2. Into an 8-mL vial, was placed a mixture of methyl (S)-2-(3-(4-((tert-butoxycarbonyl)amino)butanamido)phenyl)-2-(isoindolin-2-yl)acetate (850 mg, 1 Eq, 1.82 mmol), trimethyltinhydroxide (986 mg, 3.00 Eq, 5.45 mmol), and DCE (10 mL). The reaction mixture was stirred at 90° C. for 16 h. The mixture was directly purified by MPLC to provide (S)-2-(3-(4-((tert-butoxycarbonyl)amino)butanamido)phenyl)-2-(isoindolin-2-yl)acetic acid (330 mg, 728 μmol, 40.0%) as a yellow oil. $[M+H]^+$=454.2.

Step 3. (S)-2-(3-(4-((tert-butoxycarbonyl)amino)butanamido)phenyl)-2-(isoindolin-2-yl)acetic acid was treated with Intermediate E, NHS, DCC, and DIEA in a manner similar to Step 3 of the synthesis of Compound 1, to provide the product as two isomers. The back peak was isolated to provide a single isomer of tert-butyl (4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)carbamate (240 mg, 269 μmol, 36.9%) as a light yellow solid. $[M+H]^+$ =893.3. The front peak was isolated to provide the other single isomer of tert-butyl (4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)carbamate (175 mg).

Step 4. tert-Butyl (4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)carbamate from one peak was treated with TFA in a manner similar to Step 2 in the synthesis of Compound 1 to provide (2R)-2-(3-(4-aminobutanamido)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (190 mg, 0.19 mmol, 90%) as a light yellow oil, which was used directly in the next step without any purification. $[M+H]^+$=793.8.

Step 5. (2R)-2-(3-(4-aminobutanamido)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide was treated with DIEA and 3,4-diethoxycyclobut-3-ene-1,2-dione in a manner similar to Example 6, Step 8 to provide the crude (2R)—N-(2,6-difluoro-4-hydroxybenzyl)-2-(2-(3-(4-((2-ethoxy-3,4-dioxocyclobut-1-en-1-yl)amino)butanamido)phenyl)-2-(isoindolin-2-yl)acetamido)-5-((Z)-2-((2-propionamidoethyl)carbamoyl)guanidino)pentanamide, which was used directly in the next step without purification. $[M+H]^+$=917.7.

Step 6. To the crude product (2R)—N-(2,6-difluoro-4-hydroxybenzyl)-2-(2-(3-(4-((2-ethoxy-3,4-dioxocyclobut-1-en-1-yl)amino)butanamido)phenyl)-2-(isoindolin-2-yl)acetamido)-5-((Z)-2-((2-propionamidoethyl)carbamoyl)guanidino)pentanamide was added DIEA and tert-butyl (6-aminohexyl)carbamate (46 mg, 3.0 Eq, 0.21 mmol). The reaction mixture was stirred at 25° C. for 1 hour. The mixture was directly purified by MPLC to provide tert-butyl (6-((2-((4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3,4-dioxocyclobut-1-en-1-yl)amino)hexyl)carbamate (45 mg, 41 μmol, 58%) as a white solid. $[M+H]^+$=1087.8.

Steps 7-8. tert-Butyl (6-((2-((4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3,4-dioxocyclobut-1-en-1-yl)amino)hexyl)carbamate was treated with TFA in a manner similar to Step 2 in the synthesis of Compound 1, then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the formic acid salt of 2,2',2"-(10-(2-((6-((2-((4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3,4-dioxocyclobut-1-en-1-yl)amino)hexyl)amino)-2-oxoethyl)-1,4,7,10-tetraazacyclododecane-1,4,7-triyl)triacetic acid (25.1 mg, 17.7 μmol, 50%) as a white solid. MS: Calc'd for $C_{65}H_{90}F_2N_{16}O_{15}$: 1372.7, found $[M+H]^+$: 1373.5.

Example 37: A single isomer of 2,2',2"-(10-(2-((6-((2-((4-((3-((1R,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3,4-dioxocyclobut-1-en-1-yl)amino)hexyl)amino)-2-oxoethyl)-1,4,7,10-tetraazacyclododecane-1,4,7-triyl)triacetic acid (Compound 31B)

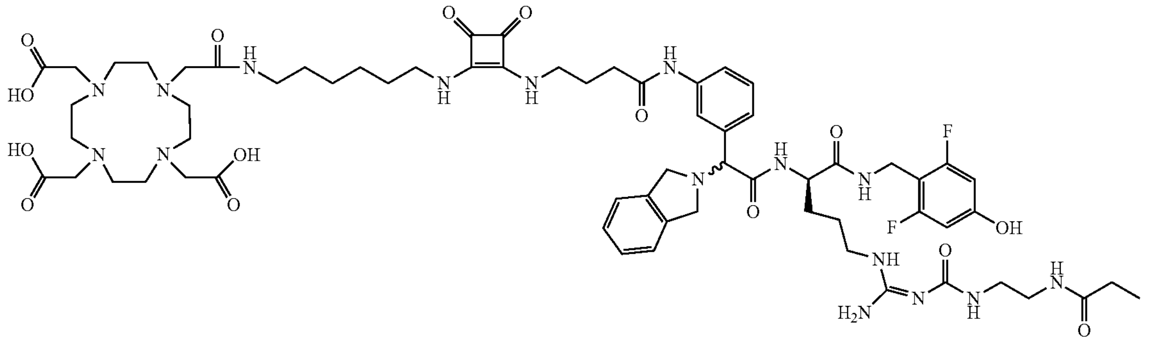 [SMILES: CCC(=O)NCCNC(=O)/N=C(/N)NCCC[C@@H](NC(=O)C(c1cccc(NC(=O)CCCNc2c(NCCCCCCNC(=O)CN3CCN(CC(=O)O)CCN(CC(=O)O)CCN(CC(=O)O)CC3)c(=O)c2=O)c1)N1Cc2ccccc2C1)C(=O)NCc1c(F)cc(O)cc1F]

Steps 1-4. The other single isomer of 2,2',2"-(10-(2-((6-((2-((4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3,4-dioxocyclobut-1-en-1-yl)amino)hexyl)amino)-2-oxoethyl)-1,4,7,10-tetraazacyclododecane-1,4,7-triyl)triacetic acid was synthesized from tert-butyl (4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)carbamate from the other peak (Example 37, Step 3) in a manner similar to Steps 4-8 of Example 37 to provide the trifluoroacetic acid salt of the product (47.3 mg, 31.8 μmol, 70%) as a white solid. MS: Calc'd for $C_{65}H_{90}F_2N_{16}O_{15}$: 1372.7, found $[M+H]^+$: 1373.5.

Example 38: A single isomer of 2,2',2"-(10-(2-((3-(((R)-1-((4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3-hydroxy-1-oxopropan-2-yl)amino)-3-oxopropyl)amino)-2-oxoethyl)-1,4,7,10-tetraazacyclododecane-1,4,7-triyl)triacetic acid (Compound 32A)

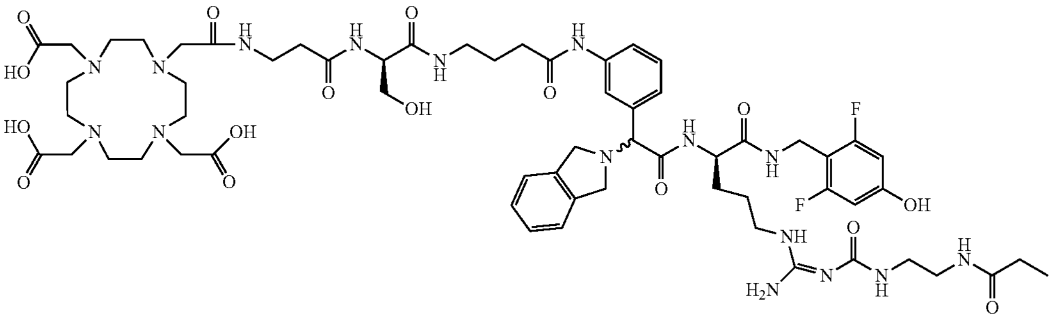 [SMILES: CCC(=O)NCCNC(=O)/N=C(/N)NCCC[C@@H](NC(=O)C(c1cccc(NC(=O)CCCNC(=O)[C@@H](CO)NC(=O)CCNC(=O)CN2CCN(CC(=O)O)CCN(CC(=O)O)CCN(CC(=O)O)CC2)c1)N1Cc2ccccc2C1)C(=O)NCc1c(F)cc(O)cc1F]

Step 1. (2R)-2-(2-(3-(4-aminobutanamido)phenyl)-2-(isoindolin-2-yl)acetamido)-N-(4-hydroxybenzyl)-5-((Z)-2-((2-propionamidoethyl)carbamoyl)guanidino)pentanamide (from one peak from Example 37, Step 4) was treated with (3-((((9H-fluoren-9-yl)methoxy)carbonyl)amino)propanoyl)-D-serine, DIEA, and HATU in a manner similar to Step 3 in the synthesis of Compound 1, to provide a single isomer of (9H-fluoren-9-yl)methyl (3-(((R)-1-((4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3-hydroxy-1-oxopropan-2-yl)amino)-3-oxopropyl)carbamate (32 mg, 27 μmol, 32%) as a yellow oil. $[M+H]^+$=1173.7.

Step 2. The single isomer of (9H-fluoren-9-yl)methyl (3-(((R)-1-((4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3-hydroxy-1-oxopropan-2-yl)amino)-3-oxopropyl)carbamate was treated with DBU in a manner similar to Example 7, Step 4 to provide a single isomer of (2R)-2-(2-(3-(4-(R)-2-(3-aminopropanamido)-3-hydroxypropanamido)butanamido)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (20 mg, 21 mol, 77%), which was directly used in the next step without any purification.

Step 3. The single isomer of (2R)-2-(2-(3-(4-((R)-2-(3-aminopropanamido)-3-hydroxypropanamido)butanamido)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the formic acid salt of a single isomer of 2,2',2"-(10-(2-((3-(((R)-1-((4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3-hydroxy-1-oxopropan-2-yl)amino)-3-oxopropyl)amino)-2-oxoethyl)-1,4,7,10-tetraazacyclododecane-1,4,7-triyl)triacetic acid (19.2 mg, 13.9 μmol, 66%) as a white solid. MS: Calc'd for $C_{61}H_{86}F_2N_{16}O_{16}$: 1407.45, found $[M+H-TFA]^+$: 1337.5.

Example 39: A single isomer of 2,2',2"-(10-(2-((3-(((R)-1-((4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3-hydroxy-1-oxopropan-2-yl)amino)-3-oxopropyl)amino)-2-oxoethyl)-1,4,7,10-tetraazacyclododecane-1,4,7-triyl)triacetic acid (Compound 32B)

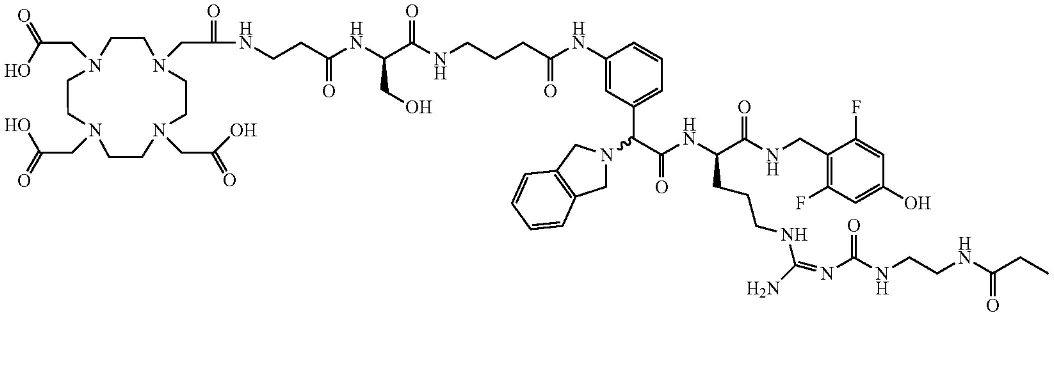 [SMILES: CCC(=O)NCCNC(=O)/N=C(/N)NCCC[C@@H](NC(=O)C(c1cccc(NC(=O)CCCNC(=O)[C@@H](CO)NC(=O)CCNC(=O)CN2CCN(CC(=O)O)CCN(CC(=O)O)CCN(CC(=O)O)CC2)c1)N1Cc2ccccc2C1)C(=O)NCc1c(F)cc(O)cc1F]

Steps 1-3. A single isomer of 2,2',2"-(10-(2-((3-(((R)-1-((4-((3-((4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenyl)amino)-4-oxobutyl)amino)-3-hydroxy-1-oxopropan-2-yl)amino)-3-oxopropyl)amino)-2-oxoethyl)-1,4,7,10-tetraazacyclododecane-1,4,7-triyl)triacetic acid was synthesized from a single isomer of (2R)-2-(2-(3-(4-aminobutanamido)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (from the other peak from Example 37, Step 4) in a manner similar to Step 1-3 of Example 39 to provide the trifluoroacetic salt of the product as a white solid. MS: Calc'd for $C_{61}H_{86}F_2N_{16}O_{16}$: 1336.63, found $[M+H]^+$: 1337.5.

Example 40: 2,2',2"-(10-(2-((6-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-6-oxohexyl)amino)-2-oxoethyl)-1,4,7,10-tetraazacyclododecane-1,4,7-triyl)triacetic acid (Compound 33)

Step 1. Into a 500-mL round bottom flask, was placed a mixture of methyl (S)-2-amino-2-phenylacetate (4.0 g, 1.5 Eq, 24 mmol), 1,2-bis(bromomethyl)-3-nitrobenzene (5.0 g, 1 Eq, 16 mmol), $KHCO_3$ (4.9 g, 3.0 Eq, 49 mmol), to which was added ACN (250 mL). The reaction mixture was stirred at 80° C. for 16 hours. The reaction mixture was filtered through a pad of celite, the filtrate was concentrated and the crude product was purified by MPLC to provide methyl (S)-2-(4-nitroisoindolin-2-yl)-2-phenylacetate (3.3 g, 11 mmol, 65%) as a yellow solid. $[M+H]^+$=313.1.

Step 2. Into a 100-mL round-bottom flask purged and maintained under an inert atmosphere of nitrogen, was placed methyl (S)-2-(4-nitroisoindolin-2-yl)-2-phenylacetate (1.3 g, 1 Eq, 4.2 mmol) and i-PrOH (15 mL), to which was carefully added Pd/C (89 mg, 0.20 Eq, 0.84 mmol). The flask was evacuated and flushed with hydrogen three times. The mixture was stirred at 25° C. for 16 hours under $H_2$. The reaction mixture was filtered through a pad of celite and the filtrate was concentrated to provide methyl (S)-2-(4-aminoisoindolin-2-yl)-2-phenylacetate (1.06 g, 3.75 mmol, 90%) as a yellow oil. $[M+H]^+$=283.2.

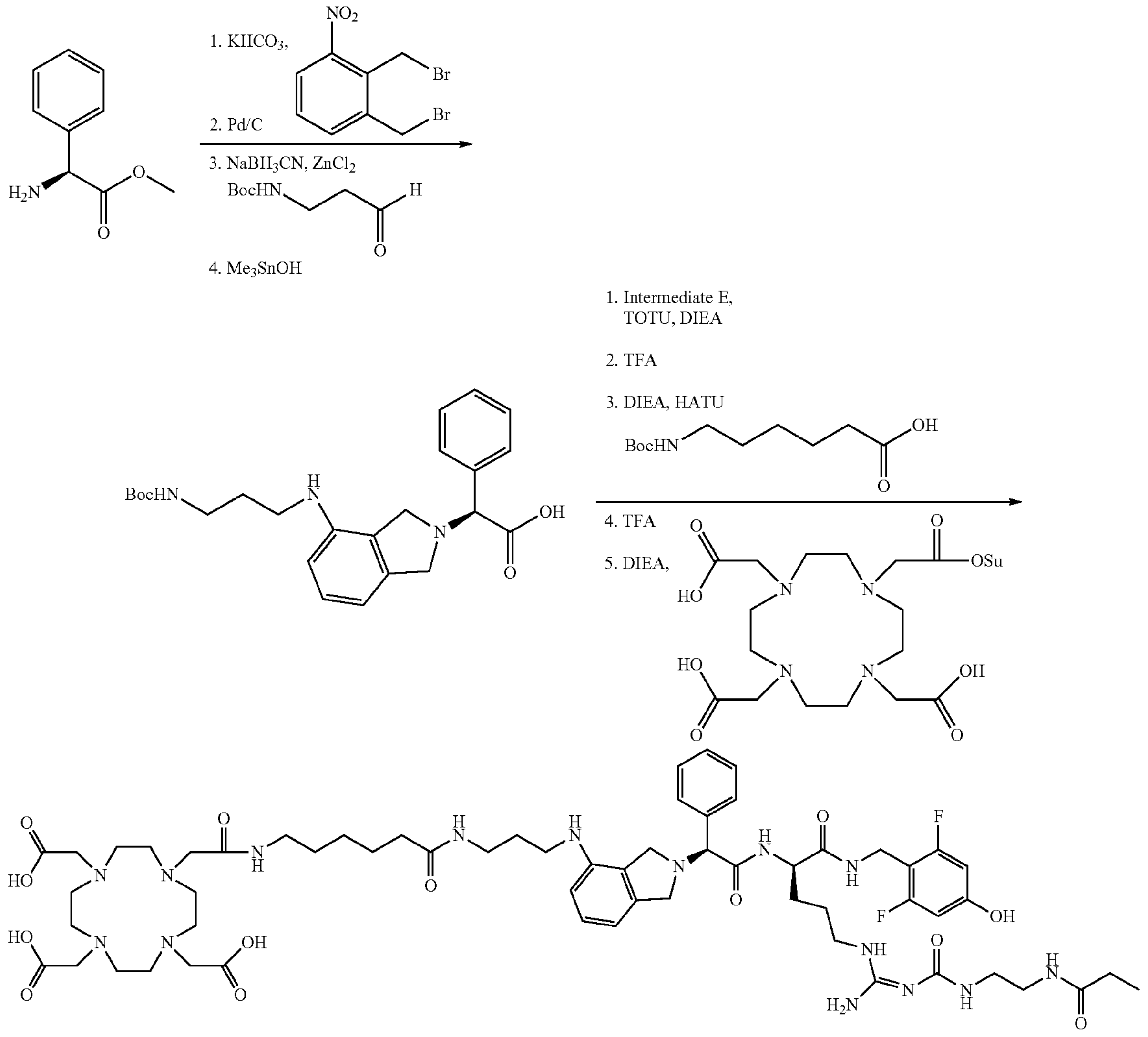

Step 3. Into a 40-mL vial, was placed a mixture of methyl (S)-2-(4-aminoisoindolin-2-yl)-2-phenylacetate (910 mg, 1 Eq, 3.22 mmol), zinc chloride (878 mg, 414 μL, 2.00 Eq, 6.44 mmol), tert-butyl (3-oxopropyl)carbamate (837 mg, 1.50 Eq, 4.83 mmol) and DCE (10 mL), to which was added $NaBH_3CN$ (608 mg, 3.00 Eq, 9.68 mmol). The reaction mixture was stirred at 25° C. for 3 hours. The mixture was diluted with 10 mL of MeOH and concentrated under reduced pressure. The mixture was directly purified by MPLC to provide methyl (S)-2-(4-((3-((tert-butoxycarbonyl)amino)propyl)amino)isoindolin-2-yl)-2-phenylacetate (600 mg, 1.37 mmol, 42.4%) as a yellow oil. $[M+H]^+$=440.2.

Step 4. Into a 40-mL vial, was placed a mixture of methyl (S)-2-(4-((3-((tert-butoxycarbonyl)amino)propyl)amino)isoindolin-2-yl)-2-phenylacetate (522 mg, 1 Eq, 1.19 mmol) and DCE (6 mL), to which was added $Me_3SnOH$ (215 mg, 1 Eq, 1.19 mmol). The reaction mixture was stirred at 90° C. for 16 hours. The mixture was directly purified by MPLC to provide (S)-2-(4-((3-((tert-butoxycarbonyl)amino)propyl)amino)isoindolin-2-yl)-2-phenylacetic acid (370 mg, 870 μmol, 73.2%) as a white solid. $[M+H]^+$=426.2.

Step 5. (S)-2-(4-((3-((tert-butoxycarbonyl)amino)propyl)amino)isoindolin-2-yl)-2-phenylacetic acid was treated with Intermediate E, DIEA and TOTU in a manner similar to Step 1 of the synthesis of Compound 1 to provide tert-butyl (3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)carbamate (300 mg, 347 μmol, 67.1%) as a yellow oil. $[M+H]^+$=865.5.

Step 6. tert-Butyl (3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)carbamate was treated with TFA in a manner similar to Step 2 in the synthesis of Compound 1 to provide (R)-2-((S)-2-(4-((3-aminopropyl)amino)isoindolin-2-yl)-2-phenylacetamido)-N-(2,6-difluoro-4-hydroxybenzyl)-5-((Z)-2-((2-propionamidoethyl)carbamoyl)guanidino)pentanamide (165 mg, 216 μmol, 93.3%) as a yellow oil. $[M+H]^+$=765.3.

Step 7. (R)-2-((S)-2-(4-((3-aminopropyl)amino)isoindolin-2-yl)-2-phenylacetamido)-N-(2,6-difluoro-4-hydroxybenzyl)-5-((Z)-2-((2-propionamidoethyl)carbamoyl)guanidino)pentanamide was treated with 6-((tert-butoxycarbonyl)amino)hexanoic acid, HATU and DIEA in a manner similar to Step 3 of the synthesis of Compound 1, to provide tert-butyl (6-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-6-oxohexyl)carbamate (60 mg, 61 μmol, 59%) as a yellow oil. $[M+H]^+$=978.4.

Steps 8-9. tert-Butyl (6-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-6-oxohexyl)carbamate was treated with TFA in a manner similar to Step 2 in the synthesis of Compound 1, then treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2''-(10-(2-((6-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-6-oxohexyl)amino)-2-oxoethyl)-1,4,7,10-tetraazacyclododecane-1,4,7-triyl)triacetic acid (38.7 mg, 28.1 μmol, 55%) as a white solid. $[M+H]^+$=1264.5.

Example 41: 2,2',2''-(10-(2-((6-((2-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-3,4-dioxocyclobut-1-en-1-yl)amino)hexyl)amino)-2-oxoethyl)-1,4,7,10-tetraazacyclododecane-1,4,7-triyl)triacetic acid (Compound 34)

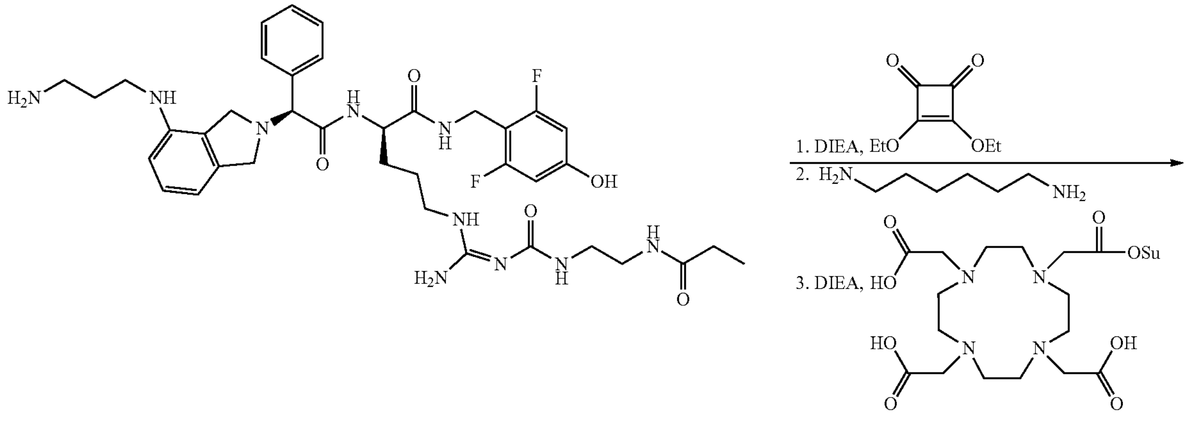

-continued

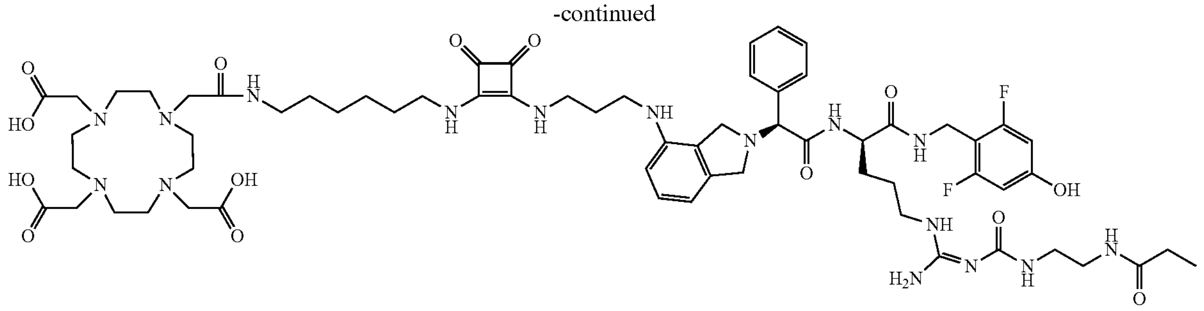

Step 1. (R)-2-((S)-2-(4-((3-aminopropyl)amino)isoindolin-2-yl)-2-phenylacetamido)-N-(2,6-difluoro-4-hydroxybenzyl)-5-((Z)-2-((2-propionamidoethyl)carbamoyl)guanidino)pentanamide was treated with DIEA and 3,4-diethoxycyclol-3-ene-1,2-dione in a manner similar to Example 6, Step 8 to provide (R)—N-(2,6-difluoro-4-hydroxybenzyl)-2-((S)-2-(4-((3-((2-ethoxy-3,4-dioxocyclobut-1-en-1-yl)amino)propyl)amino)isoindolin-2-yl)-2-phenylacetamido)-5-((Z)-2-((2-propionamidoethyl)carbamoyl)guanidino)pentanamide, which was used directly in the next step without purification. $[M+H]^+$=889.3.

Step 2. (R)—N-(2,6-difluoro-4-hydroxybenzyl)-2-((S)-2-(4-((3-((2-ethoxy-3,4-dioxocyclobut-1-en-1-yl)amino)propyl)amino)isoindolin-2-yl)-2-phenylacetamido)-5-((Z)-2-((2-propionamidoethyl)carbamoyl)guanidino)pentanamide was treated with hexane-1,6-diamine in a manner similar to Example 6, Step 9 to provide (R)-2-((S)-2-(4-((3-((2-((6-aminohexyl)amino)-3,4-dioxocyclobut-1-en-1-yl)amino)propyl)amino)isoindolin-2-yl)-2-phenylacetamido)-N-(2,6-difluoro-4-hydroxybenzyl)-5-((Z)-2-((2-propionamidoethyl)carbamoyl)guanidino)pentanamide (45 mg, 33 mmol, 49%) as a white solid. [M+Na]*=981.4.

Step 3. (R)-2-((S)-2-(4-((3-((2-((6-aminohexyl)amino)-3,4-dioxocyclobut-1-en-1-yl)amino)propyl)amino)isoindolin-2-yl)-2-phenylacetamido)-N-(2,6-difluoro-4-hydroxybenzyl)-5-((Z)-2-((2-propionamidoethyl)carbamoyl)guanidino)pentanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-((6-((2-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-3,4-dioxocyclobut-1-en-1-yl)amino)hexyl)amino)-2-oxoethyl)-1,4,7,10-tetraazacyclododecane-1,4,7-triyl)triacetic acid (17.1 mg, 11.7 μmol, 32%) as a white solid. MS: Calc'd for $C_{64}H_{90}F_2N_{16}O_{14}$: 1344.67, found $[M+H]^+$: 1345.6.

Example 42: 2,2',2"-(10-(2-((6-(4-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazin-1-yl)piperidin-1-yl)-6-oxohexyl)amino)-2-oxoethyl)-1,4,7,10-tetraazacyclododecane-1,4,7-triyl)triacetic acid (Compound 35)

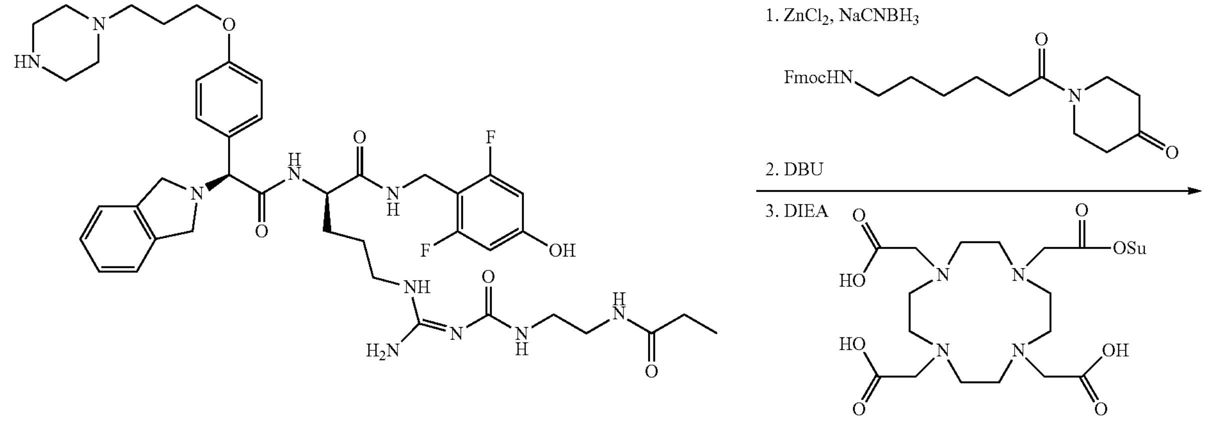

-continued

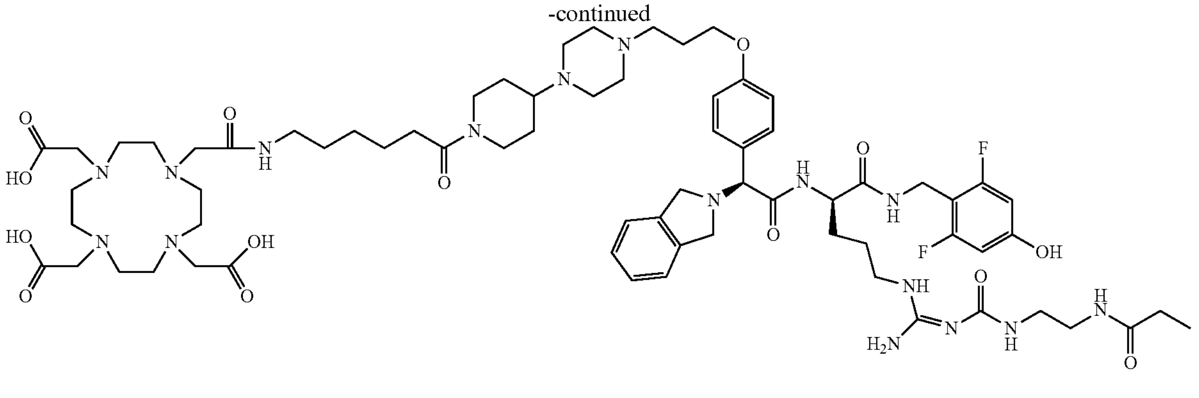

Step 1. Into a 8-mL vial, was placed a mixture of (R)—N-(2,6-difluoro-4-hydroxybenzyl)-2-((S)-2-(isoindolin-2-yl)-2-(4-(3-(piperazin-1-yl)propoxy)phenyl)acetamido)-5-((Z)-2-((2-propionamidoethyl)carbamoyl)guanidino)pentanamide (80 mg, 90% Wt, 1 Eq, 86 mol), (9H-fluoren-9-yl)methyl (6-oxo-6-(4-oxopiperidin-1-yl)hexyl) carbamate (37 mg, 1 Eq, 86 μmol), TEA (8.7 mg, 12 μL, 1 Eq, 86 μmol), zinc(II) chloride (12 mg, 1 Eq, 86 μmol), sodium cyanoborohydride (5.4 mg, 5.0 μL, 1 Eq, 86 μmol) and MeOH (0.8 mL). The reaction mixture was stirred at 25° C. for 16 hours. The mixture was directly purified by MPLC to provide (9H-fluoren-9-yl)methyl (6-(4-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazin-1-yl)piperidin-1-yl)-6-oxohexyl)carbamate (60 mg, 48 μmol, 56%) as a yellow oil. $[M+H]^+$=1254.8.

Step 2. (9H-fluoren-9-yl)methyl (6-(4-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazin-1-yl)piperidin-1-yl)-6-oxohexyl)carbamate was treated with DBU in a manner similar to Example 7, Step 4 to provide ((R)-2-((S)-2-(4-(3-(4-(1-(6-aminohexanoyl)piperidin-4-yl)piperazin-1-yl)propoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide as a crude product which was used directly in the next step without any purification. $[M+H]^+$=1031.5.

Step 3. ((R)-2-((S)-2-(4-(3-(4-(1-(6-aminohexanoyl)piperidin-4-yl)piperazin-1-yl)propoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-((6-(4-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazin-1-yl)piperidin-1-yl)-6-oxohexyl)amino)-2-oxoethyl)-1,4,7,10-tetraazacyclododecane-1,4,7-triyl)triacetic acid. MS: Calc'd for $C_{69}H_{102}F_2N_{16}O_{14}$: 1416.8, found $[M+H]^+$: 1417.6.

Example 43: 2,2',2"-(10-(2-((6-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)amino)-2-oxoethyl)-1,4,7,10-tetraazacyclododecane-1,4,7-triyl)triacetic acid (Compound 36)

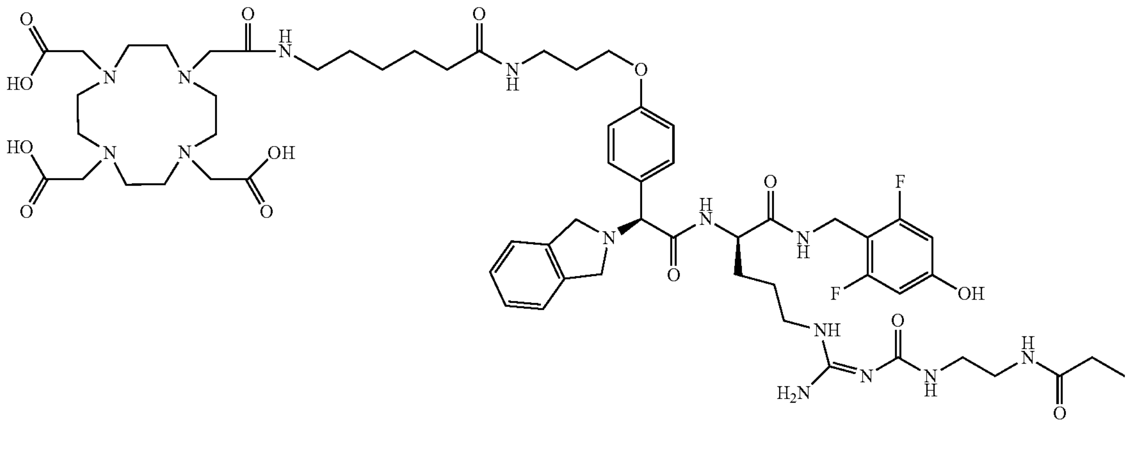 [SMILES: CCC(=O)NCCNC(=O)/N=C(/N)NCCC[C@@H](NC(=O)[C@H](c1ccc(OCCCNC(=O)CCCCCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F]

Step 1. (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (made according to Example 11) was treated with 6-((tert-butoxycarbonyl)amino)hexanoic acid, HATU, and DIEA in a manner similar to Step 3 of the synthesis of Compound 1, to provide tert-butyl (6-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)carbamate (24 mg, 25 μmol, 42%) as a yellow oil. $[M+H]^+$=979.4.

Step 2. tert-butyl (6-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)carbamate was treated with TFA in a manner similar to Step 2 in the synthesis of Compound 1 to provide 6-amino-N-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)hexanamide (24 mg, 25 μmol, 100%) as a yellow oil. $[M+H]^+$=879.7.

Step 3. 6-amino-N-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)hexanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the formic acid salt of 2,2',2"-(10-(2-((6-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-6-oxohexyl)amino)-2-oxoethyl)-1,4,7,10-tetraazacyclododecane-1,4,7-triyl)triacetic acid (7 mg, 5 μmol, 20%) as a white solid. MS: Calc'd for $C_{61}H_{88}F_2N_{14}O_{16}$: 1310.64, found $[M+H-FA]^+$: 1266.4.

Example 44: 2,2',2"-(10-(2-((6-((2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3,4-dioxocyclobut-1-en-1-yl)amino)hexyl)amino)-2-oxoethyl)-1,4,7,10-tetraazacyclododecane-1,4,7-triyl)triacetic acid (Compound 37)

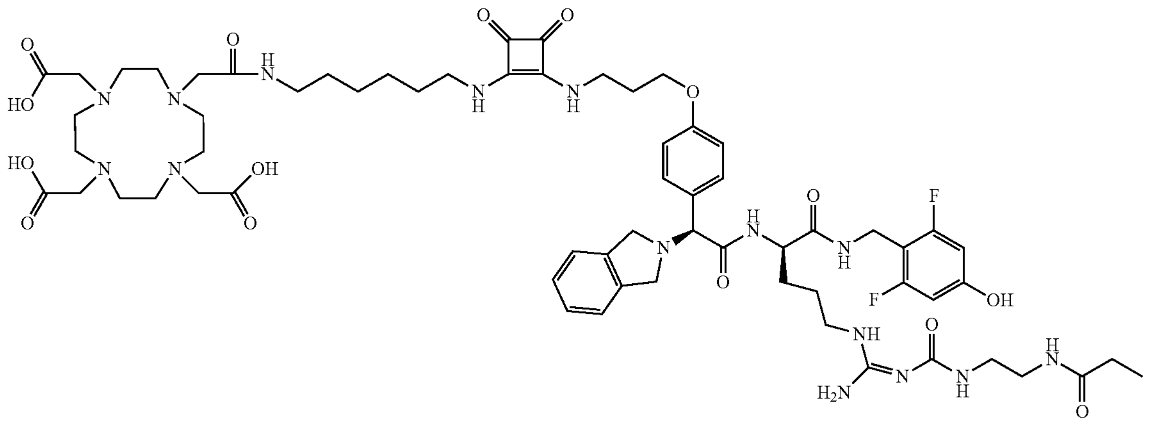

Steps 1-3. 2,2',2"-(10-(2-((6-((2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3,4-dioxocyclobut-1-en-1-yl)amino)hexyl)amino)-2-oxoethyl)-1,4,7,1letraazacyclododecane-1,4,7-triyl)triacetic acid was synthesized from (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide in a manner similar to Example 42, Steps 1-3 to provide the product (33.6 mg, 25.0 μmol, 60%) as a white solid. MS: Calc'd for $C_{64}H_{89}F_2N_{15}O_{15}$: 1345.7, found $[M+H]^+$: 1346.5.

Example 45: 2,2',2"-(10-(2-((3-((2R,5R)-5-(2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-3,6-dioxopiperazin-2-yl)propyl)amino)-2-oxoethyl)-1,4,7,10-tetraazacyclododecane-1,4,7-triyl)triacetic acid (Compound 38)

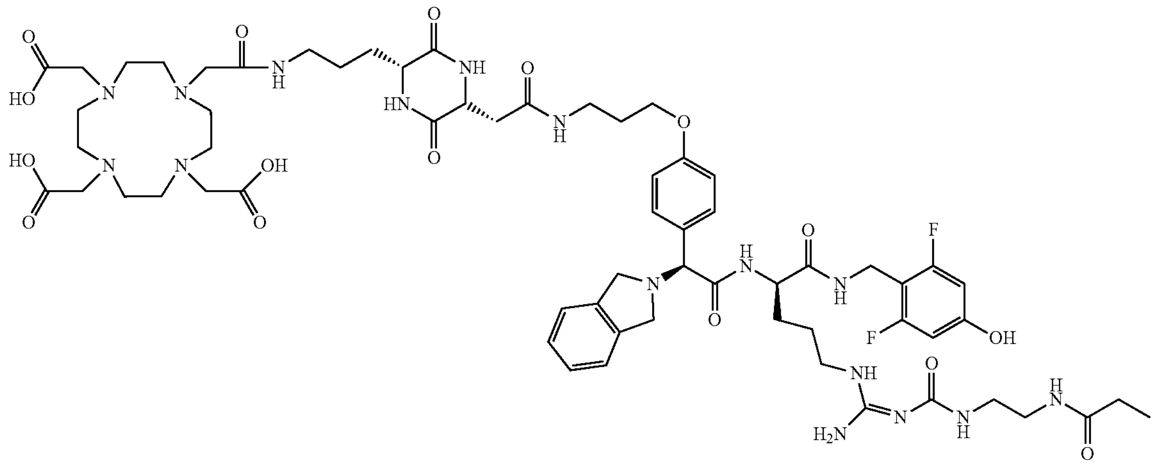

Step 1. (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide was treated with 2-((2R,5R)-5-(3-((((9H-fluoren-9-yl)methoxy)carbonyl)amino)propyl)-3,6-dioxopiperazin-2-yl)acetic acid, HATU and DIEA in a manner similar to Step 3 of the synthesis of Compound 1, to provide (9H-fluoren-9-yl)methyl (3-((2R,5R)-5-(2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-3,6-dioxopiperazin-2-yl)propyl)carbamate (35 mg, 29 μmol, 41%) as a yellow oil. $[M+H]^+=1199.6$.

Step 2. (9H-fluoren-9-yl)methyl (3-((2R,5R)-5-(2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-3,6-dioxopiperazin-2-yl)propyl)carbamate was treated with DBU in a manner similar to Example 7, Step 4 to provide (R)-2-((S)-2-(4-(3-(2-((2R,5R)-5-(3-aminopropyl)-3,6-dioxopiperazin-2-yl)acetamido)propoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (30 mg, 31 μmol, 110%) without any purification for next step. $[M+H]^+=977.5$.

Step 3. (R)-2-((S)-2-(4-(3-(2-((2R,5R)-5-(3-aminopropyl)-3,6-dioxopiperazin-2-yl)acetamido)propoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-((3-((2R,5R)-5-(2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-3,6-dioxopiperazin-2-yl)propyl)amino)-2-oxoethyl)-1,4,7,10-tetraazacyclododecane-1,4,7-triyl)triacetic acid (12.8 mg, 8.66 μmol, 28%) as a white solid. MS: Calc'd for $C_{63}H_{88}F_2N_{16}O_{16}$: 1362.7, found $[M+H-TFA]^+$: 1363.3.

Example 46: 2,2',2"-(10-(2-((6-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazin-1-yl)-6-oxohexyl)amino)-2-oxoethyl)-1,4,7,10-tetraazacyclododecane-1,4,7-triyl)triacetic acid (Compound 39)

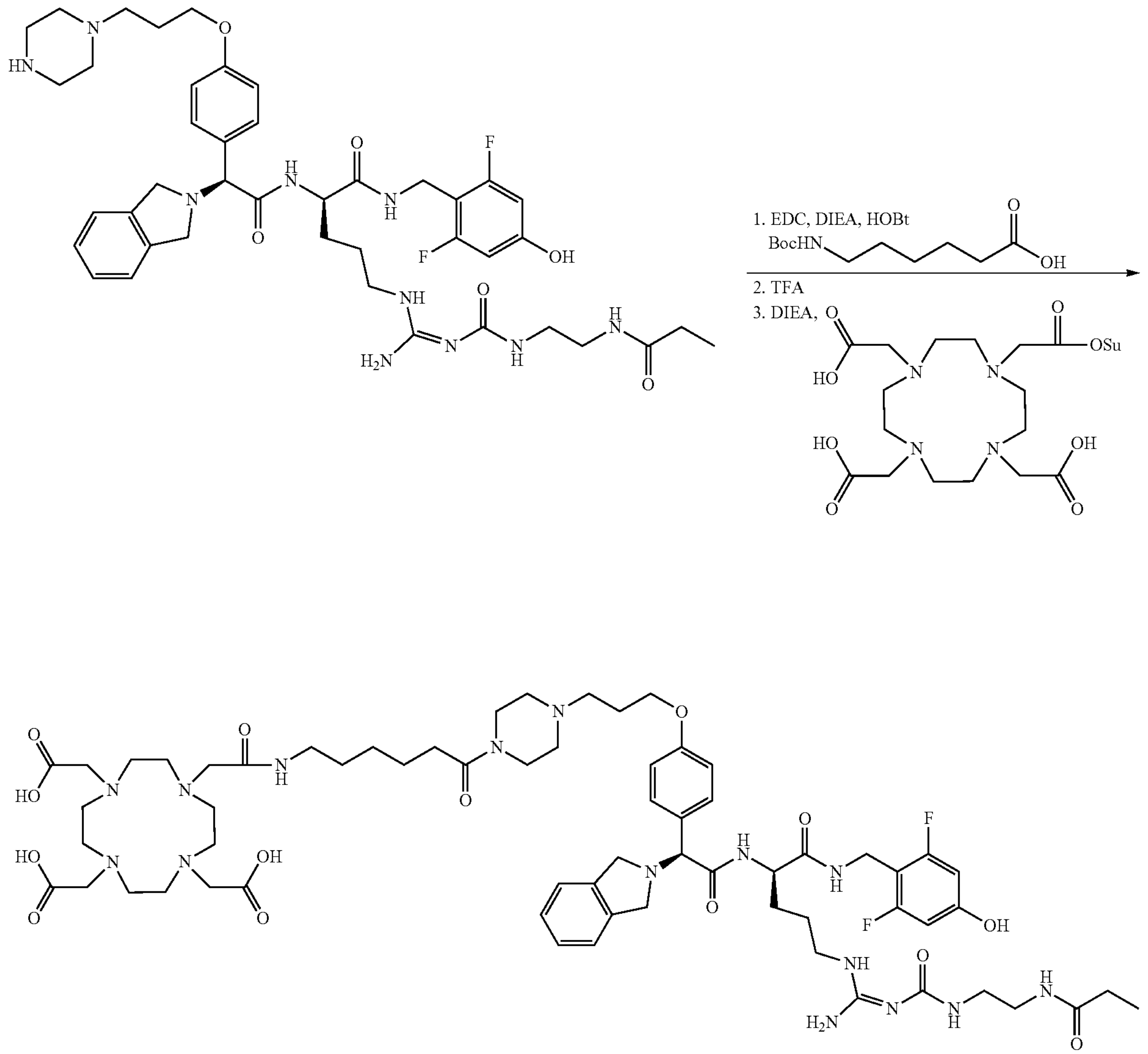

Step 1. (R)—N-(2,6-difluoro-4-hydroxybenzyl)-2-((S)-2-(isoindolin-2-yl)-2-(4-(3-(piperazin-1-yl)propoxy)phenyl)acetamido)-5-((Z)-2-((2-propionamidoethyl)carbamoyl)guanidino)pentanamide was treated with HOBt, EDCI, and DIEA in a manner similar to Example 23, Step 3 to provide tert-butyl (6-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazin-1-yl)-6-oxohexyl)carbamate (45 mg, 43 mol, 56%) as a yellow oil. $[M+H]^+$=1048.8.

Steps 2-3. tert-butyl (6-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazin-1-yl)-6-oxohexyl)carbamate was treated with TFA in a manner similar to Step 2 in the synthesis of Compound 1, then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-((6-(4-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)piperazin-1-yl)-6-oxohexyl)amino)-2-oxoethyl)-1,4,7,10-tetraazacyclododecane-1,4,7-triyl)triacetic acid (18.1 mg, 12.5 μmol, 31%) as a white solid. MS: Calc'd for $C_{64}H_{93}F_2N_{15}O_{14}$: 1333.7, found $[M+H]^+$: 1334.5.

Example 47: 2,2',2"-(10-(2-((3-((2R,5R)-5-(2-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-2-oxoethyl)-3,6-dioxopiperazin-2-yl)propyl)amino)-2-oxoethyl)-1,4,7,10-tetraazacyclododecane-1,4,7-triyl)triacetic acid (Compound 40)

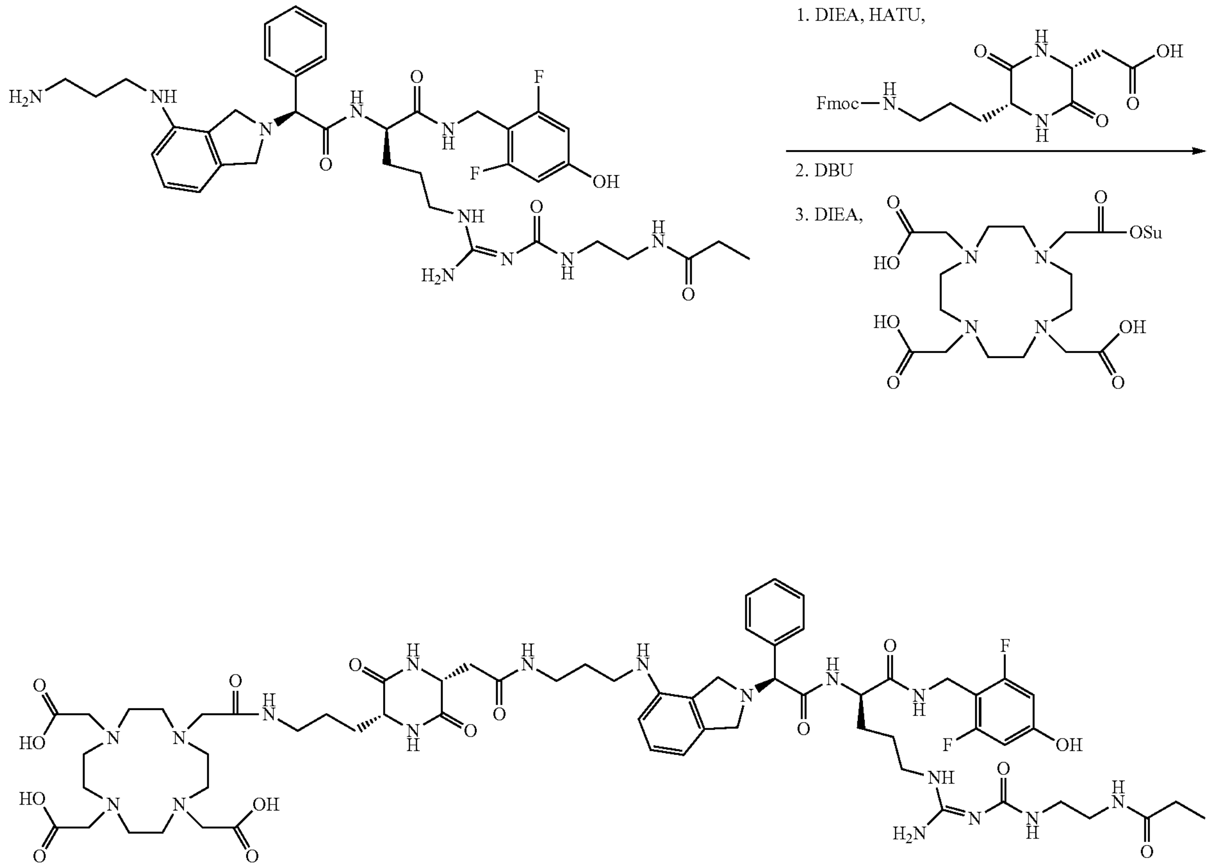

Step 1. (R)-2-((S)-2-(4-((3-aminopropyl)amino)isoindolin-2-yl)-2-phenylacetamido)-N-(2,6-difluoro-4-hydroxybenzyl)-5-((Z)-2-((2-propionamidoethyl)carbamoyl)guanidino)pentanamide was treated with 2-((2R,5R)-5-(3-((((9H-fluoren-9-yl)methoxy)carbonyl)amino)propyl)-3,6-dioxopiperazin-2-yl)acetic acid, HATU and DIEA in a manner similar to Step 3 of the synthesis of Compound 1, to provide (9H-fluoren-9-yl)methyl (3-((2R,5R)-5-(2-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-2-oxoethyl)-3,6-dioxopiperazin-2-yl)propyl)carbamate (40 mg, 33 μmol, 51%) as a yellow oil. $[M+H]^+=1198.4$.

Step 2. (9H-fluoren-9-yl)methyl (3-((2R,5R)-5-(2-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-2-oxoethyl)-3,6-dioxopiperazin-2-yl)propyl)carbamate was treated with DBU in a manner similar to Example 7, Step 4 to provide (R)-2-((S)-2-(4-((3-(2-((2R,5R)-5-(3-aminopropyl)-3,6-dioxopiperazin-2-yl)acetamido)propyl)amino)isoindolin-2-yl)-2-phenylacetamido)-N-(2,6-difluoro-4-hydroxybenzyl)-5-((Z)-2-((2-propionamidoethyl)carbamoyl)guanidino)pentanamide (32 mg, 33 mol, 98%) as a light yellow oil, which was used directly in the next step without any purification. $[M+H]^+=976.6$.

Step 3. (R)-2-((S)-2-(4-((3-(2-((2R,5R)-5-(3-aminopropyl)-3,6-dioxopiperazin-2-yl)acetamido)propyl)amino)isoindolin-2-yl)-2-phenylacetamido)-N-(2,6-difluoro-4-hydroxybenzyl)-5-((Z)-2-((2-propionamidoethyl)carbamoyl)guanidino)pentanamide 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-((3-((2R,5R)-5-(2-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-2-oxoethyl)-3,6-dioxopiperazin-2-yl)propyl)amino)-2-oxoethyl)-1,4,7,10-tetraazacyclododecane-1,4,7-triyl)triacetic acid (24.6 mg, 16.7 μmol, 51%) as a white solid. MS: Calc'd for $C_{63}H_{89}F_2N_{17}O_{15}$: 1361.7, found $[M+H-TFA]^+$: 1362.5.

Example 48: 2,2',2"-(10-(2-(((3R,5R)-7-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-3,5-dihydroxy-7-oxoheptyl)amino)-2-oxoethyl)-1,4,7,10-tetraazacyclododecane-1,4,7-triyl)triacetic acid (Compound 41)

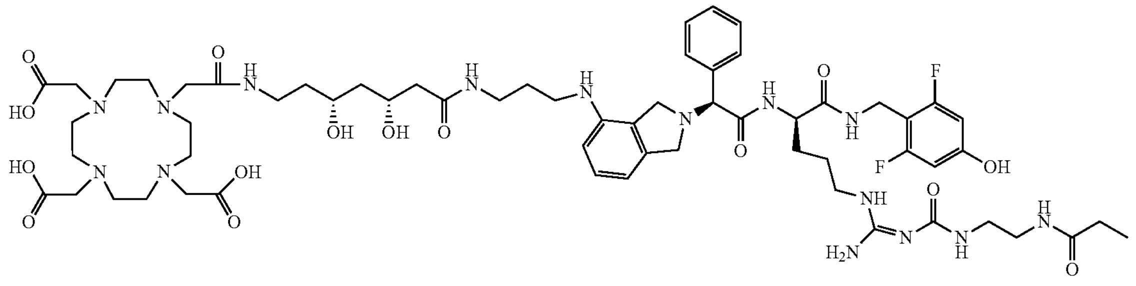 [SMILES: CCC(=O)NCCNC(=O)/N=C(/N)NCCC[C@@H](NC(=O)[C@H](c1ccccc1)N1Cc2cccc(NCCCNC(=O)C[C@H](O)C[C@H](O)CCNC(=O)CN3CCN(CC(=O)O)CCN(CC(=O)O)CCN(CC(=O)O)CC3)c2C1)C(=O)NCc1c(F)cc(O)cc1F]

Step 1. (R)-2-((S)-2-(4-((3-aminopropyl)amino)isoindolin-2-yl)-2-phenylacetamido)-N-(2,6-difluoro-4-hydroxybenzyl)-5-((Z)-2-((2-propionamidoethyl)carbamoyl)guanidino)pentanamide was treated with 2-((4R,6R)-6-(2-((tert-butoxycarbonyl)amino)ethyl)-2,2-dimethyl-1,3-dioxan-4-yl)acetic acid, HATU and DIEA in a manner similar to Step 3 of the synthesis of Compound 1, to provide tert-butyl (2-((4R,6R)-6-(2-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-2-oxoethyl)-2,2-dimethyl-1,3-dioxan-4-yl)ethyl)carbamate (36 mg, 34 μmol, 52%) as a yellow oil. $[M+H]^+$=1064.5.

Steps 2-3. tert-butyl (2-((4R,6R)-6-(2-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-2-oxoethyl)-2,2-dimethyl-1,3-dioxan-4-yl)ethyl)carbamate was treated with TFA in a manner similar to Step 2 in the synthesis of Compound 1, then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-(((3R,5R)-7-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-3,5-dihydroxy-7-oxoheptyl)amino)-2-oxoethyl)-1,4,7,10-tetraazacyclododecane-1,4,7-triyl)triacetic acid (19.0 mg, 13.3 μmol, 48%) as a white solid. MS: Calc'd for $C_{61}H_{89}F_2N_{15}O_{15}$: 1309.66, found $[M+H]^+$: 1310.6.

Example 49: 2,2',2"-(10-(2-((2-(4-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-4-oxobutanamido)ethyl)amino)-2-oxoethyl)-1,4,7,10-tetraazacyclododecane-1,4,7-triyl)triacetic acid (Compound 42)

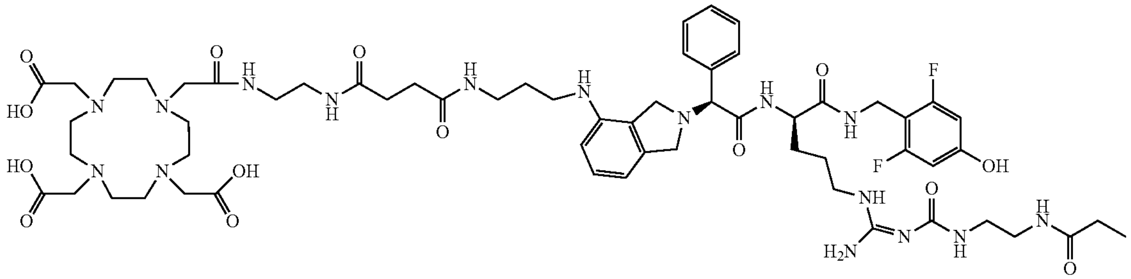 [SMILES: CCC(=O)NCCNC(=O)/N=C(/N)NCCC[C@@H](NC(=O)[C@H](c1ccccc1)N1Cc2cccc(NCCCNC(=O)CCC(=O)NCCNC(=O)CN3CCN(CC(=O)O)CCN(CC(=O)O)CCN(CC(=O)O)CC3)c2C1)C(=O)NCc1c(F)cc(O)cc1F]

Step 1. (R)-2-((S)-2-(4-((3-aminopropyl)amino)isoindolin-2-yl)-2-phenylacetamido)-N-(2,6-difluoro-4-hydroxybenzyl)-5-((Z)-2-((2-propionamidoethyl)carbamoyl)guanidino)pentanamide was treated with 2-((4R,6R)-6-(2-((tert-butoxycarbonyl)amino)ethyl)-2,2-dimethyl-1,3-dioxan-4-yl)acetic acid, HATU and DIEA in a manner similar to Step 3 of the synthesis of Compound 1, to provide tert-butyl (2-(4-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-4-oxobutanamido)ethyl)carbamate (40 mg, 40 µmol, 61%) as a yellow oil. $[M+H]^+=1007.5$.

Steps 2-3. tert-butyl (2-(4-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-4-oxobutanamido)ethyl) carbamatewas treated with TFA in a manner similar to Step 2 in the synthesis of Compound 1, then treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2''-(10-(2-((2-(4-((3-((2-((1S,4R,Z)-9-amino-4-((2,6-difluoro-4-hydroxybenzyl)carbamoyl)-2,11,16-trioxo-1-phenyl-3,8,10,12,15-pentaazaoctadec-9-en-1-yl)isoindolin-4-yl)amino)propyl)amino)-4-oxobutanamido)ethyl)amino)-2-oxoethyl)-1,4,7,10-tetraazacyclododecane-1,4,7-triyl)triacetic acid (26.7 mg, 19.0 µmol, 54%) as a white solid. MS: Calc'd for $C_{60}H_{86}F_2N_{16}O_{14}$: 1292.64, found $[M+H]^+$: 1293.5.

Example 50: 2,2',2''-(10-(17-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-2,10,13-trioxo-6-oxa-3,9,14-triazaheptadecyl)-1,4,7,10-tetraazacyclododecane-1,4,7-triyl)triacetic acid (Compound 43)

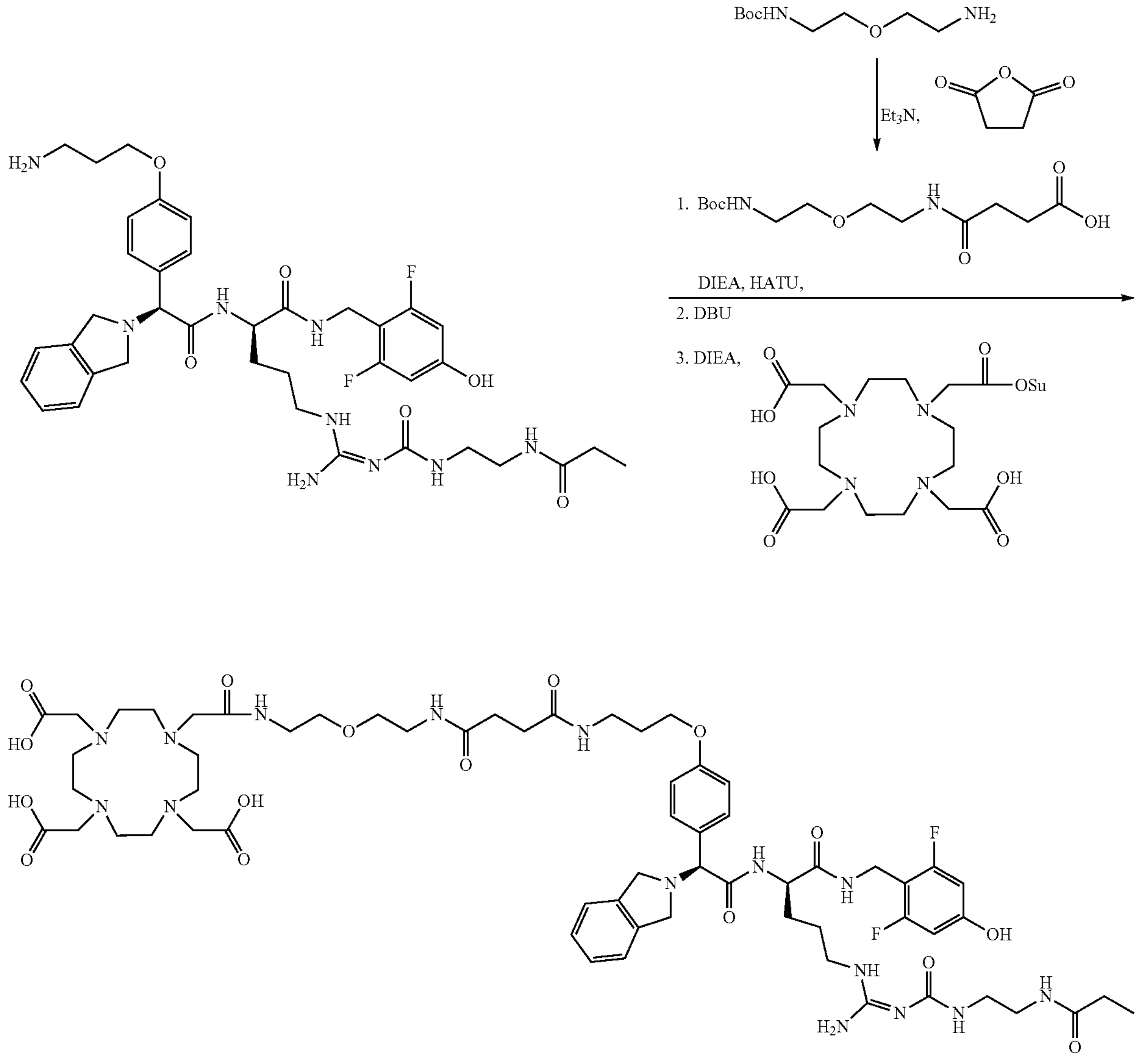

Step 1. Into a 40-mL vial, was placed a mixture of tert-butyl (2-(2-aminoethoxy)ethyl)carbamate (525 mg, 1 Eq, 2.57 mmol) and THE (5 mL), to which was added TEA (1.30 g, 1.79 mL, 5.00 Eq, 12.8 mmol) and dihydrofuran-2,5-dione (386 mg, 1.50 Eq, 3.86 mmol). The reaction mixture was stirred at 20° C. for 1 hour. The crude product was purified by Prep-HPLC to provide 2,2-dimethyl-4,12-dioxo-3,8-dioxa-5,11-diazapentadecan-15-oic acid (800 mg, 2.1 mmol, 82%) as a yellow oil. $[M+H]^+$=305.1.

Step 2. (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide was treated with 2,2-dimethyl-4,12-dioxo-3,8-dioxa-5,11-diazapentadecan-15-oic acid, HATU and DIEA in a manner similar to Step 3 of the synthesis of Compound 1, to provide tert-butyl (2-(2-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-4-oxobutanamido)ethoxy)ethyl)carbamate (80 mg, 49 μmol, 37%) as a yellow oil. $[M+H]^+$=1052.6.

Steps 3-4. tert-butyl (2-(2-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-4-oxobutanamido)ethoxy)ethyl)carbamate was treated with TFA in a manner similar to Step 2 in the synthesis of Compound 1, then treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2''-(10-(17-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-2,10,13-trioxo-6-oxa-3,9,14-triazaheptadecyl)-1,4,7,10-tetraazacyclododecane-1,4,7-triyl)triacetic acid (29.8 mg, 20.5 μmol, 30%) as a white solid. MS: Calc'd for $C_{62}H_{89}F_2N_{15}O_{16}$: 1337.65, found $[M+H]^+$: 1339.0.

Example 51: 2,2',2''-(10-(14-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-2,6,10-trioxo-8-oxa-3,7,11-triazatetradecyl)-1,4,7,10-tetraazacyclododecane-1,4,7-triyl)triacetic acid (Compound 44)

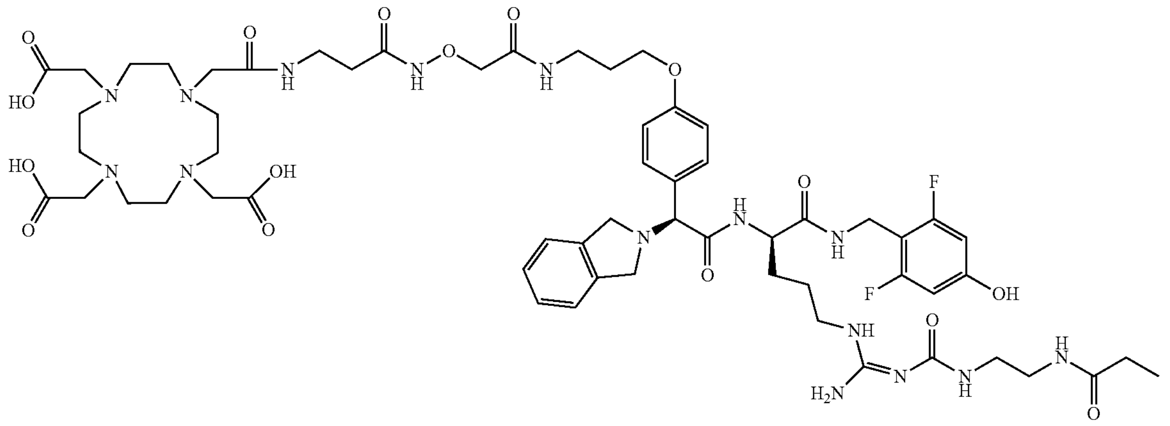 [SMILES: CCC(=O)NCCNC(=O)/N=C(/N)NCCC[C@@H](NC(=O)[C@H](c1ccc(OCCCNC(=O)CONC(=O)CCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F]

Step 1. The trifluoroacetic acid salt of 2,2',2''-(10-(14-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-2,6,10-trioxo-8-oxa-3,7,11-triazatetradecyl)-1,4,7,1-tetraazacyclododecane-1,4,7-triyl)triacetic acid was synthesized from (R)-2-((S)-2-(4-(3-(2-((3-aminopropanamido)oxy)acetamido)propoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide and 1-(9H-fluoren-9-yl)-3,7-dioxo-2,9-dioxa-4,8-diazaundecan-11-oic acid in a manner similar to Example 51, Steps 2-4 to provide the product (37.9 mg, 26.9 μmol, 70%) as a white solid. MS: Calc'd for $C_{59}H_{83}F_2N_{15}O_{16}$: 1295.4, found $[M+H]^+$: 1296.5.

Example 52: 2,2',2"-(10-(12-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-2,8-dioxo-4-oxa-3,7,9-triazadodecyl)-1,4,7,10-tetraazacyclododecane-1,4,7-triyl)triacetic acid (Compound 45)

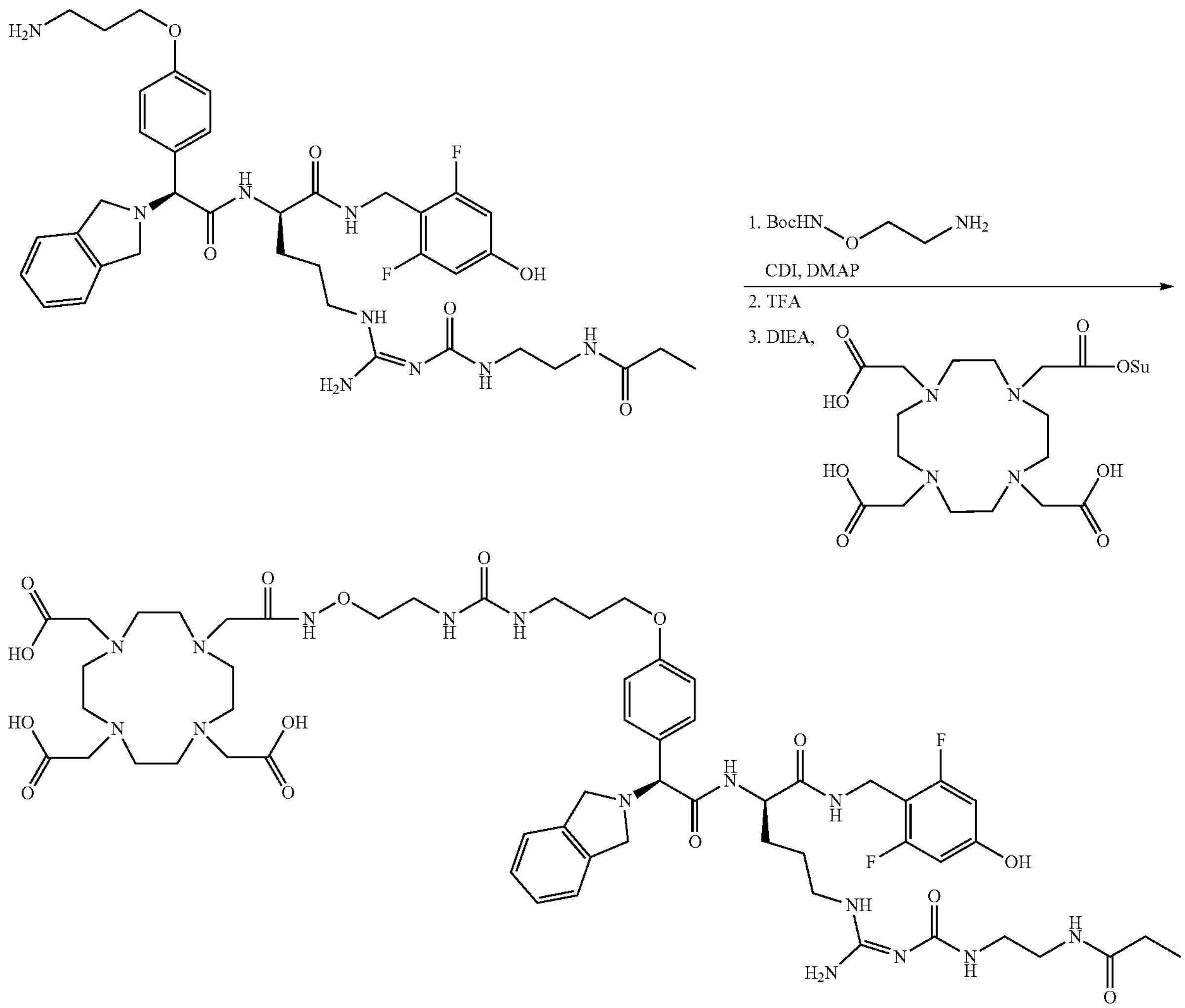

Step 1. Into a 8-mL vial, was placed a mixture of tert-butyl (2-aminoethoxy)carbamate (12 mg, 1.0 Eq, 68 μmol), CDI (10 mg, 0.94 Eq, 62 μmol), and ACN (1 mL). The reaction mixture was stirred at 25° C. for 10 minutes, then (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (50 mg, 1 Eq, 65 μmol) and DMAP (2 mg, 0.3 Eq, 0.02 mmol) were added and the reaction mixture was stirred at 50° C. for an additional 16 hours. The mixture was directly purified by MPLC to provide tert-butyl (2-(3-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)ureido)ethoxy)carbamate (60 mg, 62 μmol, 95%) as a white solid. $[M+H]^+$=968.6.

Steps 2-3. tert-Butyl (2-(3-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)ureido)ethoxy)carbamate was treated with TFA in a manner similar to Step 2 in the synthesis of Compound 1, then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(12-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-2,8-dioxo-4-oxa-3,7,9-triazadodecyl)-1,4,7,10-tetraazacyclododecane-1,4,7-triyl)triacetic acid (25.2 mg, 18.4 μmol, 32%) as a white solid. MS: Calc'd for $C_{57}H_{81}F_2N_{15}O_{15}$: 1253.6, found $[M+H]^+$: 1254.4.

Example 53: 2,2',2"-(10-(15-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-3,6,9-trimethyl-2,5,8,11-tetraoxo-3,6,9,12-tetraazapentadecyl)-1,4,7,10-tetraazacyclododecane-1,4,7-triyl)triacetic acid (Compound 46)

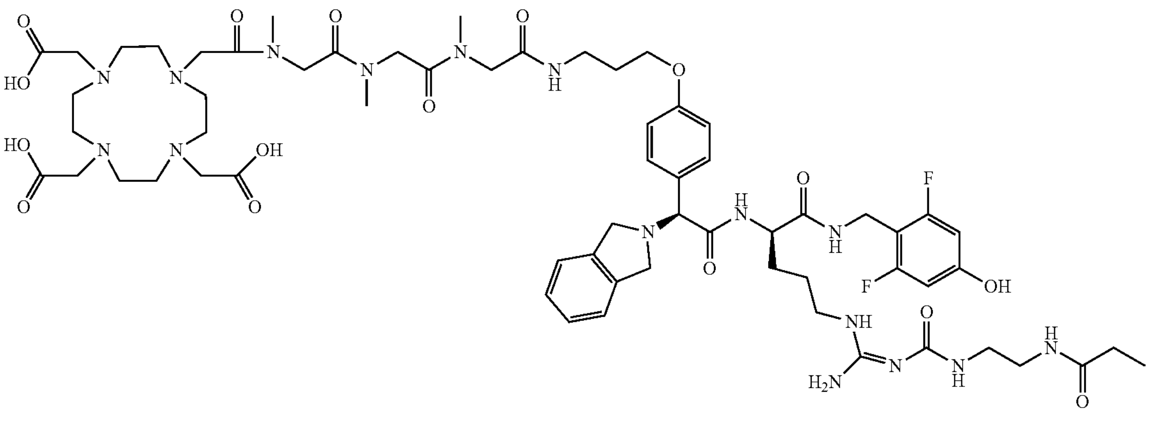 [SMILES: CCC(=O)NCCNC(=O)/N=C(/N)NCCC[C@@H](NC(=O)[C@H](c1ccc(OCCCNC(=O)CN(C)C(=O)CN(C)C(=O)CN(C)C(=O)CN2CCN(CC(=O)O)CCN(CC(=O)O)CCN(CC(=O)O)CC2)cc1)N1Cc2ccccc2C1)C(=O)NCc1c(F)cc(O)cc1F]

Step 1A. Into a 8-mL vial, was placed a mixture of 1-(9H-fluoren-9-yl)-4,7,10-trimethyl-3,6,9-trioxo-2-oxa-4,7,10-triazadodecan-12-oic acid (50 mg, 1.5 Eq, 0.11 mmol), DCC (25 mg, 1.7 Eq, 0.12 mmol), NHS (15 mg, 1.8 Eq, 0.13 mmol) and THE (0.5 mL). The reaction mixture was stirred at 25° C. for 1 hour. The mixture was added to the reaction mixture in Step 1B, and transferred with THF. Step 1B. Into another 8-mL vial, was placed a mixture of the crude product from Step 1A, (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino) pentanamide (55 mg, 1 Eq, 72 μmol), DIEA (46 mg, 62 μL, 5.0 Eq, 0.36 mmol) and THF (0.5 mL). The reaction mixture was stirred at 25° C. for 2 hours. The mixture was directly purified by MPLC to afford (9H-fluoren-9-yl)methyl (2-((2-((2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl) amino)-2-oxoethyl)(methyl)amino)-2-oxoethyl)(methyl) amino)-2-oxoethyl)(methyl)carbamate (60 mg, 43 μmol, 60%) as an off-white solid. $[M+H]^+$=1201.7.

Steps 2-3. (9H-fluoren-9-yl)methyl (2-((2-((2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)(methyl)amino)-2-oxoethyl)(methyl)amino)-2-oxoethyl)(methyl)carbamate was treated with DBU in a manner similar to Example 7, Step 4 then 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide 2,2',2"-(10-(15-(4-((1S,4R,Z)-9-amino-4-((2,6-difluoro-4-hydroxybenzyl) carbamoyl)-1-(isoindolin-2-yl)-2,11,16-trioxo-3,8,10,12,15-pentaazaoctadec-9-en-1-yl)phenoxy)-3,6,9-trimethyl-2,5,8,11-tetraoxo-3,6,9,12-tetraazapentadecyl)-1,4,7,10-tetraazacyclododecane-1,4,7-triyl)triacetic acid (18.7 mg, 12.3 μmol, 33%) as an off-white solid. MS: Calc'd for $C_{63}H_{90}F_2N_{16}O_{16}$: 1364.62, found $[M+H]^+$: 1365.5.

Example 54: 2,2',2"-(10-(2-((3-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropyl)amino)-2-oxoethyl)-1,4,7,10-tetraazacyclododecane-1,4,7-triyl)triacetic acid (Compound 47)

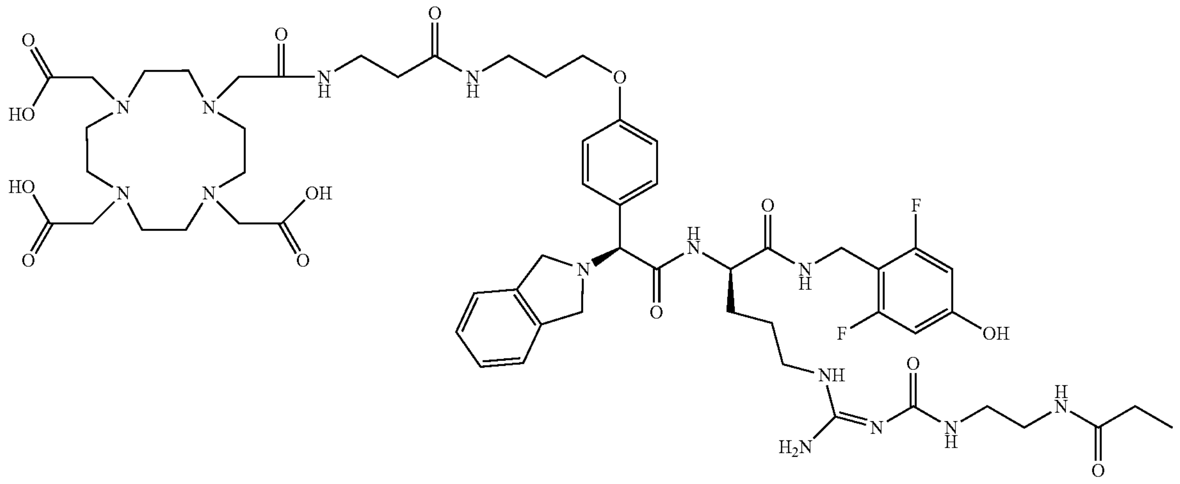 [SMILES: CCC(=O)NCCNC(=O)/N=C(/N)NCCC[C@@H](NC(=O)[C@H](c1ccc(OCCCNC(=O)CCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F]

Step 1. Into an 8-mL vial, was placed a mixture of (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (40 mg, 1 Eq, 52 μmol), 2,5-dioxopyrrolidin-1-yl 3-((tert-butoxycarbonyl)amino)propanoate (18 mg, 1.2 Eq, 63 μmol), DIEA (20 mg, 27 μL, 3.0 Eq, 0.15 mmol) and DMF (0.5 mL). The reaction mixture was stirred at 25° C. for 2 hours. The mixture was directly purified by MPLC to afford tert-butyl (3-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropyl)carbamate (34 mg, 33 μmol, 63%) as an off-white solid. $[M+H]^+$=937.8.

Steps 2-3. tert-Butyl (3-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropyl)carbamate was treated with TFA in a manner similar to Step 2 in the synthesis of Compound 1, then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-((3-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropyl)amino)-2-oxoethyl)-1,4,7,10-tetraazacyclododecane-1,4,7-triyl)triacetic acid (16 mg, 12 μmol, 32%) as a white solid. MS: Calc'd for $C_{57}H_{80}F_2N_{14}O_{14}$: 1222.59, found $[M+H]^+$: 1223.5.

Example 55: 2,2',2"-(10-(2-((3-(((R)-1-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-hydroxy-1-oxopropan-2-yl)amino)-3-oxopropyl)amino)-2-oxoethyl)-1,4,7,10-tetraazacyclododecane-1,4,7-triyl)triacetic acid (Compound 48)

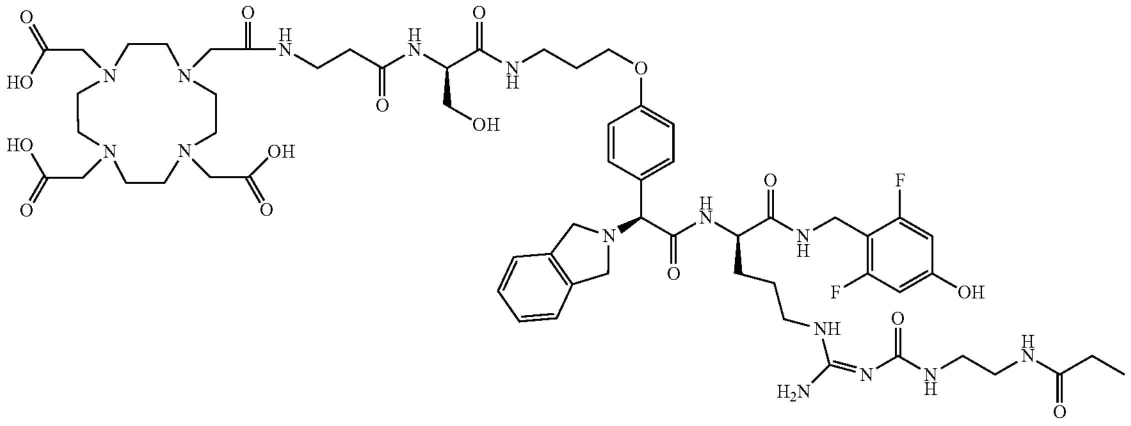 [SMILES: CCC(=O)NCCNC(=O)/N=C(/N)NCCC[C@@H](NC(=O)[C@H](c1ccc(OCCCNC(=O)[C@@H](CO)NC(=O)CCNC(=O)CN2CCN(CC(=O)O)CCN(CC(=O)O)CCN(CC(=O)O)CC2)cc1)N1Cc2ccccc2C1)C(=O)NCc1c(F)cc(O)cc1F]

Steps 1-3. The trifluoroacetic acid salt of 2,2',2"-(10-(2-((3-(((R)-1-((3-(4-((1 S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-hydroxy-1-oxopropan-2-yl)amino)-3-oxopropyl)amino)-2-oxoethyl)-1,4,7,10-tetraazacyclododecane-1,4,7-triyl)triacetic acid was synthesized from 3-((((9H-fluoren-9-yl)methoxy)carbonyl)amino)propanoyl)-D-serine and (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide in a manner similar to Step 1 of the synthesis of Compound 1, Step 4 of Example 7, then Step 5 of Example 1, to provide the product (25.0 mg, 17.6 μmol, 54%) as a white solid. MS: Calc'd for $C_{60}H_{85}F_2N_{15}O_{16}$: 1309.63, found $[M+H]^+$: 1310.6.

Example 56: 2,2',2"-(10-(4-((2-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-4-oxobutanamido)ethyl)amino)-1-carboxy-4-oxobutyl)-1,4,7,10-tetraazacyclododecane-1,4,7-triyl)triacetic acid (Compound 49)

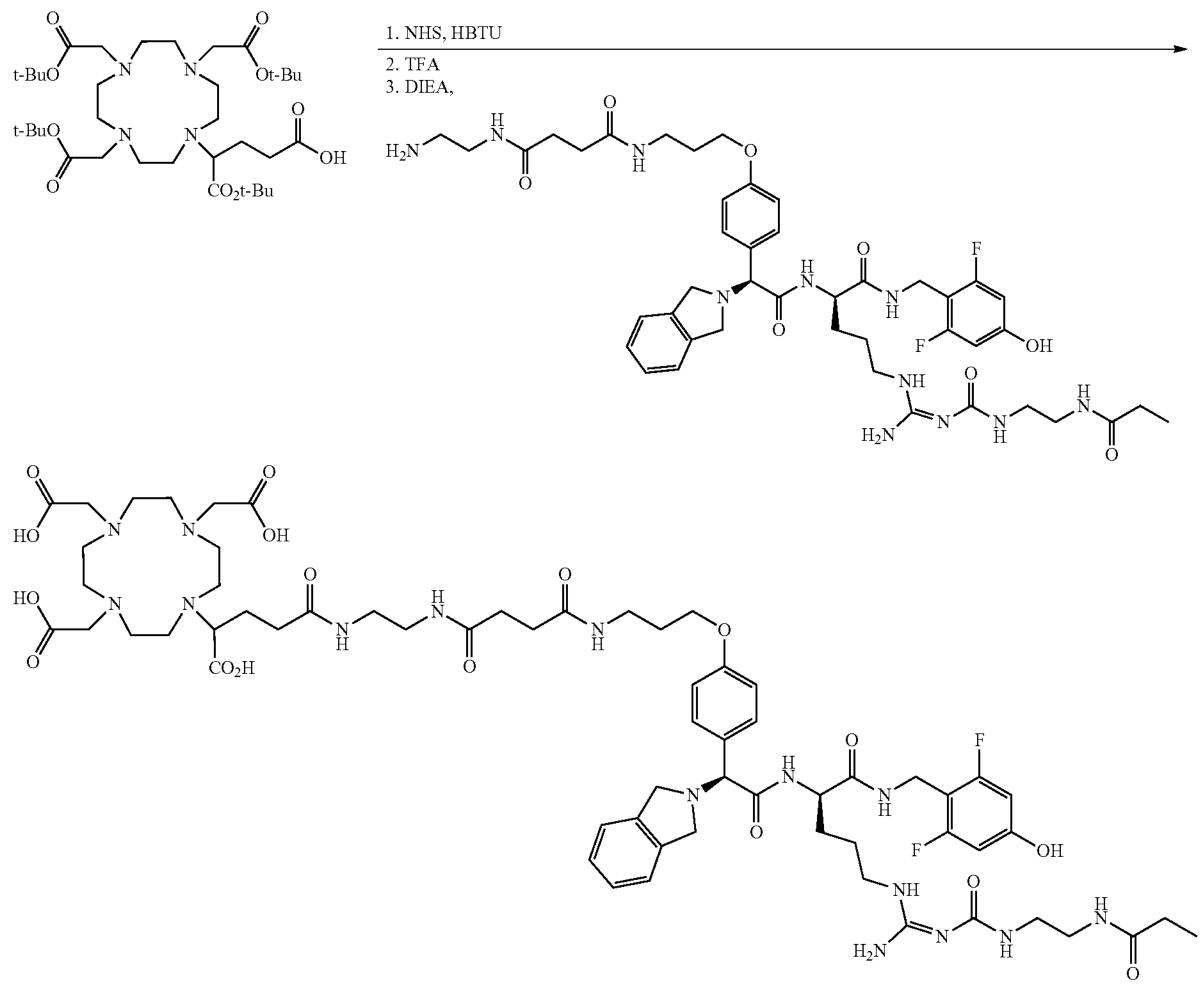

Step 1. Into an 8-mL vial, was placed a mixture of 5-(tert-butoxy)-5-oxo-4-(4,7,10-tris(2-(tert-butoxy)-2-oxoethyl)-1,4,7,10-tetraazacyclododecan-1-yl)pentanoic acid (200 mg, 1 Eq, 285 μmol), NHS (45 mg, 1.4 Eq, 0.39 mmol), HBTU (150 mg, 1.39 Eq, 396 μmol) and ACN (3 mL). The reaction mixture was stirred at 25° C. for 1 hour. The crude product was purified by MPLC to provide 1-(tert-butyl) 5-(2,5-dioxopyrrolidin-1-yl) 2-(4,7,10-tris(2-(tert-butoxy)-2-oxoethyl)-1,4,7,10-tetraazacyclododecan-1-yl)pentanedioate (150 mg, 0.13 mmol, 46%) as a yellow solid. $[M+H]^+$=798.7.

Step 2. Into an 8-mL vial, was placed a mixture of 1-(tert-butyl) 5-(2,5-dioxopyrrolidin-1-yl) 2-(4,7,10-tris(2-(tert-butoxy)-2-oxoethyl)-1,4,7,10-tetraazacyclododecan-1-yl)pentanedioate (150 mg, 70% Wt, 1 Eq, 132 μmol) and DCM (1 mL), to which was added TFA (0.5 mL). The reaction mixture was stirred at 25° C. for 24 hours. The mixture was concentrated under reduced pressure to afford 2,2',2"-(10-(1-carboxy-4-((2,5-dioxopyrrolidin-1-yl)oxy)-4-oxobutyl)-1,4,7,10-tetraazacyclododecane-1,4,7-triyl)triacetic acid (150 mg, 0.12 mmol, 89%) as a light yellow solid, which was used directly in the next step without any purification. $[M+Na]^+$=574.3.

Step 3. Into an 8-mL vial, was placed a mixture of N1-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)-N4-(2-aminoethyl)succinamide (50 mg, 1 Eq, 55 mol) (from Example 12), 2,2',2"-(10-(1-carboxy-4-((2,5-dioxopyrrolidin-1-yl)oxy)-4-oxobutyl)-1,4,7,10-tetraazacyclododecane-1,4,7-triyl)triacetic acid (90 mg, 2.8 Eq, 0.16 mmol) and DMF (1 mL), to which was added DIEA (22 mg, 30 L, 3.1 Eq, 0.17 mmol). The reaction mixture was stirred at 25° C. for 1 hour. The mixture was directly purified by Prep-HPLC to provide the trifluoroacetic acid salt of 2,2',2"-(10-(4-((2-(4-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-4-oxobutanamido)ethyl)amino)-1-carboxy-4-oxobutyl)-1,4,7,10-tetraazacyclododecane-1,4,7-triyl)triacetic acid (35.0 mg, 23.6 μmol, 43%) as a white solid. MS: Calc'd for $C_{63}H_{89}F_2N_{15}O_{17}$: 1365.65, found $[M+H]^+$: 1366.5.

Example 57: 2,2',2''-(10-(2-((3-(((R)-4-amino-1-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-1,4-dioxobutan-2-yl)amino)-3-oxopropyl)amino)-2-oxoethyl)-1,4,7,10-tetraazacyclododecane-1,4,7-triyl)triacetic acid (Compound 50)

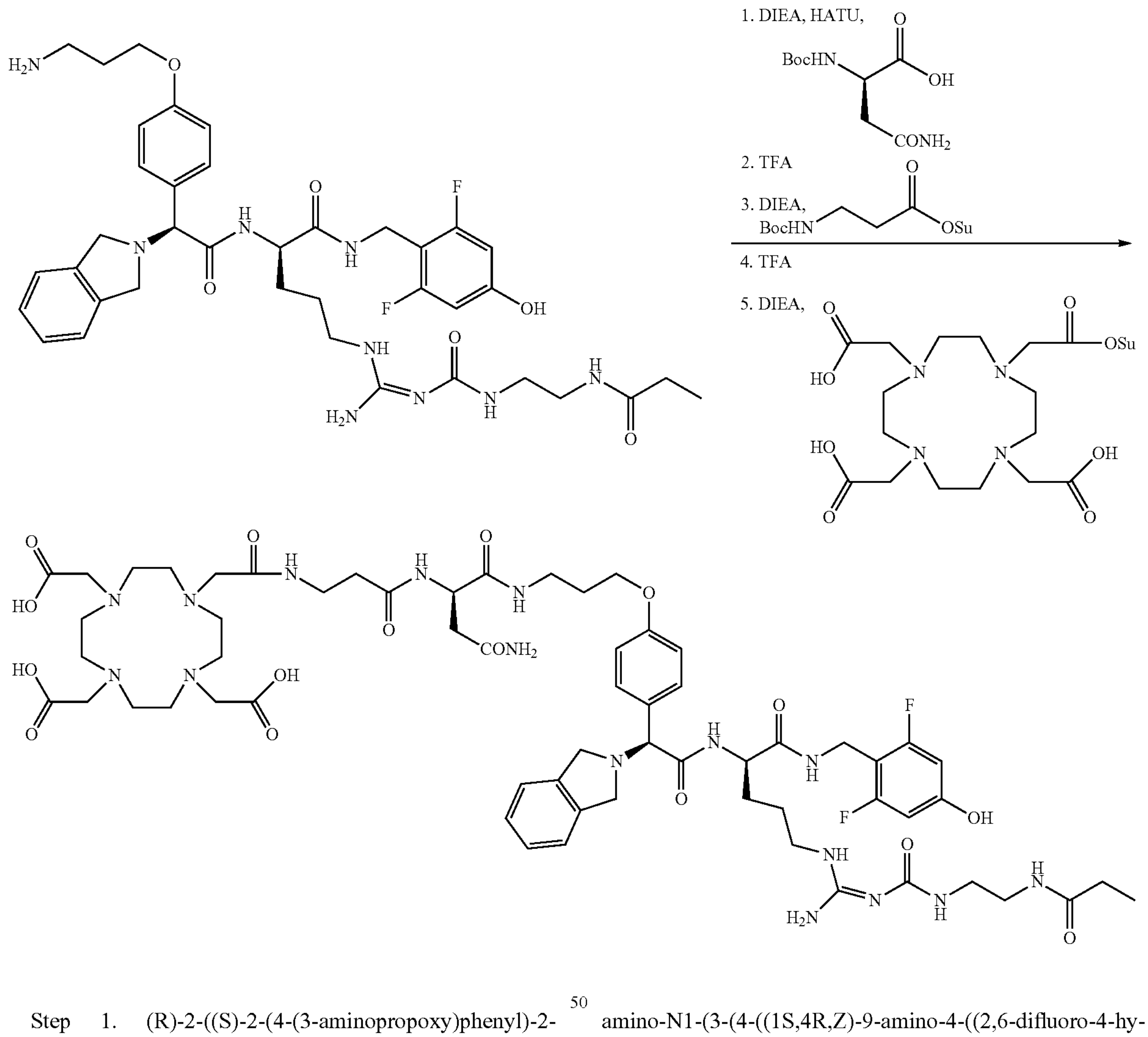

Step 1. (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide was treated with (tert-butoxycarbonyl)-D-asparagine, HATU and DIEA in a manner similar to Step 3 of the synthesis of Compound 1, to provide tert-butyl ((R)-4-amino-1-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-1,4-dioxobutan-2-yl)carbamate (180 mg, 184 μmol, 70.3%) as a yellow oil. $[M+H]^+$=980.4.

Step 2. tert-butyl ((R)-4-amino-1-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-1,4-dioxobutan-2-yl)carbamate was treated with TFA in a manner similar to Step 2 in the synthesis of Compound 1 to provide (R)-2-amino-N1-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)succinamide (160 mg, 182 μmol, 99.0%) as a crude oil without any purification. $[M+H]^+$=880.4.

Step 3. Into an 8-mL vial, was placed a mixture of (R)-2-amino-N1-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)succinamide (80 mg, 1 Eq, 91 μmol), DIEA (35 mg, 47 μL, 3.0 Eq, 0.27 mmol) and DMF (1 mL), to which was added 2,5-dioxopyrrolidin-1-yl 3-((tert-butoxycarbonyl)amino)propanoate (21 mg, 0.81 Eq, 73 μmol). The reaction mixture was stirred at 25° C. for 2 hours. The mixture was directly purified by MPLC to provide tert-butyl (3-(((R)-4-amino-1-((3-(4-((1S,4R,Z)-9-amino-4-((2,6-difluoro-4-hydroxybenzyl)carbamoyl)-1-(isoindolin-2-yl)-2, 11,16-trioxo-3,8,10,12,15-pentaazaoctadec-9-en-1-yl)phenoxy)propyl)amino)-1,4-dioxobutan-2-yl)amino)-3-oxopropyl)carbamate (50 mg, 48 mol, 52%) as a white solid. $[M+H]^+$=1051.4.

Steps 4-5. tert-butyl (3-(((R)-4-amino-1-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-1,4-dioxobutan-2-yl)amino)-3-oxopropyl)carbamate was treated with TFA in a manner similar to Step 2 in the synthesis of Compound 1, then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-(2-((3-(((R)-4-amino-1-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-1,4-dioxobutan-2-yl)amino)-3-oxopropyl)amino)-2-oxoethyl)-1,4,7,10-tetraazacyclododecane-1,4,7-triyl)triacetic acid (21.7 mg, 15.0 μmol, 36%) as a white solid. MS: Calc'd for $C_{61}H_{86}F_2N_{16}O_{16}$: 1336.63, found $[M+H]^+$: 1337.5.

Example 58: 2,2',2"-(10-((8R,11R)-11-(2-amino-2-oxoethyl)-16-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-8-(hydroxymethyl)-2,6,9,12-tetraoxo-3,7,10,13-tetraazahexadecyl)-1,4,7,10-tetraazacyclododecane-1,4,7-triyl)triacetic acid (Compound 51)

Step 1. (R)-2-Amino-N1-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)succinimide was treated with (3-((((9H-fluoren-9-yl)methoxy)carbonyl)amino)propanoyl)-D-serine, HATU and DIEA in a manner similar to Step 3 in the synthesis of Compound 1, to provide (9H-fluoren-9-yl)methyl (3-(((R)-1-(((R)-4-amino-1-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-1,4-dioxobutan-2-yl)amino)-3-hydroxy-1-oxopropan-2-yl)amino)-3-oxopropyl)carbamate (40 mg, 32 μmol, 35%) as a yellow oil. $[M+H]^+$=1260.5.

Steps 2-3. (9H-fluoren-9-yl)methyl (3-(((R)-1-(((R)-4-amino-1-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-1,4-dioxobutan-2-yl)amino)-3-hydroxy-1-oxopropan-2-yl)amino)-3-oxopropyl)carbamate was treated with DBU in a manner similar to Example 7, Step 4 then 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-((8R,11R)-11-(2-amino-2-oxoethyl)-16-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)

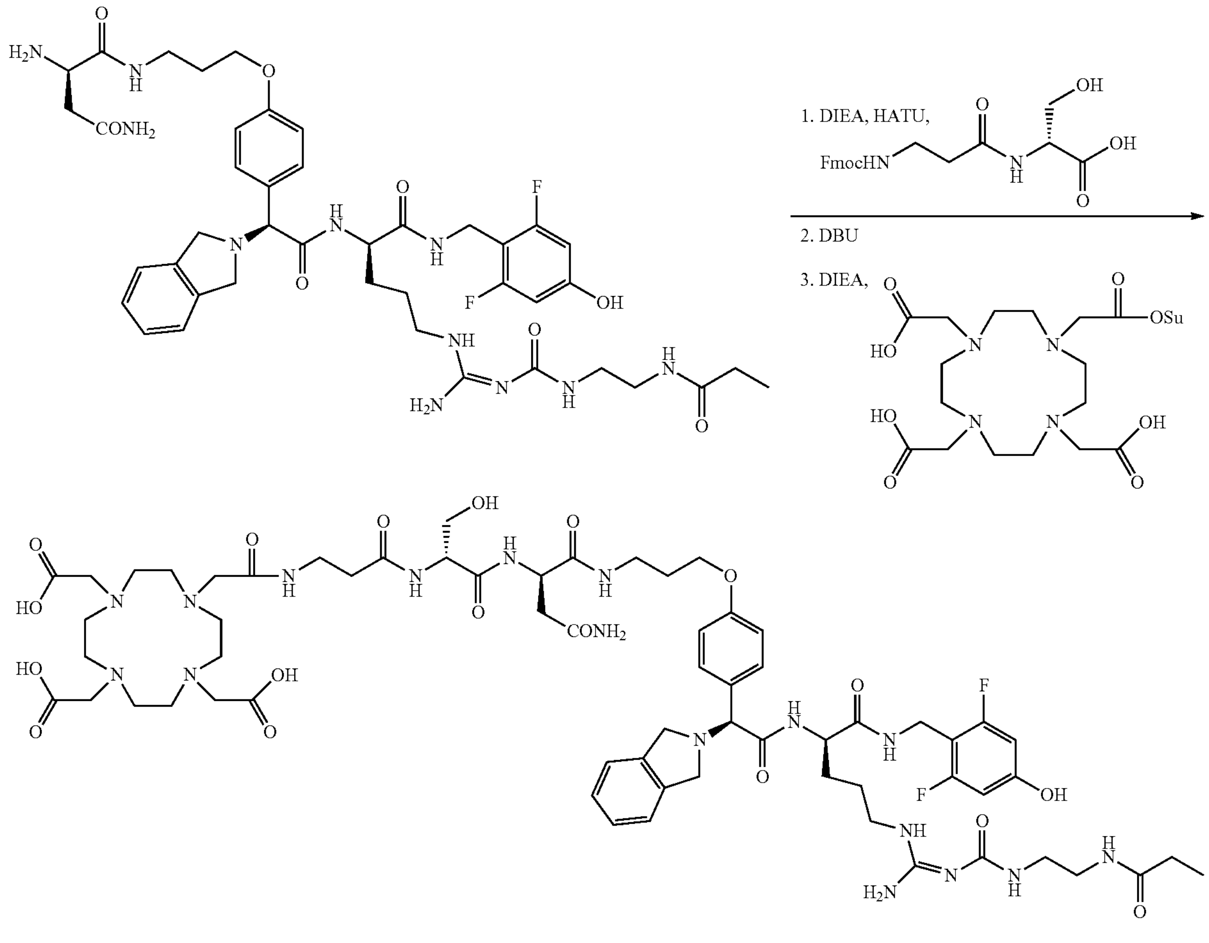

phenoxy)-8-(hydroxymethyl)-2,6,9,12-tetraoxo-3,7,10,13-tetraazahexadecyl)-1,4,7,10-tetraazacyclododecane-1,4,7-triyl)triacetic acid (3.3 mg, 2.1 μmol, 11%) as a white solid. MS: Calc'd for $C_{64}H_{91}F_2N_{17}O_{18}$: 1423.66, found $[M+H]^+$: 1424.4.

Example 59: 2,2',2"-(10-(2-((2-((2R,5R)-5-(2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-3,6-dioxopiperazin-2-yl)ethyl)amino)-2-oxoethyl)-1,4,7,10-tetraazacyclododecane-1,4,7-triyl)triacetic acid (Compound 52)

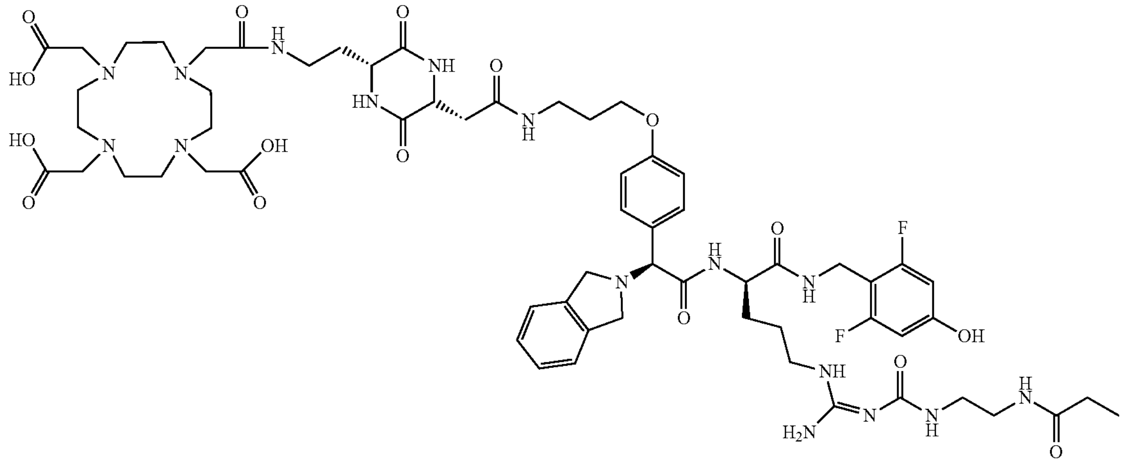

Steps 1-3. The trifluoroacetic acid salt of 2,2',2"-(10-(2-((2-((2R,5R)-5-(2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-3,6-dioxopiperazin-2-yl)ethyl)amino)-2-oxoethyl)-1,4,7,10-tetraazacyclododecane-1,4,7-triyl)triacetic acid was prepared from (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide and 2-((2R,5R)-5-(2-((((9H-fluoren-9-yl)methoxy)carbonyl)amino)ethyl)-3,6-dioxopiperazin-2-yl)acetic acid in a manner similar to Example 46, Steps 1-3 to provide the trifluoroacetic acid salt of 2,2',2"-(10-(2-((2-((2R,5R)-5-(2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-3,6-dioxopiperazin-2-yl)ethyl)amino)-2-oxoethyl)-1,4,7,10-tetraazacyclododecane-1,4,7-triyl)triacetic acid (21.3 mg, 13.4 μmol, 46%) as a white solid. MS: Calc'd for $C_{62}H_{86}F_2N_{16}O_{16}$: 1348.63, found $[M+H]^+$: 1349.5.

Example 60: 2,2',2"-(10-((14R,16R)-22-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-14,16-dihydroxy-2,7,10,18-tetraoxo-3,6,11,19-tetraazadocosyl)-1,4,7,10-tetraazacyclododecane-1,4,7-triyl)triacetic acid (Compound 53)

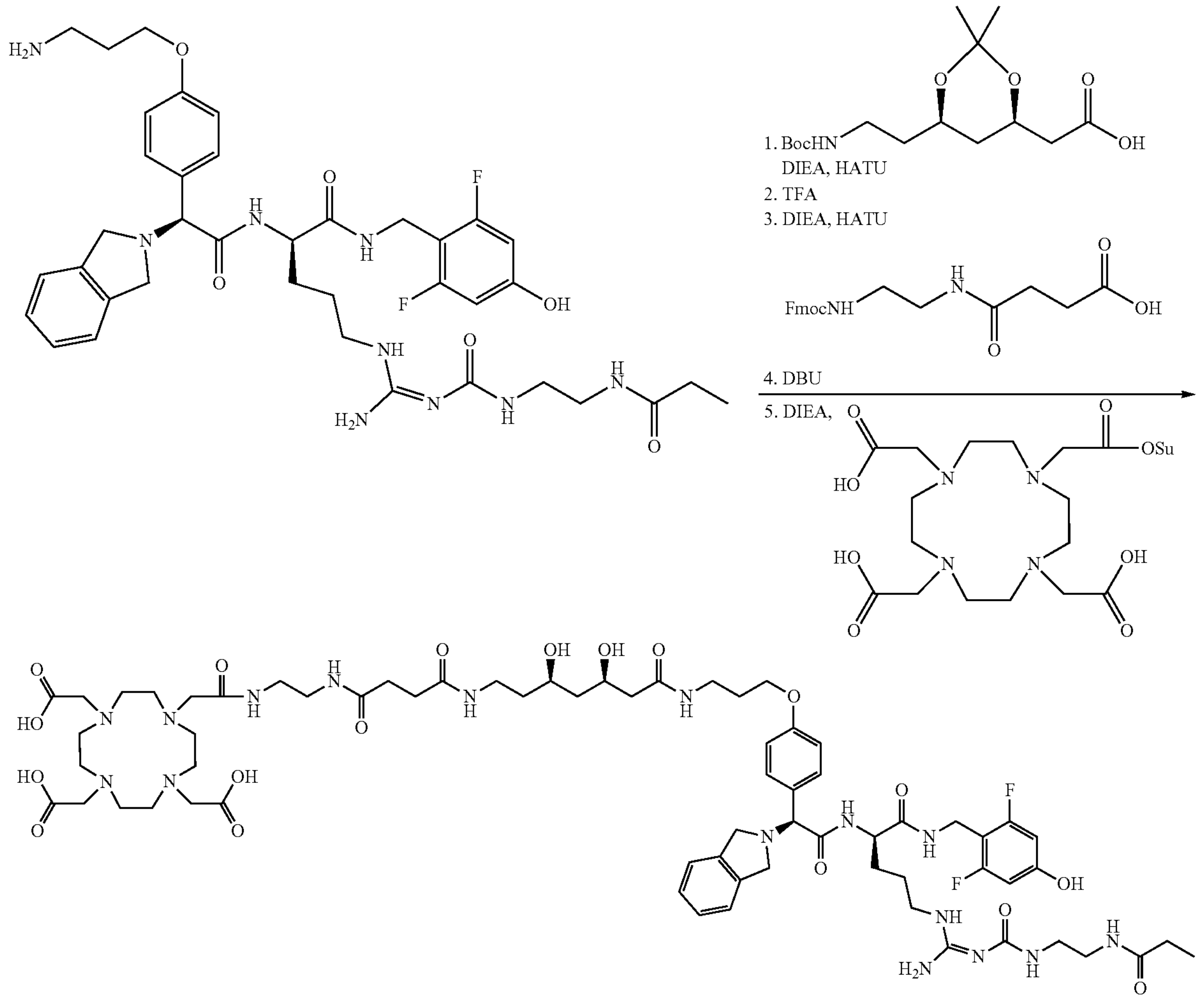

Step 1. (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino) pentanamide was treated with 2-((4R,6R)-6-(2-((tert-butoxycarbonyl)amino)ethyl)-2,2-dimethyl-1,3-dioxan-4-yl)acetic acid, HATU and DIEA in a manner similar to Step 3 of the synthesis of Compound 1, to provide tert-butyl (2-((4R,6R)-6-(2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-2,2-dimethyl-1,3-dioxan-4-yl)ethyl)carbamate (60 mg, 56 μmol, 51%) as a white solid. $[M+H]^+$=1065.7.

Step 2. tert-butyl (2-((4R,6R)-6-(2-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-2,2-dimethyl-1,3-dioxan-4-yl)ethyl)carbamate was treated with TFA in a manner similar to Step 2 in the synthesis of Compound 1 to provide (3R,5R)-7-amino-N-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)-3,5-dihydroxyheptanamide (50 mg, 54 μmol, 96%) as a yellow oil. $[M+H]^+$=925.6

Step 3. (3R,5R)-7-amino-N-(3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)-3,5-dihydroxyheptanamide was treated with 4-((2-((((9H-fluoren-9-yl)methoxy)carbonyl)amino)ethyl)amino)-4-oxobutanoic acid, HATU and DIEA in a manner similar to Step 3 of the synthesis of Compound 1, to provide (9H-fluoren-9-yl)methyl (2-(4-(((3R,5R)-7-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3,5- dihydroxy-7-oxoheptyl)amino)-4-oxobutanamido)ethyl) carbamate (30 mg, 23 μmol, 43%) as a white solid. $[M+H]^+$ =1290.4.

Step 4. (9H-fluoren-9-yl)methyl (2-(4-(((3R,5R)-7-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3,5-dihydroxy-7-oxoheptyl)amino)-4-oxobutanamido)ethyl) carbamate was treated with DBU in a manner similar to Example 7, Step 4 to provide N1-((3R,5R)-7-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3,5-dihydroxy-7-oxoheptyl)-N4-(2-aminoethyl)succinamide (20 mg, 19 μmol, 81%), which was used directly in the next step without any purification.

Step 5. N1-((3R,5R)-7-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3,5-dihydroxy-7-oxoheptyl)-N4-(2-aminoethyl)succinimide was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the trifluoroacetic acid salt of 2,2',2"-(10-((14R,16R)-22-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-14,16-dihydroxy-2,7,10,18-tetraoxo-3,6,11,19-tetraazadocosyl)-1,4,7,10-tetraazacyclododecane-1,4,7-triyl)triacetic acid (14.6 mg, 9.31 μmol, 40%) as a yellow oil. MS: Calc'd for $C_{67}H_{98}F_2N_{16}O_{18}$: 1452.72, found $[M+H]^+$: 1453.5.

Example 61: 2,2',2"-(10-((8R,11R,14R)-19-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-8,11,14-tris(hydroxymethyl)-2,6,9,12,15-pentaoxo-3,7,10,13,16-pentaazanonadecyl)-1,4,7,10-tetraazacyclododecane-1,4,7-triyl)triacetic acid (Compound 54)

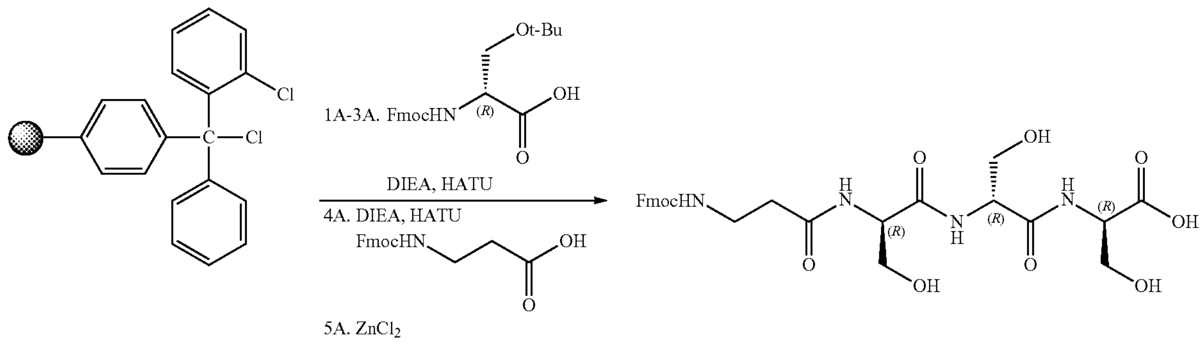

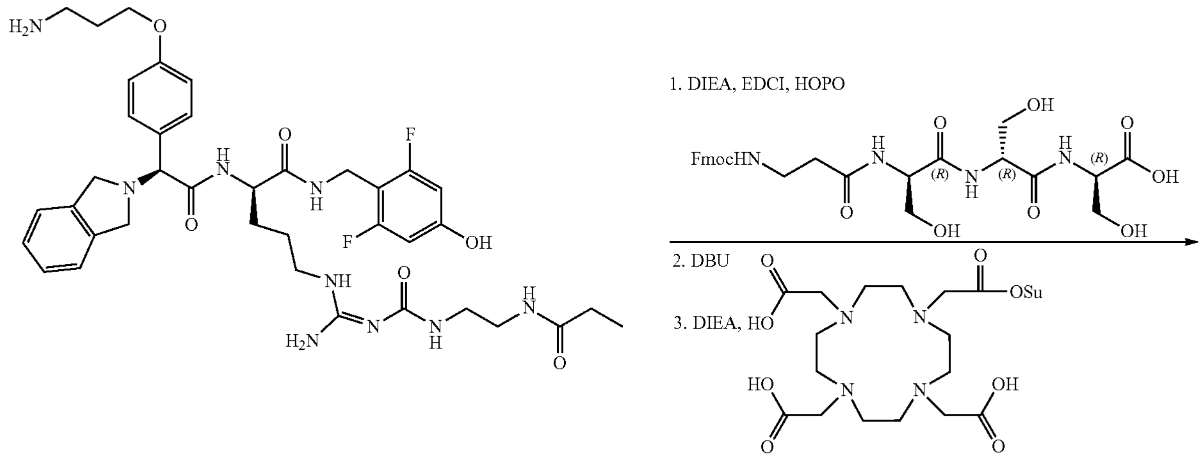

-continued

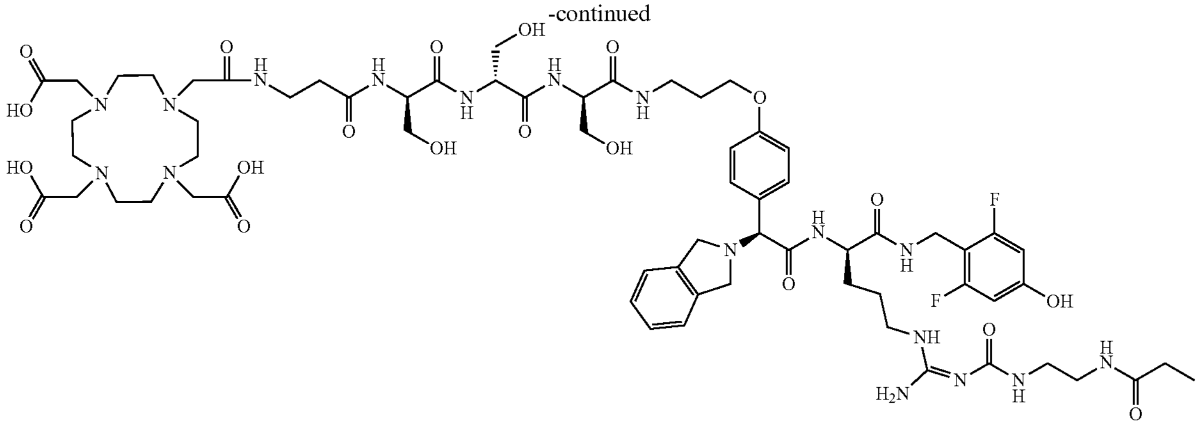

Step 1. General SPPS procedure:

Step 1A, Resin swelling: The resin (1-chloro-2-(chloro(phenyl)(p-tolyl)methyl)benzene (1.0 g, 1 Eq, 3.1 mmol) 500 mg/tube) was swelled in DCM (2 mL/tube) for 30 minutes at room temperature under nitrogen atmosphere. The resin was then washed 4 times with DCM (500 mL/tube).

Step 1B, Substitution: 1-chloro-2-(chloro(phenyl)(p-tolyl)methyl)benzene (1.0 g, 1 Eq, 3.1 mmol), Amino acid (4 equiv, N-(((9H-fluoren-9-yl)methoxy)carbonyl)-O-(tert-butyl)-D-serine (750 mg, 1.96 mmol)), and DIPEA (8 equiv) in DMF (10 mL) for 2 h at 30° C.

Step 1C, Fmoc de-protection: The resin (N-(((9H-fluoren-9-yl)methoxy)carbonyl)-O-(tert-butyl)-D-serine (750 mg, 0.64 Eq, 1.96 mmol) 500 mg/tube) was treated with 20% of piperidine in NMP (1 mL) for 20 minutes at room temperature under nitrogen atmosphere. Then, the resin was washed 4 times with NMP (1 mL/tube).

Step 1D, Capping: The resin (100 mg/tube) was capped with the solution (v/v/v $Ac_2O$/DIPEA/NMP=31.5:8.5:160) for 1 hours at room temperature under nitrogen atmosphere. Then, the resin was washed 4 times with NMP (1 mL/tube).

Step 1E, $2^{nd}$-$4^{th}$ HATU coupling: Peptide was prepared from previous peptide by standard Fmoc-based SPPS procedures (General SPPS procedure 2-3-2). $2^{nd}$ and $3^{rd}$ coupling with N-(((9H-fluoren-9-yl)methoxy)carbonyl)-O-(tert-butyl)-D-serine (750 mg, 0.64 Eq, 1.96 mmol) and $4^{th}$ coupling with 3-((((9H-fluoren-9-yl)methoxy)carbonyl)amino)propanoic acid (700 mg, 0.74 Eq, 2.25 mmol).

Step 1F, Cleavage & Centrifuging: Crude peptide was cleaved from the resin with the solution (v/v=TFA/DCM=1/20) for 2 hours at room temperature. The mixture was filtered, and the filtrate was concentrated under reduced pressure. After the residue was precipitated with cold ether (6 mL), the precipitates were collected by centrifugation, three repetitions of centrifuging are required.

Step 1G, Purification: The crude product was dissolved in DMF (5 mL) and purified by prep-HPLC with the following conditions: Column: SunFire prep OBD 19*150 mm Sum; Mobile Phase A: Water (0.05% TFA); Mobile Phase B: ACN; Gradient: 25% B to 65% B in 8 min; Flow rate: 20 mL/min; Wave Length: 220 nm. The collected fractions were dried by lyophilization. This resulted in N—(N—(N-(3-((((9H-fluoren-9-yl)methoxy)carbonyl)amino)propanoyl)-O-(tert-butyl)-D-seryl)-O-(tert-butyl)-D-seryl)-O-(tert-butyl)-D-serine (750 mg, 1.01 mmol, 33%) as a white solid. $[M+H]^+$=741.5.

Step 2. Into a 100 mL round bottom, was placed a mixture of N—(N—(N-(3-((((9H-fluoren-9-yl)methoxy)carbonyl)amino)propanoyl)-O-(tert-butyl)-D-seryl)-O-(tert-butyl)-D-seryl)-O-(tert-butyl)-D-serine (750 mg, 1 Eq, 1.01 mmol) and EtOAc (50 mL), to which was added zinc(II) bromide (2.1 g, 9.2 Eq, 9.3 mmol). The reaction mixture was stirred at 50° C. for 16 hours. The mixture was concentrated under reduced pressure and the crude product was purified by MPLC to provide (3-((((9H-fluoren-9-yl)methoxy)carbonyl)amino)propanoyl)-D-seryl-D-seryl-D-serine (150 mg, 262 μmol, 25.9%) as a white solid. $[M+H]^+$=573.3.

Step 3. Into an 8-mL vial, was placed a mixture of (3-((((9H-fluoren-9-yl)methoxy)carbonyl)amino)propanoyl)-D-seryl-D-seryl-D-serine (50 mg, 1 Eq, 87 μmol), DIEA (40 mg, 54 μL, 3.5 Eq, 0.31 mmol), EDCI (40 mg, 2.4 Eq, 0.21 mmol), HOPO (20 mg, 2.1 Eq, 0.18 mmol) and DMF (1 mL). The reaction mixture was stirred at 20° C. for 10 minutes, then (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (100 mg, 1.5 Eq, 131 μmol) was added and the reaction mixture was stirred at 25° C. for an additional 1 hour. The crude product (9H-fluoren-9-yl)methyl ((5R,8R,11R)-16-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-5,8,11-tris(hydroxymethyl)-3,6,9,12-tetraoxo-4,7,10,13-tetraazahexadecyl)carbamate (40 mg, 30 μmol, 35%) was used directly in the next step without purification. $[M+H]^+$=1320.8.

Steps 4-5. The formic acid salt of 2,2',2"-(10-((8R,11R,14R)-19-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-8,11,14-tris(hydroxymethyl)-2,6,9,12,15-pentaoxo-3,7,10,13,16-pentaazanonadecyl)-1,4,7,10-tetraazacyclododecane-1,4,7-triyl)triacetic acid was synthesized from (9H-fluoren-9-yl)methyl ((5R,8R,11R)-16-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)-5,8,11-tris(hydroxymethyl)-3,6,9,12-tetraoxo-4,7,10,13-tetraazahexadecyl)carbamate in a manner similar to Step 4 of Example 7, then Step 5 of Example 1, to provide the product (13.2 mg, 8.62 μmol, 31%) as a white solid. MS: Calc'd for $C_{66}H_{95}F_2N_{17}O_{20}$: 1483.69, found $[M+H]^+$: 1484.5.

Example 62: 2,2',2"-(10-(2-((2-((3-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropyl)(methyl)amino)ethyl)amino)-2-oxoethyl)-1,4,7,10-tetraazacyclododecane-1,4,7-triyl)triacetic acid (Compound 55)

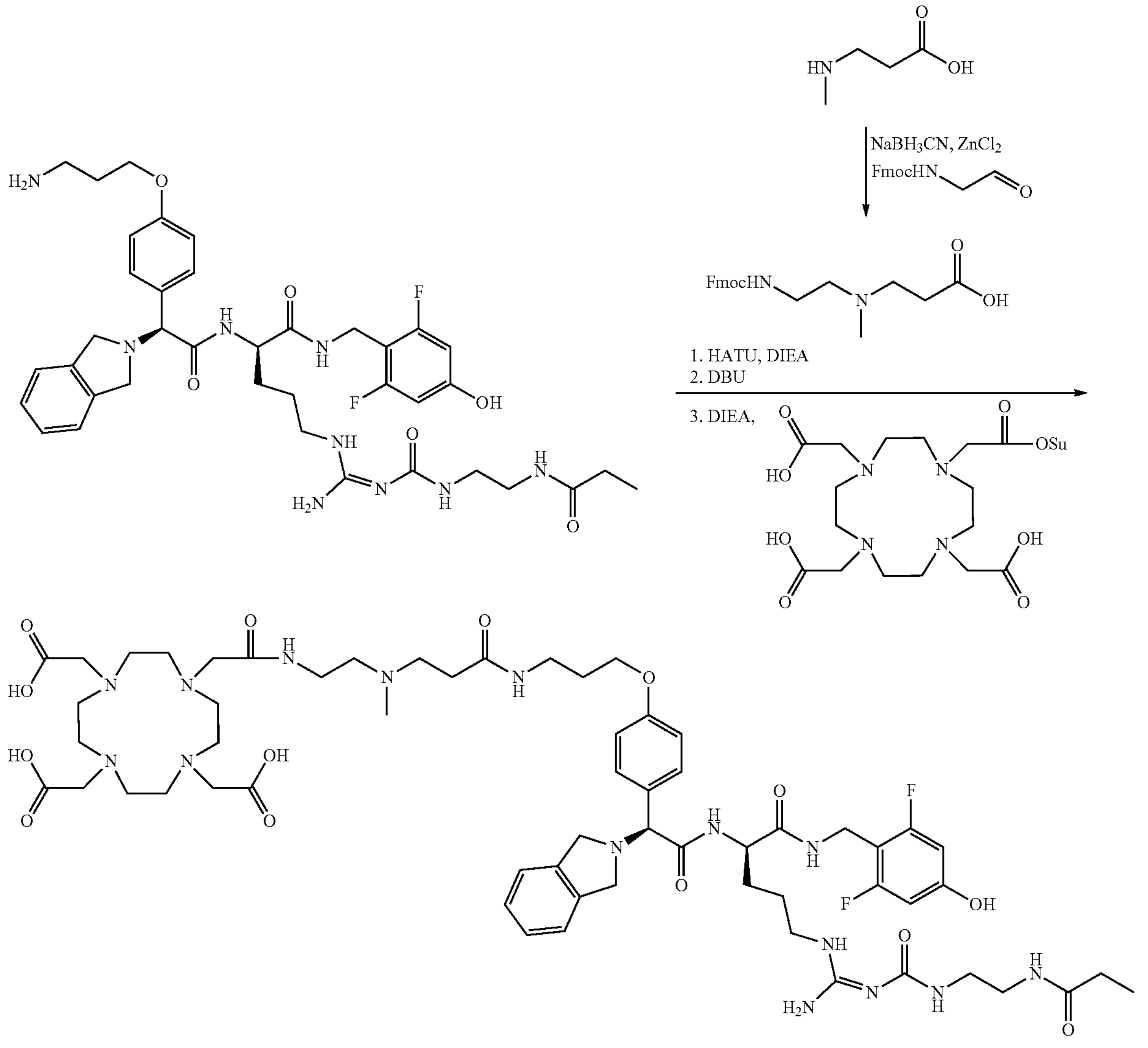

Step 1. Into a 8-mL vial, was placed a mixture of 3-(methylamino)propanoic acid (500 mg, 1 Eq, 4.85 mmol), (9H-fluoren-9-yl)methyl (2-oxoethyl)carbamate (3.5 g, 2.6 Eq, 12 mmol), zinc chloride (1.5 g, 0.68 mL, 2.3 Eq, 11 mmol) and MeOH (10 mL). The reaction mixture was stirred at 0° C. for 10 minutes, then $NaBH_3CN$ (450 mg, 1.48 Eq, 7.16 mmol) was added and the reaction mixture was stirred at 25° C. for an additional 3 hours. The mixture was directly purified by MPLC to provide 3-((2-((((9H-fluoren-9-yl)methoxy)carbonyl)amino)ethyl)(methyl)amino)propanoic acid (600 mg, 1.63 mmol, 33.6%) as a yellow oil. $[M+H]^+$ =369.1.

Steps 2-4. The trifluoroacetic acid salt of 2,2',2"-(10-(2-((2-((3-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)amino)-3-oxopropyl)(methyl)amino)ethyl)amino)-2-oxoethyl)-1,4,7,10-tetraazacyclododecane-1,4,7-triyl)triacetic acid was synthesized from (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide and 3-((2-((((9H-fluoren-9-yl)methoxy)carbonyl)amino)ethyl)(methyl)amino)propanoic acid in a manner similar to Step 3 of the synthesis of Compound 1, Step 4 of Example 7, then Step 5 of Example 1, to provide the product as a white solid. MS: Calc'd for $C_{60}H_{87}F_2N_{15}O_{14}$: 1279.65, found $[M+H]^+$: 1280.5.

Example 63: 2,2',2"-(10-(2-((5-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)(methyl)amino)pentyl)amino)-2-oxoethyl)-1,4,7,10-tetraazacyclododecane-1,4,7-triyl)triacetic acid (Compound 56)

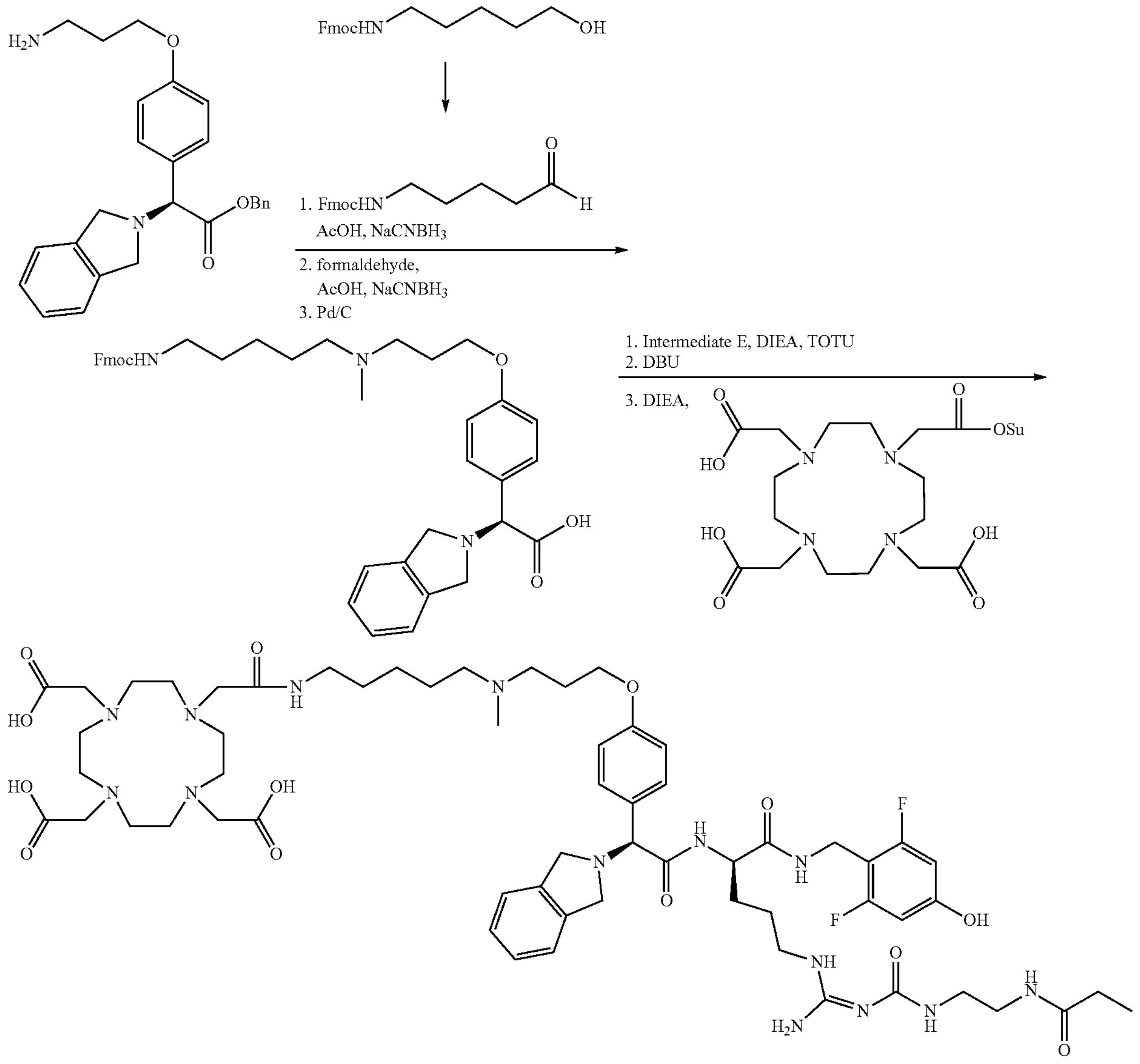

Step 1. Into a 50-mL three-necked round bottom flask, purged and maintained with an inert atmosphere of nitrogen, was placed a mixture of DCM (15 mL) and oxalyl dichloride (1.6 g, 1.4 Eq, 13 mmol), to which was added DMSO (5 mL) dropwise at −60° C. over 5 min. The reaction mixture was stirred at −60° C. for 1 hour, then (9H-fluoren-9-yl)methyl (5-hydroxypentyl)carbamate (3.0 g, 1 Eq, 9.2 mmol) was added dropwise at −60° C. over 5 min. The reaction mixture was stirred at −60° C. for 1 hour, then DIEA (4.8 g, 6.5 mL, 4.0 Eq, 37 mmol) was added dropwise at −60° C. over 5 mins. The reaction mixture was stirred at −60° C. for 1 hour. The mixture was quenched with an aqueous solution of $NH_4Cl$ (50 mL), extracted with EtOAc (50 mL×3), the combined organic layers were washed with brine (50 mL), dried over anhydrous $Na_2SO_4$ and concentrated under reduced pressure to provide (9H-fluoren-9-yl)methyl (5-oxopentyl)carbamate (3.7 g, 7.4 mmol, 81%) as a yellow oil, which was used directly in the next step without any purification. $[M+H]^+$=324.1.

Step 2. Into a 8-mL vial, was placed a mixture of benzyl (S)-2-(4-(3-aminopropoxy)phenyl)-2-(isoindolin-2-yl)acetate (2.1 g, 1 Eq, 5.0 mmol) (9H-fluoren-9-yl)methyl (5-oxopentyl)carbamate (2.1 g, 1.3 Eq, 6.5 mmol), AcOH (30 mg, 29 L, 0.099 Eq, 0.50 mmol) and MeOH (20 mL). The reaction mixture was stirred at 25° C. for 10 min then $NaCNBH_3$ (0.95 g, 3.0 Eq, 15 mmol) was added and the reaction mixture was stirred at 25° C. for an additional 1 hour. The mixture was directly purified by MPLC to afford benzyl (S)-2-(4-(3-((5-((((9H-fluoren-9-yl)methoxy)carbonyl)amino)pentyl)amino)propoxy)phenyl)-2-(isoindolin-2-yl)acetate (1.2 g, 1.7 mmol, 33%) as a light yellow solid. $[M+H]^+$=724.9.

Step 3. Benzyl (S)-2-(4-(3-((5-((((9H-fluoren-9-yl)methoxy)carbonyl)amino)pentyl)amino)propoxy)phenyl)-2-(isoindolin-2-yl)acetate (700 mg, 1 Eq, 967 μmol) was treated with paraformaldehyde in a manner similar to Step 2 to afford benzyl (S)-2-(4-(3-((5-((((9H-fluoren-9-yl)methoxy)carbonyl)amino)pentyl)(methyl)amino)propoxy)phenyl)-2-(isoindolin-2-yl)acetate (550 mg, 745 μmol, 77.1%) as a light yellow solid. $[M+H]^+$=724.9.

Step 4. Benzyl (S)-2-(4-(3-((5-((((9H-fluoren-9-yl)methoxy)carbonyl)amino)pentyl)(methyl)amino)propoxy)phenyl)-2-(isoindolin-2-yl)acetate was treated with Pd/C in a manner similar to Step 4 of Example 13 to provide (S)-2-(4-(3-((5-((((9H-fluoren-9-yl)methoxy)carbonyl)amino)pentyl)(methyl)amino)propoxy)phenyl)-2-(isoindolin-2-yl)acetic acid (380 mg, 587 μmol, 78.7%) as a white solid. $[M+H]^+$=648.8.

Step 5. (S)-2-(4-(3-((5-((((9H-fluoren-9-yl)methoxy)carbonyl)amino)pentyl)(methyl)amino)propoxy)phenyl)-2-(isoindolin-2-yl)acetic acid was treated with Intermediate E, DIEA and TOTU in a manner similar to Step 1 of the synthesis of Compound 1 to provide (9H-fluoren-9-yl)methyl (5-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)(methyl)amino)pentyl)carbamate (40 mg, 37 μmol, 34%) as a yellow oil. $[M+H]^+$=1088.2.

Steps 6-7. (9H-fluoren-9-yl)methyl (5-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)(methyl)amino)pentyl) carbamate was treated with DBU in a manner similar to Example 7, Step 4 then treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the TFA salt of 2,2',2"-(10-(2-((5-((3-(4-((1S,4R,Z)-9-amino-4-((2,6-difluoro-4-hydroxybenzyl)carbamoyl)-1-(isoindolin-2-yl)-2,11,16-trioxo-3,8,10,12,15-pentaazaoctadec-9-en-1-yl)phenoxy)propyl)(methyl)amino)pentyl)amino)-2-oxoethyl)-1,4,7,10-tetraazacyclododecane-1,4,7-triyl)triacetic acid (16.0 mg, 11.7 μmol, 41%) as a white solid. MS: Calc'd for $C_{60}H_{88}F_2N_{14}O_{13}$: 1364.65, found $[M+H]^+$: 1365.6.

Example 64: 2,2',2"-(10-(2-((6-((4-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)butyl)amino)-6-oxohexyl)amino)-2-oxoethyl)-1,4,7,10-tetraazacyclododecane-1,4,7-triyl)triacetic acid (Compound 57)

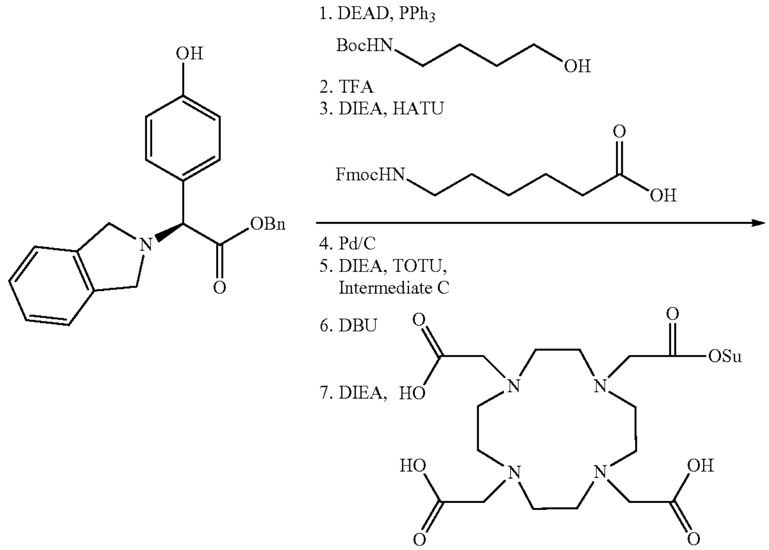

-continued

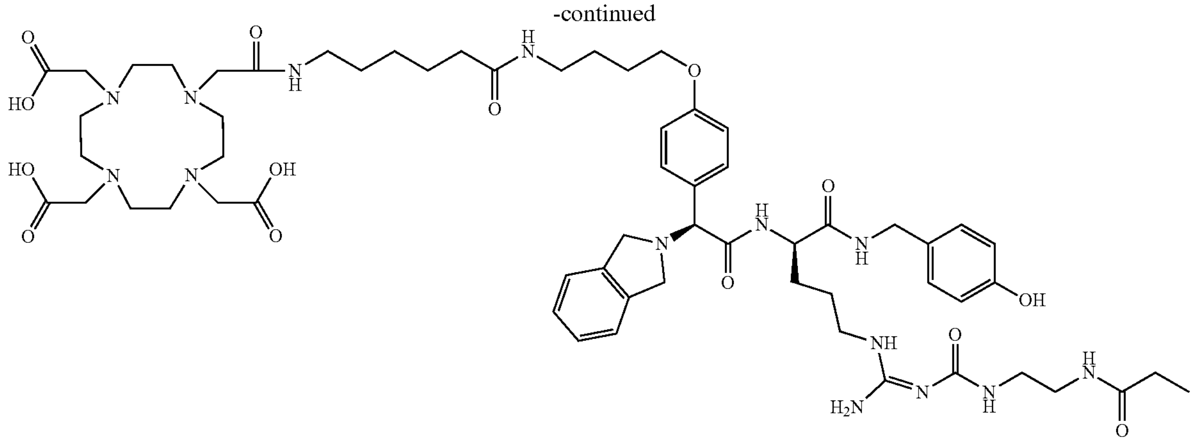

Step 1. Benzyl (S)-2-(4-hydroxyphenyl)-2-(isoindolin-2-yl)acetate was treated with DEAD, $PPh_3$, and tert-butyl (4-hydroxybutyl)carbamate in a manner similar to Step 2 in the synthesis of Intermediate D to provide benzyl (S)-2-(4-(4-((tert-butoxycarbonyl)amino)butoxy)phenyl)-2-(isoindolin-2-yl)acetate (120 mg, 226 μmol, 54.2%) as a yellow oil. $[M+H]^+$=531.6

Step 2. Benzyl (S)-2-(4-(4-((tert-butoxycarbonyl)amino)butoxy)phenyl)-2-(isoindolin-2-yl)acetate was treated with TFA in a manner similar to Step 2 in the synthesis of Compound 1 to provide benzyl (S)-2-(4-(4-aminobutoxy)phenyl)-2-(isoindolin-2-yl)acetate (120 mg, 0.21 mmol, 92%) as a light yellow solid, which was used directly in the next step without any purification. $[M+H]^+$=431.5.

Step 3. Benzyl (S)-2-(4-(4-aminobutoxy)phenyl)-2-(isoindolin-2-yl)acetate was treated with 6-((((9H-fluoren-9-yl)methoxy)carbonyl)amino)hexanoic acid, DIEA and HATU in a manner similar to Step 3 of the synthesis of Compound 1, to provide benzyl (S)-2-(4-(4-(6-((((9H-fluoren-9-yl)methoxy)carbonyl)amino)hexanamido)butoxy)phenyl)-2-(isoindolin-2-yl)acetate (110 mg, 144 μmol, 68.7%) as a yellow oil. $[M+H]^+$=766.6.

Step 4. Benzyl (S)-2-(4-(4-(6-((((9H-fluoren-9-yl)methoxy)carbonyl)amino)hexanamido)butoxy)phenyl)-2-(isoindolin-2-yl)acetate was treated with Pd/C in a manner similar to Step 4 of Example 13 to provide (S)-2-(4-(4-(6-((((9H-fluoren-9-yl)methoxy)carbonyl)amino)hexanamido)butoxy)phenyl)-2-(isoindolin-2-yl)acetic acid (90 mg, 0.13 mmol, 93%) as a white solid. $[M+H]^+$=676.3.

Step 5. (S)-2-(4-(4-(6-((((9H-fluoren-9-yl)methoxy)carbonyl)amino)hexanamido)butoxy)phenyl)-2-(isoindolin-2-yl)acetic acid was treated with Intermediate C, DIEA and TOTU in a manner similar to Step 1 of the synthesis of Compound 1 to provide (9H-fluoren-9-yl)methyl (6-((4-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)butyl)amino)-6-oxohexyl)carbamate (50 mg, 46 μmol, 63%) as a yellow oil. $[M+H]^+$=1079.9.

Steps 6-7. (9H-fluoren-9-yl)methyl (6-((4-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)butyl)amino)-6-oxohexyl)carbamate was treated with DBU in a manner similar to Example 7, Step 4 then treated with 2,2',2''-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 to provide the TFA salt of 2,2',2''-(10-(2-((6-((4-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)butyl)amino)-6-oxohexyl)amino)-2-oxoethyl)-1,4,7,10-tetraazacyclododecane-1,4,7-triyl)triacetic acid as a white solid. MS: Calc'd for $C_{61}H_{90}F_2N_{14}O_{14}$: 1242.68, found $[M+H]^+$: 1243.4.

Example 65: 2,2',2"-(10-(2-((6-((2-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)ethyl)amino)-6-oxohexyl)amino)-2-oxoethyl)-1,4,7,10-tetraazacyclododecane-1,4,7-triyl)triacetic acid (Compound 58)

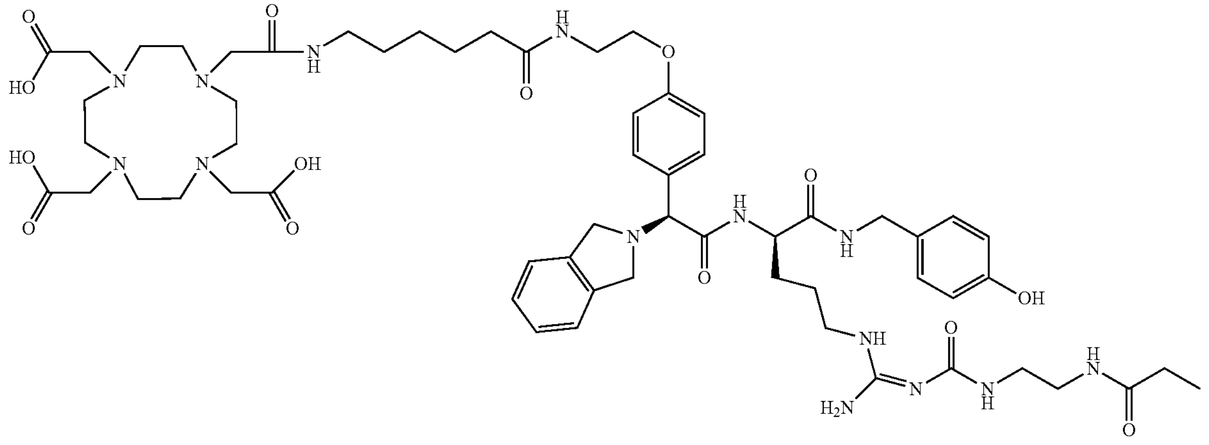 [SMILES: CCC(=O)NCCNC(=O)/N=C(/N)NCCC[C@@H](NC(=O)[C@H](c1ccc(OCCNC(=O)CCCCCNC(=O)CN2CCN(CC(=O)O)CCN(CC(=O)O)CCN(CC(=O)O)CC2)cc1)N1Cc2ccccc2C1)C(=O)NCc1ccc(O)cc1]

Steps 1-7. 2,2',2"-(10-(2-((6-((2-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)ethyl)amino)-6-oxohexyl)amino)-2-oxoethyl)-1,4,7,10-tetraazacyclododecane-1,4,7-triyl)triacetic acid was synthesized from benzyl (S)-2-(4-hydroxyphenyl)-2-(isoindolin-2-yl)acetate and tert-butyl (2-hydroxyethyl)carbamate in a manner similar to Example 65 to provide the trifluoroacetic acid salt of 2,2',2"-(10-(2-((6-((2-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)ethyl)amino)-6-oxohexyl)amino)-2-oxoethyl)-1,4,7,10-tetraazacyclododecane-1,4,7-triyl)triacetic acid (32.5 mg, 24.4 μmol, 54%) as a white solid. MS: Calc'd $C_{57}H_{85}N_{14}O_{12}$: 1214.64, found $[M+H]^+$: 1215.4.

Example 66: 2,2',2"-(10-(2-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-1,4,7,10-tetraazacyclododecane-1,4,7-triyl)triacetic acid (Compound 59)

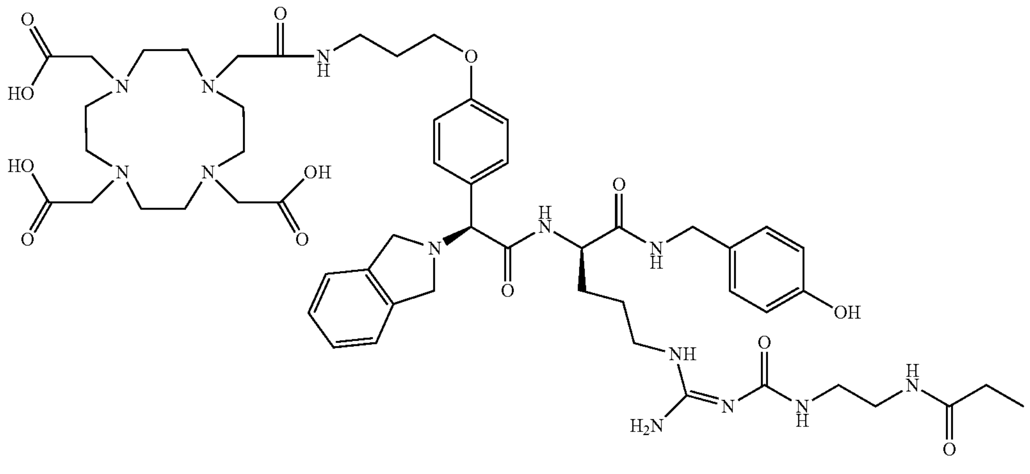 [SMILES: CCC(=O)NCCNC(=O)/N=C(/N)NCCC[C@@H](NC(=O)[C@H](c1ccc(OCCCNC(=O)CN2CCN(CC(=O)O)CCN(CC(=O)O)CCN(CC(=O)O)CC2)cc1)N1Cc2ccccc2C1)C(=O)NCc1ccc(O)cc1]

Steps 1-3. The trifluoroacetic salt of 2,2',2"-(10-(2-((3-(4-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenoxy)propyl)amino)-2-oxoethyl)-1,4,7,10-tetraazacyclododecane-1,4,7-triyl)triacetic acid was synthesized from (S)-2-(4-(3-((tert-butoxycarbonyl)amino)propoxy)phenyl)-2-(isoindolin-2-yl)acetic acid in a manner similar to Step 1 in the synthesis of Compound 1, then Step 2 in the synthesis of Compound 1, then Step 5 in Example 1 to provide the product (32.3 mg, 26.3 µmol, 38%) as a white solid. MS: Calc'd for $C_{54}H_{77}N_{13}O_{13}$: 1115.57, found $[M+H]^+$: 1116.5.

Example 67: (2R)—N-(4-hydroxybenzyl)-2-(2-(isoindolin-2-yl)-2-phenylacetamido)-5-((Z)-2-((2-propionamidoethyl)carbamoyl)guanidino)pentanamide (Compound 60)

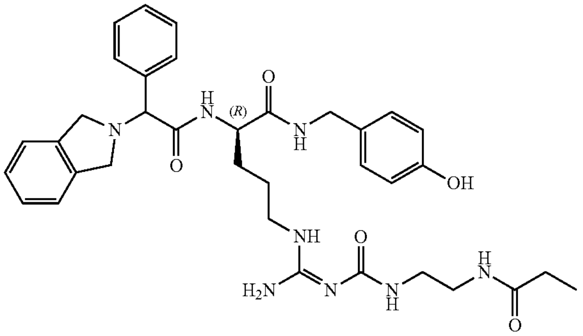

Into a 4-mL vial, was placed a mixture of (R)—N-(4-hydroxybenzyl)-2-((S)-2-(isoindolin-2-yl)-2-phenylacetamido)-5-((Z)-2-((2-propionamidoethyl)carbamoyl)guanidino) pentanamide 2,2,2-trifluoroacetate (Compound 60A, 3.5 mg, 1 Eq, 4.5 µmol) and (R)—N-(4-hydroxybenzyl)-2-((R)-2-(isoindolin-2-yl)-2-phenylacetamido)-5-((Z)-2-((2-propionamidoethyl)carbamoyl)guanidino)pentanamide 2,2,2-trifluoroacetate (Compound 60B, 3.5 mg, 1.0 Eq, 4.5 µmol), to which was added $ACN/H_2O$=1:1 (1.5 mL). The mixture was dried by lyophilization to provide (2R)—N-(4-hydroxybenzyl)-2-(2-(isoindolin-2-yl)-2-phenylacetamido)-5-((Z)-2-((2-propionamidoethyl)carbamoyl)guanidino)pentanamide 2,2,2-trifluoroacetate (6.3 mg, 8.2 µmol, 180%) as a white solid. MS: Calc'd for $C_{35}H_{44}N_8O_5$: 656.34, found $[M+H]^+$: 657.2.

Example 68: (R)—N-(4-hydroxybenzyl)-2-((S)-2-(isoindolin-2-yl)-2-phenylacetamido)-5-((Z)-2-((2-propionamidoethyl)carbamoyl)guanidino)pentanamide (Compound 60A)

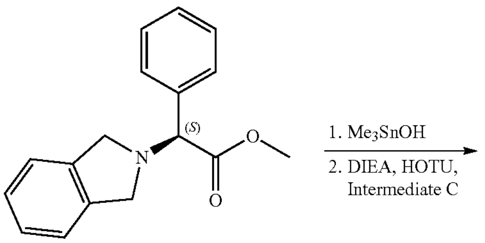

-continued

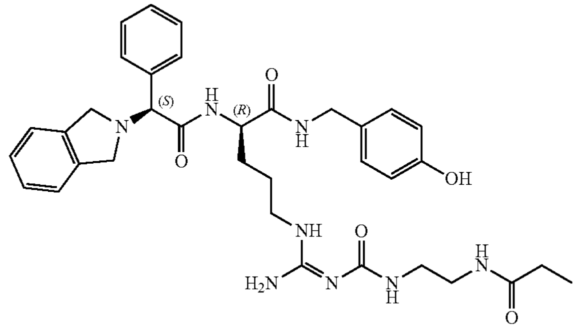

Step 1. Into an 8-mL vial, was placed a mixture of methyl (S)-2-(isoindolin-2-yl)-2-phenylacetate (250 mg, 1 Eq, 935 µmol) and DCE (4 mL), to which was added trimethyltin-hydroxide (676 mg, 4.00 Eq, 3.74 mmol). The reaction mixture was stirred at 90° C. for 16 hours. The reaction mixture was filtered through a pad of celite, then the filtrate was concentrated and purified by MPLC to provide (S)-2-(isoindolin-2-yl)-2-phenylacetic acid (150 mg, 592 µmol, 63.3%) as a brown oil. $[M+H]^+$=254.1.

Step 2. Into an 8-mL vial, was placed a mixture of (S)-2-(isoindolin-2-yl)-2-phenylacetic acid (25 mg, 1 Eq, 99 µmol), HOTU (32 mg, 0.99 Eq, 98 µmol), DIEA (38 mg, 51 L, 3.0 Eq, 0.29 mmol) and DMF (1 mL). The reaction mixture was stirred at 20° C. for 10 minutes, then (R,Z)-2-amino-N-(4-hydroxybenzyl)-5-(2-((2-propionamidoethyl)carbamoyl)guanidino)pentanamide (54 mg, 1.3 Eq, 0.13 mmol) was added and the reaction mixture was stirred at 25° C. for 10 min. The mixture was directly purified by Prep-HPLC to provide the trifluoroacetic acid salt of (R)—N-(4-hydroxybenzyl)-2-((S)-2-(isoindolin-2-yl)-2-phenylacetamido)-5-((Z)-2-((2-propionamidoethyl)carbamoyl)guanidino)pentanamide (12.8 mg, 16.6 µmol, 17%) as a white solid. MS: Calc'd for $C_{35}H_{44}N_8O_5$: 656.34, found $[M+H]^+$: 657.2.

Example 69: (R)—N-(4-hydroxybenzyl)-2-((R)-2-(isoindolin-2-yl)-2-phenylacetamido)-5-((Z)-2-((2-propionamidoethyl)carbamoyl)guanidino)pentanamide (Compound 60B)

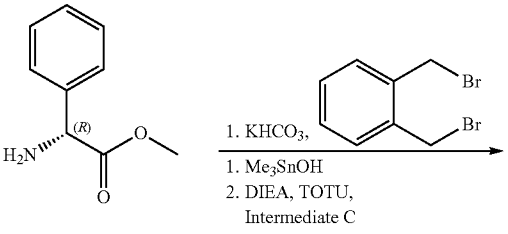

-continued

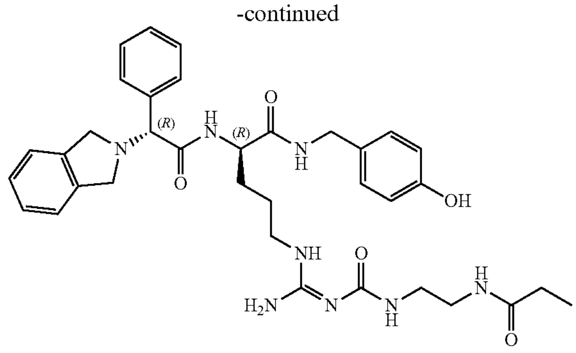

Step 1. Methyl (R)-2-amino-2-phenylacetate hydrochloride was treated with bis(bromomethyl)benzene and potassium bicarbonate in a manner similar to step 1 of the synthesis of Intermediate D (Example 1) to provide methyl (R)-2-(isoindolin-2-yl)-2-phenylacetate (450 mg, 1.68 mmol, 67.9%) as a yellow solid.

Step 2. Methyl (R)-2-(isoindolin-2-yl)-2-phenylacetate was treated with trimethyltinhydroxide in a manner similar to Example 69 to provide (R)-2-(isoindolin-2-yl)-2-phenylacetic acid (45 mg, 0.18 mmol, 47%) as a brown solid. $[M+H]^+$=254.2.

Step 3. (R)-2-(Isoindolin-2-yl)-2-phenylacetic acid was treated with Intermediate C, TOTU, and DIEA in a manner similar to Step 1 in the synthesis of Compound 1A to provide the trifluoroacetic acid salt of (R)—N-(4-hydroxybenzyl)-2-((R)-2-(isoindolin-2-yl)-2-phenylacetamido)-5-((Z)-2-((2-propionamidoethyl)carbamoyl)guanidino)pentanamide (16.0 mg, 20.8 μmol, 13%) as a white solid. MS: Calc'd for $C_{35}H_{44}N_8O_5$: 656.34, found $[M+H]^+$: 657.3.

Example 70: (R)—N-(2,6-difluoro-4-hydroxybenzyl)-2-((S)-2-(isoindolin-2-yl)-2-phenylacetamido)-5-((Z)-2-((2-propionamidoethyl)carbamoyl)guanidino)pentanamide (Compound 61A)

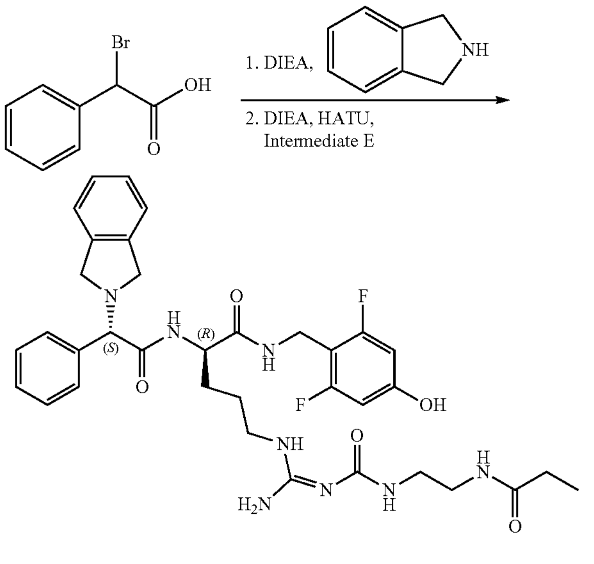

Step 1. Into an 8-mL vial, was placed a mixture of 2-bromo-2-phenylacetic acid (50 mg, 1 Eq, 0.23 mmol), DIEA (90 mg, 0.12 mL, 3.0 Eq, 0.70 mmol), isoindoline (30 mg, 1.1 Eq, 0.25 mmol) and ACN (0.5 mL). The reaction mixture was stirred at 80° C. for 1 hour. The mixture was directly purified by MPLC to afford 2-(isoindolin-2-yl)-2-phenylacetic acid (48 mg, 0.17 mmol, 73%) as an off-white solid. $[M+H]^+$=254.1.

Step 2. Into an 8-mL vial, was placed a mixture of 2-(isoindolin-2-yl)-2-phenylacetic acid (45 mg, 1 Eq, 0.18 mmol), DIEA (110 mg, 148 μL, 4.8 Eq, 851 μmol), HATU (70 mg, 1.0 Eq, 0.18 mmol) and DMF (0.5 mL). The reaction mixture was stirred at 20° C. for 10 minutes, then (R,Z)-2-amino-N-(2,6-difluoro-4-hydroxybenzyl)-5-(2-((2-propionamidoethyl)carbamoyl)guanidino)pentanamide (80 mg, 0.98 Eq, 0.17 mmol) was added and the reaction mixture was stirred at 25° C. for an additional 2 hours. The mixture was directly purified by Prep-HPLC to provide two isomers as two separate peaks. The front peak fractions were combined to provide the formic acid salt of (R)—N-(2,6-difluoro-4-hydroxybenzyl)-2-((S)-2-(isoindolin-2-yl)-2-phenylacetamido)-5-((Z)-2-((2-propionamidoethyl)carbamoyl)guanidino)pentanamide (11.3 mg, 15.0 μmol, 8.4%) (assumed) as a white solid. MS: Calc'd for $C_{35}H_{42}F_2N_8O_5$: 692.32, found $[M+H]^+$: 693.2.

Example 71: (R)—N-(2,6-difluoro-4-hydroxybenzyl)-2-((R)-2-(isoindolin-2-yl)-2-phenylacetamido)-5-((Z)-2-((2-propionamidoethyl)carbamoyl)guanidino)pentanamide (Compound 61B)

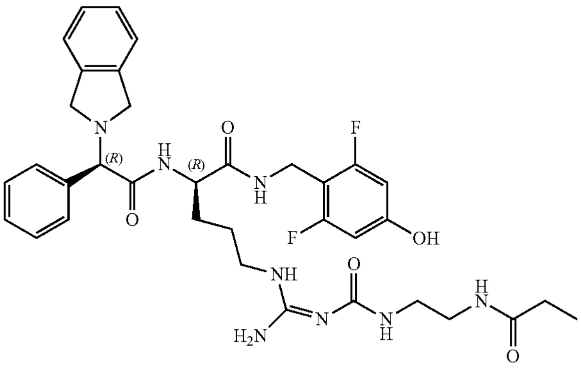

The back peak fractions (from Example 71, Step 2) were combined to provide the formic acid salt of (R)—N-(2,6-difluoro-4-hydroxybenzyl)-2-((R)-2-(isoindolin-2-yl)-2-phenylacetamido)-5-((Z)-2-((2-propionamidoethyl)carbamoyl)guanidino)pentanamide (13.5 mg, 17.1 μmol, 9.6%) (assumed) as a white solid. MS: Calc'd for $C_{35}H_{42}F_2N_8O_5$: 692.32, found $[M+H]^+$: 693.2.

Example 72: (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide (Compound 62)

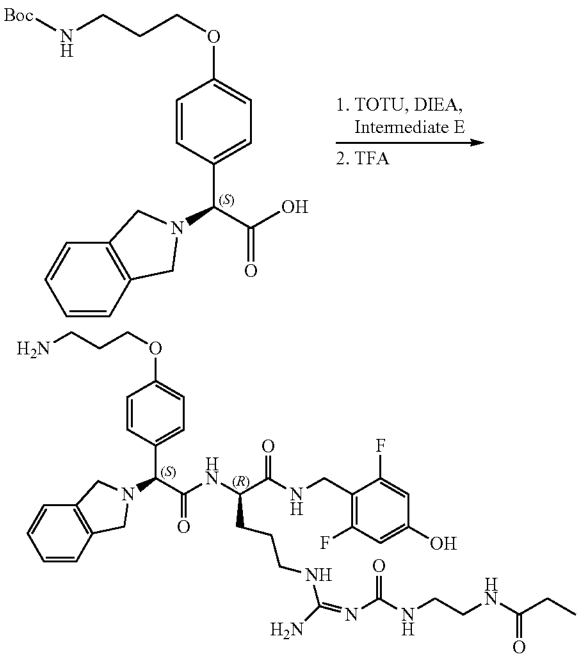

Steps 1 and 2. (S)-2-(4-(3-((tert-butoxycarbonyl)amino)propoxy)phenyl)-2-(isoindolin-2-yl)acetic acid was treated with Intermediate E, DIEA and TOTU in a manner similar to Step 1 of the synthesis of Compound 1, then treated with TFA in a manner similar to Step 2 in the synthesis of Compound 1 to provide the trifluoroacetic acid salt of (R)-2-((S)-2-(4-(3-aminopropoxy)phenyl)-2-(isoindolin-2-yl)acetamido)-N-(2,6-difluoro-4-hydroxybenzyl)-5-((Z)-2-((2-propionamidoethyl)carbamoyl)guanidino)pentanamide as a white solid. MS: Calc'd for $C_{38}H_{49}F_2N_9O_6$: 765.37, found $[M+H]^+$: 766.2.

Example 73: (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide (Compound 63)

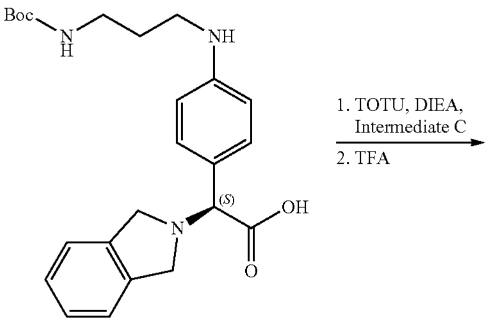

-continued

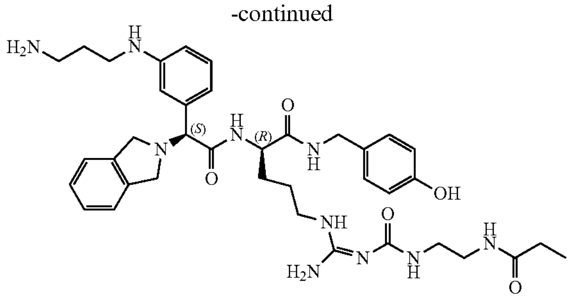

Step 1. Into a 40-mL vial, was placed (S)-2-(3-((3-((tert-butoxycarbonyl)amino)propyl)amino)phenyl)-2-(isoindolin-2-yl)acetic acid (580 mg, 1 Eq, 1.36 mmol), 1-hydroxypyrrolidine-2,5-dione (235 mg, 1.50 Eq, 2.04 mmol) and THE (6 mL). To the mixture was added DCC (422 mg, 1.50 Eq, 2.05 mmol) under $N_2$. The reaction mixture was stirred at 25° C. for 2 hours then the reaction mixture was filtered. The filtrate was concentrated below 35° C. to provide crude white oil (660 mg). Into a 8-mL vial, was placed a mixture of (R,Z)-2-amino-N-(4-hydroxybenzyl)-5-(2-((2-propionamidoethyl)carbamoyl)guanidino)pentanamide (1.15 g, 2.00 Eq, 2.73 mmol), N-ethyl-N-isopropylpropan-2-amine (529 mg, 3.00 Eq, 4.09 mmol) and THE (6 mL). A solution of the crude white oil in THE (0.5 mL) was dropwise added into the mixture at 25° C. The reaction mixture was stirred at 50° C. for 4 hours. The reaction mixture was directly purified by Prep-HPLC to provide two isomers as two peaks. The front peak fractions were dried by lyophilization to afford tert-butyl (3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)carbamate (500 mg, 603 μmol, 44.2%) as a white solid. [M+H+]=829.2.

Step 2. tert-butyl (3-((3-((1S,4R,Z)-9-amino-4-((4-hydroxybenzyl)carbamoyl)-1-(isoindolin-2-yl)-2,11,16-trioxo-3,8,10,12,15-pentaazaoctadec-9-en-1-yl)phenyl)amino)propyl)carbamate was treated with TFA in a manner similar to Step 2 in the synthesis of Compound 1 to provide the trifluoroacetic acid salt of (R)-2-((S)-2-(3-((3-aminopropyl)amino)phenyl)-2-(isoindolin-2-yl)acetamido)-N-(4-hydroxybenzyl)-5-((Z)-2-((2-propionamidoethyl)carbamoyl)guanidino)pentanamide (290 mg, 344 μmol, 57.0%) as a white solid. MS: Calc'd for $C_{40}H_{53}F_3N_{10}O_7$: 842.40, found $[M+H-TFA]^+$: 729.5.

Example 74: (R)-2-((S)-2-(4-(3-aminopropoxy)phenyl)-2-(isoindolin-2-yl)acetamido)-N-(4-hydroxybenzyl)-5-((Z)-2-((2-propionamidoethyl)carbamoyl)guanidino)pentanamide (Compound 64A)

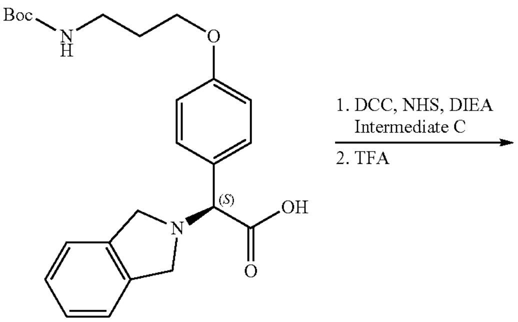

-continued

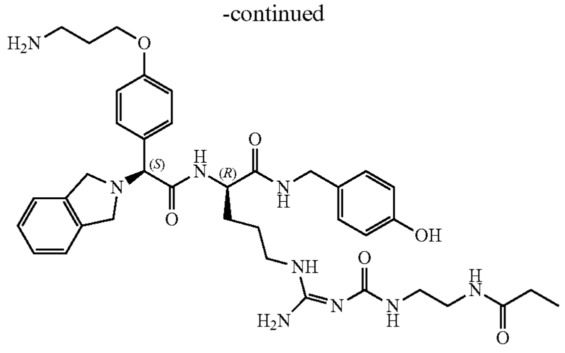

(S)-2-(4-(3-((tert-butoxycarbonyl)amino)propoxy)phenyl)-2-(isoindolin-2-yl)acetic acid was treated with NHS and DCC in a manner similar to Example 7, Step 3, then TFA in a manner similar to Step 2 in the synthesis of Compound 1 to provide the trifluoroacetic acid salt of (R)-2-((S)-2-(4-(3-aminopropoxy)phenyl)-2-(isoindolin-2-yl)acetamido)-N-(4-hydroxybenzyl)-5-((Z)-2-((2-propionamidoethyl)carbamoyl)guanidino)pentanamide (6.0 mg, 7.1 μmol, 59%) as a white solid. MS: Calc'd for $C_{40}H_{52}F_3N_9O_8$: 843.38, found $[M+H-TFA]^+$: 730.4.

Example 75: (R)-2-((R)-2-(4-(3-aminopropoxy)phenyl)-2-(isoindolin-2-yl)acetamido)-N-(4-hydroxybenzyl)-5-((Z)-2-((2-propionamidoethyl)carbamoyl) guanidinopentanamide (Compound 64B)

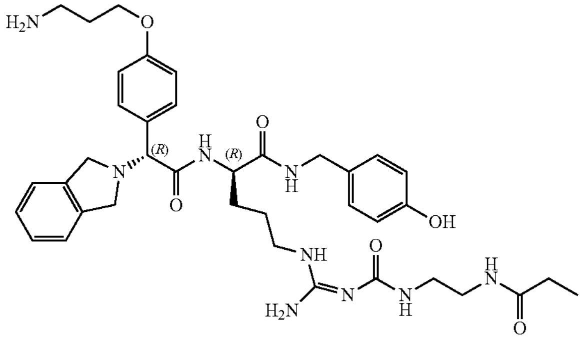

(R)-2-(4-(3-((tert-butoxycarbonyl)amino)propoxy)phenyl)-2-(isoindolin-2-yl)acetic acid was treated with NHS and DCC in a manner similar to Example 7, Step 3, then TFA in a manner similar to Step 2 in the synthesis of Compound 1 to provide the trifluoroacetic acid salt of (R)-2-((R)-2-(4-(3-aminopropoxy)phenyl)-2-(isoindolin-2-yl)acetamido)-N-(4-hydroxybenzyl)-5-((Z)-2-((2-propionamidoethyl)carbamoyl)guanidino)pentanamide (7.0 mg, 8.3 mol, 69%) as a white solid. MS: Calc'd for $C_{40}H_{52}F_3N_9O_8$: 843.38, found $[M+H-TFA]^+$: 730.3.

Example 76: (R)-2-((S)-2-(4-((3-aminopropyl) amino)isoindolin-2-yl)-2-phenylacetamido)-N-(2,6-difluoro-4-hydroxybenzyl)-5-((Z)-2-(ethylcarbamoyl)guanidino)pentanamide (Compound 65)

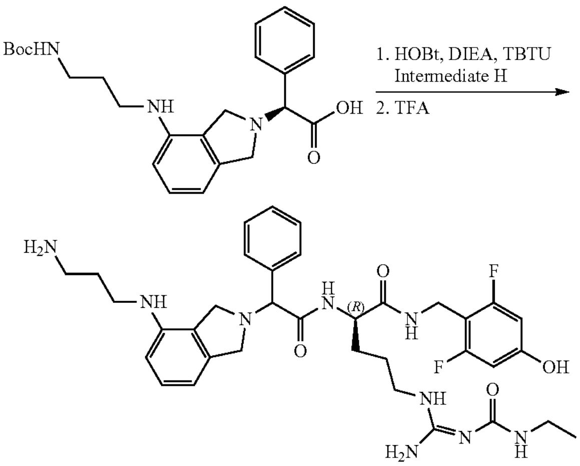

Step 1. (S)-2-(4-((3-((tert-Butoxycarbonyl)amino)propyl) amino)isoindolin-2-yl)-2-phenylacetic acid was treated with (R,Z)-2-amino-N-(2,6-difluoro-4-hydroxybenzyl)-5-(2-(ethylcarbamoyl)guanidino)pentanamide (Intermediate H), HOBt, TBTU, and DIEA in manner similar to Step 5 of Example 13 to provide tert-butyl (3-((2-((11R,Z)-6-amino-11-((2,6-difluoro-4-hydroxybenzyl)carbamoyl)-4,13-dioxo-14-phenyl-3,5,7,12-tetraazatetradec-5-en-14-yl)isoindolin-4-yl)amino)propyl)carbamate (12 mg, 12 μmol, 21%) as an off-white solid. $[M+H]^+$=794.7.

Step 2. tert-Butyl (3-((2-((11R,Z)-6-amino-11-((2,6-difluoro-4-hydroxybenzyl)carbamoyl)-4,13-dioxo-14-phenyl-3,5,7,12-tetraazatetradec-5-en-14-yl)isoindolin-4-yl)amino) propyl)carbamate was treated with TFA in a manner similar to Step 2 in the synthesis of Compound 1 to provide the trifluoroacetic salt of (R)-2-((S)-2-(4-((3-aminopropyl) amino)isoindolin-2-yl)-2-phenylacetamido)-N-(2,6-difluoro-4-hydroxybenzyl)-5-((Z)-2-(ethylcarbamoyl)guanidino)pentanamide (9.8 mg, 12 μmol, 79%) as a white solid. The LCMS of the final product showed two isomers, as the final product is a racemate because the compound racemized during the synthesis. MS: Calc'd for $C_{35}H_{45}F_2N_9O_4$: 693.36, found $[M+H-TFA]^+$: 694.2.

Example 77: (R)-2-((S)-2-(5-((3-aminopropyl)amino)isoindolin-2-yl)-2-phenylacetamido)-N-(2,6-difluoro-4-hydroxybenzyl)-5-((Z)-2-(ethylcarbamoyl)guanidino)pentanamide (Compound 65A)

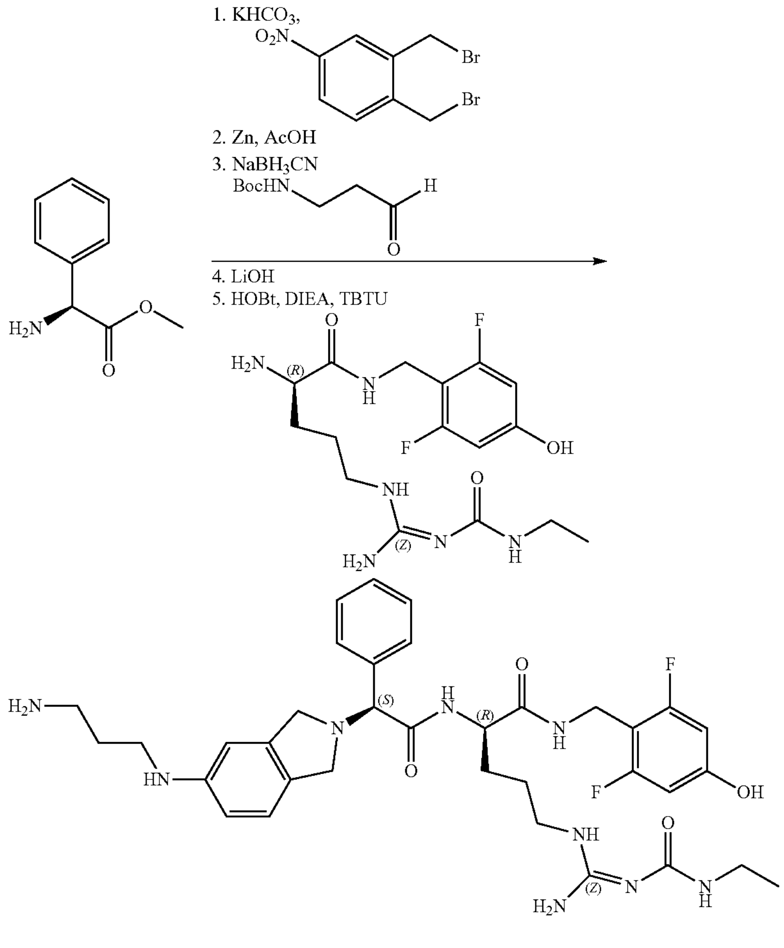

Step 1. Into a 40-mL vial, was placed a mixture of methyl (S)-2-amino-2-phenylacetate hydrochloride (700 mg, 1 Eq, 3.47 mmol), 1,2-bis(bromomethyl)-4-nitrobenzene (1.18 g, 1.10 Eq, 3.82 mmol), potassium bicarbonate (1.04 g, 479 μL, 2.99 Eq, 10.4 mmol) and ACN (7 mL). The reaction mixture was stirred at 80° C. for 6 hours. The mixture was directly purified by MPLC to afford methyl (S)-2-(5-nitroisoindolin-2-yl)-2-phenylacetate (680 mg, 2.1 mmol, 61%) as a brown oil. $[M+H]^+$=313.1.

Step 2. Into a 40-mL vial, was placed a mixture of methyl (S)-2-(5-nitroisoindolin-2-yl)-2-phenylacetate (680 mg, 1 Eq, 2.18 mmol) and AcOH (7 mL), to which was added zinc (1.42 g, 272 μL, 9.98 Eq, 21.7 mmol). The reaction mixture was stirred at 25° C. for 2 hours. The mixture was concentrated under reduced pressure. The crude product was purified by MPLC to afford methyl (S)-2-(5-aminoisoindolin-2-yl)-2-phenylacetate (420 mg, 1.49 mmol, 68.3%) as a yellow oil. $[M+H]^+$=283.1.

Step 3. Into a 40-mL vial, was placed a mixture of methyl (S)-2-(5-aminoisoindolin-2-yl)-2-phenylacetate (410 mg, 1 Eq, 1.45 mmol), tert-butyl (3-oxopropyl)carbamate (201 mg, 0.799 Eq, 1.16 mmol), $NaBH_3CN$ (274 mg, 3.00 Eq, 4.36 mmol) and MeOH (4.1 mL). The reaction mixture was stirred at 25° C. for 1 hour. The mixture was directly purified by MPLC to afford methyl (S)-2-(5-((3-((tert-butoxycarbonyl)amino)propyl)amino)isoindolin-2-yl)-2-phenylacetate (100 mg, 228 μmol, 15.7%) as a yellow oil. $[M+H]^+$=440.4.

Step 4. Into an 8-mL vial, was placed a mixture of methyl (S)-2-(5-((3-((tert-butoxycarbonyl)amino)propyl)amino)isoindolin-2-yl)-2-phenylacetate (40 mg, 1 Eq, 91 mol), LiOH (22 mg, 10 Eq, 0.92 mmol), MeOH (1 mL) and $H_2O$ (0.5 mL). The reaction mixture was stirred at 25° C. for 16 hours. The reaction mixture was concentrated under reduced pressure to remove most of the MeOH, the residue was diluted with water (10 mL), the pH value was adjusted to 6.0 by addition of a saturated $NaHSO_4$ solution. The aqueous solution was extracted with DCM (10 mL×3), dried over anhydrous $Na_2SO_4$, then concentrated under reduced pressure to afford methyl (S)-2-(5-((3-((tert-butoxycarbonyl)amino)propyl)amino)isoindolin-2-yl)-2-phenylacetic acid (12 mg, 28 μmol, 31%) as a light yellow solid, which was used directly in the next step without any purification. $[M+H]^+$=426.4.

Step 5. Methyl (S)-2-(5-((3-((tert-butoxycarbonyl)amino)propyl)amino)isoindolin-2-yl)-2-phenylacetic acid was treated with (R,Z)-2-amino-N-(2,6-difluoro-4-hydroxybenzyl)-5-(2-(ethylcarbamoyl)guanidino)pentanamide, HOBt, TBTU, and DIEA in manner similar to Step 5 of Example 13, then was treated with TFA in a manner similar to Step 2 in the synthesis of Compound 1 to provide the trifluoroacetic salt of (R)-2-((S)-2-(5-((3-aminopropyl)amino)isoindolin-2-yl)-2-phenylacetamido)-N-(2,6-difluoro-4-hydroxybenzyl)-5—((Z)-2-(ethylcarbamoyl)guanidino)pentanamide (6.9 mg, 8.5 μmol, 100%) as an off-white solid. MS: Calc'd for $C_{35}H_{45}F_2N_9O_4$: 693.36, found $[M+H]^+$: 694.2.

Example 78: (R)-2-((S)-2-(3-((3-aminopropyl)amino)phenyl)-2-(isoindolin-2-yl)acetamido)-N-(2,6-difluoro-4-hydroxybenzyl)-5-((Z)-2-(ethylcarbamoyl)guanidino)pentanamide (Compound 66A)

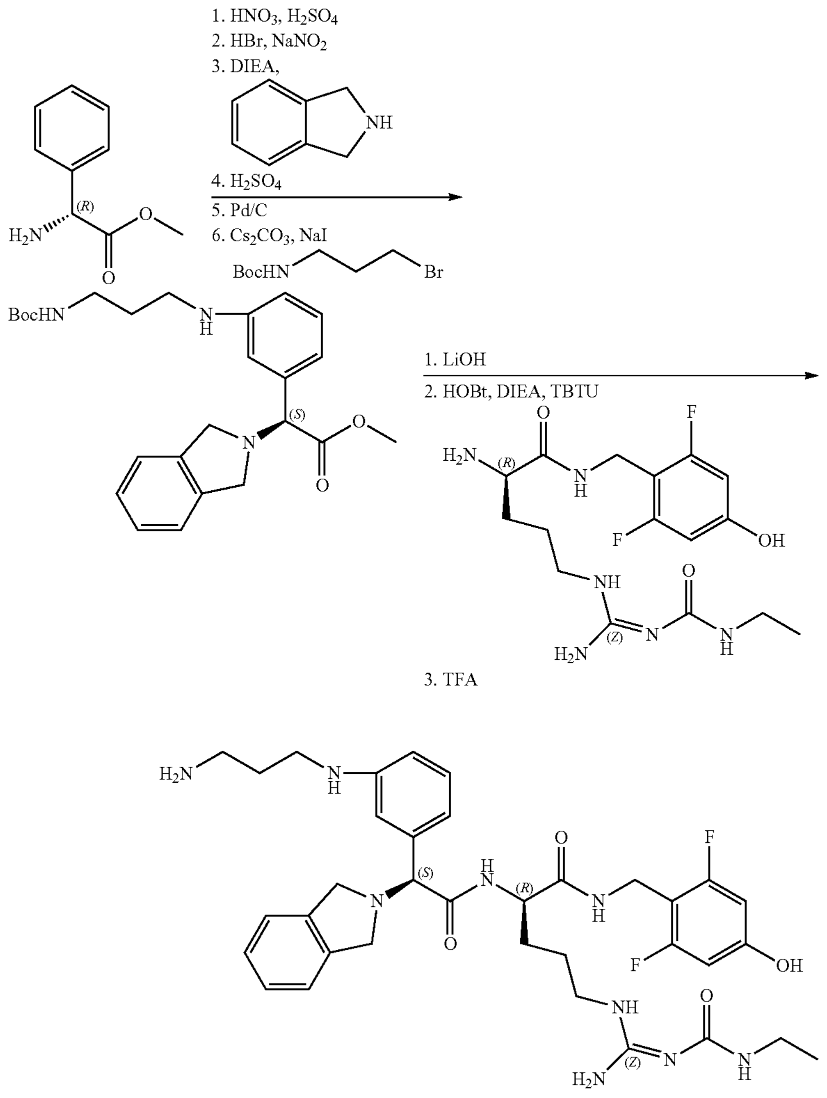

Step 1. Into a 250-mL round bottom flask, was placed a mixture of (R)-2-amino-2-phenylacetic acid (5 g, 1 Eq, 0.03 μmol) and $H_2SO_4$ (40 mL), to which was dropwise added nitric acid (5 g, 4 mL, 2 Eq, 0.08 μmol) at 0° C. The reaction mixture was stirred at 0° C. for 30 min. The mixture was quenched with ice-water (500 g) and the pH was adjusted to pH=7 by addition of 2N NaOH, then the aqueous solution was extracted with EtOAc (200 mL×3). The combined organic layers were washed with water (200 mL×2) and brine (200 mL), dried over anhydrous $Na_2SO_4$ and concentrated under reduced pressure to provide crude (R)-2-amino-2-(3-nitrophenyl)acetic acid (5.5 g, 28 mmol, 80%) as a yellow oil, which was used directly in the next step without purification. [M+H]=196.7.

Step 2. Into a 250-mL round bottom flask, was placed a mixture of HBr (4.4 g, 3.0 mL, 1.9 Eq, 54 mmol), (R)-2-amino-2-(3-nitrophenyl)acetic acid (5.5 g, 1 Eq, 28 mmol) and $H_2O$ (40 mL), to which was dropwise added nitric acid (5 g, 4 mL, 2 Eq, 0.08 μmol) at 0° C. The reaction mixture was stirred at −15° C. for 30 min. To which was dropwise added a solution of sodium nitrite (3.9 g, 2.4 mL, 2.0 Eq, 57 mmol) in $H_2O$ (10 mL) at 0° C. The reaction mixture was stirred at 25° C. The mixture was quenched with 400 g ice-water, then extracted with EtOAc (200 mL×3). The combined organic layers were washed with water (200 mL×2) and brine (200 mL), dried over anhydrous $Na_2SO_4$ and concentrated under reduced pressure to provide (R)-2- bromo-2-(3-nitrophenyl)acetic acid (6.8 g, 26 mmol, 93%) as a yellow solid, which was used directly in the next step without purification.

Step 3. Into a 100-mL round bottom flask, was placed a mixture of (R)-2-bromo-2-(3-nitrophenyl)acetic acid (4.4 g, 1 Eq, 17 mmol), DIEA (6.6 g, 8.9 mL, 3.0 Eq, 51 mmol), isoindoline (3.0 g, 1.5 Eq, 25 mmol) and DMF (40 mL). The reaction mixture was stirred at 25° C. for 2 hours. The mixture was diluted with water (250 mL), extracted with EtOAc (100 mL×3), then the combined organic layers were washed with water (100 mL×2) and brine (50 mL), dried over anhydrous $Na_2SO_4$ and concentrated under reduced pressure to provide (S)-2-(isoindolin-2-yl)-2-(3-nitrophenyl)acetic acid (5.0 g, 10 mmol, 59%) as a yellow solid. [M+H]=298.7.

Step 4. Into a 250-mL round bottom flask, was placed a mixture of (S)-2-(isoindolin-2-yl)-2-(3-nitrophenyl)acetic acid (5.0 g, 60% Wt, 1 Eq, 10 mmol), $H_2SO_4$ (9 g, 5 mL, 9 Eq, 0.09 mol) and MeOH (50 mL). The reaction mixture was stirred at 70° C. for 16 hours. The mixture was diluted with water (300 mL), then extracted with EtOAc (100 mL×5). The combined organic layers were washed with water (100 mL×2), brine (100 mL), dried over anhydrous $Na_2SO_4$ and concentrated under reduced pressure. The crude product was purified by MPLC to provide methyl (S)-2-(isoindolin-2-yl)-2-(3-nitrophenyl)acetate (2.1 g, 6.7 mmol, 67%) as a yellow solid. [M+H−56]=313.2.

Step 5. Methyl (S)-2-(isoindolin-2-yl)-2-(3-nitrophenyl) acetate (2.1 g, 1 Eq, 6.7 mmol) was treated with Pd/C in a manner similar to Step 4 of Example 13 to provide methyl (S)-2-(3-aminophenyl)-2-(isoindolin-2-yl)acetate (1.5 g, 5.3 mmol, 79%) as a yellow oil. [M+H]=282.8.

Step 6. Into a 40-mL vial, was placed a mixture of methyl (S)-2-(3-aminophenyl)-2-(isoindolin-2-yl)acetate (1.5 g, 1 Eq, 5.3 mmol), $Cs_2CO_3$ (5.2 g, 3.0 Eq, 16 mmol), sodium iodide (1.6 g, 2.0 Eq, 11 mmol), tert-butyl (3-bromopropyl) carbamate (1.9 g, 1.5 Eq, 8.0 mmol) and DMF (10 mL). The reaction mixture was stirred at 100° C. for 16 hours. The mixture was directly purified by MPLC to provide methyl (S)-2-(3-((3-((tert-butoxycarbonyl)amino)propyl)amino) phenyl)-2-(isoindolin-2-yl)acetate (750 mg, 1.71 mmol, 32%) as a yellow oil. [M+H]=440.6.

Step 7. Methyl (S)-2-(3-((3-((tert-butoxycarbonyl)amino) propyl)amino)phenyl)-2-(isoindolin-2-yl)acetate was treated with LiOH in a manner similar to Step 2 of Example 35 to provide (S)-2-(3-((3-((tert-butoxycarbonyl)amino)propyl)amino)phenyl)-2-(isoindolin-2-yl)acetic acid (600 mg, 1.41 mmol, 88.5%) as a yellow oil. [M+H−56]=426.2.

Steps 8-9. (S)-2-(3-((3-((tert-butoxycarbonyl)amino)propyl)amino)phenyl)-2-(isoindolin-2-yl)acetic acid was treated with 2,2',2"-(10-(2-((2,5-dioxopyrrolidin-1-yl)oxy)-2-oxoethyl)-1,4,7,10-tetraazacyclododecane-1,4,7-triyl)triacetic acid and DIEA in a manner similar to Example 1, Step 5 then treated with TFA in a manner similar to Step 2 in the synthesis of Compound 1 to provide the product as two isomers, which were separated by prep-HPLC. The front peak fractions were combined to provide the trifluoroacetic salt of (R)-2-((S)-2-(3-((3-aminopropyl)amino)phenyl)-2-(isoindolin-2-yl)acetamido)-N-(2,6-difluoro-4-hydroxybenzyl)-5-((Z)-2-(ethylcarbamoyl)guanidino)pentanamide (6.0 mg, 7.4 µmol, 70%) as a white solid. MS: Calc'd for $C_{37}H_{46}F_5N_9O_6$: 807.35, found $[M+H-TFA]^+$: 694.4.

Example 79: (R)-2-((R)-2-(3-((3-aminopropyl) amino)phenyl)-2-(isoindolin-2-yl)acetamido)-N-(2,6-difluoro-4-hydroxybenzyl)-5-((Z)-2-(ethylcarbamoyl)guanidino)pentanamide (Compound 66B)

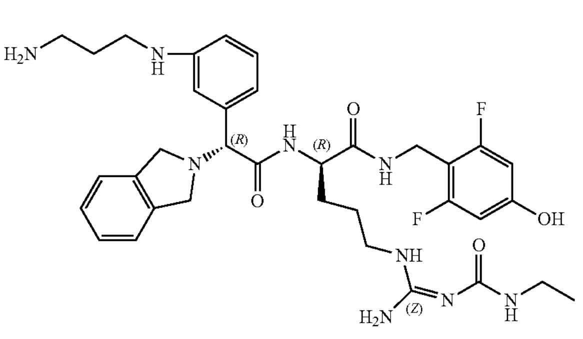

The back peak fractions from Example 79 were combined to provide the trifluoroacetic salt of (R)-2-((R)-2-(3-((3-aminopropyl)amino)phenyl)-2-(isoindolin-2-yl)acetamido)-N-(2,6-difluoro-4-hydroxybenzyl)-5-((Z)-2-(ethylcarbamoyl)guanidino)pentanamide (2.4 mg, 3.0 µmol, 60%) as a white solid. MS: Calc'd for $C_{37}H_{46}F_5N_9O_6$: 807.35, found $[M+H-TFA]^+$: 694.4.

Example 80: (2R)—N-(2,6-difluoro-4-hydroxybenzyl)-5-((Z)-2-(ethylcarbamoyl)guanidino)-2-(2-(isoindolin-2-yl)-2-phenylacetamido)pentanamide (Compound 67)

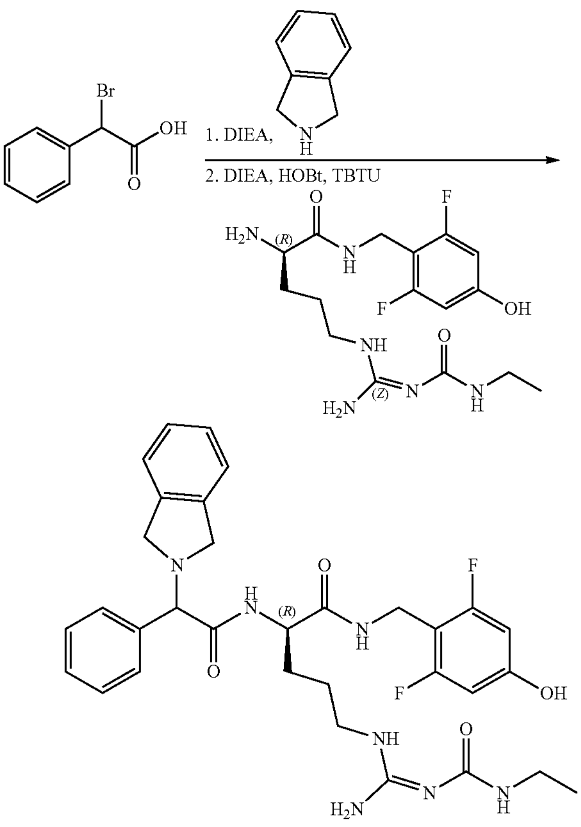

Step 1. Into an 8-mL vial, was placed a mixture of 2-bromo-2-phenylacetic acid (200 mg, 1 Eq, 930 μmol), DIEA (361 mg, 487 μL, 3.00 Eq, 2.79 mmol), isoindoline (167 mg, 1.51 Eq, 1.40 mmol) and MeCN (2 mL). The reaction mixture was stirred at 25° C. for 2 hours. The mixture was directly purified by MPLC to provide 2-(isoindolin-2-yl)-2-phenylacetic acid (150 mg, 0.45 mmol, 48%) as a white solid. [M+H]=253.9.

Step 2. Into an 8-mL vial, was placed a mixture of 2-(isoindolin-2-yl)-2-phenylacetic acid (25 mg, 1 Eq, 99 μmol), TBTU (50 mg, 1.6 Eq, 0.16 mmol), HOBt (23 mg, 1.5 Eq, 0.15 mmol), (R,Z)-2-amino-N-(2,6-difluoro-4-hydroxybenzyl)-5-(2-(ethylcarbamoyl)guanidino)pentanamide (39 mg, 1.0 Eq, 0.10 mmol), DIEA (38 mg, 51 μL, 3.0 Eq, 0.29 mmol) and DMF (0.5 mL). The reaction mixture was stirred at 25° C. for 1 hour. The crude product was purified by Prep-HPLC to provide the trifluoroacetic acid salt of (2R)—N-(2,6-difluoro-4-hydroxybenzyl)-5-((Z)-2-(ethylcarbamoyl)guanidino)-2-(2-(isoindolin-2-yl)-2-phenylacetamido)pentanamide (21 mg, 27 μmol, 27%) as an off-white solid. MS: Calc'd for $C_{34}H_{38}F_5N_7O_6$: 735.28, found [M+H−TFA]$^+$: 622.3.

Example 81: (2R)-5-guanidino-N-(4-hydroxybenzyl)-2-(2-(isoindolin-2-yl)-2-phenylacetamido)pentanamide (Compound 68)

MPLC to provide tert-butyl (R)-(1-((4-(tert-butoxy)benzyl)amino)-5-guanidino-1-oxopentan-2-yl)carbamate (350 mg, 804 μmol, 45.2%) as a yellow oil. [M+H]=437.5.

Step 2. Into an 8-mL vial, was placed a mixture of tert-butyl (R)-(1-((4-(tert-butoxy)benzyl)amino)-5-guanidino-1-oxopentan-2-yl)carbamate (150 mg, 1 Eq, 344 μmol) and DCM (1.5 mL), to which was added TFA (0.3 mL). The reaction mixture was stirred at 20° C. for 20 min. The mixture was concentrated under reduced pressure to afford (R)-2-amino-5-guanidino-N-(4-hydroxybenzyl)pentanamide (140 mg, 501 μmol, 146%) as colorless oil, which was used directly in the next step without any purification. [M+H]=280.3.

Step 3. Into a 8-mL vial, was placed a mixture of 2-bromo-2-phenylacetic acid (50 mg, 1 Eq, 0.23 mmol), DIEA (90 mg, 0.12 mL, 3.0 Eq, 0.70 mmol), isoindoline (56 mg, 2.0 Eq, 0.47 mmol) and ACN (0.5 mL). The reaction mixture was stirred at 80° C. for 1 hour. The mixture was directly purified by MPLC to provide 2-(isoindolin-2-yl)-2-phenylacetic acid (55 mg, 0.22 mmol, 93%) as a colorless oil. [M+H]=254.3.

Step 4. Into an 8-mL vial, was placed a mixture of 2-(isoindolin-2-yl)-2-phenylacetic acid (16 mg, 1 Eq, 63 μmol), HOBt (11 mg, 1.1 Eq, 72 μmol), 0-(Benzotriazol-1-yl)-N,N,N',N'-tetramethyluroniumTetrafluoroborate (TBTU) (23 mg, 1.1 Eq, 72 μmol), DIEA (25 mg, 34 μL, 3.1

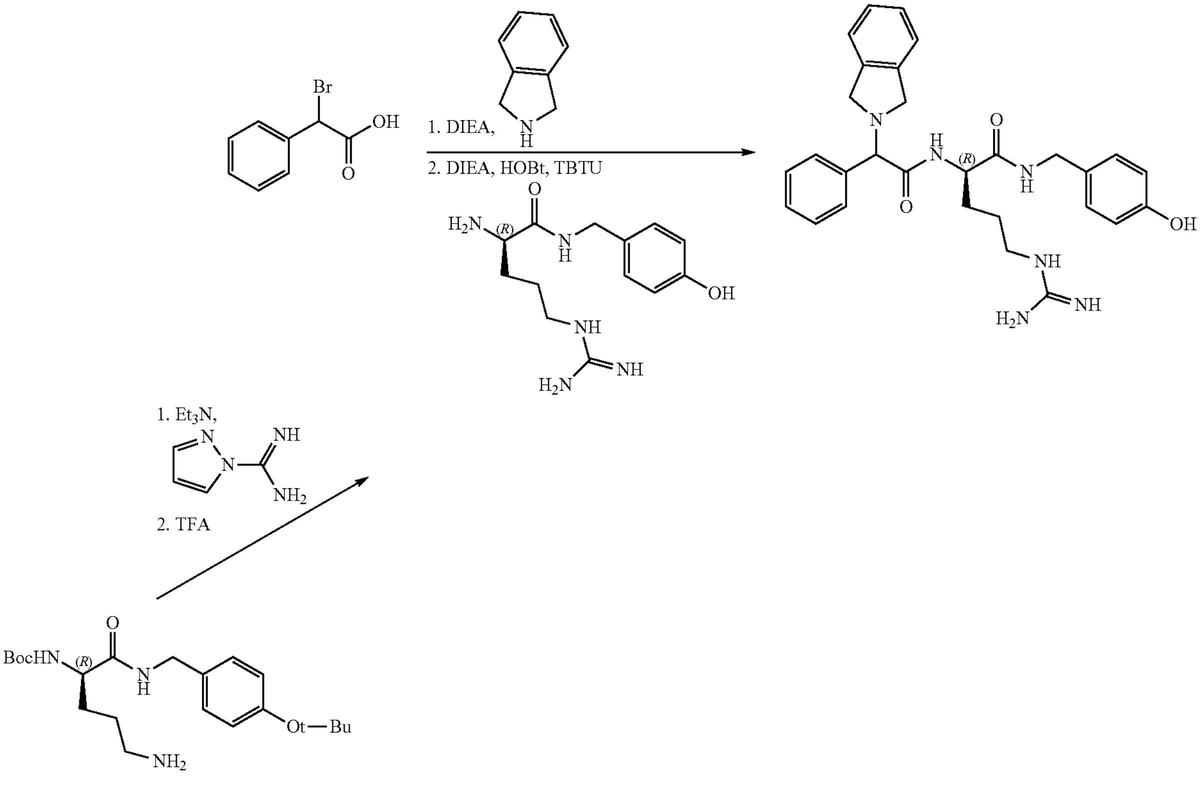

Step 1. Into a 40-mL vial, was placed a mixture of tert-butyl (R)-(5-amino-1-((4-(tert-butoxy)benzyl)amino)-1-oxopentan-2-yl)carbamate (700 mg, 1 Eq, 1.78 mmol), TEA (540 mg, 744 μL, 3.00 Eq, 5.34 mmol), 1H-pyrazole-1-carboximidamide (200 mg, 1.02 Eq, 1.82 mmol) and ACN (10 mL). The reaction mixture was stirred at 20° C. for an additional 2 hours. The mixture was directly purified by Eq, 0.19 mmol) and DMF (0.5 mL). The reaction mixture was stirred at 20° C. for 10 minutes, then (R)-2-amino-5-guanidino-N-(4-hydroxybenzyl)pentanamide (20 mg, 1.1 Eq, 72 μmol) was added and the reaction mixture was stirred at 25° C. for an additional 1 hour. The reaction mixture was purified by Prep-HPLC to provide the trifluoroacetic acid salt of (2R)-5-guanidino-N-(4-hydroxybenzyl)-2-(2-(isoindolin-2-yl)-2-phenylacetamido)pentanamide (21.2 mg, 33.7 μmol, 53%) as a white solid. MS: Calc'd for $C_{31}H_{35}F_3N_6O_5$: 628.26, found $[M+H-TFA]^+$: 515.3.

Example 82: (R)—N-(2,6-difluoro-4-hydroxybenzyl)-5-guanidino-2-((S)-2-(isoindolin-2-yl)-2-phenylacetamido)pentanamide (Compound 69)

Step 2. Benzyl tert-butyl (5-((2,6-difluoro-4-hydroxybenzyl)amino)-5-oxopentane-1,4-diyl)(R)-dicarbamate was treated with Pd/C in MeOH in a manner similar to Example 13, Step 4 to provide tert-butyl (R)-(5-amino-1-((2,6-difluoro-4-hydroxybenzyl)amino)-1-oxopentan-2-yl)carbamate (300 mg, 0.72 mmol, 73%) as a white solid. $[M+H]^+$=374.4.

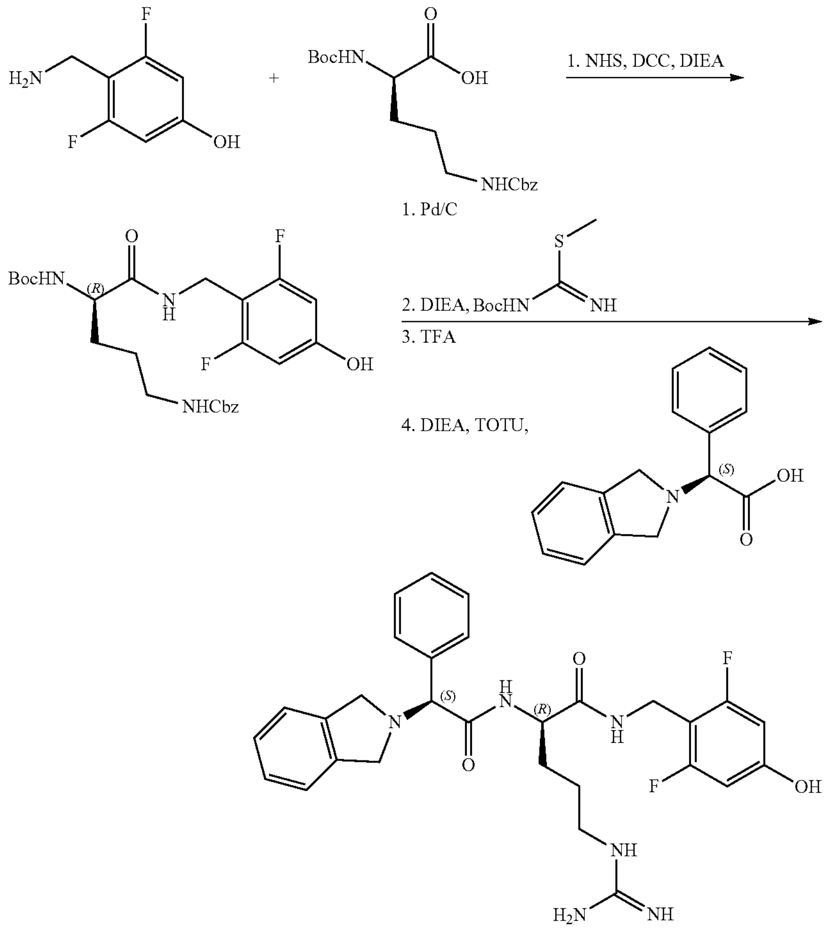

Step 1. Into a 250-mL round bottom flask, was placed (R)-5-(((benzyloxy)carbonyl)amino)-2-((tert-butoxycarbonyl)amino)pentanoic acid (8.1 g, 1 Eq, 22 mmol), N-hydroxysuccinimide (2.5 g, 1 Eq, 22 mmol) and THE (80 mL). To the mixture was added dicyclohexylcarbodiimide (4.5 g, 3.9 mL, 1 Eq, 22 mmol) under $N_2$. The reaction mixture was stirred at 25° C. for 1 hour. Into another 250-mL round bottom flask, was placed a mixture of 4-(aminomethyl)-3,5-difluorophenol (3.5 g, 1 Eq, 22 mmol), DIEA (2.8 g, 3.8 mL, 1 Eq, 22 mmol) and THE (30 mL). The first solution was added dropwise into the $2^{nd}$ mixture at 25° C. The reaction mixture was stirred at 25° C. for 2 hours. The mixture was diluted with 100 mL of water, extracted with EtOAc (100 mL×3), then the combined organic layers were washed with water (100 mL×2) and brine (80 mL), dried over anhydrous $Na_2SO_4$ and concentrated under reduced pressure. The crude product was purified by MPLC to provide benzyl tert-butyl (5-((2,6-difluoro-4-hydroxybenzyl)amino)-5-oxopentane-1,4-diyl)(R)-dicarbamate (9.0 g, 14 mmol, 65%) as an off-white solid. [M+H]=508.1.

Step 3. Into an 8 mL vial, was placed a mixture of tert-butyl (R)-(5-amino-1-((2,6-difluoro-4-hydroxybenzyl)amino)-1-oxopentan-2-yl)carbamate (300 mg, 1 Eq, 803 mol), Intermediate A (185 mg, 1.21 Eq, 972 μmol), DIEA (312 mg, 420 μL, 3.00 Eq, 2.41 mmol) and EtOH (3 mL). The reaction mixture was stirred at 80° C. for 4 hours. The mixture was concentrated under reduced pressure and directly purified by MPLC to afford the product (330 mg, 0.58 mmol, 72%) as an off-white solid. $[M+H]^+$=516.5.

Step 4. The product from Step 3 was treated with TFA in a manner similar to Step 2 in the synthesis of Compound 1 to provide (R)-2-amino-N-(2,6-difluoro-4-hydroxybenzyl)-5-guanidinopentanamide 2,2,2-trifluoroacetate (380 mg, 0.62 mmol, 97%) as a light yellow solid, which was used directly in the next step without any purification. $[M+H]^+$=316.1.

Step 5. (R)-2-Amino-N-(2,6-difluoro-4-hydroxybenzyl)-5-guanidinopentanamide 2,2,2-trifluoroacetate was treated with (S)-2-(isoindolin-2-yl)-2-phenylacetic acid, HOBt, TBTU, and DIEA in a manner similar to Step 4 of Example 82 to provide the trifluoroacetic acid salt of (R)—N-(2,6-difluoro-4-hydroxybenzyl)-5-guanidino-2-((S)-2-(isoindolin-2-yl)-2-phenylacetamido)pentanamide (11.0 mg, 15.5 μmol, 19%) as a white solid. MS: Calc'd for $C_{29}H_{32}F_{3}N_{6}O_{3}$: 550.25, found $[M+H]^+$: 551.2.

Example 83: (R)-5-guanidino-N-(4-hydroxybenzyl)-2-((S)-2-(isoindolin-2-yl)-2-phenylacetamido)pentanamidICompound 70)

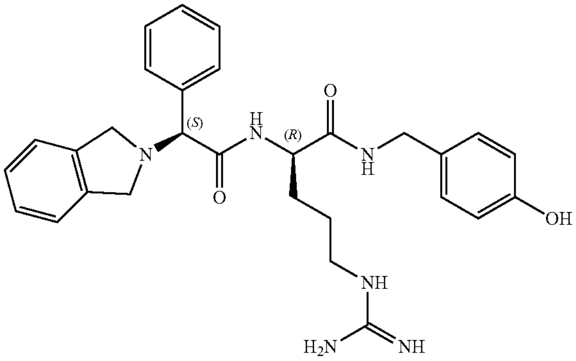

Steps 1-4. (R)-5-guanidino-N-(4-hydroxybenzyl)-2-((S)-2-(isoindolin-2-yl)-2-phenylacetamido)pentanamide was synthesized from benzyl tert-butyl (5-((4-(tert-butoxy)benzyl)amino)-5-oxopentane-1,4-diyl)(R)-dicarbamate in a manner similar to Steps 2-5 of Example 83 to provide the trifluoroacetic acid salt (R)-5-guanidino-N-(4-hydroxybenzyl)-2-((S)-2-(isoindolin-2-yl)-2-phenylacetamido)pentanamide (15.1 mg, 24.0 mmol, 15%) as a white solid. MS: Calc'd for $C_{29}H_{34}N_{6}O_{3}$: 514.27, found $[M+H]^+$: 515.2.

Example 84: (R)-5-guanidino-N-(4-hydroxybenzyl)-2-((S)-2-(1-oxoisoindolin-2-yl)-2-phenylacetamido)pentanamide (Compound 71A)

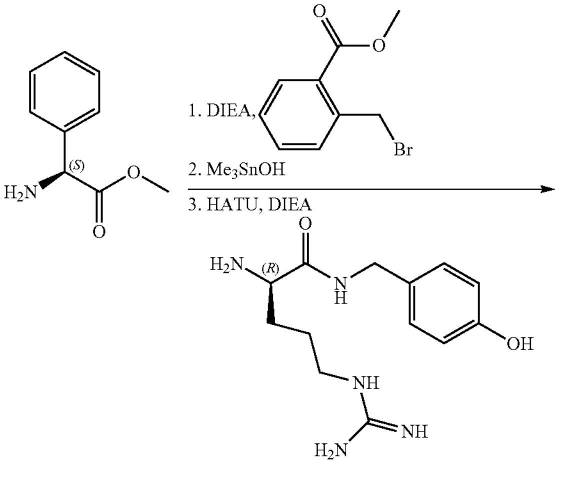

-continued

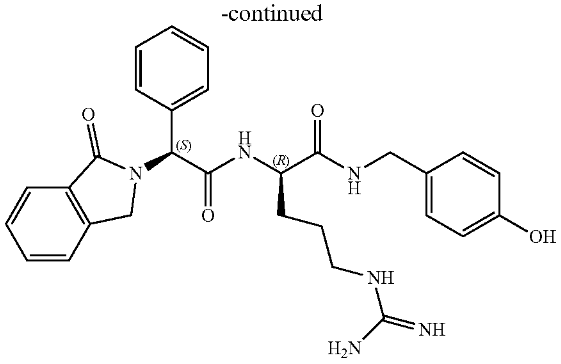

Step 1. Into a 40-mL vial, was placed a mixture of methyl (S)-2-amino-2-phenylacetate (500 mg, 1 Eq, 3.03 mmol), methyl 2-(bromomethyl)benzoate (763 mg, 1.10 Eq, 3.33 mmol), DIEA (782 mg, 1.05 mL, 2.00 Eq, 6.05 mmol) and DMF (5 mL). The reaction mixture was stirred at 80° C. for 16 hours. The mixture was directly purified by MPLC to provide methyl (S)-2-(1-oxoisoindolin-2-yl)-2-phenylacetate (200 mg, 711 μmol, 23.5%) as a yellow oil. $[M+H]^+$=282.1.

Step 2. Into a 8-mL vial, was placed a mixture of methyl (S)-2-(1-oxoisoindolin-2-yl)-2-phenylacetate (100 mg, 1 Eq, 355 μmol) and DCE (1 mL), to which was added trimethyltinhydroxide (129 mg, 2.01 Eq, 713 μmol). The reaction mixture was stirred at 90° C. for 16 hours. The mixture was concentrated under reduced pressure then purified by MPLC to provide (S)-2-(1-oxoisoindolin-2-yl)-2-phenylacetic acid (45 mg, 0.17 mmol, 47%) as a white solid. $[M+H]^+$=268.2.

Step 3. Into a 8-mL vial, was placed a mixture of (S)-2-(1-oxoisoindolin-2-yl)-2-phenylacetic acid (45 mg, 1 Eq, 0.17 mmol), HATU (64 mg, 1.0 Eq, 0.17 mmol), DIEA (65 mg, 88 μL, 3.0 Eq, 0.50 mmol) and DMF (0.5 mL). The reaction mixture was stirred at 20° C. for 10 minutes, then (R)-2-amino-5-guanidino-N-(4-hydroxybenzyl)pentanamide (47 mg, 1.0 Eq, 0.17 mmol) was added and the reaction mixture was stirred at 25° C. for an additional 1 hour. The crude product was purified by Prep-HPLC to provide two isomers as two peaks. The front peak fractions were combined to provide the formic acid salt of (R)-5-guanidino-N-(4-hydroxybenzyl)-2-((S)-2-(1-oxoisoindolin-2-yl)-2-phenylacetamido)pentanamide (15.4 mg, 26.8 μmol, 16%) (assumed) as a white solid. MS: Calc'd for $C_{29}H_{32}N_{6}O_{4}$: 528.25, Ind $[M+H]^+$: 529.2.

Example 85: (R)-5-guanidino-N-(4-hydroxybenzyl)-2-((R)-2-(1-oxoisoindolin-2-yl)-2-phenylacetamido)pentanamide (Compound 71B)

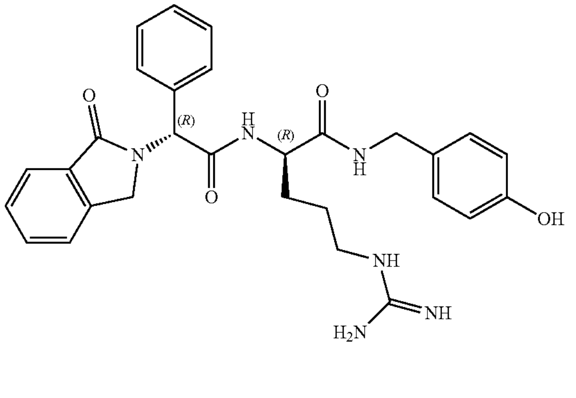

The back peak fractions from Step 3 of Example 85 were combined to provide the formic acid salt of (R)-5-guanidino-N-(4-hydroxybenzyl)-2-((R)-2-(1-oxoisoindolin-2-yl)-2-phenylacetamido)pentanamide (6.0 mg, 10 μmol, 6.2%) (assumed) as a white solid. MS: Calc'd for $C_{29}H_{32}N_6O_4$: 528.25, found $[M+H]^+$: 529.2.
Example 86: (2R)-5-guanidino-N-(4-hydroxybenzyl)-2-(2-phenyl-2-(piperidin-1-yl)acetamido)pentanamide (Compound 72)
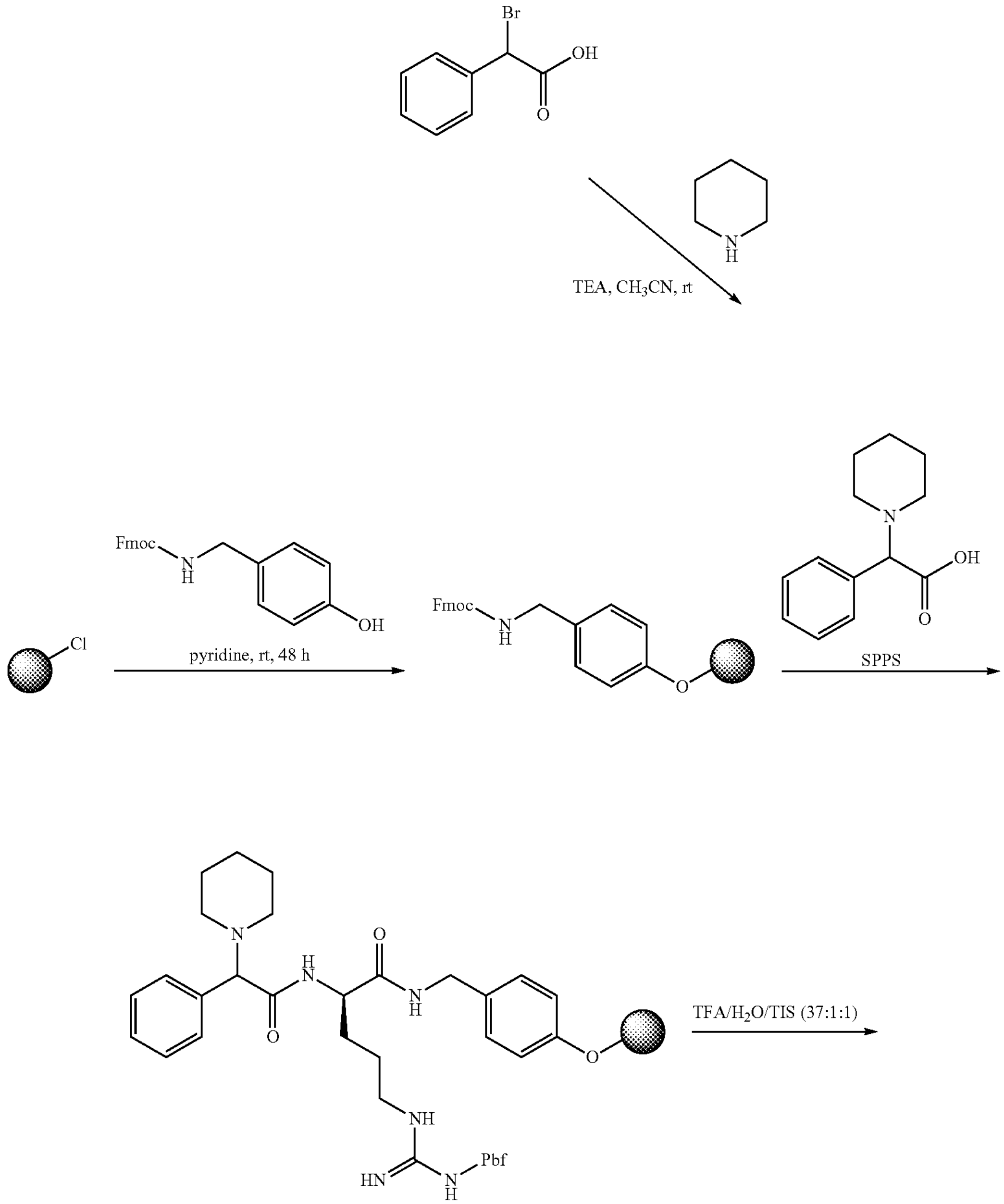

-continued

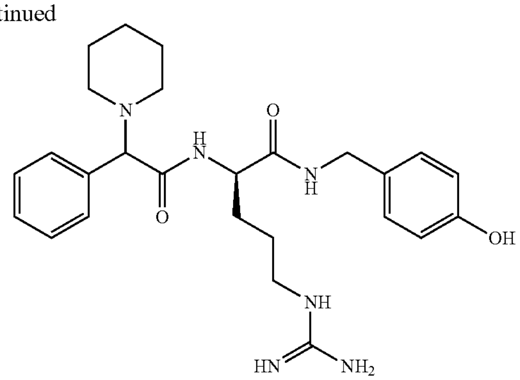

General SPPS procedure: (A) Resin swelling: the resin (100 mg) was swelled in NMP (1 mL) for 15 min at room temperature under nitrogen atmosphere. The resin was then washed with NMP (1 mL×4). (B: Fmoc de-protection: the resin (100 mg) was treated with 20% of piperidine in NMP (1 mL) for 20 min at room temperature under nitrogen atmosphere. The resin was then washed with NMP (1 mL×4). (C): HATU coupling: the resin (100 mg) was treated with the mixture of amino acid (4 equiv), HATU (4 equiv) and DIPEA (8 equiv) in NMP (1 mL) for 45 min at 30° C. under nitrogen atmosphere unless otherwise noted. The resin was then washed with NMP (1 mL×4). (D): Cleavage & purification: the crude peptide was cleaved from the resin with the solution (2 mL, v/v/v TFA/$H_2O$/TIS=37:1:1) for 2 h at room temperature. The mixture was filtered, and the filtrate was concentrated under reduced pressure. After the residue was precipitated with cold ether, the precipitation was collected by centrifugation and purified by RP-HPLC. The desired fractions were combined and dried by lyophilization.

Step 1. Synthesis of 2-phenyl-2-(piperidin-1-yl)acetic acid: A solution of bromo(phenyl)acetic acid (500 mg, 2.32 mmol, 1.0 equiv), piperidine (297.0 mg, 3.49 mmol, 1.5 equiv) and TEA (470.6 mg, 4.65 mmol, 2.0 equiv) in $CH_3CN$ (1 mL) was stirred overnight at room temperature under a nitrogen atmosphere. After the solvent was removed in vacuo, the residue was purified by reversed-phase flash chromatography (column: $C_{18}$ silica gel; mobile phase A: water (0.1% formic acid), mobile phase B: $CH_3CN$, 10% to 100% gradient mobile phase B in 40 min; detector wavelength: UV 220 nm). The collected fractions were combined and concentrated in vacuo to afford 2-phenyl-2-(piperidin-1-yl)acetic acid (180 mg, 35.3%) as a white solid. LCMS m z: $[M+H]^+$=220.1.

Step 2. 2-Chlorotrityl chloride resin (5.0 g, 1.52 mmol/g) was swollen in pyridine (30 mL) for 30 min at room temperature. After the solvent was removed by filtration, a solution of (9H-fluoren-9-yl)methyl (4-hydroxybenzyl)carbamate (5.2 g, 15.07 mmol, 2.0 equiv) in pyridine (40 mL) was added to the resin. The mixture was incubated for 48 h at room temperature. The resin was washed with dichloromethane (30 mL×4) and ether (30 mL×4).

Step 3: (2R)-5-guanidino-N-(4-hydroxybenzyl)-2-(2-phenyl-2-(piperidin-1-yl)acetamido)pentanamide was synthesized using the general SPPS procedure described above. In Step (C), HATU coupling of D-Arg, followed by HATU coupling of 2-phenyl-2-(piperidin-1-yl)acetic acid. (General SPPS procedure Step B-C). The crude peptide product was cleaved from the resin and purified by RP-HPLC (General SPPS procedure Step D). The desired fractions were combined and lyophilized to afford (2R)-5-guanidino-N-(4-hydroxybenzyl)-2-(2-phenyl-2-(piperidin-1-yl)acetamido)pentanamide as a white solid (overall yield 2.0%, 99.1% purity). MS: Calc'd for $C_{26}H_{36}N_6O_3$: 480.28, found $[M+H]^+$=481.2.

Example 87: (2R)-5-guanidino-N-(4-hydroxybenzyl)-2-(2-phenyl-2-(4-(trifluoromethyl)piperidin-1-yl)acetamido)pentanamide (Compound 73)

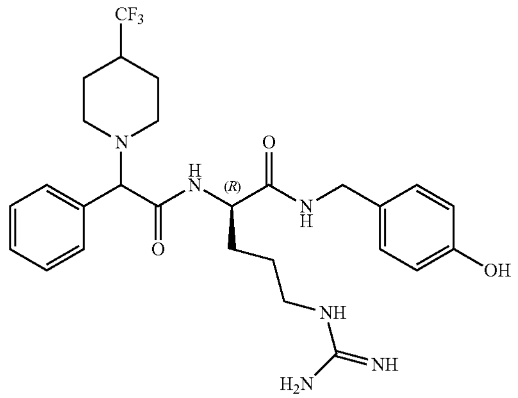

Step 1. Phenyl[4-(trifluoromethyl) piperidin-1-yl]acetic acid was synthesized from bromo(phenyl)acetic acid and 4-(trifluoromethyl)piperidine in a manner similar to Step 1 of Example 87 to provide the product (350 mg, 52.4%) as a white solid. $[M+H]^+$=288.1.

Steps 2-3. (2R)-5-guanidino-N-(4-hydroxybenzyl)-2-(2-phenyl-2-(4-(trifluoromethyl)piperidin-1-yl)acetamido)pentanamide was synthesized from phenyl[4-(trifluoromethyl) piperidin-1-yl]acetic acid in a manner similar to Steps 2-3 of Example 87 to provide the product. MS: Calc'd for $C_{27}H_{35}F_3N_6O_3$: 548.27, found $[M+H]^+$=549.2.

Example 88: (2R)-2-(2-(4,4-dimethylpiperidin-1-yl)-2-phenylacetamido)-5-guanidino-N-(4-hydroxybenzyl)pentanamide (Compound 74)

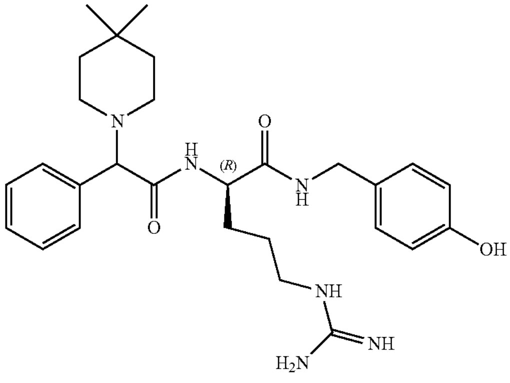

Step 1. (4,4-Dimethylpiperidin-1-yl) (phenyl)acetic acid was synthesized from bromo(phenyl)acetic acid and 4,4-dimethylpiperidine in a manner similar to Step 1 of Example 87 to provide the product (210 mg, 36.4% yield) as a white solid. $[M+H]^+$=248.1.

Steps 2-3. (2R)-2-(2-(4,4-dimethylpiperidin-1-yl)-2-phenylacetamido)-5-guanidino-N-(4-hydroxybenzyl)pentanamide was synthesized from phenyl[4-(trifluoromethyl) piperidin-1-yl]acetic acid in a manner similar to Steps 2-3 of Example 87 to provide the product. MS: Calc'd for $C_{28}H_{40}N_6O_3$: 508.32, found $[M+H]^+$=509.2.

Example 89: (2R)-2-(2-(3,3-dimethylpiperidin-1-yl)-2-phenylacetamido)-5-guanidino-N-(4-hydroxybenzyl)pentanamide (Compound 75)

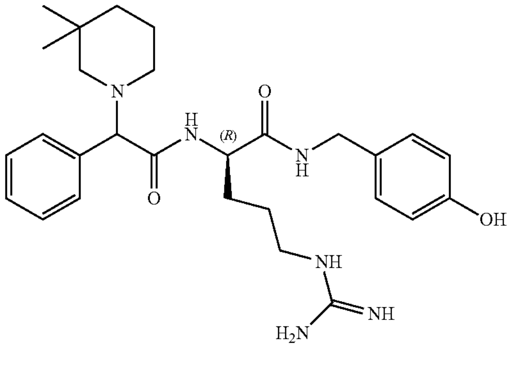

Step 1. (3,3-Dimethylpiperidin-1-yl) (phenyl)acetic acid was synthesized from bromo(phenyl)acetic acid and 3,3-dimethylpiperidine in a manner similar to Step 1 of Example 87 to provide the product (232 mg, 35.2%) as a white solid. [M+H]=248.1.

Steps 2-3. (2R)-2-(2-(3,3-dimethylpiperidin-1-yl)-2-phenylacetamido)-5-guanidino-N-(4-hydroxybenzyl)pentanamide was synthesized from (3,3-dimethylpiperidin-1-yl) (phenyl)acetic acid in a manner similar to Steps 2-3 of Example 87 to provide the product. MS: Calc'd for $C_{28}H_4N_6O_3$: 508.32, found $[M+H]^+$=509.2.

Example 90: (2R)-5-guanidino-N-(4-hydroxybenzyl)-2-(2-phenyl-2-(4-phenylpiperazin-1-yl)acetamido)pentanamide (Compound 76)

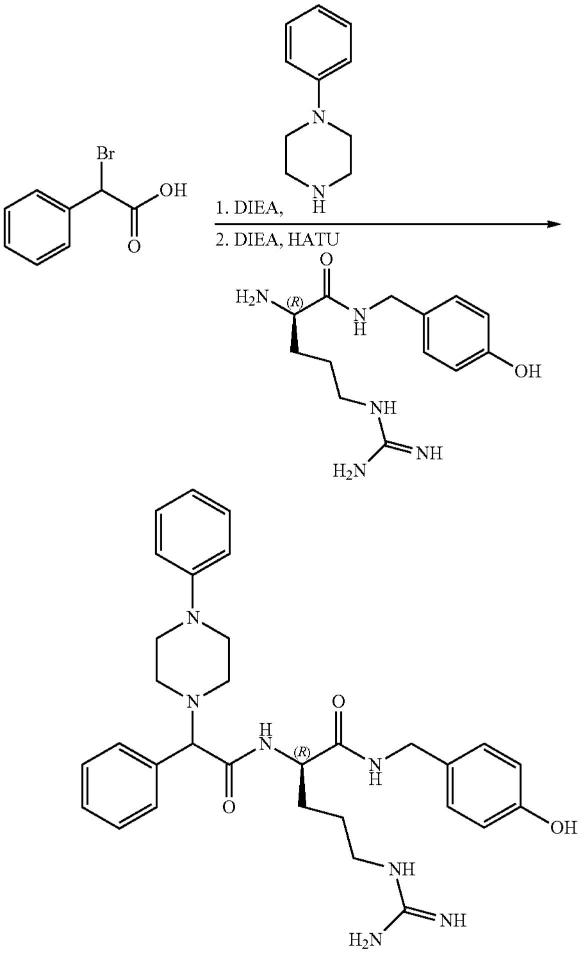

Step 1. Into an 8-mL vial, was placed a mixture of 2-bromo-2-phenylacetic acid (40 mg, 1 Eq, 0.19 mmol), DIEA (72 mg, 97 L, 3.0 Eq, 0.56 mmol), 1-phenylpiperazine (60 mg, 2.0 Eq, 0.37 mmol) and ACN (1.0 mL). The reaction mixture was stirred at 25° C. for 2 hours. The mixture was directly purified by MPLC to provide 2-phenyl-2-(4-phenylpiperazin-1-yl)acetic acid (35 mg, 0.12 mmol, 63%) as a yellow oil. [M+H]=297.2.

Step 2. Into a 8-mL vial, was placed a mixture of 2-phenyl-2-(4-phenylpiperazin-1-yl)acetic acid (35 mg, 1 Eq, 0.12 mmol), 2-(3H-[1,2,3]triazolo[4,5-b]pyridin-3-yl)-1,1,3,3-tetramethylisouronium hexafluorophosphate(V) (52 mg, 1.2 Eq, 0.14 mmol), N-ethyl-N-isopropylpropan-2-amine (45 mg, 2.9 Eq, 0.35 mmol) and DMF (1.0 mL). The reaction mixture was stirred at 20° C. for 10 minutes, then (R)-2-amino-5-guanidino-N-(4-hydroxybenzyl)pentanamide (40 mg, 1.2 Eq, 0.14 mmol) was added and the reaction mixture was stirred at 25° C. for an additional 2 hours. The crude product was purified by Prep-HPLC to provide the trifluoroacetic acid salt of (2R)-5-guanidino-N-(4-hydroxybenzyl)-2-(2-phenyl-2-(4-phenylpiperazin-1-yl)acetamido)

pentanamide (7 mg, 0.01 mmol, 9%) as an off-white solid. MS: Calc'd for $C_{33}H_{40}F_3N_7O_5$: 671.34, found [M+H−TFA]$^+$: 558.3.

Example 91: (2R)-5-guanidino-N-(4-hydroxybenzyl)-2-(2-(4-isopropylpiperidin-1-yl)-2-phenylacetamido)pentanamide (Compound 77)

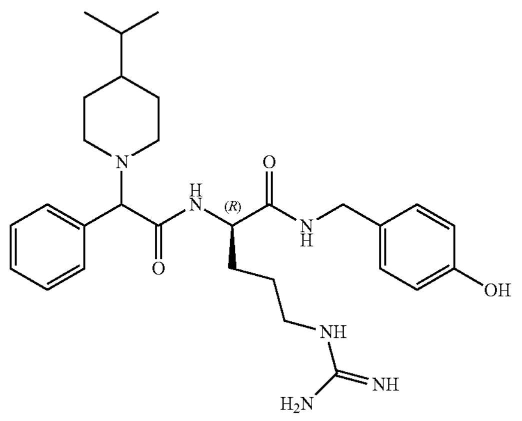

(2R)-5-guanidino-N-(4-hydroxybenzyl)-2-(2-(4-isopropylpiperidin-1-yl)-2-phenylacetamido)pentanamide was synthesized from 2-bromo-2-phenylacetic acid and 4-isopropylpiperidine in a manner similar to Example 91 to provide the trifluoroacetic acid salt of the product (7.5 mg, 12 μmol, 9.6%) as an off-white solid. MS: Calc'd for $C_{31}H_{43}F_3N_6O_5$: 636.32, found [M+H−TFA]$^+$: 523.3.

Example 92: (R)-5-guanidino-N-(4-hydroxybenzyl)-2-((S)-2-phenyl-2-(4-propylpiperidin-1-yl)acetamidlentanamide (Compound 78)

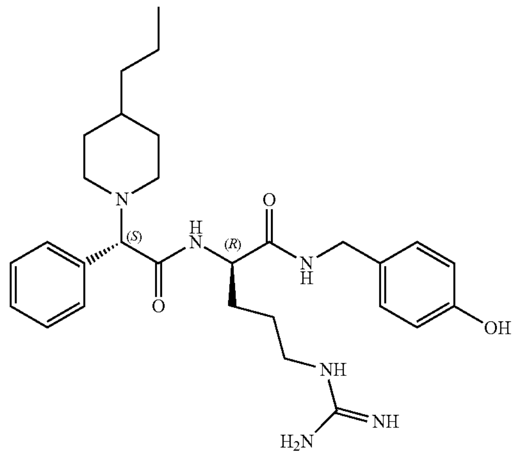

(R)-5-guanidino-N-(4-hydroxybenzyl)-2-((S)-2-phenyl-2-(4-propylpiperidin-1-yl)acetamido)pentanamide was synthesized from 2-bromo-2-phenylacetic acid and 4-propylpiperidine in a manner similar to Example 91. The product was purified by Prep-HPLC to provide two isomers as two distinct peaks. The front peak fractions were combined to provide the formic acid salt of the product (3.2 mg, 3.9 μmol, 2.9%) as an off-white solid. MS: Calc'd for $C_{30}H_{44}N_6O_5$: 568.34, found [M+H−FA]$^+$: 523.3.

Example 93: (R)-5-guanidino-N-(4-hydroxybenzyl)-2-((R)-2-phenyl-2-(4-propylpiperidin-1-yl)acetamido)pentanamide (Compound 78A)

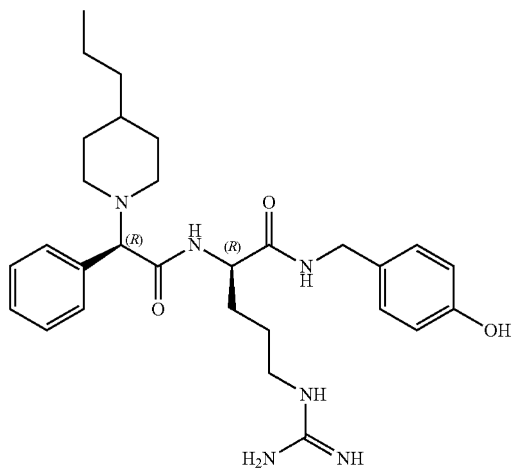

The formic acid salt of (R)-5-guanidino-N-(4-hydroxybenzyl)-2-((R)-2-phenyl-2-(4-propylpiperidin-1-yl)acetamido)pentanamide was obtained by combining the back peak fractions from Example 93 to provide the product (5.4 mg, 9.5 μmol, 7.1%) as an off-white solid. MS: Calc'd for $C_{30}H_{44}N_6O_5$: 568.34, found [M+H−FA]$^+$: 523.3.

Example 94: (2R)-2-(2-(4-ethylpiperidin-1-yl)-2-phenylacetamido)-5-guanidino-N-(4-hydroxybenzyl)pentanamide (Compound 79)

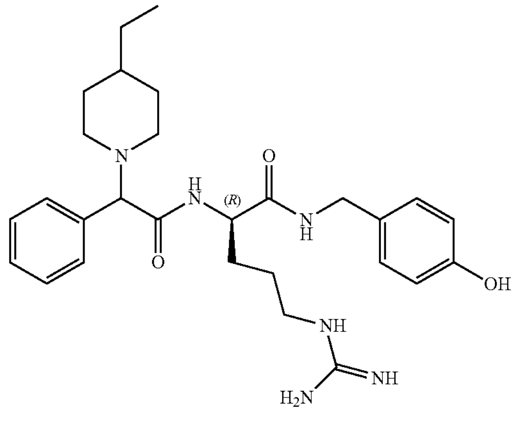

(2R)-2-(2-(4-ethylpiperidin-1-yl)-2-phenylacetamido)-5-guanidino-N-(4-hydroxybenzyl)pentanamide was synthesized from 2-bromo-2-phenylacetic acid and 4-ethylpiperidine in a manner similar to Example 91. The product was purified by Prep-HPLC to provide the trifluoroacetic acid of the product (17.1 mg, 27.5 μmol, 23%) as a white solid. MS: Calc'd for $C_{28}H_{40}N_6O_3$: 508.32, found [M+H−TFA]$^+$: 509.3.

Example 95: (2R)-2-(2-(4-(tert-butyl)piperidin-1-yl)-2-phenylacetamido)-5-guanidino-N-(4-hydroxybenzyl)pentanamide (Compound 80)

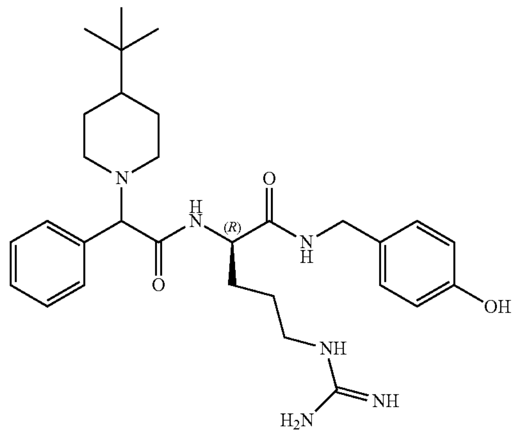

(2R)-2-(2-(4-(tert-butyl)piperidin-1-yl)-2-phenylacetamido)-5-guanidino-N-(4-hydroxybenzyl)pentanamide was synthesized from 2-bromo-2-phenylacetic acid and 4-(tert-butyl)piperidine in a manner similar to Example 91. The product was purified by Prep-HPLC to provide the formic acid of the product (6.5 mg, 11 μmol, 9.8%) as a white solid. MS: Calc'd for $C_{31}H_{46}N_6O_5$: 582.35, found $[M+H-FA]^+$: 537.3.

Example 96: (2R)-2-(2-(4-cyclopropylpiperidin-1-yl)-2-phenylacetamido)-5-guanidino-N-(4-hydroxybenzyl)pentanamide (Compound 81)

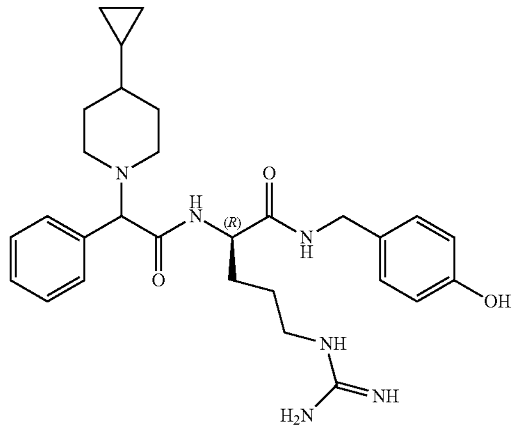

(2R)-2-(2-(4-cyclopropylpiperidin-1-yl)-2-phenylacetamido)-5-guanidino-N-(4-hydroxybenzyl)pentanamide was synthesized from 2-bromo-2-phenylacetic acid and 4-cyclopropylpiperidine in a manner similar to Example 91. The product was purified by Prep-HPLC to provide the trifluoroacetic acid of the product (12.0 mg, 18.9 μmol, 14%) as a white solid. MS: Calc'd for $C_{31}H_{41}F_3N_6O_5$: 634.31, found $[M+H-TFA]^+$: 521.3.

Example 97: (2R)-5-guanidino-N-(4-hydroxybenzyl)-2-(2-(4-isobutylpiperidin-1-yl)-2-phenylacetamido)pentanamide (Compound 82)

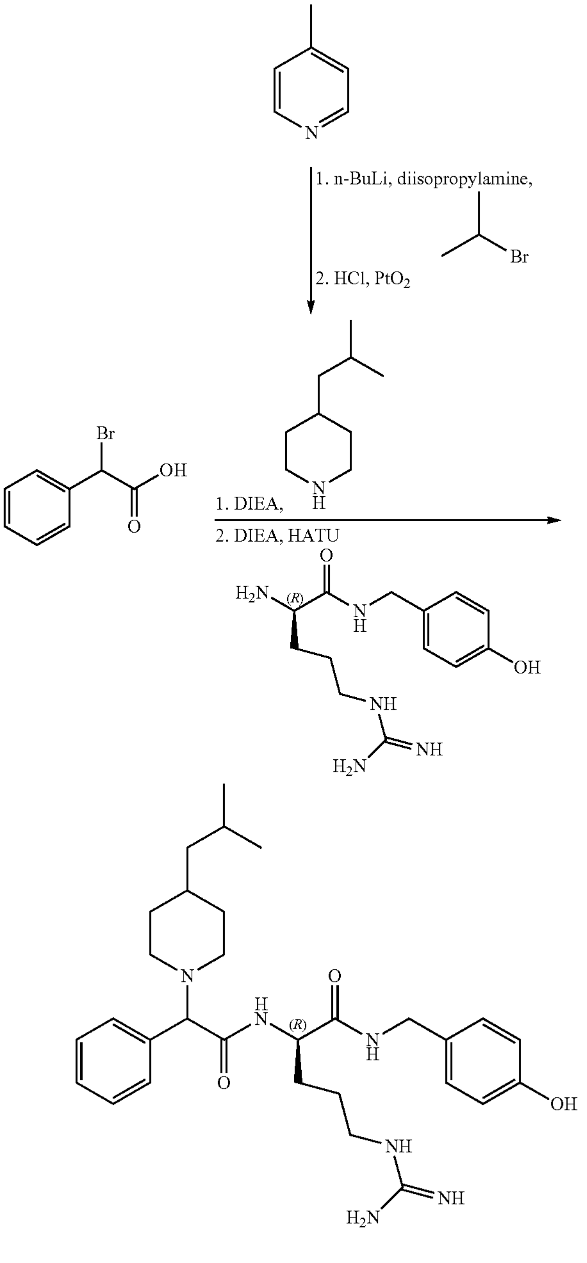

Step 1. Into a 250-mL three-necked round bottom flask, purged and maintained with an inert atmosphere of nitrogen, was placed a mixture of diisopropylamine (4 g, 5 mL, 3 Eq, 0.04 mol) in THE (50 mL), to which was added n-butyllithium (2.1 g, 13 mL, 2.5 molar, 3.0 Eq, 33 mmol) dropwise at −78° C. over 10 min. The reaction mixture was stirred at −78° C. for 30 min, then into the reaction mixture was added dropwise 4-methylpyridine (1.0 g, 1 Eq, 11 mmol) in THE (7 mL). The remaining mixture was stirred at −78° C. for 1 hour. Then 2-bromopropane (1.35 g, 1.0 Eq, 11.0 mmol) in THE (2 mL) was added dropwise. The mixture was stirred at −78° C. for an additional 1 hour. Then the mixture was allowed to warm to room temperature and stirred for an additional 12 hours. The mixture was quenched with a saturated aqueous solution of $NH_4Cl$ (50 mL), extracted with EtOAc (50 mL×3), then the combined organic layers were washed with brine (50 mL), dried over anhydrous $Na_2SO_4$ and concentrated under reduced pressure. The crude product was purified by MPLC to provide 4-isobutylpyridine (600 mg, 4.44 mmol, 41%) as a yellow oil. [M+H] =136.4.

Step 2. Into a 50-mL round bottom flask, was placed a mixture of 4-isobutylpyridine (200 mg, 1 Eq, 1.48 mmol), HCl in MeOH (0.1 g, 1 mL, 4 molar, 3 Eq, 4 mmol), platinic oxide (165 mg, 0.491 Eq, 727 μmol) and MeOH (2 mL). The flask was evacuated and flushed with hydrogen three times. The mixture was stirred at 15° C. for 16 hours under $H_2$. The reaction mixture was filtered through a pad of celite, then the filtrate was concentrated under reduced pressure to afford crude 4-isobutylpiperidine (130 mg, 920 μmol, 62.2%) as a colorless oil, which was used directly in the next step without any purification.

Steps 3-4. (2R)-5-guanidino-N-(4-hydroxybenzyl)-2-(2-(4-isobutylpiperidin-1-yl)-2-phenylacetamido)pentanamide was synthesized from 2-bromo-2-phenylacetic acid and 4-isobutylpiperidine in a manner similar to Example 91. The product was purified by Prep-HPLC to provide the trifluoroacetic acid of the product (13.2 mg, 20.3 μmol, 16%) as a white solid. MS: Calc'd for $C_{32}H_{45}F_3N_6O_5$: 650.34, found $[M+H-TFA]^+$: 537.4.

-continued

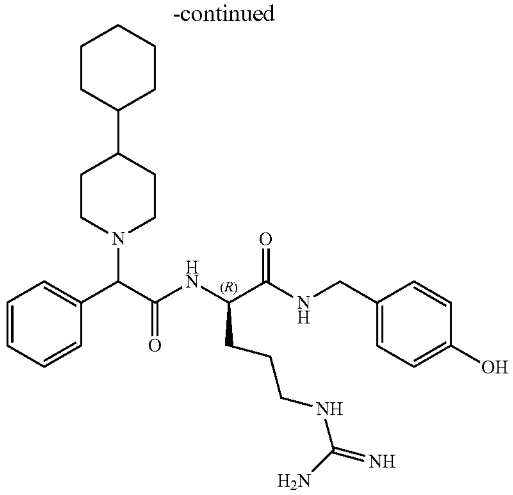

Example 98: (2R)-2-(2-(4-cyclohexylpiperidin-1-yl)-2-phenylacetamido)-5-guanidino-N-(4-hydroxybenzyl)pentanamide (Compound 83)

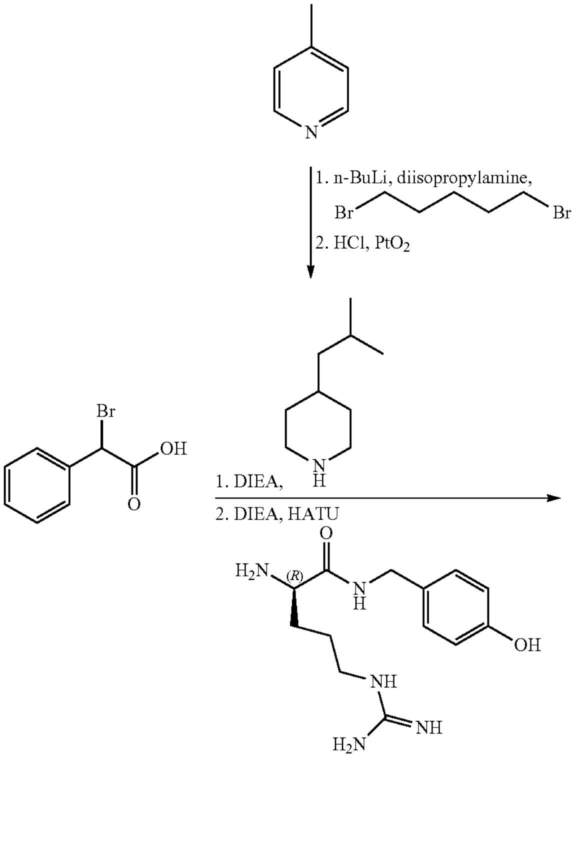

Steps 1-2. 4-cyclohexylpiperidine hydrochloride was synthesized from 4-methylpyridine and 1,5-dibromopentane in a manner similar to Steps 1-2 of Example 99 to provide the crude product as a colorless oil, which was used directly in the next step without any purification.

Steps 3-4. (2R)-2-(2-(4-cyclohexylpiperidin-1-yl)-2-phenylacetamido)-5-guanidino-N-(4-hydroxybenzyl)pentanamide was synthesized from 2-bromo-2-phenylacetic acid and 4-cyclohexylpiperidine hydrochloride in a manner similar to Example 91. The product was purified by Prep-HPLC to provide the product (13.2 mg, 20.3 μmol, 16%) as a white solid. MS: Calc'd for $C_{32}H_{46}N_6O_3$: 562.36, found $[M+H-TFA]^+$: 563.5.

Example 99: (2R)-5-guanidino-N-(4-hydroxybenzyl)-2-(2-phenyl-2-(8-azaspiro[4.5]decan-8-yl)acetamido)pentanamide (Compound 84)

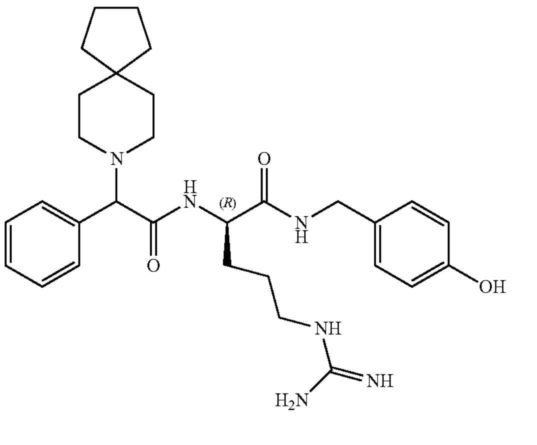

Step 1. (2R)-5-guanidino-N-(4-hydroxybenzyl)-2-(2-phenyl-2-(8-azaspiro[4.5]decan-8-yl)acetamido)pentanamide was synthesized from 2-bromo-2-phenylacetic acid and 82-azaspiro[4.5]decane hydrochloride in a manner similar to Example 91. The product was purified by Prep-HPLC to provide the formic acid salt of the product (7.8 mg, 13 μmol, 12%) as a white solid. MS: Calc'd for $C_{30}H_{42}N_6O_3$: 534.33, found $[M+H]^+$: 535.4.

Example 100: (2R)-5-guanidino-N-(4-hydroxybenzyl)-2-(2-phenyl-2-(6-azaspiro[2.5]octan-6-yl)acetamido)pentanamide (Compound 85)

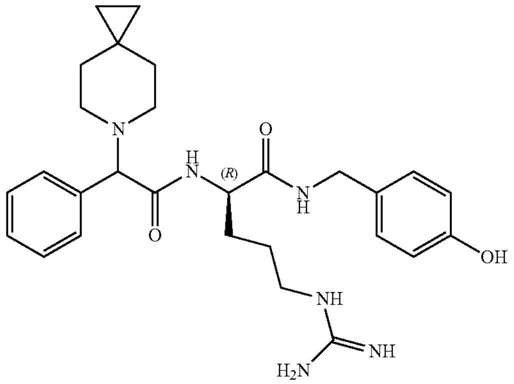

(2R)-5-guanidino-N-(4-hydroxybenzyl)-2-(2-phenyl-2-(6-azaspiro[2.5]octan-6-yl)acetamido)pentanamide was synthesized from 2-bromo-2-phenylacetic acid and 6-azaspiro[2.5]octane in a manner similar to Example 91. The product was purified by Prep-HPLC to provide the trifluoroacetic acid salt of the product (6.9 mg, 11 μmol, 9.1%) as a white solid. MS: Calc'd for $C_{30}H_{39}F_3N_6O_5$: 620.29, found $[M+H-TFA]^+$: 507.4.

Example 101: (2R)-5-guanidino-N-(4-hydroxybenzyl)-2-(2-phenyl-2-(4-phenylpiperidin-1-yl)acetamido)pentanamide (Compound 86)

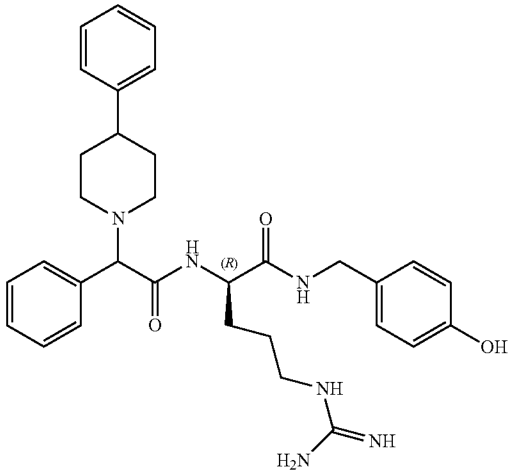

Step 1. (2R)-5-guanidino-N-(4-hydroxybenzyl)-2-(2-phenyl-2-(4-phenylpiperidin-1-yl)acetamido)pentanamide was synthesized from 2-bromo-2-phenylacetic acid and 4-phenylpiperidine in a manner similar to Example 91. The product was purified by Prep-HPLC to provide the trifluoroacetic acid salt of the product (8.9 mg, 13 μmol, 13%) as an off-white solid. MS: Calc'd for $C_{34}H_{41}F_3N_6O_5$: 670.31, found $[M+H-TFA]^+$: 557.3.

Example 102: (2R)-5-guanidino-N-(4-hydroxybenzyl)-2-(2-phenyl-2-(3-azaspiro[5.5]undecan-3-yl)acetamido)pentanamide (Compound 87)

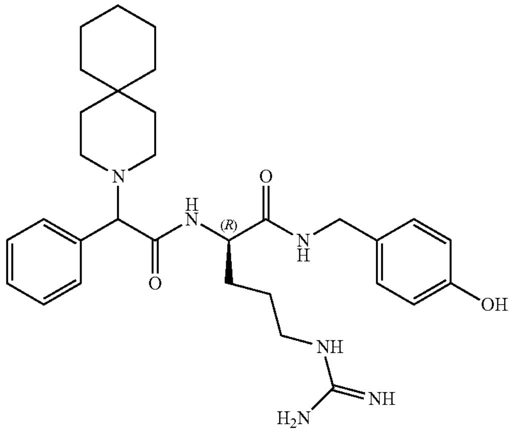

(2R)-5-guanidino-N-(4-hydroxybenzyl)-2-(2-phenyl-2-(3-azaspiro[5.5]undecan-3-yl)acetamido)pentanamide was synthesized from 2-bromo-2-phenylacetic acid and 3-azaspiro[5.5]undecane in a manner similar to Example 91. The product was purified by Prep-HPLC to provide the formic acid salt of the product (8.8 mg, 15 μmol, 11%) as an off-white solid. MS: Calc'd for $C_{32}H_{46}N_6O_5$: 594.35, found $[M+H-FA]^+$: 549.3.

Example 103: (2R)-2-((2S)-2-(6,6-dimethyl-3-azabicyclo[3.1.0]hexan-3-yl)-2-phenylacetamido)-5-guanidino-N-(4-hydroxybenzyl)pentanamide (Compound 88A)

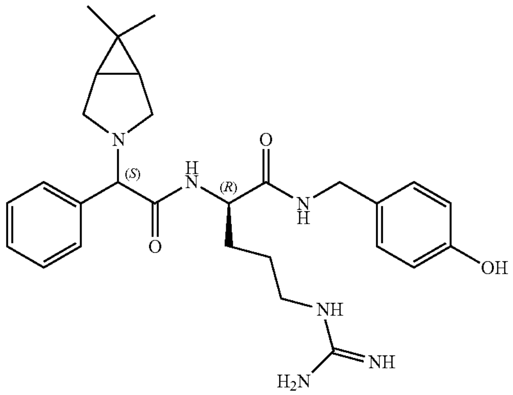

(2R)-2-((2S)-2-(6,6-dimethyl-3-azabicyclo[3.1.0]hexan-3-yl)-2-phenylacetamido)-5-guanidino-N-(4-hydroxybenzyl)pentanamide was synthesized from 2-bromo-2-phenylacetic acid and 6,6-dimethyl-3-azabicyclo[3.1.0]hexane in a manner similar to Example 91. The product was purified by Prep-HPLC to provide two isomers as two peaks. The front peak fractions were combined to provide the trifluoroacetic acid salt of the product (5.6 mg, 9.0 μmol, 14%) as a white solid. MS: Calc'd for $C_{30}H_{39}F_3N_6O_5$: 620.29, found $[M+H-TFA]^+$: 507.3.

Example 104: (2R)-2-((2R)-2-(6,6-dimethyl-3-azabicyclo[3.1.0]hexan-3-yl)-2-phenylacetamido)-5-guanidino-N-(4-hydroxybenzyl)pentanamide (Compound 88B)

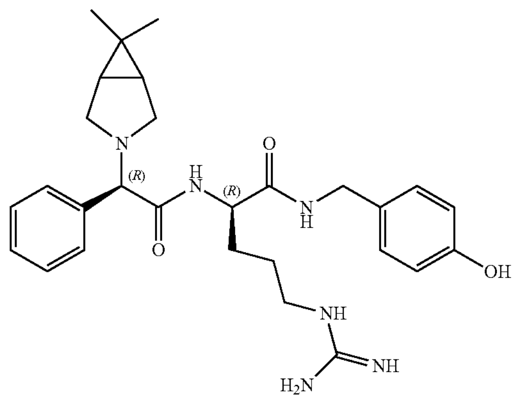

The back peak fractions from Example 104 were combined to provide the trifluoroacetic acid salt of (2R)-2-((2R)-2-(6,6-dimethyl-3-azabicyclo[3.1.0]hexan-3-yl)-2-phenylacetamido)-5-guanidino-N-(4-hydroxybenzyl)pentanamide (2.4 mg, 3.9 μmol, 5.9%) as a yellow solid. MS: Calc'd for $C_{30}H_{39}F_3N_6O_5$: 620.29, found $[M+H-TFA]^+$: 507.4.

Example 105: (2R)-5-guanidino-N-(4-hydroxybenzyl)-2-(2-phenyl-2-(7-azaspiro[3.5]nonan-7-yl)acetamido)pentanamide (Compound 89)

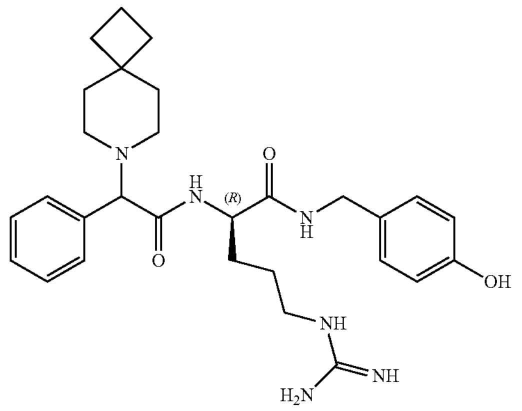

(2R)-5-guanidino-N-(4-hydroxybenzyl)-2-(2-phenyl-2-(7-azaspiro[3.5]nonan-7-yl)acetamido)pentanamide was synthesized from 2-bromo-2-phenylacetic acid and 7-azaspiro[3.5]nonane in a manner similar to Example 91. The product was purified by Prep-HPLC to provide the trifluoroacetic acid salt of the product (8.0 mg, 13 μmol, 11%) as a white solid. MS: Calc'd for $C_{31}H_{41}F_3N_6O_5$: 634.30, found $[M+H-TFA]^+$: 521.4.

Example 106: (2R)-2-(2-(2,2-difluoro-7-azaspiro[3.5]nonan-7-yl)-2-phenylacetamido)-5-guanidino-N-(4-hydroxybenzyl)pentanamide (Compound 90)

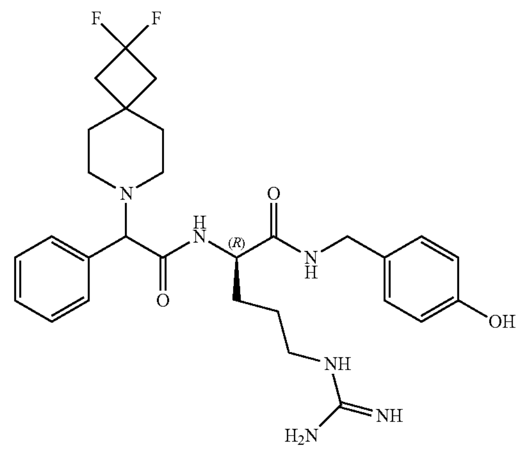

(2R)-2-(2-(2,2-difluoro-7-azaspiro[3.5]nonan-7-yl)-2-phenylacetamido)-5-guanidino-N-(4-hydroxybenzyl)pentanamide was synthesized from 2-bromo-2-phenylacetic acid and 2,2-difluoro-7-azaspiro[3.5]nonane in a manner similar to Example 91. The product was purified by Prep-HPLC to provide the trifluoroacetic acid salt of the product (11.3 mg, 16.8 μmol, 17%) as a white solid. MS: Calc'd for $C_{31}H_{39}F_5N_6O_5$: 670.29, found $[M+H-TFA]^+$: 557.3.

Example 107: (2R)-2-(2-(4-(tert-butyl)piperidin-1-yl)-2-phenylacetamido)-5-((Z)-2-(ethylcarbamoyl)guanidino)-N-(4-hydroxybenzyl)pentanamide (Compound 91)

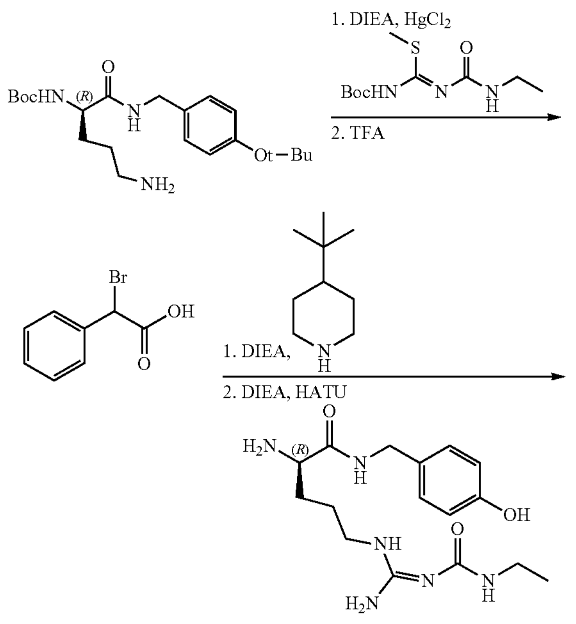

-continued

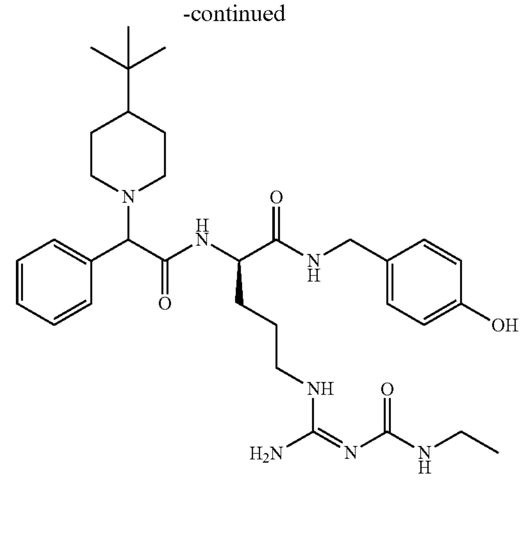

Steps 1-2. tert-butyl (R)-(5-amino-1-((4-(tert-butoxy)benzyl)amino)-1-oxopentan-2-yl)carbamate was treated with intermediate H and $HgCl_2$ in a manner similar to step 4 in the synthesis of Intermediate H (Example 19) then treated with TFA in a manner similar to step 5 in the synthesis of Intermediate H to provide (R,Z)-2-amino-5-(2-(ethylcarbamoyl)guanidino)-N-(4-hydroxybenzyl)pentanamide-2,2,2-trifluoroacetaldehyde (1/2) (1.6 g, 2.0 mmol, 89%) as an off-white solid. [M+H]=351.1.

Step 3. (2R)-2-(2-(4-(tert-butyl)piperidin-1-yl)-2-phenylacetamido)-5-((Z)-2-(ethylcarbamoyl)guanidino)-N-(4-hydroxybenzyl)pentanamide was synthesized from 2-bromo-2-phenylacetic acid and 4-(tert-butyl)piperidine in a manner similar to Step 1 of Example 91 to provide 2-(4-(tert-butyl)piperidin-1-yl)-2-phenylacetic acid (105 mg, 381 μmol, 41.0%) as a yellow oil. [M+H]=276.2.

Step 4. Into an 8-mL vial, was placed a mixture of 2-(4-(tert-butyl)piperidin-1-yl)-2-phenylacetic acid (50 mg, 1 Eq, 0.18 mmol), TBTU (70 mg, 1.2 Eq, 0.22 mmol), HOBt (33 mg, 1.2 Eq, 0.22 mmol) and DMF (0.5 mL). The reaction mixture was stirred at 25° C. for 10 minutes, then (R,Z)-2-amino-5-(2-(ethylcarbamoyl)guanidino)-N-(4-hydroxybenzyl)pentanamide (95 mg, 1.5 Eq, 0.27 mmol) was added and the reaction mixture was stirred at 25° C. for an additional 2 hours. The crude product was purified by Prep-HPLC to provide the trifluoroacetic acid salt of (2R)-2-(2-(4-(tert-butyl)piperidin-1-yl)-2-phenylacetamido)-5-((Z)-2-(ethylcarbamoyl)guanidino)-N-(4-hydroxybenzyl)pentanamide (15 mg, 21 μmol, 11%) as a white solid. MS: Calc'd for $C_{35}H_{50}F_3N_7O_6$: 721.38, found $[M+H-TFA]^+$: 608.4.

Example 108: (Compound 92)

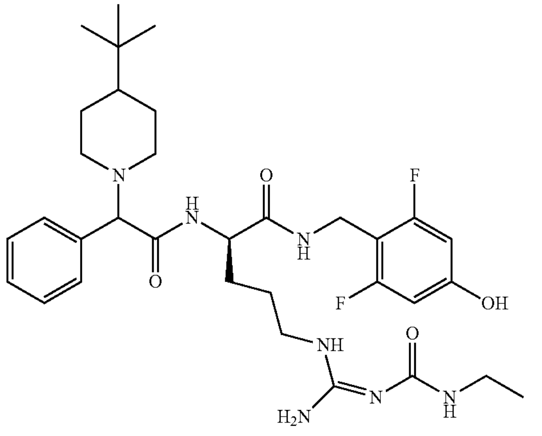 [SMILES: CCNC(=O)/N=C(/N)NCCC[C@@H](NC(=O)C(c1ccccc1)N1CCC(C(C)(C)C)CC1)C(=O)NCc1c(F)cc(O)cc1F]

Into an 8-mL vial, was placed a mixture of 2-(4-(tert-butyl)piperidin-1-yl)-2-phenylacetic acid (50 mg, 1 Eq, 0.18 mmol), TBTU (70 mg, 1.2 Eq, 0.22 mmol), DIEA (28 mg, 38 L, 1.2 Eq, 0.22 mmol) HOBt (83 mg, 3.0 Eq, 0.54 mmol) and DMF (1.0 mL). The reaction mixture was stirred at 25° C. for 10 minutes, then (R,Z)-2-amino-N-(2,6-difluoro-4-hydroxybenzyl)-5-(2-(ethylcarbamoyl)guanidino)pentanamide (Intermediate H, 90 mg, 1.3 Eq, 0.23 mmol) was added and the reaction mixture was stirred at 25° C. for an additional 2 hours. The crude product was purified by Prep-HPLC to provide the trifluoroacetic acid salt of (2R)-2-(2-(4-(tert-butyl)piperidin-1-yl)-2-phenylacetamido)-N-(2,6-difluoro-4-hydroxybenzyl)-5-((Z)-2-(ethylcarbamoyl)guanidino)pentanamide (31.5 mg, 41.6 μmol, 23%) as a white solid. [M+H−TFA]=644.4.

Example 109: Parenteral Pharmaceutical Composition

To prepare a parenteral pharmaceutical composition suitable for administration by injection (subcutaneous, intravenous), 0.001-500 mg of a compound Formula (I), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection.

Biology Examples

Example B-1: NPY1R Binding Assay

Membrane Preparation:

Crude membrane fractions are prepared from SK-N-MC cells endogenously expressing the NPY1R receptor. The cells are grown to 85-100% confluence on standard tissue culture dishes in Eagle's Minimum Essential Medium supplemented with 10% dialyzed FBS. To prepare membranes, cells are scraped and collected in 1× Dulbecco's phosphate buffered saline and then pelleted at 1000 RPM's. The cell pellet is reconstituted in membrane preparation buffer (20 mM HEPES, 6 mM $MgCl_2$ and 1 mM EGTA, protease inhibitor tablets, pH 7.4) and placed in a cell disruption vessel at 1000 PSI for 30 minutes on ice. The pressurized contents are then released and spun down at 1000 RPMs and the supernatant is collected and further centrifuged at 15,000 RPMs to pellet the membranes. The membrane pellet is resuspended in membrane preparation buffer, snap frozen and stored at −80° C. for later use. NPY1R binding assay protocol:

The SK-N-MC membrane binding assay utilizes the following components: radiolabel [$^{1251}$]-Peptide YY (human), crude SK-N-MC membranes, and competing small molecule and peptide ligands. The assay is initiated by combining in assay buffer (25 mM HEPES, 1 mM $MgCl_2$, 2.5 mM $CaCl_2$), 0.1% BSA, 0.01% bacitracin, pH 7.4) a dose response of competing ligand (the final concentrations are typically 0-10,000 nM), SK-N-MC membranes, and [$^{1251}$]Peptide YY (human) at a final concentration of 0.05 nM in a 96-well assay plate and allowed to incubate 120 min at room temperature. Assay contents are then filtered through unifilter GF/C microplates and washed with 9×400 μl of cold wash buffer (25 mM HEPES, 5 mM $MgCl_2$, 1 mM $CaCl_2$), 500 mM NaCl, 0.1% Tween-20, pH 7.4). Assay plates are read using a Top Count NXT and $K_i$ values for compounds are determined using a GraphPad Prism 6 non-linear regression analysis.

TABLE A

Representative Binding Affinity

| Compound No. | hNPY$_1$R binding Ki* |
|---|---|
| 1A | A |
| 1A-In | A |
| 1A-Lu | A |
| 1A-Ga | A |
| 1B | C |
| 2 | A |
| 3A | A |
| 3B | A |
| 4 | A |
| 5 | A |
| 6 | A |
| 7 | A |
| 8A | A |
| 8B | B |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 25 | A |
| 26 | A |
| 27 | A |
| 28 | A |
| 29 | A |
| 30 | A |
| 31A | A |
| 31B | A |
| 32A | A |
| 32B | A |
| 33 | A |
| 34 | A |
| 35 | A |
| 36 | A |
| 37 | A |
| 38 | A |
| 39 | A |

TABLE A-continued

Representative Binding Affinity

| Compound No. | hNPY$_1$R binding Ki* |
|---|---|
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 60A | A |
| 60B | B |
| 61A | A |
| 61B | A |
| 62 | A |
| 63 | A |
| 64A | A |
| 64B | B |
| 65 | A |
| 65A | A |
| 66A | A |
| 66B | A |
| 67 | A |
| 68 | B |
| 69 | A |
| 70 | B |
| 71A | D |
| 71B | D |
| 72 | C |
| 73 | C |
| 74 | C |
| 75 | C |
| 76 | D |
| 77 | B |
| 78 | C |
| 78A | D |
| 79 | B |
| 80 | B |
| 81 | C |
| 82 | C |
| 83 | D |
| 84 | C |
| 85 | B |
| 86 | C |
| 87 | C |
| 88A | C |
| 88B | D |
| 89 | B |
| 90 | C |
| 91 | A |
| 92 | A |

*A is <10 nM; B is 10-100 nM; C is 100 nM-1 μM; D is >1 μM

Example B-2: Biodistribution of $^{111}$In[In] Complex of Compound 1A in Wister Han Rats

TABLE B

Rat Biodistribution Study Outline

| Treatment | N value | Dose (MBq/Rat) | Dose (nmol/mouse) | Time (h) |
|---|---|---|---|---|
| $^{111}$In[In]-Compound 1A | 4 | 5-7 | 1 | 0.5-1 |
| $^{111}$In[In]-Compound 1A | 4 | 5-7 | 1 | 2-3 |
| $^{111}$In[In]-Compound 1A | 4 | 5-7 | 1 | 5-6 |
| $^{111}$In[In]-Compound 1A | 4 | 5-7 | 1 | 22-24 |
| $^{111}$In[In]-Compound 1A | 4 | 5-7 | 1 | 70-72 |

*Treatment schedule is Q1Dx1(IV)

Study Details: 24 h prior to the start of the biodistribution Compound IA was radiolabeled.

Animals were randomized based on their individual body weight into 6 groups of 4 rats. Animals received a single IV injection of 200 μL into the caudal vein via a catheter with 5-7 MBq of $^{111}$In[In] Compound 1A (1 nMol) per animal. For the competition study arm, 1 nMol of $^{111}$In[In]-Compound 1 was co injected with 100 nMol of unlabeled Compound 1A.

After drug administration, animals were euthanized at timepoints (0.5-1 h, 2-3 h, 5-6 h, 22-24 h and 70-72 h) and organs (blood, heart, kidneys, adrenals, liver, spleen, lungs, stomach, small intestine, large intestine, bone (femur), brain, and muscle) were collected, weighed, and ÿ radioactivity assessed in each organ/tissue. Activity was quantitated and expressed as % ID/g (Percentage of Initial Dose/gram of tissue).

Example B-3: Biodistribution of $^{111}$In[In] Complex of Compound 1A in Mouse Tumor Model

TABLE C

Tumor bearing mice Biodistribution Study Outline

| Treatment | N value | Dose (MBq/Rat) | Dose (nmol/mouse) | Time (h) |
|---|---|---|---|---|
| 177Lu[Lu]-Compound 1A | 4 | 10-15 | 1 | 0.5-1 |
| 177Lu[Lu]-Compound 1A | 4 | 10-15 | 1 | 2-3 |
| 177Lu[Lu]-Compound 1A | 4 | 10-15 | 1 | 5-6 |
| 177Lu[Lu]-Compound 1A | 5 | 10-15 | 1 | 22-24 |
| 177Lu[Lu]-Compound 1A | 4 | 10-15 | 1 | 168-170 |

*Treatment schedule is Q1Dx1(IV)

Prior to initiation of the biodistribution study, female Swiss nude mice were subcutaneously inoculated with $10\times10^6$ human cancer cells.

When tumors were between 150-300 $mm^3$, animals were randomized and received a single IV injection of 200 μL into the caudal vein via a catheter with 10-15 MBq of $^{177}$Lu [Lu]-Compound 1A (1 nMol) per animal.

After drug administration, animals were euthanized at timepoints (0.5-1 h, 2-3 h, 5-6 h, 22-24 h and 168-170 h) and organs (blood, heart, muscle, lungs, intestines, spleen, bone, brain, kidneys, liver and tumor) were collected, weighed, and ÿ radioactivity assessed in each organ/tissue. Activity was quantitated and expressed as % ID/g (Percentage of Initial Dose/gram of tissue).

Example B-4: Biodistribution, Safety and Dosimetry Study in Patients with Breast Cancer A non-limiting example of a phase 1 safety and dosimetry study of $^{68}$Ga-complex of a compound of Formula (I) in patients with breast cancer is described below.

This is an open-label, first-in-human, Phase 1 study of $^{68}$Ga-complex of a compound of Formula (I) designed to characterize its biodistribution, safety, radiation dosimetry and PET imaging properties in patients diagnosed with breast cancer. In some embodiments, a 68G-complex of a compound of Formula (I) is used to localize to NPY1R-expressing lesions and identify breast cancer patients with NPY1R-expressing tumors who may benefit from treatment with NPY1R-targeting therapeutic agents, such as $^{177}$Lu-complex of a compound of Formula (I). In healthy humans, NPY1R is found primarily in the central and peripheral nervous systems and across a variety of different cell types, albeit at lower levels, such as smooth muscle cells, adipocytes, macrophages and other immune cells. NPY1R is highly expressed in breast cancer, particularly in luminal A and B subtypes.

This study will enroll approximately 18-24 evaluable subjects in total. Breast cancer patients with locally recurrent or metastatic, estrogen or progesterone receptor positive disease with at least one CT-measurable target lesion by Response Evaluation Criteria in Solid Tumors (RECIST) v1.1 target lesion criteria are eligible to participate if they meet all inclusion criteria and none of the exclusion criteria.

Study Populations: Patients with locally recurrent or metastatic, estrogen or progesterone receptor positive breast cancer.

Primary Objectives: To evaluate the biodistribution of $^{68}$Ga-complex of a compound of Formula (I).

Secondary Objectives: To describe the safety of $^{68}$Ga-complex of a compound of Formula (I), to determine tumor uptake of $^{68}$Ga-complex of a compound of Formula (I) by timepoint and location in subjects with breast cancer. To assess the pharmacokinetic (PK) profile of a $^{68}$Ga-complex of a compound of Formula (I). To describe organ and whole-body dosimetry of $^{68}$Ga-complex of a compound of Formula (I) positron emission tomography/computed tomography (PET/CT) scans. To compare a $^{68}$Ga-complex of a compound of Formula (I) imaging to anatomic imaging in detecting tumor lesions.

Exploratory Objective: To evaluate the expression of tumor markers in tumor tissue.

Primary Endpoints: Number and location of tumors identified by a $^{68}$Ga-complex of a compound of Formula (I) PET/CT. Maximum standard uptake value ($SUV_{max}$) of each tumor and $SUV_{mean}$ of organs. Ratio of the tumor SUV over reference region SUV.

Secondary Endpoints: Incidence of adverse events (AE) characterized overall and by type, frequency, seriousness, relationship to the study drug, timing, and severity, graded according to the National Cancer Institute (NCI) Common Terminology Criteria for Adverse Events (CTCAE), Version 5.0. Absolute values and changes in clinical laboratory parameters. Absorbed dose coefficients (milliGray [mGy]/megabecquerel [MBq]) in target organs and the effective dose coefficient (milliSievert [mSv]/MBq). Whole-body absorbed dose coefficient (Gy/MBq). Number and location of tumors identified by a $^{68}$Ga-complex of a compound of Formula (I) PET/CT and by anatomic imaging (contrastenhanced diagnostic CT). PK parameters and radioactive blood counts from serial blood samples.

Exploratory Endpoint: Expression of tumor markers (e.g., neuropeptide $Y_1$ receptor [NPY1R], other) in the histology samples from biopsy and surgical tumor specimens from subjects with breast cancer, as measured by immunohistochemistry or other methods.

Study Design: This study will enroll up to approximately 24 evaluable patients. Patients who receive study drug and complete all scheduled imaging procedures are considered evaluable.

There are three patient cohorts in the study: Cohort 1: patients with estrogen or progesterone receptor (ER/PR) positive locoregionally recurrent or metastatic breast cancer who have not yet received treatment for recurrent or metastatic disease; Cohort 2: patients with estrogen or progesterone receptor (ER/PR) positive locoregionally recurrent or metastatic breast cancer who are currently receiving treatment that includes hormonal therapy; Cohort 3: patients with estrogen or progesterone receptor (ER/PR) positive locoregionally recurrent or metastatic breast cancer who are refractory to existing therapies. Patients are enrolled into the three cohorts in parallel. Each cohort will enroll at least six evaluable patients. If at least one patient is deemed positive among the six evaluable patients per PET/CT evaluation, the cohort is expanded with two more patients. All patients will be evaluated for eligibility prior to enrollment (56-day screening period). All patients should have at least one target lesion by Response Evaluation Criteria in Solid Tumors (RECIST) v1.1 on a recent examination. Each eligible patient enrolled will receive a single intravenous injection of a $^{68}$Ga-complex of a compound of Formula (I) on Day 1 of the study at a dose of approximately 5 mCi (185 MBq). The first six evaluable patients (regardless of cohort assignment) will take part in the Imaging Optimization/Dosimetry part of the study where patients will undergo dynamic PET imaging for the first 20 minutes post-injection of $^{68}$Ga-complex of a compound of Formula (I) with camera centered over a selected tumor lesion, followed by whole-body PET/CT scans at 30-, 60-, 120- and 180-minutes post-dose. In this part of the study, serial blood samples will be collected for PK and dosimetry analyses, along with urine sample collected for dosimetry at the completion of imaging. In the Expansion part of the study, patients will be imaged with a whole-body PET/CT scan at a single timepoint that is selected in the Imaging Optimization/Dosimetry part of the study.

All subjects with breast cancer will undergo a contrast-enhanced diagnostic CT scan of chest, abdomen, and pelvis (or magnetic resonance imaging [MRI] if subject is allergic to CT contrast media) within 14 days of the study drug injection.

In order to assess the expression of NPY1R and other markers of interest and to compare to SUV, tumor samples (frozen, paraffin blocks or processed slides) will be obtained from patients with breast cancer who have had prior tumor biopsies or resections.

All patients must meet all the inclusion eligibility criteria and none of the exclusion eligibility criteria, as appropriate and provided below.

Inclusion Criteria: Pathologically confirmed breast cancer. Locally recurrent or metastatic breast cancer that is positive for expression of estrogen or progesterone receptor as assessed by local histological criteria with at least 1 measurable target lesion per RECIST v1.1 criteria (Cohort 1 patients only: no treatment for locally recurrent or metastatic breast cancer; Cohort 2 patients only: currently on treatment for locally recurrent or metastatic breast cancer that includes hormonal treatment; Cohort 3 patients only: refractory to existing therapies). Male or non-pregnant, non-lactating female subjects age ≥18 years. Subjects who are sexually active must agree to use adequate method(s) of effective contraception during their participation in the study. Eastern Cooperative Oncology Group (ECOG) Performance Status ≤2. Adequate hepatic function as defined by a) serum alanine aminotransaminase (ALT)/aspartate aminotransaminase (AST)≤3×upper limit of normal (ULN) or ≤5×ULN if liver metastases are present or received prior mitotane therapy, and b) serum bilirubin–total≤1.5×ULN (unless due to Gilbert's syndrome or hemolysis in which case total≤3.0×ULN). Adequate renal function as measured by creatinine clearance calculated by the Cockcroft-Gault formula (≥60 mL/minute). Able to understand and willing to sign a written informed consent form.

Exclusion Criteria: Administered a radionuclide within a period of time corresponding to less than 10 physical half-lives of the radionuclide prior to study Day 1. Radiotherapy≤14 days prior to study Day 1. Major surgery≤21 days prior to study Day 1 or has not recovered from adverse effects of such procedure. History of cerebrovascular accident within 6 months or that resulted in ongoing neurologic instability. History of other previous or concurrent cancer that would interfere with the determination of safety. Any other condition that in the opinion of the Investigator would place the subject at an unacceptable risk or cause the subject to be unlikely to fully participate or comply with study procedures.

Study Drug, Dose, and Mode of Administration

Study Drug: The study drug is a $^{68}$Ga-complex of a compound of Formula (I). In some embodiments, the $^{68}$Ga-complex is a $^{68}$Ga-complex of a compound of Formula (I). In some embodiments, the $^{68}$Ga-complex is a $^{68}$Ga-complex of Compound 1. In some embodiments, the $^{68}$Ga-complex is a $^{68}$Ga-complex of Compound 1A. In some embodiments, the $^{68}$Ga-complex is a $^{68}$Ga-complex of Compound 1B. In some embodiments, the $^{68}$Ga-complex is a $^{68}$Ga-complex of Compound 2. In some embodiments, the $^{68}$Ga-complex is a $^{68}$Ga-complex of Compound 3. In some embodiments, the $^{68}$Ga-complex is a $^{68}$Ga-complex of Compound 3A. In some embodiments, the $^{68}$Ga-complex is a $^{68}$Ga-complex of Compound 3B. In some embodiments, the $^{68}$Ga-complex is a $^{68}$Ga-complex of Compound 4. In some embodiments, the $^{68}$Ga-complex is a $^{68}$Ga-complex of Compound 5. In some embodiments, the $^{68}$Ga-complex is a $^{68}$Ga-complex of Compound 6. In some embodiments, the $^{68}$Ga-complex is a $^{68}$Ga-complex of Compound 7.

Dose: 5.0 mCi (±20%); Total carrier mass of the compound of Formula (I): not more than (NMT) 90 μg/dose.

Mode of Administration: Intravenous

Duration of Participation: A 56-day screening window will be utilized where the subject will undergo study assessments to deem the subject eligible for the study. Once confirmed, subjects will receive the study drug, $^{68}$Ga-complex of a compound of Formula (I), and PET/CT imaging on Day 1. The subjects will return to the clinical site on Day 2 (+2 days) for a safety evaluation.

Study Duration: The start of the study will be the date on which the first subject provides informed consent. The end of the study will be the last subject's last assessment.

The examples and embodiments described herein are for illustrative purposes only and various modifications or changes suggested to persons skilled in the art are to be included within the purview of this application and scope of the appended claims.

What is claimed is:

1. A compound of Formula (If), or a pharmaceutically acceptable salt thereof:

Formula (If)

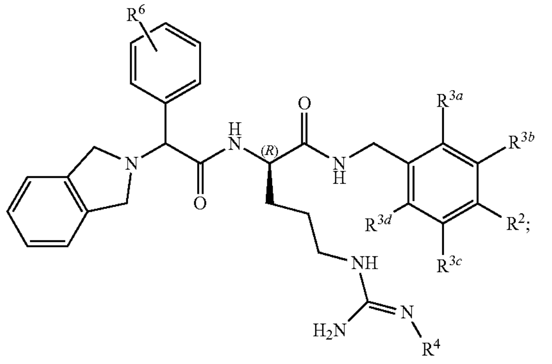

wherein, $R^2$ is —OH, —$NH_2$, —C(=O)$NH_2$ or —$CH_2$NHC(=O)$NH_2$;

$R^{3a}$, $R^{3b}$, $R^{3c}$, and $R^{3d}$ are each independently selected from the group consisting of H, F, Cl, Br, I, —CN, substituted or unsubstituted —$C_1$-$C_6$ alkyl, and substituted or unsubstituted —$C_1$-$C_6$ alkoxy;

$R^4$ is H, —C(=O)$R^{10}$, —C(=O)NH$R^{10}$ or —C(=O)N($CH_3$)$R^{10}$;

$R^{10}$ is substituted or unsubstituted —$C_1$-$C_6$ alkyl, substituted or unsubstituted 2 to 6-membered heteroalkyl, or —$(CH_2)_t$NHC(=O)$(CH_2)_u$$CH_3$;

t is 1, 2, 3, 4, 5, or 6;

u is 1, 2, 3, or 4;

$R^6$ is —$Z^A$—$L^A$—$R^A$;

$Z^A$ is absent, —$C_1$-$C_6$ alkylene-, —$C_1$-$C_6$ alkylene-O—, —O—$C_1$-$C_6$ alkylene-, —C(=O)N$R^{12}$—, —N$R^{12}$C(=O)—, —O—, or —N$R^{12}$—;

$L^A$ is a linker;

$R^A$ is a chelating moiety or a radionuclide complex thereof; and $R^{12}$ is H or unsubstituted —$C_1$-$C_4$ alkyl;

wherein $R^A$ is selected from the group consisting of:

1,4,7,10-tetraazacyclododecane-1,4,7,10-tetraacetic acid (DOTA);

2,2',2"-(10-(2-amino-2-oxoethyl)-1,4,7,10-tetraazacyclododecane-1,4,7-triyl)triacetic acid (PSC);

1,4,7,10-tetraazacyclododecane-1,4,7-triacetic acid (DO3A);

1,4,7,10-tetraazacyclododecane-1,7-diacetic acid (DO2A);

α,α',α",α'"-tetramethyl-1,4,7,10-tetraazacyclododecane-1,4,7,10-tetraacetic acid (DOTMA);

1,4,7,10-tetrakis (carbamoylmethyl)-1,4,7,10-tetraazacyclododecane (DOTAM);

1,4,7,10-tetraazacyclododecane-1,4,7,10-tetrapropionic acid (DOTPA);

2,2',2"-(10-(2-amino-2-oxoethyl)-1,4,7,10-tetraazacyclododecane-1,4,7-triyl)triacetic acid;

benzyl-1,4,7,10-tetraazacyclododecane-1,4,7,10-tetraacetic acid (Bn-DOTA);

p-hydroxy-benzyl-1,4,7,10-tetraazacyclododecane-1,4,7,10-tetraacetic acid (p-OH-Bn-DOTA);

6,6'-(((pyridine-2,6-diylbis(methylene))bis((carboxymethyl) azanediyl))bis(methylene))dipicolinic acid ($H_4$pypa);

$H_4$pypa-benzyl;

6,6',6",6"-(((pyridine-2,6-diylbis(methylene))bis (azanetriyl))tetrakis(methylene))tetrapicolinic acid ($H_4py_4pa$);

$H_4py_4pa$-benzyl;

2,2',2"-(1,4,7-triazacyclononane-1,4,7-triyl)triacetic acid (NOTA);

6,6'-((1,4,10,13-tetraoxa-7,16-diazacyclooctadecane-7,16-diyl)bis(methylene))dipicolinic acid (macropa);

2,2',2",2'"-(1,10-dioxa-4,7,13,16-tetraazacyclooctadecane-4,7,13,16-tetrayl)tetraacetic acid (crown);

6,6'-((ethane-1,2-diylbis ((carboxymethyl) azanediyl))bis (methylene))dipicolinic acid ($H_4$octapa);

$H_4$octapa-benzyl; and 3,6,9,12-tetrakis (carboxymethyl)-3,6,9,12-tetraazatetradecanedioic acid (TTHA);

or a radionuclide complex thereof;

wherein the radionuclide of the chelator-radionuclide complex is:

111-indium ($^{111}$In), 115-indium ($^{115}$In), 67-gallium ($^{67}$Ga), 68-gallium ($^{68}$Ga), 69-gallium ($^{69}$Ga), 71-gallium ($^{71}$Ga), 225-actinium ($^{225}$Ac), 175-lutetium ($^{175}$Lu), 177-lutetium ($^{177}$Lu), 204-lead ($^{204}$Pb), 206-lead ($^{206}$Pb), 207-lead ($^{207}$Pb), 208-lead ($^{208}$Pb), 212-lead ($^{212}$Pb), 63-copper ($^{63}$Cu), 64-copper ($^{64}$Cu), 65-copper ($^{65}$Cu), or 67-copper ($^{67}$Cu).

2. The compound of claim 1, or a pharmaceutically acceptable salt thereof, wherein $Z^A$ is $C_1$-$C_6$ alkylene, —O—, —NH—, —N(—$CH_3$)—, or —NHC(=O).

3. The compound of claim 2, or a pharmaceutically acceptable salt thereof, wherein $R^{3a}$, $R^{3b}$, $R^{3c}$, and $R^{3d}$ are each independently selected from the group consisting of H, F, Cl, Br, I, —CN, —$CH_3$, —$CF_3$, and —$OCH_3$; and $Z^A$ is —$CH_2$—, —O—, —NH—, —N(—$CH_3$)—, or —NHC(=O)—.

4. The compound of claim 3, wherein the compound has the structure of Formula (Iz) or Formula (Iaa), or a pharmaceutically acceptable salt thereof:

(Iz)

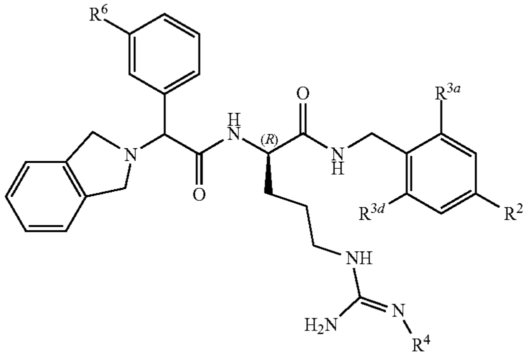

or

-continued (Iaa)

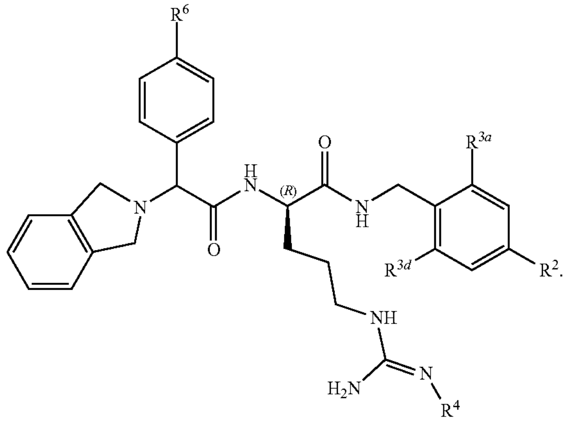

5. The compound of claim 2, wherein the compound has the following structure, or a pharmaceutically acceptable salt thereof:

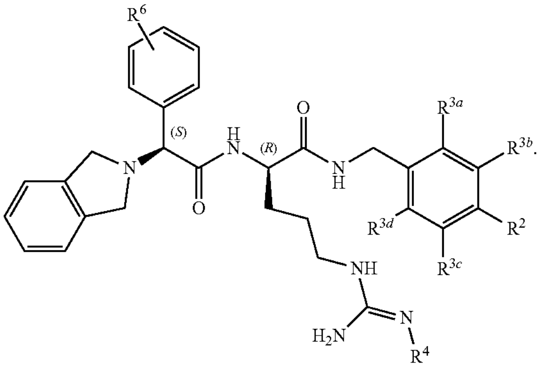

6. A compound that has the following structure, or a pharmaceutically acceptable salt thereof:

or a radionuclide complex thereof;

wherein, $R^1$ is H;

$R^2$ is —OH;

each $R^3$ is independently selected from the group consisting of H, F, Cl, Br, I, —CN, —$CH_3$, —$CF_3$, and —$OCH_3$;

$R^4$is —C(=O)NH$R^{10}$;

$R^{10}$ is unsubstituted —$C_1$-$C_6$ alkyl or —$(CH_2)_t$NHC(=O)$(CH_2)_u$$CH_3$;

t is 1, 2, 3, or 4;

u is 1 or 2;

$Z^A$ is absent, —$C_1$-$C_6$ alkylene-, —$C_1$-$C_6$ alkylene-O—, —O—$C_1$-$C_6$ alkylene-, —C(=O)NR $^{12}$-, —N$R^{12}$C(=O)—, —O—, or —NR $^{12}$-;

$L^A$ is a linker:

$R^9$ is H;

$R^{12}$ is H or unsubstituted —$C_1$-$C_4$ alkyl;

n is 0, 1, 2, 3, or 4;

m is 0; and p is 0;

wherein the radionuclide of the chelator-radionuclide complex is:

111-indium ($^{111}$In), 115-indium ($^{115}$In), 67-gallium ($^{67}$Ga), 68-gallium ($^{68}$Ga), 69-gallium ($^{69}$Ga), 71-gallium ($^{71}$Ga), 225-actinium ($^{225}$Ac), 175-lutetium ($^{175}$Lu), 177-lutetium ($^{177}$Lu), 204-lead ($^{204}$Pb), 206-lead ($^{206}$Pb), 207-lead ($^{207}$Pb), 208-lead ($^{208}$Pb), 212-lead ($^{212}$Pb), 63-copper ($^{63}$Cu), 64-copper ($^{64}$Cu), 65-copper ($^{65}$Cu), or 67-copper ($^{67}$Cu).

7. The compound of claim 5, or a pharmaceutically acceptable salt thereof, wherein $R^2$ is —OH;

$R^{3a}$ and $R^{3d}$ are F or Cl and $R^{3b}$ and $R^{3c}$ are H;

$R^4$ is —C(=O)NH$R^{10}$;

$R^{10}$ is unsubstituted —$C_1$-$C_6$ alkyl or —$(CH_2)_t$NHC(=O)$(CH_2)_u$$CH_3$;

t is 1, 2, 3, or 4; and u is 1 or 2.

8. The compound of claim 6, or a pharmaceutically acceptable salt thereof, wherein $R^A$ is:

1,4,7,10-tetraazacyclododecane-1,4,7,10-tetraacetic acid (DOTA);

α,α',α",α'"-tetramethyl-1,4,7,10-tetraazacyclododecane-1,4,7,10-tetraacetic acid (DOTMA);

1,4,7,10-tetrakis (carbamoylmethyl)-1,4,7,10-tetraazacyclododecane (DOTAM); or benzyl-1,4,7,10-tetraazacyclododecane-1,4,7,10-tetraacetic acid (Bn-DOTA);

or a radionuclide complex thereof.

9. The compound of claim 1, or a pharmaceutically acceptable salt thereof, wherein $R^A$ is

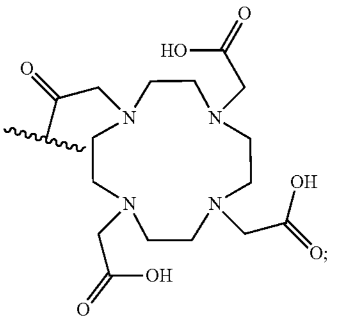 [SMILES: *C(=O)CN1CCN(CC(=O)O)CCN(CC(=O)O)CCN(CC(=O)O)CC1]

or a radionuclide complex thereof.

10. The compound of claim 9, or a pharmaceutically acceptable salt thereof, wherein $L^A$ is independently selected from -$L^2$-, -$L^3$-, -$L^4$-, -$L^5$-, -$L^6$-, -$L^7$-, -$L^2$-$L^3$-, -$L^2$-$L^7$-, -$L^4$-$L^7$-, -$L^2$-$L^4$-$L^7$-, -$L^2$-$L^6$-$L^7$-, -$L^2$-$L^3$-$L^4$-$L^7$-, -$L^2$-$L^4$-$L^5$-$L^7$-, -$L^2$-$L^4$-$L^6$-$L^7$-, or -$L^2$-$L^4$-$L^5$-$L^6$-$L^7$-;

$L^2$ is absent, substituted or unsubstituted —$C_1$-$C_{20}$ alkylene-N$R^{16}$—, substituted or unsubstituted —$C_1$-$C_{20}$ alkylene-N$R^{16}$C(=O)—, or —$(CH_2CH_2O)_w$—$CH_2CH_2$—;

each $R^{16}$ is independently selected from H and $C_1$-$C_4$ alkyl;

w is 1, 2, 3, 4, 5, or 6;

$L^3$ is absent or a natural or unnatural amino acid or peptide that is formed from two or more independently selected natural and unnatural amino acids, wherein when two or more amino acids are present then the N atom of the amide linking the amino acids is optionally substituted with —$C_1$-$C_6$ alkyl;

$L^4$ is absent, substituted or unsubstituted 2 to 10-membered heteroalkylene, —$(CH_2)_v$-, —$(CH_2CH_2O)_v$—$CH_2CH_2$—, —C(=O)$CH_2CH_2$—, —$(CH_2)_v$—N$R^{17}$C(=O)—, —$CH_2CH_2$C(=O)NH$CH_2CH_2$—, —$CH_2CH_2$—C(=O)NH—$(CH_2CH_2O)_v$$CH_2CH_2$—, —$(CH_2)_x$—N$R^{17}$—$(CH_2)_v$-, —NHC(=O)NH—O—

$(CH_2)_v$-, —NHC(═O)NH—$(CH_2)_v$-, —$(CH_2)_x$—NHC(═O)NH—$(CH_2)_v$-, —$(CH_2)_x$—NHC(═O)—$(CH_2)_v$-, —$(CH_2)_x$—C(═O)NH—$(CH_2)_v$-, —$CH_2$CH(═OH) $CH_2$—CH(OH)—$CH_2CH_2$—, —$CH_2$CH(═OH)$CH_2$—CH(OH)—$CH_2CH_2$—NHC(═O)$CH_2CH_2$C(═O)—NH$CH_2CH_2$—, or —NHC(═O)$CH_2$—O—NH—C(═O)$(CH_2)_v$-;

each $R^{17}$ is H or —$C_1$-$C_6$ alkyl;

each x is independently 1, 2, 3, 4, 5, or 6;

each v is independently 1, 2, 3, 4, 5, 6, 7, 8, 9, or 10;

$L^5$ is absent, —O—, or —$NR^{13}$C(═O); $R^{13}$ is H or —$C_1$-$C_4$ alkyl;

$L^6$is absent or -$L^8$-$L^9$-L $^{10}$-;

$L^8$ is absent, —$(CH_2)_r$-, —$(CH_2)_r$—$NR^{14}$—, or substituted or unsubstituted heterocycloalkylene;

r is 0, 1, 2, or 3;

$L^9$ is substituted or unsubstituted cycloalkylene, substituted or unsubstituted cycloalkenylene, substituted or unsubstituted heterocycloalkylene, or substituted or unsubstituted arylene;

$L^{10}$ is absent, —$(CH_2)_q$-, —$NR^{15}$—$(CH_2)_q$-, or —C(═O)—$(CH_2)_q$-; q is 1, 2, 3, 4, 5 or 6;

$R^{14}$ and $R^{15}$ are each independently selected from H or —$C_1$-$C_6$ alkyl; and $L^7$ is —NH—.

11. The compound of claim 10, or a pharmaceutically acceptable salt thereof, wherein $L^2$ is substituted or unsubstituted —$C_1$-$C_{20}$ alkylene-NH— or substituted or unsubstituted —$C_1$-$C_{20}$ alkylene —NHC(═O)—;

$L^3$ is absent or $L^3$ is a natural amino acid, an unnatural amino acid, or peptide that is formed from two or more independently selected amino acids selected from the group consisting of alanine (Ala), 3-(2-Naphthyl)-alanine (2-Nal), arginine (Arg), asparagine (Asn), aspartate (Asp), cysteine (Cys), cysteic acid, glutamine (Gln), glutamate (Glu), gamma-Carboxyglutamate (Gla), glycine (Gly), histidine (His), isoleucine (Ile), leucine (Leu), lysine (Lys), hydroxylysine (Hyl), ornithine (Orn), methionine (Met), phenylalanine (Phe), p-phenyl phenylalanine (Bip), proline (Pro), hydroxyproline (Hyp), serine (Ser), homoserine (Hse), sarcosine (Sar), threonine (Thr), tryptophan (Trp), tyrosine (Tyr), and valine (Val), wherein when two or more amino acids are present then the N atom of the amide linking the amino acids is optionally substituted with —$CH_3$;

$L^4$ is —$(CH_2)_v$-, —$(CH_2CH_2O)_v$—$CH_2CH_2$—, —$(CH_2)_v$—$NR^{17}$C(═O)—, —$CH_2CH_2$C(═O)NH$CH_2CH_2$—, —$CH_2CH_2$—C(═O)NH—$(CH_2CH_2O)_v$$CH_2CH_2$—, —$(CH_2)_v$—$NR^{17}$—$(CH_2)_v$-, —NH(C═O)NH—O—$(CH_2)_v$-, —NHC(═O)NH—$(CH_2)_v$-, —$(CH_2)_x$—NHC(═O)NH—$(CH_2)_v$-, —$CH_2$CH(OH)$CH_2$—CH(OH)—$CH_2CH_2$—, —$CH_2$CH(OH)$CH_2$—CH(OH)—$CH_2CH_2$—NHC(═O)$CH_2CH_2$C(═O)—NH$CH_2CH_2$—, or —NHC(═O)$CH_2$—O—NH—C(═O)$(CH_2)_v$-;

v is 1, 2, 3, 4, 5, or 6;

$L^6$ is absent or -$L^8$-$L^9$-$L^{10}$-;

$L^8$ is absent, —$(CH_2)_r$-, or —$(CH_2)_r$—$NR^{14}$—;

r is 1 or 2;

$L^9$ is substituted or unsubstituted 4 to 6-membered heterocycloalkylene, an unsubstituted or substituted $C_4$-$C_8$ cycloalkylene, an unsubstituted or substituted $C_4$-$C_8$ cycloalkenylene, or unsubstituted phenylene; and $L^{10}$ is absent, —$(CH_2)_q$-, —NH—$(CH_2)_q$-, or —C(═O)—$(CH_2)_q$-.

12. The compound of claim 11, or a pharmaceutically acceptable salt thereof, wherein $L^9$ is azetidinylene, pyrrolidinylene, piperidinylene, piperazinylene, or

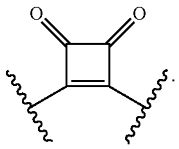 [SMILES: *c1c(*)c(=O)c1=O]

.

13. The compound of claim 10, or a pharmaceutically acceptable salt thereof, wherein:

-$L^2$-$L^3$-$R^A$;

$L^2$ is unsubstituted —$C_1$-$C_6$ alkylene-NH—; and $L^3$ is a natural or unnatural amino acid, wherein the N atom of the amide linking the amino acids is optionally substituted with —$CH_3$.

14. The compound of claim 10, or a pharmaceutically acceptable salt thereof, wherein:

-$L^A$-$R^A$ is -$L^2$-$L^7$-$R^A$;

$L^2$ is —$(CH_2CH_2O)_w$—$CH_2CH_2$—; and $L^7$ is —NH—.

15. The compound of claim 10, or a pharmaceutically acceptable salt thereof, wherein:

-$L^A$-$R^A$ is -$L^2$-$L^4$-$L^7$-$R^A$, $L^2$ is unsubstituted —$C_1$-$C_6$ alkylene- or unsubstituted —$C_1$-$C_6$ alkylene-NHC(═O)—;

$L^4$ is —$(CH_2)_v$—, —$(CH_2CH_2O)_v$—$CH_2CH_2$—, —$(CH_2)_v$—$NR^{17}$—$(CH_2)_v$, —NHC(═O)NH—O—$(CH_2)_v$—NHC(═O)$CH_2$—O—NH—C(═O)qj$(CH_2)_v$—, —$CH_2$CH(═OH) $CH_2$—CH(OH)—$CH_2CH_2$—, —$CH_2CH_2$C(═O)NH$CH_2CH_2$—, —$CH_2CH_2$—C(═O)NH—$(CH_2CH_2O)_v$$CH_2CH_2$—, or —$CH_2$CH(—OH)$CH_2$—CH(OH)—$CH_2CH_2$—NHC(═O)$CH_2CH_2$C(═O)—NH$CH_2CH_2$; and $L^7$ is —NH—.

16. The compound of claim 10, or a pharmaceutically acceptable salt thereof, wherein:

-$L^A$-$R^A$ is -$L^2$-$L^6$-$L^7$-$R^A$;

$L^2$ is unsubstituted —$C_1$-$C_6$ alkylene-, unsubstituted —$C_1$-$C_6$ alkylene-NH—, or unsubstituted —$C_1$-$C_6$ alkylene-NHC(═O)—;

$L^6$ is -$L^8$-$L^9$-$L^{10}$-; and $L^7$ is —NH—.

17. The compound of claim 10, or a pharmaceutically acceptable salt thereof, wherein $L^A$ is:

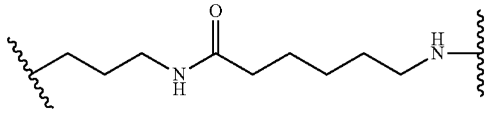

,

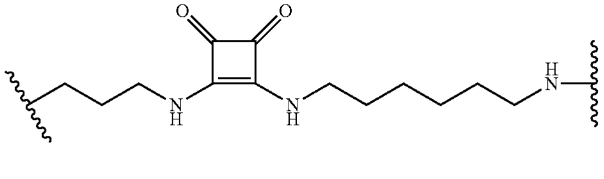

,

-continued
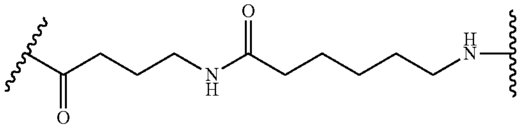,
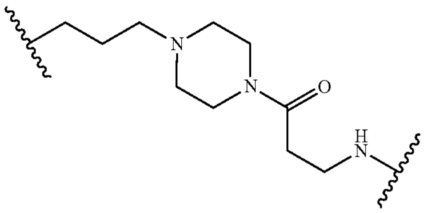,
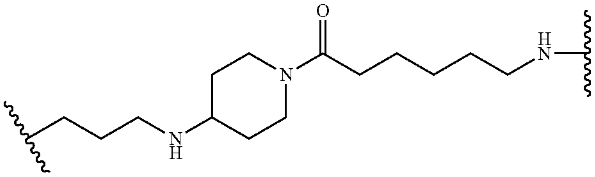,
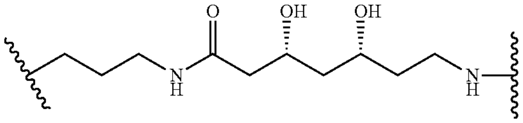,
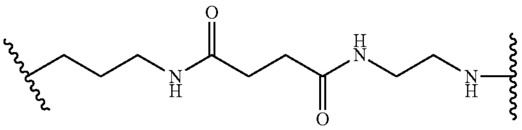,
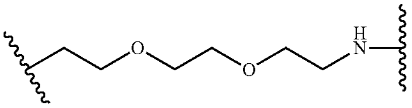,
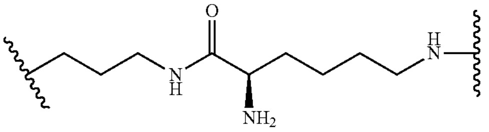,
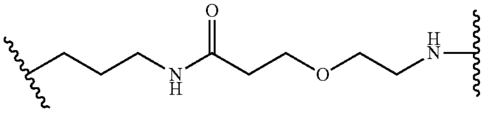,
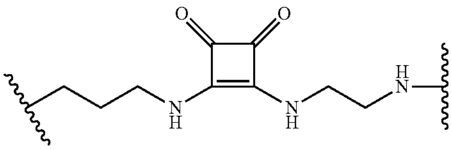,
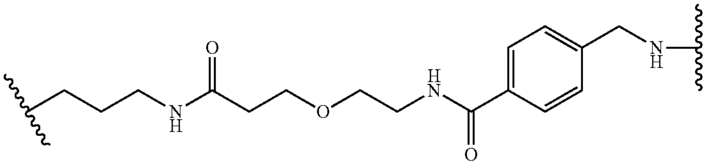,
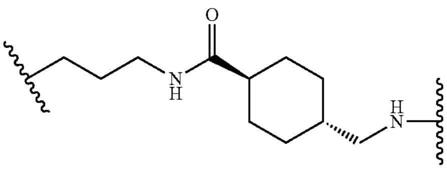,
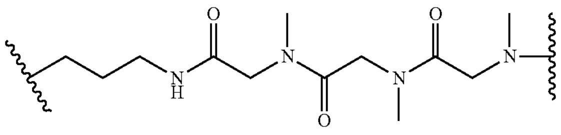,
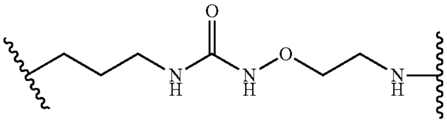,
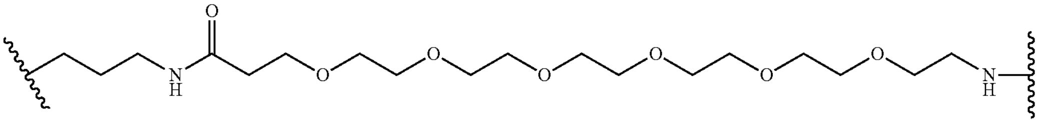,
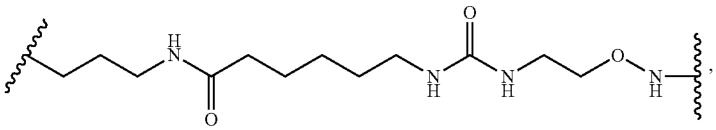,
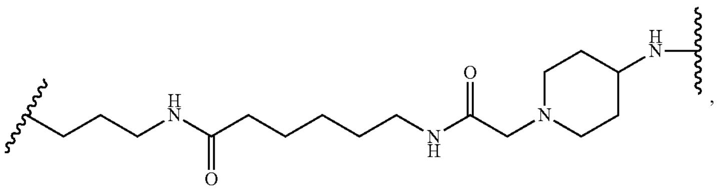, -continued
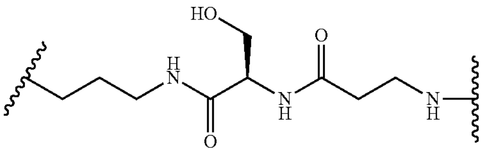, 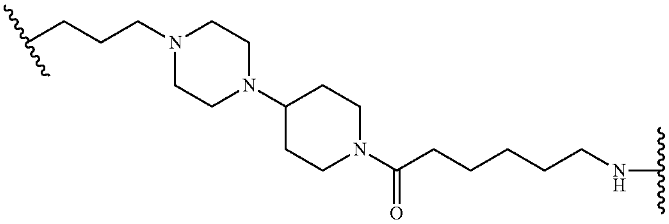,
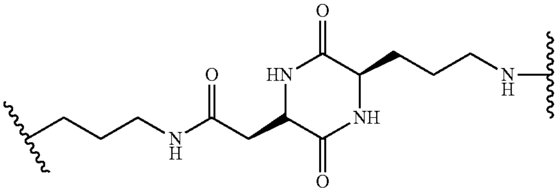, 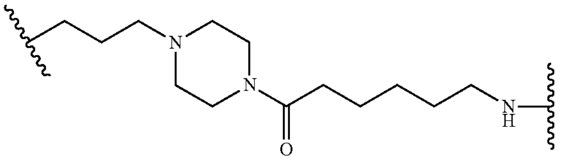,
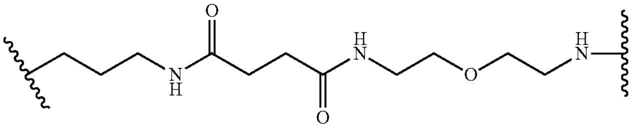, 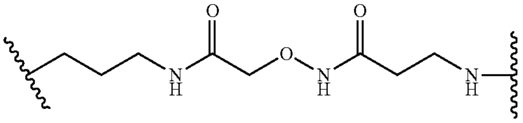,
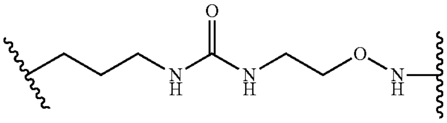, 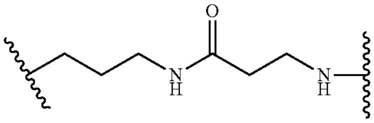,
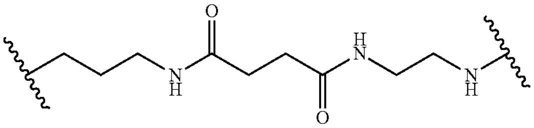, 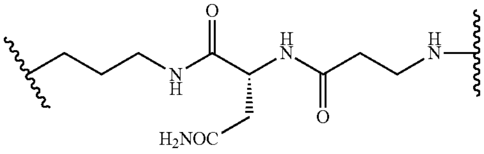,
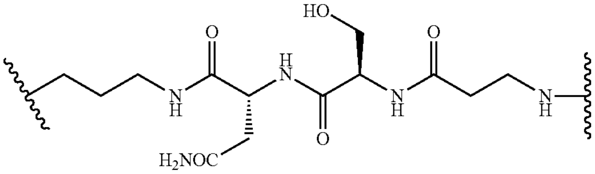, 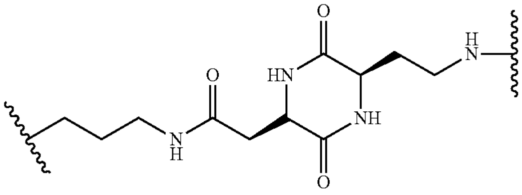,
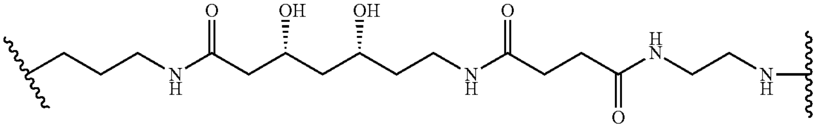,
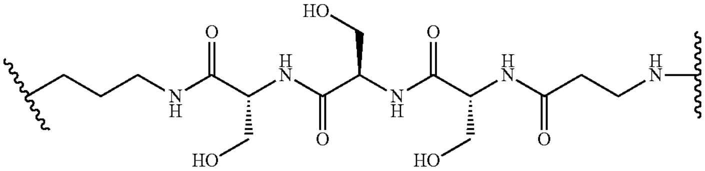,
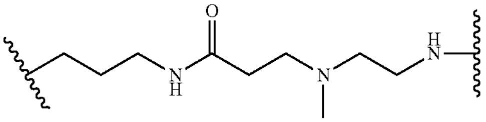, 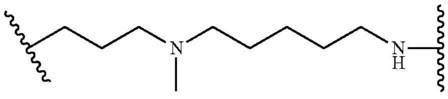,
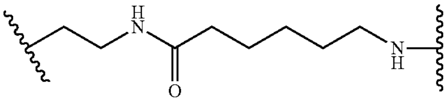, or 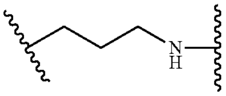.

18. The compound of claim 1, or a pharmaceutically acceptable salt thereof, wherein:

$R^1$ is H;

$R^2$ is —OH;

$R^{3a}$ and $R^{3d}$ are F or Cl and $R^{3b}$ and $R^{3c}$ are H;

$R^4$ is —C(═O)NHR$^{10}$;

$R^{10}$ is unsubstituted —$C_1$-$C_6$ alkyl or —$(CH_2)_t$NHC(═O)$(CH_2)_u$$CH_3$;

t is 1, 2, 3, or 4; u is 1 or 2;

$R^6$ is —$Z^A$-$L^A$-$R^A$;

and $Z^A$ is —O—, —NH—, —N(—$CH_3$)—, —NHC(—O)— or —$CH_2$—.

19. The compound of claim 18, or a pharmaceutically acceptable salt thereof, wherein -$L^A$-$R^A$ is:

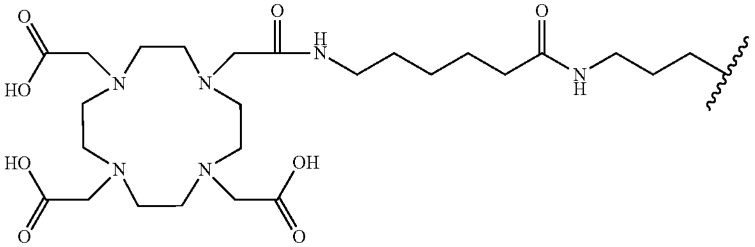
,

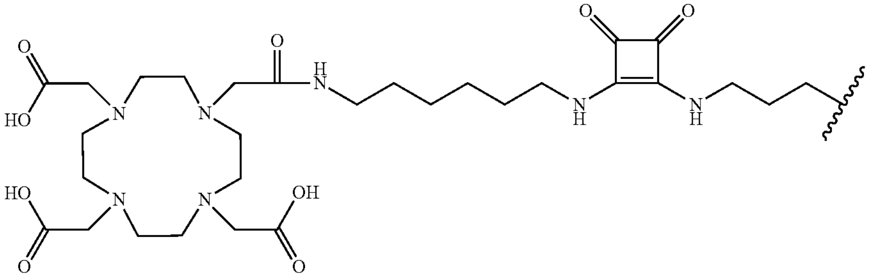
,

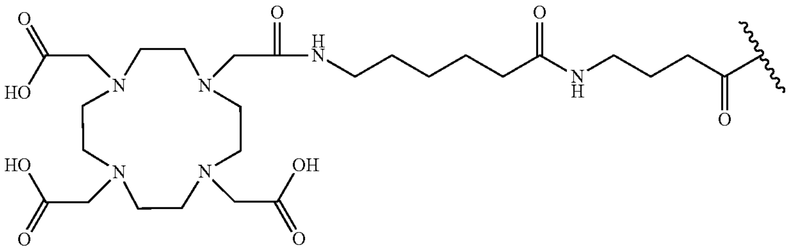
,

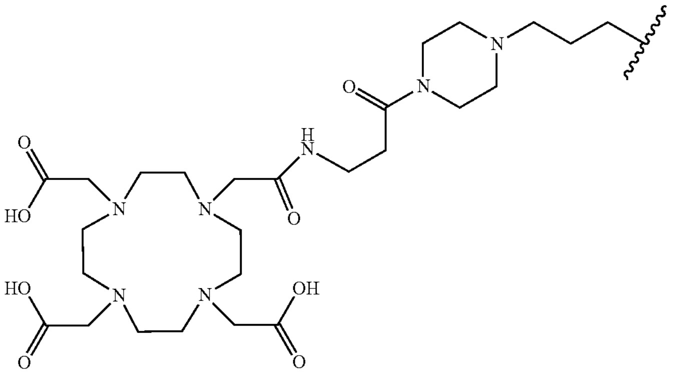
,

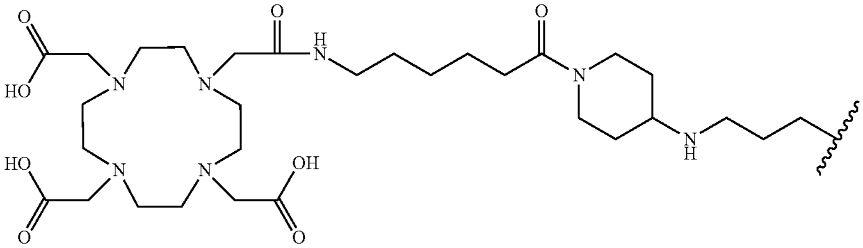
,

-continued
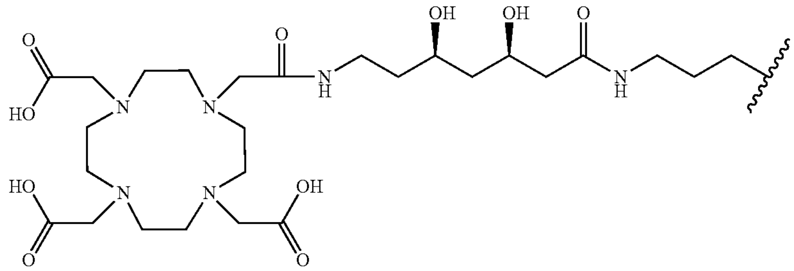
,
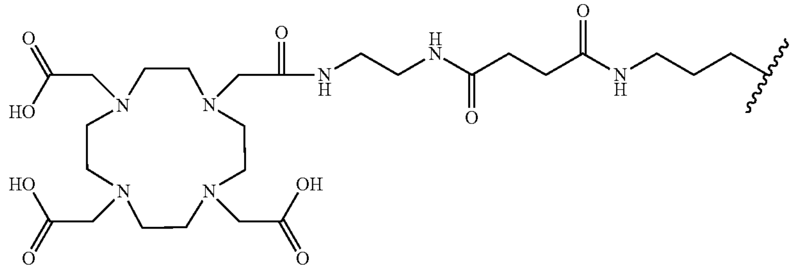
,
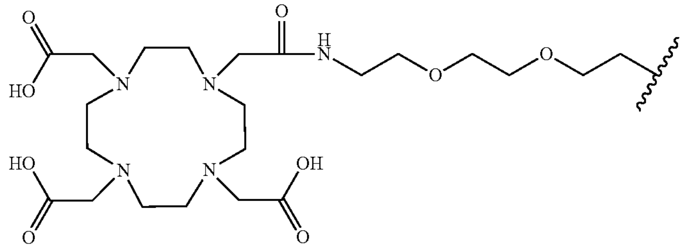
,
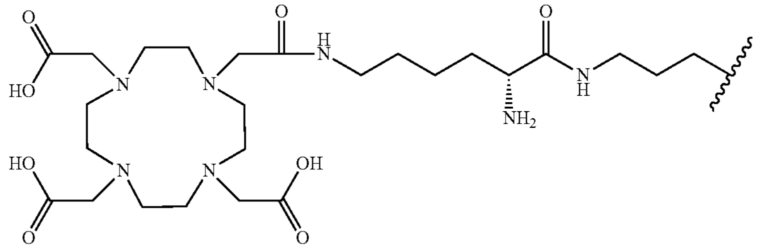
,
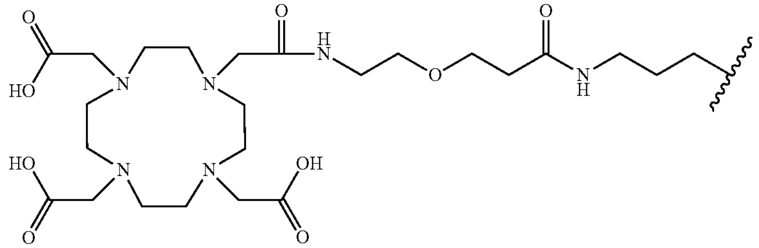
,
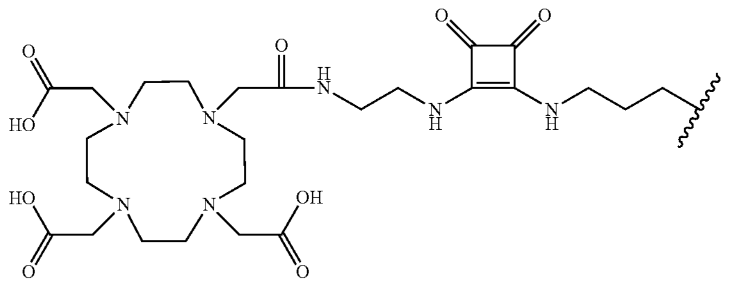
, -continued
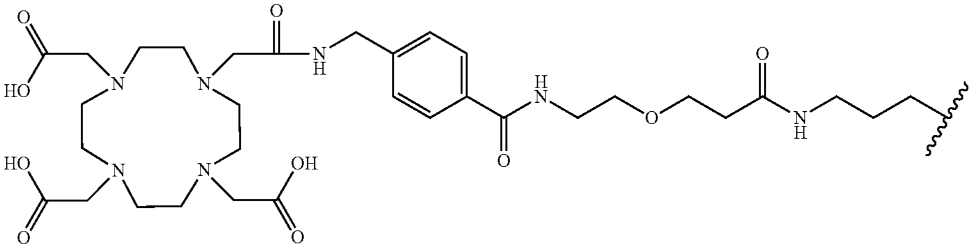,
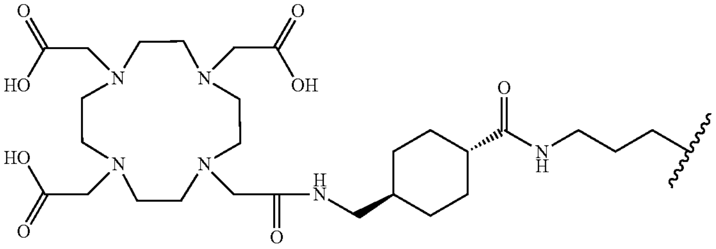,
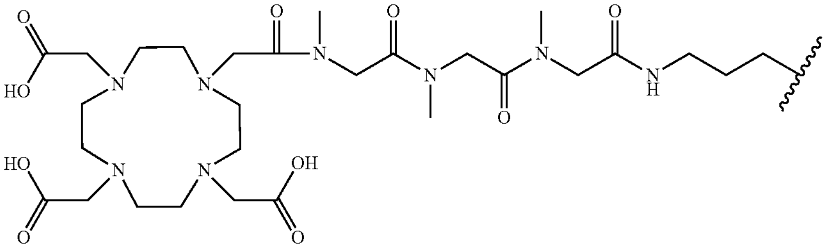,
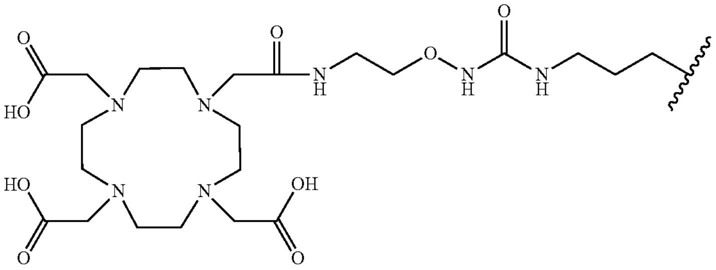,
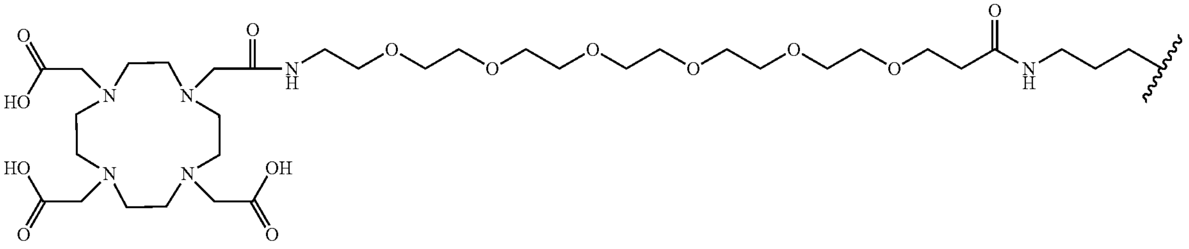,
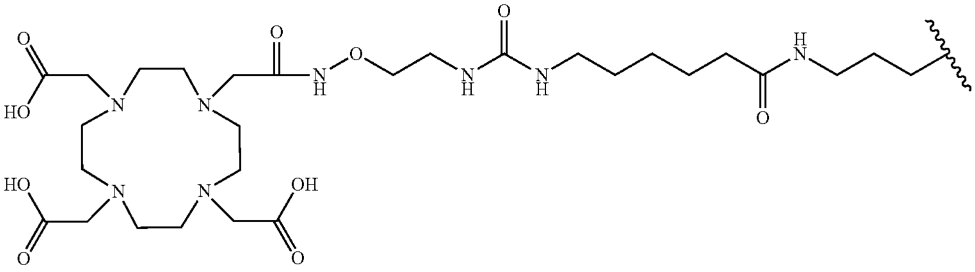, -continued
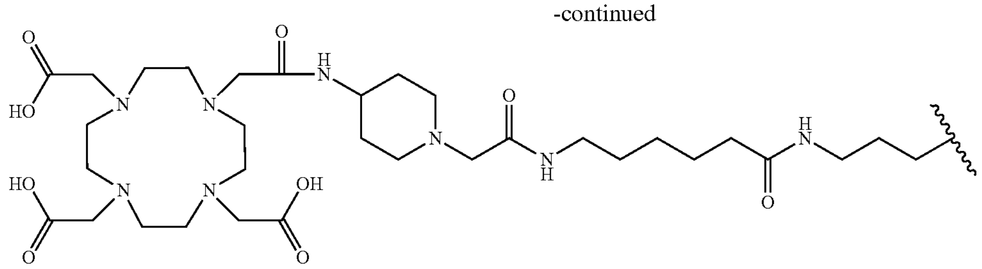
,
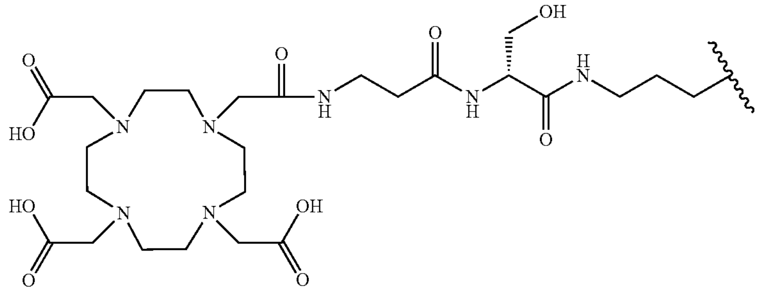
,
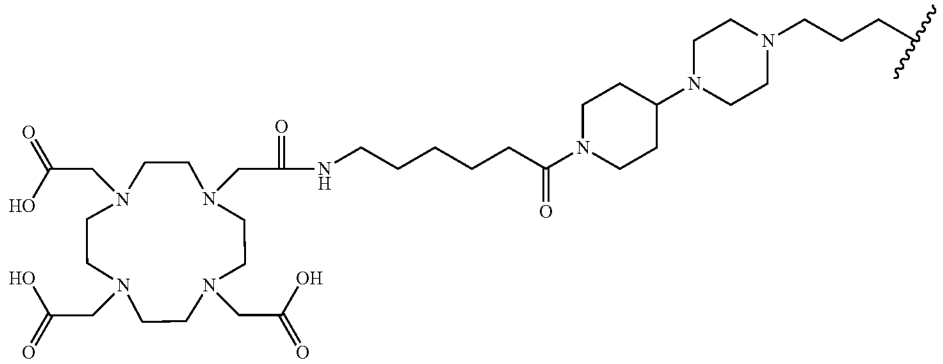
,
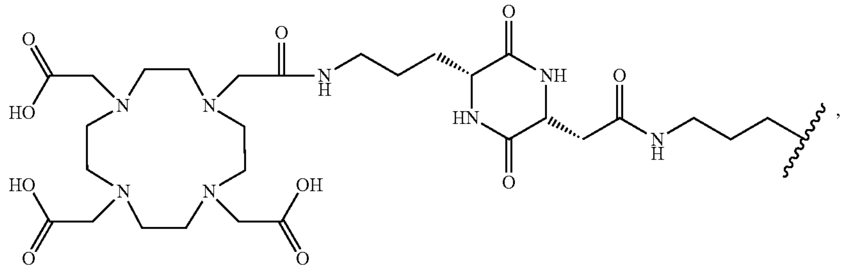
,
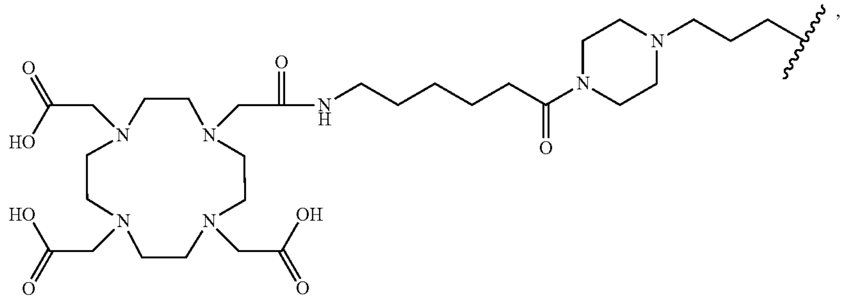
,
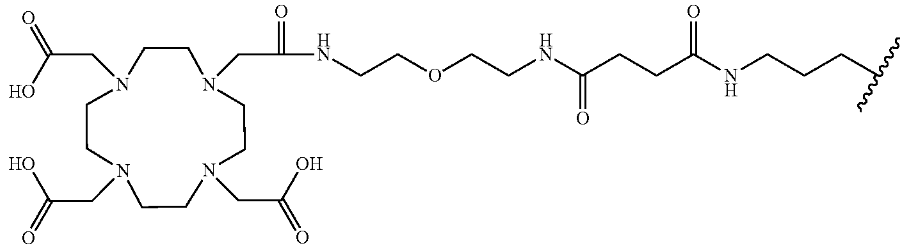
, -continued
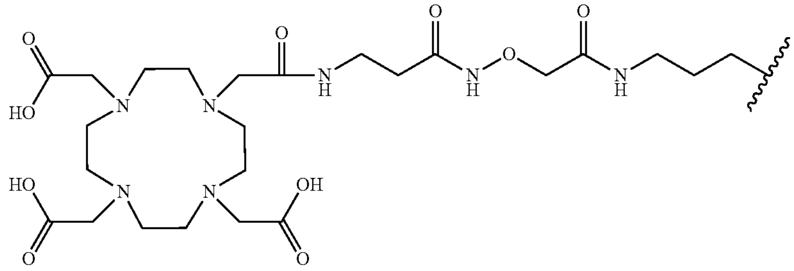
,
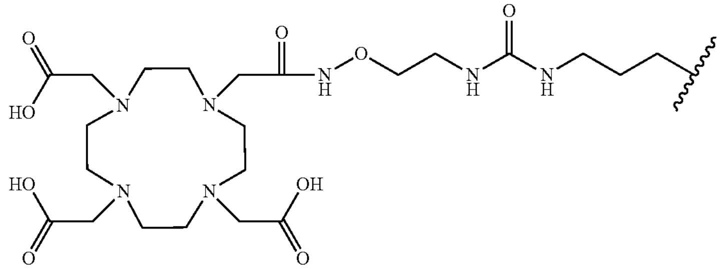
,
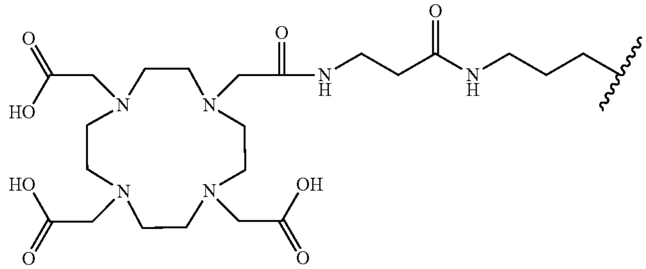
,
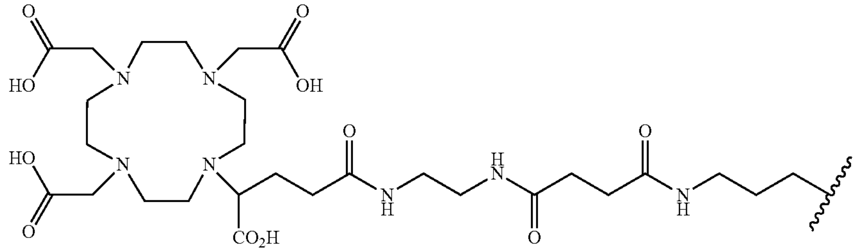
,
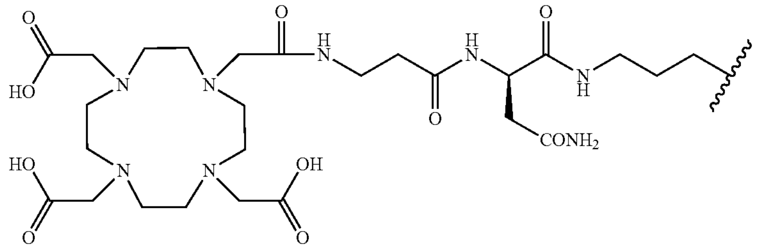
,
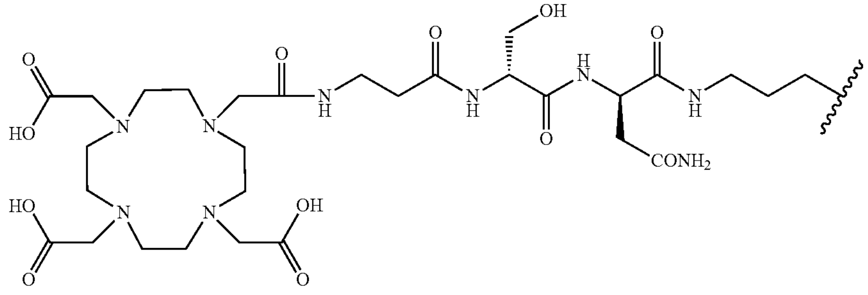
, -continued
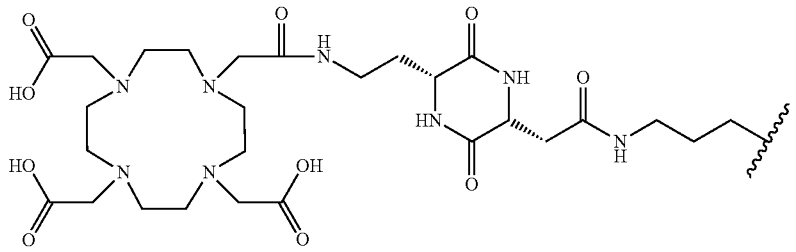
,
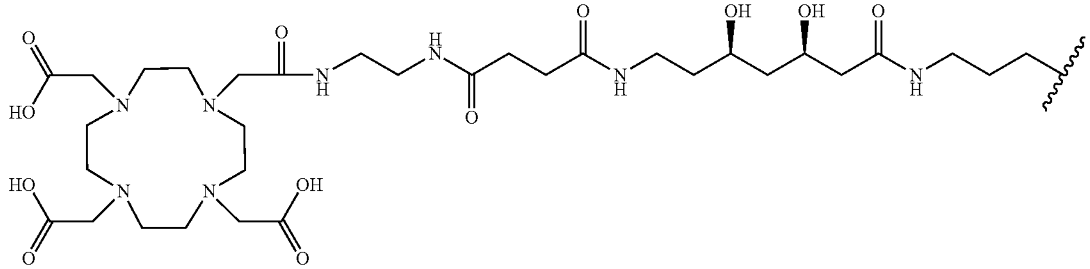
,
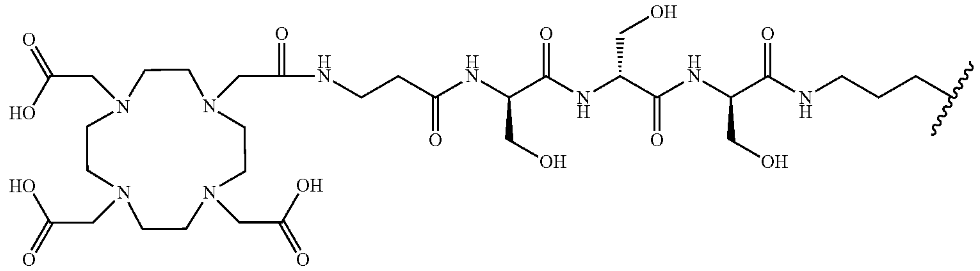
,
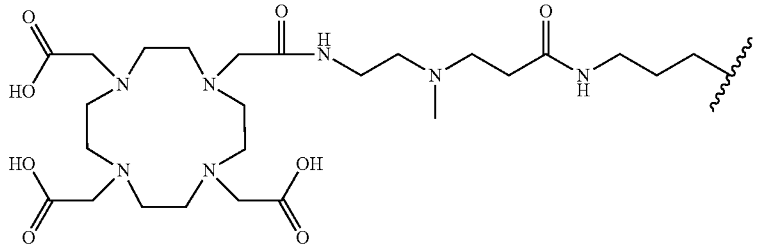
,
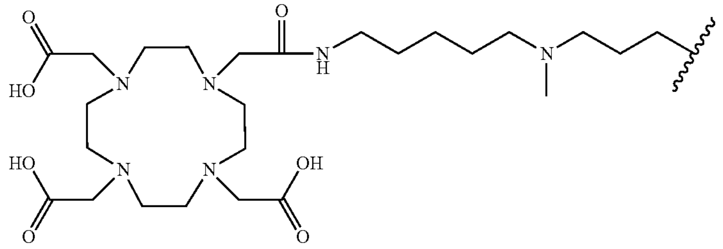
,
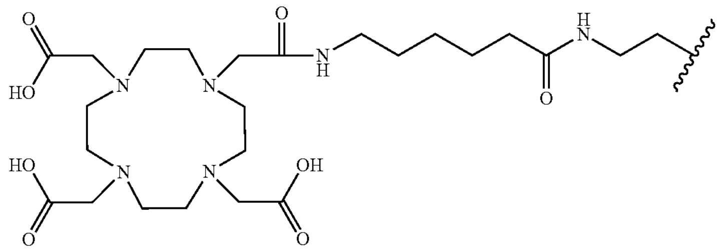
, or -continued
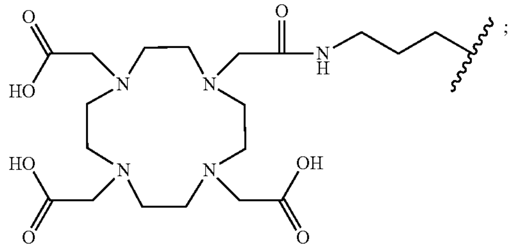
or a radionuclide complex thereof.
20. A compound that has one of the following structures, or a pharmaceutically acceptable salt thereof:
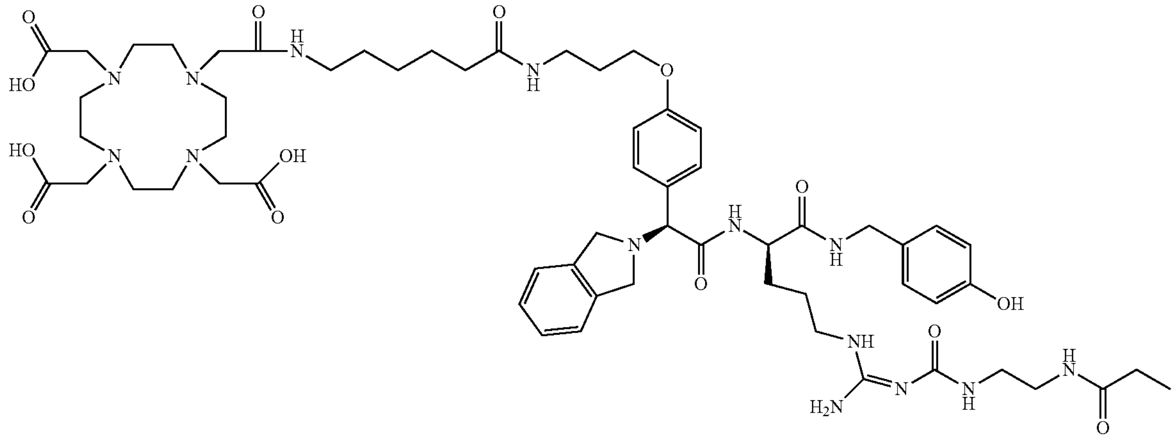
,
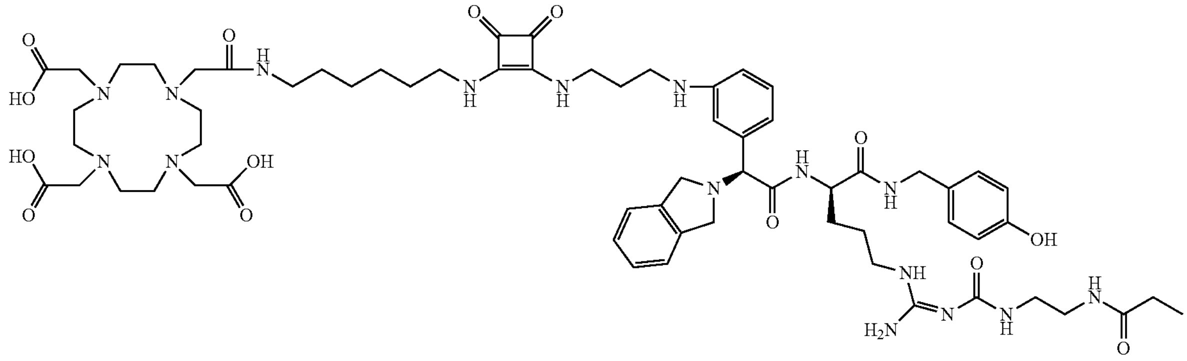
,
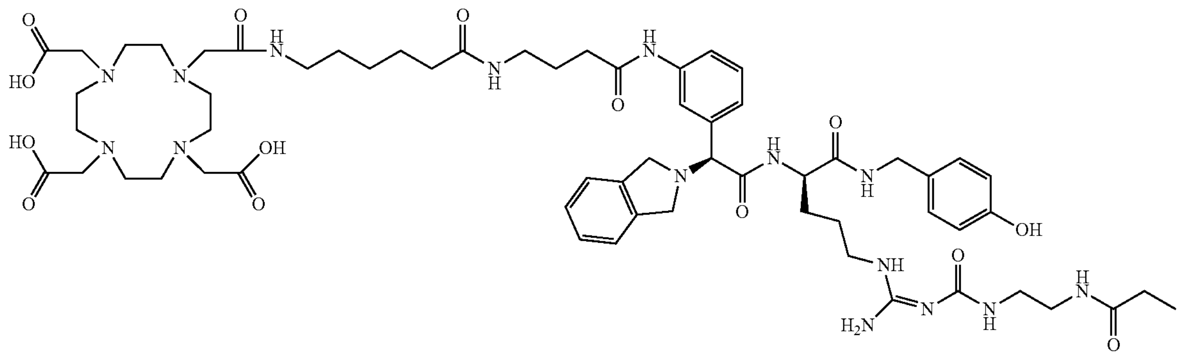
, -continued
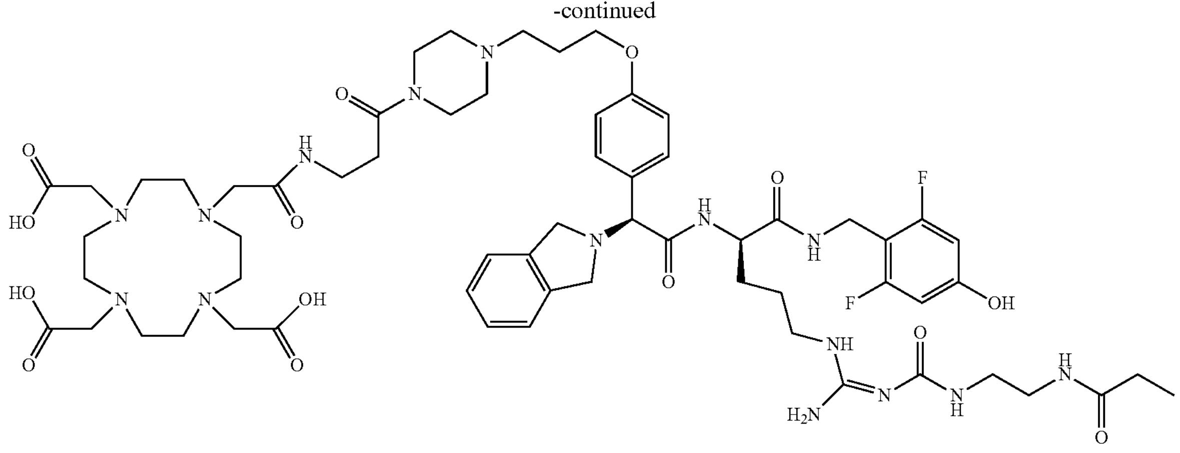
,
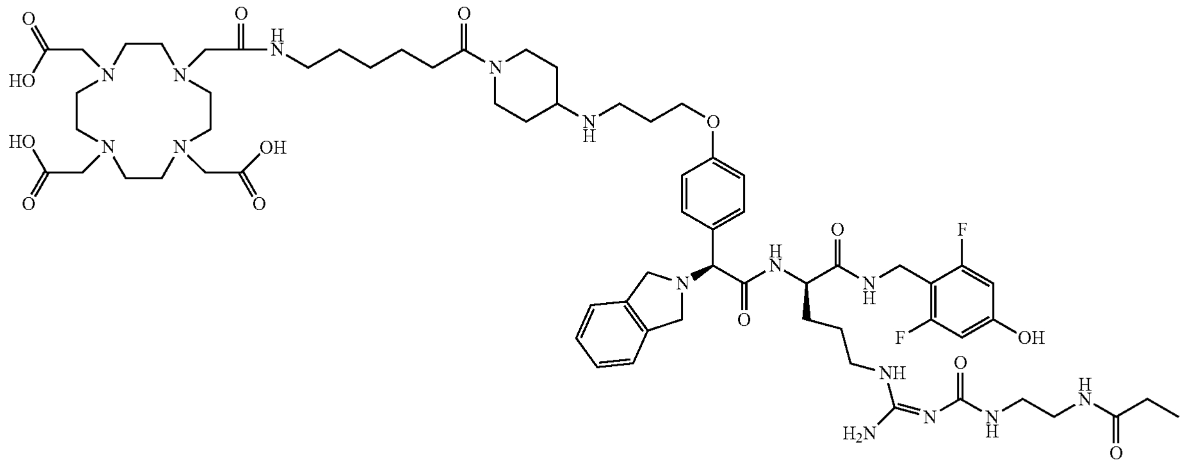
,
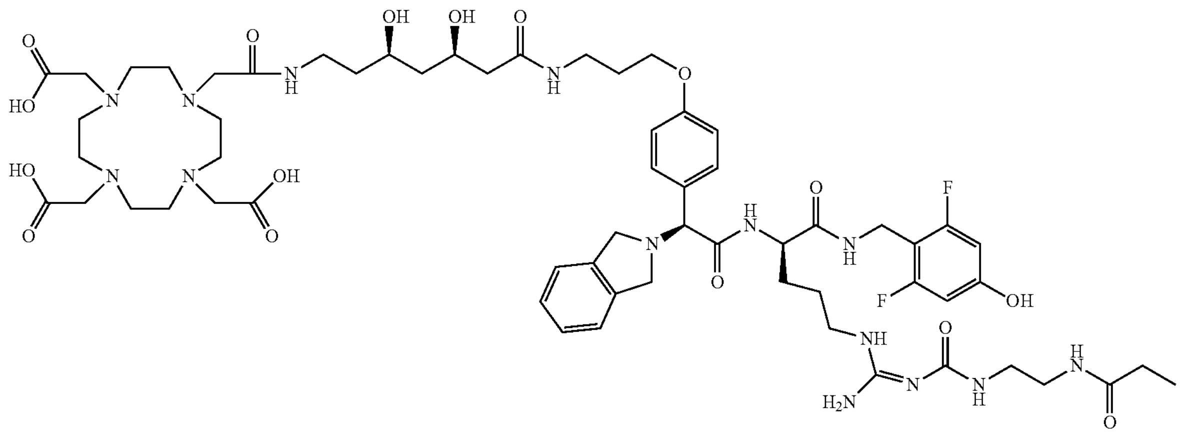
, -continued
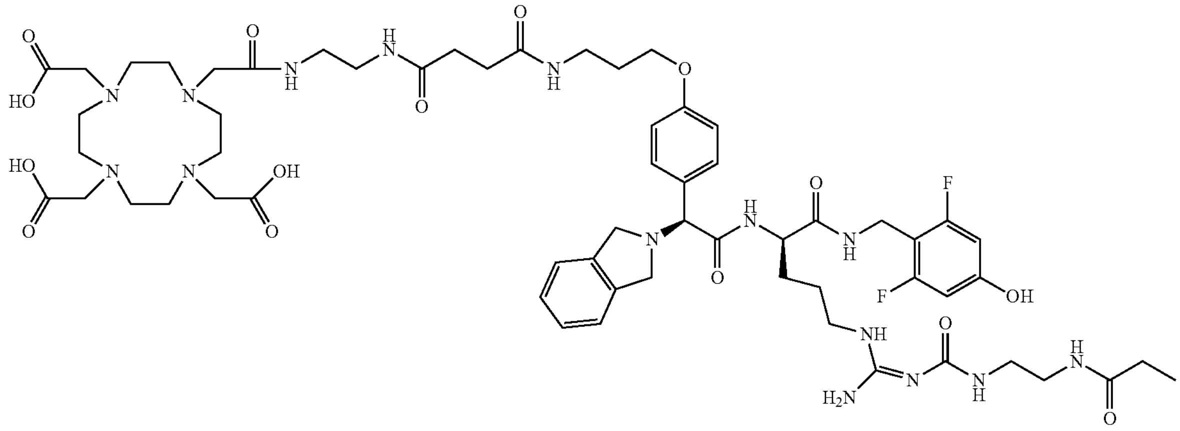
,
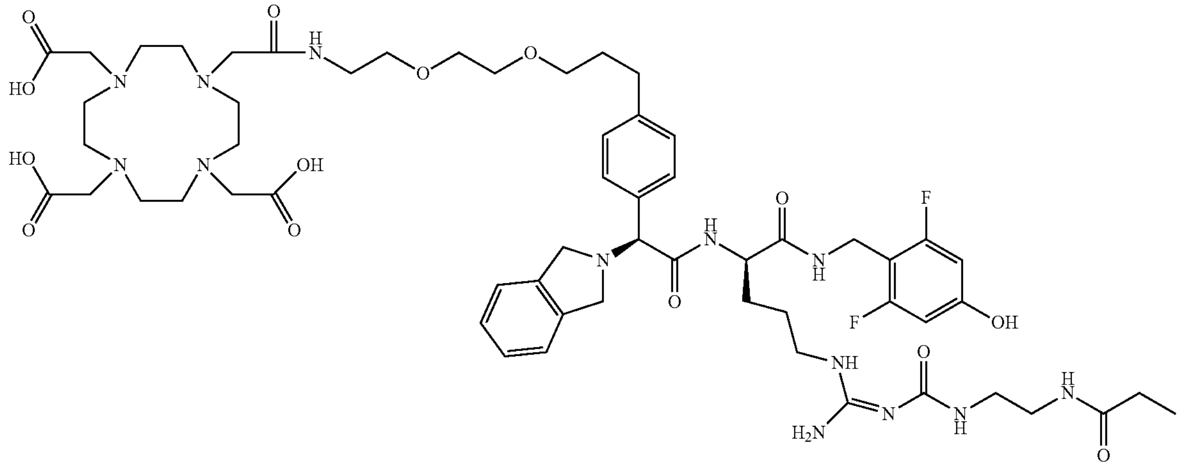
,
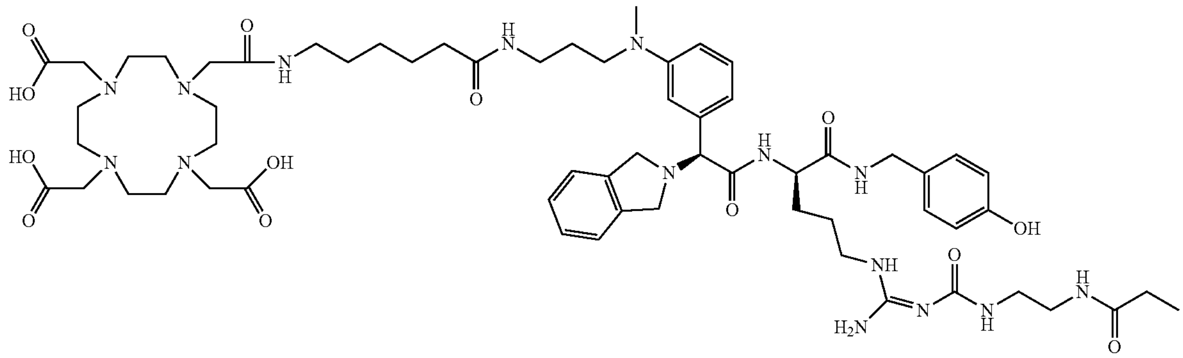
,
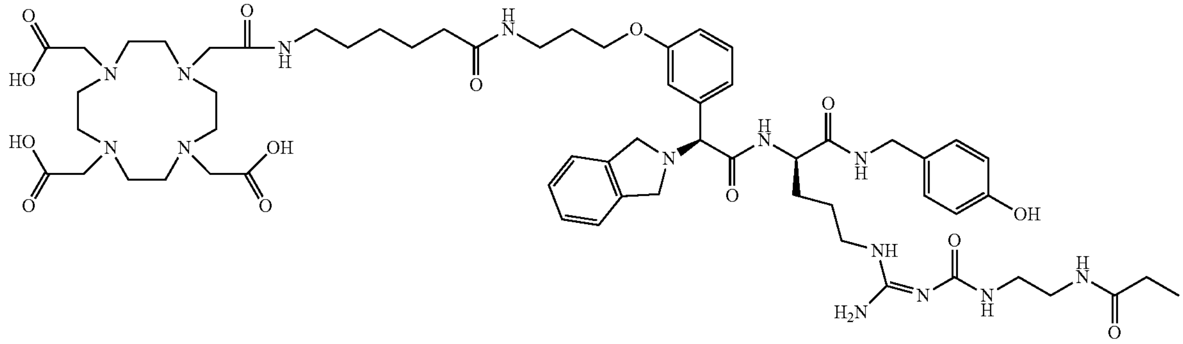
, -continued
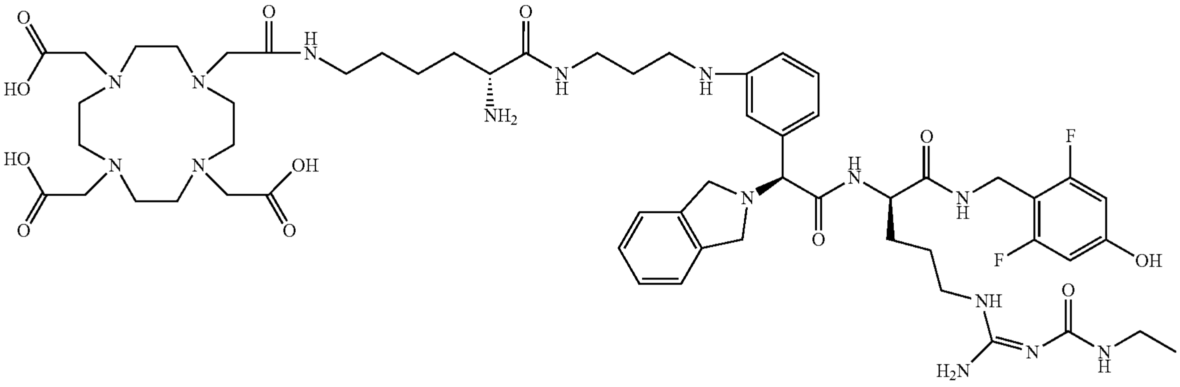
,
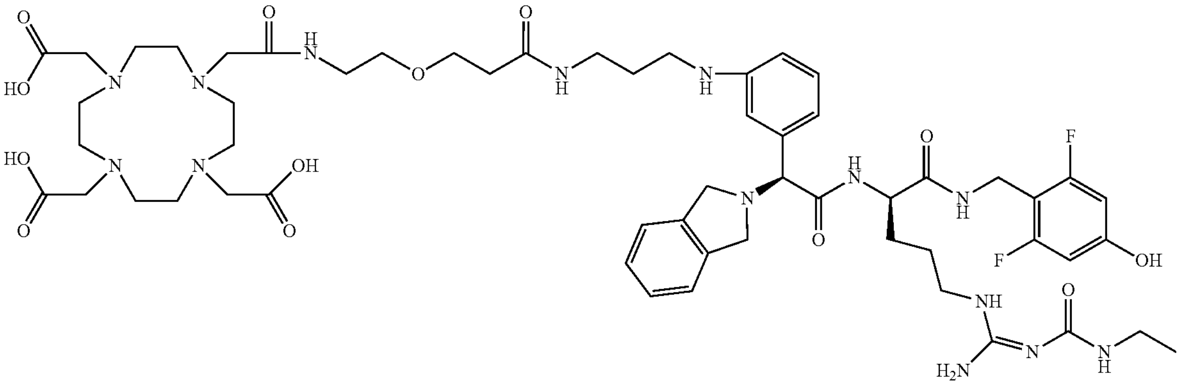
,
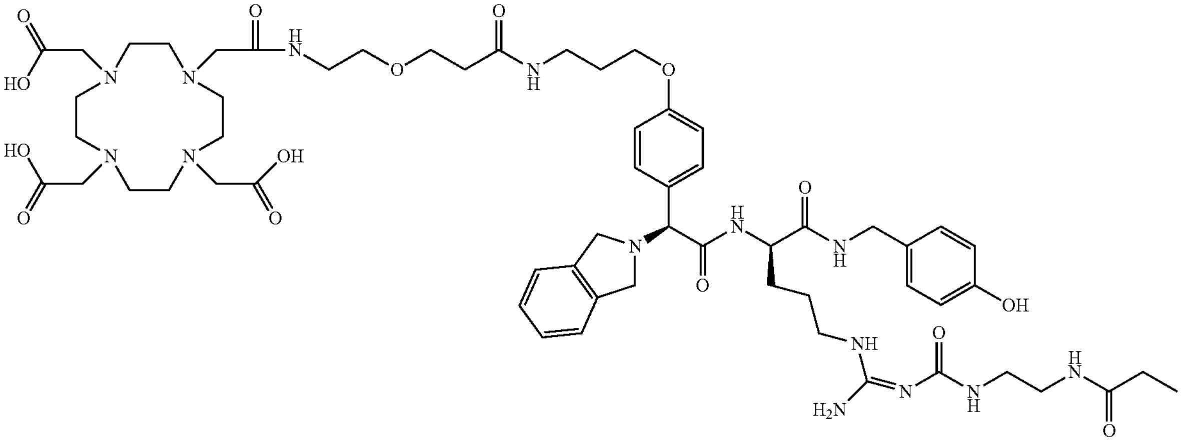
,
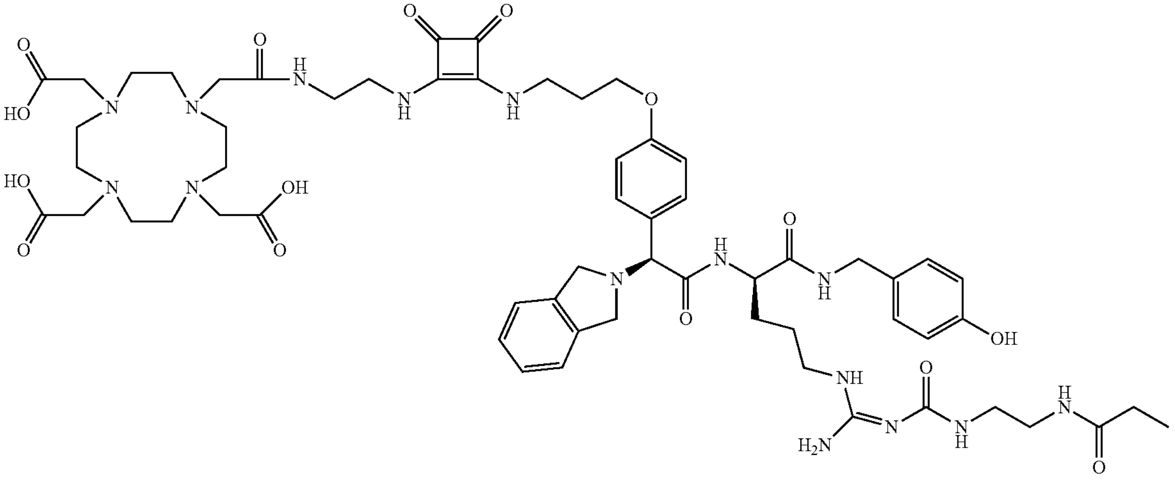
, -continued
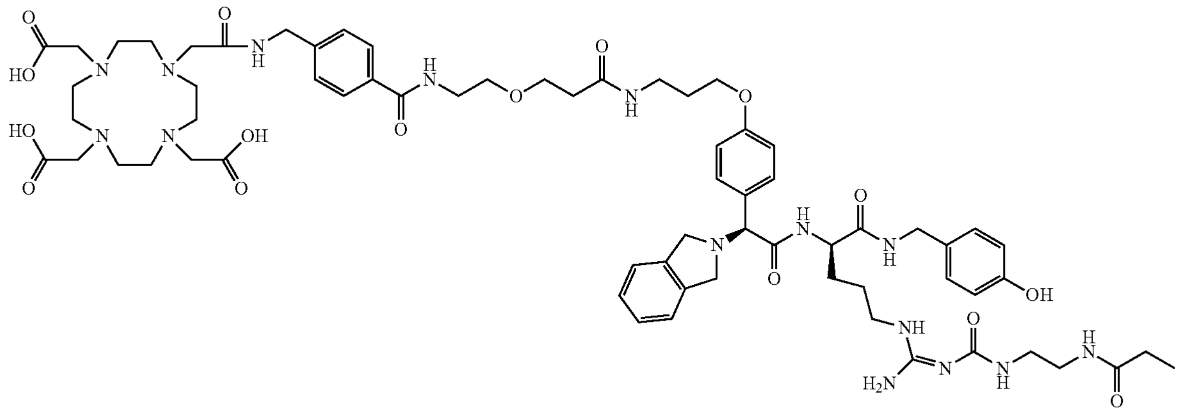
,
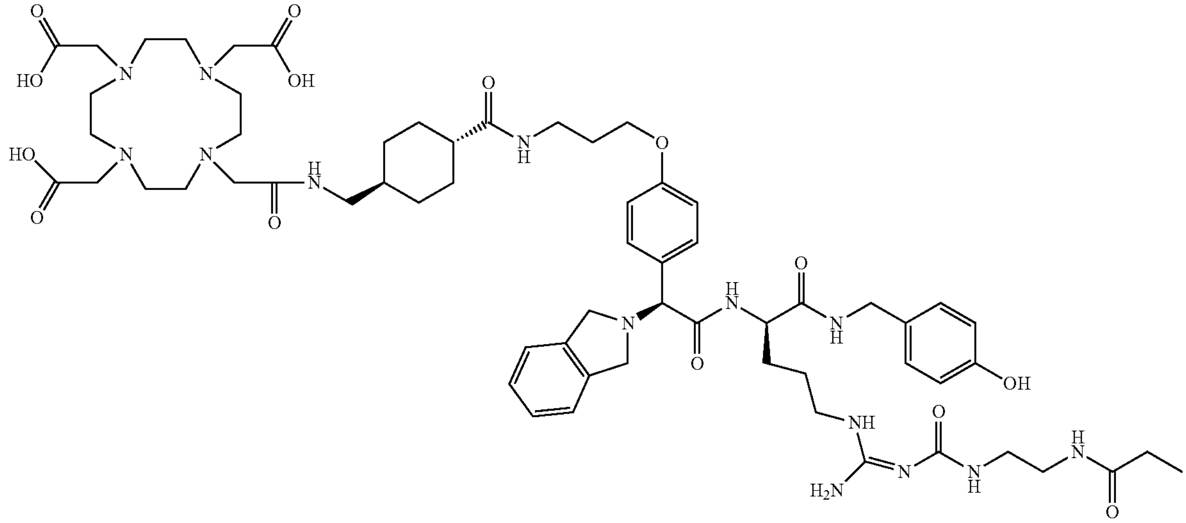
,
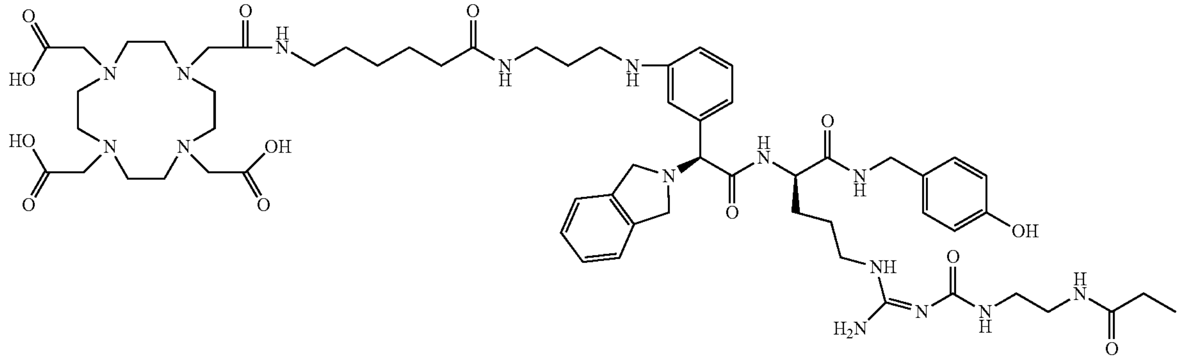
,
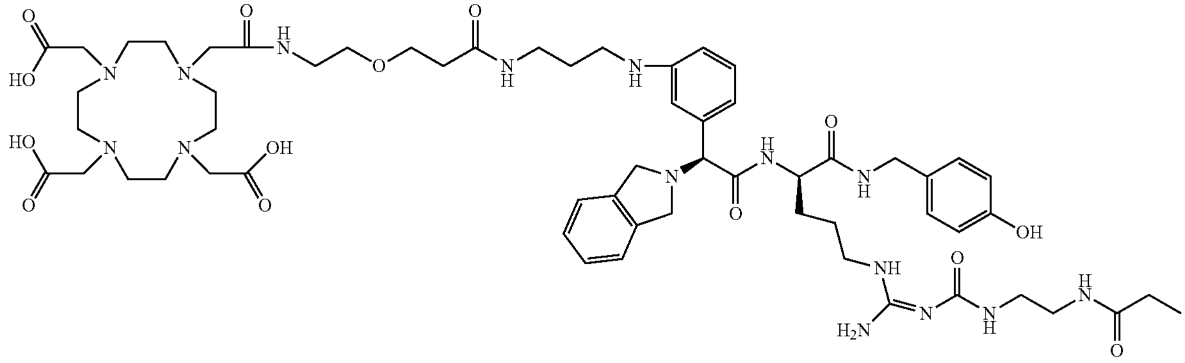
, -continued
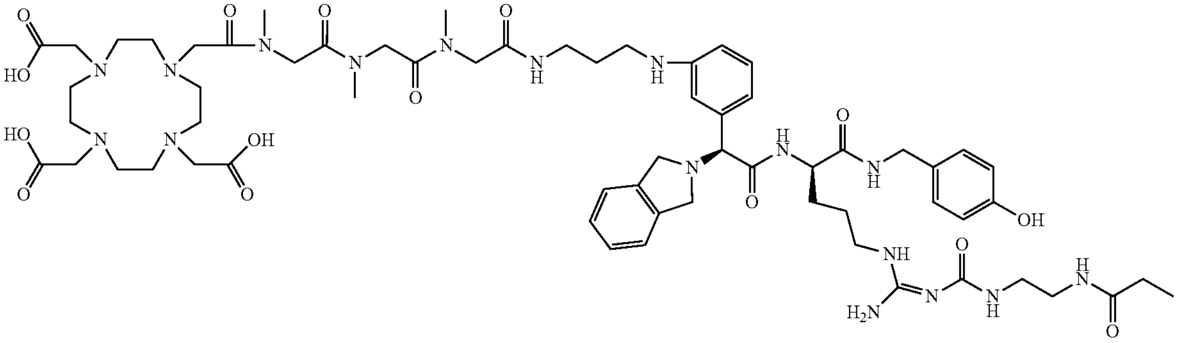
,
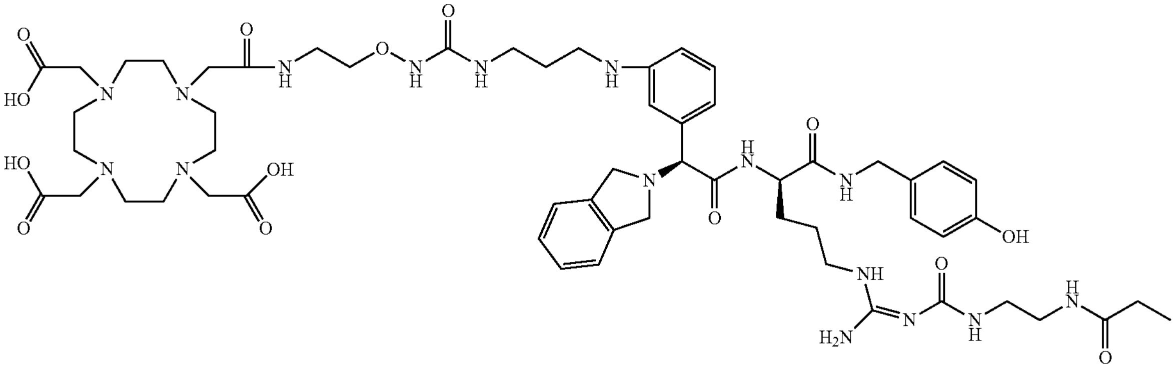
,
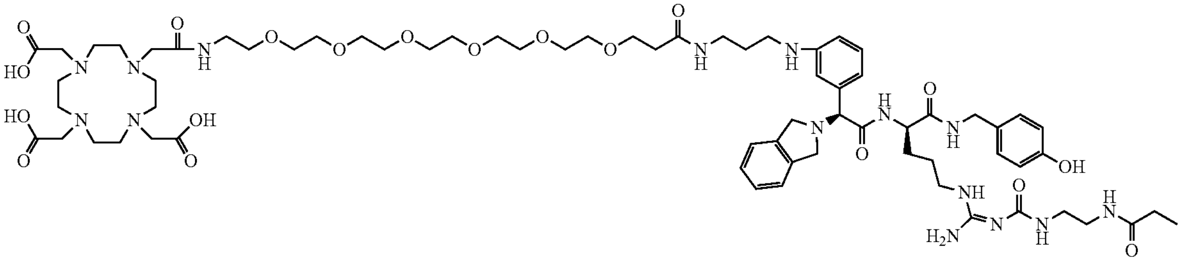
,
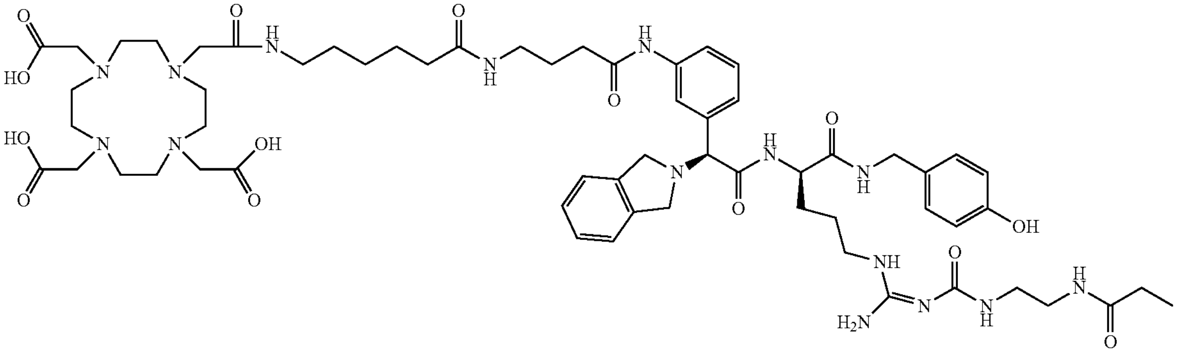
,
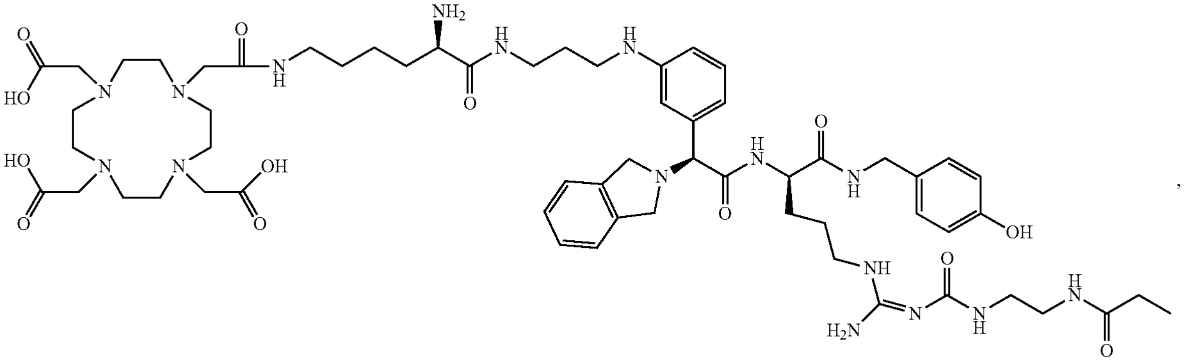
, -continued
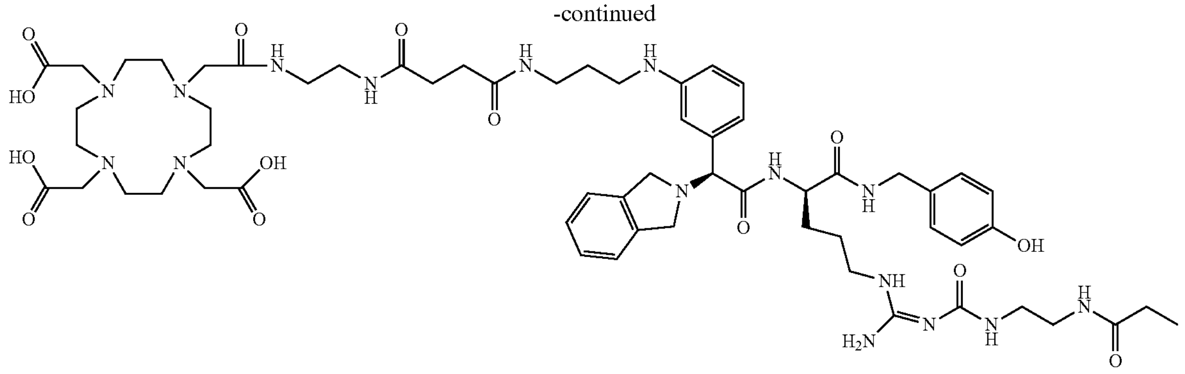
,
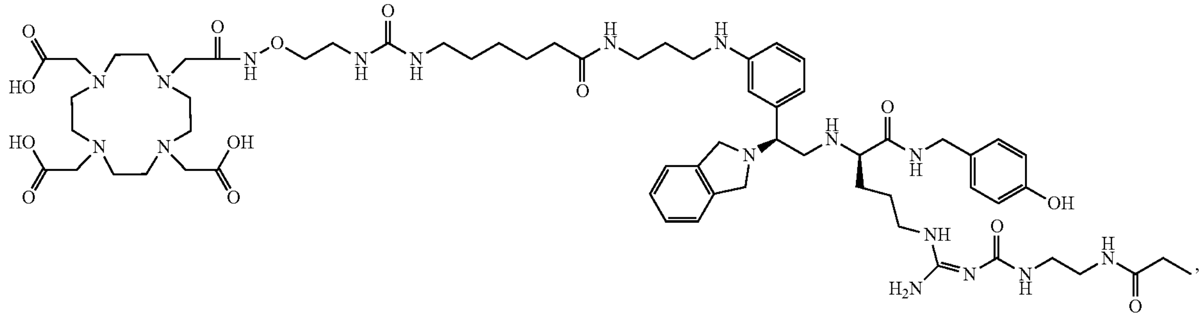
,
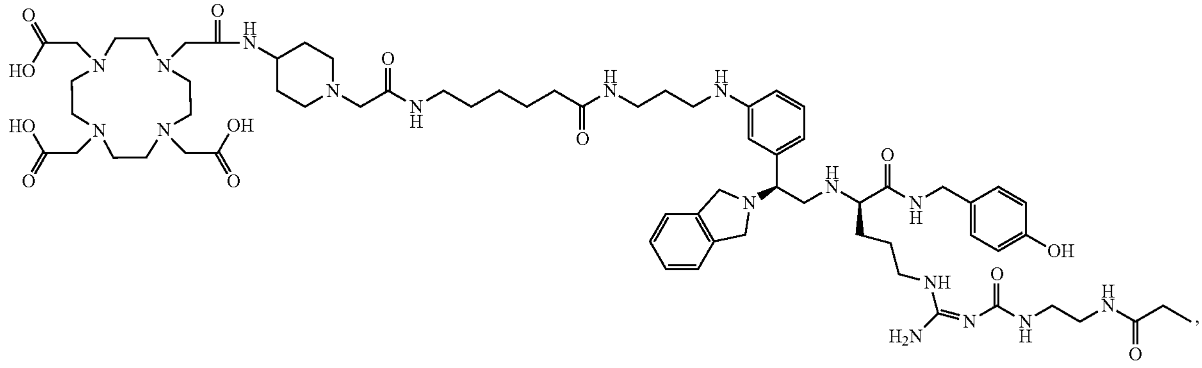
,
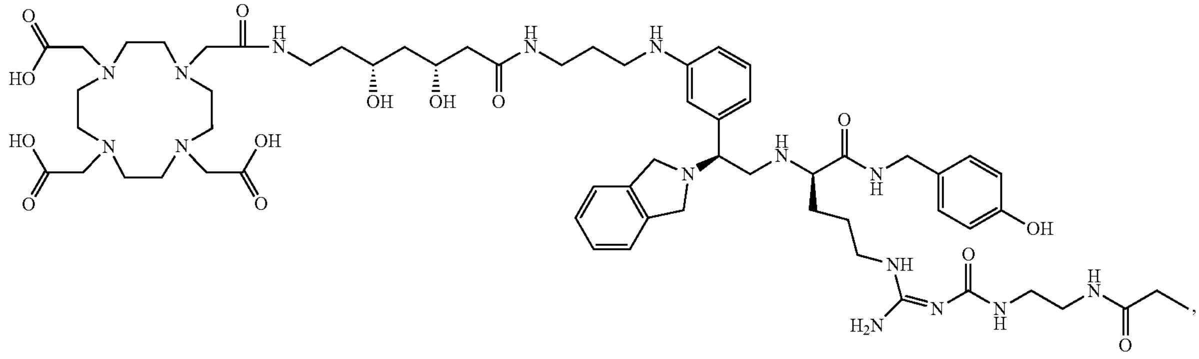
, -continued
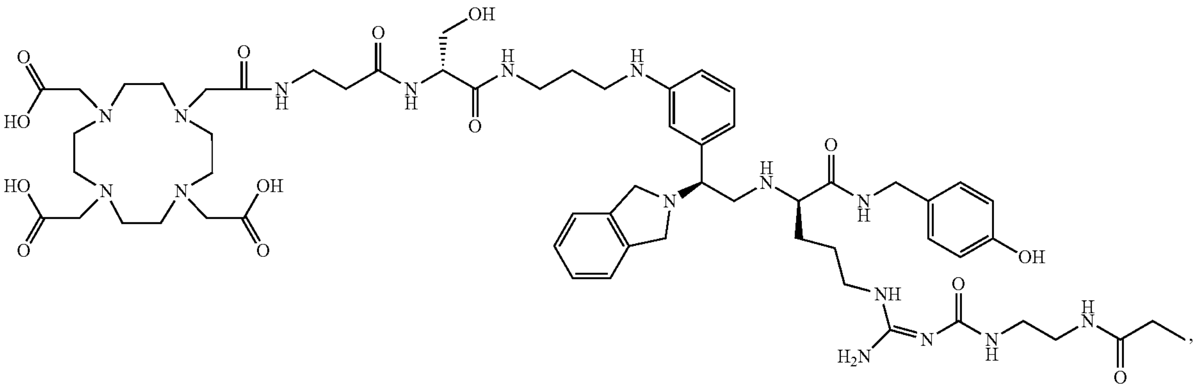
,
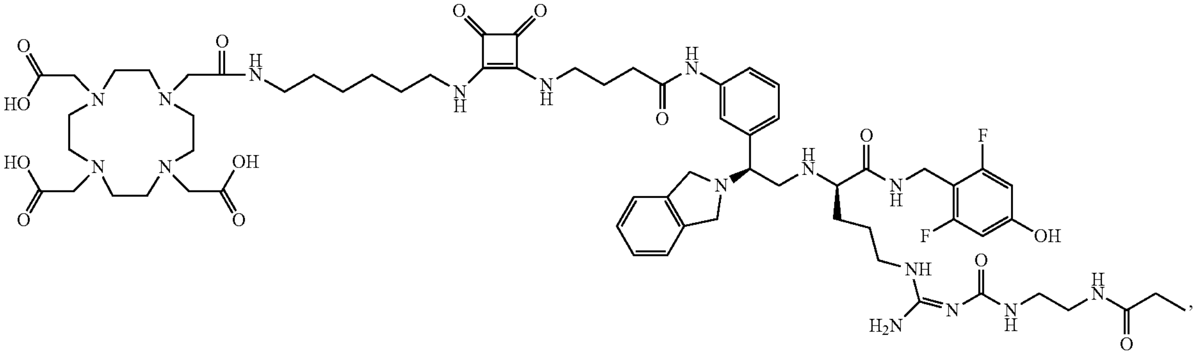
,
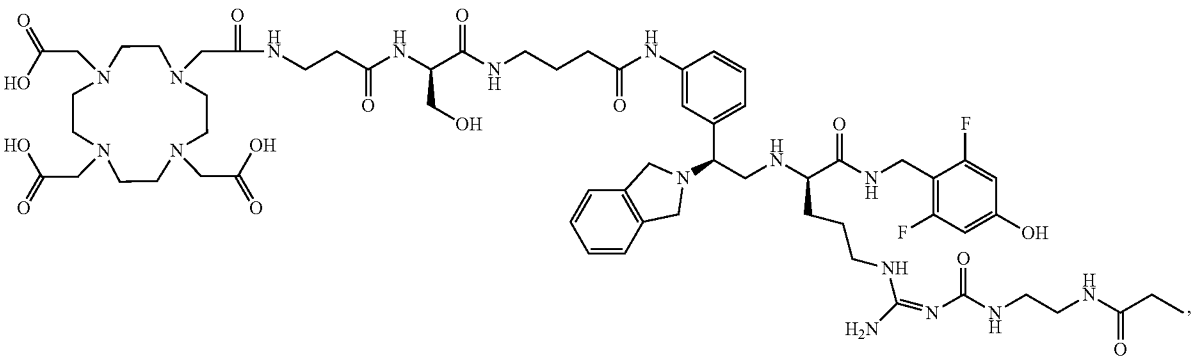
,
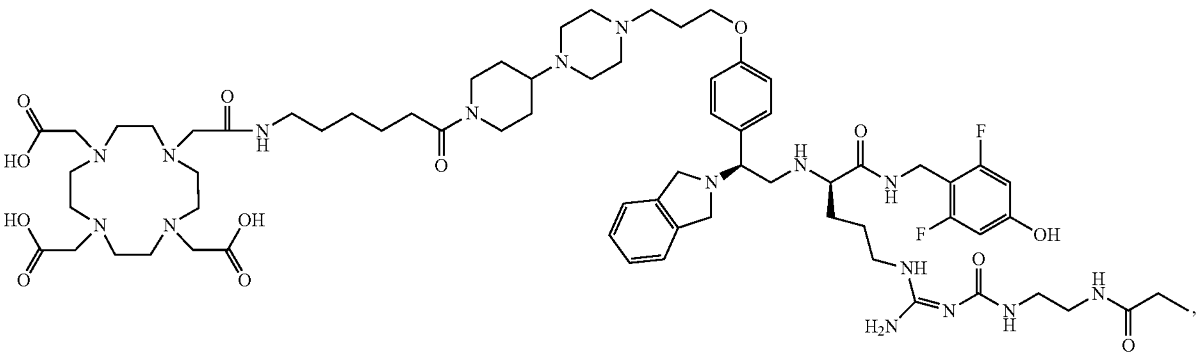
, -continued
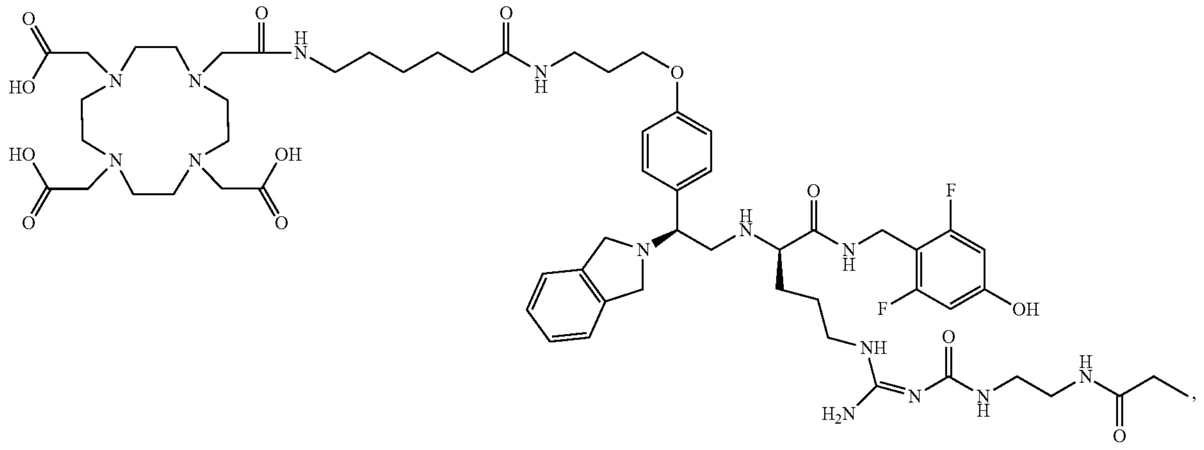
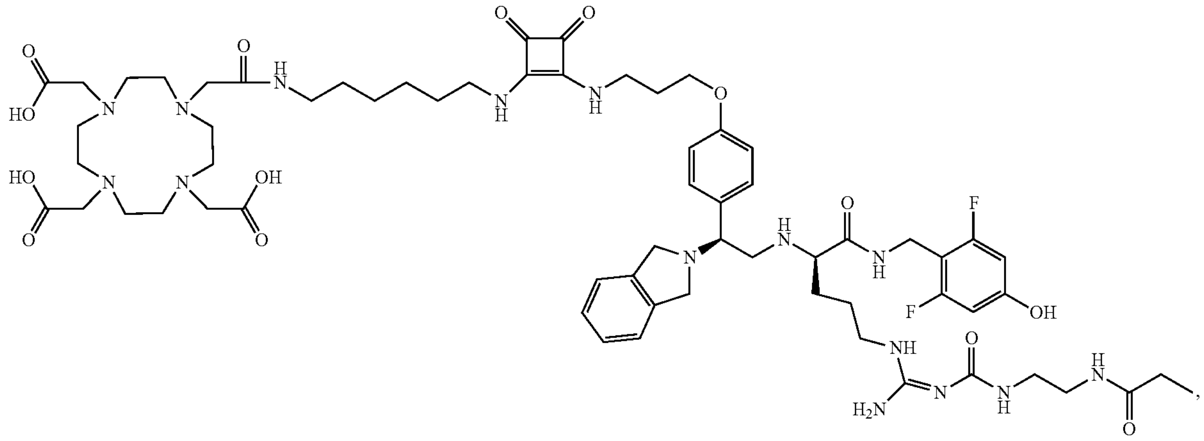
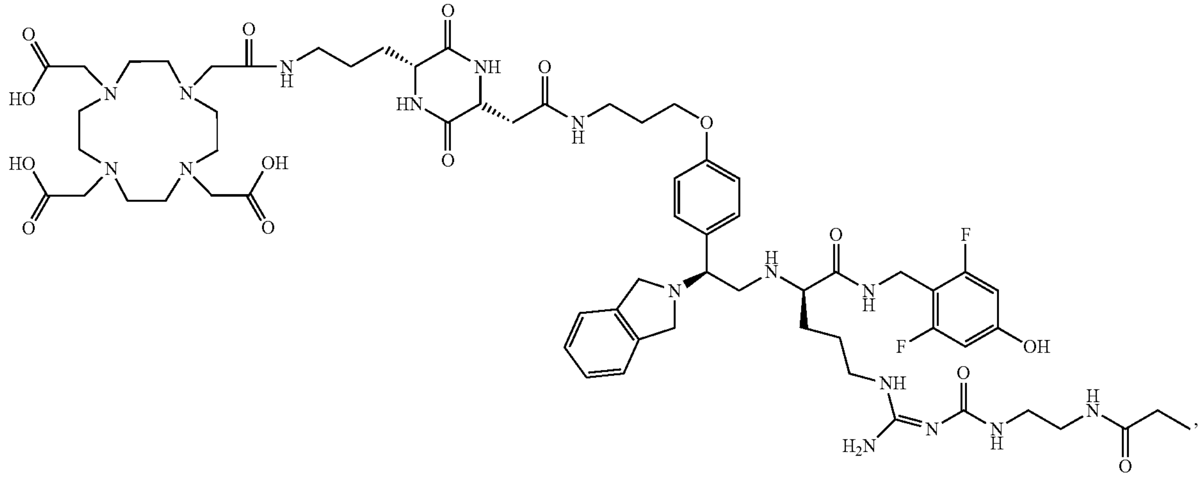

-continued
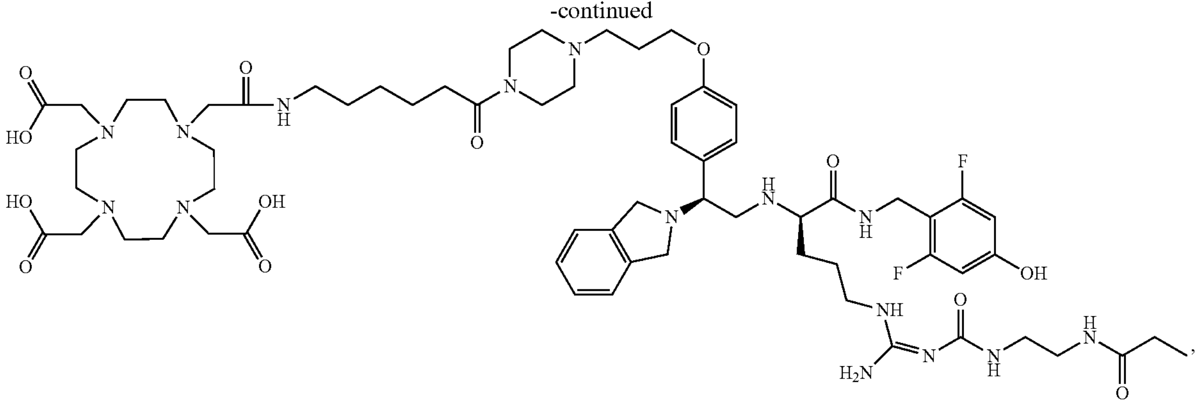
,
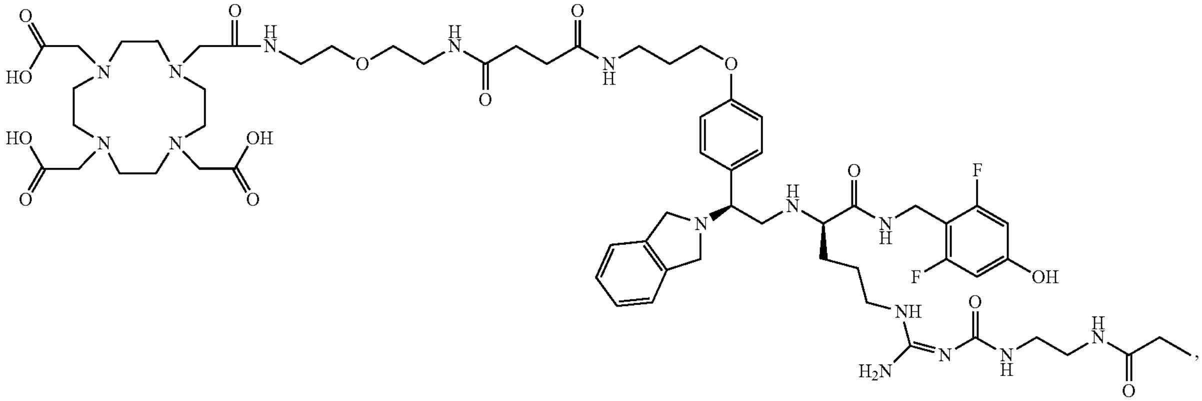
,
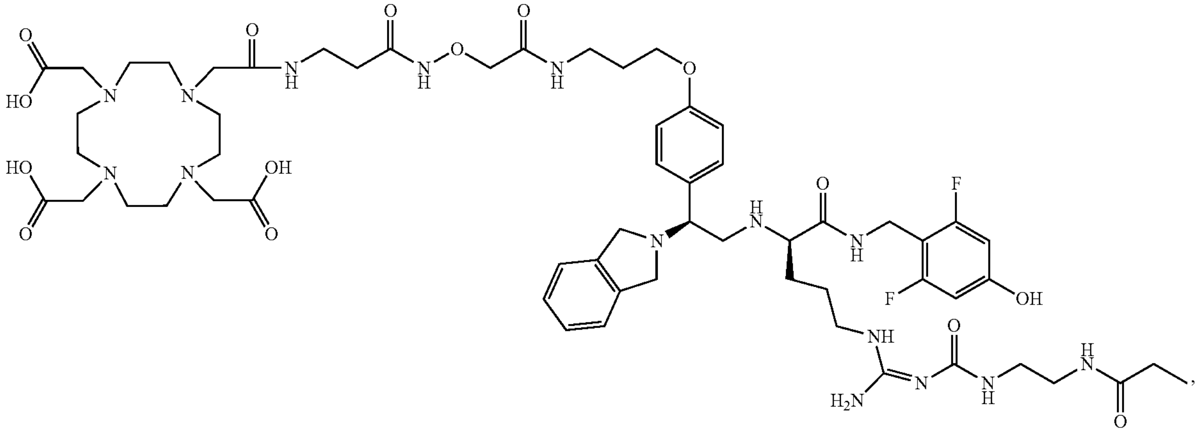
,
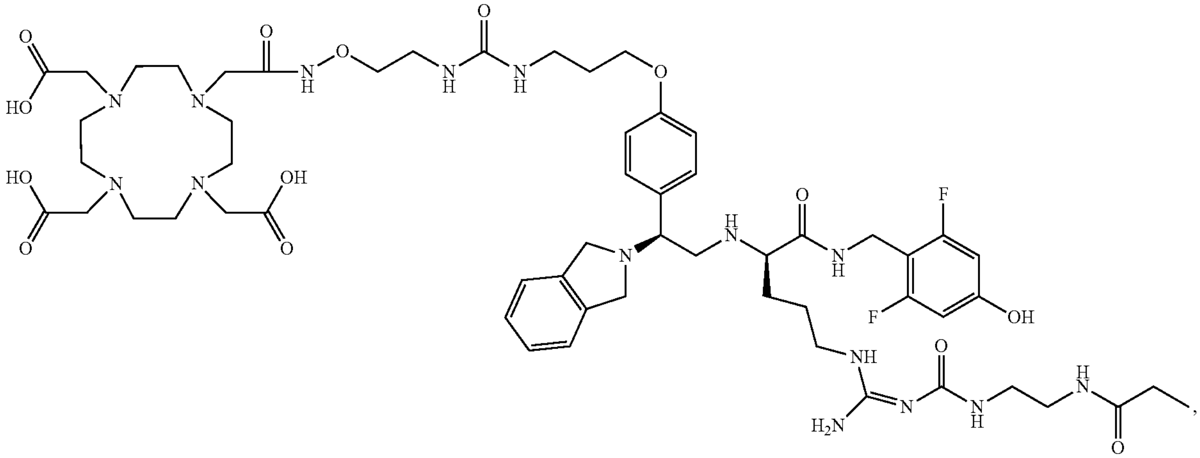
,

-continued
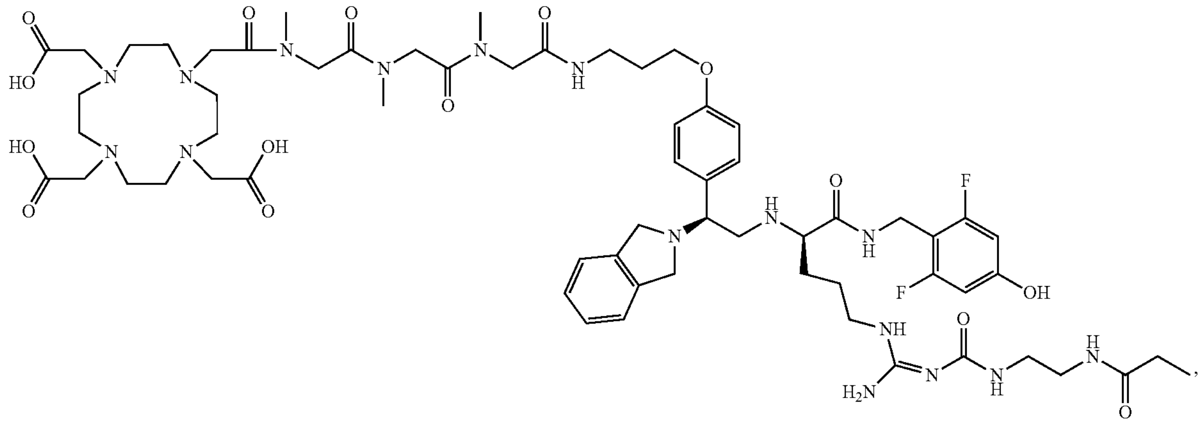
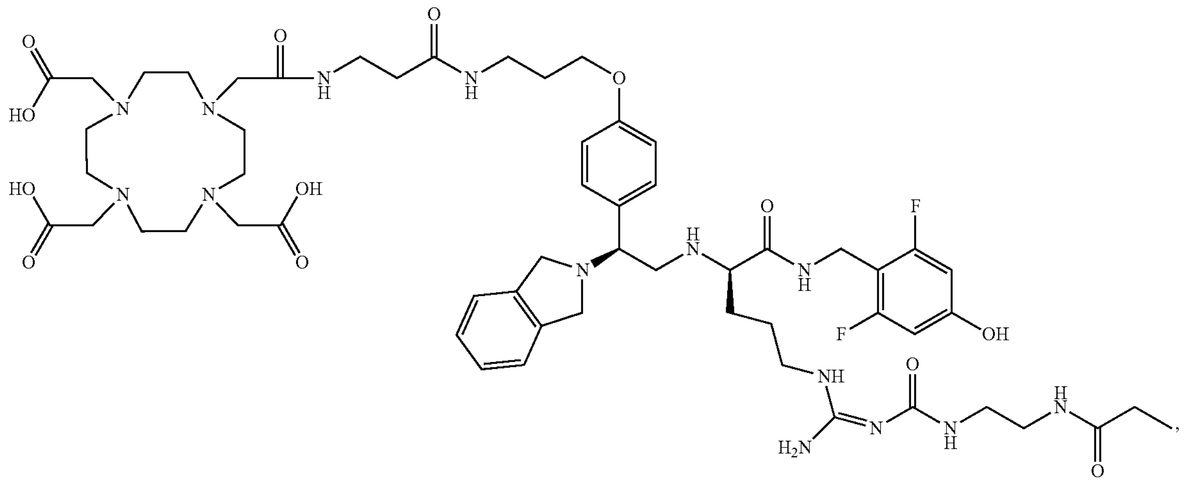
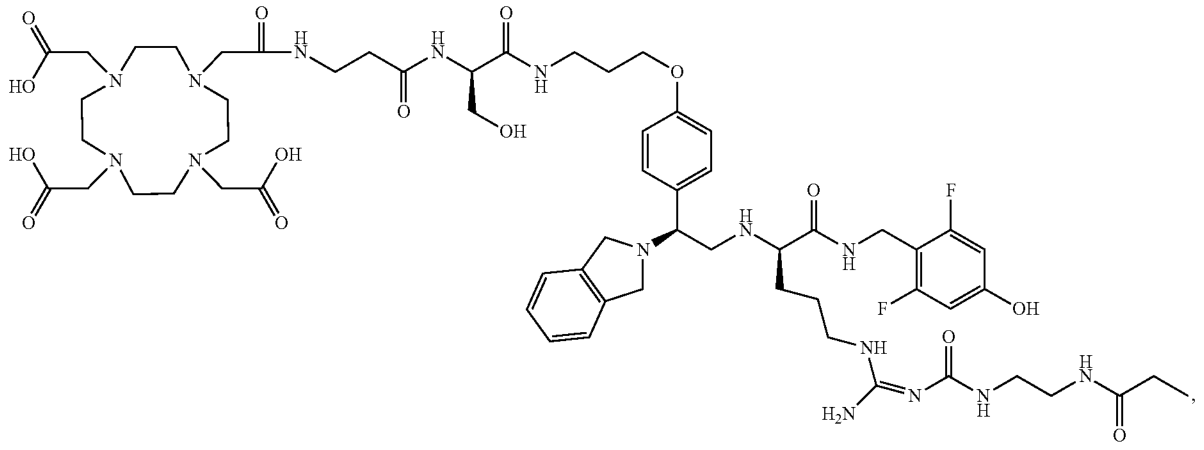

-continued
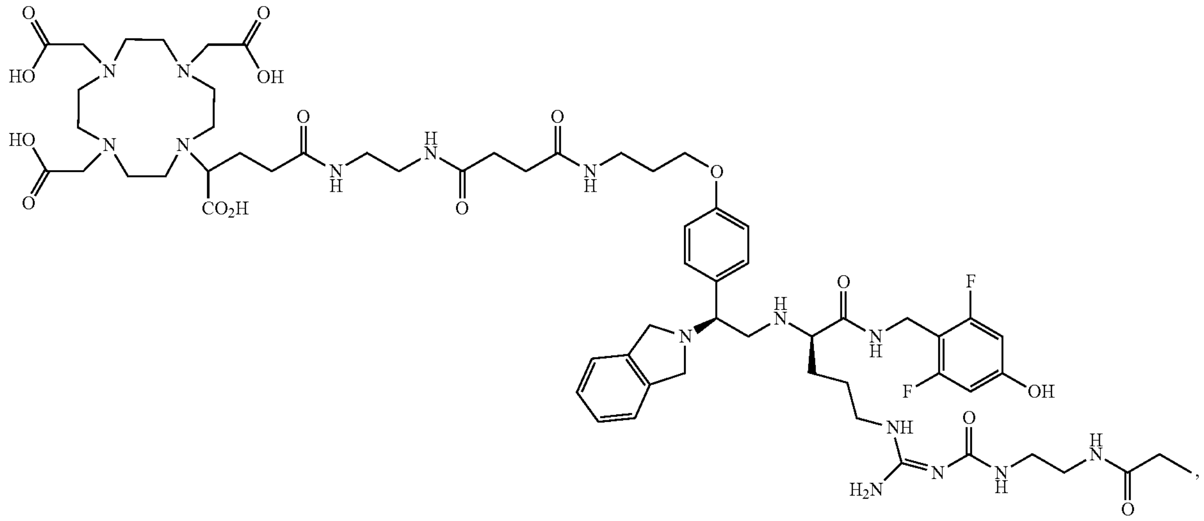
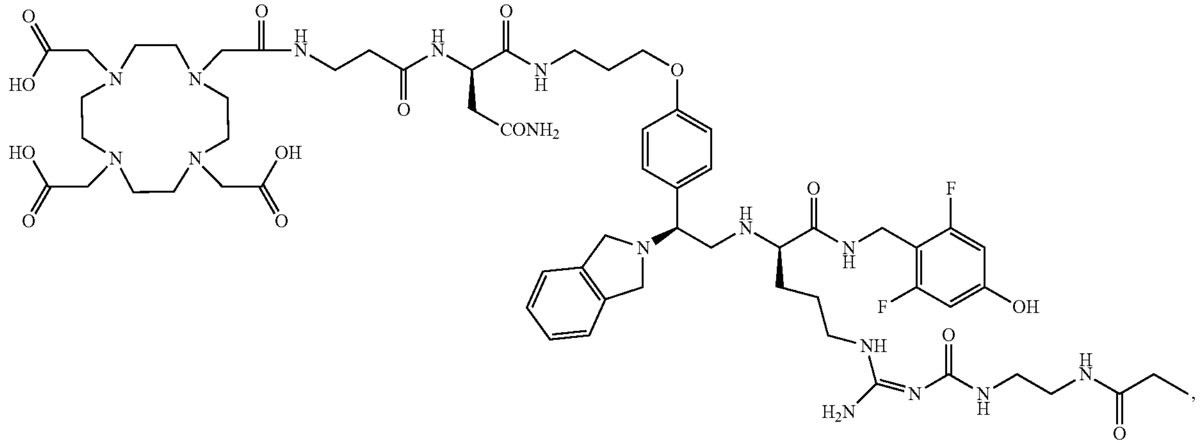
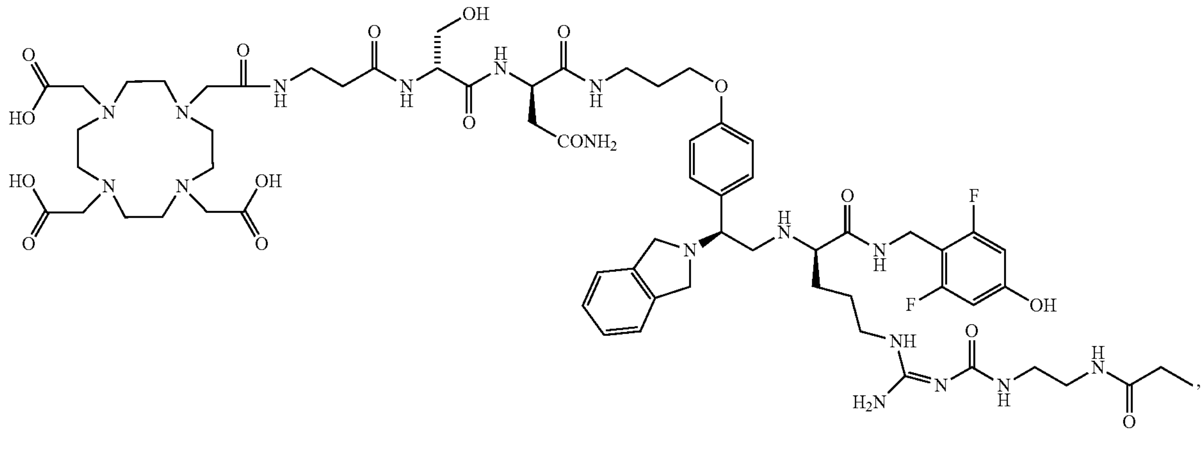

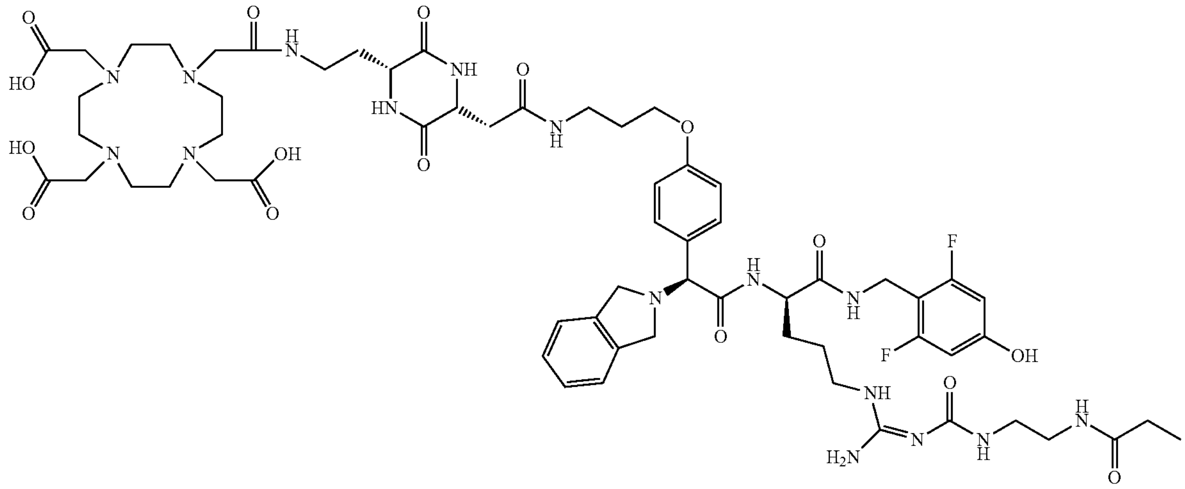
,
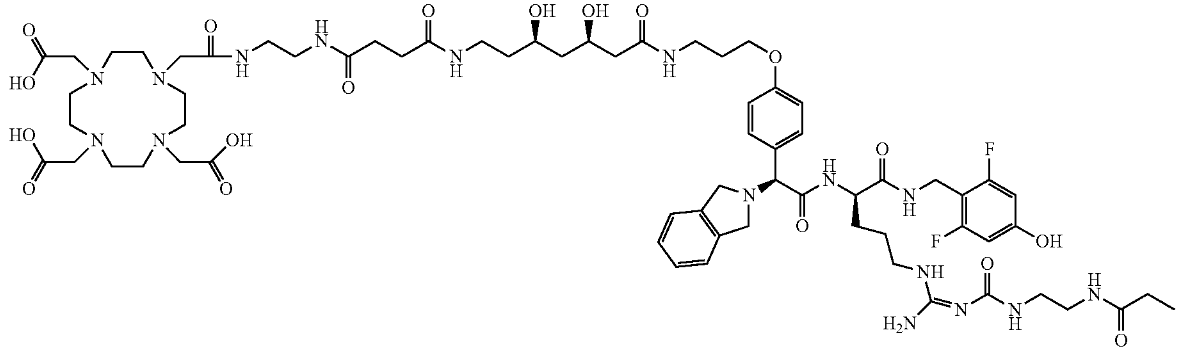
,
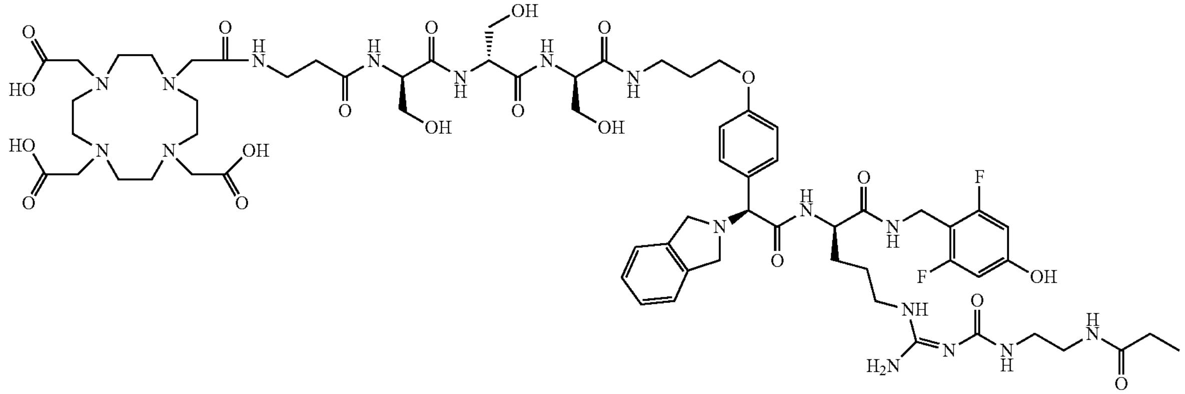
,
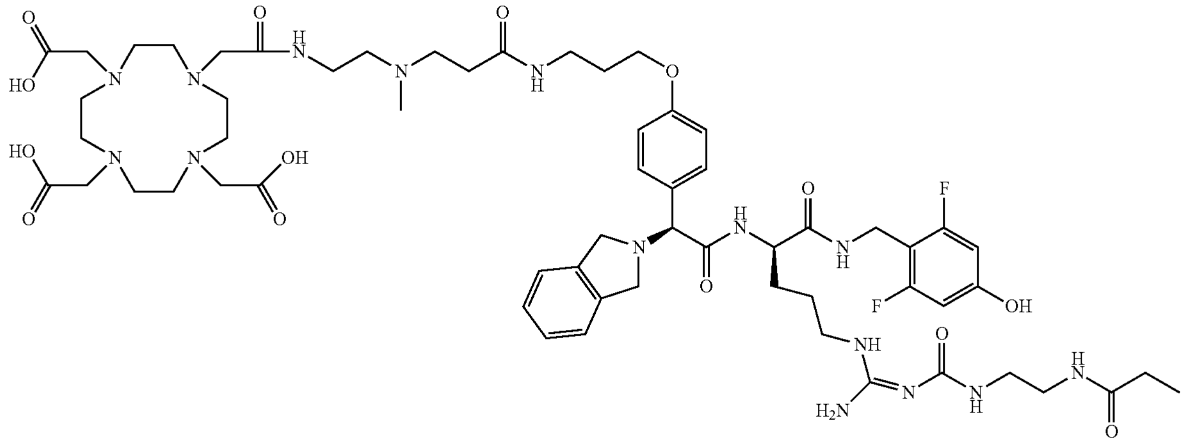
,

-continued
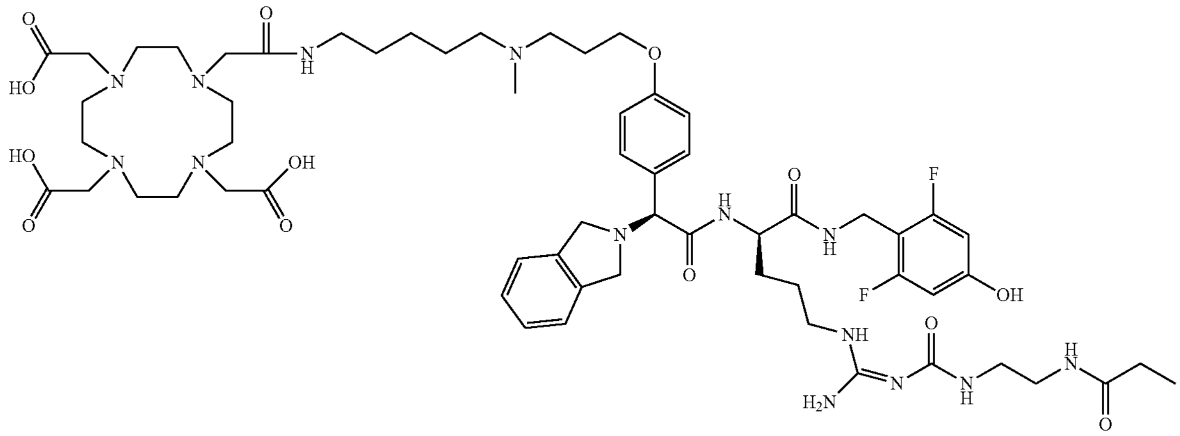
,
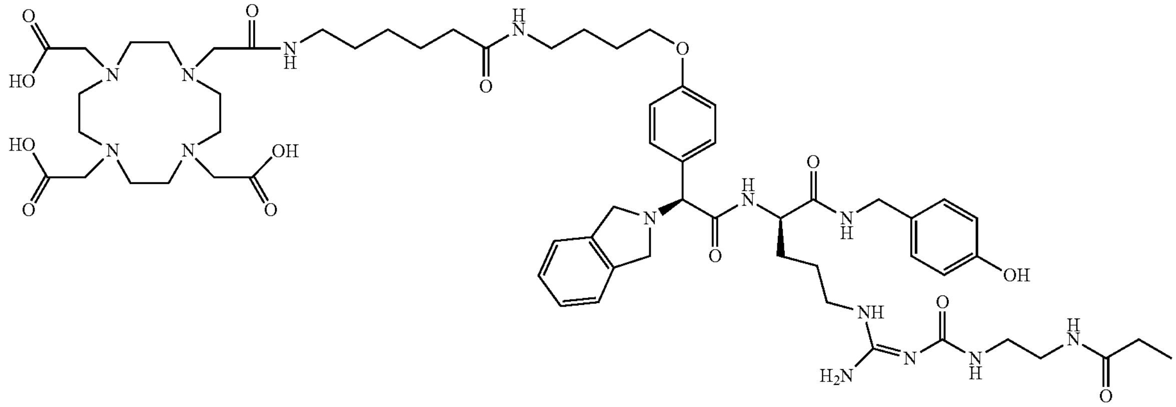
,
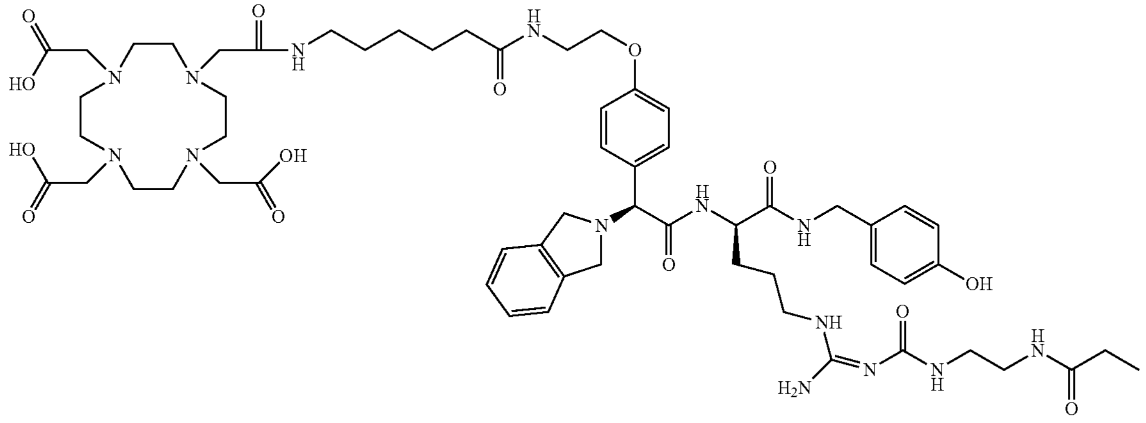
, or

-continued

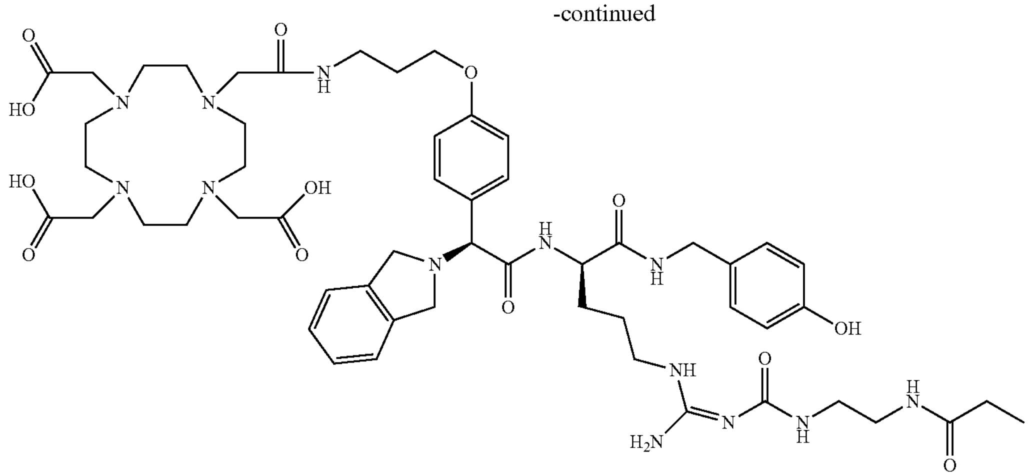

, or a radionuclide complex thereof;

wherein the radionuclide of the chelator-radionuclide complex is:

111-indium ($^{111}In$), 115-indium ($^{115}In$), 67-gallium ($^{67}Ga$), 68-gallium ($^{68}Ga$), 69-gallium ($^{69}Ga$), 71-gallium ($^{71}Ga$), 225-actinium ($^{225}Ac$), 175-lutetium ($^{175}Lu$), 177-lutetium ($^{177}Lu$), 204-lead ($^{204}Pb$), 206-lead ($^{206}Pb$), 207-lead ($^{207}Pb$), 208-lead ($^{208}Pb$), 212-lead ($^{212}Pb$), 63-copper ($^{63}Cu$), 64-copper ($^{64}Cu$), 65-copper ($^{65}Cu$), or 67-copper ($^{67}Cu$).

21. The compound of claim 1, or a pharmaceutically acceptable salt thereof, wherein the compound of Formula (If) has one of the following structures, or a pharmaceutically acceptable salt thereof:

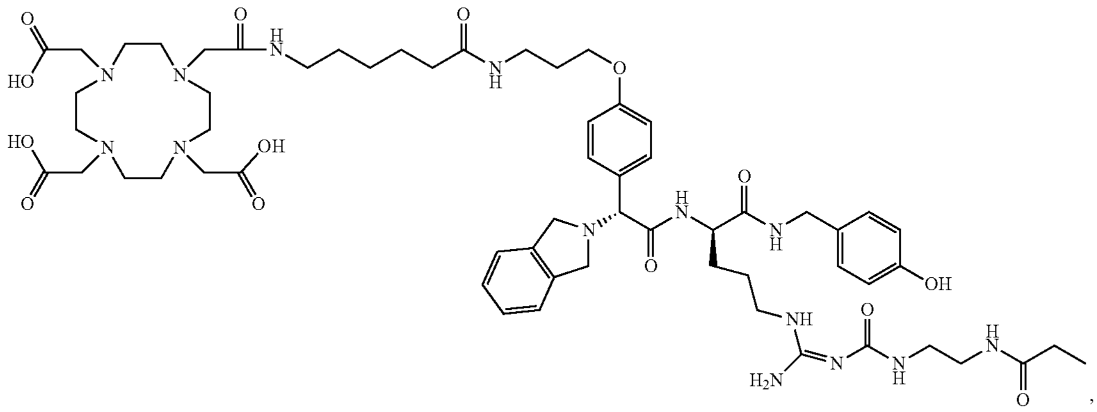

,

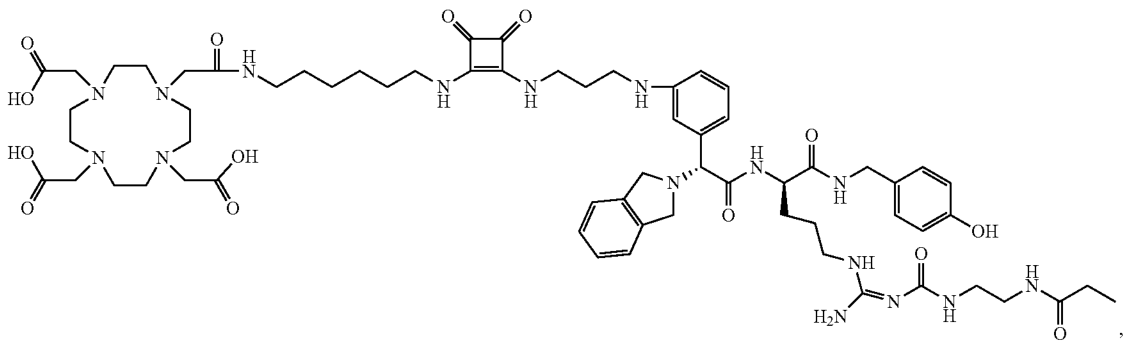

,

-continued
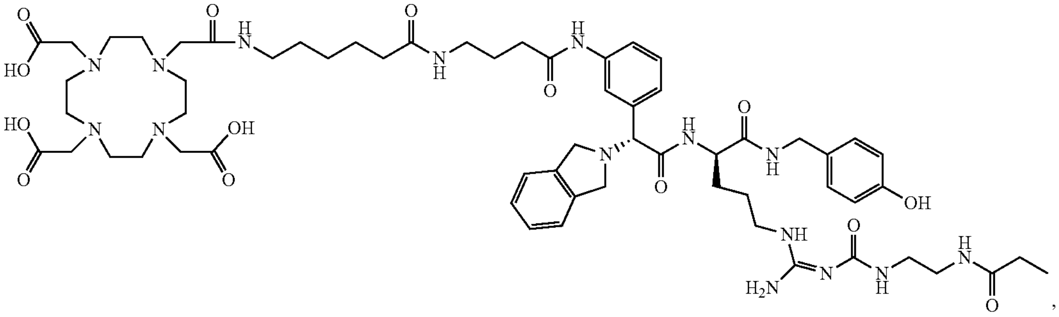
,
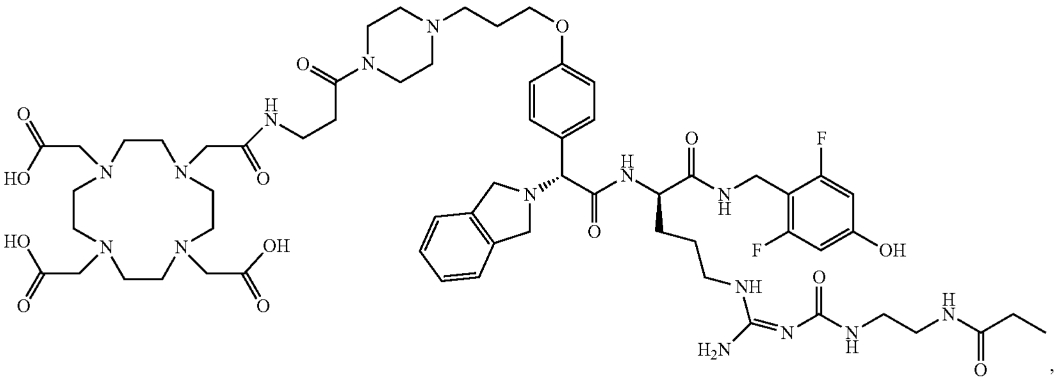
,
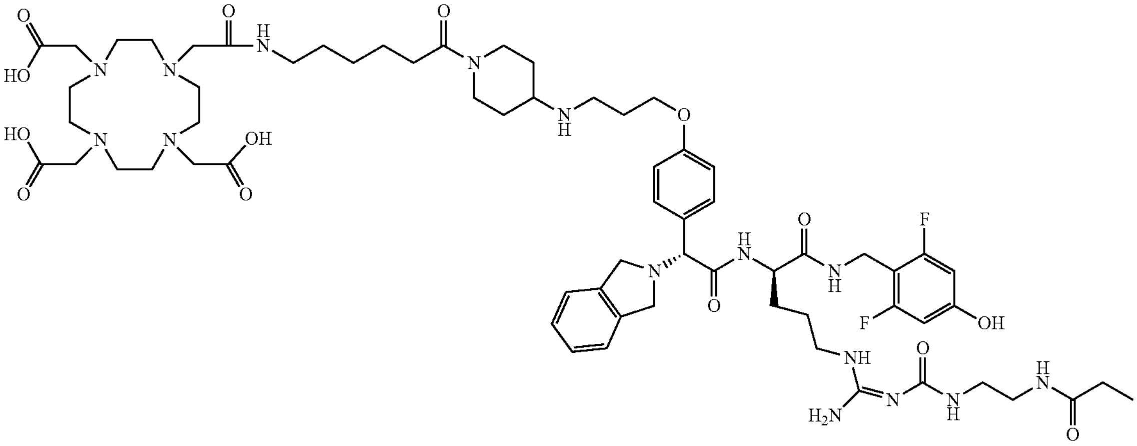
,
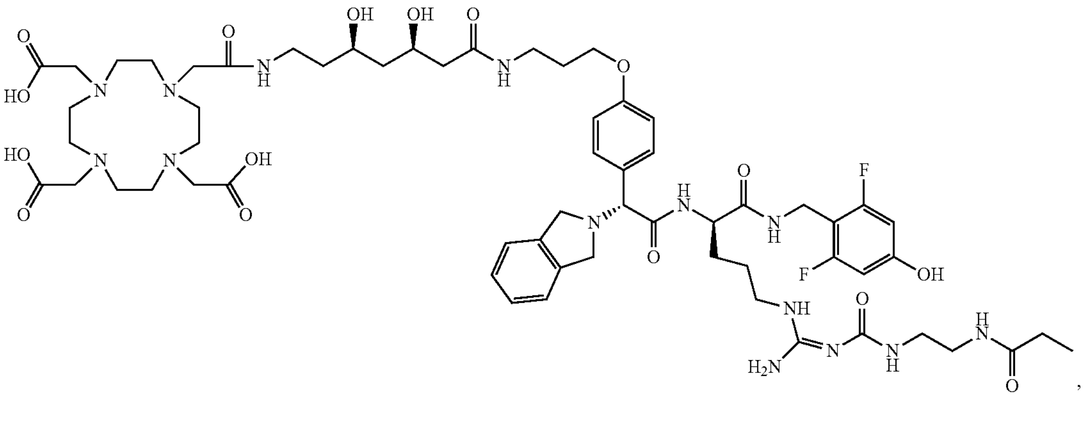
,

-continued

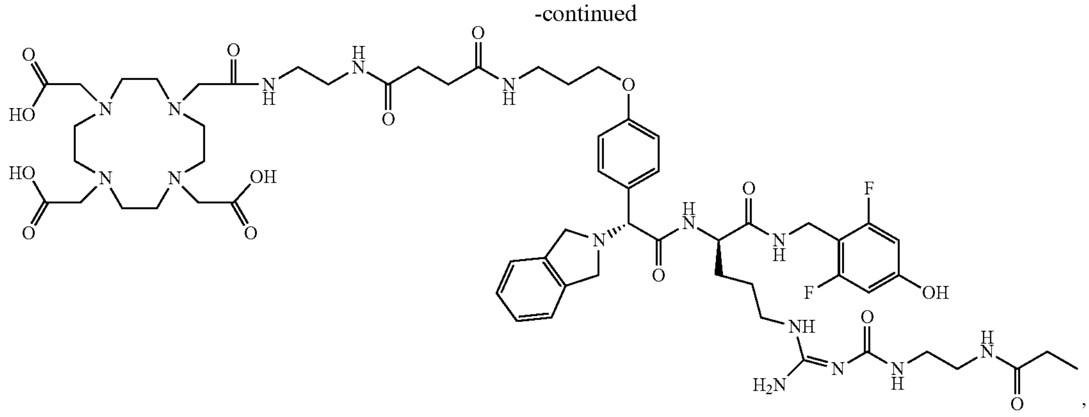

,

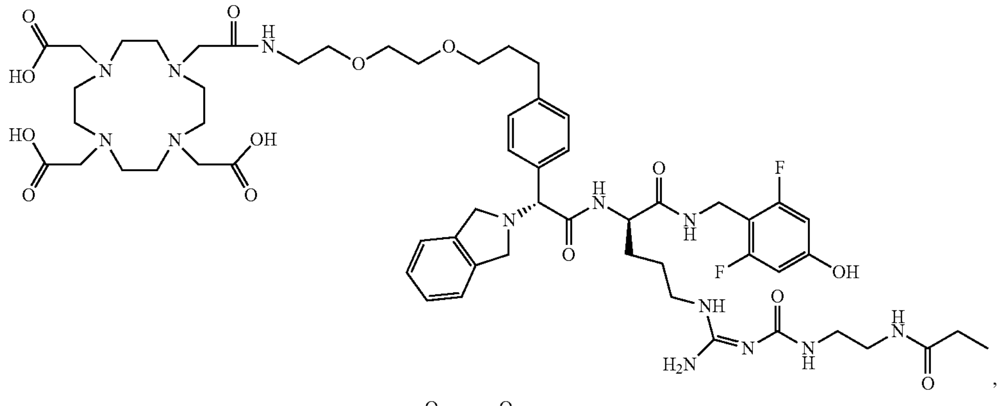

,

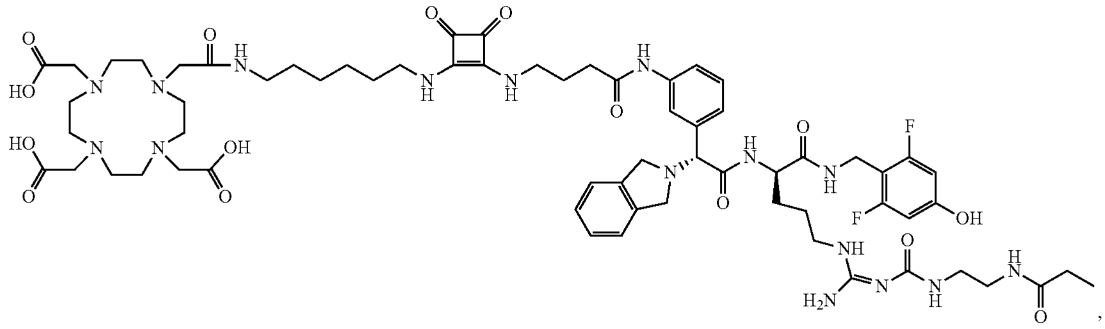

, or

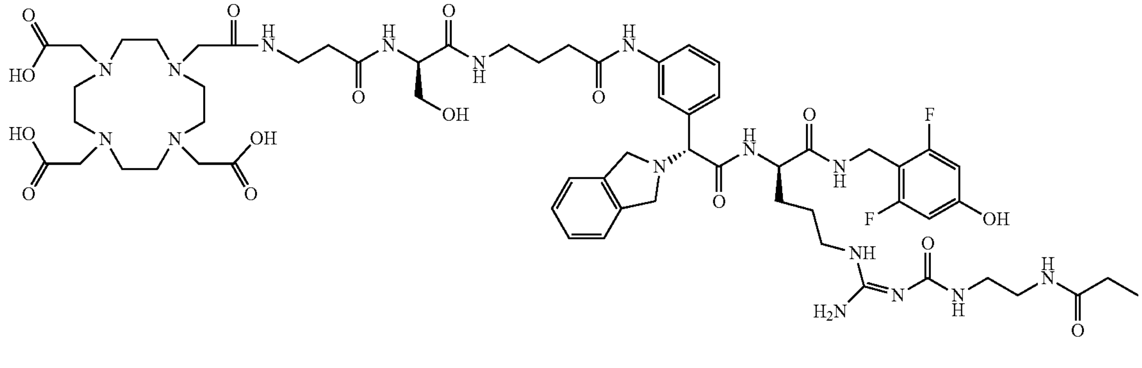

, or a radionuclide complex thereof.

22. The compound of claim 20, or a pharmaceutically acceptable salt thereof, wherein the compound comprises a chelator-radionuclide complex and the radionuclide of the chelator-radionuclide complex is: 225-actinium ($^{225}Ac$), 212-lead ($^{212}Pb$), or 177-lutetium ($^{177}Lu$).

23. The compound of claim 20, or a pharmaceutically acceptable salt thereof, wherein: the compound comprises a chelator-radionuclide complex and the radionuclide of the chelator-radionuclide complex is 111-indium ($^{111}In$), 115-indium ($^{115}In$), 67-gallium ($^{67}Ga$), 68-gallium ($^{68}Ga$), 225-actinium ($^{225}Ac$), 175-lutetium ($^{175}Lu$), or 177-lutetium ($^{177}Lu$).

24. A pharmaceutical composition comprising a compound of claim 1, or a pharmaceutically acceptable salt thereof, and at least one pharmaceutically acceptable excipient.

25. A method for the treatment of cancer comprising administering to a mammal with cancer an effective amount of a compound of claim 1, or a pharmaceutically acceptable salt thereof; wherein the compound comprises a chelator-radionuclide complex and the radionuclide of the chelator-radionuclide complex is:

an α-emitting radionuclide that is 225-actinium ($^{225}Ac$), or 212-lead ($^{212}Pb$); or a β-emitting radionuclide that is 177-lutetium ($^{177}Lu$), 64-copper ($^{64}Cu$), or 67-copper ($^{67}Cu$).

26. The method of claim 25, wherein the cancer is breast cancer, kidney cancer, ovarian cancer, melanoma, gastrointestinal stromal tumor (GIST), Ewing's sarcoma, nephroblastoma, or adrenal gland tumors.

27. A method of killing tumors in a mammal that overexpress the neuropeptide $Y_1$ receptor ($NPY_1R$) comprising administering to the mammal a compound of claim 1, or a pharmaceutically acceptable salt thereof, wherein the compound comprises a chelator-radionuclide complex and the radionuclide of the chelator-radionuclide complex is:

an α-emitting radionuclide that is 225-actinium ($^{225}Ac$), 213-bismuth ($^{213}Bi$), 223-radium ($^{223}Ra$), or 212-lead ($^{212}Pb$); or a β-emitting radionuclide that is 90-yttrium ($^{90}Y$), 177-lutetium ($^{177}Lu$), 64-copper ($^{64}Cu$), 67-copper ($^{67}Cu$), or 153-samarium ($^{153}Sm$).

28. The method of claim 27, wherein the mammal has been diagnosed with breast cancer, kidney cancer, ovarian cancer, melanoma, gastrointestinal stromal tumor (GIST), Ewing's sarcoma, nephroblastoma, or adrenal gland tumors.

29. A compound that has one of the following structures, or a pharmaceutically acceptable salt thereof:

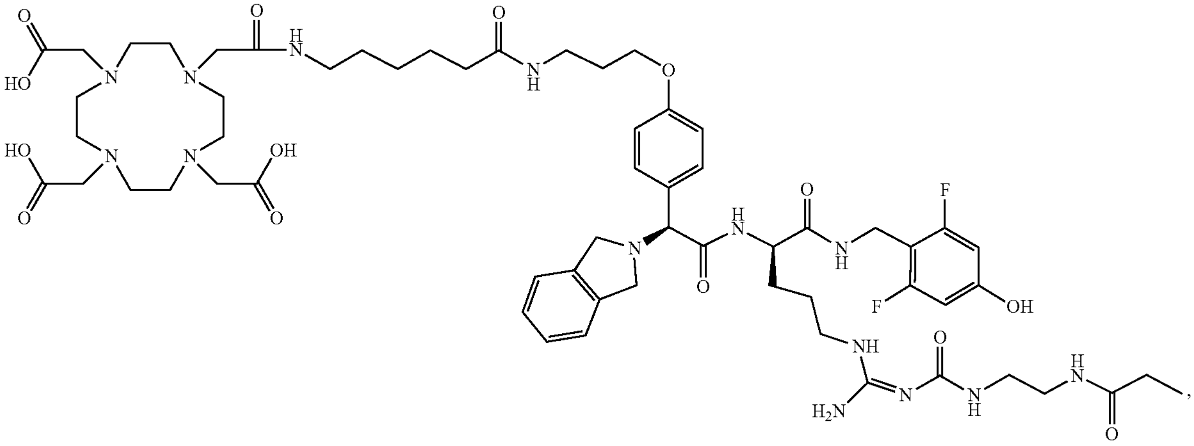

,

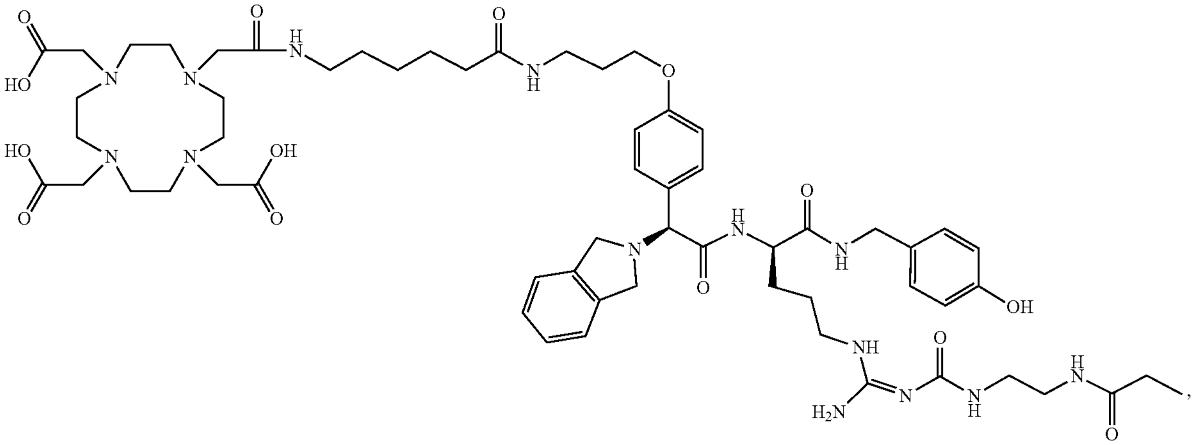

,

-continued
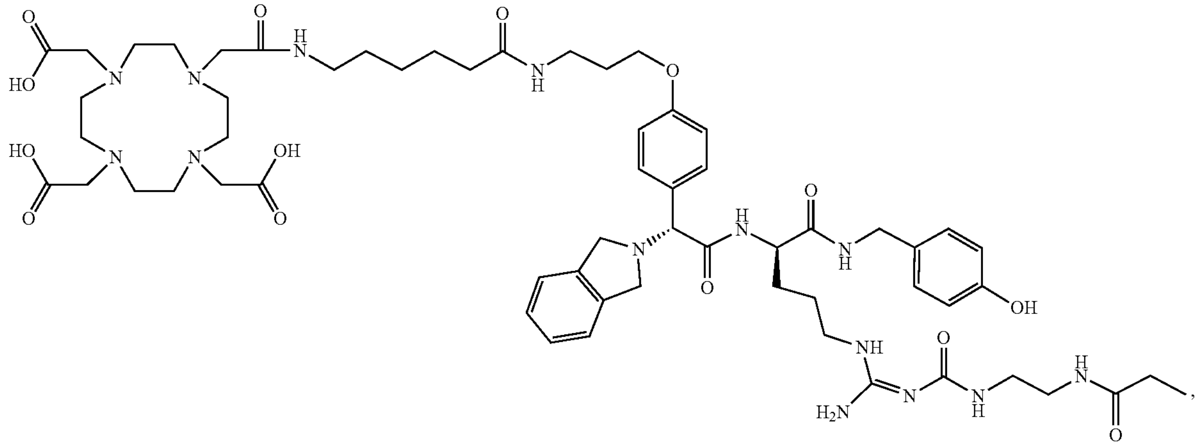
,
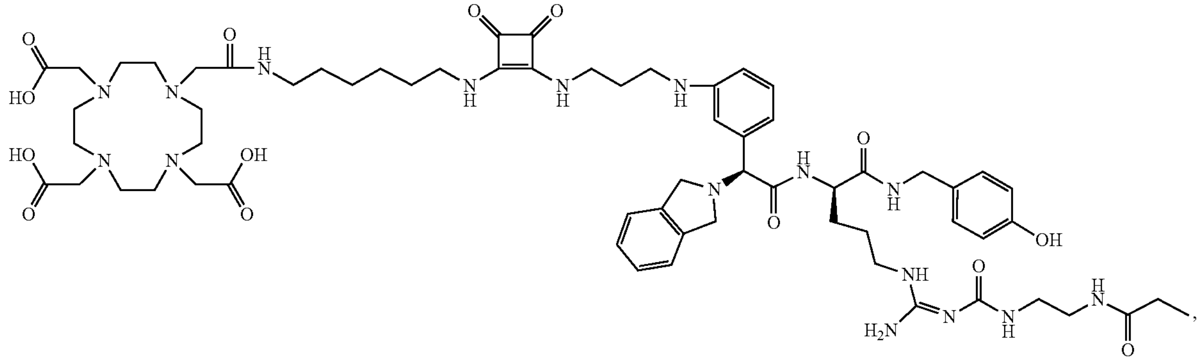
,
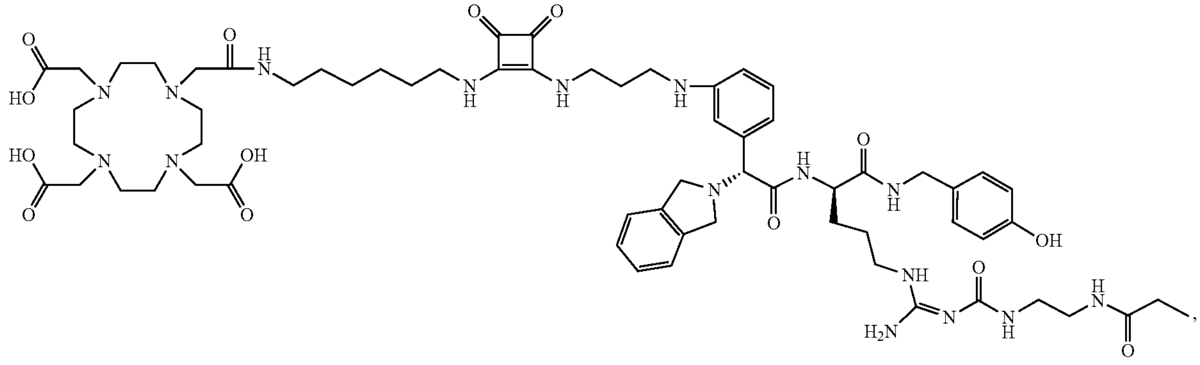
,
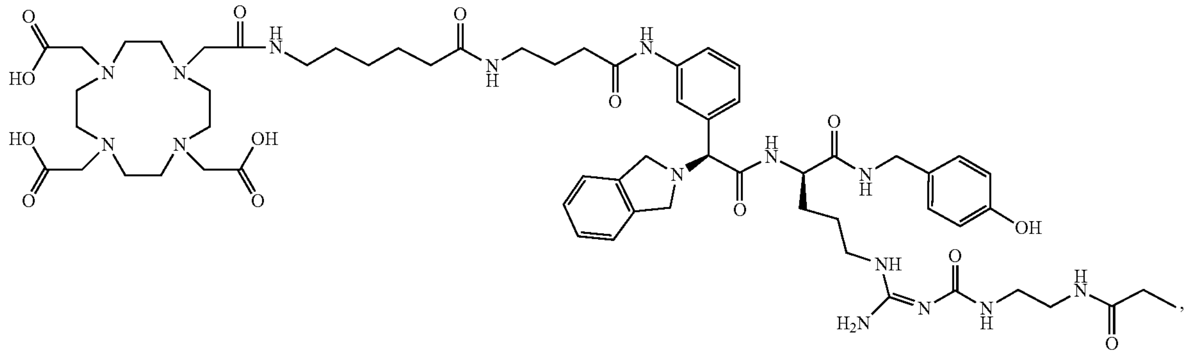
,

-continued
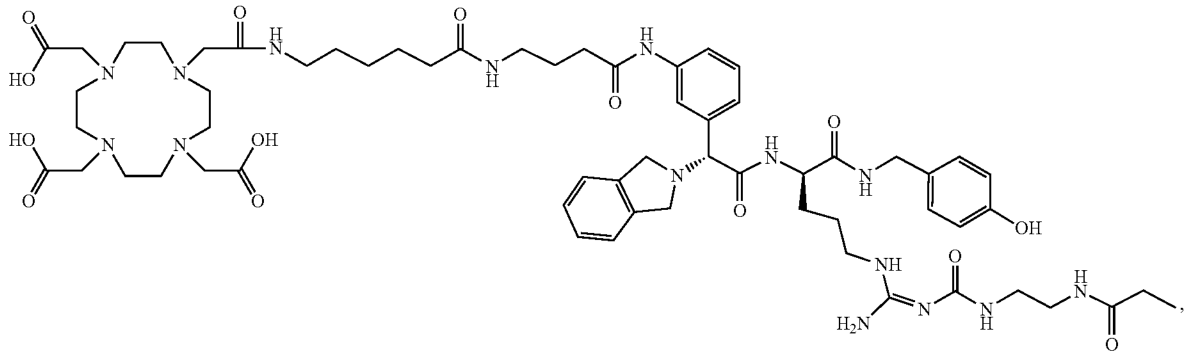
,
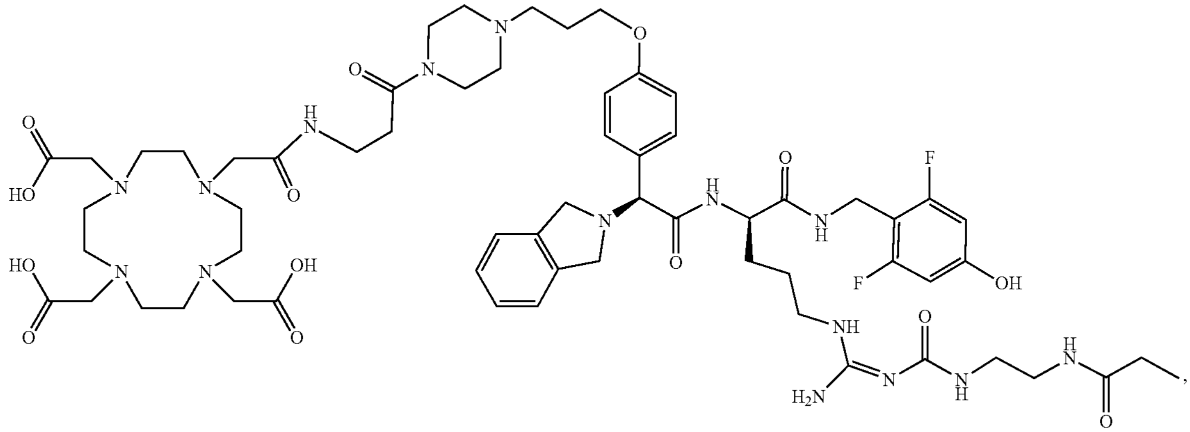
,
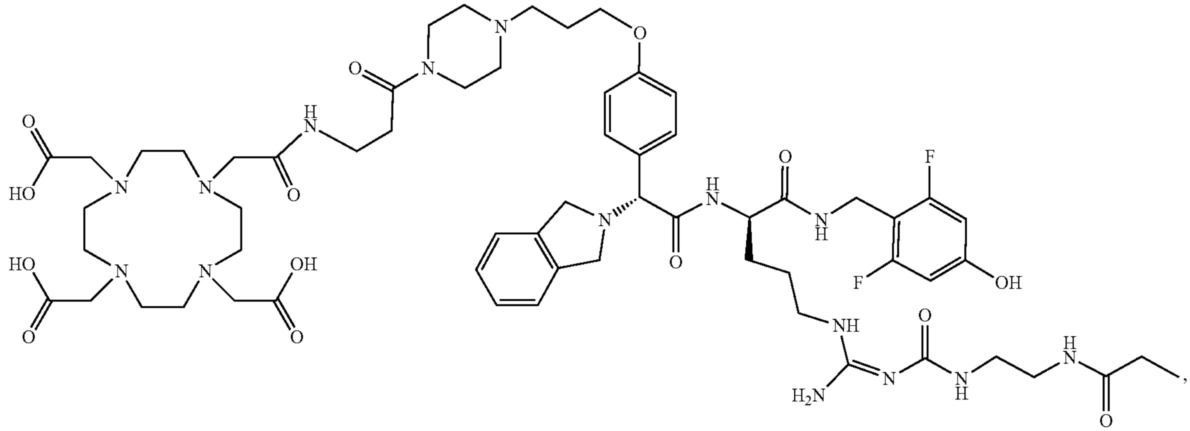
,
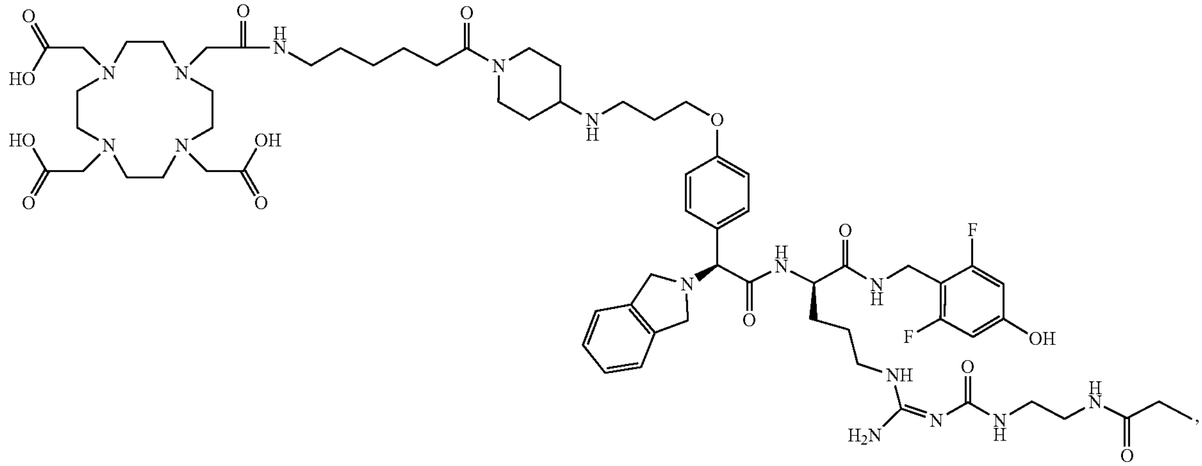
,

-continued
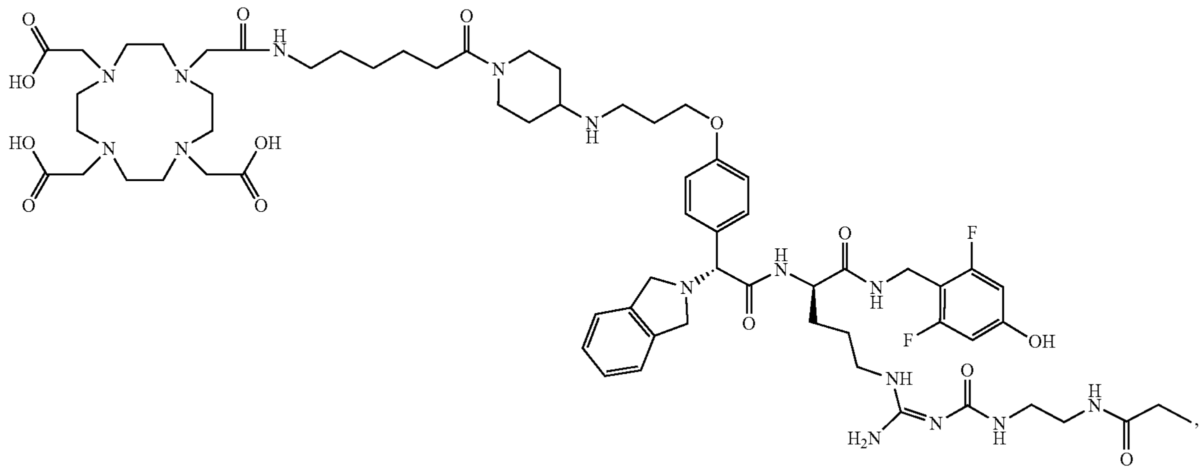
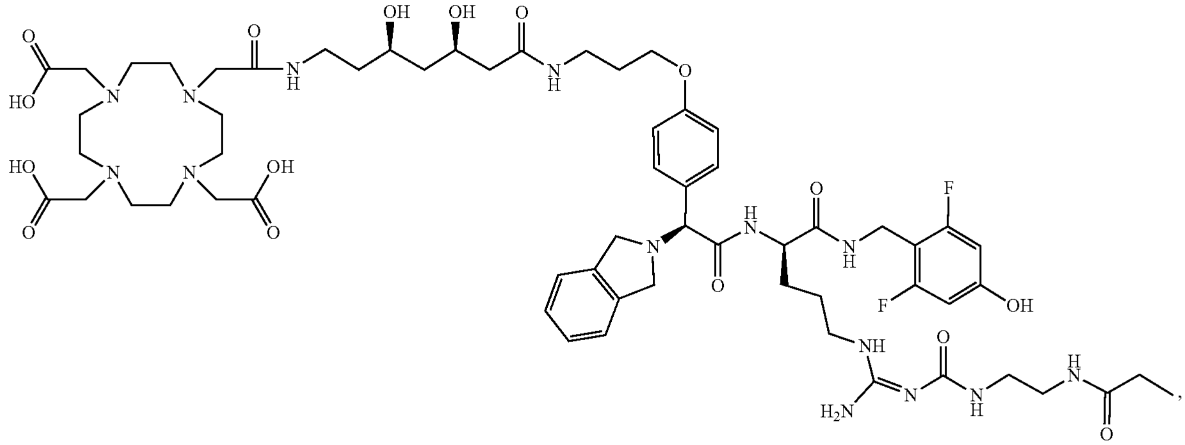
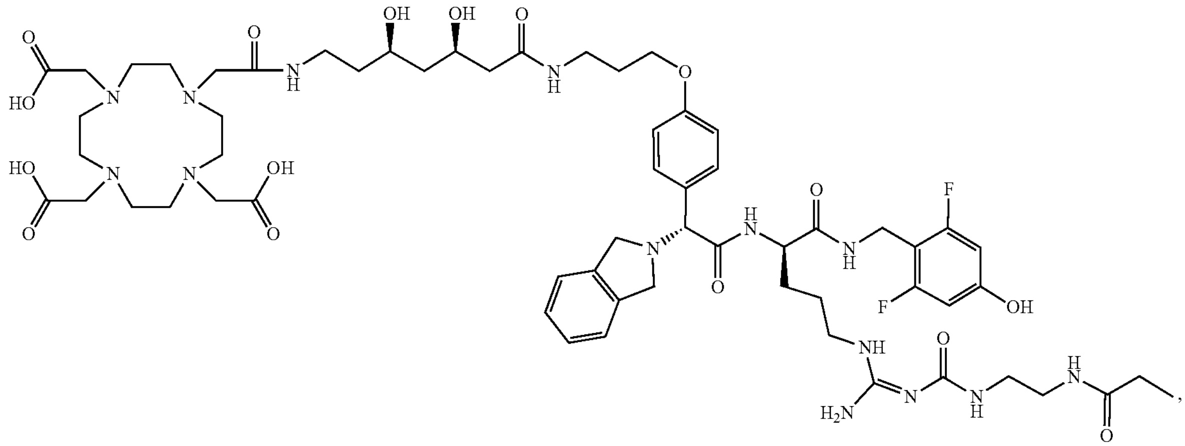

-continued
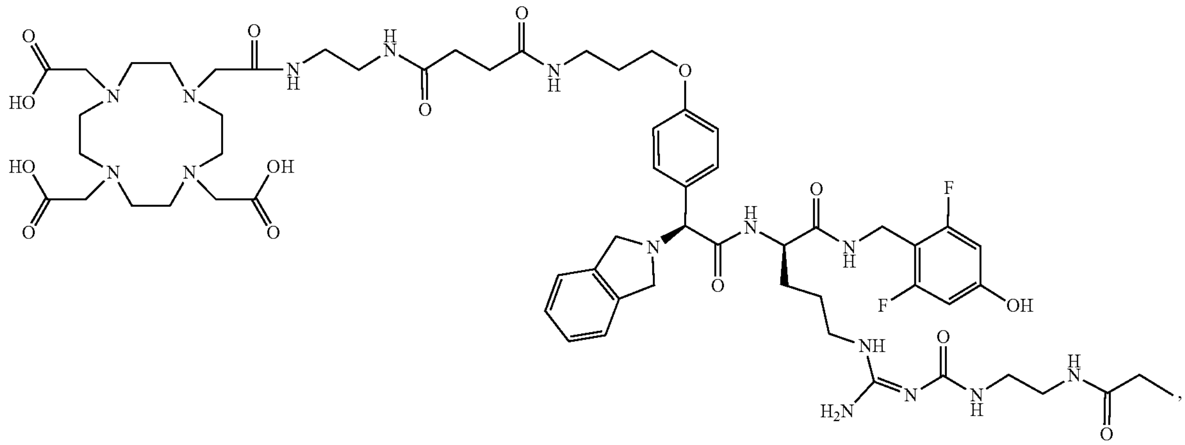
,
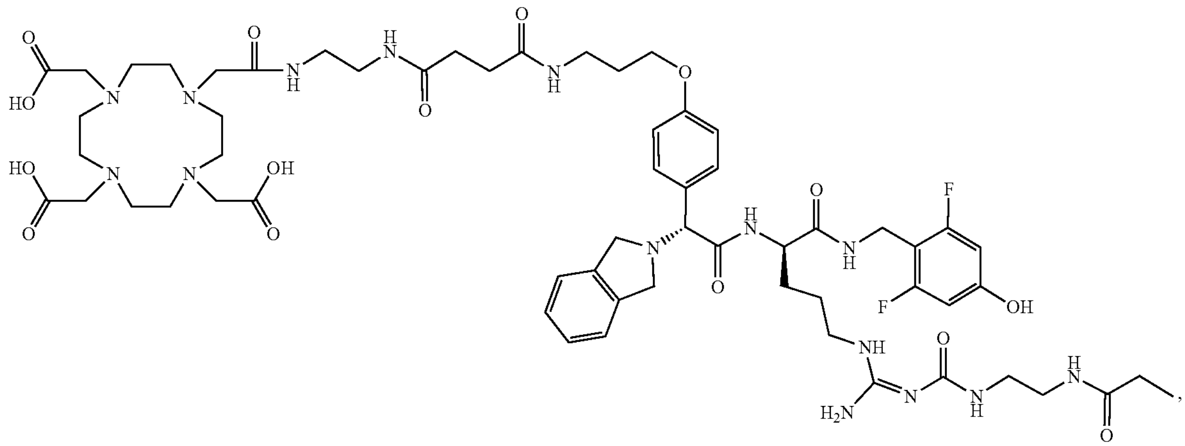
,
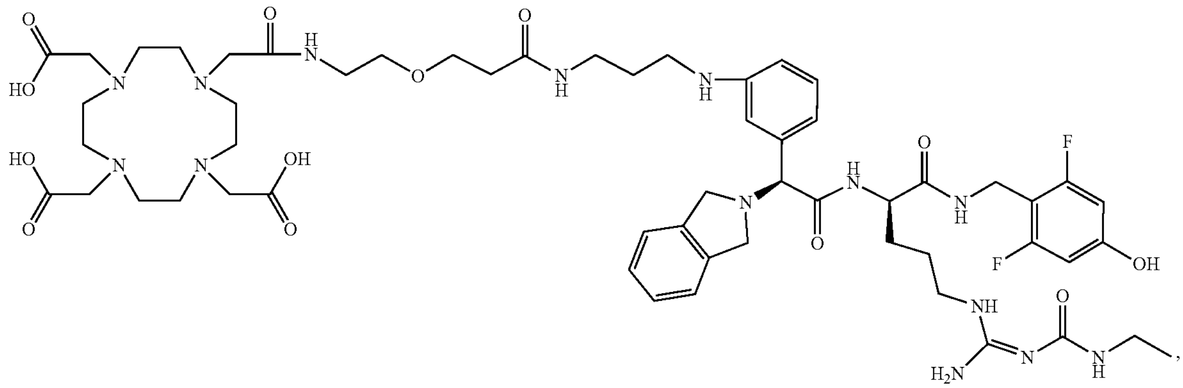
,

-continued
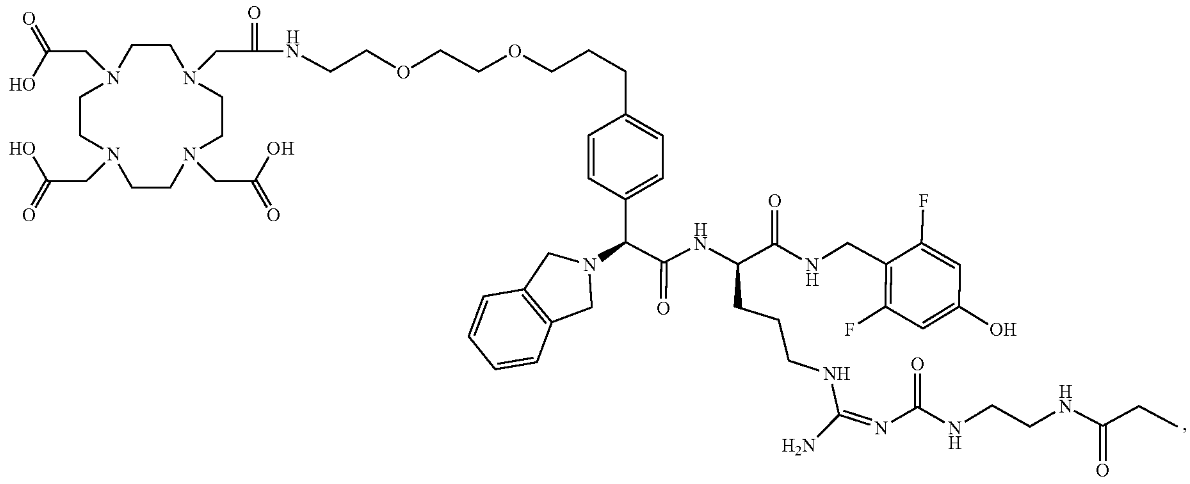
,
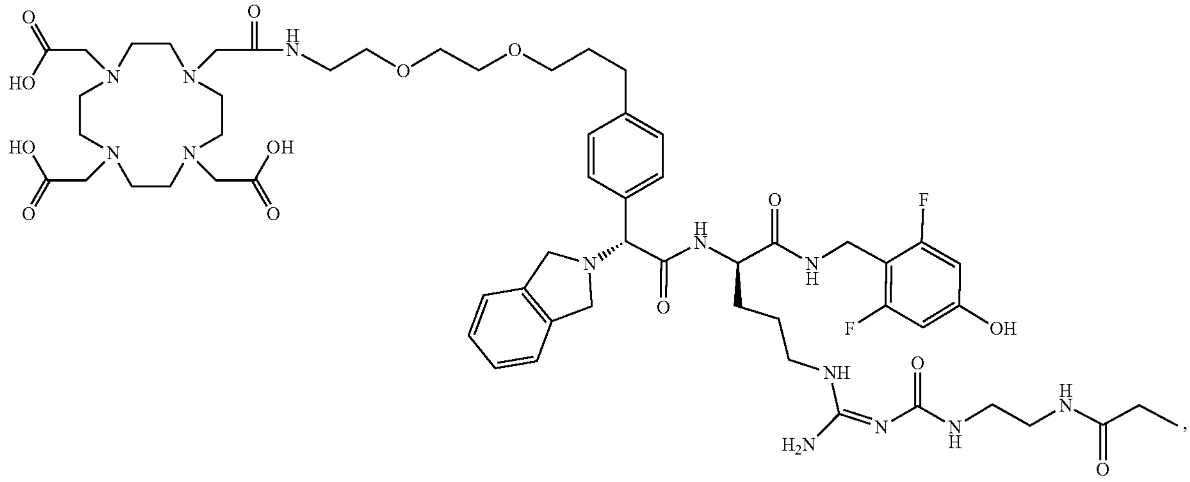
,
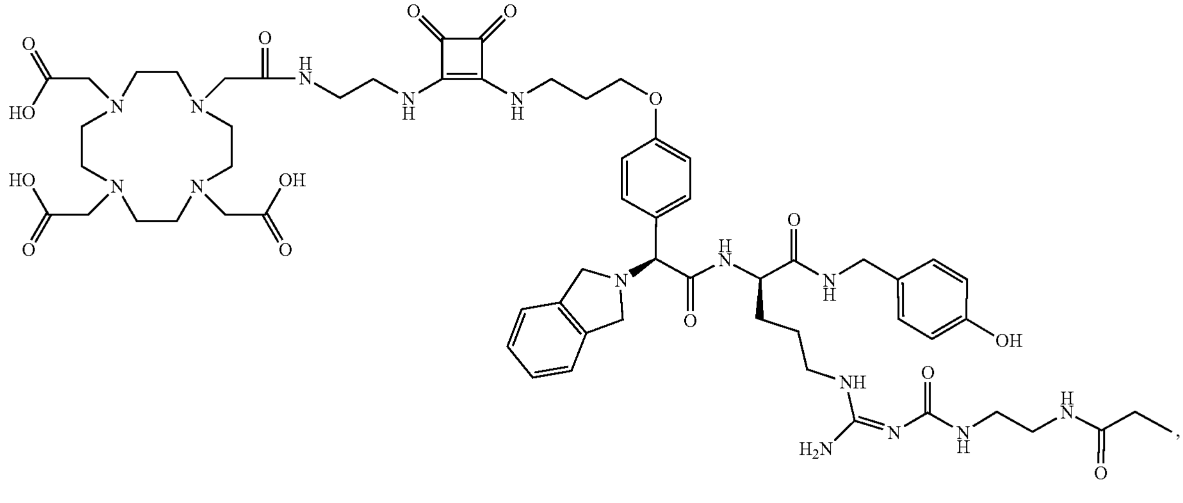
,

-continued
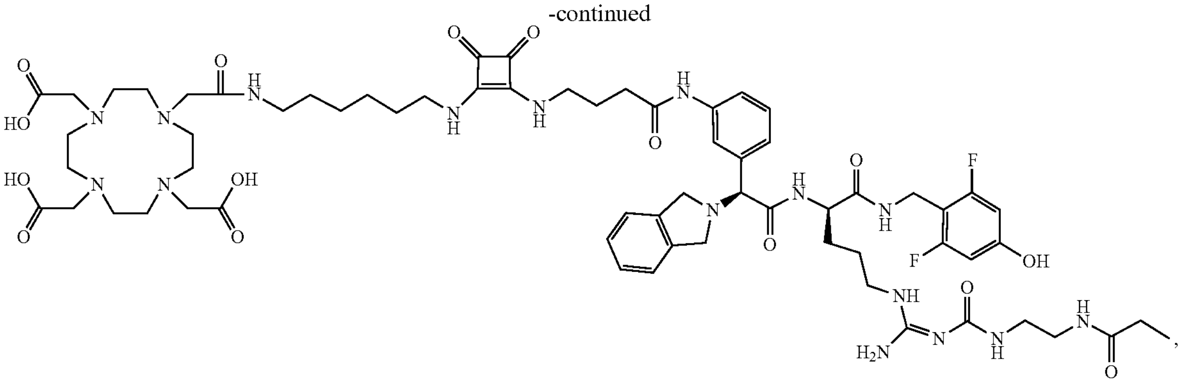
,
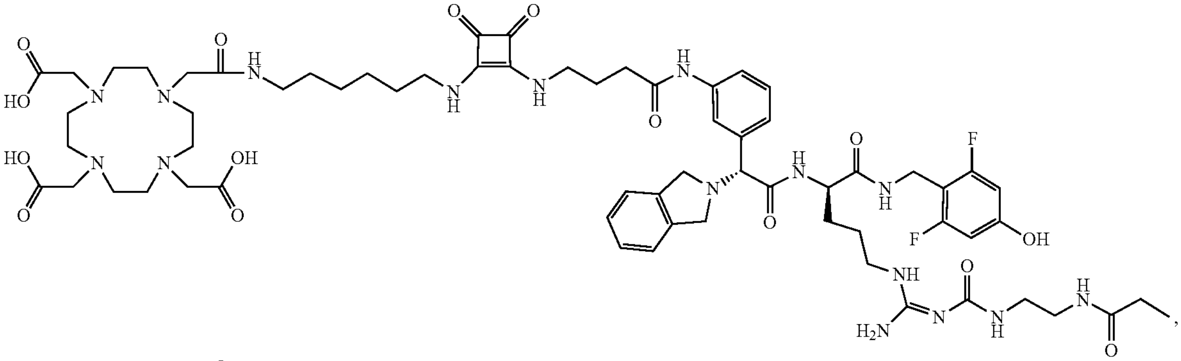
,
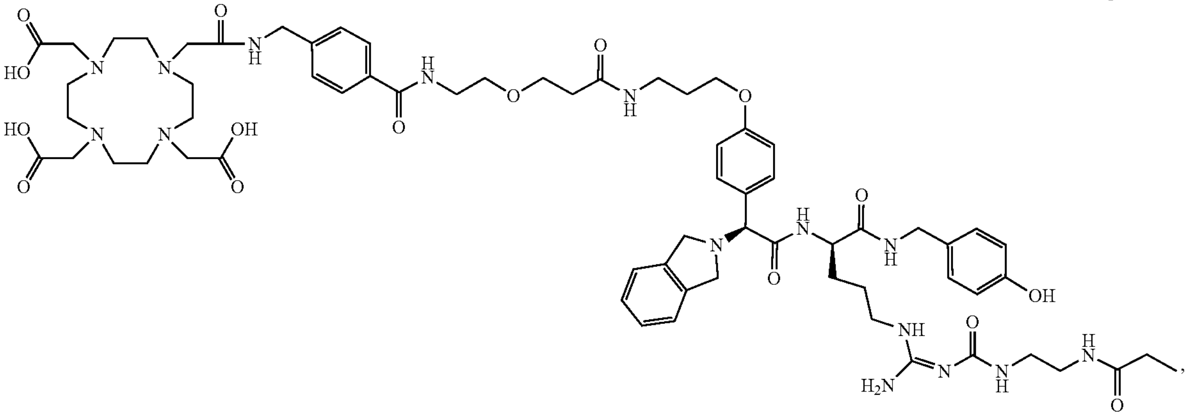
,
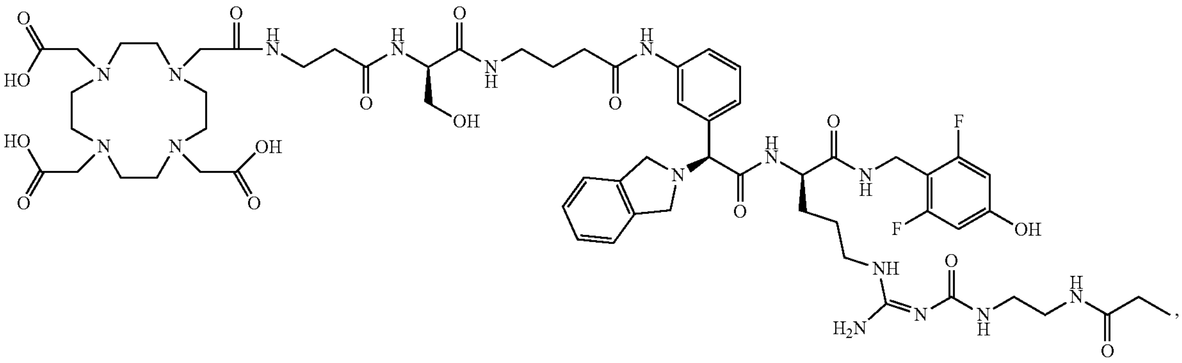
,

-continued
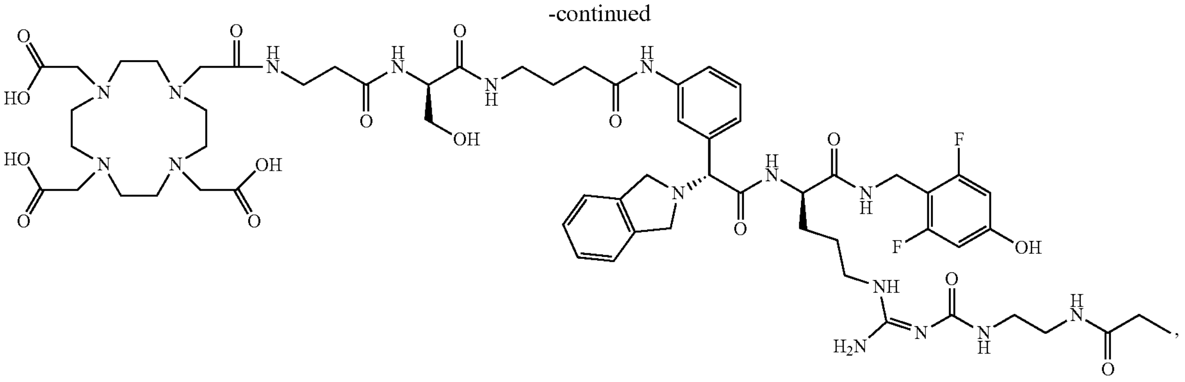
or a radionuclide complex thereof;
wherein the radionuclide of the chelator-radionuclide complex is:
111-indium ($^{111}In$), 115-indium ($^{115}In$), 67-gallium ($^{67}Ga$), 68-gallium ($^{68}Ga$), 69-gallium ($^{69}Ga$), 71-gallium ($^{71}Ga$), 225-actinium ($^{225}Ac$), 175-lutetium ($^{175}Lu$), 177-lutetium ($^{177}Lu$), 204-lead ($^{204}Pb$), 206-lead ($^{206}Pb$), 207-lead ($^{207}Pb$), 208-lead ($^{208}Pb$), 212-lead ($^{212}Pb$), 63-copper ($^{63}Cu$), 64-copper ($^{64}Cu$), 65-copper ($^{65}Cu$), or 67-copper ($^{67}Cu$).
* * * * *